US008420104B2

(12) United States Patent
Charneau et al.

(10) Patent No.: US 8,420,104 B2
(45) Date of Patent: Apr. 16, 2013

(54) LENTIVIRAL GENE TRANSFER VECTORS AND THEIR MEDICINAL APPLICATIONS

(75) Inventors: Pierre Charneau, Paris (FR); Anne-Sophie Beignon, Paris (FR); Frederic Philippe Coutant, Rodez (FR); Karine Courbeyrette, Massy (FR)

(73) Assignees: Institut Pasteur, Paris (FR); Centre National de la Recherche Scientifique, Paris (FR); Theravectys, Paris (FR)

( * ) Notice: Subject to any disclaimer, the term of this patent is extended or adjusted under 35 U.S.C. 154(b) by 451 days.

(21) Appl. No.: 12/671,898

(22) PCT Filed: Aug. 1, 2008

(86) PCT No.: PCT/IB2008/002930
§ 371 (c)(1),
(2), (4) Date: Apr. 22, 2010

(87) PCT Pub. No.: WO2009/019612
PCT Pub. Date: Feb. 12, 2009

(65) Prior Publication Data
US 2010/0297168 A1    Nov. 25, 2010

(30) Foreign Application Priority Data

Aug. 3, 2007    (EP) .................................... 07290979
Aug. 3, 2007    (EP) .................................... 07290980
Oct. 12, 2007    (EP) .................................... 07291251
May 16, 2008    (EP) .................................... 08156405

(51) Int. Cl.
*A61K 39/12*    (2006.01)
*A61K 39/21*    (2006.01)
*A61K 39/205*    (2006.01)
*C12Q 1/70*    (2006.01)

(52) U.S. Cl.
USPC ................... 424/204.1; 424/208.1; 424/224.1; 435/5

(58) Field of Classification Search .................... None
See application file for complete search history.

(56) References Cited

U.S. PATENT DOCUMENTS

2003/0203489 A1 * 10/2003 Yonemitsu et al. ........... 435/456
2008/0089863 A1    4/2008 Mallet et al.
2010/0047276 A1    2/2010 Heeney et al.

FOREIGN PATENT DOCUMENTS

| EP | 1403374 A1 | 3/2004 |
|---|---|---|
| WO | WO-02/22080 A2 | 3/2002 |
| WO | WO-02/090558 A | 11/2002 |
| WO | WO-03/037919 A2 | 5/2003 |
| WO | WO-2004/110485 A1 | 12/2004 |
| WO | WO-2005/028634 A2 | 3/2005 |
| WO | WO-2006/010834 A1 | 2/2006 |
| WO | WO-2007/012691 A1 | 2/2007 |
| WO | WO-2007/054792 A1 | 5/2007 |
| WO | WO-2007/071994 A2 | 6/2007 |
| WO | WO-2007/071997 A2 | 6/2007 |
| WO | WO-2007/091066 A1 | 8/2007 |

OTHER PUBLICATIONS

Gupta et al., Journal of Virology, 1979, 30(3):735-745.*
Wilks et al., Archives of Virology, 1985, 86:335-340.*
Morikawa et al., The Journal of Biological Chemistry, 1996, 271(5):2868-2873.*
Zennou et al., Nature Biotechnology, 2001, 19:446-450.*
Baliga et al., "Vaccination of mice with replication-defective human immunodeficiency virus induces cellular and humoral immunity and protects against vaccinia virus-gag challenge", Molecular Therapy, Academic Press, San Diego, CA, USA, vol. 14, No. 3, Aug. 12, 2006, pp. 432-441.
Iglesias Maria Candela et al., "Lentiviral vectors encoding HIV-1 polyepitopes induce broad CTL responses invivo", Molecular Therapy, Academic Press, San Diego, CA, USA, vol. 15, No. 6, Jun. 1, 2007, pp. 1203-1210.
Delenda C, "Lentiviral vectors: Optimization of packaging, transduction and gene expression", Journal of Gene Medicine, Wiley, USA, vol. 6, No. Suppl 1, Feb. 2004, pp. S125-S138.
Pichlmair Andreas et al., "Tubulovesicular structures within vesicular stomatitis virus G protein-pseudotyped lentiviral vector preparations carry DNA and stimulate antiviral responses via toll-like receptor 9", Journal of Virology, vol. 81, No. 2, Jan. 2007, pp. 539-547.
Buffa Viviana et al., "Evaluation of a self-inactivating lentiviral vector expressing simian immunodeficiency virus gag for induction of specific immune responses in vitro and in vivo", Viral Immunology Winter 2006, vol. 19, No. 4, Jan. 2006, pp. 690-701.
Negri Donatella RM et al., "Successful immunization with a single injection of non-integrating lentiviral vector", Molecular Therapy, Academic Press, San Diego, CA, USA, vol. 15, No. 9, Jun. 26, 2007, pp. 1716-1723.

(Continued)

Primary Examiner — Stacy B. Chen
(74) Attorney, Agent, or Firm — Law Office of Salvatore Arrigo and Scott Lee, LLP

(57) ABSTRACT

The present invention relates to the design of gene transfer vectors and especially provides lentiviral gene transfer vectors suitable for either a unique administration or, for iterative administration in a host, and to their medicinal application (such as vaccination against Immunodeficiency Virus, especially suitable in human hosts). Gene transfer vectors are either integrative or non-integrative (NI) vectors, dependently upon the purpose of their use. The invention relates to the use of gene transfer vectors for unique or for multiple in vivo administration into a host in need thereof. The field of application of the present application concerns in particular animal treatment or treatment of human being (e.g. prophylactic or therapeutic or symptomatic or curative treatment), gene therapy or vaccination in vivo. These vectors may be used to elicit an immune response to prevent or to treat a pathogenic state, including virus infections (for example treatment or prevention against Immunodeficiency Virus and especially against AIDS), parasite and bacterial infections or cancers, and preferably to elicit a protective, long-lasting immune response.

40 Claims, 170 Drawing Sheets

OTHER PUBLICATIONS

Figure 2A:
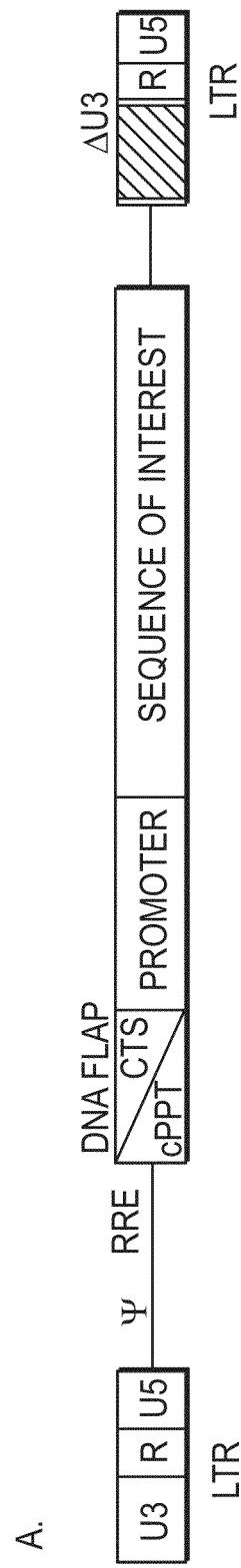

Buffa Viviana et al., "A single administration of lentiviral vectors expressing either full-length human immunodeficiency virus 1 (HIV-1)(HXB2) Rev/Env or codon-optimized HIV-1(JR-FL) gp120 generates durable immune responses in mice", Journal of General Virology, vol. 87, No. Part 6, Jun. 2006, pp. 1625-1634.

Gomez et al., "Head-to-head comparison on the immunogenicity of two HIV/AIDS vaccine candidates based on the attenuated poxvirus strains MVA and NYVAC co-expressing in a single locus the HIV-1BX08 gp120 and HIV-1IIIB Gag-Pol-Nef proteins of clade B", Vaccine, Butterworth Scientific, Guildford, GB, vol. 25, No. 15, Mar. 16, 2007, pp. 2863-2885.

Feng Gao et al., "Codon usage optimization of HIV type 1 subtype C Gag, Pol, Env, and Nef genes: In vitro expression and immune responses in DNA-vaccinated mice", AIDS Research and Human Retroviruses, Mary Ann Liebert, US, vol. 19, No. 9, Jan. 1, 2003, pp. 817-823.

Keil W et al., "Epitope mapping by deletion mutants and chimeras of two vesicular stomatitis virus glycoprotein genes expressed by a vaccinia virus vector", Virology, vol. 170, No. 2, 1989, pp. 392-407.

Rollman et al., "The rationale behind a vaccine based on multiple HIV antigens", Microbes and Infection, Elsevier, Paris, FR, vol. 7, No. 14, Nov. 2005, pp. 1414-1423.

Chen et al. "Induction of primary anti-HIV CD4 and CD8 T cell responses by dendritic cells transduced with self-inactivating lentiviral vectors", Cellular Immunology, Academic Press, San Diego, CA, USA, vol. 243, No. 1, Feb. 22, 2007, pp. 10-18.

Philpott Nicola J et al., "Use of nonintegrating lentiviral vectors for gene therapy", Human Gene Therapy, vol. 18, No. 6, Jun. 2007, pp. 483-489.

Iglesias Maria Candela et al., "A single immunization with a minute dose of a lentiviral vector-based vaccine is highly effective at eliciting protective humoral immunity against West Nile virus", Journal of Gene Medicine, Wiley, USA, vol. 8, No. 3, Mar. 2006, pp. 265-274.

Leavitt A D et al., "Human immunodeficiency virus type 1 integrase mutants retain in vitro integrase activity yet fail to integrate viral DNA efficiently during infection", Journal of Virology, The American Society for Microbiology, USA, vol. 70, No. 2, Feb. 1996, pp. 721-728.

Iglesias C et al., "Lentiviral vectors as potential tools for theraputic vaccination against aids", Gene Therapy, Macmillan Press LTD., Basingstoke, GB, vol. 11, No. Suppl. 1, Feb. 1, 2004, pp. S131.

Young et al., "Virus-like particles: esigning an effective AIDS vaccine", Methods : A Companion to Methods in Enzymology, Academic Press Inc., New York, NY, US, vol. 40, No. 1, Sep. 2006, pp. 98-117.

* cited by examiner

CAEV
GTTCCAGCCACAATTTGTCGCTGTAGAATCAGCCATAGCAGCAGCCCTAGTCGC
CATAAATATAAAAGAAAGGGTGGGCTGGGGACAAGCCCTATGGATATTTTAT
ATATAATAAAGAACAGAAAAGAATAAATAATAAATATAATAAAAATTCTCAAAA
AATTCAATTCTGTTATTACAGAATAAGGAAAAGAGGAC (SEQ ID NO: 1)

EIAV
CTTGTAACAAAGGGAGGGAAAGTATGGGAGGACAGACACCATGGGAAGTATTTA
TCACTAATCAAGCACAAGTAATACATGAGAAACTTTTACTACAGCAAGCACAAT
CCTCCAAAAAATTTTGTTTTTACAAAATCCCTGGTGAACATGATTGGAAGGGAC
CTACTAGGGTGCTGTGGAAGGGTGATGGTGCAGTAGTA (SEQ ID NO: 2)

VISNA
GGACCCTCATTACTCTAAATATAAAAAGAAAGGGTGGGCTAGGGACAAGCCCTA
TGGATATATTTATATTTAATAAGGAACAACAAAGAATACAGCAACAAAGTAAAT
CAAAACAAGAAAAAATTCGATTTTGTTATTACAGAACAAGAAAAAGAGGGCATC
CAGGAGAGTGGCAAGGACCAACACAGGTACTTTGGGGC (SEQ ID NO: 3)

SIV$_{AGM}$
TACTGATGGCTTGCATACTTCACAATTTTAAAAGAAAGGGAGGAATAGGGGGAC
AGACTTCAGCAGAGAGACTAATTAATATAATAACAACACAATTAGAAATACAAC
ATTTACAAACCAAAATTCAAAAAATTTTAAATTTTAGAGTCTACTACAGAGAAG
GGAGAGACCCTGTGTGGAAAGGACCGGCACAATTAATC (SEQ ID NO: 4)

HIV-2 ROD
TGCATGAATTTTAAAAGAAGGGGGGGAATAGGGGATATGACTCCATCAGAAAGA
TTAATCAATATGATCACCACAGAACAAGAGATACAATTCCTCCAAGCCAAAAAT
TCAAAATTAAAAGATTTTCGGGTCTATTTCAGAGAAGGCAGAGATCAGTTGTGG
AAAGGACCTGGGGAACTACTGTGGAAGGAGAAGGAGC (SEQ ID NO: 5)

HIV-1 LAI
CAGTATTCATCCACAATTTTAAAAGAAAAGGGGGGATTGGGGGGTACAGTGCAG
GGGAAAGAATAGTAGACATAATAGCAACAGACATACAAACTAAAGAATTACAAA
AACAAATTACAAAAATTCAAAATTTTCGGGTTTATTACAGGGACAGCAGAGATC
CACTTTGGAAAGGACCAGCAAAGCTCCTCTGGAAAGGT (SEQ ID NO: 6)

HIV1
TTTTAAAAGAAAAGGGGGGATTGGGGGGTACAGTGCAGGGGAAAGAATAGTAGA
CATAATAGCAACAGACATACAAACTAAAGAATTACAAAAACAAATTACAAAAAT
TCAAAATTTTC (SEQ ID NO: 7)

*FIG. 1*

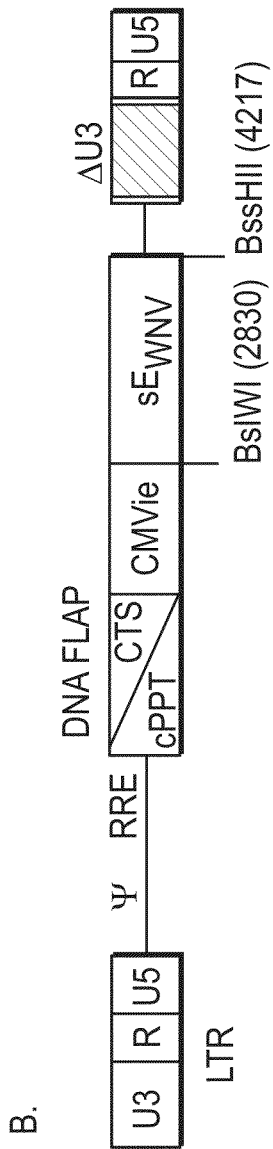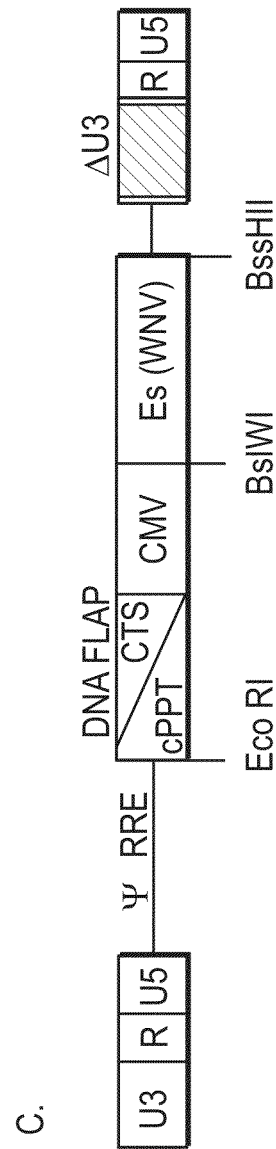
FIG. 2B
FIG. 2C

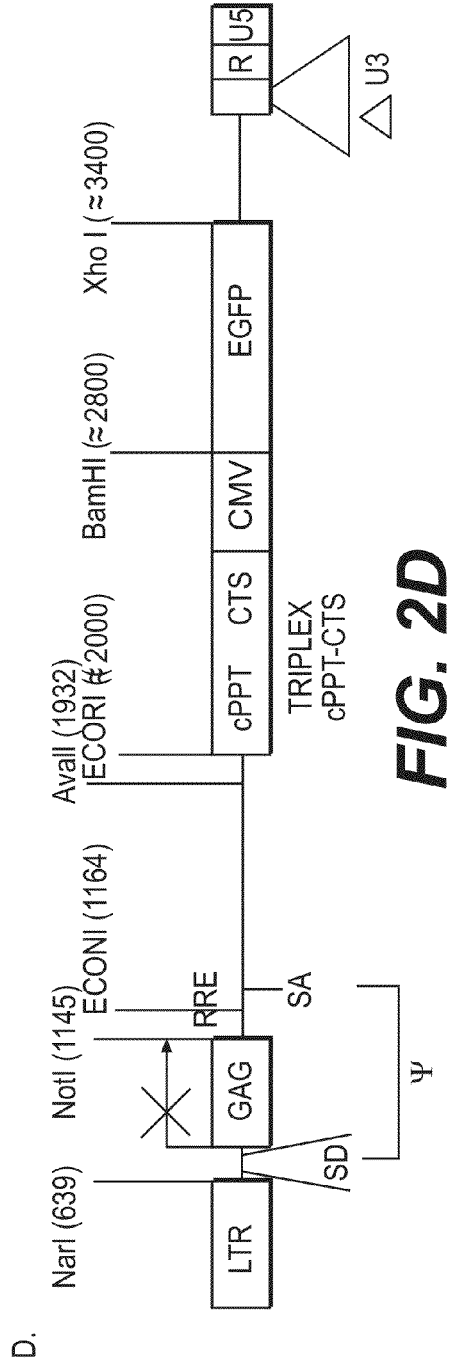
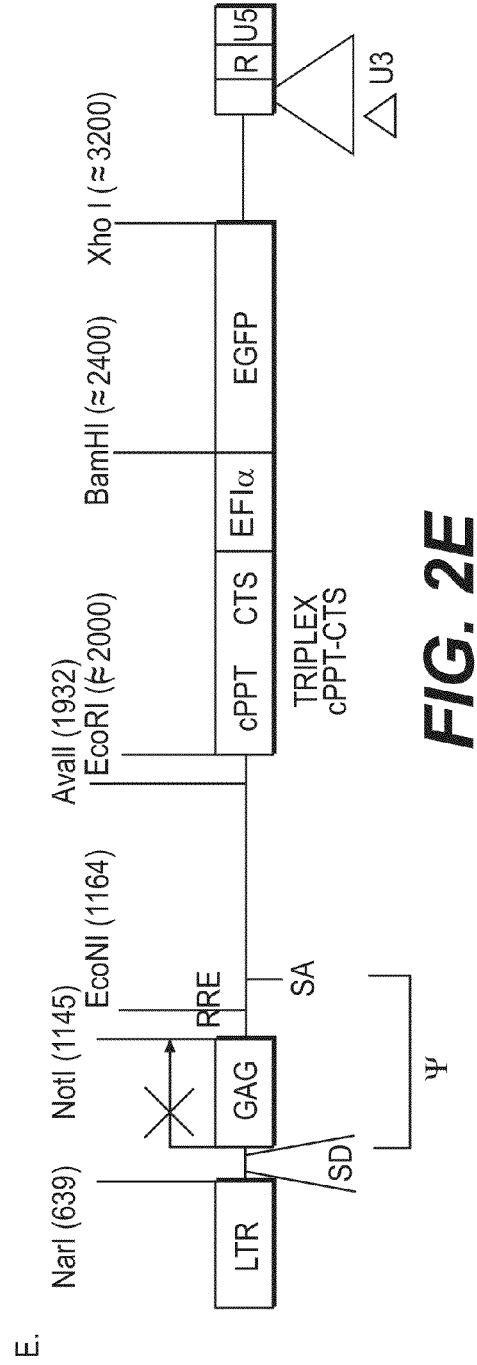
FIG. 2D
FIG. 2E

```
CHP     MTSSVTISVVLLISFITPLYSYLSIAFPENTKLDWKPVTKNTRYCPMGGEWFLEPGLQEESFLSSTPIGATPSKSD
COCAL     MNFLLLTFIVLPLCSHAKFSIVFPQSQKGNWKNVPSSYHYCPSSSDQNWHNDLLGITMKVKMPKTHKAIQAD
IND        MKCLLYLAFLFIGVNCKFTIVFPHNQKGNWKNVPSNYHYCPSSSDLNWHNDLVGTALQVKMPKSHKAIQAD
NJ          MLSYLILAIVVSPILGKIEIVFPQHTTGDWKRVPHEYNYCPTSADKNSHGTQTGIPIELTMPKGLTTHQVD
ISFA    MTSVLFMVGVLLGAFGSTHCSIQIVFPSETKLVWKPVLKGTRYCPQSAELNLEPDLKTMAFDSKVPIGITPSNSD
PIRY          MTDTVLGKFQIVFPDQNELEWTPVVGDSRHCPQSSEMQFDGSRSQTILTGKAPVGITPSKSD
SVCV     MSIISYIAFLLLIDSTLGIPIFVPSGQNISWQPVIQPFDYQCPIHGNLPNTMGLSATKLTIKSPSVFSTDKVS

CHP     GFLCHAAKWVTTCDFRWYGPKYITHSIHNIKPTRSDCDTALASYKSGTLVSLGFPPESCGYASVTDSEFLVIMITP
COCAL   GWMCHAAKWITTCDFRWYGPKYITHSIHSIQPTSEQCKESIKQTKQGTWMSPGFPPQNCGYATVTDSVAVVVQATP
IND     GWMCHASKWVTTCDFRWYGPKYITHSIRSFTPSVEQCKESIEQTKQGTWLNPGFPPQSCGYATVTDAEAAIVQVTP
NJ      GFMCHSALWMTTCDFRWYGPKYITHSIHNEEPTDYQCLEAIKAYKDGVSFNPGFPPQSCGYGTVTDAEAHIITVTP
ISFA    GYLCHAAKWVTTCDFRWYGPKYITHSVHSLRPTVSDCKAAVEAYNAGTLMYPGFPPESCGYASITDSEFYVMLVTP
PIRY    GFICHAAKWVTTCDFRWYGPKYITHSIHHLRPTTSDCETALQRYKDGSLINLGFPPESCGYATVTDSEAMLVQVTP
SVCV    GWICHAAEWKTTCDYRWYGPQYITHSIHPISPTIDECKRIISRIASGTDEDLGFPPQSCGWASVTTVSNTNYKVVP

CHP     HHVGVDDYRGHWVDPLFVGGECDQSYCDTIHNSSVWIPADQTKKNICGQSFTPLTVTVAYDKTK--EIAAGGIVFK
COCAL   HHVLVDEYTGEWIDSQFPNGKCETEECETVHNSTVWYSDYKV-TGLCDATLVDTEITFFSEDGKKESIGKPNTGYR
IND     HHVLVDEYTGEWVDSQFINGKCSNYICPTVHNSTTWHSDYKV-KGLCDSNLISMDITFFSEDGELSSLGKKGTGFR
NJ      HSVKVDEYTGEWIDPHFIGGRCKGQICETVHNSTKWFTSSDG-ESVCSQLFTLVGGTFFSDSEEITSMGLPETGIR
ISFA    HPVGVDDYRGHWVDPLFPTSECNSNFCETVHNATMWIPKDLKTHDVCSQDFQTIRVSVMYPQTK--PTKGADLTLK
PIRY    HHVGVDDYRGHWIDPLFPGGECSTNFCDTVHNSSVWIPKSQK-TDICAQSFKNIKMTASYPSEG--ALVSDRFAFH
SVCV    HSVHLEPYGGHWIDHDFNGGECREKVCEMKGNHSIWITDETV-QHECEKHIEEVEGIMYGNAPR-GDAIYINNFII

CHP     SKYHSHMEGARTCRLSYCGRNGIKFPNGEWVSLMLKLRSKRNLYFPCLKMCPTGIRGEIYPSIRWAQVLTSEIQRI
COCAL   SNYFAYEKGDKVCKMNYCKHAGVRLPSGVWFEFVDQDVYAAAK----LPECPVGATISAPTQTSVDVSLILDVERI
IND     SNYFAYETGDKACKMQYCKHWGVRLPSGVWFEMADKDLFAAAR----FPECPEGSSISAPSQTSVDVSLIQDVERI
NJ      SNYFPYISTEGICKMPFCRKPGYKLKNDLWFQITDPDLDKTVRDLPHIKDCDLSSSIITPGEHATDISLISDVERI
ISFA    SKFHAHMKGDRVCKMKFCNKNGLRLGNGEWIEVGDEVMLDNSKLLSLFPDCLVGSVVKSTLLSEGVQTALWETDRL
PIRY    SAYHPNMPGSTVCIMDFCEQKGLRFTNGEWMGLNVEQSIREKKISAIFPNCVAGTEIRATLESEGARTLTWETQRM
SVCV    DKHHRVYRFGGSCRMKFCNKDGIKFTRGDWVEKTAGTLTNIYEN---IPECADGTLVSGHRPGLDLIDTVFNLENV
```

*FIG. 3A*

```
CHP    LDYSLCQNTWDKVERKEPLSPLDLSYLASKSPGKGLAYTVINGTLSFAHTRYVRMWIDGPVLKEPKGKRESPSGIS
COCAL  LDYSLCQETWSKIRSKQPVSPVDLSYLAPKNPGTGPAFTIINGTLKYFETRYIRIDIDNPIISKMVGKISG-SQTE
IND    LDYSLCQETWSKIRAGLPISPVDLSYLAPKNPGTGPVFTIINGTLKYFETRYIRVDIAAPILSRMVGMISG-TTTE
NJ     LDYSLCQNTWSKIEAGEPITPVDLSYLGPKNPGVGPVFTIINGSLHYFTSKYLRVELENPVIPRMEGRVAG-TRIV
ISFA   LDYSLCQNTWEKIDRKEPLSAVDLSYLAPRSPGKGMAYIVANGSLMSAPARYIRVWIDSPILKEIKGKKESASGID
PIRY   LDYSLCQNTWDKVSRKEPLSPLDLSYLSPRAPGKGMAYTVINGTLHSAHAKYIRTWIDYGEMKEIKGGRGEYSKAP
SVCV   VEYTLCEGTKRKINKQEKLTSVDLSYLAPRIGGFGSVFRVRNGTLERGSTTYIRIEVEGPVVDSLNGIDPR-TNAS

CHP    SDIWTQWFKYGDMEIGPNGLLKTAGGYKFPWHLIGMIVDNELHELSEANPLDHPQLPHAQSIADDS---EEIFFG
COCAL  RELWTEWFPYEGVEIGPNGILKTPTGYKFPLFMIGHGMLDSDLHKTSQAEVFEHPHLAEAPKQLPEE---ETLFFG
IND    RVLWDDWAPYEDVEIGPNGVLRTSSGYKFPLYMIGHGMLDSDLHLSSKAQVFEHPHIQDAASQLPDD---ETLFFG
NJ     RQLWDQWFPFGEAEIGPNGVLKTKQGYKFPLHIIGTGEVDSDIKMERVVKHWEHPHIEAAQTFLKKDDTGEVLYYG
ISFA   TVLWEQWLPFNGMELGPNGLIKTKSGYKFPLYLLGMGIVDQDLQELSSVNPVDHPHVPIAQAFVSEG---EEVFFG
PIRY   ELLWSQWFDFGPFKIGPNGLLHTGKTFKFPLYLIGAGIIDEDLHELDEAAPIDHPQMPDAKSVLPED---EEIFFG
SVCV   RVFWDDWELDGNIYQGFNGVYKGKDGKIHIPLNMIESGIIDDELQHAFQADIIPHPHYDDDEIREDD-----IFFD

CHP    DTGVSKNPVELVTGWFTSWKESLAAGSCPDLRCPPLFPGIVYYLQKAQME-------ERGERSDSFEMRIFKPNNM
COCAL  DTGISKNPVELIEGWFSSWKSTVVTFFFAIGVFILLYVVARIVIAVRYRYQGS----NNKRIYNDIEMSRFRK---
IND    DTGLSKNPIEFVEGWFSSWKSSIASFFFIIGLIIGLFLVLRVGIYLCIKLKHT----KKRQIYTDIEMNRLGK---
NJ     DTGVSKNPVELVEGWFSGWRSSIMGVLAVIIGFVILIFLIRLIGVLSSLFRPK----RRPIYKSDVEMAHFR----
ISFA   DTGVSKNPIELISGWFSDWKETAAALGFAAISVILIIGLMRLLPLLCRRRK------QKKVIYKDVELNSFDPRQA
PIRY   DTGVSKNPIELIQGWFSNWRESVMAIVGIVLLIVVTFLAIKTVRVLNCLWRPRKKRIVRQEVDVESRLNHFEMRGF
SVCV   NTGENGNPVDAVVEWVSGWGTSLKFFGMTLVALILIFLLIRCCVACTYLMK------KSKRPATESHEMRSLV
                       TRANSMEMBRANE DOMAIN
CHP    RARV-- (SEQ ID NO: 15)
COCAL  ------ (SEQ ID NO: 16)
IND    ----   (SEQ ID NO: 17)
NJ     ----   (SEQ ID NO: 18)
ISFA   FHR--- (SEQ ID NO: 19)
PIRY   PEYVKR (SEQ ID NO: 20)
SVCV          (SEQ ID NO: 21)
```

FIG. 3A (CONTINUED)

Indiana Virus
MKCLLYLAFLFIGVNCKFTIVFPHNQKGNWKNVPSNYHYCPSSSDLNWHNDLIGTAIQVKMPKSHKAIQADGWMCHASKWVTT
CDFRWYGPKYITQSIRSFTPSVEQCKESIEQTKQGTWLNPGFPPQSCGYATVTDAEAVIVQVTPHHVLVDEYTGEWVDSQFIN
GKCSNYICPTVHNSTTWHSDYKVKGLCDSNLISMDITFFSEDGELSSLGKEGTGFRSNYFAYETGGKACKMQYCKHWGVRLPS
GVWFEMADKDLFAAARFPECPEGSSISAPSQTSVDVSLIQDVERILDYSLCQETWSKIRAGLPISPVDLSYLAPKNPGTGPAF
TIINGTLKYFETRYIRVDIAAPILSRMVGMISGTTTERELWDDWAPYEDVEIGPNGVLRTSSGYKFPLYMIGHGMLDSDLHLS
SKAQVFEHPHIQDAASQLPDDESLFFGDTGLSKNPIELVEGWFSSWKSSIASFFFIIGLIIGLFLVLRVGIHLCIKLKHTKKR
QIYTDIEMNRLGK  (SEQ ID NO:15)

Chandipura Virus
MTSSVTISVVLLISFITPLYSYLSIAFPENTKLDWKPVTKNTRYCPMGGEWFLEPGLQEESFLSSTPIGATPSKSDGFLCHAA
KWVTTCDFRWYGPKYITHSIHNIKPTRSDCDTALASYKSGTLVSLGFPPESCGYASVTDSEFLVIMITPHHVGVDDYRGHWVD
PLFVGGECDQSYCDTIHNSSVWIPADQTKKNICGQSFTPLTVTVAYDKTKEIAAGGIVFKSKYHSHMEGARTCRLSYCGRNGI
KFPNGEWVSLMLKLRSKRNLYFPCLKMCPTGIRGEIYPSIRWAQVLTSEIQRILDYSLCQNTWDKVERKEPLSPLDLSYLASK
SPGKGLAYTVINGTLSFAHTRYVRMWIDGPVLKEPKGKRESPSGISSDIWTQWFKYGDMEIGPNGLLKTAGGYKFPWHLIGMG
IVDNELHELSEANPLDHPQLPHAQSIADDSEEIFFGDTGVSKNPVELVTGWFTSWKESLAAGSCPDLRCPPLFPGIVYYLQKA
QMEERGERSDSFEMRIFKPNNMRARV (SEQ ID NO:16)

Piry Virus
MDLFPILVVVLMTDTVLGKFQIVFPDQNELEWRPVVGDSRHCPQSSEMQFDGSRSQTILTGKAPVGITPSKSDGFICHAAKWV
TTCDFRWYGPKYITHSIHHLRPTTSDCETALQRYKDGSLINLGFPPESCGYATVTDSEAMLVQVTPHHVGVDDYRGHWIDPLF
PGGECSTNFCDTVHNSSVWIPKSQKTDICAQSFKNIKMTASYPSEGALVSDRFAFHSAYHPNMPGSTVCIMDFCEQKGLRFTN
GEWMGLNVEQSIREKKISAIFPNCVAGTEIRATLESEGARTLTWETQRMLDYSLCQNTWDKVSRKEPLSPLDLSYLSPRAPGK
GMAYTVINGTLHSAHAKYIRTWIDYGEMKEIKGGRGEYSKAPELLWSQWFDFGPFKIGPNGLLHTGKTFKFPLYLIGAGIIDE
DLHELDEAAPIDHPQMPDAKSVLPEDEEIFFGDTGVSKNPIELIQGWFSNWRESVMAIVGIVLLIVVTFLAIKTVRVLNCLWR
PRKKRIVRQEVDVESRLNHFEMRGFPEYVKR (SEQ ID NO:17)

New Jersey Virus
MLSYLIFALAVSPILGKIEIVFPQHTTGDWKRVPHEYNYCPTSADKNSHGTQTGIPVELTMPKGLTTHQVEGFMCHSALWMTT
CDFRWYGPKYITHSIHNEEPTDYQCLEAIKSYKDGVSFNPGFPPQSCGYGTVTDAEAHIVTVTPHSVKVDEYTGEWIDPHFIG
GRCKGQICETVHNSTKWFTSSDGESVCSQLFTLVGGIFFSDSEEITSMGLPETGIRSNYFPYISTEGICKMPFCRKQGYKLKN
DLWFQIMDPDLDKTVRDLPHIKDCDLSSSIITPGEHATDISLISDVERILDYALCQNTWSKIESGEPITPVDLSYLGPKNPGV
GPVFTIINGSLHYFTSKYLRVELESPVIPRMEGKVAGTRIVRQLWDQWFPFGEVEIGPNGVLKTKQGYKFPLHIIGTGEVDSD
IKMERVVKHWEHPHIEAAQTFLKKDDTGEVLYYGDTGVSKNPVELVEGWFSGWRSSLMGVLAVIIGFVILMFLIKLIGVLSSL
FRPKRRPIYKSDVEMAHFR (SEQ ID NO:18)

*FIG. 3B*

Cocal Virus
MNFLLLTFIVLPLCSHAKFSIVFPQSQKGNWKNVPSSYHYCPSSSDQNWHNDLLGITMKVKMPKTHKAIQADGWMCHAAKWIT
TCDFRWYGPKYITHSIHSIQPTSEQCKESIKQTKQGTWMSPGFPPQNCGYATVTDSVAVVVQATPHHVLVDEYTGEWIDSQFP
NGKCETEECETVHNSTVWYSDYKVTGLCDATLVDTEITFFSEDGKKESIGKPNTGYRSNYFAYEKDKVCKMNYCKHAGVRLPS
GVWFEFVDQDVYAAAKLPECPVGATISAPTQTSVDVSLILDVERILDYSLCQETWSKIRSKQPVSPVDLSYLAPKNPGTGPAF
TIINGTLKYFETRYIRIDIDNPIISKMVGKISGSQTERELWTEWFPYEGVEIGPNGILKTPTGYKFPLFMIGHGMLDSDLHKT\
SQAEVFEHPHLAEAPKQLPEEETLFFGDTGISKNPVELIEGWFSSWKSTVVTFFFAIGVFILLYVVARIVIAVRYRYQGSNNK
RIYNDIEMSRFRK (SEQ ID NO:19)

Isfahan Virus
MTSVLFMVGVLLGAFGSTHCSIQIVFPSETKLVWKPVLKGTRYCPQSAELNLEPDLKTMAFDSKVPIGITPSNSDGYLCHAAK
WVTTCDFRWYGPKYITHSVHSLRPTVSDCKAAVEAYNAGTLMYPGFPPESCGYASITDSEFYVMLVTPHPVGVDDYRGHWVDP
LFPTSECNSNFCETVHNATMWIPKDLKTHDVCSQDFQTIRVSVMYPQTKPTKGADLTLKSKFHAHMKGDRVCKMKFCNKNGLR
LGNGEWIEVGDEVMLDNSKLLSLFPDCLVGSVVKSTLLSEGVQTALWETDRLLDYSLCQNTWEKIDRKEPLSAVDLSYLAPRS
PGKGMAYIVANGSLMSAPARYIRVWIDSPILKEIKGKKESASGIDTVLWEQWLPFNGMELGPNGLIKTKSGYKFPLYLLGMGI
VDQDLQELSSVNPVDHPHVPIAQAFVSEGEEVFFGDTGVSKNPIELISGWFSDWKETAAALGFAAISVILIIGLMRLLPLLCR
RRKQKKVIYKDVELNSFDPRQAFHR (SEQ ID NO:20)

SVCV Virus
MSIISYIAFLLLIDSTFGIPIFVPSGQNISWQPVIQPFDYQCPIHGNLPNTMGLSATKLTIKSPSVFSTDKVSGWICHAAEWK
TTCDYRWYGPQYITHSIHPISPTIDECKRIISRIASGTDEDLGFPPQSCGWASVTTVSNTNYKVVPHSVHLEPYGGHWIDHEF
NGGECREKVCEMKGNHSIWITDETVQHECEKHIEEVEGIMYGNAPRGDAIYINNFIIDKHHRVYRFGGSCRMKFCNKDGIKFT
RGDWVEKTAETLTNIYANIPECADGTLVSGHRPGLDLIDTVFNLENVVEYTLCEGTKRKINNQEKLTSVDLSYLAPRIGGFGS
VFRVRNGTLERGSTTYIKIEVEGPIVDSLNGTDPRTNASRVFWDDWELDGNIYQGFNGVYKGKDGKIHIPLNMIESGIIDDEL
QHAFQADIIPHPHYDDDEIREDDIFFDNTGENGNPVDAVVEWVSGWGTSLKFFGTTLVALILIFLLIRCCVACTYLMKKSKRP
ATESHEMRSFV (SEQ ID NO:21)

FIG. 3B
*(CONTINUED)*

```
TGGAAGGGCTAATTCACTCCCAACGAAGACAAGATATCCTTGATCTGTGG
ATCTACCACACACAAGGCTACTTCCCTGATTAGCAGAACTACACACCAGG
GCCAGGGATCAGATATCCACTGACCTTTGGATGGTGCTACAAGCTAGTAC
CAGTTGAGCCAGAGAAGTTAGAAGAAGCCAACAAAGGAGAGAACACCAGC
TTGTTACAACCTGTGAGCCTGCATGGGATGGATGACCCGGAGAGAGAAGT
GTTAGAGTGGAGGTTTGACAGCCGCCTAGCATTTCATCACGGTGGCCCGA
GAGCTGCATCCGGAGTACTTCAAGAACTGCTGATATCGAGCTTGCTACAA
GGGACTTTCCGCTGGGGGACTTTCCAGGGAGGCGTGGCCTGGGCGGGACT
GGGGAGTGGCGAGCCCTCAGATCCTGCATATAAGCAGCTGCTTTTTGCCT
GTACTGGGTCTCTCTGGTTAGACCAGATCTGAGCCTGGGAGCTCTCTGGC
TAACTAGGGAACCCACTGCTTAAGCCTCAATAAAGCTTGCCTTGAGTGCT
TCAAGTAGTGTGTGCCCGTCTGTTGTGTGACTCTGGTAACTAGAGATCCC
TCAGACCCTTTTAGTCAGTGTGGAAAATCTCTAGCAGTGGCGCCCGAACA
GGGACTTGAAAGCGAAAGGGAAACCAGAGGAGCTCTCTCGACGCAGGACT
CGGCTTGCTGAAGCGCGGAATTCCGCGCCACGGCAAGAGGCGAGGGGCGG
CGACTGGTGAGTACGCCAAAAATTTTGACTAGCGGAGGCTAGAAGGAGAG
AGATGGGTGCGAGAGCGTCAGTATTAAGCGGGGAGAATTAGATCGCGAT
GGGAAAAAATTCGGTTAAGGCCAGGGGGAAAGAAAAAATATAAATTAAAA
CATATAGTATGGGCAAGCAGGGAGCTAGAACGATTCGCAGTTAATCCTGG
CCTGTTAGAAACATCAGAAGGCTGTAGACAAATACTGGGACAGCTACAAC
CATCCCTTCAGACAGGATCAGAAGAACTTAGATCATTATATAATACAGTA
GCAACCCTCTATTGTGTGCATCAAAGGATAGAGATAAAAGACACCAAGGA
AGCTTTAGACAAGATAGAGGAAGAGCAAAACAAAAGTAAGACCACCGCAC
AGCAAGCGGCCGCTGATCTTCAGACCTGGAGGAGGAGATATGAGGGACAA
TTGGAGAAGTGAATTATATAAATATAAAGTAGTAAAAATTGAACCATTAG
GAGTAGCACCCACCAAGGCAAAGAGAAGAGTGGTGCAGAGAGAAAAAAGA
GCAGTGGGAATAGGAGCTTTGTTCCTTGGGTTCTTGGGAGCAGCAGGAAG
CACTATGGGCGCAGCGTCAATGACGCTGACGGTACAGGCCAGACAATTAT
TGTCTGGTATAGTGCAGCAGCAGAACAATTTGCTGAGGGCTATTGAGGCG
```

*FIG. 4A*

```
CAACAGCATCTGTTGCAACTCACAGTCTGGGGCATCAAGCAGCTCCAGGC
AAGAATCCTGGCTGTGGAAAGATACCTAAAGGATCAACAGCTCCTGGGGA
TTTGGGGTTGCTCTGGAAAACTCATTTGCACCACTGCTGTGCCTTGGAAT
GCTAGTTGGAGTAATAAATCTCTGGAACAGATTTGGAATCACACGACCTG
GATGGAGTGGGACAGAGAATTAACAATTACACAAGCTTAATACACTCCT
TAATTGAAGAATCGCAAAACCAGCAAGAAAAGAATGAACAAGAATTATTG
GAATTAGATAAATGGGCAAGTTTGTGGAATTGGTTTAACATAACAAATTG
GCTGTGGTATATAAAATTATTCATAATGATAGTAGGAGGCTTGGTAGGTT
TAAGAATAGTTTTTGCTGTACTTTCTATAGTGAATAGAGTTAGGCAGGGA
TATTCACCATTATCGTTTCAGACCCACCTCCCAACCCCGAGGGGACCCGA
CAGGCCCGAAGGAATAGAAGAAGAAGGTGGAGAGAGAGACAGAGACAGAT
CCATTCGATTAGTGAACGGATCTCGACGGTATCGCCGAATTCACAAATGG
CAGTATTCATCCACAATTTTaaaagaaaagggggATTGGGGGGTACAGT
GCAGGGGAAAGAATAGTAGACATAATAGCAACAGACATACAAACTAAAGA
ATTACAAAAACAAATTACaaaaattcaaaattttCGGGTTTATTACAGGG
ACAGCAGAGATCCACTTTGGGGCGATAAGCTTGGGAGTTCCGCGTTACAT
AACTTACGGTAAATGGCCCGCCTGGCTGACCGCCCAACGACCCCCGCCCA
```

FIG. 4A
*(CONTINUED)*

```
TTGACGTCAATAATGACGTATGTTCCCATAGTAACGCCAATAGGGACTTT
CCATTGACGTCAATGGGTGGAGTATTTACGGTAAACTGCCCACTTGGCAG
TACATCAAGTGTATCATATGCCAAGTACGCCCCCTATTGACGTCAATGAC
GGTAAATGGCCCGCCTGGCATTATGCCCAGTACATGACCTTATGGGACTT
TCCTACTTGGCAGTACATCTACGTATTAGTCATCGCTATTACCATGGTGA
TGCGGTTTTGGCAGTACATCAATGGGCGTGGATAGCGGTTTGACTCACGG
GGATTTCCAAGTCTCCACCCCATTGACGTCAATGGGAGTTTGTTTTGGCA
CCAAAATCAACGGGACTTTCCAAAATGTCGTAACAACTCCGCCCCATTGA
CGCAAATGGGCGGTAGGCGTGTACGGTGGGAGGTCTATATAAGCAGAGCT
CGTTTAGTGAACCGTCAGATCGCCTGGAGACGCCATCCACGCTGTTTTGA
CCTCCATAGAAGACACCGACTCTAGAggaCGTACGATGAGAGTTGTGTTT
GTCGTGCTATTGCTTTTGGTGGCCCCAGCTTACAGCTTCAACTGCCTTGG
AATGAGCAACAGAGACTTCTTGGAAGGAGTGTCTGGAGCAACATGGGTGG
ATTTGGTTCTCGAAGGCGACAGCTGCGTGACTATCATGTCTAAGGACAAG
CCTACCATCGATGTGAAGATGATGAATATGGAGGCGGTCAACCTGGCAGA
GGTCCGCAGTTATTGCTATTTGGCTACCGTCAGCGATCTCTCCACCAAAG
CTGCGTGCCCGACCATGGGAGAAGCTCACAATGACAAACGTGCTGACCCA
GCTTTTGTGTGCAGACAAGGAGTGGTGGACAGGGGCTGGGGCAACGGCTG
CGGATTATTTGGCAAAGGAAGCATTGACACATGCGCCAAATTTGCCTGCT
CTACCAAGGCAATAGGAAGAACCATCTTGAAAGAGAATATCAAGTACGAA
GTGGCCATTTTTGTCCATGGACCAACTACTGTGGAGTCGCACGGAAACTA
CTCCACACAGGTTGGAGCCACTCAGGCAGGGAGATTCAGCATCACTCCTG
CGGCGCCTTCATACACTAAAGCTTGGAGAATATGGAGAGGTGACAGTG
GACTGTGAACCACGGTCAGGGATTGACACCAATGCATACTACGTGATGAC
TGTTGGAACAAAGACGTTCTTGGTCCATCGTGAGTGGTTCATGGACCTCA
ACCTCCCTTGGAGCAGTGCTGGAAGTACTGTGTGGAGGAACAGAGAGACG
TTAATGGAGTTTGAGGAACCACACGCCACGAAGCAGTCTGTGATAGCATT
GGGCTCACAAGAGGGAGCTCTGCATCAAGCTTTGGCTGGAGCCATTCCTG
TGGAATTTTCAAGCAACACTGTCAAGTTGACGTCGGGTCATTTGAAGTGT
AGAGTGAAGATGGAAAAATTGCAGTTGAAGGGAACAACCTATGGCGTCTG
TTCAAAGGCTTTCAAGTTTCTTGGGACTCCGCAGACACAGGTCACGGCA
CTGTGGTGTTGGAATTGCAGTACACTGGCACGGATGGACCTTGCAAAGTT
CCTATCTCGTCAGTGGCTTCATTGAACGACCTAACGCCAGTGGGCAGATT
GGTCACTGTCAACCCTTTTGTTTCAGTGGCCACGGCCAACGCTAAGGTCC
```

*FIG. 4B*

TGATTGAATTGGAACCACCCTTTGGAGACTCATACATAGTGGTGGGCAGA
GGAGAACAACAGATCAATCACCATTGGCACAAGTCTGGAAGCAGCATTGG
CAAAGCCTTTACAACCACCCTCAAAGGAGCGCAGAGACTAGCCGCTCTAG
GAGACACAGCTTGGGACTTTGGATCAGTTGGAGGGGTGTTCACCTCAGTT
GGGAAGGCTGtctaatgcgcgcGGTACCTTTAAGACCAATGACTTACAAG
GCAGCTGTAGATCTTAGCCACTTTTTAAAAGAAAAGGGGGACTGGAAGG
GCTAATTCACTCCCAACGAAGACAAGatcgtcgagAGATGCTGCATATAA
GCAGCTGCTTTTTGCTTGTACTGGGTCTCTCTGGTTAGACCAGATCTGAG
CCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTA
GCAGT (SEQ ID NO: 29)

FIG. 4B
(CONTINUED)

```
TGGAAGGGCTAATTCACTCCCAACGAAGACAAGATATCCTTGATCTGTGG
ATCTACCACACACAAGGCTACTTCCCTGATTAGCAGAACTACACACCAGG
GCCAGGGATCAGATATCCACTGACCTTTGGATGGTGCTACAAGCTAGTAC
CAGTTGAGCCAGAGAAGTTAGAAGAAGCCAACAAAGGAGAGAACACCAGC
TTGTTACAACCTGTGAGCCTGCATGGATGGATGACCCGGAGAGAGAAGT
GTTAGAGTGGAGGTTTGACAGCCGCCTAGCATTTCATCACGGTGGCCCGA
GAGCTGCATCCGGAGTACTTCAAGAACTGCTGATATCGAGCTTGCTACAA
GGGACTTTCCGCTGGGGACTTTCCAGGGAGGCGTGGCCTGGGCGGGACT
GGGGAGTGGCGAGCCCTCAGATCCTGCATATAAGCAGCTGCTTTTTGCCT
GTACTGGGTCTCTCTGGTTAGACCAGATCTGAGCCTGGGAGCTCTCTGGC
TAACTAGGGAACCCACTGCTTAAGCCTCAATAAAGCTTGCCTTGAGTGCT
TCAAGTAGTGTGTGCCCGTCTGTTGTGTGACTCTGGTAACTAGAGATCCC
TCAGACCCTTTTAGTCAGTGTGGAAAATCTCTAGCAGTGGCGCCCGAACA
GGGACTTGAAAGCGAAAGGGAAACCAGAGGAGCTCTCTCGACGCAGGACT
CGGCTTGCTGAAGCGCGCACGGCAAGAGGCGAGGGGCGGCGACTGGTGAG
TACGCCAAAAATTTTGACTAGCGGAGGCTAGAAGGAGAGAGATGGGTGCG
AGAGCGTCAGTATTAAGCGGGGAGAATTAGATCGCGATGGGAAAAAATT
CGGTTAAGGCCAGGGGGAAAGAAAAAATATAAATTAAAACATATAGTATG
GGCAAGCAGGGAGCTAGAACGATTCGCAGTTAATCCTGGCCTGTTAGAAA
CATCAGAAGGCTGTAGACAAATACTGGGACAGCTACAACCATCCCTTCAG
ACAGGATCAGAAGAACTTAGATCATTATATAATACAGTAGCAACCCTCTA
TTGTGTGCATCAAAGGATAGAGATAAAAGACACCAAGGAAGCTTTAGACA
AGATAGAGGAAGAGCAAAACAAAAGTAAGACCACCGCACAGCAAGCGGCC
GCTGATCTTCAGACCTGGAGGAGGAGATATGAGGGACAATTGGAGAAGTG
AATTATATAAATATAAAGTAGTAAAAATTGAACCATTAGGAGTAGCACCC
ACCAAGGCAAAGAGAAGAGTGGTGCAGAGAGAAAAAAGAGCAGTGGGAAT
AGGAGCTTTGTTCCTTGGGTTCTTGGGAGCAGCAGGAAGCACTATGGGCG
CAGCGTCAATGACGCTGACGGTACAGGCCAGACAATTATTGTCTGGTATA
GTGCAGCAGCAGAACAATTTGCTGAGGGCTATTGAGGCGCAACAGCATCT
GTTGCAACTCACAGTCTGGGGCATCAAGCAGCTCCAGGCAAGAATCCTGG
CTGTGGAAAGATACCTAAAGGATCAACAGCTCCTGGGGATTTGGGGTTGC
TCTGGAAAACTCATTTGCACCACTGCTGTGCCTTGGAATGCTAGTTGGAG
TAATAAATCTCTGGAACAGATTTGGAATCACACGACCTGGATGGAGTGGG
ACAGAGAAATTAACAATTACACAAGCTTAATACACTCCTTAATTGAAGAA
TCGCAAAACCAGCAAGAAAAGAATGAACAAGAATTATTGGAATTAGATAA
```

FIG. 5A

```
ATGGGCAAGTTTGTGGAATTGGTTTAACATAACAAATTGGCTGTGGTATA
TAAAATTATTCATAATGATAGTAGGAGGCTTGGTAGGTTTAAGAATAGTT
TTTGCTGTACTTTCTATAGTGAATAGAGTTAGGCAGGGATATTCACCATT
ATCGTTTCAGACCCACCTCCCAACCCCGAGGGGACCCGACAGGCCCGAAG
GAATAGAAGAAGAAGGTGGAGAGAGAGACAGAGACAGATCCATTCGATTA
GTGAACGGATCTCGACGGTATCGCCGAATTCACAAATGGCAGTATTCATC
CACAATTTTaaaagaaaagggggATTGGGGGGTACAGTGCAGGGGAAAG
AATAGTAGACATAATAGCAACAGACATACAAACTAAAGAATTACAAAAAC
AAATTACaaaaattcaaaattttCGGGTTTATTACAGGGACAGCAGAGAT
CCACTTTGGGGCGATAAGCTTGGGAGTTCCGCGTTACATAACTTACGGTA
AATGGCCCGCCTGGCTGACCGCCCAACGACCCCCGCCCATTGACGTCAAT
```

FIG. 5A
*(CONTINUED)*

```
AATGACGTATGTTCCCATAGTAACGCCAATAGGGACTTTCCATTGACGTC
AATGGGTGGAGTATTTACGGTAAACTGCCCACTTGGCAGTACATCAAGTG
TATCATATGCCAAGTACGCCCCTATTGACGTCAATGACGGTAAATGGCC
CGCCTGGCATTATGCCCAGTACATGACCTTATGGGACTTTCCTACTTGGC
AGTACATCTACGTATTAGTCATCGCTATTACCATGGTGATGCGGTTTTGG
CAGTACATCAATGGGCGTGGATAGCGGTTTGACTCACGGGGATTTCCAAG
TCTCCACCCCATTGACGTCAATGGGAGTTTGTTTTGGCACCAAAATCAAC
GGGACTTTCCAAAATGTCGTAACAACTCCGCCCCATTGACGCAAATGGGC
GGTAGGCGTGTACGGTGGGAGGTCTATATAAGCAGAGCTCGTTTAGTGAA
CCGTCAGATCGCCTGGAGACGCCATCCACGCTGTTTTGACCTCCATAGAA
GACACCGACTCTAGAggatccccaccggtcgccaccatggtgagcaaggg
cgaggagctgttcaccggggtggtgcccatcctggtcgagctggacggcg
acgtaaacggccacaagttcagcgtgtccggcgagggcgagggcgatgcc
acctacggcaagctgaccctgaagttcatctgcaccaccggcaagctgcc
cgtgccctggcccaccctcgtgaccaccctgacctacggcgtgcagtgct
tcagccgctaccccgaccacatgaagcagcacgacttcttcaagtccgcc
atgcccgaaggctacgtccaggagcgcaccatcttcttcaaggacgacgg
caactacaagacccgcgccgaggtgaagttcgagggcgacaccctggtga
accgcatcgagctgaagggcatcgacttcaaggaggacggcaacatcctg
gggcacaagctggagtacaactacaacagccacaacgtctatatcatggc
cgacaagcagaagaacggcatcaaggtgaacttcaagatccgccacaaca
tcgaggacggcagcgtgcagctcgccgaccactaccagcagaacacccc
atcggcgacggccccgtgctgctgcccgacaaccactacctgagcaccca
gtccgccctgagcaaagaccccaacgagaagcgcgatcacatggtcctgc
tggagttcgtgaccgccgccgggatcactctcggcatggacgagctgtac
aagtaaagcggccggactctagctcgagACCTAGAAAAACATGGAGCAAT
CACAAGTAGCAATACAGCAGCTACCAATGCTGATTGTGCCTGGCTAGAAG
CACAAGAGGAGGAGGAGGTGGGTTTTCCAGTCACACCTCAGGTACCTTTA
AGACCAATGACTTACAAGGCAGCTGTAGATCTTAGCCACTTTTTAAAAGA
AAAGGGGGGACTGGAAGGGCTAATTCACTCCCAACGAAGACAAGatcgtc
gagAGATGCTGCATATAAGCAGCTGCTTTTTGCTTGTACTGGGTCTCTCT
GGTTAGACCAGATCTGAGCCTGGGAGCTCTCTGGCTAACTAGGGAACCCA
CTGCTTAAGCCTCAATAAAGCTTGCCTTGAGTGCTTCAAGTAGTGTGTGC
CCGTCTGTTGTGTGACTCTGGTAACTAGAGATCCCTCAGACCCTTTTAGT
CAGTGTGGAAAATCTCTAGCAGT (SEQ ID NO: 30)
```

FIG. 5B

A.
MKCLLYLAFLFIGVNCKFTIVFPHNQKGNWKNVPSNYHYCPSSSDLNWHNDLVGTALQVKMPKSHKAIQ
ADGWMCHASKWVTTCDFRWYGPKYITHSIRSFTPSVEQCKESIEQTKQGTWLNPGFPPQSCGYATVTDA
EAAIVQVTPHHVLVDEYTGEWVDSQFINGKCSNYICPTVHNSTTWHSDYKVKGLCDSNLISMDITFFSE
DGELSSLGKKGTGFRSNYFAYETGDKACKMQYCKHWGVRLPSGVWFEMADKDLFAAARFPECPEGSSIS
APSQTSVDVSLIQDVERILDYSLCQETWSKIRAGLPISPVDLSYLAPKNPGTGPVFTIINGTLKYFETR
YIRVDIAAPILSRMVGMISGTTTERVLWDDWAPYEDVEIGPNGVLRTSSGYKFPLYMIGHGMLDSDLHL
SSKAQVFEHPHIQDAASQLPDDETLFFGDTGLSKNPIEFVEGWFSSWKSSIASFFFIIGLIIGLFLVLR
VGIYLCIKLKHTKKRQIYTDIEMNRLGK (GENBANK # M11048)

FIG. 6A

B.

```
      M   K   C   L   L   Y   L   A   F   L   F   I   G   V   N   C   K   F   T   I   V   F   P   H   N   Q   K   G   N   W   K   N   V   P
  1  ATGAAATGCC TGCTCTATCT GGCCTTCCTC TTTATCGGGG TCAACTGTAA GTTCACCATC GTGTTCCCC ACAATCAGAA GGGAAACTGG AACAACGTTC
     TACTTTACGG ACCAGATAGA CCGGAAGGAG AAATAGCCCC AGTTGACATT CAAGTGCTAG CACAAAGGG TGTTAGTCTT CCCTTTGACC TTCTTGCAGG

.   S   N   Y   H   Y   C   P   S   S   S   D   L   N   W   H   N   D   L   I   G   T   A   I   Q   V   K   M   P   K   S   H   K   A   .
 101 CGAGCAACTA CCACTACTGC CCTAGCTCAA GCGACACGAA CTGGCACAAC GACCTGATCG GCACCGCTAT CCAGGTGAAG ATGCCAAAGA GCCACAAGGC
     GCTCGTTGAT GGTGATGACG GGATCGAGTT CGCTGTGCTT GACCACGTTG CTGGACTAGC CGTGGCGATA GGTCCACTTC TACGGTTTCT CGGTGTTCCG

.   I   Q   A   D   G   W   M   C   H   A   S   K   W   V   T   T   C   D   F   R   W   Y   G   P   K   Y   I   T   Q   S   I   R   S
 201 CATCCAAGCC GACGGCTGGA TGTGTCACGC CAGCAAATGG GTGACGACGT GCGATTTTCG CTGGTATGGC CCCAAGTACA TCACCCAAAT AATCCGCTCA
     GTAGGTTCGG CTGCCGACCT ACACAGTGCG GTCGTTTACC CACTGCTGCA CGCTAAAAGC GACCATACCG GGGTTCATGT AGTGGGTTAG TTAGGCGAGT

F   T   P   S   V   E   Q   C   K   E   S   I   E   Q   T   K   Q   G   T   W   L   N   P   G   F   P   P   Q   S   C   G   Y   A   T   .
 301 TTTACACCCA GGGTGGAGCA ATGTAAGGAG AGCATCGAGC AGACCAAGCA GGGGACCTGG CTCAACCCCG GCTTCCCACC GCAAAGCTGC GGATACGCCA
     AAATGTGGGT CCCACCTCGT TACATTCCTC TCGTAGCTCG TCTGGTTCGT CCCCTGGACC GAGTTGGGGC CGAAGGGTGG CGTTTCGACG CCTATGCGGT

.   V   T   D   A   E   A   V   I   V   Q   V   T   P   H   H   V   L   V   D   E   Y   T   G   E   M   V   D   S   Q   F   I   N   G   .
 401 CCGTGACCGA CGCTGAGGCC GTCATCGTGC AGGTGACCCC ACACCACGTG CTGGTGGACG AGTACACCGG CGAGTGGGTG GATTCACAGT TTATCAACGG
     GGCACTGGCT GCGACTCCGG CAGTAGCACG TCCACTGGGG TGTGGTGCAC GACCACCTGC TCATGTGGCC GCTCACCCAC CTAAGTGTCA AATAGTTGCC

.   K   C   S   N   Y   I   C   P   T   V   H   N   S   T   T   W   H   S   D   Y   K   V   K   G   L   C   D   S   N   L   I   S   M
 501 AAAGTGCTAG AATTACATCT GCCCCACCGT GCACAACAGC ACCACCTGGC ACTCAGACTA TAAGGTGAAG GGCCTCTGCG ACAGCAATCT GATCTCAATG
     TTTCACGATC TTAATGTAGA CGGGGTGGCA CGTGTTGTCG TGGTGGACCG TGAGTCTGAT ATTCCACTTC CCGGAGACGC TGTCGTTAGA CTAGAGTTAC

D   I   F   F   S   E   D   G   E   L   S   S   L   G   K   E   G   T   G   F   R   S   N   Y   F   A   Y   E   T   G   G   K   A   .
 601 GACATCACCT TCTTTAGCGA AGACGGCGAA CTCTCAAGCC TCGGAAAGGAA GGCACCGGG TTCCCAGCA ATTACTTTGC TTACGAAACC GGGGGCAAGG
     CTGTAGTGGA AGAAATCGCT TCTGCCGCTT GAGAGTTCGG AGCCCTTCCT AAGGGTGCCC AAGGGTCGT TAATGAAAGA ATGCTTTGG CCCCGTTCC
```

FIG. 6B

```
              .  C   K   M       Q   Y   C       K   H   W   G       V   R   L       P   S   G       V   N   F   E       M   A   D       K   D   L       F   A   A   A   R   F   P   .
  701         CCTGCAAGAT GCAATACTGC AAGCACTGGG GGGTGCGCCT GCCAAGCGGC GTGTGGTTTG AGATGGCTGA TAAGGACCTG TTCGCGGCTG CCCGCTTCCC
              CGACGTTCTA CGTTATGACG TTCGTGACCC CCACGCGGGA CGGTTCGCCG CACACCAAAC TCTACCGACT ATTCCTGGAC AAGCGCCGAC GGGCGAAGGG

.  E   C   P       E   G   S   S       I   S   A       P   S   Q       T   S   V   D       V   S   L       I   Q   D       V   E   R   I   L   D   Y       S   L   C
  801         GGAATGCCCC GAGGGCAGCA GCATCAGCGC CCCCAGCCAG ACATCAGTGG AGTTAGCCTA GATCCAGGAT GTGGAAGCGA TCCTGGACTA CAGCCTGTGT
              CCTTACGGGG CTCCCGTCGT CGTAGTCGCG GGGGTCGGTC TGTAGTCACC TCAATCGGAT CTAGGTCCTA CACCTTCGCT AGGACCTGAT GTCGGACACA

.  Q   E   T   W       S   K   I       R   A   G       L   P   I   S       P   V   D       L   S   Y       L   A   P   K       N   P   G       T   G   P       A   F   T   I
  901         CAGGAAAACGT GGACCAAGAT CCGCGCCGGA CTGCCTATCA GCCCCGTGGA TCTCAGCTAC CTGGCCCCAA AGAACCCAGG CACCGGACCC GCCTTTACAA
              GTCCTTTTGCA CCTGGTTCTA GGCGCGGCCT GACGGATAGT CGGGGCACCT AGAGTCGATG GACCGGGGTT TCTTGGGTCC GTGGCCTGGG CGGAAATGTT

.  I   N   G       T   L   K       Y   F   E   T       R   Y   I       A   A   P       I   L   S       R   M   V       G   M   I   S       G   T   T
  1001        TCATCAACGG CACCCTGAAG TACTTTGAAA CACGCTACAT CGCCGCTCCC ATCCTGTCTC AGGCATGGTG TGGTATGATA TCAGGACGAC
              AGTAGTTGCC GTGGGACTTC ATGAAACTTT GTGCGATGTA GCGGCGAGGG TAGGACAGAG TCCGTACCAC ACCATACTAT AGTCCTGCTG

.  T   E   R       E   L   W   D       D   W   A       P   Y   E       D   V   E   I       G   P   N       G   V   L       R   T   S   S       G   Y   K       F   P   L
  1101        CACGGAGCGC GAGCTGTGGG ATGACTGGGC CCCGTATGAA GATGTGGAGA TCGGACCTAA CGGGGTGCTG CGGACATCAA GCGGTACAA GTTCCCCTG
              GTGCCTCGCG CTCGACACCC TACTGACCCG GGGCATACTT CTACACCTCT AGCCTGGATT GCCCCACGAC GCCTGTAGTT CGCCATGTT CAAGGGGAC

.  Y   M   I   G       H   G   M       L   D   S       D   L   H   L       S   S   K       A   Q   V       F   E   H   P       H   I   Q       D   A   A       S   Q   L   P
  1201        TACATGATCG GCCATGGCAT GCTGGACAGC GACCTGCACC TCAGCAGC AAGGCCCAGGTC TTTGAGCACC CACACATCCA GGACGCTGCC AGCCAGCTCC
              ATGTACTACC CGGTACCGTA CGACCTGTCG CTGGACGTGG AGTCGAGTT TCCGGGTCCAG AAACTCGTGG GTGTGTAGGT CCTGCGACGG TCGGTCGAGG

.  D   D   E       S   L   F       F   G   D   T       G   L   S       K   N   P       I   E   L   V       E   G   W       F   S   S       W   K   S   S       I   A   S
  1301        CCGACGACGA AGCCCTGTTC TTTGGAGATA CAGGGCTCAG CAAGAACCCC ATCGAGCTGG TGGAGGGCTG GTTCTCAAGC TGGAAGAGCA GCATCGCTTC
              GGCTGCTGCT TCGGGACAAG AAACCTCTAT GTCCCGAGTC GTTCTTGGGG TAGCTCGACC ACCTCCCGAC CAAGAGTTCG ACCTTCTCGT CGTAGCGAAG

.  F   F   F       I   I   G       L   I   I   G       L   F   L       V   L   R   V       G   I   H       L   C   I       K   L   K   H       T   K   K       R   Q   I
  1401        ATTTTTTTTC ATCATCGGCC TCATCATCGG GCTGTTTCTG GTCCTGCGCG TGGGCATCCA CCTGTGCATC AAGCTGAAGC ACACCAAGAA GCGCCAGATC
              TAAAAAAAAG TAGTAGCCGG AGTAGTAGCC CGACAAAGAC CAGGACGCGC ACCCGTAGGT GGACACGTAG TTCGACTTCG TGTGGTTCTT CGCGGTCTAG

Y   T   D   I       E   M   N       R   L   G       K   *
  1501        TATACCGACA TCGAGATGAA TCGCCTGGGG AAGTAA
              ATATGGCTGT AGCTCTACTT AGCGGACCCC TTCATT
```

*FIG. 6B*  
*(CONTINUED)*

C.

Plasmid map of pTHV-VSV.G (IND-CO), 5144 bp, with features: EcoRI (1), NotI (28), XhoI (34), WPRE/ATG, XhoI (644), XbaI (650), BGH pA, KanR, NcoI (1644), pUC ORI, NdeI (3146), NcoI (3272), CMV, NheI (3557), HindIII (3573), KpnI (3583), BamHI (3591), PvuI (3667), BstEII (4040), VSV/G IND CO, BglII (5104).

CNCM I-3842

FIG. 6C

A.

MLSYLILAIVVSPILGKIEIVFPQHTTGDWKRVPHEYNYCPTSADKNSHGTQTGIPIELTMPKGLTTHQ
VDGFMCHSALWMTTCDFRWYGPKYITHSIHNEEPTDYQCLEAIKAYKDGVSFNPGFPPQSCGYGTVTDA
EAHIITVTPHSVKVDEYTGEWIDPHFIGGRCKGQICETVHNSTKWFTSSDGESVCSQLFTLVGGTFFSD
SEEITSMGLPETGIRSNYFPYISTEGICKMPFCRKPGYKLKNDLWFQITDPDLDKTVRDLPHIKDCDLS
SSIITPGEHATDISLISDVERILDYSLCQNTWSKIEAGEPITPVDLSYLGPKNPGVGPVFTIINGSLHY
FTSKYLRVELENPVIPRMEGRVAGTRIVRQLWDQWFPFGEAEIGPNGVLKTKQGYKFPLHIIGTGEVDS
DIKMERVVKHWEHPHIEAAQTFLKKDDTGEVLYYGDTGVSKNPVELVEGWFSGWR<u>SSIMGVLAVIIGFV
ILIFLI</u>RLIGVLSSLFRPKRRPIYKSDVEMAHFR (GenBank # AF170624)

*FIG. 7A*

B.

```
      M  L  S  Y  L  I  F     A  L  A     V  S  P  I  L  G  K     I  E  I     V  F  P  Q     H  T  T     G  D  W     K  R  V  P .
  1   ATGCTGTCAT ATCTGATCTT TGCCCTGCTT GTGAGCCCAA TCCTCGGAAA GATCGAAATC GTGTTCCCAC AACACCACCAC AGGGACTGG AAGCGGTGC
      TACGACAGTA TAGACTAGAA ACGGGACGA CACTCGGGTT AGGAGCCTTT CTAGCTTTAG CACAAGGGTG TTGTGGTG TCCCTGACC TTCCGCACG
      .  H  E  Y     N  Y  C     P  T  S     A  D  K  N     S  H  G     T  Q  T  G     I  P  V     E  L  T     M  P  K  G     L  T  T .
 101  CCCACCAGTA CAACTACTGC CCGACCAGC CGGACAACGAA TAGCCACGGC ACCCAGACCG GGATCCCTGT GGAGCTGACC ATGCCCAAGG GGCTCACAAC
      GGGTGGTCAT GTTGATGACG GGCTGGAGTC GCCTGTTCTT ATCGGTGCCG TCGGTCTGGC CTCCACTG TACGGGTTCC CCGAGTGTTG
      .  H  Q  V     E  G  F  M     C  H  S     A  L  W     M  T  T  C     D  F  R     W  Y  G     P  K  Y  I     T  H  S     I  H  N .
 201  CACCAAGTC GAAGGCTTCA TGTGCCACAG CGCTCTCTGG ATGACAACCT GCGATTTTCG CTGGTATGGC CCCAAGTACA TCACCCACAG CATCCACAAT
      CGTGGTTCAG CTTCCGAAGT ACACGGGTGTC GCGAGAGACC TACTGTTGGA CGCTAAAAGC GACCATACCG GGGTCATGT AGTGGGTGTC GTAGGTGTTA
      E  E  P  T     D  Y  Q     C  L  E     A  I  K  S     Y  K  D     G  V  S     F  N  P  G     F  P  P     Q  S  C     G  Y  G  T .
 301  GAGGAACCAA CGGACTACCA GTGCCTCGAA GCCATCAAGT CATACAAGGA TGGCGTTGAC TTCAACCCG GCTTCCCGCC CAATCAATGT GGCTACGGCA
      CTCCTTGGTT GCCTGATGGT CACGGAGCTT CGGTAGTTCA GTATGTTCCT ACCCCACTG AAGTTGGGC CGAAGGGCGG GGTAGTACA CCGATGCCGT
      .  V  T  D     A  E  A     H  I  V  T     V  T  P     H  S  V     K  V  D  E     Y  T  G     E  W  I     D  P  H  F     I  G  G .
 401  CGGTGACCGA CGCCGAGGCC CACATCGTCA CCGTGACACC CCACTCAGTC AAGGTCGACG AGTACACAGG CGAATGGATC GACCCCCACT TCATCGGGG
      GCCACTGGCT GCGGCTCCGG GTGTAGCAGT GGCACTGTGG GGTGAGTCAG TTCCAGCTGC TCATGTGTCC GCTTACCTAG CTGGGGGTGA AGTAGCCCC
      .  R  C  K     G  Q  I  C     E  T  V     H  N  S     T  K  W  F     T  S  S     D  G  E     S  V  C  S     Q  L  F     T  L  V .
 501  CGGCTGTAAG GGCCAAATCT GCGAGACCGT GCACAACAGC ACCAAGTGGT TTACGTCATC AGACGGCGAA AGCGTGTGCA GCCAACTGTT TACCCTGGTG
      GCCGACATTC CCGGTTTAGA CGCTCTGGCA CGTGTTGTCG TGGTTCACCA AATGCAGTAG TCTGCCGCTT TCGCACACGT CGGTTGACAA ATGGGACCAC
```

FIG. 7B

FIG. 7B (CONTINUED-1)

```
      G  G  I  F  F  S  D   S  E  E   I  T  S  M  G  L  P   E  T  G   I  R  S  N  Y  F  P   Y  I  S   T  E  G  I  .
 601  GGGGCAICT TCTTTTAGCA CAGGAGGAG AICACCAGCA TGGGCICCC GGAGACAGGA AICCGAGGA ACTACTITCC GTACAICAGC ACGAGGAA
      CCCCGTAGA AGAAAATCCT GTCGTCCTC TAGTGGTCGT ACCCGAGGG CCTCTGTCCT TAGGCTCCT TGATGAAAGG CATGTAGTCG TGCCTCCCTT
      .  C  K  M   P  F  C   R  K  Q  G   Y  K  L   K  N  D   L  W  F  Q  I  M  D   P  D  L   D  K  T  V  R  D  L  .
 701  TCTGTAAGAT GCCTTTTTGC CGAAGACGCT GATATAAGCT CTTCTTTACTTGA CTTGGTTCC AGATCATTGA CCCCGACCTG GACAAGACCG TCCGCGATCT
      AGACATTCTA CGGAAAAACG GCTTCTGCGA CTATATTCGA GAAGAAATGA GAACCAAGG TCTAGTACTT GGGCCTGGAC CTGTTCTGGC AGGCGCTAGA
      .  P  H  I  K  D  C  D   L  S  S   S  I  I  T  P  G  E  H  A  T   D  I  S   L  I  S  D  V  E  R   I  L  D   .
 801  GCCCCACATC AAGGACTGTG ATCTGTCATC AGCATCATC ACCCCGAG GAACATCAGC CTCATCAGCG ATGTGGAGCG CATCCTCGAC
      CGGGGTGTAG TTCCTGACAC TAGACAGTAG TCGTAGTAG TGGGGCCTC CTTGTAGTCG GAGTAGTCGC TACACCTCGC GTAGGAGCTG
      Y  A  L  C  Q  N  T   W  S  K   I  E  S  G  E  P  I   T  P  V   D  L  S  Y  L  G  P   K  N  P   G  V  G  P  .
 901  TACGCTCTCT GCCAGAACAC ATGGAGCAAG ATCGAGAGCG GCGAACCAT ACACCCCAGTG GACCTGAGCT ATCTCGGACCC AAGAACCCC GGGTGGGC
      ATGCGAGAGA CGGTCTTGTG TACCTCGTTC TAGCTCTCGC CGCTTGGTA CGGGTCAC CTGGACTCGA TAGACCCTGG TTCTTGGG CCCACCCG
      .  V  F  T   I  I  N   G  S  L  H   Y  F  T   S  K  Y   L  R  V  E  L  E  S   P  V  I   P  R  M  E   G  K  V  .
1001  CGGTGTTCAC CATCATCAAC GGGAGCCTGC ACTACTTTAC AAGCAAGTAT CTCGCGGTGG AGCTCGAAAG CCCAGTCATC CCCCGGATG AGGGAAGT
      GCCACAAGTG GTAGTAGTTG CCCTCGGACG TGATGAAATG TTCGTTCATA GAGCGCCACC TCGAGCTTTC GGGTCAGTAG GGGGCCTAC TCCCCTTCA
      .  A  G  T   R  I  V  R   Q  L  W   D  Q  W   F  P  F  G   E  V  E   I  G  P   N  G  V  L  K  T  K   Q  G  Y  .
1101  GGGCCGGAC CGCATGCGTC GCCAGCTGTG GGACCAGTGG TTCCCTTTTG GCGAGGTGGA AATCGGCCCC AACGGGGTC TGAAGACCAA GCAAGGATAT
      CCCGGCCCTG GCGTACGCAG CGGTCGACAC CCTGGTCACC AAGGGAAAAC CGCTCCACCT TTAGCCGGGG TTGCCCCAG ACTTCTGGTT CGTTCCTATA
      K  F  P  L  H  I   I  G  T  G   E  V  D  S   D  I  K   M  E  R   V  V  K  H   W  E  H   P  H  I   E  A  A  Q  .
1201  AAGTTCCCG TGCACACATC GGGACGGGC GAAGTGCACA GCGATATCAA GATGGAGCGC GTGGTGAAGC ACTGGAGCA CCCACACATC GAGGCTGCTC
      TTCAAGGGC ACGTGTGTAG CCCTGCCCG CTTCACGTGT CGCTATAGTT CTACCTCGCG CACCAGTTCG TGACCCTCGT GGGTGTGTAG CTCCGACGAG
```

```
     . T F L   K K D   D T G E   V L Y   Y G D   T G V S   K N P   V E L   V E G W   F S G .
1301 AGACCTTTCT CAAGAAGGAC GATACCGGCG AAGTCCTGTA TTACGGGGAT ACGGGAGTGA GCAAGAACCC TGTGGACCTG GTGGAAGGCT GGTTCAGCGG
     TCTGAAAGA GTTCTTCCTG CTATGGCCGC TTCAGGACAT AATGCCCCTA TGCCCTCACT CGTTCTTGGG ACACCTGGAC CACCTTCCGA CCAAGTCGCC
     . W R S   S L M G   V L A   V I I   G F V I   L M F   L I K   L I G V   L S S   L F R .
1401 ATGGCGCTCA AGCCTGATGG CCGTTCTGGC CGTCATCATC GGATTTGTGA TCCTGATGTT CCTCATCAAG CTGATCGGCG TGCTGTCGGC CCTGTTCCGC
     TACCGCGAGT TCGGACTACC GGCACGACCG GCAGTAGTAG CCTAAACACT AGGACTACAA GGAGTAGTTC GACTAGCCGC ACGACAGTTC GGACAAGGCG
     . P K R R   P I Y   K S D   V E M A   H F R   *
1501 CCTAAGCGGC GCCCAATCTA CAAGAGCGAC GTCGAGATGG CCCACTTTCG CTAA
     GGATTCGCCG CGGGTTAGAT GTTCTCGCTG CAGCTCTACC GGGTGAAAGC GATT
```

*FIG. 7B*
*(CONTINUED-2)*

EcoRI (1)
PmeI (55)
BGH pA
KanR
VSV/G NJ CO
NcoI (103)

pThV-VSV.G (IND-CO)
4552 bp

BamHI (2981)
PmeI (2956)
CMV
NcoI (2662)
NdeI (2536)
SpeI (2301)
pUC ORI

CNCM 1-4058

FIG. 7C
*(CONTINUED)*

A.

MTSSVTISVVLLISFITPLYSYLSIAFPENTKLDWKPVTKNTRYCPMGGEWFLEPGLQEESFLSSTPIG
ATPSKSDGFLCHAAKWVTTCDFRWYGPKYITHSIHNIKPTRSDCDTALASYKSGTLVSLGFPPESCGYA
SVTDSEFLVIMITPHHVGVDDYRGHWVDPLFVGGECDQSYCDTIHNSSVWIPADQTKKNICGQSFTPLT
VTVAYDKTKEIAAGGIVFKSKYHSHMEGARTCRLSYCGRNGIKFPNGEWVSLMLKLRSKRNLYFPCLKM
CPTGIRGEIYPSIRWAQVLTSEIQRILDYSLCQNTWDKVERKEPLSPLDLSYLASKSPGKGLAYTVING
TLSFAHTRYVRMWIDGPVLKEPKGKRESPSGISSDIWTQWFKYGDMEIGPNGLLKTAGGYKFPWHLIGM
GIVDNELHELSEANPLDHPQLPHAQSIADDSEEIFFGDTGVSKNPVELVTGWFTSWK<u>ESLAAGSCPDLR</u>
<u>CPPLFPGI</u>VYYLQKAQMEERGERSDSFEMRIFKPNNMRARV (GENBANK # J04350)

FIG. 8A

FIG. 8B

```
     · K S K   Y H S H   H M E G   A R T   C R L S   Y C G   R N G   I K F P   N G E   M V S
 701 CAAGAGCAAG TACCACAGCC ACATGGAAGG CGCCAGGACC TGCAGACTGT CCTACTGCGG CGGAACGGC ATCAAGTTCC CCAACGGGA GTGGTGTC
     GTTCTCGTTC ATGGTGTCGG TGTACCTTCC GCGGTCCTGG ACGTCTGACA GGATGACGCC GCCTTGCCG TAGTTCAAGG GGTTGCCCT CACCCACAG
     L M L K L R S   K R N   L Y F P   C L K   M C P   T G I R   G E I   Y P S   I R W A
 801 CTGATGCTGA AGTCGGGAG CAAGGGGAAC CTGTACTTCC CCTGCCTGAA GATGTGCCCC ACCGGCATCC GGGGCGAGAT CTACCCCAGC ATCAGATGG
     GACTACGACT TCAGCCCCTC GTTCCCCTTG GACATGAAGG GGACGGACTT CTACACGGGG TGGCCGTAGG CCCCGCTCTA GATGGGGTCG TAGTCTACC
     · Q V L   T S E   I Q R I   L D Y   S L C   Q N T W   D K V   E R K   E P L S   P L D
 901 CCCAGGTGCT GACCTCAGAG ATCCAGAGGA TCCTGGACTA CAGCCTGTGC CAGAACACCT GGGACAAGGT GAGCGGGAAA GAGCCCCTGA GCCCCCTGGA
     GGGTCCACGA CTGGAGTCTC TAGGTCTCCT AGGACCTGAT GTCGGACACG GTCTTGTGGA CCCTGTTCCA CTCGCCCTTT CTCGGGGACT CGGGGGACCT
     · L S Y   L A S K   S P G   K G L   A Y T V   I N G   T L S   F A H T   R Y V   R M W
1001 CCTGAGCTAC CTGGCCAGCA AGTCCCCAGG CAAGGGCCTG GCCTACACCG TGATCAACGG CACCCTGAGC TTCGCCCACA CCAGATACGT GGGGATGTGG
     GGACTCGATG GACCGGTCGT TCAGGGGTCC GTTCCCGGAC CGGATGTGGC ACTAGTTGCC GTGGGACTCG AAGCGGGTGT GGTCTATGCA CCCCTACACC
     I D G P   V L K   E P K   G K R E   S P S   G I S   S D I W   T Q W   F K Y   G D M E
1101 ATCGACGGCC CCGTGCTGAA AGAGCCCAAG GGCAAGAGAG AGAGCCCTAG CGGCATCAGC AGCGACATCT GGACCCAGTG GTTCAAGTAC GGCGACATGG
     TAGCTGCCGG GGCACGACTT TCTCGGGTTC CCGTTCTCTC TCTCGGGATC GCCGTAGTCG TCGCTGTAGA CCTGGGTCAC CAAGTTCATG CCGCTGTACC
     · I G P   N G L   L K T A   G G Y   K F P   W H L I   G M G   I V D   N E L H   E L S
1201 AAATCGGCCC CAACGGCCTG CTGAAAACAG CCGGCGGATA CAAGTTTCCT TGGCACCTGA TCGGCATGGG CATCGTGGAC AACGAGCTGC ACGAGCTGTC
     TTTAGCCGGG GTTGCCGGAC GACTTTTGTC GGCCGCCTAT GTTCAAAGGA ACCGTGGACT AGCCGTACCC GTAGCACCTG TTGCTCGACG TGCTCGACAG
     · E A N   P L D H   P Q L   P H A   Q S I A   D D S   E E I   F F G D   T G V   S K N
1301 CGAGGCCAAC CCCCTGGATC ACCCCCAGCT GCCCCACGCC CAGAGCATTG CCGACGACAG CGAGGAAATC TTCTTCGGCG ACACCGGGGT GAGCAAGAAC
     GCTCCGGTTG GGGGACCTAG TGGGGGTCGA CGGGGTGCGG GTCTCGTAAC GGCTGCTGTC GCTCCTTTAG AAGAAGCCGC TGTGGCCCA CTCGTTCTTG
```

FIG. 8B
*(CONTINUED-1)*

```
              P  V  E  L  V  T  G   W  F  T   S  W  K  E  S   L  A   A  G  S   C  P  D  L  R  C  P   P  L  F   P  G  I  V  .
1401 CCCGTGGAAC TGGTGACAGG CTGTTCACC AGCTGGAAAG AGAGCCTGGC CCCGGATCT TGCCCCCACC TGCCGTGCCC CCCTCTGTTC CCCGGCATCG
     GGGCACCTTG ACCACTGTCC GACAAGTGG TCGACCTTTC TCTCGGACCG GCGCCTAGA ACGGGGGTGG ACGGCAGGG GGGAGACAAG GGGCCGTAGC

.  Y  Y  L   Q  K  A   Q  M  E  E  R  G  E   R  S  D   S  F  E  M  R  I  F   K  P  N   N  M  R  A  R  V  *  .
1501 TGTACTACCT GCAGAAAGCC CAGATGGAAG AGCGGGGCGA GCGGAGCGAC AGCTTCGAGA TGCGGATCTT CAAGCCCAAC AACATGCGG CCAGAGTGTG
     ACATGATGGA CGTCTTTCGG GTCTACCTTC TCGCCCCGCT CGCCTCGCTG TCGAAGCTCT AGCCCTAGAA GTTCGGGTTG TTGTACGCC GGTCTCACAC
                EcoRI
                ~~~~~~~~
                  .  *  .
1601 ATGAGAATTC TTAATTAA
     TACTCTTAAG AATTAATT
```

FIG. 8B
(CONTINUED-2)

C.

Plasmid map: pTHV-VSV.G (CHANDI-CO), 5186 bp

Features and sites:
- EcoRI (1)
- NotI (28)
- XhoI (34)
- WPRE/ΔATG
- XhoI (644)
- XbaI (650)
- BGH pA
- KanR
- NcoI (1644)
- pUC ORI
- NdeI (3146)
- NcoI (3272)
- CMV
- NheI (3557)
- HindIII (3573)
- KpnI (3583)
- BamHI (3591)
- NcoI (3745)
- BstEII (3863)
- VSV.G CHANDIPURA CO
- BglII (4459)

*FIG. 8C*

Xho I (34)
EcoRI (1)
PmeI (55)
BGH pA
KanR
VSV.G CHANDIPURA CO
NcoI (103)
pThV-VSV.G (CHANDI-CO)
4576 bp
NcoI (3135)
BamHI (2981)
PmeI (2956)
CMV
NcoI (2662)
NdeI (2536)
pUC ORI

FIG. 8C
(CONTINUED)

A.

MNFLLLTFIVLPLCSHAKFSIVFPQSQKGNWKNVPSSYHYCPSSSDQNWHNDLLGITMKVKMPKTHKAI
QADGWMCHAAKWITTCDFRWYGPKYITHSIHSIQPTSEQCKESIKQTKQGTWMSPGFPPQNCGYATVTD
SVAVVVQATPHHVLVDEYTGEWIDSQFPNGKCETEECETVHNSTVWYSDYKVTGLCDATLVDTEITFFS
EDGKKESIGKPNTGYRSNYFAYEKGDKVCKMNYCKHAGVRLPSGVWFEFVDQDVYAAAKLPECPVGATI
SAPTQTSVDVSLILDVERILDYSLCQETWSKIRSKQPVSPVDLSYLAPKNPGTGPAFTIINGTLKYFET
RYIRIDIDNPIISKMVGKISGSQTERELWTEWFPYEGVEIGPNGILKTPTGYKFPLFMIGHGMLDSDLH
KTSQAEVFEHPHLAEAPKQLPEEETLFFGDTGISKNPVELIEGWFSSWKSTVVTFFFAIGVFILLYVVA
RIVIAVRYRYQGSNNKRIYNDIEMSRFRK (GenBank # AF045556)

FIG. 9A

B.

BamHI

M   N   F   L   L   L   T   F   I   V   L   P   L   C   S   H   A   K   F   S   I   V   F   P   Q  .
  1  GGCGCGCCCG ATCCTGATCA GCCACCATGA ACTTTCTGCT GCTGACATTC ATCGTCCTGC CTCTGTGCAG CCACGCCAAG TTCAGCATCG TGTTCCCCCA
     CCGCGCGGGC TAGGACTAGT CGGTGGTACT TGAAAGACGA CGACTGTAAG TAGCAGGACG GAGACACGTC GGTGCGGTTC AAGTCGTAGC ACAAGGGGT

S   Q   K   G   N   W   K   N   V   P   S   S   Y   H   Y   C   P   S   S   S   D   Q   N   W   H   N   D   L   L   G   I   T   M
101  GAGCCAGAAG GGCAACTGGA AGAACGTGCC CAGCAGCTAC CACTACTGCC CCAGCAGCAG CGACCAGAAC TGGCACAACG ACCTGCTGGG CATCACCATG
     CTCGGTCTTC CCGTTGACCT TCTTGCACGG GTCGTCGATG GTGATGACGG GGTCGTCGTC GCTGGTCTTG ACCGTGTTGC TGGACGACCC GTAGTGGTAC

K   V   K   M   P   K   T   H   K   A   I   Q   A   D   G   W   M   C   H   A   A   K   W   I   T   T   C   D   F   R   W   Y   G   P  .
201  AAGGTGAAAA TGCCCAAGAC CCACAAGGCC ATCCAGGCTG ACGGCTGGAT GTGCCACGCC GCCAAGTGGA TCACCACCTG CGACTTCCGG TGGTACGGCC
     TTCCACTTTT ACGGGTTCTG GGTGTTCCGG TAGGTCCGAC TGCCGACCTA CACGGTGCGG CGGTTCACCT AGTGGTGGAC GCTGAAGGCC ACCATGCCGG

K   Y   I   T   H   S   I   Q   P   T   S   E   Q   C   K   E   S   I   K   Q   T   K   Q   G   T   W   M   S   P   G  .
301  CCAAGTACAT CACCCACAGC ATCCAGCCCA CCAGCGAGCA GTGCAAAGAG AGCATCAAGC AGACCAAGCA GGGCACCTGG ATGAGCCCCG GCACCCCCG
     GGTTCATGTA GTGGGTGTCG TAGGTCGGGT GGTCGCTCGT CACGTTTCTC TCGTAGTTCG TCTGGTTCGT CCCGTGGACC TACTCGGGGC CGTGGGGGCC

F   P   P   Q   N   C   G   Y   A   T   V   T   D   S   V   A   V   V   V   Q   A   T   P   H   H   V   L   V   D   E   Y   T   G  .
401  CTTCCCACCC CAGAACTGCG GCTACGCCAC CGTGACCGAC AGCGTGGCCG TGGTGGTCCA GGCCACCCCC CACCACGTGC TGGTGGACGA GTACACCGGC
     GAAGGGTGGG GTCTTGACGC CGATGCGGTG GCACTGGCTG TCGCACCGGC ACCACCAGGT CCGGTGGGGG GTGGTGCACG ACCACCTGCT CATGTGGCCG

E   W   I   D   S   Q   F   P   N   G   K   C   E   T   E   E   C   E   T   V   H   N   S   T   V   W   Y   S   D   Y   K   V   T   G  .
501  GAGTGGATCG ACAGCCAGTT CCCCAACGGC AAGTGCGAGA CAGAGGAATG CGAGACAGTA CACAACAGCA CCGTGTGGTA CAGCGACTAC AAGGTGACCG
     CTCACCTAGC TGTCGGTCAA GGGGTTGCCG TTCACGCTCT GTCTCCTTAC GCTCTGTCAT GTGTTGTCGT GGCACACCAT GTCGCTGATG TTCCACTGGC

FIG. 9B

FIG. 9B (CONTINUED-1)

```
     . L  C  D  A  T  L  V  D  T  E  I  T  F  F  S  E  D  G  K  K  E  S  I  G  K  P  N  T  G  Y  R  S  N .
601   GCCTGTGCGA CGCCACCCTG GTGGACACCG AGATCACCTT TTTCAGCGAG GACGGCAAGA AAGAGTCCAT CGGCAAGCCC AACACCGGCT ACAGAAGCAA
      CGGACACGCT GCGGTGGGAC CACCTGTGGC TCTAGTGGAA AAAGTCGCTC CTGCCGTTCT TTCTCAGGTA GCCGTTCGGG TTGTGGCCGA TGTCTTCGTT

. Y  F  A  Y  E  K  G  D  K  V  C  K  M  N  Y  C  K  H  A  G  V  R  L  P  S  G  V  W  F  E  F  V  D .
701   CTACTTCGCC TACGAGAAGG GCGACAAAGT GTGCAAGATG AACTACTGCA AGCATGCCGG AGTGAGGCTG CCTAGCGGCG TGTGGTTCGA GTTCGTGGAC
      GATGAAGCGG ATGCTCTTCC CGCTGTTTCA CACGTTCTAC TTGATGACGT TCGTACGGTT TCGTACGGCC TCACTCCGAC GGATCGCCGC ACACCAAGCT CAAGCACCTG

. Q  D  V  Y  A  A  A  K  L  P  E  C  P  V  G  A  T  I  S  A  P  T  Q  T  S  V  D  V  S  L  I  L  D  V .
801   CAGGACGTGT ACGCCGCCGC CAAGCTGCCC GAGTGCCCCG TGGGCGCCAC CATCAGCGCC CCCACCCAGA CCAGCGTGGA CGTGAGCCTG ATCCTGGACG
      GTCCTGCACA TGCGGCGGCG GTTCGACGGG CTCACGGGGC ACCCGCGGTG GTAGTCGCGG GGGTGGGTCT GGTCGCACCT GCACTCGGAC TAGGACCTGC

. E  R  I  L  D  Y  S  L  C  Q  E  T  W  S  K  I  R  S  K  Q  P  V  S  P  V  D  L  S  Y  L  A  P  K .
901   TGGAGAGAAT CCTGGACTAC AGCCTGTGTC AGGAAACCTG GTCCAAGATC AGATCCAAGC AGCCCGTCAG CCCTGTCGAC CTGAGCTACC TGGCCCCTAA
      ACCTCTCTTA GGACCTGATG TCGGACACAG TCCTTTGGAC CAGGTTCTAG TCTAGGTTCG TCGGGCAGTC GGGACAGCTG GACTCGATGG ACCGGGGATT

. N  P  G  T  G  P  A  F  T  I  I  N  G  T  L  K  Y  F  E  T  R  Y  I  R  I  D  I  D  N  P  I  I  S .
1001  GAACCCCGGC ACCGGCCCTG CCTTCACCAT CATCAACGGC ACCCTGAAGT ACTTCGAGAC ACGGTACATC CGGATCGACA TCGACAACCC CATCATCAGC
      CTTGGGGCCG TGGCCGGGAC GGAAGTGGTA GTAGTTGCCG TGGGACTTCA TGAAGCTCTG TGCCATGTAG GCCTAGCTGT AGCTGTTGGG GTAGTAGTCG

. K  M  V  G  K  I  S  G  S  Q  T  E  R  E  L  W  T  E  M  F  P  Y  E  G  V  E  I  G  P  N  G  I  L  K .
1101  AAGATGGTGG GCAAGATCAG CGGCAGCCAG ACCGAGCGG AGCTGTGGAC CGAGATGTTC CCCTACGAGG GCGTGGAGAT CGGCCCCAAT GGCATCCTGA
      TTCTACCACC CGTTCTAGTC GCCGTCGGTC TGGCTCGCC TCGACACCTG GCTCTACAAG GGGATGCTCC CGCACCTCTA GCCGGGGTTA CCGTAGGACT
```

```
       . T  P  T  G  Y  K     F  P  L  F  M  I  G  H  G  M     L  D  S  D  L  H  K     T  S  Q     A  E  V  F  E  H  P .
1201 AAACCCTAC CGGCTACAAG TTCCCCCTGT TCATGATCGG CCACGGCATG CTGGACAGCG ACCTGCACAA GACCTCCCAG GCCGAGGTGT TCGAGCACCC
     TTTGGGGATG GCCGATGTTC AAGGGGGACA AGTACTAGCC GGTGCCGTAC GACCTGTCGC TGGAGGGTGT TCTGGAGGGTC CGGCTCCACA AGCTCGTGGG

. H  L  A     E  A  P  K     Q  L  P     E  E  E     T  L  F  F  G  D  T     G  I  S     K  N  P  V  E  L  I     E  G  W
1301 CCACTGGCC GAGGCCCCA AGCAGCTGCC CGAAGAGGAA ACCCTGTTCT TCGGCGACAC CGGCATCTCC AAGAACCCTG TGGAGCTGAT CGAGGGCTGG
     GGTGACCGG CTCCGGGGT TCGTCGACGG GCTTCTCCTT TGGGACAAGA AGCCGCTGTG GCCGTAGAGG TTCTTGGGAC ACCTCGACTA GCTCCCGACC

. F  S  S  W  K  S  T     V  V  T     F  F  F  A  I  G  V     F  I  L     L  Y  V  V     A  R  I     V  I  A     V  R  Y  R .
1401 TTCAGCAGCT GGAAGAGCAC CGTGGTGACC TTTTTCTTCG CCATCGGCGT GTTCATCCTG CTGTACGTGG TGGCCCGGAT CGTGATCGCC GTGCGGTACA
     AAGTCGTCGA CCTTCTCGTG GCACCACTGG AAAAAGAAGC GGTAGCCGCA CAAGTAGGAC GACATGCACC ACCGGGCCTA GCACTAGCGG CACGCCATGT

EcoRI
       . Y  Q  G     S  N  N     K  R  I  Y     N  D  I     E  M  S     R  F  R  K     *     *
1501 GATACCAGGG CAGCAACAAC AAGCGGATCT ACAACGACAT CGAGATGAGC CGGTTCCGGA AGTGATGAGA ATTCTTTAATT AA
     CTATGGTCCC GTCGTTGTTG TTCGCCTAGA TGTTGCTGTA GCTCTACTCG GCCAAGGCCT TCACTACTCT TAAGAAATTAA TT
```

*FIG. 9B (CONTINUED-2)*

A.

MTDTVLGKFQIVFPDQNELEWTPVVGDSRHCPQSSEMQFDGSRSQTILTGKAPVGITPSKSDGFICHAA
KWVTTCDFRWYGPKYITHSIHHLRPTTSDCETALQRYKDGSLINLGFPPESCGYATVTDSEAMLVQVTP
HHVGVDDYRGHWIDPLFPGGECSTNFCDTVHNSSVWIPKSQKTDICAQSFKNIKMTASYPSEGALVSDR
FAFHSAYHPNMPGSTVCIMDFCEQKGLRFTNGEWMGLNVEQSIREKKISAIFPNCVAGTEIRATLESEG
ARTLTWETQRMLDYSLCQNTWDKVSRKEPLSPLDLSYLSPRAPGKGMAYTVINGTLHSAHAKYIRTWID
YGEMKEIKGGRGEYSKAPELLWSQWFDFGPFKIGPNGLLHTGKTFKFPLYLIGAGIIDEDLHELDEAAP
IDHPQMPDAKSVLPEDEEIFFGDTGVSKNPIELIQGWFSNWRE<u>SVMAIVGIVLLIVVTFLAIK</u>TVRVLN
CLWRPRKKRIVRQEVDVESRLNHFEMRGFPEYVKR (GenBank # D26175)

FIG. 10A

B.

BamHI

```
                    M  T  D  T  V  L  G  K   F  Q  I  V  F  P  D   Q  N  E  L  E  W  T  P  V  V  .
  1  GGGGGACCCG ATCCTGATCA GCCACCATGA CCGATACAGT GCTGGCAAG TTCCAGATCG TGTTCCCGA CCAGAACGAG CTGGAATGGA CCCCGGTCGT
     CCCCCTGGGC TAGGACTAGT CGGTGGTACT GGCTATGTCA CGACCGTTC AAGGTCTAGC ACAAGGGCT GGTCTTGCTC GACCTTACCT GGGGCCACAA
     .  G  D  S  R  H  C  P  Q  S  S   E  M  Q  F  D  G  S   R  S  Q  T  I  L   T  G  K  A  P  V  G  I  T  P
101  GGGGGACAGC CGGCATTGCC CGAGATGCAG TTCGACGGCA GCAGAAGCCA GACACTGACC GGAAAGGCT CCCGTGGG CATCACACC
     CCCCCTGTCG GCCGTAACGG GCTCTACGTC AAGCTGCCGT CGTCTTCGGT CTGTGACTGG CCTTTCCGA GGGCACCC GTAGTGTGG
                                                                                                                 .
     S  K  S  D  G  F  I   C  H  A  A  K  W  V  T  T  C   D  F  R  W  Y  G  P   K  Y  I  T  H  S   I  H  H  L  .
201  AGCAAGAGCG ACGGCTTCAT CTGCCACGCC GCCAAGTGGG TGACCACCTG CGACTTCCGC TGGTACGGCC CCAAGTACAT CACCCACAGC ATCCACACAC
     TCGTTCTCGC TGCCGAAGTA GACGGTGCGG CGGTTCACCC ACTGGTGGAC GCTGAAGGCG ACCATGCCGG GGTTCATGTA GTGGGTGTCG TAGGTGTG
     .  R  P  T   T  S  D  C  E  T  A   L  Q  R  Y  K  D   G  S  L  I  N  L  G   F  P  P  E  S  C   G  Y  A  T  .
301  TCCGGCCCAC CACCTCGGAC TGCGAGACAG CCCTGCAGCG GTACAAAGAC GGCAGCCTGA TCAACCTGGG CTTCCCTCCC GAGAGCTGG GCTACGCCAC
     AGGCCGGGTG GTGGAGCCTG ACGCTCTGTC GGGACGTCGC CATGTTTCTG CCGTCGGACT AGTTGGACCC GAAGGGAGG CTCTCGACC CGATGCGGTG
     .  V  T  D   S  E  A  M  L  V  Q   V  T  P  H  H  V  G  V  D  D  Y  R  G   H  W  I  D  P  L  F   P  G  G  .
401  CGTCACAGAC AGCGAGGCCA TGCTGGTGCA GGTCACCCCC CACCACGTGG GGTGGACGA CGATTACCGC CACTGGATCG ACCCGCTGT CCCTGGGGGC
     GCAGTGTCTG TCGCTCCGGT ACGACCACGT CCAGTGGGGG GTGGTGCACC CCACCTGCT GCTAATGGCG GTGACCTACC TGGGGACA GGGACCCGG
     .  E  C  S  T   N  F  C  D  T  V   H  N  S  S  V  W   I  P  K  S   Q  K  T  D   I  C  A  Q  S  F   K  N  I  K  .
501  CGAGTGCAGCA CCAATTTCTG CGATACCGTG CACAACAGCA GCGTGTGGAT TCCCAAGAGC CAGAAAACG ACATCTGCG CCCAGAGCTTC AAGAACATCA
     GCTCACGTCGT GGTTAAAGAC GCTATGGCAC GTGTTGTCGT CGCACACCTA AGGGTTCTCG GTCTTTTGC TGTAGACGC GGGTCTCGAAG TTCTTGTAGT
```

FIG. 10B

. M T A S Y P S E G A L V S D R F A F H S A Y H P N M P G S T V C I .
601 AGATGACCGC CACCTACCCC AGCGAGGGAG CCCTGGTGTC CGACCGGTTC GCCTTCCACA GCGCCTACCA CCCCAACATG CCCGGCACCA CCGTGTGCAT
      TCTACTGGCG GTGGATGGGG TCGCTCCCTC GGGACCACAG GCTGGCCAAG CGGAAGGTGT CGCGGATGGT GGGGTTGTAC GGGCCGTGGT GGCACACGTA

. M D F C E Q K G L R F T N G E W M G L N V E Q S I R E K K I S A I .
701 CATGGATTTC TGCGAGCAGA AGGGCCTGCG GTTCACCAAC GGCGAGTGGA TGGGCCTGAA CGTGGAGCAG AGCATCCGGG AGAAGAAGAT CAGCGCCATC
      GTACTACAAG ACGCTCGTCT TCCCGGACGC CAAGTGGTTG CCGCTCACCT CAAGTGGTTG GCACCTCGTC TCGTAGGCCC TCTTCTTCTA GTCGCGGTAG

. F P N C V A G T E I R A T L E S E G A R T L T W E T Q R M L D Y S L .
801 TTCCCCAACT GCGTGGCCGG CACCGAGATC CGGGCCACCC TGGAATCCGA GGGCGCCAGG ACCCTGACCT GGGAGACACA GCGGATGCTG GACTACAGCC
      AAGGGGTTGA CGCACCGGCC GTGGCTCTAG GCCCGGTGGG ACCTTAGGCT CCCGCGGTCC TGGGACTGGA CCCTCTGTGT CGCCTACGAC CTGATGTCGG

. C Q N T W D K V S R K E P L S P L D L S Y L S P R A P G K G M A Y .
901 TGTGCCAGAA CACCTGGGAC AAGGTGTCCC GGAAAGAGCC CCTTTCTCCG CTTGACCTGA GCTACCTGAG CCCTAGAGCC CCTGGAAAAG GCATGGCCTA
      ACACGGTCTT GTGGACCCTG TTCCACAGGG CCTTTCTCGG GGAAAGAGGC GAACTGGACT CGATGGACTC GGGATCTCGG GGACCTTTTC CGTACCGGAT

. T V I N G T L H S A H A K Y I R T W I D Y G E M K E I K G G R G E .
1001 CACCGTGATC AACGGCACC CTGCACAGCG CCCACGCCAAG TATATCCGA CCTTGGATCGA CTACGGCGAG ATGAAAGAGA TCAAGGGCGG CAGGGGCGAG
      GTGGCACTAG TTGCCGTGGG GACGTGTCGC GGGTGCGGTTC ATATAGGCT ATATAGGCT GAACCTAGCT GATGCCGCTC TACTTTCT AGTTCCCGCC GTCCCGCTC

FIG. 10B
*(CONTINUED-1)*

```
         Y  S  K  A  P  E  L  L  W  S     Q  W  F  D     F  G  P     F  K  I     G  P  N  G     L  L  H     T  G  K     T  F  K  F  .
1101  TACACCAAG CCCCTGACT GCTGTGGAGC CAGTGGTTCG ACTTCGGCCC CTTCAAGATC GGCCCCAACG GCCTGCTGCA CACCGGCAAG ACCTTCAAGT
      ATGTGGTTC GGGACTGA CGACACCTCG GTCACCAAGC TGAAGCCGGG GAAGTTCTAG CCGGGGTTGC CCGGACGAGT GTGGCCGTTC TGGAAGTTCA

.  P  L  Y     L  I  G     A  G  I  I     D  E  D     L  H  E     L  D  E  A     A  P  I     D  H  P     Q  M  P  D     A  K  S
1201  TCCCCCTGTA TCTGATCGGA GCCGGAATCA TCGACGAGGA CCTGCACGAG CTGGACGAAG CGCCCATCGA CCACCCCCAG CAGATGCCCG ACGCCAAGAG
      AGGGGGACAT AGACTAGCCT CGGCCTTAGT AGCTGCTCCT GGACGTGCTC GACCTGCTTC GCGGGTAGCT GGTGGGGGTC GTCTACGGGC TGCGGTTCTC

.  V  L  P     E  D  E  E     I  F  F     G  D  T     G  V  S  K     N  P  I     E  L  I     Q  G  W  F     S  N  W     R  E  S
1301  CGTGCTGCCC GAGGACGAGG AAATCTTCTT CGGCGACACC GGCGTGAGCA AGAACCCCAT CGAGCTGATC CAGGGCTGGT TCAACTGGCG GGAGAGC
      GCACGACGGG CTCCTGCTCC TTTAGAAGAA GCCGCTGTGG CCGCACTCGT TCTTGGGGTA GCTCGACTAG GTCCCGACCA AGTTGACCGC CCTCTCTCG

V  M  A  I     V  G  I     V  L  L     I  V  V  T     F  L  A     I  K  T     V  R  V  L     N  C  L     W  R  P     R  K  K  R  .
1401  GTGATGGCCA TCGTGGGCAT CGTGCTGCTG ATCGTGGTCA CCTTCCTGGC CATCAAGACC GTGCGGGTGC TGAACTGCCT GTGGCGGCCC AGGAAGAAAC
      CACTACCGGT AGCACCCGTA GCACGACGAC TAGCACCAGT GGAAGGACCG GTAGTTCTGG CACGCCCACG ACTTGACGGA CACCGCCGGG TCCTTCTTTG

EcoRI
         .  I  V  R     Q  E  V     D  V  E  S     R  L  N     H  F  E     M  R  G  F     P  E  Y     V  K  R     *  *
1501  GGATCGTCCG GCAGGAAGTG GACGTCGAGA GCCGCCTGAA CCACTTCGAA ATGAGAGGCT TCCCCGAGTA CGTGAAGCGG TGATGAGAAT TCTTAATTAA
      CCTAGCAGGC CGTCCTTCAC CTGCAGCTCT CGGCGGACTT GGTGAAGCTT TACTCTCCGA AGGGGCTCAT GCACTTCGCC ACTACTCTTA AGAATTAATT
```

FIG. 10B
*(CONTINUED-2)*

A.

MTSVLFMVGVLLGAFGSTHCSIQIVFPSETKLVWKPVLKGTRYCPQSAELNLEPDLKTMAFDSKVPIG
ITPSNSDGYLCHAAKWVTTCDFRWYGPKYITHSVHSLRPTVSDCKAAVEAYNAGTLMYPGFPPESCGY
ASITDSEFYVMLVTPHPVGVDDYRGHWVDPLFPTSECNSNFCETVHNATMWIPKDLKTHDVCSQDFQT
IRVSVMYPQTKPTKGADLTLKSKFHAHMKGDRVCKMKFCNKNGLRLGNGEWIEVGDEVMLDNSKLLSL
FPDCLVGSVVKSTLLSEGVQTALWETDRLLDYSLCQNTWEKIDRKEPLSAVDLSYLAPRSPGKGMAYI
VANGSLMSAPARYIRVWIDSPILKEIKGKKESASGIDTVLWEQWLPFNGMELGPNGLIKTKSGYKFPL
YLLGMGIVDQDLQELSSVNPVDHPHVPIAQAFVSEGEEVFFGDTG11VSKNPIELISGWFSDWK<u>ETAA</u>
<u>ALGFAAISVILIIGLM</u>RLLPLLCRRRKQKKVIYKDVELNSFDPRQAFHR (genBank # AJ810084)

FIG. 11A

B.

BamHI

```
                            M  T  D  T  V     L  G  K     F  Q  I  V  F  P  D     Q  N  E     L  E  W  T  P  V  V  .
  1  GGGCGGCCGCG ATCCTGATCA GCCACCATGA CCGATACAGT CCTGGGCAAG TTCCAGAACG TGTTCCCCGA CCAGAACCAG CTGGAATGGA CCCCCGTCGT
     CCCGCGGCGC TAGGACTAGT CGGTGGTACT GGCTATGTCA GGACCCGTTC AAGGTCTTGC ACAAGGGGCT GGTCTTGGTC GACCTTACCT GGGGCAGCA
                            .  G  D  S     R  H  C  P     Q  S  S     E  M  Q     F  D  G  S     R  S  Q     T  I  L     T  G  K  A  P  V  G     I  T  P
101  GGGCGGACAGC CGGCATTGCC CTCAGTCCAG CAAGATGCAG TTCGACGGCA GCAGAAGCCA GACCATCCTG ACCGGCAAGG CCCCCGTCGG CATCACACCC
     CCCGCCTGTCG GCCGTAACGG GAGTCAGGTC GTTCTACGTC AAGCTGCCGT CGTCTTCGGT CTGGTAGGAC TGGCCGTTCC GGGGCAGCC GTAGTGTGG
           S  K  S  D     G  F  I     C  H  A     A  K  W  V     T  T  C     D  F  R     W  Y  G  P  K  Y  I     T  H  S     I  H  H  L  .
201  AGCAAGAGCG ACGGCTTCAT CTGCCACGCC GCCAAGTGGG TGACCACCTG CGACTTCCGG TGGTACGGCC CCAAGTACAT CACCCACAGC ATCCACCACC
     TCGTTCTCGC TGCCGAAGTA GACGGTGCGG CGGTTCACCC ACTGGTGGAC GCTGAAGGCC ACCATGCCGG GGTTCATGTA GTGGGTGTCG TAGGTGGTGG
     .  R  P  T     T  S  D     C  E  T  A     L  Q  R     Y  K  D     G  S  L  I  N  L  G     F  P  P     E  S  C  G     Y  A  T     .
301  TGCGGCCCAC CACCTCCGAC TGCGAGACAG CCCTGCAGCG GTACAAGGAC GGCAGCCTGA TCAACCTGGG CTTCCCTCCC GAGAGCTGCG GCTACGCCAC
     ACGCCGGGTG GTGGAGGCTG ACGCTCTGTC GGGACGTCGC CATGTTCCTG CCGTCGGACT AGTTGGACCC GAAGGGAGGG CTCTCGACGC CGATGCGGTG
     .  V  T  D     S  E  A  M     L  V  Q     V  T  P     H  H  V  G     V  D  D     Y  R  G     H  M  I  D     P  L  F     P  G  G
401  CGTGACAGAC AGGGAGGCCA TGCTGGTGCA GGTGACCCCC CACCACGTGG GCGTGGACGA CTACCGGGGC CACATGATCG ACCCCCTGTT CCCTGGGGGC
     GCACTGTCTG TCCCTCCGGT ACGACCACGT CCACTGGGGG GTGGTGCACC CGCACCTGCT GATGGCCCCG GTGTACTAGC TGGGGGACAA GGGACCCCCG
     E  C  S  T     N  F  C     D  T  V     H  N  S  S     V  W  I     P  K  S     Q  K  T  D     I  C  A     Q  S  F     K  N  I  K  .
501  GAGTGCAGCA CCAATTTCTG CGATACCGTG CACAACAGCA GCGTGTGGAT TCCCAAGAGC CAGAAAACCG ACATCTGCGC CCAGAGCTTC AAGAACATCA
     CTCACGTCGT GGTTAAAGAC GCTATGGCAC GTGTTGTCGT CGCACACCTA AGGGTTCTCG GTCTTTTGGC TGTAGACGCG GGTCTCGAAG TTCTTGTAGT
```

*FIG. 11B*

FIG. 11B
(CONTINUED-1)

```
       . M  T  A    S  Y  P    S  E  G  A    L  V  S    D  R  F    A  F  H  S    A  Y  H    P  N  M    P  G  S    T  V  C  I .
 601  AGATGACCGC CAGCTACCCC AGCGAGGAG CCCTGGTGTC CGACCGGTTC GCCTTCCACA GCGCCTACCA CCCCAACATG CCCGGCAGCA CCGTGTGCAT
      TCTACTGGCG GTCGATGCGG TCGCTCCCTC GGGGACCACAG GCTGGCCAAG CGGAAGTGT CGGGATTGTAC GGGTTGTAC GGGCCGTCGT GGCACACGTA

. M  D  F    C  E  Q  K    G  L  R    F  T  N    G  E  W  M    G  L  N    V  E  Q    S  I  R  E    K  K  I    S  A  I
 701  CATGGATTTC TGCGAGCAGA AGGGCCTGCG GTTCACCAAC GGCGAGTGGA TGGGCCTGAA CGTGGAGCAG AGCATCCGGG AGAAGAAGAT CAGCGCCATC
      GTACCTAAAG ACGCTCGTCT TCCCGGACGC CAAGTGGTTG CCGCTCACCT ACCCGGACTT GCACCTCGTC TCGTAGGCCC TCTTCTTCTA GTCGCGGTAG

F  P  N  C    V  A  G    T  E  I    R  A  T    L  E  S  E    G  A  R    T  L  T  W    E  T  Q    R  M  L    D  Y  S  L .
 801  TTCCCCAACT GCGTGGCCGG CACCGAGATC CGGGCCACCC TGGAATCCGA GGGCGCCCGG ACCCTGACCT GGGAGACACA GCGGATGCTG GACTACAGCC
      AAGGGGTTGA CGCACCGGCC GTGGCTCTAG GCCCGGTGGG ACCTTAGGCT CCCGCGGGCC TGGGACTGGA CCCTCTGTGT CGCCTACGAC CTGATGTCGG

. C  Q  N    T  W  D    K  V  S  R    K  E  P    L  S  P    L  D  L  S    Y  L  S    P  R  A    P  G  K  G    M  A  Y .
 901  TGTGCCAGAA CACCTGGGAC AAGGTGTCCC GGAAAGAGCC CCTGTCCCCC CTGGACCTGA GCTACCTGTCG CCCTAGAGCC CCTGGCAAGG GCATGGCCTA
      ACACGGTCTT GTGGACCCTG TTCCACAGGG CCTTTCTCGG GGACAGGGGG GACCTGGACT CGATGGACT CGGATCTCGG GGACGTTCC CGTACCGGAT

. T  V  I    N  G  T  L    H  S  A    H  A  K    Y  I  R  T    W  I  D    Y  G  E    M  K  E  I    K  G  G    R  G  E
1001  CACCGTGATC AACGGCACCC TGCACAGCGC CCACGCCAAG TATATCCGGA CCTGGATCGA CTACGGCGAG ATGAAAGAGA TCAAGGGCGG CAGGGGCGAG
      GTGGCACTAG TTGCCGTGGG ACGTGTCGCG GGTGCGGTTC ATATAGGCCT GGACCTAGCT GATGCCGCTC TACTTTCTCT AGTTCCCGCC GTCCCCGCTC

Y  S  K  A    P  E  L    L  W  S    Q  W  F  D    F  G  P    F  K  I    G  P  N  G    L  L  H    T  G  K    T  F  K  F .
1101  TACAGCAAGG CCCCTGAGCT GCTGTGGAGC CAGTGGTTCG ACTTCGGCCC CTTCAAGATC GGCCCCAACG GCCTGCTGCA CACCGGCAAG ACCTTCAAGT
      ATGTCGTTCC GGGGACTCGA CGACACCTCG GTCACCAAGC TGAAGCCGGG GAAGTTCTAG CCGGGGGTTGC CGGACGACGT GTGGCCGTTC TGGAAGTTCA
```

```
       .  P  L  Y     L  I  G     A  G  I  I  D  E  D     L  H  E     L  D  E  A     A  P  I     D  H  P     Q  M  P  D     A  K  S  .
1201 TCCCTCTGTA TCTGATCGGA GCCGGCATCA TCGACGAGGA CCTGCACGAG CTGGACGAAG CCGCCCCTAT CGACCACCCC CAGATGCCCG ACGCCAAGAG
     AGGGAGACAT AGACTAGCCT CGGGCCGTAGT AGCTGCTCCT GGACGTGCTC GACCTGCTTC GGCGGGGATA GCTGGTGGGG GTCTACGGGC TGCGGTTCTC

.  V  L  P     E  D  E  E     I  F  F     G  D  T     G  V  S  K     N  P  I     E  L  I     Q  G  W  F     S  N  W     R  E  S
1301 CGTGCTGCCC GAGGACGAGG AAATCTTCTT CGGCGACACC GGGGTGAGCA AGAACCCCAT CGAGCTGATC CAGGGCTGGT TCAGCAACTG GCGGGAGAGC
     GCACGACGGG CTCCTGCTCC TTTAGAAGAA GCCGCTGTGG CCCACTCGT TCTTGGGGTA GCTCGACTAG GTCCCGACCA AGTCGTTGAC CGCCCTCTCG

V  M  A  I  V  G  I     V  L  L     I  V  V  T     F  L  A     I  K  T     V  R  V  L  N  C  L     W  R  P     R  K  K  R  .
1401 GTGATGGCCA TCGTGGGCAT CGTCCTGCTG ATCGTGGTGA CCTTCCTGGC CATCAAGACC GTGGGGGTGC TGAACTGCCT GTGGCGGCCC AGGAAGAAAC
     CACTACCGGT AGCACCCGTA GCAGGACGAC TAGCACCACT GGAAGGACCG GTAGTTCTGG CACCCCCACG ACTTGACGGA CACCGCCGGG TCCTTCTTTG

EcoRI
       .  I  V  R     Q  E  V     D  V  E  S     R  L  N     H  F  E     M  R  G  F     P  E  Y     V  K  R   *    *
1501 GGATCGTCCG GCAGGAAGTG GACGTCGAGA GCCGGCTGAA CCACTTCGAG ATGAGAGGCT TCCCCGAGTA CGTGAAGCGG TGATGAGAAT TCTTTAATTAA
     CCTAGCAGGC CGTCCTTCAC CTGCAGCTCT CGGCCGACTT GGTGAAGCTC TACTCTCCGA AGGGGCTCAT GCACTTCGCC ACTACTCTTA AGAAATTAATT
```

*FIG. 11B*
*(CONTINUED-2)*

C.

pThzV-VSV.G (ISFA-CO)
5168bp

- EcoRI (1)
- NotI (28)
- XhoI (34)
- WPRE/ΔATG
- XhoI (644)
- XbaI (650)
- BGH pA
- KanR
- NcoI (1644)
- pUC ORI
- NcoI (3272)
- NdeI (3146)
- CMV
- NheI (3557)
- HindIII (3573)
- KpnI (3583)
- BamHI (3591)
- BstEII (3821)
- BstEII (4013)
- VSV.G PIRY CO
- BspEI (4627)
- BspEI (5018)

FIG. 11C

A.

MSIISYIAFLLLIDSTLGIPIFVPSGQNISWQPVIQPFDYQCPIHGNLPNTMGLSATKLTIKSPSVFSTDKVSGW
ICHAAEWKTTCDYRWYGPQYITHSIHPISPTIDECKRIISRIASGTDEDLGFPPQSCGWASVTTVSNTNYKVVPH
SVHLEPYGGHWIDHDFNGGECREKVCEMKGNHSIWITDETVQHECEKHIEEVEGIMYGNAPRGDAIYINNFIIDK
HHRVYRFGGSCRMKFCNKDGIKFTRGDWVEKTAGTLTNIYENIPECADGTLVSGHRPGLDLIDTVFNLENVVEYT
LCEGTKRKINKQEKLTSVDLSYLAPRIGGFGSVFRVRNGTLERGSTTYIRIEVEGPVVDSLNGIDPRTNASRVFW
DDWELDGNIYQGFNGVYKGKDGKIHIPLNMIESGIIDDELQHAFQADIIPHPHYDDDEIREDDIFFDNTGENGNP
VDAVVEWVSGWGTSLKFFGMTLVALILIFLLIRCCVACTYLMKKSKRPATESHEMRSLV  (GenBank
AAZ20272)

FIG. 12A

B.

BamHI

```
                 M  S  I  I  S  Y  I  A  F  L  L  L  I  D  S     T  L  G     I  P  I  F  V  P  S  .
  1  GGCGCGCCCG ATCCTGATCA GCCACCATGA GCATCATCAG CTATATCGCC TTTCTCCTGC TGATCGACAG CACCCTGGGC ATCCCCATCT TCGTGCCCAG
     CCGCGCGGCC TAGGACTAGT CGGTGGTACT CGTAGTAGTC GATATAGCGG AAAGAGGACG ACTAGCTGTC GTGGGACCCG TAGGGGTAGA AGCACGGGTC

·  G  Q  N     I  S  W  Q  P  V  I     Q  P  F     D  Y  Q  C     P  I  H     G  N  L     P  N  T  M     G  L  S     A  T  K
 101 CGGCCAGAAC ATCAGCTGGC AGCCCGTGAT CCAGCCCTTC GACTACCAGT GCCCCATCCA CGGCAACCTG CCCAACACCA TGGGCCTGAG CGCCACCAAG
     GCCGGTCTTG TAGTCGACCG TCGGGCACTA GGTCGGGAAG CTGATGGTCA CGGGGTAGGT GCCGTTGGAC GGGTTGTGGT ACCCGGACTC GCGGTGGTTC

L  T  I  K  S  P  S     V  F  S     T  D  K  V     S  G  W     I  C  H     A  A  E  W     K  T  T     C  D  Y     R  W  Y  G  .
 201 CTGACCATCA AGAGCCCCAG CGTGTTCAGC ACCGACAAGG TGTCCGGCTG GATCTGCCAC GCCGCCGAGT GGAAAACCAC CTGCGACTAC CGGTGGTACG
     GACTGGTAGT TCTCGGGGTC GCACAAGTCG TGGCTGTTCC ACAGGCCGAC CTAGACGGTG CGGCGGCTCA CCTTTTGGTG GACGCTGATG GCCACCATGC

·  P  Q  Y     I  T  H     S  I  H  P     I  S  P     T  I  D     E  C  K  R     I  I  S     R  I  A     S  G  T  D     E  D  L  .
 301 GCCCCCAGTA CATCACCCAC AGCATCCAC CCCATCAGCC CCACCATCGA CGAGTGCAAG CGGATCATCAG CCGTAGCGCC AGCGGCACCG ACGAGGACCT
     CGGGGGTCAT GTAGTGGGTG TCGTAGGTGG GGTAGTCGG GGTGGTAGCT GCTCACGTTC GCCTAGTAGTC GGCATCGCGG TCGCCGTGGC TGCTCCTGGA

·  G  F  P     P  Q  S  C     G  W  A     S  V  T     T  V  S     N  T  N  Y     K  V  V     P  H  S  V     H  L  E     P  Y  G
 401 GGGCTTCCCA CCCCAGAGCT GCGGCTGGGC CAGCGTGACC ACCGTGAGCA ACACCAACTA CAAGGTGGTG CCCCACAGCG TGCACCTGGA ACCCTACGGC
     CCCGAAGGGT GGGGTCTCGA CGCCGACCCG GTCGCACTGG TGGCACTCGT TGTGGTTGAT GTTCCACCAC GGGGTGTCGC ACGTGGACCT TGGGATGCCG
```

FIG. 12B

. G H W I D H D    F N G  G E C R  E K V  C E M  K G N H  S I W  I T D  E T V Q .
    501   GGCCACTGGA TCGACCACGA CTTCAACGGC GGGAGTGCC GGGAGAAAGT GTGCGAGATG AAGGCAACC ACAGCATCTG GATCACCGAC GAGACAGTGC
          CCGGTGACCT AGCTGGTGCT GAAGTTGCCG CCCTCACGG CCCTCTTTCA TTCCGTTGG TGTCGTAGAC CTAGTGGCTG CTCTGTCACG

. H E C E K H    I E E V  E G I  M Y G  N A P R  G D A  I Y I  N N F I I D K .
    601   AGCAGAGTGC CGAAGAGCAC ATCGAGGAAG TGGAGGGCAT CATGTACGGC AACCCCCGA GGGGCCACGC CATCTACATC AACAACTTCA TCATCGACAA
          TCGTCTCACG GCTTCCTCGTG TAGCTCCTTC ACTCCCGTA GTACATGCCG TTGCGGGGCT CCCCGGTGCG GTAGATGTAG TTGTTGAAGT AGTAGCTGTT

. H H R V Y R F    G G S  C R M  K F C N  K D G  I K F  T R G D  W V E K T A
    701   GCACCACCGG GTGTACCGG TTCGGGAGCTC CGTCCGGATG AAGTTCTGCA ACAAGGACGG CATCAAGTTC ACCAGAGGCG ACTGGGTGGA GAAAACCGCC
          CGTGGTGGCC CACATGGCCA AGCCCGAGAG GCAGGCCTAC TTCAAGACGT TGTTCCTGCC GTAGTTCAAG TGGTCTCCGC TGACCCACCT CTTTTGGCGG

. G T L T N I Y    E N I  P E C A  D G T  L V S  G H R P  G L D  L I D  T V F N .
    801   GGCACCCTGA CCAACATCTA CGAGAACATC CCGGAGTGCG CCGACGGCAC ACTGGTGTCC GGCCACAGAC CCGGCCTGGA CCTGATCGAC ACCGTGTTCA
          CCGTGGGACT GGTTGTAGAT GCTCTTGTAG GGCCTCACGC GGCTGCCGTG TGACCACAGG CCGGTGTCTG GGCCGGACCT GGACTACTG TGGCACAAGT

. L E N V V E    Y T L C  E G T  K R K  I N K Q  E K L  T S V  D L S Y L A P .
    901   ACCTGGAAAA CGTGGTGGAG TACACCCTGT GCGAGGGCAC CAAGCGGAAG ATCAACAAGC AGGAAAAGCT GACCAGCGTC GACCTGAGCT ACCTGGCCCC
          TGGACCTTTT GCACCACCTC ATGTGGGACA CGCTCCCGTG GTTCGCCTTC TAGTTGTTCG TCCTTTTCGA CTGGTCGCAG CTGGACTCGA TGGACCGGGG

. R I G G F G S    V F R  V R N  G T L E  R G S  T T Y  I R I E  V E G  P V V
    1001  CAGGATCGGC GGCTTCGGCA GCGTGTTCCG CGTTGGGAAT GGCACCCTGG AAAGGAGGAAG CACCACATAC ATTCGGATCG AAGTGGAAGG CCCCGTGGTG
          GTCCTAGCCG CCGAAGCCGT CGCACAAGGC GCACGCCTTA CCGTGGGACC TTTCTCCTTC GTGGTGTATG TAAGCCTAGC TTCACCTTCC GGGGCACCAC

*FIG. 12B*
                              *(CONTINUED-1)*

```
             D  S  L  N   G  I  D    P  R  T   N  A  S  R   V  F  W   D  D  W   E  L  D  G   N  I  Y    Q  G  F   N  G  V  Y  .
1101  GACAGCCTGA ACGGATCGA CCCCGGACC AACGCCAGCC GGGTGTTCTG GACGACTGG GAGCTGGACG GCAACATCTA CCAGGGCTTC AATGGGGTGT
      CTGTCCGACT TGCCCTAGCT GGGGGCCTGG TTGCGGTCGG CCCACAAGAC CTGCTGACC CTCGACCTGC CGTTGTAGAT GGTCCCGAAG TTACCCACA

.  K  G  K    D  G  K    I  H  I  P   L  N  M   I  E  S    G  I  I  D    D  E  L    Q  H  A    F  Q  A  D   I  I  P  .
1201  ACAAGGGCAA GGATGGCAAG ATCCACATCC CCCTGAACAT GATCGAGAGC GGCATCATCG ACGACGAGCT GCAGCACGCC TTCCAGGCCG ACATCATCCC
      TGTTCCCGTT CCTACCGTTC TAGGTGTAGG GGGACTTGTA CTAGCTCTCG CCGTAGTAGC CTGCTGCTCGA CGTCGTGCGG AAGGTCCGGC TGTAGTAGGG

.  H  P  H    Y  D  D  D    E  I  R    E  D  D    I  F  F  D   N  T  G    E  N  G    N  P  V  D    A  V  V   E  W  V
1301  CCACCCCCAC TACGACGACG AGGAGATCCG GGAGGACGAC ATCTTCTTCG ACAACACCGG CGAGAACGGC AACCCCGTGG ACGCCGTGGT GGAATGGGTG
      GGTGGGGGTG ATGCTGCTGC TCCTCTAGGC CCTCCTGCTG TAGAAGAAGC GCTGTTGTGGCC GCTCTTGCCG TTGGGCACC TGCGGCACCA CCTTACCCAC

S  G  W  G   T  S  L    K  F  F    G  M  T  L    V  A  L    I  L  I    F  L  L  I   R  C  C    V  A  C    T  Y  L  M  .
1401  TCCGGATGGG GCACCAGCCT GAAGTTCTTC GGCATGACCC TGGTGGCCCT GATCCTGATC TTCCTGCTGA TCCGCTGCTG CGTGGCCTGC ACCTACCTGA
      AGGCCTACCC CGTGGTCGGA CTTCAAGAAG CCGTACTGGG ACCACCGGGA CTAGGACTAG AAGGACGACT AGGCGACGAC GCACCGGACG TGGATGGACT

EcoRI
             .  K  K  S    K  R  P    A  T  E  S    H  E  M    R  S  L   V  *  *
1501  TGAAGAAGAG CAAGAGGCCC GCCACCGAGA GCCACGAGAT GGGGAGCCTG GTGTGATGAG AATTCTTAAT TAA
      ACTTCTTCTC GTTCTCCGGG CGGTGGCTCT CGGTGCTCTA CCCCTCGGAC CACACTACTC TTAAGAATTA ATT
```

FIG. 12B (CONTINUED-2)

C.

Plasmid map: pThV-VSV.G (SVCV-CO), 5141 bp

Features labeled:
- EcoRI (1)
- NotI (28)
- XhoI (34)
- WPRE∆ATG
- XhoI (644)
- XbaI (650)
- BGH pA
- KanR
- NcoI (1644)
- pUC ORI
- NdeI (3146)
- NcoI (3272)
- CMV
- NheI (3557)
- HindIII (3573)
- KpnI (3583)
- BamHI (3591)
- NcoI (3760)
- VSV.G SVCV-CO
- BspEI (4983)

FIG. 12C

1 -    Indiana PCR fragment

VSV-G$_{Indiana}$ sequence (optimized codons)
   BamH1
5'CTC GGATCC TGATCAGCCACCATGAAATGCCTGCTCTATCTGGCCTTCCTCTTTATCGGCGTGAACTGTAAGTTCACGATC
GTGTTTCCCCACAATCAGAAGGGAAACTGGAAGAACGTCCCGAGCAACTACCACTACTGCCCTAGCTCAAGCGACCTGAACTG
GCACAACGACCTGATCGGCACCGCTATCCAGGTGAAGATGCCAAAGAGCCACAAGGCCATCCAAGCCGACGGCTGGATGTGTC
ACGCCAGCAAATGGGTGACGACGTGCGATTTTCGCTGGTATGGCCCCAAGTACATCACCCAATCAATCCGCTCATTTACACCC
AGCGTGGAGCAATGTAAGGAGAGCATCGAGCAGACCAAGCAGGGGACCTGGCTCAACCCCGGCTTCCCACCGCAAAGCTGCGG
ATACGCCACCGTGACCGACGCTGAGGCCGTCATCGTGCAGGTGACCCCGCACCACGTGCTGGTGGACGAGTACACCGGCGAGT
GGGTGGATTCACAGTTTATCAACGGAAAGTGTAGCAATTACATCTGCCCCACCGTGCACAACAGCACCACCTGGCACTCAGAC
TATAAGGTGAAGGGCCTCTGCGACAGCAATCTGATCTCAATGGACATCACCTTCTTTAGCGAAGACGGCGAACTCTCAAGCCT
CGGGAAGGAAGGCACCGGGTTCCGCAGCAATTACTTTGCTTACGAAACCGGCGGCAAGGCCTGCAAGATGCAATACTGCAAGC
ACTGGGGCGTGCGCCTGCCAAGCGGCGTGTGGTTTGAGATGGCTGATAAGGACCTGTTCGCCGCTGCCCGCTTCCCGGAATGC
CCCGAGGGGAGCAGCATCAGCGCCCCAGCCAGACATCAGTGGACGTGAGCCTGATCCAGGATGTGGAACGCATCCTGGACTA
CAGCCTGTGTCAGGAAACGTGGAGCAAGATCCGCGCCGGACTGCCTATCAGCCCCGTGGATCTCAGCTACCTGGCCCCAAAGA
ACCCAGGCACCGGACCCGCCTTTACAATCATCAACGGCACCCTGAAGTACTTTGAAACACGCTACATCCGCGTCGACATCGCC
GCTCCCATCCTCTCACGCATGGTGGGCATGATCTCAGGGACGACCACGGAGCGCGAGCTGTGGGATGACTGGGCCCCGTATGA
AGATGTGGAGATCGGACCTAACGGCGTGCTGCGCACATCAAGCGGGTACAAGTTCCCGCTGTACATGATCGGCCACGGCATGC
TGGACAGCGACCTGCACCTCAGCTCAAAGGCCCAGGTCTTTGAGCACCCACACATCCAGGACGCTGCCAGCCAGCTCCCCGAC
GACGAAAGCCTGTTCTTTGGAGATACAGGGCTCAGCAAGAACCCCATCGAGCTGGTCGAGGGCTGGTTCTCAAGCTGGAAG**AG
CAGCATCGCTTCATTTTTTTTTCATCATCGGCCTCATCATCGGGCTGTTTCTGGTGC**TGCGCGTCGGCATCCACCTGTGCATCA
AGCTGAAGCACACCAAGAAGCGCCAGATCTATACCGACATCGAGATGAATCGCCTGGGGAAGTAA GAATTC GCAGATATCCA
GCA-3' (SEQ ID NO: 45)                                                          EcoR1

Oligonucleotides Indiana
-    1 (5'-AGCAGCATCGCTTCATTTTTTTTTCATCATCGG-3') (SEQ ID NO:46)
-    2 (5'-GCTGGATATCTGCAGAATTCTTACTTCCCCAGGCG-3') (SEQ ID NO:47)

*FIG. 13A*

PCR fragment (160bp):
    Indiana Transmembrane Domain
5'AGCAGCATCGCTTCATTTTTTTTTCATCATCGGCCTCATCATCGGGCTGTTTCTGGTGCTGCGCGTCGGCATCCACCTGTGC
ATCAAGCTGAAGCACACCAAGAAGCGCCAGATCTATACCGACATCGAGATGAATCGCCTGGGGAAG<u>TAA</u>GAATTCTGCA3'
(SEQ ID NO:48)
    2.  NewJersey PCR fragment VSV-G<sub>NewJersey</sub> sequence (optimized codons)
        BamH1
5' TACCGAGCTCGGATCCTGATCAGCCACCATGCTGTCATATCTGATCTTTGCCCTGGCTGTGAGCCCAATCCTCGGAAAGAT
CGAAATCGTGTTCCCACAACACACCACAGGGGACTGGAAGCGCGTGCCCCACGAGTACAACTACTGCCCGACCTCAGCCGACA
AGAATAGCCACGGCACGCAGACCGGCATCCCTGTGGAGCTGACCATGCCCAAGGGGCTCACAACGCACCAAGTCGAAGGCTTC
ATGTGCCACAGCGCTCTCTGGATGACZAACCTGCGATTTTCGCTGGTATGGCCCCAAGTACATCACGCACAGCATCCACAATGA
GGAACCAACCGACTACCAGTGCCTCGAAGCCATCAAGTCATACAAGGATGGGGTGAGCTTCAACCCCGGCTTCCCGCCCCAAT
CATGTGGCTACGGCACCGTGACCGACGCCGAGGCCCACATCGTGACCGTGACACCCCACTCAGTCAAGGTGGACGAGTACACA
GGCGAATGGATCGACCCCCACTTCATCGGGGCCGCTGTAAGGGCCAAATCTGCGAGACCGTGCACAACAGCACCAAGTGGTT
TACGTCATCAGACGGCGAAAGCGTGTGCAGCCAACTGTTTACGCTCGTGGGCGGCATCTTCTTTAGCGACAGCGAGGAGATCA
CCAGCATGGGCCTCCCGGAGACAGGAATCCGCAGCAACTACTTTCCGTACATCAGCACCGAGGGAATCTGTAAGATGCCTTTT
TGCCGCAAGCAGGGATATAAGCTGAAGAATGACCTGTGGTTCCAGATCATGGACCCGGACCTGGACAAGACCGTCCGCGATCT
GCCCCACATCAAGGACTGTGATCTGTCATCAAGCATCATCACCCCCGGAGAACACGCCACGGACATCAGCCTCATCAGCGATG
TGGAGCGCATCCTCGACTACGCTCTCTGCCAGAACACATGGAGCAAGATCGAAAGCGGCGAACCCATCACCCCAGTGGACCTG
AGCTATCTCGGCCCAAAGAACCCCGGCGTGGGGCCCGTGTTCACCATCATCAACGGGAGCCTGCACTACTTTACAAGCAAGTA
TCTGCGCGTGGAGCTCGAAAGCCCAGTCATCCCCCGCATGGAGGGGAAGGTGGCCGGGACCCGCATCGTGCGCCAGCTGTGGG
ACCAGTGGTTCCCTTTTGGCGAGGTGGAAATCGGCCCCAACGGCGTGCTGAAGACCAAGCAAGGATATAAGTTCCCGCTGCAC
ATCATCGGGACGGGCGAAGTGGACAGCGATATCAAGATGGAGCGCGTGGTCAAGCACTGGGAGCACCCACACATCGAGGCTGC
TCAGACCTTTCTCAAGAAGGACGATACCGGCGAAGTCCTGTATTACGGGGATACGGGAGTGAGCAAGAACCCTGTGGAGCTGG
TGGAAGGCTGGTTCAGCGGATGGCGC**TCAAGCCTGATGGGCGTGCTGGCCGTCATCATCGGATTTGTGATCCTGATGTTCCTC
AT**CAAGCTGATCGGCGTGCTGTCAAGCCTGTTCCGCCCTAAGCGCCGCCCAATCTACAAGAGCGACGTCGAGATGGCCCACTT
TCGC<u>TAA</u>AATTCTGCAGATAT-3' (SEQ ID NO:49)
    EcoR1

*FIG. 13A*
*(CONTINUED)*

Oligonucleotides NewJersey:
- 3 (5'-CGAGCTCGGATCCTGATCAGCCACCATGCTGTC-3') (SEQ ID NO:50)
- 4 (5'-GAAAAAAAATGAAGCGATGCTGCTGCGCCATCCGCTGAACCAGCCTTCCAC-3'). (SEQ ID NO:51)

The bold and underlined part of oligo 4 corresponds to the 28 first
Indiana transmembrane domain nucleotides.

PCR NewJersey (1446bp):

```
        BamH1
5' CGAGCTCGGATCCTGATCAGCCACCATGCTGTCATATCTGATCTTTGCCCTGGCTGTGAGCCCAATCCTCGGAAAGATCGA
AATCGTGTTCCCACAACACACCACAGGGGACTGGAAGCGCGTGCCCCACGAGTACAACTACTGCCCGACCTCAGCCGACAAGA
ATAGCCACGGCACGCAGACCGGCATCCCTGTGGAGCTGACCATGCCCAAGGGGCTCACAACGCACCAAGTCGAAGGCTTCATG
TGCCACAGCGCTCTCTGGATGACAACCTGCGATTTTCGCTGGTATGGCCCCAAGTACATCACGCACAGCATCCACAATGAGGA
ACCAACCGACTACCAGTGCCTCGAAGCCATCAAGTCATACAAGGATGGGGTGAGCTTCAACCCCGGCTTCCCGCCCCAATCAT
GTGGCTACGGCACCGTGACCGACGCCGAGGCCCACATCGTGACCGTGACACCCCACTCAGTCAAGGTGGACGAGTACACAGGC
GAATGGATCGACCCCCACTTCATCGGGGCCGCTGTAAGGGCCAAATCTGCGAGACCGTGCACAACAGCACCAAGTGGTTTAC
GTCATCAGACGGCGAAAGCGTGTGCAGCCAACTGTTTACGCTCGTGGGCGGCATCTTCTTTAGCGACAGCGAGGAGATCACCA
GCATGGGCCTCCCGGAGACAGGAATCCGCAGCAACTACTTTCCGTACATCAGCACCGAGGGAATCTGTAAGATGCCTTTTTGC
CGCAAGCAGGGATATAAGCTGAAGAATGACCTGTGGTTCCAGATCATGGACCCGGACCTGGACAAGACCGTCCGCGATCTGCC
CCACATCAAGGACTGTGATCTGTCATCAAGCATCATCACCCCCGGAGAACACGCCACGGACATCAGCCTCATCAGCGATGTGG
AGCGCATCCTCGACTACGCTCTCTGCCAGAACACATGGAGCAAGATCGAAAGCGGCGAACCCATCACCCCAGTGGACCTGAGC
TATCTCGGCCCAAAGAACCCCGGCGTGGGGCCCGTGTTCACCATCATCAACGGGAGCCTGCACTACTTTACAAGCAAGTATCT
GCGCGTGGAGCTCGAAAGCCCAGTCATCCCCCGCATGGAGGGGAAGGTGGCCGGGACCCGCATCGTGCGCCAGCTGTGGGACC
AGTGGTTCCCTTTTGGCGAGGTGGAAATCGGCCCCAACGCGCTGCTGAAGACCAAGCAAGGATATAAGTTCCCGCTGCACATC
ATCGGGACGGGCGAAGTGGACAGCGATATCAAGATGGAGCGCGTGGTCAAGCACTGGGAGCACCCACACATCGAGGCTGCTCA
GACCTTTCTCAAGAAGGACGATACCGGCGAAGTCCTGTATTACGGGGATACGGGAGTGAGCAAGAACCCTGTGGAGCTGGTGG
AAGGCTGGTTCAGCGGATGGCGCAGCAGCATCGCTTCATTTTTTTTC-3' (SEQ ID NO:52)
                        Indiana TransMembrane domain
```

FIG. 13B

3. Overlapping PCR (1620bp)

PCR with oligonucleotides 2 and 3

Oligo 3
BamH1

5'GAGCTCGGATCCTGATCAGCCACCATGCTGTCATATCTGATCTTTGCCCTGGCTGTGAGCCCAATCCTCGGAAAGATCGAA
ATCGTGTTCCCACAACACACCACAGGGGACTGGAAGCGCGTGCCCCACGAGTACAACTACTGCCCGACCTCAGCCGACAAGAA
TAGCCACGGCACGCAGACCGGCATCCCTGTGGAGCTGACCATGCCCAAGGGGCTCACAACGCACCAAGTCGAAGGCTTCATGT
GCCACAGCGCTCTCTGGATGACAACCTGCGATTTTCGCTGGTATGGCCCCAAGTACATCACGCACAGCATCCACAATGAGGAA
CCAACCGACTACCAGTGCCTCGAAGCCATCAAGTCATACAAGGATGGGGTGAGCTTCAACCCCGGCTTCCCGCCCCAATCATG
TGGCTACGGCACCGTGACCGACGCCGAGGCCCACATCGTGACCGTGACACCCCACTCAGTCAAGGTGGACGAGTACACAGGCG
AATGGATCGACCCCCACTTCATCGGGGGCCGCTGTAAGGGCAAATCTGCGAGACCGTGCACAACAGCACCAAGTGGTTTACG
TCATCAGACGGCGAAAGCGTGTGCAGCCAACTGTTTACGCTCGTGGGCGGCATCTTCTTTAGCGACAGCGAGGAGATCACCAG
CATGGGCCTCCCCGGAGACAGGAATCCGCAGCAACTACTTTCCGTACATCAGCACCGAGGGAATCTGTAAGATGCCTTTTTGCC
GCAAGCAGGGATATAAGCTGAAGAATGACCTGTGGTTCCAGATCATGGACCCGGACCTGGACAAGACCGTCCGCGATCTGCCC
CACATCAAGGACTGTGATCTGTCATCAAGCATCATCACCCCCGGAGAACACGCCACGGACATCAGCCTCATCAGCGATGTGGA
GCGCATCCTCGACTACGCTCTCTGCCAGAACACATGGAGCAAGATCGAAAGCGGCGAACCCATCACCCCAGTGGACCTGAGCT
ATCTCGGCCCAAAGAACCCCGGCGTGGGGCCCGTGTTCACCATCATCAACGGGAGCCTGCACTACTTTACAAGCAAGTATCTG
CGCGTGGAGCTCGAAAGCCCAGTCATCCCCCGCATGGAGGGGAAGGTGGCCGGGACCCGCATCGTGCGCCAGCTGTGGGACCA
GTGGTTCCCTTTTGGCGAGGTGGAAATCGGCCCCAACGGCGTGCTGAAGACCAAGCAAGGATATAAGTTCCCGCTGCACATCA
TCGGGACGGGCGAAGTGGACAGCGATATCAAGATGGAGCGCGTGGTCAAGCACTGGGAGCACCCACACATCGAGGCTGCTCAG
ACCTTTCTCAAGAAGGACGATACCGGCGAAGTCCTGTATTACGGGGATACGGGAGTGAGCAAGAACCCTGTGGAGCTGGTGGA
AGGCTGGTTCAGCGGATGGCGCAGCAGCATCGCTTCATTTTTTTTTC
                                 AGCAGCATCGCTTCATTTTTTTTTCATCATCGGCCTCATCATCGGGCTGTTTCTGGTGCTG
CGCGTCGGCATCCACCTGTGCATCAAGCTGAAGCACACCAAGAAGCGCCAGATCTATACCGACATCGAGATGAAATCGCCTGGG
GAAGTAAGAATTCTGCA-3'  (SEQ ID NO:53)
       EcoR1
OLIGO 2

```
       M  N  F  L  L  T  F  I  V  L     P  L  C  S     H  A  K  F  S  I     V  F  P  Q  S  Q  K     G  N  W
3601   ATG AACTTCTGC TCCTGACATT CATGTGTGTG CCTCTGTGCA GCCACGCCAA GTTCAGCATC GTGTTCCCCC AGAGCCAGAA GGGCAACTGG
       TAC TTGAAGACG AGGACTGTAA GTACACACAC GGAGACACGT CGGTGCGGTT CAAGTCGTAG CACAAGGGGG TCTCGGTCTT CCCGTTGACC

K  N  V  P  S  S  Y     H  Y  C     P  S  S  S     D  Q  N     W  H  N     D  L  L  G     I  T  M     K  V  K     M  P  K  T
3701   AAGAACGTGCC CCAGCAGCTA CCACTACTGC CCCAGCAGCA GCCAACCAGAA CTGGCACAAC GACCTGCTGG GCATCACCAT GAAGGTGAAA ATGCCCAAGA
       TTCTTGCACG GGTCGTCGAT GGTGATGACG GGGTCGTCGT CGGTTGGTCT GACCGTGTTG CTGGACGACC CGTAGTGGTA CTTCCACTTT TACGGGTTCT

.  H  K  A     I  Q  A     D  G  W     M  C  H  A     A  K  W     I  T  C     D  F  R     W  Y  G     P  K  Y  I  T  H  S
3801   CCCAGAAGGC CATTCAGGCT GACGGCTGGA TGTGCCACGC CGCCAAGTGG ATCACCACCT GGGACTTCGG GTGGTACGGC CCCAAGTACA TCACCCACAG
       GGGTCTTCCG GTAAGTCCGA CTGCCGACCT ACACGGTGCG GCGGTTCACC TAGTGGTGGA CCCTGAAGCC CACCATGCCG GGGTTCATGT AGTGGGTGTC

.  I  H  S     I  Q  P  T     S  E  Q     C  K  E     S  I  K  Q     T  K  Q     G  T  W     M  S  P  G     F  P  P     Q  N  C
3901   CATCCACTCC ATCCAGCCCA CCTCCGAGCA GTGCAAAGAG AGCATCAAGC AGACCAAGCA GGGCACCTGG ATGAGCCCCG GCTTCCCACC CCAGAACTGC
       GTAGGTGAGG TAGGTCGGGT GGAGGCTCGT CACGTTTCTC TCGTAGTTCG TCTGGTTCGT CCCGTGGACC TACTCGGGGC CGAAGGGTGG GGTCTTGACG

G  Y  A  T  V  T  D     S  V  A     V  V  V  Q     A  T  P     H  H  V     L  V  D  E  Y  T  G     E  W  I     D  S  Q  F
4001   GGCTACGCCA CCGTGACCGA CAGCGTGGCT GTGGTGGTGC AGGCCACGCC CCACCACGTG CTGGTCGACG AGTACACCGG CGAGTGGATC GACAGCCAGT
       CCGATGCGGT GGCACTGGCT GTCGCACCGA CACCACCACG TCCGGTGCGG GGTGGTGCAC GACCAGCTGC TCATGTGGCC GCTCACCTAG CTGTCGGTCA

.  P  N  G     K  C  E     T  E  E  C     E  T  V     H  N  S     T  V  W  Y     S  D  Y     K  V  T     G  L  C  D     A  T  L
4101   TCCCCAACGG CAAGTGCGAG ACAGAAGAGT GCGAGACAGT CCACAACAGC ACCGTGTGGT ACAGCGACTA CAAGGTGACC GGCCTGTGCG ACGCCACCCT
       AGGGGTTGCC GTTCACGCTC TGTCTTCTCA CGCTCTGTCA GGTGTTGTCG TGGCACACCA TGTCGCTGAT GTTCCACTGG CCGGACACGC TGCGGTGGGA

.  V  D  T     E  I  T  F     F  S  E     D  G  K     K  E  S  I     G  K  P     N  T  G     Y  R  S  N     Y  F  A     Y  E  K
4201   GGTTGACACC GAGATCACCT TTTTCAGCGA GGACGGCAAG AAAGAGTCCA TCGGCAAGCC CAACACCGGC TACAGAAGCA ACTACTTCGC CTACGAGAAG
       CCAACCTGTGG CTCTAGTGGA AAAAGTCGCT CCTGCCGTTC TTTCTCAGGT AGCCGTTCGG GTTGTGGCCG ATGTCTTCGT TGATGAAGCG GATGCTCTTC

G  D  K  V     C  K  M     N  Y  C     K  H  A  G     V  R  L     P  S  G     V  W  F  E     F  V  D     Q  D  V     Y  A  A  A
4301   GGGGACAAAG TGTGCAAGAT GAACTACTGC AAGCATGCCG GAGTCAGGCT GCCTAGCGGC GTGTGGTTCG AGTTCGTGGA CCAGGACGTG TACGCCGCCG
       CCCCTGTTTC ACACGTTCTA CTTGATGACG TTCGTACGGC CTCAGTCCGA CGGATCGCCG CACACCAAGC TCAAGCACCT GGTCCTGCAC ATGCGGCGGC

.  K  L  P     E  C  P     V  G  A  T     I  S  A     P  T  Q     T  S  V  D     V  S  L     I  L  D     V  E  R  I  L  D  Y
4401   CCAAGCTGCC CGAGTGCCCC GTGGGAGCCA CCATCAGCGC CCCGACCCAG ACCAGCGTGG ACGTGAGCCT GATCCTGGAC GTGGAGAGAA TCCTGGACTA
       GGTTCGACGG GCTCACGGGG CACCCTCGGT GGTAGTCGCG GGGCTGGGTC TGGTCGCACC TGCACTCGGA CTAGGACCTG CACCTCTCTT AGGACCTGAT
```

pThV-VSV.G (COCAL/IND)CO
5147bp

- EcoRI (1)
- BglII (5107)
- NotI (28)
- BspEI (4651)
- XhoI (34)
- WPRE/ΔATG
- XhoI (644)
- XbaI (650)
- VSV.G COCAL/INDIANA CO
- BstEII (4175)
- BGH pA
- KanR
- NcoI (1644)
- BamHI (3591)
- KpnI (3583)
- HindIII (3573)
- NheI (3557)
- CMV
- NcoI (3272)
- NdeI (3146)
- pUC ORI

*FIG. 15C*

A.

```
             M   T   D   T   V   I   L   G   K   F   Q   I   V   F   P   D   Q   N   E   L   E   W   T   P   V   V   G   D   S   R   H   C
3601         ATG ACC GAT ACA GTG CTG GGC AAG TTC CAG ATC GTG TTC CCC GAC CAG AAC GAA CTG GAA TGG ACC CCC GTG GTG GGC GAC AGC CGG CAT TGC
             TAC TGG CTA TGT CAC GAC CCG TTC AAG GTC TAG CAC AAG GGG CTG TCT TGC TTG ACC TTA CCT GGG GCA CCA CCG CTG TCG GCC GTA ACG

P   Q   S   E   M   Q   F   D   G   S   R   S   Q   T   I   L   T   G   K   A   P   V   G   I   T   P   S   K   S   D   G   F   I
3701         CCT CAG TCA GCG GAG ATG CAG TTC GAC GGC AGC AGA AGC CAG AGA CCA TCC TGA CCG GCA AGG CCC CGT GGG CAT CAC ACC AGC AAG AGC GAC GGC TTC A
             GGA GTC AGT CGC CTC TAC GTC AAG CTG CCG TCG TCT TCG GTC TCT GGT AGG ACT GGC CGT TCC GGG GCA CCC GTA GTG TGG TCG TTC TCG CTG CCG AAG T

. C  H   A   A   K   W   V   T   T   C   D   F   R   W   Y   G   P   K   Y   I   T   H   S   I   H   H   L   R   P   T   T   S   D
3801         TCT GCC ACG CGC CAA GTG GGT GAC CAC CTG CGA CTT CCG GTG GTA CGG CCC AAG TAC ATC ACC CAC AGC ATC CAC CAC CTG CGG CCC CAC CTC CGA
             AGA CGG TGC GCG GTT CAC CCA CTG GTG GAC GCT GAA GGC CAC CAT GCC GGG TTC ATG TAG TGG GTG TCG TAG GTG GTG GAC GCC GGG TGG AGG CT

. C  E   T   A   L   Q   R   Y   K   D   G   S   L   I   N   L   G   F   P   P   E   S   C   G   Y   A   T   V   T   D   S   E   A
3901         CTG CGA GAC AGC CCT GCA GCG GTA CAA GGA CGG CAG CCT GAT CAA CCT GGG CTT CCC TCC GAG AGC TGC GGC TAC GCC ACC GTG ACC GAC AGC GAG GCC
             GAC GCT CTG TCG GGA CGT CGC CAT GTT CCT GCC GTC GGA CTA GTT GGA CCC GAA GGG AGG CTC TCG ACG CCG ATG CGG TGG CAC TGG CTG TCG CTC CGG

M   L   V   Q   V   T   P   H   H   V   G   V   D   D   Y   R   G   D   P   L   F   P   G   G   E   C   S   T   N   F   C
4001         ATG CTG GTG CAG GTG ACC CCA CCA CCA CAC CAC GTG GGG GTG GAC GAC TAC CGG GGC GAC CCC CTG TTC CCT GCC GGG GAG TGC AGC ACC AAT TTC T
             TAC GAC CAC GTC CAC TGG GGT GGT GGT GTG GTG CAC CCC CAC CTG CTG ATG GCC CCG CTG GGG GAC AAG GGA CGG CCC CTC ACG TCG TGT TAA AGA

. D  T   V   H   N   S   S   V   N   I   P   K   S   D   I   C   A   Q   S   F   K   N   I   K   M   T   A   S   Y   P
4101         GCA CTA CCG TCC ACA ACA GCA GCG TGA ACA TCC CCA AGA GCG ACA TCT GCG CCC AGA GCT TCA AGA ACA TCA AGA TGA CCG CAG CTA CCC
             CGT CAT GGC AGG TGT GTC GTC GCA CTT GTG AGG GGT TCT CGC TGT AGA CGC GGG TCT CGA AGT TCT TGT AGT TCT ACT GGC GTC GAT GGG

. S  E   G   A   L   V   S   D   R   F   A   F   H   S   A   Y   H   P   N   M   P   G   S   T   V   C   I   M   D   F   C   E   Q
4201         CAG GAG GGA GCC CTG GTG TCT GAC CGG TTC GCC TTC CAC AGC GCC TAC CAT CCC AAC ATG CCC GGC AGC ACC GTG TGC ATC ATG GAT TTC TGC GAG CAG
             GTC CTC CCT CGG GAC CAC AGA CTG GCC AAG CGG AAG GTG TCG CGG ATG GTA GGG TTG TAC GGG CCG TCG TGG CAC ACG TAG TAC TAA CCT AAA GAC GCT CGT C

K   G   L   R   F   T   N   G   E   W   M   G   L   N   V   E   Q   E   K   K   I   S   A   I   F   P   N   C   V   A   G
4301         AAG GGC CTG CGG TTC ACC AAC GGG GAG TGG ATG GGC CTG AAC GTG GAG CAG GAG AAG AAG ATC TCA GGC GCC ATC TTC CCC AAC TGC GTG GCC GG
             TTC CCG GAC GCC AAG TGG TTG CCC CTC ACC TAC CCG GAC TTG CAC CTC GTC CTC TTC TTC TAG AGT CCG CGG TAG AAG GGG TTG ACG CAC CGG CC

. T  E   I   R   A   T   L   E   S   E   G   A   R   T   L   T   W   E   T   Q   R   M   L   D   Y   S   L   C   Q   N   T   W   D
4401         GCA CCG AGA TCC GGG CCA CCC TGG AAT CCG AGG GCG CCC GCA CCC TCA CCT GGG AGA CCC AGC GGA TGC TGG ACT ACA GCC TGT GCC AGA ACA CCT GGG AC
             CGT GGC TCT AGG CCC GGT GGG ACC TTA GGC TCC CGC GGG CGT GGG AGT GGA CCC TCT GGG TCG CCT ACG ACC TGA TGT CGG ACA CGG TCT TGT GGA CCC T
```

FIG. 16A

```
                  · K  V  S     R  K  E  P     L  S  P     L  D  L     S  Y  L  S     P  R  A     P  G  K     G  M  A  Y     T  V  I  N  G  T
4501  CAAGGTGTCC CGGAAAGAGC CTCTGTCCCC CCTTGGACCTG AGCTACCTGA GCCCTAGAGC CCCTGCCAAG CCCTACCGGA GGCATGGCCT ACACCGTCAT CAACGGCACC
      GTTCCACAGG GCCTTTCTCG GAGACAGGGG GGAACCTGGAC TCGATGGACT CGGGATCTCG GGGACGGTTC CGGTACCGGA TGTGGCAGTA GTTGCCGTGG

L  H  S  A     H  A  K     Y  I  R     T  W  I  D     Y  G  E     M  K  E     I  K  G  G     R  G  E     Y  S  K     A  P  E  L ·
4601  CTGCACAGCG CCCACGCCAA GTATATCCGG ACCTGGATCG ACTACGGCGA GATGAAAGAG ATCAAGGGCG GCAGGGGCGA GTACAGCAAG GCCCCTGAGC
      GACGTGTCGC GGGTGCGGTT CATATAGGCC TGGACCTAGC TGATGCCGCT CTACTTTCTC TAGTTCCCGC CGTCCCCGCT CATGTCGTTC CGGGACTCG

· L  W  S     Q  W  F     D  F  G  P     F  K  I     G  P  N     G  L  L  H     T  G  K     T  F  K     F  P  L  Y     L  I  G
4701  TGCTGTGGAG CCAGTGGTTC GACTTCGGCC CCTTCAAGAT CGGCCCCAAC GGCCTGCTGC ACACCGGCAA GACCTTCAAG TTCCCTCTGT ATCTGATCGG
      ACGACACCTC GGTCACCAAG CTGAAGCCGG GGAAGTTCTA GCCGGGGTTG CCGGACGACG TGTGGCCGTT CTGGAAGTTC AAGGGAGACA TAGACTAGCC

· A  G  I     I  D  E  D     L  H  E     A  A  P  I     D  H  P     Q  M  P     D  A  K  S     V  L  P     E  D  E
4801  AGCCGGCATC ATCGACGAGA ACCTGCACGA GCTGCACACA GCCGCCCCTA TCGACCACCC CCAGATGCCC GACGCCAAGA GCGTGCTGCC CGAGGACGAG
      TCGGCCGTAG TAGCTGCTCT TGGACGTGCT CGACGTGTGT CGGCGGGGAT AGCTGGTGGG GGTCTACGGG CTGCGGTTCT CGCACGACGG GCTCCTGCTC

E  I  F  F     G  D  T     G  V  S     K  N  P  I     E  L  I     Q  G  W     F  S  N  W     R  S  S     I  A  S     F  F  F  I
4901  GAAATCTTCT TCGGCGACAC CGGCGTGTCG AAGAACCCCA TCGAGCTGAT CCAGGGCTGG TTCAGCAACT GGCGGAGCAG CATCGCCTCC TTTTTTTTCA
      CTTTAGAAGA AGCCGCTGTG GCCGCACAGC TTCTTGGGGT AGCTCGACTA GGTCCCGACC AAGTCGTTGA CCGCCTCGTC GTAGCGGAGT AAAAAAAAGT

· I  G  L     I  G     L  F  L  V     L  R  V     G  I  H     L  C  I  K     L  K  H     T  K  K     R  Q  I  Y     T  D  I
5001  TCATCGGCCT CATCATCGGG CTGTTTCTGG TGCTGCGGGT CGGCATCCAC CTGTGTATCA AGCTGAAGCA CACCAAGAAG CGGCAGATCT ATACCGACAT
      AGTAGCCGGA GTAGTAGCCC GACAAAGACC ACGACGCCCA GCCGTAGGTG GACACATAGT TCGACTTCGT GTGGTTCTTC GCCGTCTAGA TATGGCTGTA

· E  M  N     R  L  G  K     *
5101  CGAGATGAAT CGGCTGGGGA AGTAA
      GCTCTACTTA GCCGACCCCT TCATT
```

*FIG. 16B*

A.

```
              M   T   S   V   L   F   M   V       G   V   L       L   G   A   F   G   S   T       H   C   S       I   Q   I   V   F   P   S       E   T   K
3601         ATG ACA TCC GTG CTG TTT ATG GTG GGG CGT GCT CTG GGA GCT TTC GGA TCT ACC CCA CTG CAG CAT CCA GAT CGT GTT CCC CAG CGA GAC AAA G
             TAC TGT AGG CAC GAC AAA TAC CAC CCC GCA CGA GAC CCT CGA AAG CCT AGA TGG GGT CTA GTC GTA GGT CTA GCA CAA GGG TC

L   V   W   K   P   V   L       K   G   T           R   Y   C   P       Q   S   A       E   L   N       L   E   P   D   L   K   T       M   A   F       D   S   K   V
3701         CTG GTG TGG AAG CCC GTG CTG AAG GGC ACC         CGT TAC TGC CCC CAG AGC GCC     CGA GCT CAA C         CTG GAA CCG GAC CTG AAA AAC     CAT GGC CTT C     GAC ACA AGG
             GAC CAC ACC TTC GGG CAC GAC TTC CCG TGG         GCA ATG ACG GGG GTC TCG CGG     GCT CGA GTT G         GAC CTT GGC CTG GAC TTT TTG     GTA CCG GAA G     CTG TGT TCC

P   I   G       I   T   P       S   N   S   D       G   Y   L       C   H   A       A   K   W   V   T   T   C       D   F   R       W   Y   G   P       K   Y   I
3801         CCA ATC GGG         ATC ACA CCC         AGC AAC AGC GAC GGC TAC CTG     TGC CAC GCG     GCC AAG TGG GTG ACC ACC TGC         GAC TTC CGA     TGG TAC GGC C     CAA GTA CAT
             GGT TAG CCC         TAG TGT GGG         TCG TTG TCG CTG CCG ATG GAC     ACG GTG CGC     CGG TTC ACC CAC TGG TGG ACG         CTG AAG GCT     ACC ATG CCG G     GTT CAT GTA

T   H   S       V   H   S   L       R   P   T           V   S   D           C   K   A   A       V   E   A           Y   N   A           G   T   L   M       Y   P   G           F   P   P
3901         CAC CAC AGC     GTG CAC AGC CTG     CGG CCC ACA         GTC AGC GAC         TGC AAG GCC     GCA GTG GAG         TAC AAC GCC         GGC ACC CTG ATG     TAC CCC GGA         CTT CCC CCC
             GTG GTG TCG     CAC GTG TCG GAC     GCC GGG TGT         CAG TCG CTG         ACG TTC CGG     CGT CAC CTC         ATG TTG CGG         CCG TGG GAC TAC     ATG GGG CCT         GAA GGG GGG

E   S   C   G   Y   A   S           I   T   D           S   E   F   Y   V   M   L           V   T   P           H   P   V   G           V   D   D           Y   R   G       H   W   V   D
4001         GAG AGC TGT GGC TAC GCA AGC         ATC ACG GAC         AGC GAG TTC TAC GTC ATG CTG         GTT ACA CCT         CAC CCC GTG GGG     GTC GAT GAC         TAC CGG GGC     CAC TGG GTG
             CTC TCG ACA CCG ATG CGT TCG         TAG TGC CTG         TCG CTC AAG ATG CAG TAC GAC         CAA TGT GGA         GTG GGG CAC CCC     CAG CTA CTG         ATG GCC CCG     GTG ACC CAC

P   L   F   P   T   S           E   C   N   S   N   F   C   E           E   T   V           H   N   A   T   M   W   I           P   K   D           L   K   T   H       D   V   C
4101         CCC CTC TTC CCC ACC TCC         GAG TGC AAC AGC AAC TTC TGT GAG         GAG ACA GTG         CAC AAC GCC ACC ATG TGG ATT         CCC AAG GAT         CTG AAA ACC     CAC GAC GTG TGC
             GGG GAG AAG GGG TGG AGG         CTC ACG TTG TCG TTG AAG ACA CTC         CTC TGT CAC         GTG TTG CGG TGG TAC ACC TAA         GGG TTC CTA         GAC TTT TGG     GTG CTG CAC ACG

S   Q   D           F   Q   T   I           R   V   S           V   M   Y           P   Q   T   K           P   T   K           G   A   D           L   T   L   K   S   K   F       H   A   H
4201         AGC CAG GAC         TTC CAG ACC ATC         AGA GTC TCA C         GTC ATG TAC         CCT CAG ACC AAG         CCC ACC AAG         GGA GCT GAC         CTG ACA CTG AAG AGA CAA GTT     CCA CGC CCA C
             TCG GTC CTG         AAG GTC TGG TAG         TCT CAG AGT G         CAG TAC ATG         GGA GTC TGG TTC         GGG TGG TTC         CCT CGA CTG         GAC TGT GAC TTC TCT GTT CAA     GGT GCG GGT G

M   K   G   D           R   V   C           K   M   K           F   C   N   K           N   G   L           R   L   G           N   G   E   W           I   E   V           G   D   E           V   M   L   D
4301         ATG AAG GGC GAC         AGA GTG TGC         AAG ATG AAG         TTC TGC AAC AAG         AAC GGG CTG         CGG CTG GGC         AAC GGC GAG TGG         ATC GAG GTC         GGG GAC GAG         GTG ATG CTG G
             TAC TTC CCG CTG         TCT CAC ACG         TTC TAC TTC         AAG ACG TTG TTC         TTG CCC GAC         GCC GAC CCG         TTG CCG CTC ACC         TAG CTC CAG         CCC CTG CTC         CAC TAC GAC C

N   S   K           L   L   S           L   F   P   D           C   L   V           G   S   V           V   K   S   T       L   L   S           E   G   V           Q   T   A   L   W   E   T
4401         ACA ACA GCA A         CTG CTG TCC         CTG TTC CCC GAC         TGT CTG GTG         GGC CAG TGG         GTG AAG AGC A         CAC TCT TCT         CCA GGC CCG TC     GTG GAC AGA C     ACA CCC TCT G
             TGT TGT CGT T         GAC GAC AGG         GAC AAG GGG CTG         ACA GAC CAC         CCG GTC GCC         CAC TTC TCG T         GTG AGA AGA         GGT CCG GGC AG     CAC CTG TCT G     TGT GGG AGA C
```

FIG. 17A

```
                                                                        · D R L   L D Y S   L C Q   N T W   E K I D   R K E   P L S   A V D L   S Y L   A P R
4501  AGAACCGGCTG CTGGACTACA GCCTGTGCCA GAACACCTGG GAGAAGATCG ACCGGAAAGA GCCCCTGAGC GCCGTCGACC TGAGCTACCT GGCCCCTAGA
      TCTTGGCCGAC GACCTGATGT CGGACACGGT CTTGTGGACC CTCTTCTAGC TGGCCTTTCT CGGGGACTCG CGGCAGCTGG ACTCGATGGA CCGGGGATCT

S P G K   G M A   Y I V   A N G S   L M S   A P A   R Y I R   V N I   D S P   I L K E .
4601  AGCCCCGGCA AGGGCATGGC CTACATCGTG GCCAACGGCA GCCTGATGAG CGCCCCTGCC CGGTACATCA GAGTGTGGAT CGACAGCCCC ATCCTGAAAG
      TCGGGGCCGT TCCCGTACCG GATGTAGCAC CGGTTGCCGT CGGACTACTC GCGGGGACGG GCCATGTAGT CTCACACCTA GCTGTCGGGG TAGGACTTTC

· I K G   K K E   S A S G   I D T   V L W   E Q W L   P F N   G M E   L G P N   G L I ·
4701  AGATCAAGGG CAAGAAAGAG AGCGCCAGCG GCATCGACAC CGTGCTGTGG GAGCAGTGGC TGCCCTTCAA CGGCATGGAA CTGGGCCCTA ACGGCCTGAT
      TCTAGTTCCC GTTCTTTCTC TCGCGGTCGC CGTAGCTGTG GCACGACACC CTCGTCACCG ACGGGAAGTT GCCGTACCTT GACCCGGGAT TGCCGGACTA

· K T K   S G Y K   F P L   Y L L   G M G I   V D Q   D L Q   E L S S   V N P   V D H
4801  CAAGACCAAG AGCGGCTACA AGTTCCCCCT GTACCTGCTG GGCATGGGCA TCGTGGACCA GGACCTGCAG GAACTGAGCA GCGTCAACCC CGTGGACCAC
      GTTCTGGTTC TCGCCGATGT TCAAGGGGGA CATGGACGAC CCGTACCCGT AGCACCTGGT CCTGGACGTC CTTGACTCGT CGCAGTTGGG GCACCTGGTG

P H V P   I A Q   A F V   S E G E   E V F   F G D   T G V S   K N P   I E L   I S G W
4901  CCCCACGTGC CTATCGCCCA GGCCTTCGTG AGCGAGGGCG AGGAAGTGTT CTTCGGCGAC ACCGGCGTGA GCAAGAACCC CATCGAGCTG ATCAGCGGCT
      GGGGTGCACG GATAGCGGGT CCGGAAGCAC TCGCTCCCGC TCCTTCACAA GAAGCCGCTG TGGCCGCACT CGTTCTTGGG GTAGCTCGAC TAGTCGCCGA

· F S D   W K S   I A S   F F F   L I I G   L F L   V L R   V G I H   L C I ·
5001  GGTTCAGCGA CTGGAAAAGC AGCATCGCCT CATTTTTTTT CATCATCGGC CTCTTCCTGG TGCTGCGCG  GTCGGGATCC ACCTGTGCAT
      CCAAGTCGCT GACCTTTTCG TCGTAGCGGA GTAAAAAAAA GTAGTAGCCG GAGAAGGACC ACGACGCGC  CAGCCCTAGG TGGACACGTA

· K L K   H T K   R Q I   Y T D   I E M N   R L G   K *
5101  CAAGCTGAAG CACACCAAGA ACGGCCAAGA CTATACCGAC ATCGAGATGA ATCCCCTGGG GAAGTAA
      GTTCGACTTC GTGTGGTTCT TGCCGGTTCT GATATGGCTG TAGCTCTACT TAGGGGACCC CTTCATT
```

FIG. 17B

B.

VSV.G ISFAHAN/INDIANA CO
BstEII (4052)
HindIII (3958)
BstEII (3860)
NcoI (3781)
BamHI (3591)
KpnI (3583)
HindIII (3573)
NheI (3557)
CMV
NcoI (3272)
NdeI (3146)

BglII (5128)
EcoRI (1)
NotI (28)
XhoI (34)
WPRE/ATG
XhoI (644)
XbaI (650)
BGH pA pThV-VSV.G (ISFA/IND)CO
5168bp

KanR
NcoI (1644)

pUC ORI

*FIG. 17C*

A.

```
              M   S I I S Y I A   F L L   L I D S T L G   I P I   F V P S G Q N   I S W
3601    ATG AGCATCATCA GCTATATCGC CTTTCTGCTG CTGATCGACA GCACCCTGGG CATCCCCATC TTCGTGCCCA GCCAGAATAT CATCAGCTGG
        TAC TCGTAGTAGT CGATATAGCG GAAAGACGAC GACTAGCTGT CGTGGGACCC GTAGGGGTAG AAGCACGGGT CGGTCTTA GTAGTCGACC

Q P V I Q P F   D Y Q   C P I H G N L   P N T   M G L S   A T K   L T I   K S P S
3701    CAGCCGGTGA TCCAGCCCTT CGACTACCAG TGCCCCATCC ACGGCAACCT GCCCAACACC ATGGGCCTGA GCGCCACCAA GCTGACCATC AAGAGCCCCA
        GTCGGCCACT AGGTCGGGAA GCTGATGGTC ACGGGGTAGG TGCCGTTGGA CGGGTTGTGG TACCCGGACT CGCGGTGGTT CGACTGGTAG TTCTCGGGGT

V F S   T D K   V S G W I C H   A A E   W K T T C D Y   R W Y   G P Q V I T H
3801    GCGTGTTCAG CACCGACAAG GTGTCCGGCT GGATCTGCCA CGCCGCCGAG TGGAAAACCA CCTGCGACTA CCGGTGGTAC GGCCCCCAGT ACATCACCCA
        CGCACAAGTC GTGGCTGTTC CACAGGCCGA CCTAGACGGT GCGGCGGCTC ACCTTTTGGT GGACGCTGAT GGCCACCATG CCGGGGGTCA TGTAGTGGGT

S I H   P I S P T I D   E C K   R I I S   R I A   S G T   D E D L G F P   P Q S
3901    GCGATCATCCAC CCCATCAGCC CCACCATCGA CGAGTGCAAG CGGATCATCA GCCGGATCGC CAGCGGCACC GACGAGGACC TGGGCTTCCC ACCCCAGAGC
        CGCTAGTAGTG GGGTAGTCGG GGTGGTAGCT GCTCACGTTC GCCTAGTAGT CGGCCTAGCG GTCGCCGTGG CTGCTCCTGG ACCCGAAGGG TGGGGTCTCG

C G W   A S V T   T V S   N T N Y   N K V V   P H S   V H L E   P Y G   G H W   I D H D
4001    TGCGGCTGGG CCAGCGTGAC CACCGTGAGC AACACCAACT ACAAGGTCGT GCCCCACAGC GTGCACCTGG AACCCTACGG CGGCCACTGG ATCGACCACG
        ACGCCGACCC GGTCGCACTG GTGGCACTCG TTGTGGTTGA TGTTCCACCA CGGGGTGTCG CACGTGGACC TTGGGATGCC GCCGGTGACC TAGCTGGTGC

F N G   G E C   R E K V   C E M   K G N   H S I W   I T D   E T V   Q H E C   E K H
4101    ACTTCAACGG CGGCGAGTGC CGGGAGAAAG TGTGCGAGAT GAAGGGCAAC CACAGCATCT GGATCACCGA CGAGACAGTG CAGCACGAGT GCGAAAAGCA
        TGAGTTGCCG GCCGCTCACG GCCCTCTTTC ACACGCTCTA CTTCCCGTTG GTGTCGTAGA CCTAGTGGCT GCTCTGTCAC GTCGTGCTCA CGCTTTTCGT

I E E   V E G I   M Y G   N A P   R G D A   I Y I   N N F   I I D K   H H R   V Y R
4201    CATCGAGGAA GTGGAGGGCA TCATGTACGG CAACGCCCCC AGGGGCGACG CCATCTACAT CAACAACTTC ATCATCGACA AGCACCACCG GGTGTACCGG
        GTAGCTCCTT CACCTCCCGT AGTACATGCC GTTGCGGGGG TCCCCGCTGC GGTAGATGTA GTTGTTGAAG TAGTAGCTGT TCGTGGTGGC CCACATGGCC

F G G S   C R M   K F C   N K D G   I K F   T R G   D W V E   K T A   G T L   T N I Y
4301    TTCGGCGGCT CCTGCCGGAT GAAGTTCTGC AACAAGGACG GCATCAAGTT CACCAGAGGC GACTGGGTGG AGAAAACCGC CGGCACCCTG ACCAACATCT
        AAGCCGCCGA GGACGGCCTA CTTCAAGACG TTGTTCCTGC CGTAGTTCAA GTGGTCTCCG CTGACCCACC TCTTTTGGCG GCCGTGGGAC TGGTTGTAGA

E N I   P E C   A D G T   L V S   G H R   P G L D   L I D   T V F   N L E N   V V E
4401    ACGAGAACAT CCCCGAGTGC GCCGACGGCA CACTGGTGTC CGGCCACAGA CCCGGCCTGG ACCTGATCGA CACCGTGTTC AACCTGGAAA ACGTGGTGGA
        TGCTCTTGTA GGGGCTCACG CGGCTGCCGT GTGACCACAG GCCGGTGTCT GGGACTAGCT GTGGCACAAG TTGGACCTTT TGCACCACCT
```

*FIG. 18A*

```
       . Y T L  C E G T  K R K  I N K   Q E K L  T S V  D L S   Y L A P  R I G  G F G
4501   GTACACCCTG TGCGAGGGCA CCAAGCGGAA GATCAACAAG CAGGAAAAGC TGACCAGCGT CGACCTGAGC TACCTGGCCC CCAGGATCGG CGGCTTCGGC
       CATGTGGGAC ACGCTCCCGT GGTTCGCCTT CTAGTTGTTC GTCCTTTTCG ACTGGTCGCA GCTGGACTCG ATGGACCGGG GGTCCTAGCC GCCGAAGCCG

S V F R  V R N   G T L  E R G S   T T Y  I R I   E V E G  P V V   D S L  N G I D .
4601   AGCGTGTTCC GGGTGCGGAA TGGCACCCTG GAGCGGGGCA GCACAACATA CATTCGGATC GAAGTGGAAG GCCCCGTGGT GGACAGCCTG AACGGCATCG
       TCGCACAAGG CCCACGCCTT ACCGTGGGAC CTCGCCCCGT CGTGTTGTAT GTAAGCCTAG CTTCACCTTC CGGGGCACCA CCTGTCGGAC TTGCCGTAGC

. P R T  N A S   R V F  W D D W   E L D  G N I Y   Q G F  N G V   Y K G  K D G K .
4701   ACCCCGGACA CAACCCGAGC CGGGTGTTCT GGGACGACTG GGAGCTGGAC GGCAACATCT ACCAGGGCTT CAATGGCGTG TACAAGGGCA AGGATGGCAA
       TGGGGCCTGT GTTGGGCTCG GCCCACAAGA CCCTGCTGAC CCTCGACCTG CCGTTGTAGA TGGTCCCGAA GTTACCGCAC ATGTTCCCGT TCCTACCGTT

. I H I  P L N M  I E S  G I I   D D E L  Q H A   F Q A  D I I P   H P H  Y D D .
4801   GATCCACATC CCCCTGAACA TGATCGAGAG CGGCATCATC GACGACGAGC TGCAGCAGGC CTTCCAGGCC GACATCATCC CCCACCCCA CTACGACGAC
       CTAGGTGTAG GGGGACTTGT ACTAGCTCTC GCCGTAGTAG CTGCTGCTCG AGGTCGTCCG GAAGGTCCGG CTGTAGTAGG GGGTGGGGGT GATGCTGCTG

D E I R  E D D   I F F  D N T G   E N G  N P V   D A V V  E M V   S G W  G S S I .
4901   GACGAGATCA GGGAGGACGA CATCTTCTTC GACAACACCG GCGAGAACGG GAACCCCGTG GACGCCGTGG TGGAAATGGT GTCCGGATGG GGCAGCAGCA
       CTGCTCTAGT CCCTCCTGCT GTAGAAGAAG CTGTTGTGGC CGCTCTTGCC CTTGGGGCAC CTGCGGCACC ACCTTTACCA CAGGCCTACC CCGTCGTCGT

. A S F  F I   I G L I  I G L F   L V  L R V G   I H L  C I K   L K H  T K K R .
5001   TCGCTTCATT TTTTTCATC ATCGGCCTCA TCATCGGGCT GTTCGTGCTG CTGCGGGTCG GCATCCACCT GTGCATCAAG CTGAAGCACA CCAAGAAGCG
       AGCGAAGTAA AAAAAGTAG TAGCCGGAGT AGTAGCCCGA CAAGCACGAC GACGCCCAGC CGTAGGTGGA CACGTAGTTC GACTTCGTGT GGTTCTTCGC

. Q I Y  T D I  E M N R   L G K *
5101   CCAGATCTAT ACCGACATCG AGATGAATCG CCTGGGCAAG TAA
       GGTCTAGATA TGGCTGTAGC TCTACTTAGC GGACCCGTTC ATT
```

*FIG. 18B*

B.

*Bgl*II (5104)
*Bsp*EI (4983)
*Eco*RI (1)
*Not*I (28)
*Xho*I (34)
WPRE/ATG
*Xho*I (644)
*Xba*I (650)
BGH pA

VSV.G SVC/INDIANA CO pThV-VSV.G (SVCV/IND)CO
5144bp

*Nco*I (3760)
*Bam*HI (3591)
*Kpn*I (3583)
*Hin*dIII (3573)
*Nhe*I (3557)
CMV
*Nco*I (3272)
*Nde*I (3146)

KanR
*Nco*I (1644)

pUC ORI

FIG. 18C

FIG. 19A

```
                  . L D Y   A L C Q N T W   S K I   E S G E   P I T   P V D   L S Y L   G P K   N P G
         CCTCGACTAC GCTCTCTGCC AGAACACATG GAGCAAGATC GAAAGCGGG AACCCATCAC CCCAGTGGAC CTGAGCTATC TGGGCCCAAA GAACCCGGC
4501     GGAGCTGATG CGAGAGACGG TCTTGTGTAC CTCGTTCTAG CTTTCGCCCC TTGGGTAGTG GGGTCACCTG GACTCGATAG AGCCCGGGTT CTTGGGCCG

V G P V   F T I   I N G   S L H Y   F T S   K Y L   R V E L E S P   V I P   R M E G  .
         GTGGGGCCCG TGTTCACCAT CATCAACGGG AGCCTGCACT ACTTTACAAG CAAGTATCTG CGGGTGGAGC TCGAAAGCCC AGTCATCCCC CCGATGGAGG
4601     CACCCCGGGC ACAAGTGGTA GTAGTTGCCC TCGGACGTGA TGAAATGTTC GTTCATAGAC GCCCACCTCG AGCTTTCGGG TCAGTAGGGG GGCTACCTCC

. K V A   G T R   I V R Q   L W D   Q W F   P F G E   V E I   G P N   G V L K T K Q  .
         GGAAGGTGGC CGGGACCCGC ATCGTGCGGC AGCTGTGGGA CCAGTGGTTC CCTTTTGGCG AGGTGGAAAT CGGCCCCAAC GGCGTCCTGA AGACCAAGCA
4701     CCTTCCACCG GCCCTGGGCG TAGCACGCCG TCGACACCCT GGTCACCAAG GGAAAACCGC TCCACCTTTA GCCGGGGTTG CCGCACGACT TCTGGTTCGT

. G Y K   F P L H   I I G   T G E   V D S D   I K M   E R V   V K H W   E H P   H I E  .
         GGGATATAAG TTCCCGCTGC ACATCATCGG GACGGGCGAA GTGGACAGCG ATATCAAGAT GGAGCGGGTG GTCAAGCACT GGGAGCACCC ACACATCGAG
4801     CCCTATATTC AAGGGCGACG TGTAGTAGCC CTGCCCGCTT CACCTGTCGC TATAGTTCTA CCTCGCCCAC CAGTTCGTGA CCCTCGTGGG TGTGTAGCTC

A A Q T   F L K   K D D   T G E V   L Y Y   G D T   G V S K   N P V   E L V   E G W F  .
         GCTGCTCAGA GAACCCTTCC TTTTCTCAA GAAGGACGAT ACCGGCGAAG TCCTGTATTA CGGGGATACG GGAGTGAGCA AGAACCCTGT GGAGCTGGTG GAAGGCTGGT
4901     CGACGAGTCT CTTGGGAAGG AAAAGAGTT CTTCCTGCTA TGGCCGCTTC AGGACATAAT GCCCCTATGC CCTCACTCGT TCTTGGGACA CCTCGACCAC CTTCCGACCA

. S G W   R S S   I A S F   F F I   T G L   T I G L   F L V   G T H   L C T K
         TCAGGGGATG GCCCAGCAGC ATCCCCTTCAT TTTTTTCAT TACTGGCCTC ATCATGGGC TGTTTCTGGT GCTGGCGGTC GGCATCCACC TGTGCATCAA
5001     AGTCCCCTAC CGGGTCGTCG TAGGGGAAGTA AAAAAAGTA ATGACCGGAG TAGTACCCG ACAAAGACCA CGACCGCCAG CCGTAGGTGG ACACGTAGTT

. I K H   T K R   Q I Y   T D I   E M N   R L G K  *
         GCTCGAAGCAC ACCAAGAGAC GCCAGATCTA TACCGACATC GAGATGAATC CGGCTGGGAA GTAA
5101     CGAGCTTCGTG TGGTTCTCTG CGGTCTAGAT ATGGCTGTAG CTCTACTTAG GCCGACCCTT CATT
```

FIG. 19B

EcoRI (1)
NotI (28)
XhoI (34)
WPREΔATG
XhoI (644)
XbaI (650)
VSV/G NJ CO
BGH pA pThV-VSV.G (NJ-CO)
5162bp

KanR

BamHI (3591)
KpnI (3583)
HindIII (3573)
NheI (3557)
CMV
NcoI (3272)
NdeI (3146)
NcoI (1644)

pUC ORI

EFFECT OF CODON-OPTIMIZATION UPON LENTIVIRAL VECTORS
PSEUDOTYPED WITH NEW-JERSEY VSV.G-GLYCOPROTEIN

TITER (TU/mL): 1,0E+00 to 1,0E+08

INDIANA — NEW JERSEY — NEW JERSEY CO

VSV-G GLYCOPROTEIN

*FIG. 20*

A.

MASVLSGGELDRWEKIRLRPGGKKKYKLKHIVWASRELERFAVNPGLLETSEGCRQILGQLQPSLQTGSEELRSL
YNTVATLYCVHQRIEVKDTKEALDKIEEEQNKSKKKAQQAAADTNHSSQVSQNYPIVQNLQGQMVHQAISPRTLN
AWVKVVEEKAFSPEVIPMFSALSEGATPQDLNTMLNTVGGHQAAMQMLKETINEEAAEWDRLHPVHAGPIAPGQM
REPRGSDIAGTTSTLQEQIGWMTNNPPIPVGEIYKRWIILGLNKIVRMYSPTSILDIRQGPKEPFRDYVDRFYKT
LRAEQASQEVKNWMTETLLVQNANPDCKTILKALGPAATLEEMMTACQGVGGPGHKARVLAEAMSQVTNSATIMM
QRGNFRNQRKTVKCFNCGKEGHIAKNCRAPRKKGCWKCGKEGHQMKDCTERQANFLGKIWPSHKGRPGNFLQSRP
EPTAPPEESFRFGEETTTPSQKQEPIDKELYPLASLRSLFGND (SEQ ID NO: 69)

B.

KKSVTVLDVGDAYFSVPLDKDFRKYTAFTIPSINNETPGIRYQYNVLPQGWKGSPAIFQSSMTKILEPFRKQNPD
IVIYQYMDDLYVGSDLEIGQHRTEILKEPVHGVY (SEQ ID NO: 70)

C.

VGFPVRPQVPLRPMTYKAAVDLSHFLKEKGGLEGLIYSQKRQDILDLWVYHTQGYFPDWQNYTPGPGIRYPLTFG
WCFKLVPVDPEKEVLVWKFDSRLAFHHMARELHPEYYapvkqtlnfdllklagdvesnpgp (SEQ ID NO: 66)

D.

MGARASVLSGGELDRWEKIRLRPGGKKKYKLKHIVWASRELERFAVNPGLLETSEGCRQILGQLQPSLQTGSEEL
RSLYNTVATLYCVHQRIEIKDTKEALDKIEEEQNKSKKKAQQAAADTGHSSQVSQNYPIVQNIQGQMVHQAISPR
TLNAWVKVVEEKAFSPEVIPMFSALSEGATPQDLNTMLNTVGGHQAAMQMLKETINEEAAEWDRVHPVHAGPIAP
GQMREPRGSDIAGTTSTLQEQIGWMTNNPPIPVGEIYKRWIILGLNKIVRMYSPTSILDIRQGPKEPFRDYVDRF
YKTLRAEQASQEVKNWMTETLLVQNANPDCKTILKALGPAATLEEMMTACQGVGGPGHKARVLAEAMSQVTNSAT
IMMQRGNFRNQRKIVKCFNCGKEGHIARNCRAPRKKGCWKCGKEGHQMKDCTERQANFLGKIWPSYKGRPGNFLQ
SRPEPTAPPFLQSRPEPTAPPEESFRSGVETTTPSQKQEPIDKELYPLTSLRSLFGNDPSSQ
(SEQ ID NO: 67)

FIG. 21

E.

ATGGGTGCGAGAGCGTCAGTATTAAGCGGGGGAGAATTAGATCGATGGGAAAAAATTCGGTTAAGGCCAGGGGGA
AAGAAAAAATATAAATTAAAACATATAGTATGGGCAAGCAGGGAGCTAGAACGATTCGCAGTTAATCCTGGCCTG
TTAGAAACATCAGAAGGCTGTAGACAAATACTGGGACAGCTACAACCATCCCTTCAGACAGGATCAGAAGAACTT
AGATCATTATATAATACAGTAGCAACCCTCTATTGTGTGCATCAAAGGATAGAGATAAAAGACACCAAGGAAGCT
TTAGACAAGATAGAGGAAGAGCAAAACAAAAGTAAGAAAAAAGCACAGCAAGCAGCAGCTGACACAGGACACAGC
AGCCAGGTCAGCCAAAATTACCCTATAGTGCAGAACATCCAGGGGCAAATGGTACATCAGGCCATATCACCTAGA
ACTTTAAATGCATGGGTAAAAGTAGTAGAAGAGAAGGCTTTCAGCCCAGAAGTGATACCCATGTTTTCAGCATTA
TCAGAAGGAGCCACCCCACAAGATTTAAACACCATGCTAAACACAGTGGGGGGACATCAAGCAGCCATGCAAATG
TTAAAAGAGACCATCAATGAGGAAGCTGCAGAATGGGATAGAGTGCATCCAGTGCATGCAGGGCCTATTGCACCA
GGCCAGATGAGAGAACCAAGGGGAAGTGACATAGCAGGAACTACTAGTACCCTTCAGGAACAAATAGGATGGATG
ACAAATAATCCACCTATCCCAGTAGGAGAAATTTATAAAAGATGGATAATCCTGGGATTAAATAAAATAGTAAGA
ATGTATAGCCCTACCAGCATTCTGGACATAAGACAAGGACCAAAAGAACCCTTTAGAGACTATGTAGACCGGTTC
TATAAAACTCTAAGAGCCGAGCAAGCTTCACAGGAGGTAAAAAATTGGATGACAGAAACCTTGTTGGTCCAAAAT
GCGAACCCAGATTGTAAGACTATTTTAAAAGCATTGGGACCAGCAGCTACACTAGAAGAAATGATGACAGCATGT
CAGGGAGTGGGAGGACCCGGCCATAAGGCAAGAGTTTTGGCTGAAGCAATGAGCCAAGTAACAAATTCAGCTACC
ATAATGATGCAAAGAGGCAATTTTAGGAACCAAAGAAAGATTGTTAAGTGTTTCAATTGTGGCAAAGAAGGGCAC
ATAGCCAGAAATTGCAGGGCCCCTAGGAAAAAGGGCTGTTGGAAATGTGGAAAGGAAGGACACCAAATGAAAGAT
TGTACTGAGAGACAGGCTAATTTTTTAGGGAAGATCTGGCCTTCCTACAAGGGAAGGCCAGGGAATTTTCTTCAG
AGCAGACCAGAGCCAACAGCCCCACCATTTCTTCAGAGCAGACCAGAGCCAACAGCCCCACCAGAAGAGAGCTTC
AGGTCTGGGGTAGAGACAACAACTCCCTCTCAGAAGCAGGAGCCGATAGACAAGGAACTGTATCCTTTAACTTCC
CTCAGATCACTCTTTGGCAACGACCCCTCGTCACAATAA (SEQ ID NO:68)

FIG. 21
(CONTINUED)

Figure 25A:
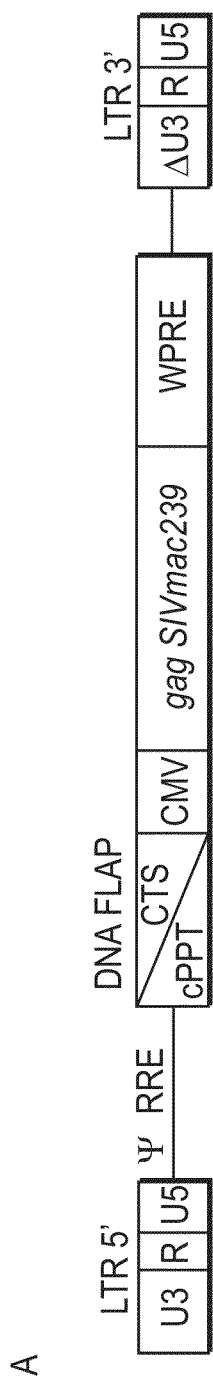

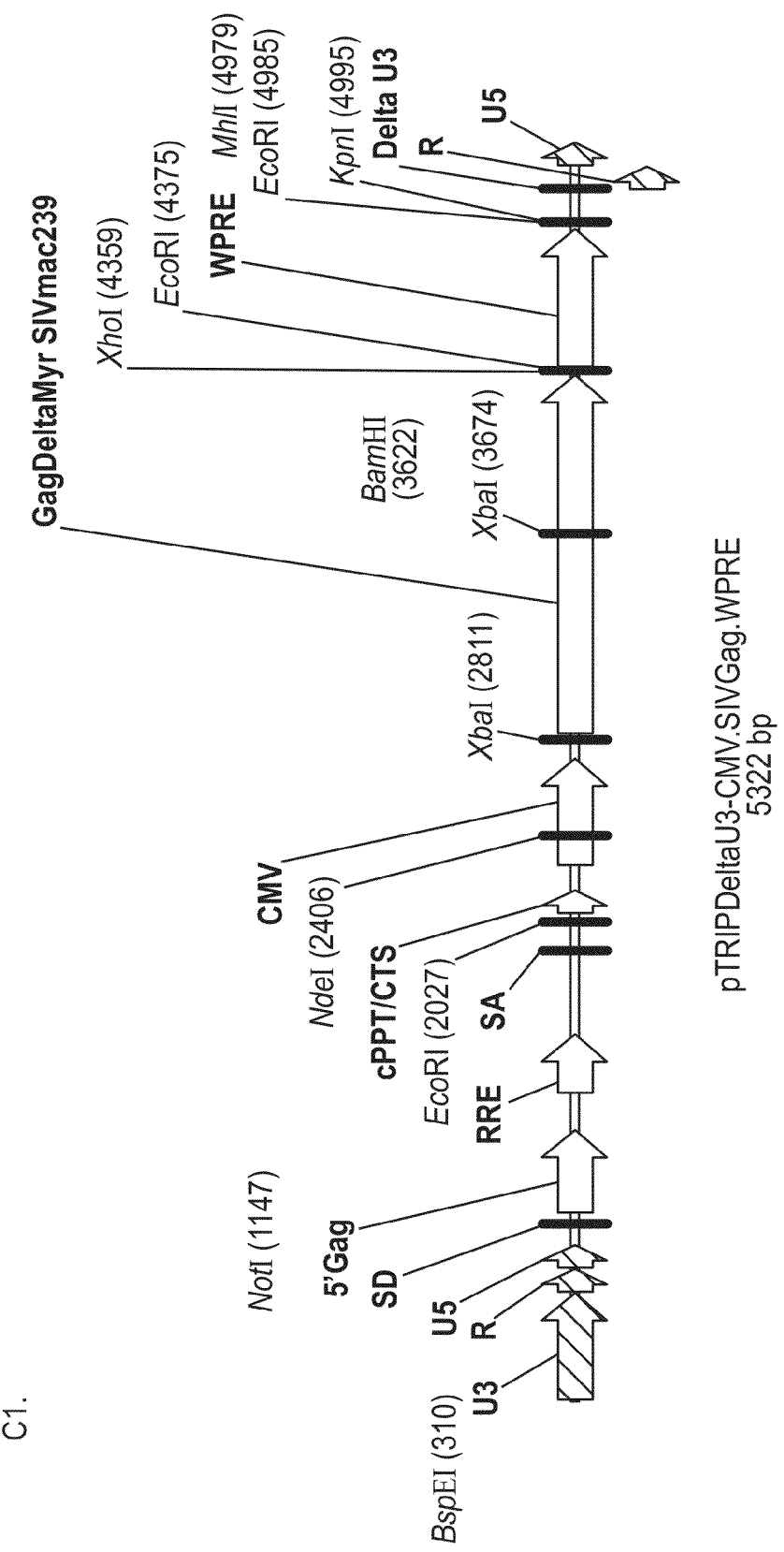
FIG. 25C(1)

C2.

tggaagggctaattcactcccaacgaagacaagatatccttgatctgtggatctaccacacacaaggc
tacttccctgattagcagaactacacaccagggccagggatcagatatccactgacctttggatggtg
ctacaagctagtaccagttgagccagagaagttagaagaagccaacaaaggagagaacaccagcttgt
tacaacctgtgagcctgcatgggatggatgacccggagagagaagtgttagagtggaggtttgacagc
cgcctagcatttcatcacggtggcccgagagctgcatccggagtacttcaagaactgctgatatcgag
cttgctacaagggactttccgctgggggactttccagggaggcgtggcctgggcgggactggggagtg
gcgagccctcagatcctgcatataagcagctgcttttgcctgtactgggtctctctggttagaccag
atctgagcctgggagctctctggctaactagggaacccactgcttaagcctcaataaagcttgccttg
agtgcttcaagtagtgtgtgcccgtctgttgtgtgactctggtaactagagatccctcagacccttt
agtcagtgtggaaaatctctagcagtggcgcccgaacagggacttgaaagcgaaagggaaaccagagg
agctctctcgacgcaggactcggcttgctgaagcgcgcacggcaagaggcgaggggcggcgactggtg
agtacgccaaaaattttgactagcggaggctagaaggagagagatgggtgcgagagcgtcagtattaa
gcgggggagaattagatcgcgatgggaaaaaattcggttaaggccagggggaaagaaaaaatataaat
taaaacatatagtatgggcaagcagggagctagaacgattcgcagttaatcctggcctgttagaaaca
tcagaaggctgtagacaaatactgggacagctacaaccatcccttcagacaggatcagaagaacttag
atcattatataatacagtagcaaccctctattgtgtgcatcaaaggatagagataaaagacaccaagg
aagctttagacaagatagaggaagagcaaaacaaaagtaagaccaccgcacagcaagcggccgctgat
cttcagacctggaggaggagatatgagggacaattggagaagtgaattatataaatataaagtagtaa
aaattgaaccattaggagtagcacccaccaaggcaaagagaagagtggtgcagagagaaaaaagagca
gtgggaataggagctttgttccttgggttcttgggagcagcaggaagcactatgggcgcagcgtcaat
gacgctgacggtacaggccagacaattattgtctggtatagtgcagcagcagaacaatttgctgaggg
ctattgaggcgcaacagcatctgttgcaactcacagtctggggcatcaagcagctccaggcaagaatc
ctggctgtggaaagatacctaaaggatcaacagctcctggggatttggggttgctctggaaaactcat
ttgcaccactgctgtgccttggaatgctagttggagtaataaatctctggaacagatttggaatcaca
cgacctggatggagtgggacagagaaattaacaattacacaagcttaatacactccttaattgaagaa
tcgcaaaaccagcaagaaaagaatgaacaagaattattggaattagataaatgggcaagtttgtggaa
ttggtttaacataacaaattggctgtggtatataaaattattcataatgatagtaggaggcttggtag
gtttaagaatagttttgctgtactttctatagtgaatagagttaggcagggatattcaccattatcg

FIG. 25C(2)

```
tttcagacccacctcccaaccccgaggggacccgacaggcccgaaggaatagaagaagaaggtggaga
gagagacagagacagatccattcgattagtgaacggatctcgacggtatcgccgaattcacaaatggc
agtattcatccacaattttaaaagaaaaggggggattgggggggtacagtgcaggggaaagaatagtag
acataatagcaacagacatacaaactaaagaattacaaaaacaaattacaaaaattcaaaattttcgg
gtttattacagggacagcagagatccactttggggcgataagcttgggagttccgcgttacataactt
acggtaaatggcccgcctggctgaccgcccaacgaccccgcccattgacgtcaataatgacgtatgt
tcccatagtaacgccaatagggactttccattgacgtcaatgggtggagtatttacggtaaactgccc
acttggcagtacatcaagtgtatcatatgccaagtacgccccctattgacgtcaatgacggtaaatgg
cccgcctggcattatgcccagtacatgaccttatgggactttcctacttggcagtacatctacgtatt
agtcatcgctattaccatggtgatgcggttttggcagtacatcaatgggcgtggatagcggtttgact
cacggggatttccaagtctccaccccattgacgtcaatgggagtttgttttggcaccaaaatcaacgg
gactttccaaaatgtcgtaacaactccgcccattgacgcaaatgggcggtaggcgtgtacggtggga
ggtctatataagcagagctcgtttagtgaaccgtcagatcgcctggagacgccatccacgctgttttg
acctccatagaagacaccgactctagaggatctgccaccatggtgagaaactccgtcttgtcagggaa
gaaagcagatgaattagaaaaaattaggctacgacccaacggaaagaaaaagtacatgttgaagcatg
tagtatgggcagcaaatgaattagatagatttggattagcagaaagcctgttggagaacaaagaagga
tgtcaaaaaatactttcggtcttagctccattagtgccaacaggctcagaaaatttaaaaagccttta
taatactgtctgcgtcatctggtgcattcacgcagaagagaaagtgaaacacactgaggaagcaaaac
agatagtgcagagacacctagtggtggaaacaggaacaacagaaactatgccaaaaacaagtagacca
acagcaccatctagcggcagaggaggaaattacccagtacaacaaataggtggtaactatgtccacct
gccattaagcccgagaacattaaatgcctgggtaaaattgatagaggaaaagaaatttggagcagaag
tagtgccaggatttcaggcactgtcagaaggttgcaccccctatgacattaatcagatgttaaattgt
gtgggagaccatcaagcggctatgcagattatcagagatattataaacgaggaggctgcagattggga
cttgcagcacccacaaccagctccacaacaaggacaacttagggagccgtcaggatcagatattgcag
gaacaactagttcagtagatgaacaaatccagtggatgtacagacaacagaaccccataccagtaggc
aacatttacaggagatggatccaactgggggttgcaaaaatgtgtcagaatgtataacccaacaaacat
tctagatgtaaaacaagggccaaaagagccatttcagagctatgtagacaggttctacaaaagttaa
gagcagaacagacagatgcagcagtaaagaattggatgactcaaacactgctgattcaaaatgctaac
ccagattgcaagctagtgctgaagggctgggtgtgaatcccaccctagaagaaatgctgacggcttg
tcaaggagtaggggggccgggacagaaggctagattaatggcagaagccctgaaagaggccctcgcac
cagtgccaatcccttttgcagcagcccaacagagggggaccaagaaagccaattaagtgttggaattgt
gggaaagagggacactctgcaaggcaatgcagagccccaagaagacagggatgctggaaatgtggaaa
```

FIG. 25C(2)
(CONTINUED-1)

```
aatggaccatgttatggccaaatgcccagacagacaggcgggttttttaggccttggtccatggggaa
agaagccccgcaatttccccatggctcaagtgcatcaggggctgatgccaactgctcccccagaggac
ccagctgtggatctgctaaagaactacatgcagttgggcaagcagcagagagaaaagcagagagaaag
cagagagaagccttacaaggaggtgacagaggatttgctgcacctcaattctctctttggaggagacc
agtagctcgagctcaagcttcgaattcccgataatcaacctctggattacaaaatttgtgaaagattg
actggtattcttaactatgttgctccttttacgctatgtggatacgctgctttaatgcctttgtatca
tgctattgcttcccgtatggctttcattttctcctccttgtataaatcctggttgctgtctctttatg
aggagttgtggcccgttgtcaggcaacgtggcgtggtgtgcactgtgtttgctgacgcaaccccact
ggttggggcattgccaccacctgtcagctcctttccgggactttcgctttccccctccctattgccac
ggcggaactcatcgccgcctgccttgccgctgctggacaggggctcggctgttgggcactgacaatt
ccgtggtgttgtcggggaagctgacgtcctttccatggctgctcgcctgtgttgccacctggattctg
cgcgggacgtccttctgctacgtcccttcggccctcaatccagcggaccttccttcccgcggcctgct
gccggctctgcggcctcttccgcgtcttcgccttcgccctcagacgagtcggatctccctttgggccg
cctccccgcgtcgacgcgtgaattcggtacctttaagaccaatgacttacaaggcagctgtagatctt
agccactttttaaaagaaaaggggggactggaagggctaattcactcccaacgaagacaagatcgtcg
agagatgctgcatataagcagctgcttttgcttgtactgggtctctctggttagaccagatctgagc
ctgggagctctctggctaactagggaacccactgcttaagcctcaataaagcttgccttgagtgcttc
aagtagtgtgtgcccgtctgttgtgtgactctggtaactagagatccctcagaccccttttagtcagtg
tggaaaatctctagcagt
```
(SEQ ID NO: 71)

FIG. 25C(2)
*(CONTINUED-2)*

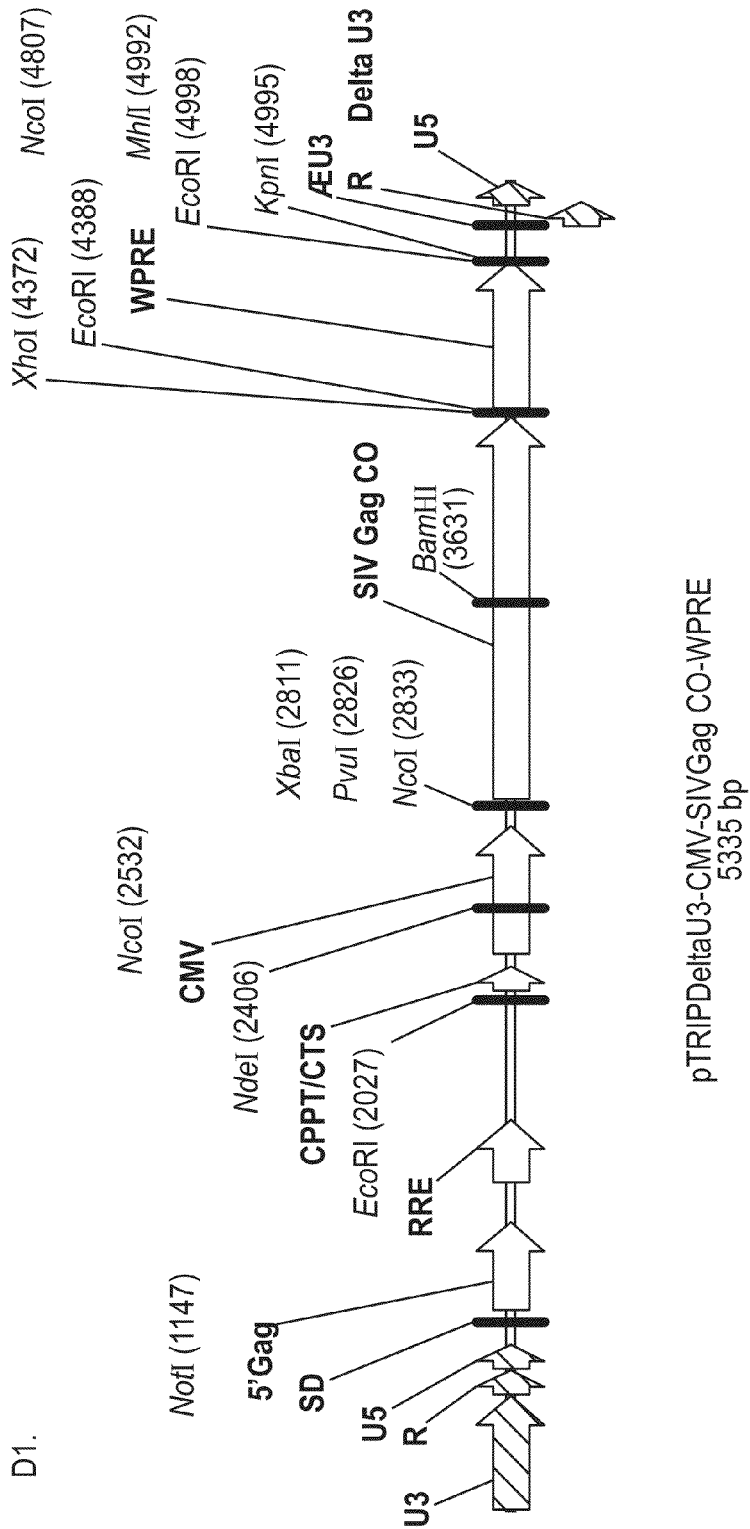
FIG. 25D(1)

D2.

```
tggaagggctaattcactcccaacgaagacaagatatccttgatctgtggatctaccacacacaaggc
tacttccctgattagcagaactacacaccagggccagggatcagatatccactgacctttggatggtg
ctacaagctagtaccagttgagccagagaagttagaagaagccaacaaaggagagaacaccagcttgt
tacaacctgtgagcctgcatgggatggatgacccggagagagaagtgttagagtggaggtttgacagc
cgcctagcatttcatcacggtggcccgagagctgcatccggagtacttcaagaactgctgatatcgag
cttgctacaagggactttccgctgggggactttccagggaggcgtggcctgggcgggactggggagtg
gcgagccctcagatcctgcatataagcagctgcttttttgcctgtactgggtctctctggttagaccag
atctgagcctgggagctctctggctaactagggaacccactgcttaagcctcaataaagcttgccttg
agtgcttcaagtagtgtgtgcccgtctgttgtgtgactctggtaactagagatccctcagacccttt
agtcagtgtggaaaatctctagcagtggcgcccgaacagggacttgaaagcgaaagggaaaccagagg
agctctctcgacgcaggactcggcttgctgaagcgcgcacggcaagaggcgaggggcggcgactggtg
agtacgccaaaaattttgactagcggaggctagaaggagagagatgggtgcgagagcgtcagtattaa
gcgggggagaattagatcgcgatgggaaaaaattcggttaaggccaggggggaaagaaaaaatataaat
taaaacatatagtatgggcaagcagggagctagaacgattcgcagttaatcctggcctgttagaaaca
tcagaaggctgtagacaaatactgggacagctacaaccatcccttcagacaggatcagaagaacttag
atcattatataatacagtagcaaccctctattgtgtgcatcaaaggatagagataaaagacaccaagg
aagctttagacaagatagaggaagagcaaaacaaaagtaagaccaccgcacagcaagcggccgctgat
cttcagacctggaggaggagatatgagggacaattggagaagtgaattatataaatataaagtagtaa
aaattgaaccattaggagtagcacccaccaaggcaaagagaagagtggtgcagagagaaaaaagagca
gtgggaataggagctttgttccttgggttcttgggagcagcaggaagcactatgggcgcagcgtcaat
gacgctgacggtacaggccagacaattattgtctggtatagtgcagcagcagaacaatttgctgaggg
ctattgaggcgcaacagcatctgttgcaactcacagtctggggcatcaagcagctccaggcaagaatc
ctggctgtggaaagataccctaaaggatcaacagctcctggggatttggggttgctctggaaaactcat
ttgcaccactgctgtgccttggaatgctagttggagtaataaatctctggaacagatttggaatcaca
cgacctggatggagtgggacagagaaattaacaattacacaagcttaatacactccttaattgaagaa
tcgcaaaaccagcaagaaaagaatgaacaagaattattggaattagataaatgggcaagtttgtggaa
ttggtttaacataacaaattggctgtggtatataaaattattcataatgatagtaggaggcttggtag
gtttaagaatagttttgctgtactttctatagtgaatagagttaggcagggatattcaccattatcg
```

FIG. 25D(2)

tttcagacccacctcccaaccccgaggggacccgacaggcccgaaggaatagaagaagaaggtggaga
gagagacagagacagatccattcgattagtgaacggatctcgacggtatcgccgaattcacaaatggc
agtattcatccacaattttaaaagaaaaggggggattgggggggtacagtgcaggggaaagaatagtag
acataatagcaacagacatacaaactaaagaattacaaaaacaaattacaaaaattcaaaattttcgg
gtttattacagggacagcagagatccactttggggcgataagcttgggagttccgcgttacataactt
acggtaaatggcccgcctggctgaccgcccaacgaccccgcccattgacgtcaataatgacgtatgt
tcccatagtaacgccaatagggactttccattgacgtcaatgggtggagtatttacggtaaactgccc
acttggcagtacatcaagtgtatcatatgccaagtacgccccctattgacgtcaatgacggtaaatgg
cccgcctggcattatgcccagtacatgaccttatgggactttcctacttggcagtacatctacgtatt
agtcatcgctattaccatggtgatgcggttttggcagtacatcaatgggcgtggatagcggtttgact
cacggggatttccaagtctccaccccattgacgtcaatgggagtttgttttggcaccaaaatcaacgg
gactttccaaaatgtcgtaacaactccgccccattgacgcaaatgggcggtaggcgtgtacggtggga
ggtctatataagcagagctcgtttagtgaaccgtcagatcgcctggagacgccatccacgctgttttg
acctccatagaagacaccgactctagaggatctcgatcggccaccatgggcgtgcgcaacagcgtgct
gagcggcaagaaggccgacgagctggagaagatccgcctgcgccccaacggcaagaagaagtacatgc
tgaagcacgtggtgtgggccgctaacgagctggaccggttcggcctggccgagagcctgctggagaac
aaggagggctgccagaagatcctgagcgtgctggcccctctggtgcccaccggcagcgagaacctgaa
gagcctgtacaacaccgtgtgcgtgatctggtgcatccacgccgaggagaaggtgaagcacaccgagg
aggccaagcagatcgtgcagcgccacctggtggtggagaccggcaccaccgagaccatgcccaagacc
agcaggcccaccgcccctagcagcggcagaggcgggaactaccccgtgcagcagatcggcggcaacta
cgtgcacctgccccctgagccccaggaccctgaacgcctgggtgaagctgatcgaggagaagaagttcg
gcgctgaggtggtgcccggcttccaggccctgagcgagggctgcacccccctacgacatcaaccagatg
ctgaactgcgtgggcgaccaccaggccgccatgcagatcatccgcgacatcatcaacgaggaagccgc
cgactgggacctgcagcaccccagcctgccccccagcagggccagctgcgcgagcccagcggctccg
acatcgccggcaccaccagcagcgtcgacgagcagatccagtggatgtaccgccagcagaacccatc
cccgtgggcaacatctaccgccgctggatccagctgggcctgcagaagtgcgtgcgcatgtacaaccc
caccaacatcctggacgtgaagcagggccccaaggagcccttccagagctacgtggaccgcttctaca
agagcctgagggccgagcagaccgatgccgccgtgaagaactggatgacccagaccctgctgatccag
aacgccaaccccgactgcaagctggtgctgaagggcctgggcgtgaaccccaccctggaggagatgct

FIG. 25D(2)
(CONTINUED-1)

```
gaccgcctgccagggcgtgggaggacctggccagaaggccaggctgatggccgaagccctgaaggagg
ccctggcccctgtgcccatccccttcgccgctgcccagcagaggggccctcgcaagcccatcaagtgt
tggaactgcggcaaggagggccacagcgccaggcagtgccgcgctccccgcaggcagggctgctggaa
gtgtgggaagatggaccacgtgatggccaagtgccccgaccgccaggccggcttcctgggcctgggcc
cctgggggaagaagccccgcaacttccctatggcgcaggtgcaccagggcctcatgcctaccgcccct
cccgaggaccctgccgtggacctgctgaagaactacatgcagctgggcaagcagcagcgcgagaagca
gcgcgagagccgcgagaagccctacaaggaggtgaccgaggacctgctgcacctgaacagcctgttcg
gcggagaccagtaatgaactcgagctcaagcttcgaattcccgataatcaacctctggattacaaaat
ttgtgaaagattgactggtattcttaactatgttgctccttttacgctatgtggatacgctgctttaa
tgcctttgtatcatgctattgcttcccgtatggctttcattttctcctccttgtataaatcctggttg
ctgtctctttatgaggagttgtggcccgttgtcaggcaacgtggcgtggtgtgcactgtgtttgctga
cgcaacccccactggttggggcattgccaccacctgtcagctcctttccgggactttcgctttccccc
tccctattgccacggcggaactcatcgccgcctgccttgcccgctgctggacaggggctcggctgttg
ggcactgacaattccgtggtgttgtcggggaagctgacgtccttttccatggctgctcgcctgtgttgc
cacctggattctgcgcgggacgtccttctgctacgtcccttcggccctcaatccagcggaccttcctt
cccgcggcctgctgccggctctgcggcctcttccgcgtcttcgccttcgccctcagacgagtcggatc
tccctttgggccgcctccccgcgtcgacgcgtgaattcggtacctttaagaccaatgacttacaaggc
agctgtagatcttagccactttttaaaagaaaaggggggactggaagggctaattcactcccaacgaa
gacaagatcgtcgagagatgctgcatataagcagctgcttttttgcttgtactgggtctctctggttag
accagatctgagcctgggagctctctggctaactagggaacccactgcttaagcctcaataaagcttg
ccttgagtgcttcaagtagtgtgtgcccgtctgttgtgtgactctggtaactagagatccctcagacc
ctttttagtcagtgtggaaaatctctagcagt (SEQ ID NO:72)
```

FIG. 25D(2)
*(CONTINUED-2)*

N TER
1
mgvmsvlsgkkadelekirlrpngkkkymlkhvvwaaneldrfglaesllenkegcqkilsvlaplvptgsenlkslyntvcviwcihaeekvkhteeakqivqrhlvvetgttetmpk
pool M (1-59)
pool N (49-107)

121
tsrptapssgrggnypvqqiggnyvhlplsprtlnawkllieekfgaevvpgfqalsegcdpyclinqmlncvgdhqaamqiirdineeaadwdlqhpqpapqqgdrepsgsdiagtt
pool O (97-155)
pool P (145-203)

241
ssvdeqiqwmyrqqnpipvgniyrwigiglqkcvrmynptnildvkqgpkepfqsyvdrfykslraeqtdaavknwmiqtlliqnanpclckmkglgvnptleemltacqgvggpgqk
pool Q (193-251)
pool R (241-299)
pool S (289-347)

361
arlmaealkealapvpipfaaaqqrgprkpikcwngkeghsarqcraprrqgcwkcgkmidhvmakcpdrqagflglpwckkprnfpmaqvhqglmptappedpavdllknymqlgkqq
pool T (337-395)
pool U (385-443)
pool V (433-491)

481
rekqresrekpykevtedllhlnslfggdq     C ter
pool W (481-511)

*FIG. 26*

A.

| PCR | OLIGOS | SEQUENCE 5'  3'→ |
|---|---|---|
| U5R FORWARD PRIMER | M667 | GGCTAACTAGGGAACCCACTG |
| U5R REVERSE PRIMER | AASM | GCTAGAGATTTTCCACACTGACTAA |
| U5R 3' END DONOR PROBE | LTR FL | CACAACAGACGGGCACACACTACTTGA-FL |
| U5R 5' END DONOR PROBE | LTR LC | LC-CACTCAAGGCAAGCTTTATTGAGGC |
| CD3 FORWARD PRIMER | CD3 IN 5' | GGCTATCATTCTTCTTCAAGGTA |
| CD3 REVERSE PRIMER | CD3 IN 3' | CCTCTCTTCAGCCATTTAAGTA |
| CD3 3' END DONOR PROBE | CD3 FL | GGCTGAAGGTTAGGGATACCAATATTCCTGTCTC-FL |
| CD3 5' END DONOR PROBE | CD3 LC | LC-CTAGTGATGGGCTCTTCCCTTGAGCCCTTC |

| STEP AND NUMBER OF CYCLES | | TEMPERATURE | DURATION |
|---|---|---|---|
| 1 CYCLE | 1: DENATURATION | 95°C | 3 MIN |
| 40 CYCLES | 2: DENATURATION | 95°C | 5 SEC |
| | 3: ANNEALING | 57°C | 10 SEC |
| | 4: ELONGATION | 72°C | 8 SEC |

B. pTRIP-CD3

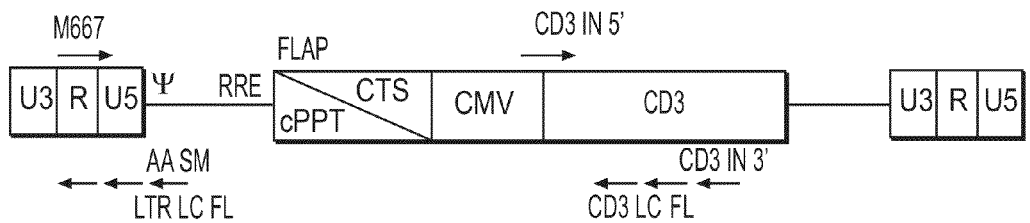

*FIG. 27*

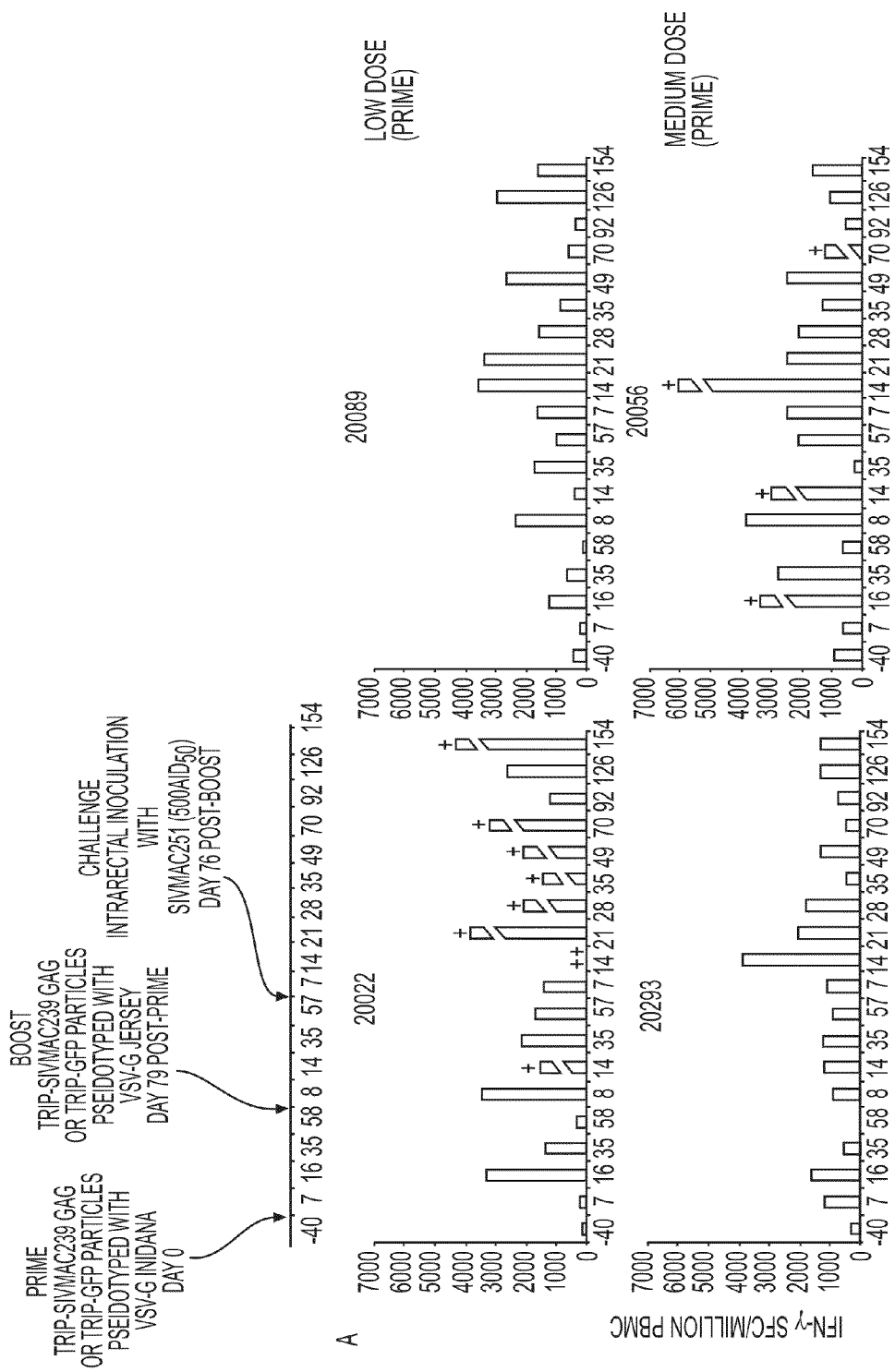
FIG. 28 (1)

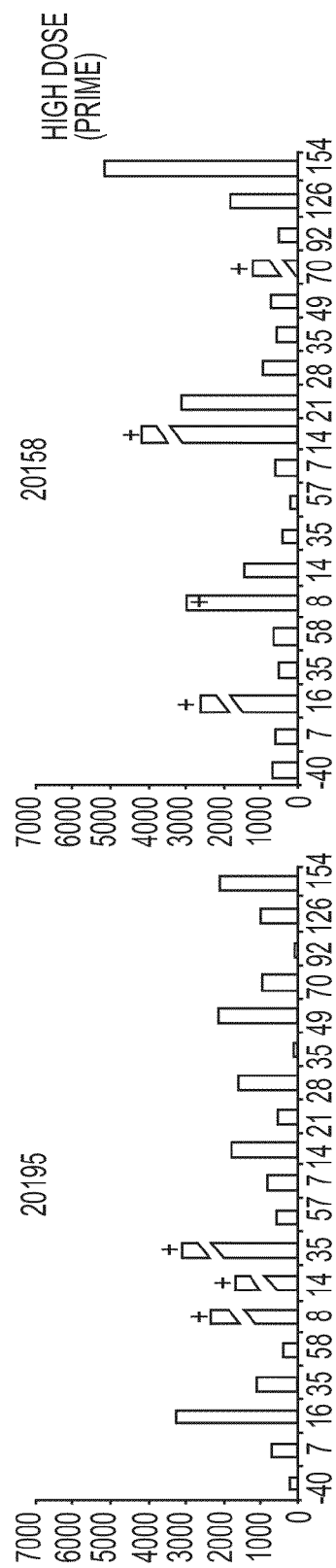
FIG. 28 (1)
(CONTINUED-1)

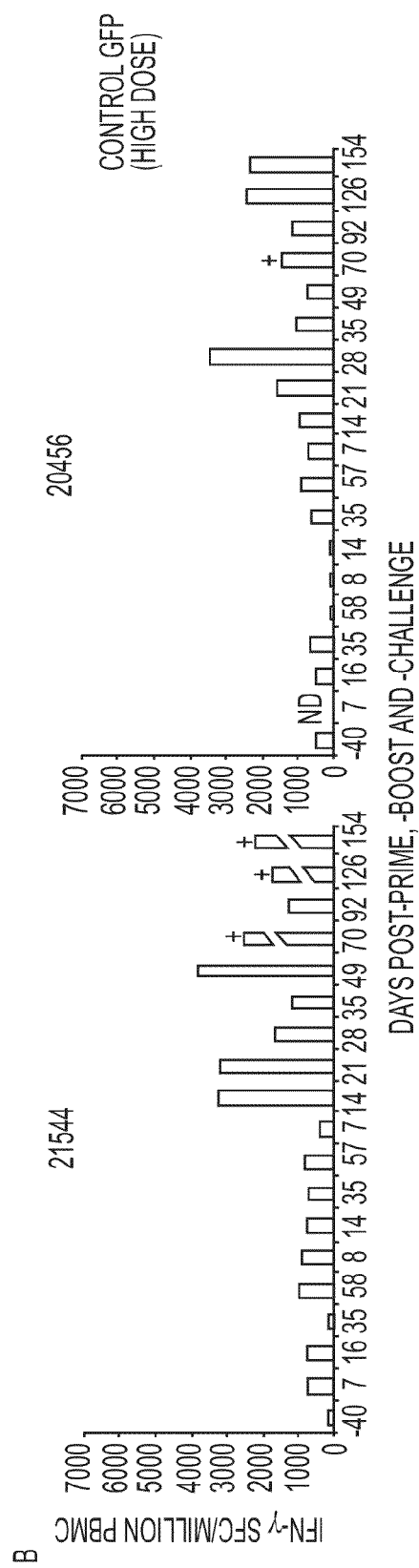
FIG. 28 (1) (CONTINUED-2)

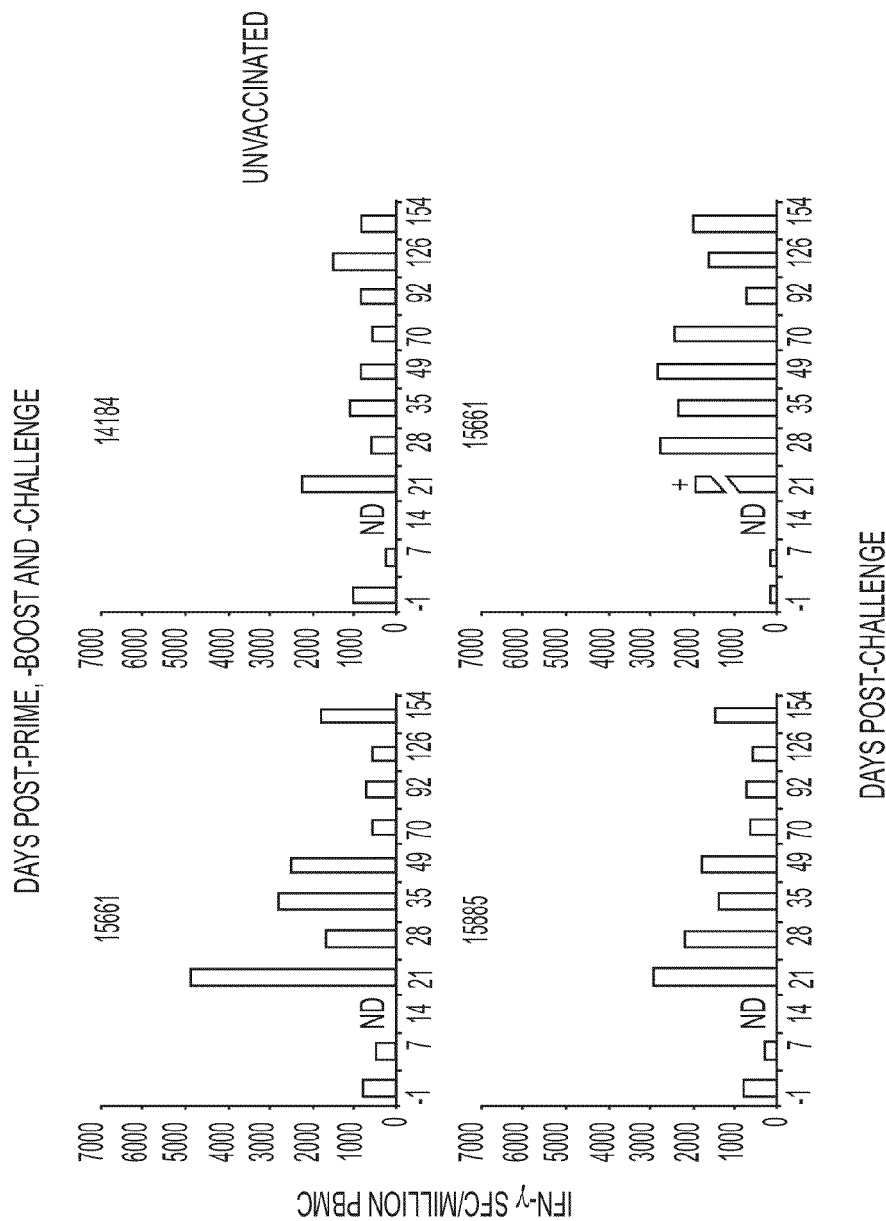
FIG. 28 (1) (CONTINUED-3)

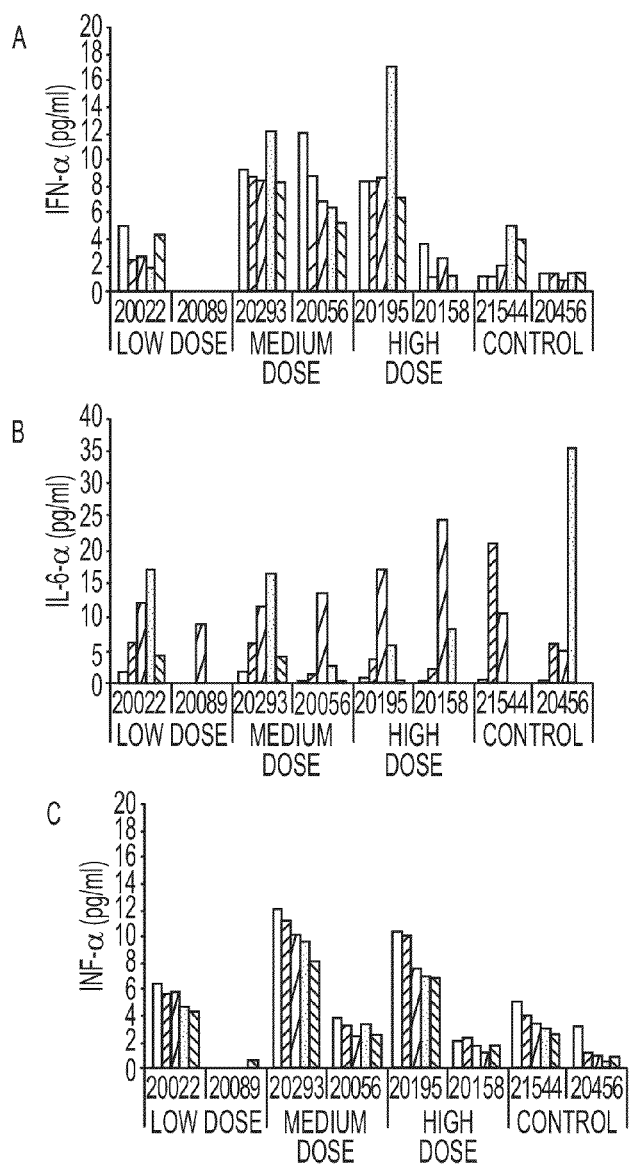
FIG. 28 (2)

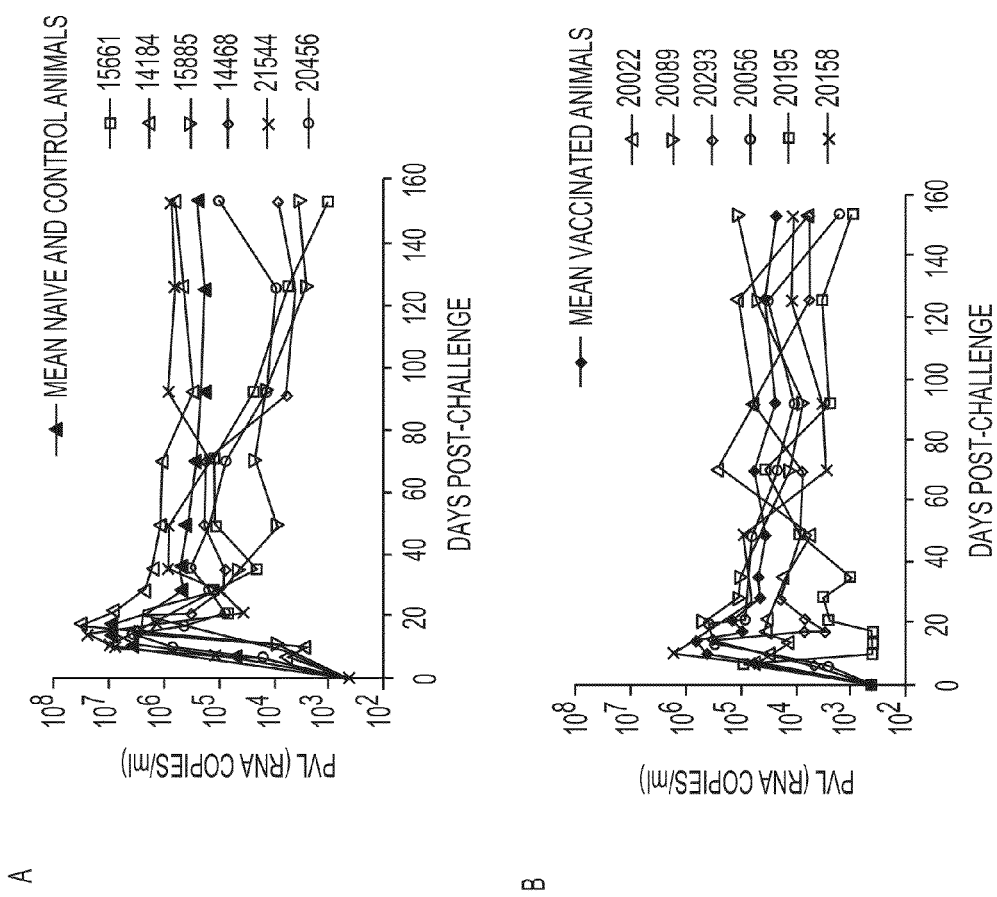
FIG. 29 (1)

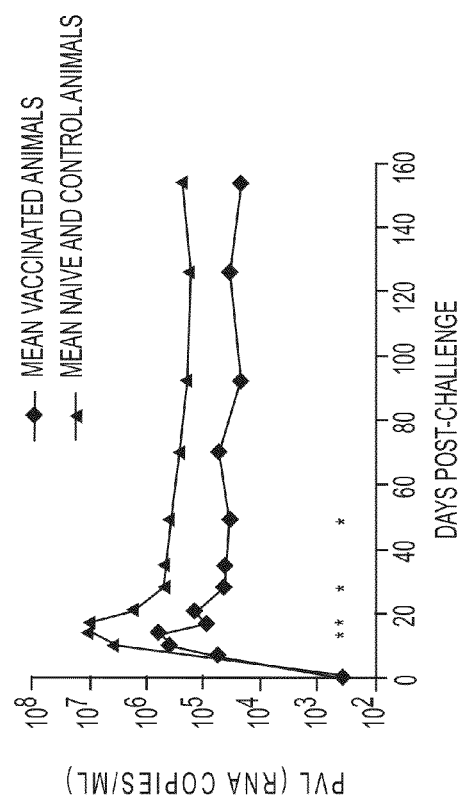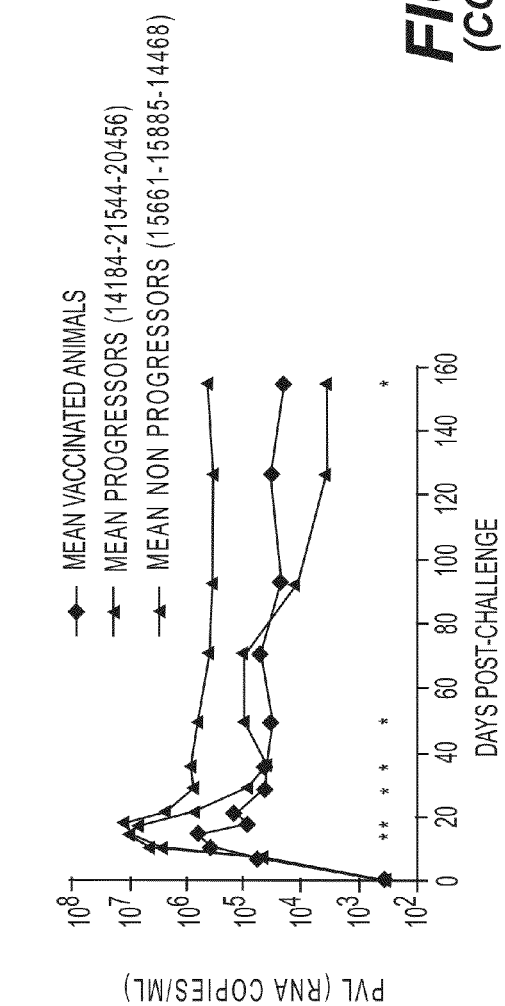
FIG. 29 (1) (CONTINUED-1)

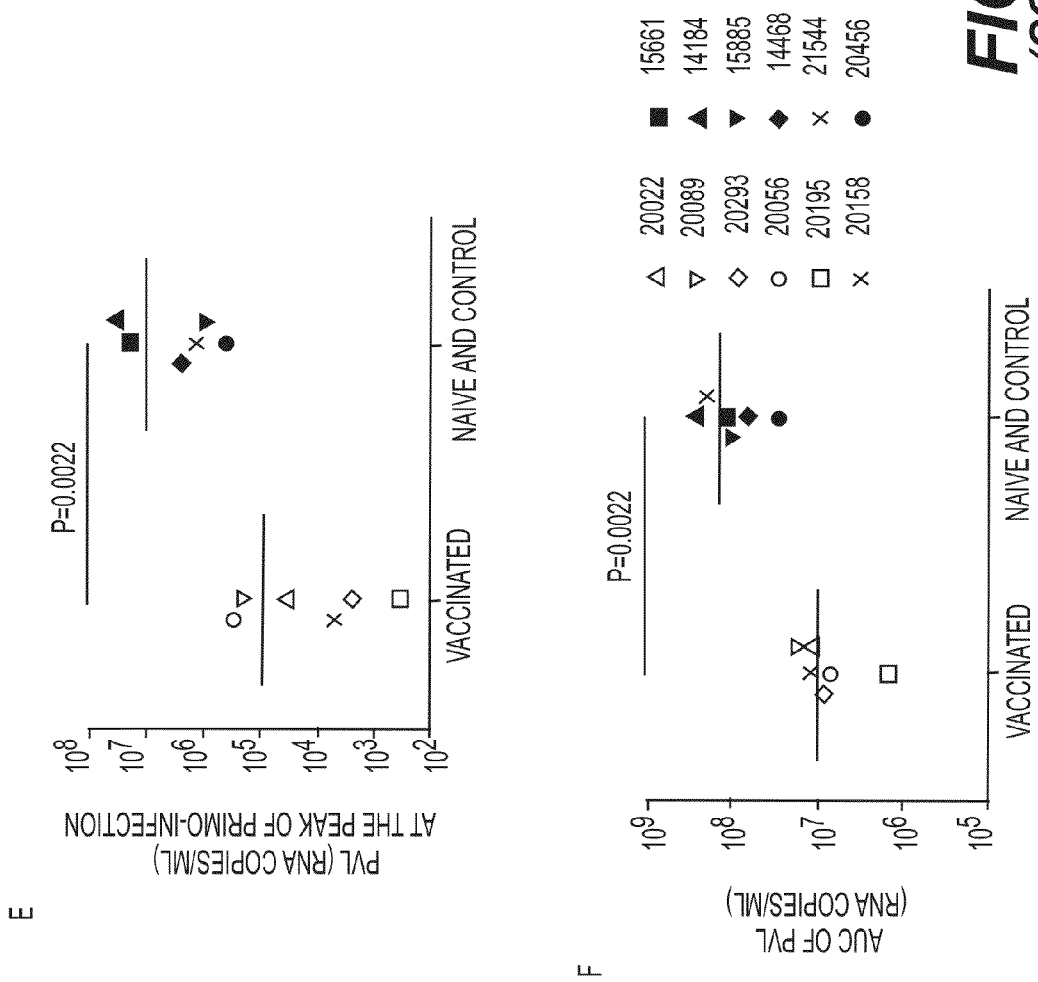
FIG. 29 (1) (CONTINUED-2)

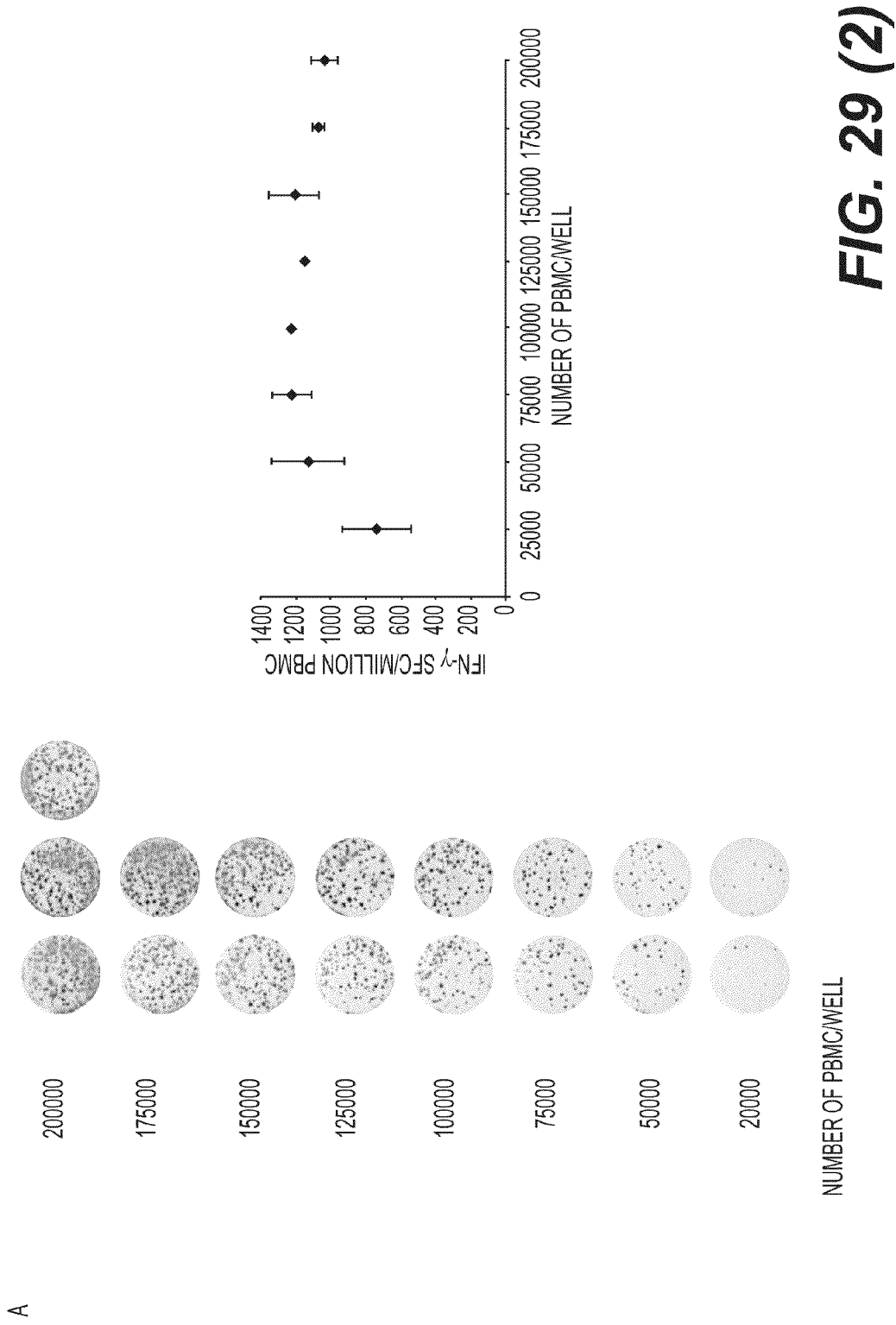
FIG. 29 (2)

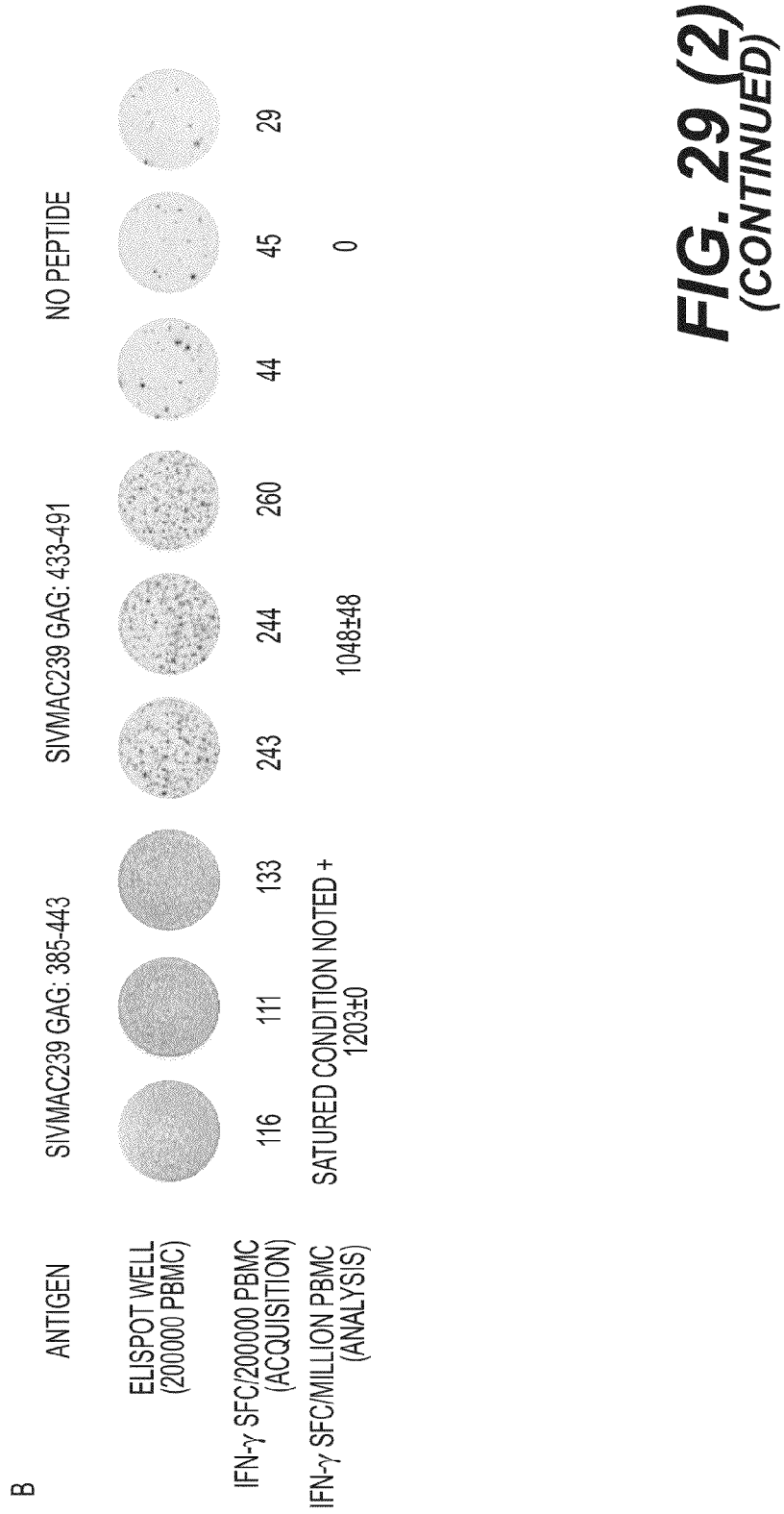

Figure 30:
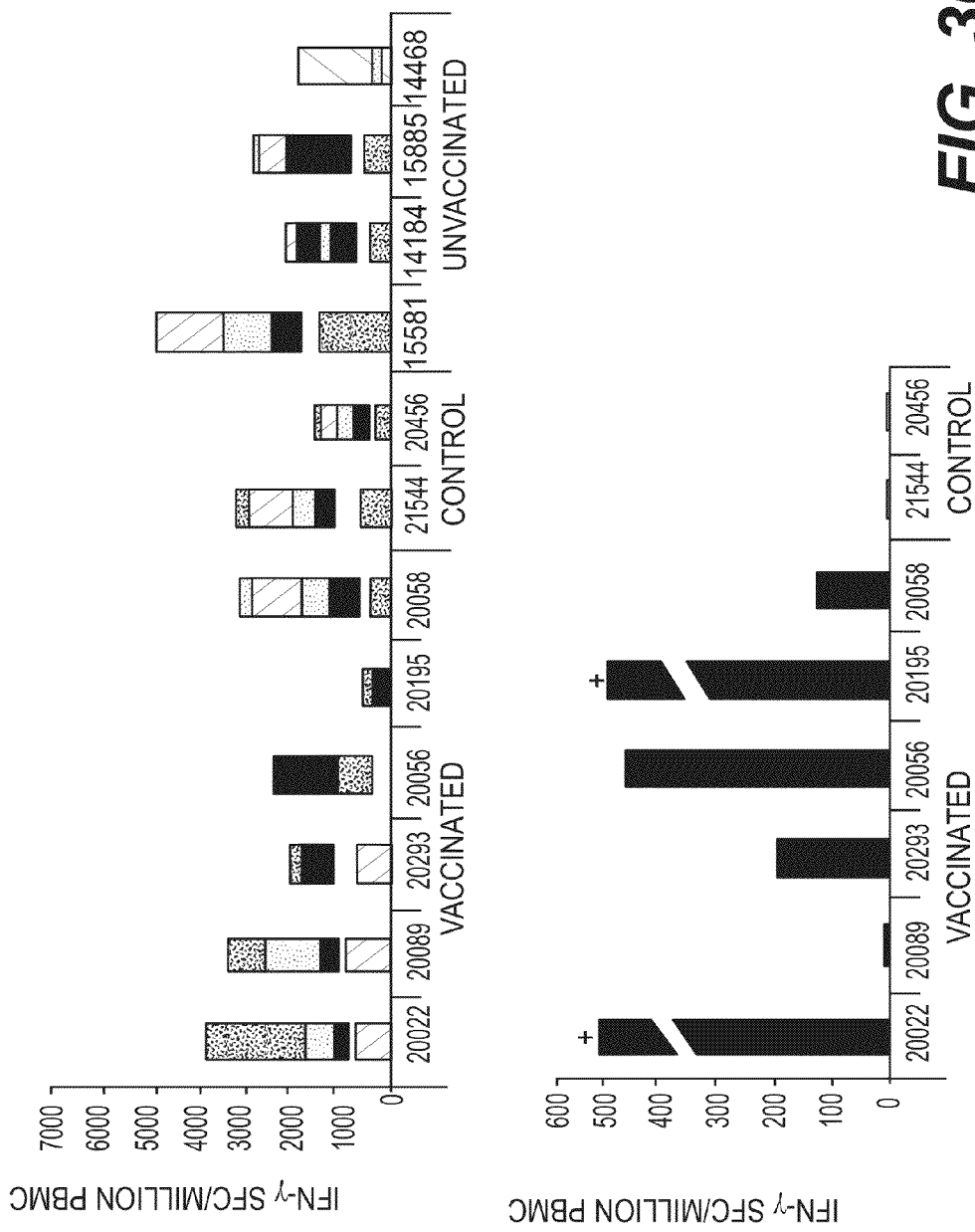

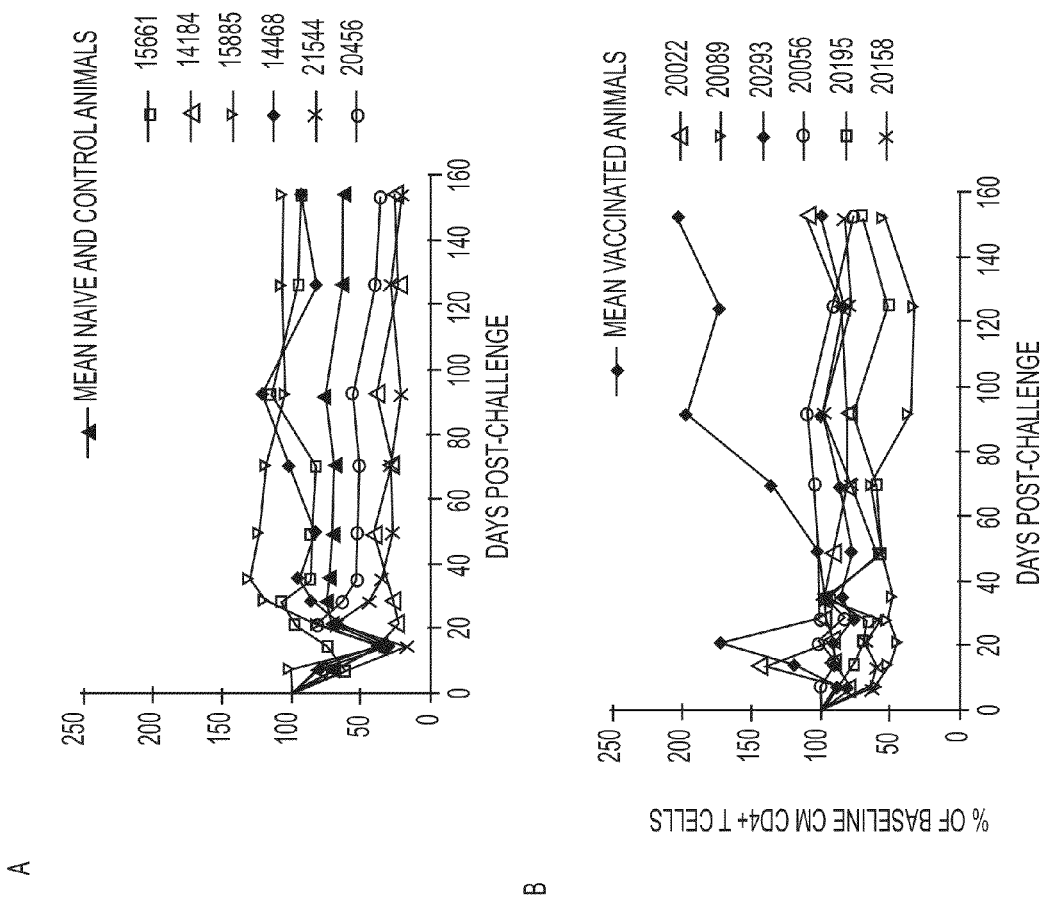
FIG. 30 (1)

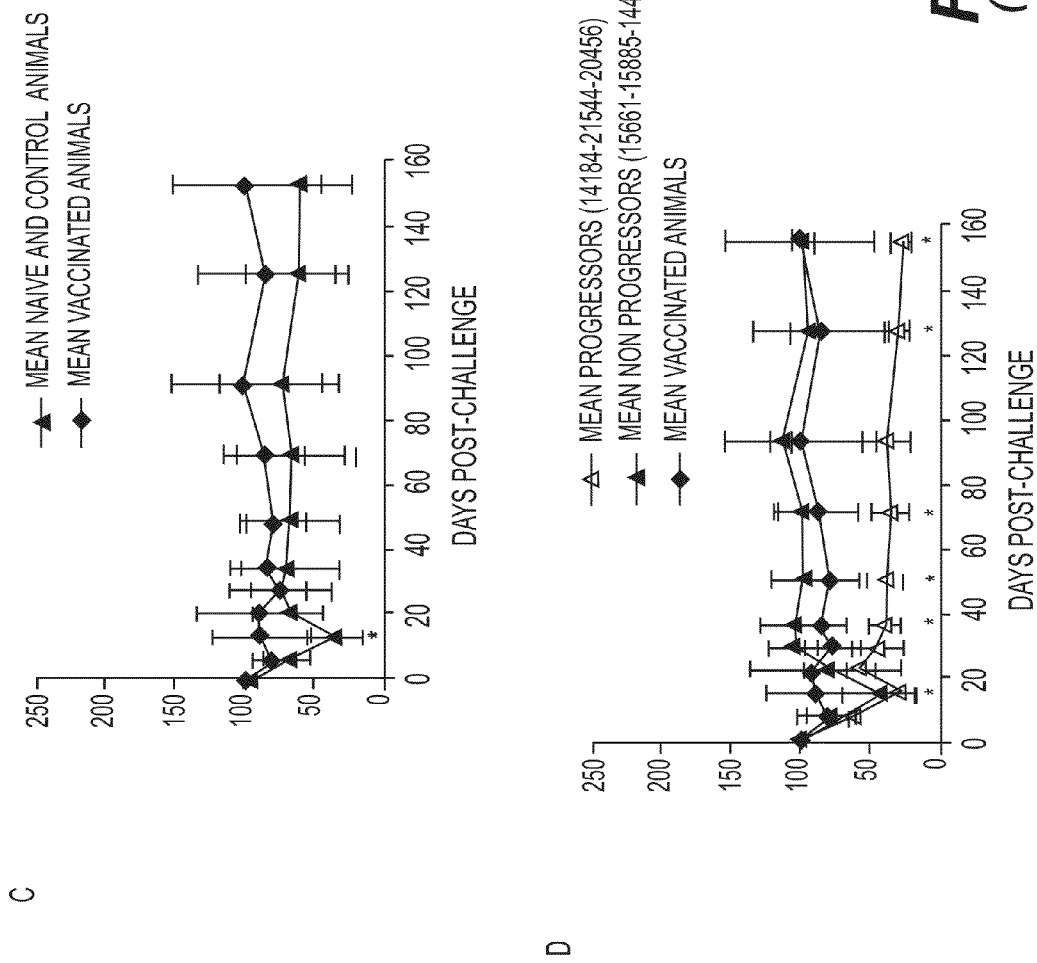
FIG. 30 (1) (CONTINUED-1)

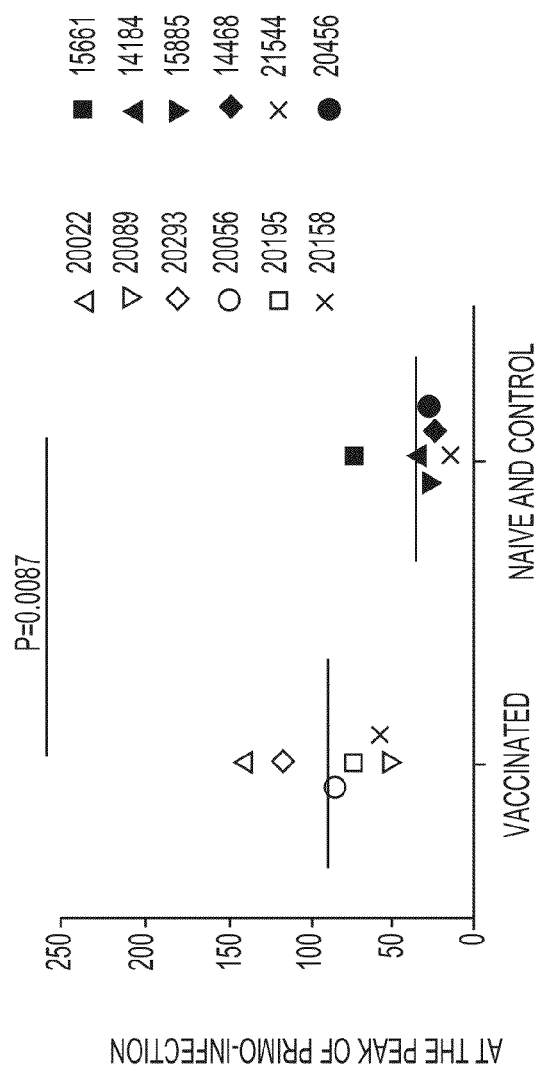
FIG. 30 (1)
(CONTINUED-2)

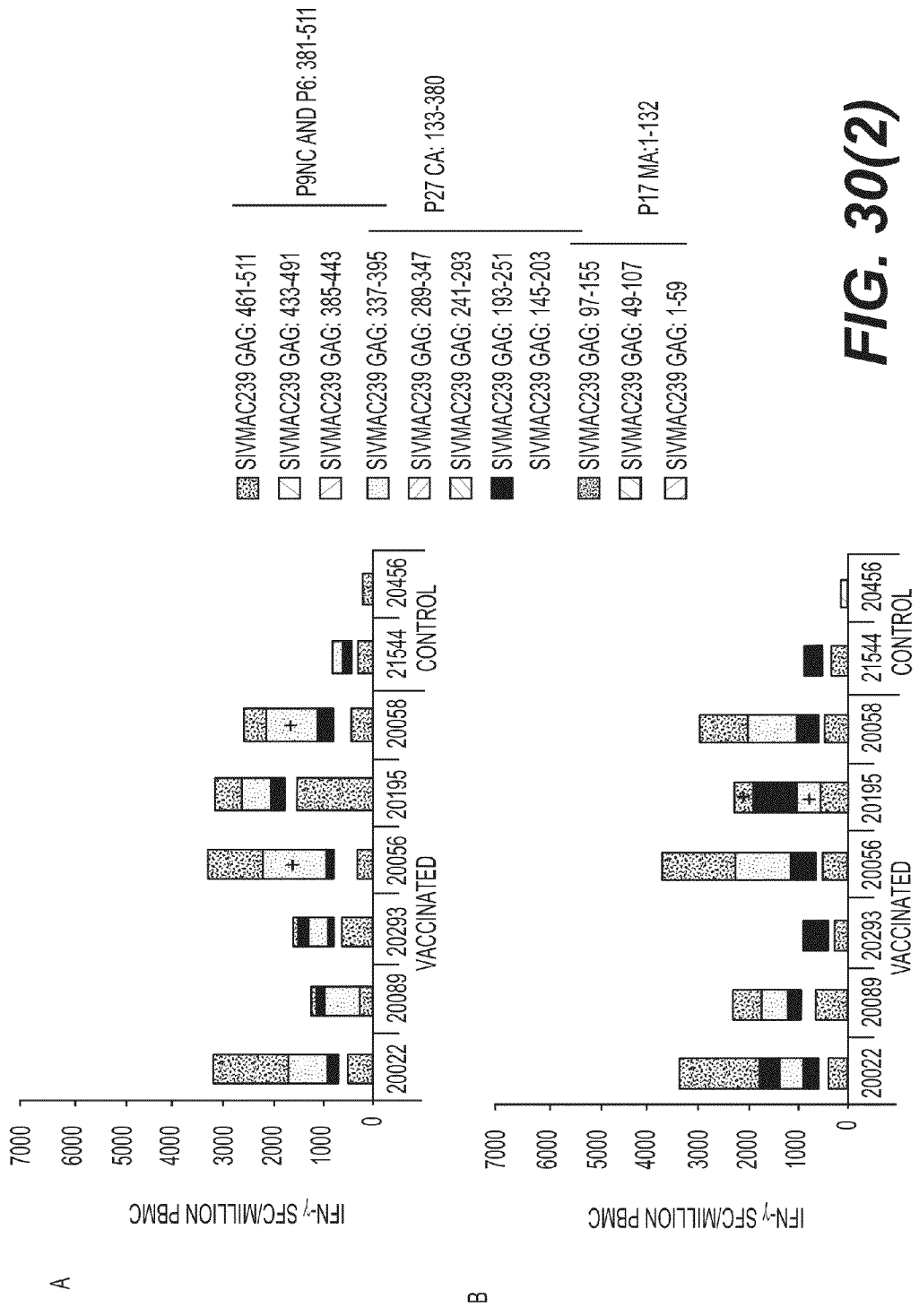

Figure 31:
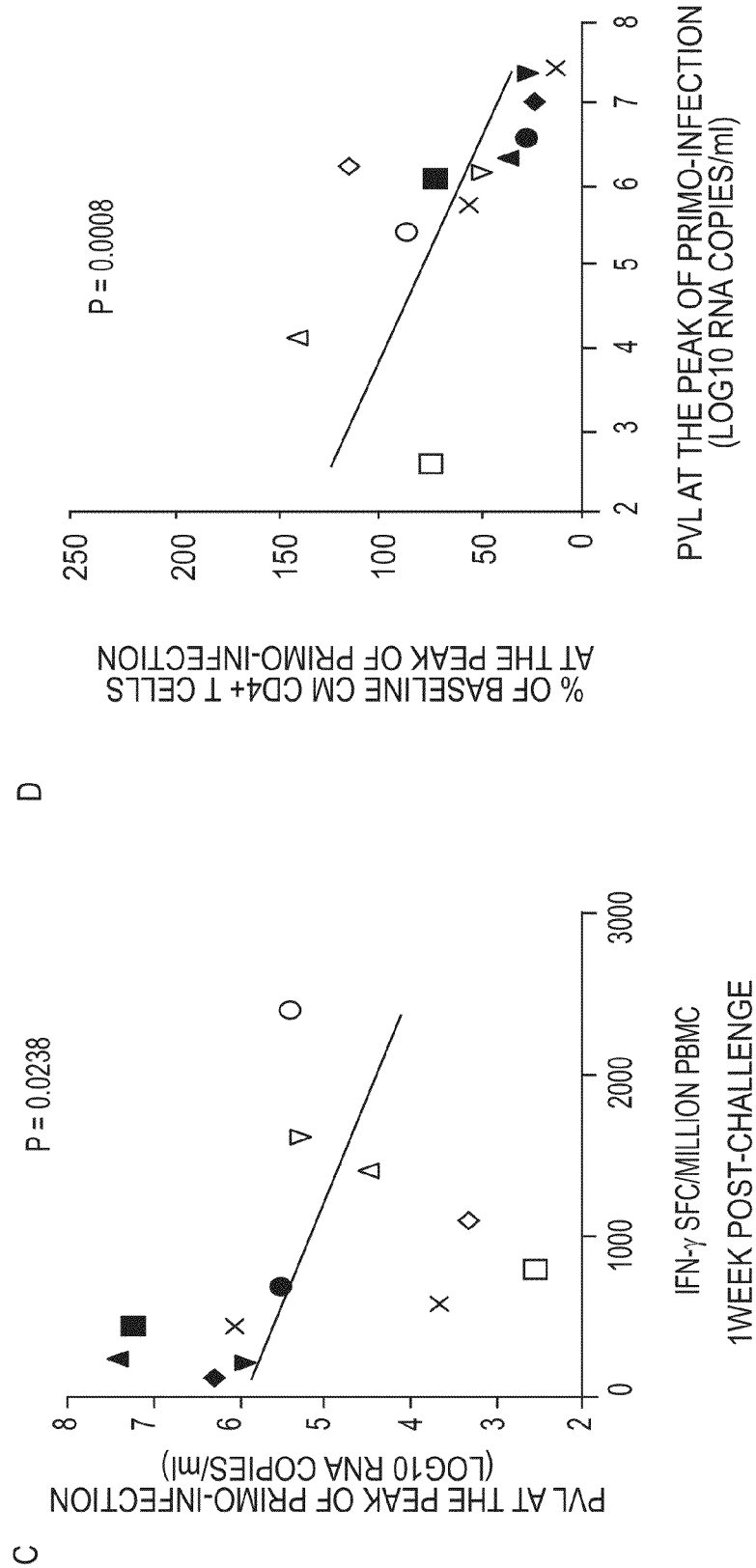
Figure 31:
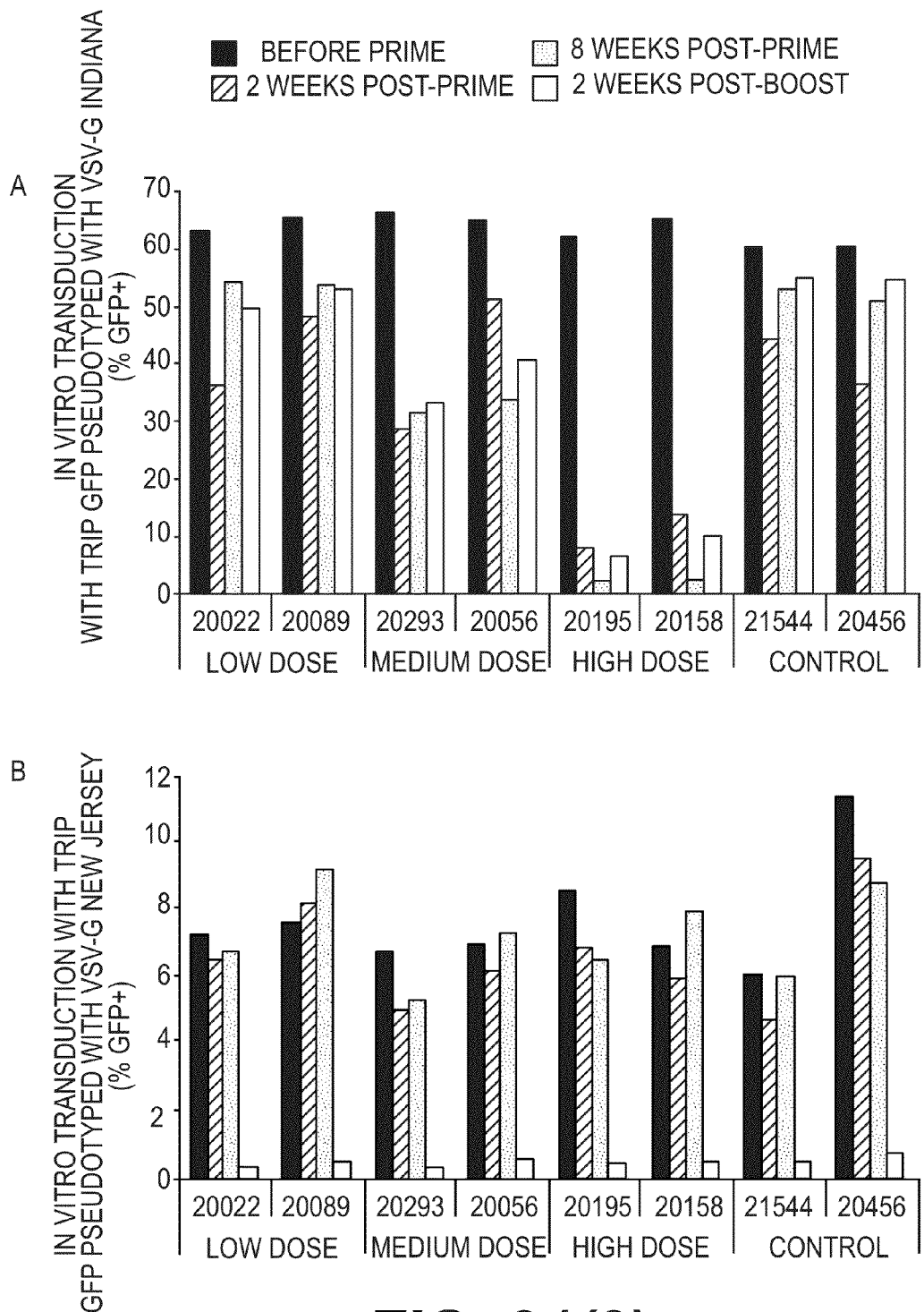

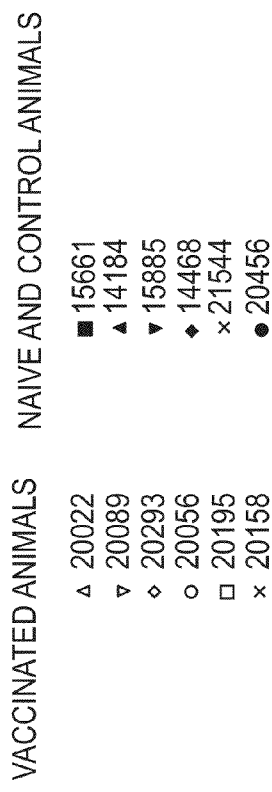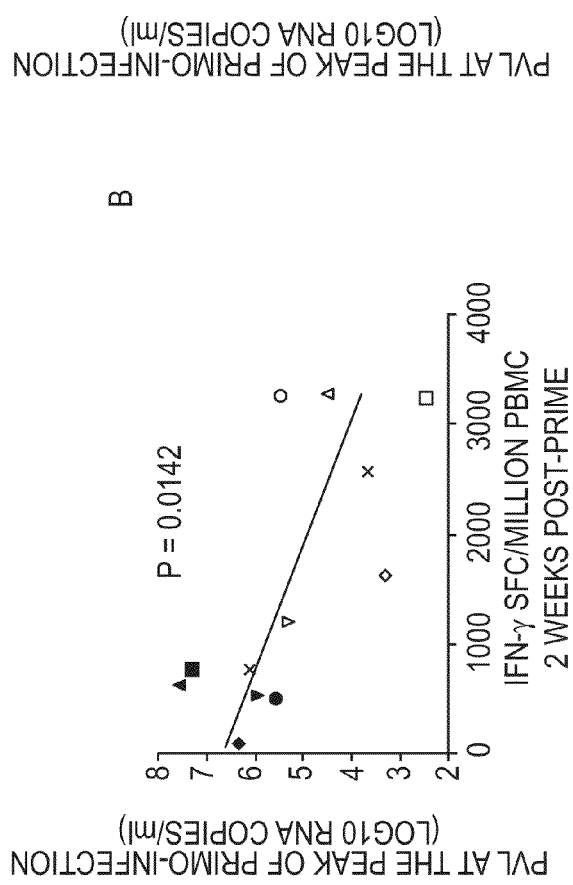
FIG. 31(1)

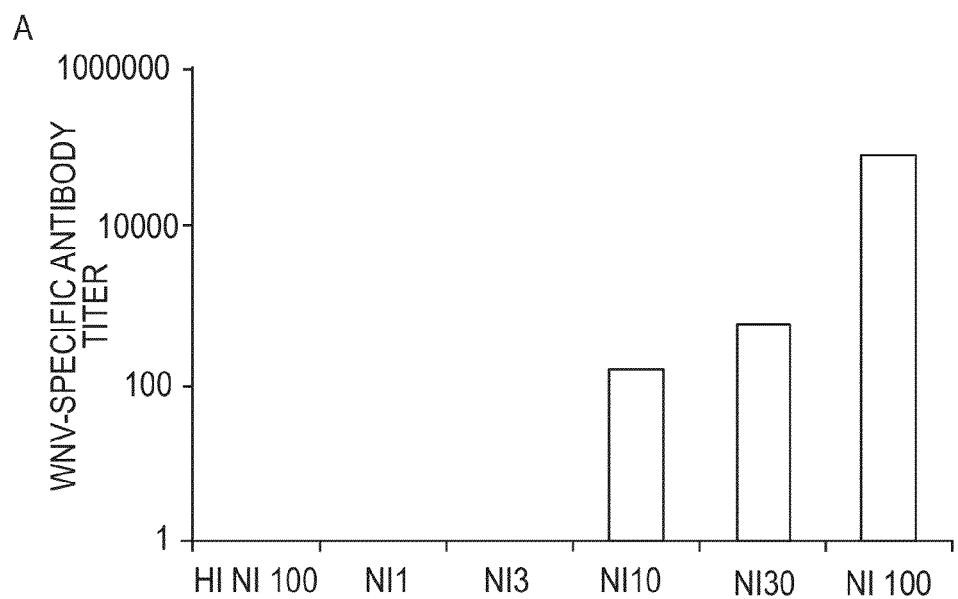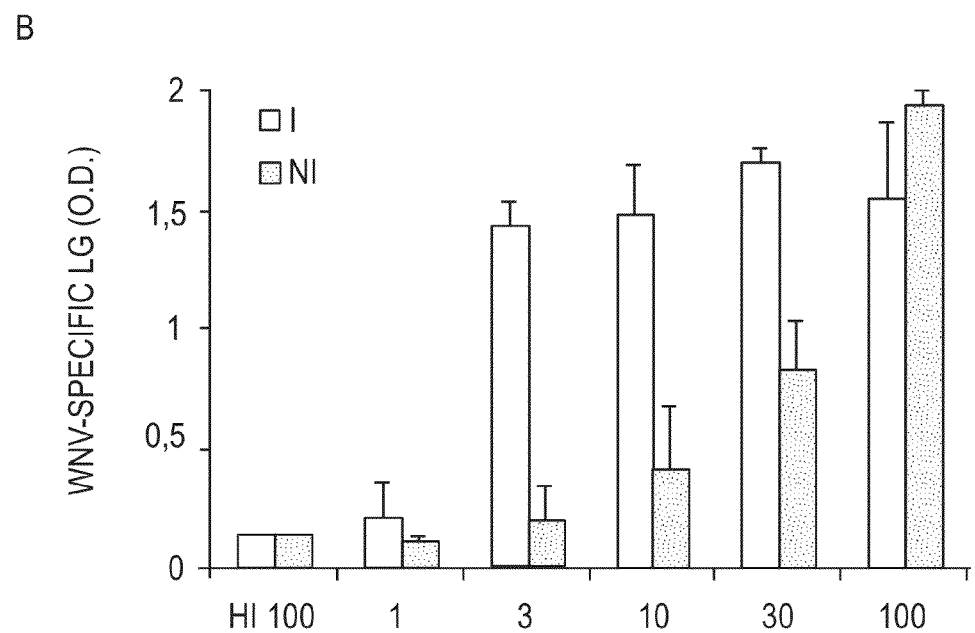
FIG. 45

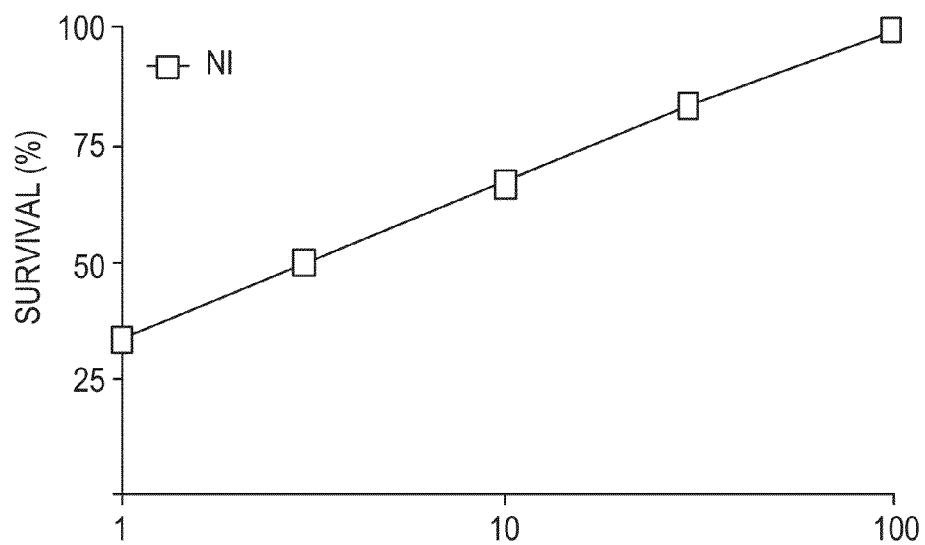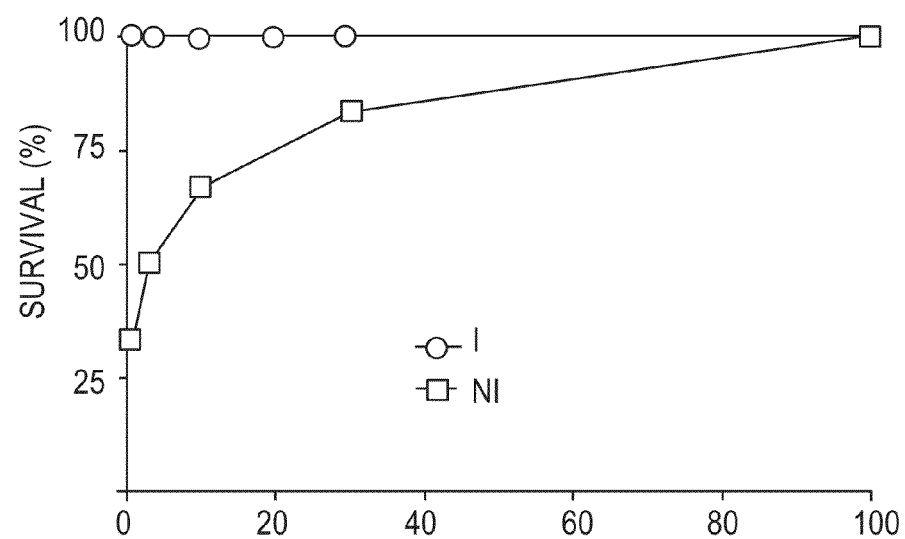
FIG. 47

FIG. 51B

| MOUSE SERA | VECTOR PARTICLES ||||| |
| --- | --- | --- | --- | --- | --- |
| | INDIANA | NEW JERSEY | ISFAHAN | SVCV | COCAL |
| INDIANA | ++ | - | - | - | - |
| NEW JERSEY | - | ++ | - | - | - |
| ISFAHAN | - | - | ++ | - | - |
| SVCV | - | - | - |

A INDIANA

| SERUM | \>75% | 50<>75% | 25<>50% | <25% | 5<>2% | <2% | TOTAL |
|---|---|---|---|---|---|---|---|
| NOT HEATED | 20 | 22 | 29 | 21 | 2 | 2 | 96 |
| HEATED | 13 | 21 | 37 | 22 | 2 | 1 | 96 |

B NEW JERSEY

| SERUM | \>75% | 50<>75% | 25<>50% | <25% | 5<>2% | <2% | TOTAL |
|---|---|---|---|---|---|---|---|
| NOT HEATED | 9 | 17 | 22 | 34 | 10 | 4 | 96 |
| HEATED | 7 | 9 | 33 | 37 | 8 | 2 | 96 |

C COCAL

| SERUM | \>75% | 50<>75% | 25<>50% | <25% | 5<>2% | <2% | TOTAL |
|---|---|---|---|---|---|---|---|
| NOT HEATED | 6 | 11 | 49 | 30 | 4 | 2 | 96 |
| HEATED | 10 | 12 | 40 | 34 | 6 | 1 | 96 |

D SVCV

| SERUM | \>75% | 50<>75% | 25<>50% | <25% | 5<>2% | <2% | TOTAL |
|---|---|---|---|---|---|---|---|
| NOT HEATED | 0 | 0 | 6 | 90 | 0 | 0 | 96 |
| HEATED | 0 | 2 | 3 | 91 | 0 | 0 | 96 |

E ISFAHAN

| SERUM | \>75% | 50<>75% | 25<>50% | <25% | 5<>2% | <2% | TOTAL |
|---|---|---|---|---|---|---|---|
| NOT HEATED | 16 | 17 | 42 | 17 | 3 | 0 | 95 |
| HEATED | 11 | 20 | 35 | 27 | 2 | 0 | 95 |

% OF TRANSDUCTION

*FIG. 58*

SEQUENCE LISTING

<160> NUMBER OF SEQ ID NOS: 84

<210> SEQ ID NO 1
<211> LENGTH: 200
<212> TYPE: DNA
<213> ORGANISM: Artificial
<220> FEATURE:
<223> OTHER INFORMATION: DNA FLAP of CAEV

<400> SEQUENCE: 1
gttccagcca caatttgtcg ctgtagaatc agccatagca gcagccctag tcgccataaa      60
tataaaaaga aagggtgggc tggggacaag ccctatggat atttttatat ataataaaga     120
acagaaaaga ataaataata aatataataa aaattctcaa aaaattcaat tctgttatta     180
cagaataagg aaaagaggac                                                 200

<210> SEQ ID NO 2
<211> LENGTH: 200
<212> TYPE: DNA
<213> ORGANISM: Artificial
<220> FEATURE:
<223> OTHER INFORMATION: DNA FLAP of EIAV

<400> SEQUENCE: 2

```
cttgtaacaa agggagggaa agtatgggag gacagacacc atgggaagta tttatcacta        60
atcaagcaca agtaatacat gagaaacttt tactacagca agcacaatcc tccaaaaaat       120
tttgttttta caaatcccct ggtgaacatg attggaaggg acctactagg gtgctgtgga       180
agggtgatgg tgcagtagta                                                    200

<210> SEQ ID NO 3
<211> LENGTH: 200
<212> TYPE: DNA
<213> ORGANISM: Artificial
<220> FEATURE:
<223> OTHER INFORMATION: DNA FLAP of VISNA

<400> SEQUENCE: 3
ggaccctcat tactctaaat ataaaaagaa agggtgggct agggacaagc cctatggata        60
tatttatatt taataaggaa caacaaagaa tacagcaaca agtaaatca aaacaagaaa        120 aaattcgatt ttgttattac agaacaagaa aaagagggca tccaggagag tggcaaggac       180
caacacaggt actttggggc                                                    200

<210> SEQ ID NO 4
<211> LENGTH: 200
<212> TYPE: DNA
<213> ORGANISM: Artificial
<220> FEATURE:
<223> OTHER INFORMATION: DNA FLAP of SIVAGM

<400> SEQUENCE: 4
tactgatggc ttgcatactt cacaatttta aagaaaggg aggaataggg ggacagactt        60
cagcagagag actaattaat ataataacaa cacaattaga aatacaacat ttacaaacca       120
aaattcaaaa aattttaaat tttagagtct actacagaga agggagagac cctgtgtgga       180
aaggaccggc acaattaatc                                                    200

<210> SEQ ID NO 5
<211> LENGTH: 200
<212> TYPE: DNA
<213> ORGANISM: Artificial
<220> FEATURE:
<223> OTHER INFORMATION: DNA FLAP of HIV-2 ROD

<400> SEQUENCE: 5
tgcatgaatt ttaaaagaag ggggggaata ggggatatga ctccatcaga aagattaatc        60
aatatgatca ccacagaaca agagatacaa ttcctccaag ccaaaaattc aaaattaaaa       120
gattttcggg tctatttcag agaaggcaga gatcagttgt ggaaaggacc tggggaacta       180
ctgtggaaag gagaaggagc                                                    200

<210> SEQ ID NO 6
<211> LENGTH: 200
<212> TYPE: DNA
<213> ORGANISM: Artificial
<220> FEATURE:
<223> OTHER INFORMATION: DNA FLAP of HIV-1 LAI

<400> SEQUENCE: 6
cagtattcat ccacaatttt aaaagaaaag ggggggattgg ggggtacagt gcagggggaaa      60 gaatagtaga cataatagca acagacatac aaactaaaga attacaaaaa caaattacaa       120
aaattcaaaa ttttcgggtt tattacaggg acagcagaga tccactttgg aaaggaccag       180
caaagctcct ctggaaaggt                                                    200
```

<210> SEQ ID NO 7
<211> LENGTH: 119
<212> TYPE: DNA
<213> ORGANISM: Artificial
<220> FEATURE:
<223> OTHER INFORMATION: DNA FLAP of HIV-1

<400> SEQUENCE: 7
ttttaaaaga aaggggggga ttgggggggta cagtgcaggg gaaagaatag tagacataat      60
agcaacagac atacaaacta aagaattaca aaaacaaatt acaaaaattc aaaattttc       119

<210> SEQ ID NO 8
<211> LENGTH: 24
<212> TYPE: PRT
<213> ORGANISM: Artificial
<220> FEATURE:
<223> OTHER INFORMATION: 2A peptide

<400> SEQUENCE: 8

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 9
<211> LENGTH: 23
<212> TYPE: DNA
<213> ORGANISM: Artificial
<220> FEATURE:
<223> OTHER INFORMATION: Forward primer

<400> SEQUENCE: 9
tgtccacctg ccattaagcc cga                                              23

<210> SEQ ID NO 10
<211> LENGTH: 24
<212> TYPE: DNA
<213> ORGANISM: Artificial
<220> FEATURE:
<223> OTHER INFORMATION: Backward primer

<400> SEQUENCE: 10
gcagaggagg aaattaccca gtac                                             24

<210> SEQ ID NO 11
<211> LENGTH: 23
<212> TYPE: DNA
<213> ORGANISM: Artificial
<220> FEATURE:
<223> OTHER INFORMATION: Internal probe

<400> SEQUENCE: 11
tgtccacctg ccattaagcc cga                                              23

<210> SEQ ID NO 12
<211> LENGTH: 15
<212> TYPE: PRT
<213> ORGANISM: Simian immunodeficiency virus

<400> SEQUENCE: 12

Gln Thr Asp Ala Ala Val Lys Asn Trp Met Thr Gln Thr Leu Leu
1               5                   10                  15

<210> SEQ ID NO 13
<211> LENGTH: 15

```
<212> TYPE: PRT
<213> ORGANISM: Simian immunodeficiency virus

<400> SEQUENCE: 13

Glu Asn Leu Lys Ser Leu Tyr Asn Thr Val Cys Val Ile Trp Cys
1               5                   10                  15

<210> SEQ ID NO 14
<211> LENGTH: 15
<212> TYPE: PRT
<213> ORGANISM: Simian immunodeficiency virus

<400> SEQUENCE: 14

Tyr Val Asp Arg Phe Tyr Lys Ser Leu Arg Ala Glu Gln Thr Asp
1               5                   10                  15

<210> SEQ ID NO 15
<211> LENGTH: 527
<212> TYPE: PRT
<213> ORGANISM: Vesicular stomatitis virus

<400> SEQUENCE: 15

Met Thr Ser Ser Val Thr Ile Ser Val Val Leu Leu Ile Ser Phe Ile
1               5                   10                  15

Thr Pro Leu Tyr Ser Tyr Leu Ser Ile Ala Phe Pro Glu Asn Thr Lys
                20                  25                  30

Leu Asp Trp Lys Pro Val Thr Lys Asn Thr Arg Tyr Cys Pro Met Gly
            35                  40                  45

Gly Glu Trp Phe Leu Glu Pro Gly Leu Gln Glu Ser Phe Leu Ser
        50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
                100                 105                 110

Cys Asp Thr Ala Leu Ala Ser Tyr Lys Ser Gly Thr Leu Val Ser Leu
            115                 120                 125

Gly Phe Pro Pro Glu Ser Cys Gly Tyr Ala Ser Val Thr Asp Ser Glu
        130                 135                 140

Phe Leu Val Ile Met Ile Thr Pro His His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
            180                 185                 190

Gln Thr Lys Lys Asn Ile Cys Gly Gln Ser Phe Thr Pro Leu Thr Val
        195                 200                 205

Thr Val Ala Tyr Asp Lys Thr Lys Glu Ile Ala Ala Gly Gly Ile Val
    210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Met Leu Lys Leu Arg Ser Lys Arg Asn Leu Tyr Phe Pro
            260                 265                 270

Cys Leu Lys Met Cys Pro Thr Gly Ile Arg Gly Glu Ile Tyr Pro Ser
        275                 280                 285
```

```
Ile Arg Trp Ala Gln Val Leu Thr Ser Glu Ile Gln Arg Ile Leu Asp
    290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
                340                 345                 350

Arg Tyr Val Arg Met Trp Ile Asp Gly Pro Val Leu Lys Glu Pro Lys
                355                 360                 365

Gly Lys Arg Glu Ser Pro Ser Gly Ile Ser Ser Asp Ile Trp Thr Gln
370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
                420                 425                 430

Pro Gln Leu Pro His Ala Gln Ser Ile Ala Asp Asp Ser Glu Glu Ile
                435                 440                 445

Phe Phe Gly Cys His Pro Asp Thr Gly Val Ser Lys Asn Pro Val Glu
                450                 455                 460

Leu Val Thr Gly Trp Phe Thr Ser Trp Lys Glu Ser Leu Ala Ala Gly
465                 470                 475                 480

Ser Cys Pro Asp Leu Arg Cys Pro Pro Leu Phe Pro Gly Ile Val Tyr
                485                 490                 495

Tyr Leu Gln Lys Ala Gln Met Glu Glu Arg Gly Glu Arg Ser Asp Ser
                500                 505                 510

Phe Glu Met Arg Ile Phe Lys Pro Asn Asn Met Arg Ala Arg Val
                515                 520                 525

<210> SEQ ID NO 16
<211> LENGTH: 512
<212> TYPE: PRT
<213> ORGANISM: Vesicular stomatitis virus

<400> SEQUENCE: 16

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
                20                  25                  30

Asn Val Pro Ser Ser Tyr His Tyr Cys Pro Ser Ser Ser Asp Gln Asn
                35                  40                  45

Trp His Asn Asp Leu Leu Gly Ile Thr Met Lys Val Lys Met Pro Lys
            50                  55                  60

Thr His Lys Ala Ile Gln Ala Asp Gly Trp Met Cys His Ala Ala Lys
65              70                  75                  80

Trp Ile Thr Thr Cys Asp Phe Arg Trp Tyr Gly Pro Lys Tyr Ile Thr
                85                  90                  95

His Ser Ile His Ser Ile Gln Pro Thr Ser Glu Gln Cys Lys Glu Ser
                100                 105                 110

Ile Lys Gln Thr Lys Gln Gly Thr Trp Met Ser Pro Gly Phe Pro Pro
            115                 120                 125

Gln Asn Cys Gly Tyr Ala Thr Val Thr Asp Ser Val Ala Val Val Val
            130                 135                 140
```

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Cys Glu
            165                 170                 175

Thr Val His Asn Ser Thr Val Trp Tyr Ser Asp Tyr Lys Val Thr Gly
            180                 185                 190

Leu Cys Asp Ala Thr Leu Val Asp Thr Glu Ile Thr Phe Phe Ser Glu
            195                 200                 205

Asp Gly Lys Lys Glu Ser Ile Gly Lys Pro Asn Thr Gly Tyr Arg Ser
210                 215                 220

Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
            245                 250                 255

Val Asp Gln Asp Val Tyr Ala Ala Ala Lys Leu Pro Glu Cys Pro Val
            260                 265                 270

Gly Ala Thr Ile Ser Ala Pro Thr Gln Thr Ser Val Asp Val Ser Leu
            275                 280                 285

Ile Leu Asp Val Glu Arg Ile Leu Asp Tyr Ser Leu Cys Gln Glu Thr
            290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
            325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
            355                 360                 365

Thr Glu Arg Glu Leu Trp Thr Glu Trp Phe Pro Tyr Glu Gly Val Glu
            370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
            405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
            435                 440                 445

Lys Asn Pro Val Glu Leu Ile Glu Gly Trp Phe Ser Ser Trp Lys Ser
450                 455                 460

Thr Val Val Thr Phe Phe Phe Ala Ile Gly Val Phe Ile Leu Leu Tyr
465                 470                 475                 480

Val Val Ala Arg Ile Val Ile Ala Val Arg Tyr Arg Tyr Gln Gly Ser
            485                 490                 495

Asn Asn Lys Arg Ile Tyr Asn Asp Ile Glu Met Ser Arg Phe Arg Lys
            500                 505                 510

<210> SEQ ID NO 17
<211> LENGTH: 511
<212> TYPE: PRT
<213> ORGANISM: Vesicular stomatitis virus

<400> SEQUENCE: 17

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Asp Leu Asn Trp
        35                  40                  45

His Asn Asp Leu Val Gly Thr Ala Leu Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
            165                 170                 175

Val His Asn Ser Thr Thr Trp His Ser Asp Tyr Lys Val Lys Gly Leu
        180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Lys Gly Thr Gly Phe Arg Ser Asn
        210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
            245                 250                 255

Asp Lys Asp Leu Phe Ala Ala Ala Arg Phe Pro Glu Cys Pro Glu Gly
        260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
        290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
            325                 330                 335

Gly Thr Leu Lys Tyr Phe Glu Thr Arg Tyr Ile Arg Val Asp Ile Ala
        340                 345                 350

Ala Pro Ile Leu Ser Arg Met Val Gly Met Ile Ser Gly Thr Thr Thr
        355                 360                 365

Glu Arg Val Leu Trp Asp Asp Trp Ala Pro Tyr Glu Asp Val Glu Ile
        370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Thr Leu Phe Phe Gly Asp Thr Gly Leu Ser Lys

```
                   435                 440                 445
Asn Pro Ile Glu Phe Val Glu Gly Trp Phe Ser Ser Trp Lys Ser Ser
450                 455                 460

Ile Ala Ser Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys
                500                 505                 510

<210> SEQ ID NO 18
<211> LENGTH: 517
<212> TYPE: PRT
<213> ORGANISM: Vesicular stomatitis virus

<400> SEQUENCE: 18

Met Leu Ser Tyr Leu Ile Leu Ala Ile Val Ser Pro Ile Leu Gly
1               5                   10                  15

Lys Ile Glu Ile Val Phe Pro Gln His Thr Thr Gly Asp Trp Lys Arg
                20                  25                  30

Val Pro His Glu Tyr Asn Tyr Cys Pro Thr Ser Ala Asp Lys Asn Ser
                35                  40                  45

His Gly Thr Gln Thr Gly Ile Pro Ile Glu Leu Thr Met Pro Lys Gly
            50                  55                  60

Leu Thr Thr His Gln Val Asp Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Gly Pro Thr Asp Tyr Gln Cys Leu Glu Ala Ile
                100                 105                 110

Lys Ala Tyr Lys Asp Gly Val Ser Phe Asn Pro Gly Phe Pro Pro Gln
            115                 120                 125

Ser Cys Gly Tyr Gly Thr Val Thr Asp Ala Glu Ala His Ile Ile Thr
130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175

Val His Asn Ser Thr Lys Trp Phe Thr Ser Asp Gly Glu Ser Val
                180                 185                 190

Cys Ser Gln Leu Phe Thr Leu Val Gly Gly Thr Phe Phe Ser Asp Ser
            195                 200                 205

Glu Glu Ile Thr Ser Met Gly Leu Pro Glu Thr Gly Ile Arg Ser Asn
            210                 215                 220

Tyr Phe Pro Tyr Ile Ser Thr Glu Gly Ile Cys Lys Met Pro Phe Cys
225                 230                 235                 240

Arg Lys Pro Gly Tyr Lys Leu Lys Asn Asp Leu Trp Phe Gln Ile Thr
                245                 250                 255

Asp Pro Asp Leu Asp Lys Thr Val Arg Asp Leu Pro His Ile Lys Asp
            260                 265                 270

Cys Asp Leu Ser Ser Ile Ile Thr Pro Gly Glu His Ala Thr Asp
            275                 280                 285

Ile Ser Leu Ile Ser Asp Val Glu Arg Ile Leu Asp Tyr Ser Leu Cys
            290                 295                 300

Gln Asn Thr Trp Ser Lys Ile Glu Ala Gly Glu Pro Ile Thr Pro Val
```

```
            305                 310                 315                 320
Asp Leu Ser Tyr Leu Gly Pro Lys Asn Pro Gly Val Gly Pro Val Phe
                325                 330                 335

Thr Ile Ile Asn Gly Ser Leu His Tyr Phe Thr Ser Lys Tyr Leu Arg
            340                 345                 350

Val Glu Leu Glu Asn Pro Val Ile Pro Arg Met Glu Gly Arg Val Ala
        355                 360                 365

Gly Thr Arg Ile Val Arg Gln Leu Trp Asp Gln Trp Phe Pro Phe Gly
    370                 375                 380

Glu Ala Glu Ile Gly Pro Asn Gly Val Leu Lys Thr Lys Gln Gly Tyr
385                 390                 395                 400

Lys Phe Pro Leu His Ile Ile Gly Thr Gly Glu Val Asp Ser Asp Ile
                405                 410                 415

Lys Met Glu Arg Val Val Lys His Trp Glu His Pro His Ile Glu Ala
            420                 425                 430

Ala Gln Thr Phe Leu Lys Lys Asp Asp Thr Gly Glu Val Leu Tyr Tyr
        435                 440                 445

Gly Asp Thr Gly Val Ser Lys Asn Pro Val Glu Leu Val Glu Gly Trp
    450                 455                 460

Phe Ser Gly Trp Arg Ser Ser Ile Met Gly Val Leu Ala Val Ile Ile
465                 470                 475                 480

Gly Phe Val Ile Leu Ile Phe Leu Ile Arg Leu Ile Gly Val Leu Ser
                485                 490                 495

Ser Leu Phe Arg Pro Lys Arg Arg Pro Ile Tyr Lys Ser Asp Val Glu
            500                 505                 510

Met Ala His Phe Arg
            515

<210> SEQ ID NO 19
<211> LENGTH: 523
<212> TYPE: PRT
<213> ORGANISM: Vesicular stomatitis virus

<400> SEQUENCE: 19

Met Thr Ser Val Leu Phe Met Val Gly Val Leu Leu Gly Ala Phe Gly
1               5                   10                  15

Ser Thr His Cys Ser Ile Gln Ile Val Phe Pro Ser Glu Thr Lys Leu
            20                  25                  30

Val Trp Lys Pro Val Leu Lys Gly Thr Arg Tyr Cys Pro Gln Ser Ala
        35                  40                  45

Glu Leu Asn Leu Glu Pro Asp Leu Lys Thr Met Ala Phe Asp Ser Lys
    50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
                85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
        115                 120                 125

Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
```

```
                165                 170                 175
Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205

Val Met Tyr Pro Gln Thr Lys Pro Thr Lys Gly Ala Asp Leu Thr Leu
    210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
            260                 265                 270

Phe Pro Asp Cys Leu Val Gly Ser Val Val Lys Ser Thr Leu Leu Ser
        275                 280                 285

Glu Gly Val Gln Thr Ala Leu Trp Glu Thr Arg Leu Leu Asp Tyr
    290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
            340                 345                 350

Tyr Ile Arg Val Trp Ile Asp Ser Pro Ile Leu Lys Glu Ile Lys Gly
        355                 360                 365

Lys Lys Glu Ser Ala Ser Gly Ile Asp Thr Val Leu Trp Glu Gln Trp
    370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Leu Gly Met Gly Ile Val
                405                 410                 415

Asp Gln Asp Leu Gln Glu Leu Ser Ser Val Asn Pro Val Asp His Pro
            420                 425                 430

His Val Pro Ile Ala Gln Ala Phe Val Ser Glu Gly Glu Glu Val Phe
        435                 440                 445

Phe Gly Asp Thr Gly Val Ser Lys Asn Pro Ile Glu Leu Ile Ser Gly
    450                 455                 460

Trp Phe Ser Asp Trp Lys Glu Thr Ala Ala Leu Gly Phe Ala Ala
465                 470                 475                 480

Ile Ser Val Ile Leu Ile Ile Gly Leu Met Arg Leu Pro Leu Leu
                485                 490                 495

Cys Arg Arg Arg Lys Gln Lys Lys Val Ile Tyr Lys Asp Val Glu Leu
            500                 505                 510

Asn Ser Phe Asp Pro Arg Gln Ala Phe His Arg
        515                 520

<210> SEQ ID NO 20
<211> LENGTH: 518
<212> TYPE: PRT
<213> ORGANISM: Vesicular stomatitis virus

<400> SEQUENCE: 20

Met Thr Asp Thr Val Leu Gly Lys Phe Gln Ile Val Phe Pro Asp Gln
1               5                   10                  15

Asn Glu Leu Glu Trp Thr Pro Val Val Gly Asp Ser Arg His Cys Pro
```

-continued

```
                20                  25                  30
Gln Ser Ser Glu Met Gln Phe Asp Gly Ser Arg Ser Gln Thr Ile Leu
         35                  40                  45
Thr Gly Lys Ala Pro Val Gly Ile Thr Pro Ser Lys Ser Asp Gly Phe
 50                  55                  60
Ile Cys His Ala Ala Lys Trp Val Thr Thr Cys Asp Phe Arg Trp Tyr
 65                  70                  75                  80
Gly Pro Lys Tyr Ile Thr His Ser Ile His His Leu Arg Pro Thr Thr
                 85                  90                  95
Ser Asp Cys Glu Thr Ala Leu Gln Arg Tyr Lys Asp Gly Ser Leu Ile
            100                 105                 110
Asn Leu Gly Phe Pro Pro Glu Ser Cys Gly Tyr Ala Thr Val Thr Asp
        115                 120                 125
Ser Glu Ala Met Leu Val Gln Val Thr Pro His His Val Gly Val Asp
    130                 135                 140
Asp Tyr Arg Gly His Trp Ile Asp Pro Leu Phe Pro Gly Gly Glu Cys
145                 150                 155                 160
Ser Thr Asn Phe Cys Asp Thr Val His Asn Ser Ser Val Trp Ile Pro
                165                 170                 175
Lys Ser Gln Lys Thr Asp Ile Cys Ala Gln Ser Phe Lys Asn Ile Lys
            180                 185                 190
Met Thr Ala Ser Tyr Pro Ser Glu Gly Ala Leu Val Ser Asp Arg Phe
        195                 200                 205
Ala Phe His Ser Ala Tyr His Pro Asn Met Pro Gly Ser Thr Val Cys
    210                 215                 220
Ile Met Asp Phe Cys Glu Gln Lys Gly Leu Arg Phe Thr Asn Gly Glu
225                 230                 235                 240
Trp Met Gly Leu Asn Val Glu Gln Ser Ile Arg Glu Lys Lys Ile Ser
                245                 250                 255
Ala Ile Phe Pro Asn Cys Val Ala Gly Thr Glu Ile Arg Ala Thr Leu
            260                 265                 270
Glu Ser Glu Gly Ala Arg Thr Leu Thr Trp Glu Thr Gln Arg Met Leu
        275                 280                 285
Asp Tyr Ser Leu Cys Gln Asn Thr Trp Asp Lys Val Ser Arg Lys Glu
    290                 295                 300
Pro Leu Ser Pro Leu Asp Leu Ser Tyr Leu Ser Pro Arg Ala Pro Gly
305                 310                 315                 320
Lys Gly Met Ala Tyr Thr Val Ile Asn Gly Thr Leu His Ser Ala His
                325                 330                 335
Ala Lys Tyr Ile Arg Thr Trp Ile Asp Tyr Gly Glu Met Lys Glu Ile
            340                 345                 350
Lys Gly Gly Arg Gly Glu Tyr Ser Lys Ala Pro Glu Leu Leu Trp Ser
        355                 360                 365
Gln Trp Phe Asp Phe Gly Pro Phe Lys Ile Gly Pro Asn Gly Leu Leu
    370                 375                 380
His Thr Gly Lys Thr Phe Lys Phe Pro Leu Tyr Leu Ile Gly Ala Gly
385                 390                 395                 400
Ile Ile Asp Glu Asp Leu His Glu Leu Asp Glu Ala Ala Pro Ile Asp
                405                 410                 415
His Pro Gln Met Pro Asp Ala Lys Ser Val Leu Pro Glu Asp Glu Glu
            420                 425                 430
Ile Phe Phe Gly Asp Thr Gly Val Ser Lys Asn Pro Ile Glu Leu Ile
        435                 440                 445
```

Gln Gly Trp Phe Ser Asn Trp Arg Glu Ser Val Met Ala Ile Val Gly
    450                 455                 460

Ile Val Leu Leu Ile Val Val Thr Phe Leu Ala Ile Lys Thr Val Arg
465                 470                 475                 480

Val Leu Asn Cys Leu Trp Arg Pro Arg Lys Lys Arg Ile Val Arg Gln
                485                 490                 495

Glu Val Asp Val Glu Ser Arg Leu Asn His Phe Glu Met Arg Gly Phe
            500                 505                 510

Pro Glu Tyr Val Lys Arg
            515

<210> SEQ ID NO 21
<211> LENGTH: 509
<212> TYPE: PRT
<213> ORGANISM: Vesicular stomatitis virus

<400> SEQUENCE: 21

Met Ser Ile Ile Ser Tyr Ile Ala Phe Leu Leu Leu Ile Asp Ser Thr
1               5                   10                  15

Leu Gly Ile Pro Ile Phe Val Pro Ser Gly Gln Asn Ile Ser Trp Gln
            20                  25                  30

Pro Val Ile Gln Pro Phe Asp Tyr Gln Cys Pro Ile His Gly Asn Leu
        35                  40                  45

Pro Asn Thr Met Gly Leu Ser Ala Thr Lys Leu Thr Ile Lys Ser Pro
    50                  55                  60

Ser Val Phe Ser Thr Asp Lys Val Ser Gly Trp Ile Cys His Ala Ala
65                  70                  75                  80

Glu Trp Lys Thr Thr Cys Asp Tyr Arg Trp Tyr Gly Pro Gln Tyr Ile
                85                  90                  95

Thr His Ser Ile His Pro Ile Ser Pro Thr Ile Asp Glu Cys Lys Arg
            100                 105                 110

Ile Ile Ser Arg Ile Ala Ser Gly Thr Asp Glu Asp Leu Gly Phe Pro
        115                 120                 125

Pro Gln Ser Cys Gly Trp Ala Ser Val Thr Thr Val Ser Asn Thr Asn
    130                 135                 140

Tyr Lys Val Val Pro His Ser Val His Leu Glu Pro Tyr Gly Gly His
145                 150                 155                 160

Trp Ile Asp His Asp Phe Asn Gly Gly Glu Cys Arg Glu Lys Val Cys
                165                 170                 175

Glu Met Lys Gly Asn His Ser Ile Trp Ile Thr Asp Thr Val Gln
            180                 185                 190

His Glu Cys Glu Lys His Ile Glu Val Glu Gly Ile Met Tyr Gly
        195                 200                 205

Asn Ala Pro Arg Gly Asp Ala Ile Tyr Ile Asn Asn Phe Ile Ile Asp
    210                 215                 220

Lys His Arg Val Tyr Arg Phe Gly Gly Ser Cys Arg Met Lys Phe
225                 230                 235                 240

Cys Asn Lys Asp Gly Ile Lys Phe Thr Arg Gly Asp Trp Val Glu Lys
                245                 250                 255

Thr Ala Gly Thr Leu Thr Asn Ile Tyr Glu Asn Ile Pro Glu Cys Ala
            260                 265                 270

Asp Gly Thr Leu Val Ser Gly His Arg Pro Gly Leu Asp Leu Ile Asp
        275                 280                 285

Thr Val Phe Asn Leu Glu Asn Val Val Glu Tyr Thr Leu Cys Glu Gly
    290                 295                 300

```
Thr Lys Arg Lys Ile Asn Lys Gln Glu Lys Leu Thr Ser Val Asp Leu
305                 310                 315                 320

Ser Tyr Leu Ala Pro Arg Ile Gly Gly Phe Gly Ser Val Phe Arg Val
                325                 330                 335

Arg Asn Gly Thr Leu Glu Arg Gly Ser Thr Thr Tyr Ile Arg Ile Glu
            340                 345                 350

Val Glu Gly Pro Val Val Asp Ser Leu Asn Gly Ile Asp Pro Arg Thr
        355                 360                 365

Asn Ala Ser Arg Val Phe Trp Asp Asp Trp Glu Leu Asp Gly Asn Ile
370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
                405                 410                 415

His Ala Phe Gln Ala Asp Ile Ile Pro His Pro His Tyr Asp Asp Asp
                420                 425                 430

Glu Ile Arg Glu Asp Asp Ile Phe Phe Asp Asn Thr Gly Glu Asn Gly
            435                 440                 445

Asn Pro Val Asp Ala Val Val Glu Trp Val Ser Gly Trp Gly Thr Ser
450                 455                 460

Leu Lys Phe Phe Gly Met Thr Leu Val Ala Leu Ile Leu Ile Phe Leu
465                 470                 475                 480

Leu Ile Arg Cys Cys Val Ala Cys Thr Tyr Leu Met Lys Lys Ser Lys
                485                 490                 495

Arg Pro Ala Thr Glu Ser His Glu Met Arg Ser Leu Val
                500                 505

<210> SEQ ID NO 22
<211> LENGTH: 511
<212> TYPE: PRT
<213> ORGANISM: Vesicular stomatitis virus

<400> SEQUENCE: 22

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
                20                  25                  30

Val Pro Ser Asn Tyr His Tyr Cys Pro Ser Ser Ser Asp Leu Asn Trp
            35                  40                  45

His Asn Asp Leu Ile Gly Thr Ala Ile Gln Val Lys Met Pro Lys Ser
50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175
```

```
Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Gly Thr Gly Phe Arg Ser Asn
    210                 215                 220

Tyr Phe Ala Tyr Glu Thr Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Arg Phe Pro Glu Cys Pro Glu Gly
            260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
    435                 440                 445

Asn Pro Ile Glu Leu Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 23
<211> LENGTH: 524
<212> TYPE: PRT
<213> ORGANISM: Vesicular stomatitis virus

<400> SEQUENCE: 23

Met Thr Ser Ser Val Thr Ile Ser Val Val Leu Leu Ile Ser Phe Ile
1               5                   10                  15

Thr Pro Leu Tyr Ser Tyr Leu Ser Ile Ala Phe Pro Glu Asn Thr Lys
            20                  25                  30

Leu Asp Trp Lys Pro Val Thr Lys Asn Thr Arg Tyr Cys Pro Met Gly
        35                  40                  45
```

-continued

```
Gly Glu Trp Phe Leu Glu Pro Gly Leu Gln Glu Ser Phe Leu Ser
     50                  55                  60

Ser Thr Pro Ile Gly Ala Thr Pro Ser Lys Ser Asp Gly Phe Leu Cys
 65                  70                  75                  80

His Ala Ala Lys Trp Val Thr Thr Cys Asp Phe Arg Trp Tyr Gly Pro
                 85                  90                  95

Lys Tyr Ile Thr His Ser Ile His Asn Ile Lys Pro Thr Arg Ser Asp
                100                 105                 110

Cys Asp Thr Ala Leu Ala Ser Tyr Lys Ser Gly Thr Leu Val Ser Leu
            115                 120                 125

Gly Phe Pro Pro Glu Ser Cys Gly Tyr Ala Ser Val Thr Asp Ser Glu
            130                 135                 140

Phe Leu Val Ile Met Ile Thr Pro His His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
            180                 185                 190

Gln Thr Lys Lys Asn Ile Cys Gly Gln Ser Phe Thr Pro Leu Thr Val
            195                 200                 205

Thr Val Ala Tyr Asp Lys Thr Lys Glu Ile Ala Ala Gly Gly Ile Val
            210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Met Leu Lys Leu Arg Ser Lys Arg Asn Leu Tyr Phe Pro
            260                 265                 270

Cys Leu Lys Met Cys Pro Thr Gly Ile Arg Gly Glu Ile Tyr Pro Ser
            275                 280                 285

Ile Arg Trp Ala Gln Val Leu Thr Ser Glu Ile Gln Arg Ile Leu Asp
            290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
            340                 345                 350

Arg Tyr Val Arg Met Trp Ile Asp Gly Pro Val Leu Lys Glu Pro Lys
            355                 360                 365

Gly Lys Arg Glu Ser Pro Ser Gly Ile Ser Ser Asp Ile Trp Thr Gln
            370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
            420                 425                 430

Pro Gln Leu Pro His Ala Gln Ser Ile Ala Asp Asp Ser Glu Glu Ile
            435                 440                 445

Phe Phe Gly Asp Thr Gly Val Ser Lys Asn Pro Val Glu Leu Val Thr
450                 455                 460

Gly Trp Phe Thr Ser Trp Lys Glu Ser Leu Ala Ala Gly Ser Cys Pro
465                 470                 475                 480
```

```
Asp Leu Arg Cys Pro Pro Leu Phe Pro Gly Ile Val Tyr Tyr Leu Gln
                485                 490                 495

Lys Ala Gln Met Glu Glu Arg Gly Glu Arg Ser Asp Ser Phe Glu Met
            500                 505                 510

Arg Ile Phe Lys Pro Asn Asn Met Arg Ala Arg Val
        515                 520

<210> SEQ ID NO 24
<211> LENGTH: 529
<212> TYPE: PRT
<213> ORGANISM: Vesicular stomatitis virus

<400> SEQUENCE: 24

Met Asp Leu Phe Pro Ile Leu Val Val Leu Met Thr Asp Thr Val
1               5                   10                  15

Leu Gly Lys Phe Gln Ile Val Phe Pro Asp Gln Asn Glu Leu Glu Trp
            20                  25                  30

Arg Pro Val Val Gly Asp Ser Arg His Cys Pro Gln Ser Ser Glu Met
            35                  40                  45

Gln Phe Asp Gly Ser Arg Ser Gln Thr Ile Leu Thr Gly Lys Ala Pro
    50                  55                  60

Val Gly Ile Thr Pro Ser Lys Ser Asp Gly Phe Ile Cys His Ala Ala
65                  70                  75                  80

Lys Trp Val Thr Thr Cys Asp Phe Arg Trp Tyr Gly Pro Lys Tyr Ile
                85                  90                  95

Thr His Ser Ile His His Leu Arg Pro Thr Thr Ser Cys Glu Thr
                100                 105                 110

Ala Leu Gln Arg Tyr Lys Asp Gly Ser Leu Ile Asn Leu Gly Phe Pro
            115                 120                 125

Pro Glu Ser Cys Gly Tyr Ala Thr Val Thr Asp Ser Glu Ala Met Leu
    130                 135                 140

Val Gln Val Thr Pro His His Val Gly Val Asp Asp Tyr Arg Gly His
145                 150                 155                 160

Trp Ile Asp Pro Leu Phe Pro Gly Gly Glu Cys Ser Thr Asn Phe Cys
                165                 170                 175

Asp Thr Val His Asn Ser Ser Val Trp Ile Pro Lys Ser Gln Lys Thr
                180                 185                 190

Asp Ile Cys Ala Gln Ser Phe Lys Asn Ile Lys Met Thr Ala Ser Tyr
            195                 200                 205

Pro Ser Glu Gly Ala Leu Val Ser Asp Arg Phe Ala Phe His Ser Ala
    210                 215                 220

Tyr His Pro Asn Met Pro Gly Ser Thr Val Cys Ile Met Asp Phe Cys
225                 230                 235                 240

Glu Gln Lys Gly Leu Arg Phe Thr Asn Gly Glu Trp Met Gly Leu Asn
                245                 250                 255

Val Glu Gln Ser Ile Arg Glu Lys Lys Ile Ser Ala Ile Phe Pro Asn
            260                 265                 270

Cys Val Ala Gly Thr Glu Ile Arg Ala Thr Leu Glu Ser Glu Gly Ala
    275                 280                 285

Arg Thr Leu Thr Trp Glu Thr Gln Arg Met Leu Asp Tyr Ser Leu Cys
    290                 295                 300

Gln Asn Thr Trp Asp Lys Val Ser Arg Lys Glu Pro Leu Ser Pro Leu
305                 310                 315                 320

Asp Leu Ser Tyr Leu Ser Pro Arg Ala Pro Gly Lys Gly Met Ala Tyr
                325                 330                 335
```

Thr Val Ile Asn Gly Thr Leu His Ser Ala His Ala Lys Tyr Ile Arg
            340                 345                 350

Thr Trp Ile Asp Tyr Gly Glu Met Lys Glu Ile Lys Gly Gly Arg Gly
            355                 360                 365

Glu Tyr Ser Lys Ala Pro Glu Leu Leu Trp Ser Gln Trp Phe Asp Phe
        370                 375                 380

Gly Pro Phe Lys Ile Gly Pro Asn Gly Leu Leu His Thr Gly Lys Thr
385                 390                 395                 400

Phe Lys Phe Pro Leu Tyr Leu Ile Gly Ala Gly Ile Ile Asp Glu Asp
                405                 410                 415

Leu His Glu Leu Asp Glu Ala Ala Pro Ile Asp His Pro Gln Met Pro
            420                 425                 430

Asp Ala Lys Ser Val Leu Pro Glu Asp Glu Ile Phe Phe Gly Asp
            435                 440                 445

Thr Gly Val Ser Lys Asn Pro Ile Glu Leu Ile Gln Gly Trp Phe Ser
    450                 455                 460

Asn Trp Arg Glu Ser Val Met Ala Ile Val Gly Ile Val Leu Leu Ile
465                 470                 475                 480

Val Val Thr Phe Leu Ala Ile Lys Thr Val Arg Val Leu Asn Cys Leu
                485                 490                 495

Trp Arg Pro Arg Lys Lys Arg Ile Val Arg Gln Glu Val Asp Val Glu
                500                 505                 510

Ser Arg Leu Asn His Phe Glu Met Arg Gly Phe Pro Glu Tyr Val Lys
            515                 520                 525

Arg

<210> SEQ ID NO 25
<211> LENGTH: 517
<212> TYPE: PRT
<213> ORGANISM: Vesicular stomatitis virus

<400> SEQUENCE: 25

Met Leu Ser Tyr Leu Ile Phe Ala Leu Ala Val Ser Pro Ile Leu Gly
1               5                   10                  15

Lys Ile Glu Ile Val Phe Pro Gln His Thr Thr Gly Asp Trp Lys Arg
            20                  25                  30

Val Pro His Glu Tyr Asn Tyr Cys Pro Thr Ser Ala Asp Lys Asn Ser
        35                  40                  45

His Gly Thr Gln Thr Gly Ile Pro Val Glu Leu Thr Met Pro Lys Gly
    50                  55                  60

Leu Thr Thr His Gln Val Glu Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Glu Pro Thr Asp Tyr Gln Cys Leu Glu Ala Ile
            100                 105                 110

Lys Ser Tyr Lys Asp Gly Val Ser Phe Asn Pro Gly Phe Pro Pro Gln
        115                 120                 125

Ser Cys Gly Tyr Gly Thr Val Thr Asp Ala Glu Ala His Ile Val Thr
    130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175

```
Val His Asn Ser Thr Lys Trp Phe Thr Ser Ser Asp Gly Glu Ser Val
                180                 185                 190

Cys Ser Gln Leu Phe Thr Leu Val Gly Gly Ile Phe Ser Asp Ser
            195                 200                 205

Glu Glu Ile Thr Ser Met Gly Leu Pro Glu Thr Gly Ile Arg Ser Asn
210                 215                 220

Tyr Phe Pro Tyr Ile Ser Thr Glu Gly Ile Cys Lys Met Pro Phe Cys
225                 230                 235                 240

Arg Lys Gln Gly Tyr Lys Leu Lys Asn Asp Leu Trp Phe Gln Ile Met
                245                 250                 255

Asp Pro Asp Leu Asp Lys Thr Val Arg Asp Leu Pro His Ile Lys Asp
                260                 265                 270

Cys Asp Leu Ser Ser Ser Ile Ile Thr Pro Gly Glu His Ala Thr Asp
            275                 280                 285

Ile Ser Leu Ile Ser Asp Val Glu Arg Ile Leu Asp Tyr Ala Leu Cys
            290                 295                 300

Gln Asn Thr Trp Ser Lys Ile Glu Ser Gly Glu Pro Ile Thr Pro Val
305                 310                 315                 320

Asp Leu Ser Tyr Leu Gly Pro Lys Asn Pro Gly Val Gly Pro Val Phe
                325                 330                 335

Thr Ile Ile Asn Gly Ser Leu His Tyr Phe Thr Ser Lys Tyr Leu Arg
                340                 345                 350

Val Glu Leu Glu Ser Pro Val Ile Pro Arg Met Glu Gly Lys Val Ala
            355                 360                 365

Gly Thr Arg Ile Val Arg Gln Leu Trp Asp Gln Trp Phe Pro Phe Gly
            370                 375                 380

Glu Val Glu Ile Gly Pro Asn Gly Val Leu Lys Thr Lys Gln Gly Tyr
385                 390                 395                 400

Lys Phe Pro Leu His Ile Ile Gly Thr Gly Glu Val Asp Ser Asp Ile
                405                 410                 415

Lys Met Glu Arg Val Val Lys His Trp Glu His Pro His Ile Glu Ala
                420                 425                 430

Ala Gln Thr Phe Leu Lys Lys Asp Asp Thr Gly Glu Val Leu Tyr Tyr
            435                 440                 445

Gly Asp Thr Gly Val Ser Lys Asn Pro Val Glu Leu Val Glu Gly Trp
450                 455                 460

Phe Ser Gly Trp Arg Ser Ser Leu Met Gly Val Leu Ala Val Ile Ile
465                 470                 475                 480

Gly Phe Val Ile Leu Met Phe Leu Ile Lys Leu Ile Gly Val Leu Ser
                485                 490                 495

Ser Leu Phe Arg Pro Lys Arg Arg Pro Ile Tyr Lys Ser Asp Val Glu
                500                 505                 510

Met Ala His Phe Arg
        515

<210> SEQ ID NO 26
<211> LENGTH: 512
<212> TYPE: PRT
<213> ORGANISM: Vesicular stomatitis virus

<400> SEQUENCE: 26

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
                20                  25                  30
```

-continued

Asn Val Pro Ser Ser Tyr His Tyr Cys Pro Ser Ser Asp Gln Asn
         35                  40                  45

Trp His Asn Asp Leu Leu Gly Ile Thr Met Lys Val Lys Met Pro Lys
 50                  55                  60

Thr His Lys Ala Ile Gln Ala Asp Gly Trp Met Cys His Ala Ala Lys
 65                  70                  75                  80

Trp Ile Thr Thr Cys Asp Phe Arg Trp Tyr Gly Pro Lys Tyr Ile Thr
                 85                  90                  95

His Ser Ile His Ser Ile Gln Pro Thr Ser Glu Gln Cys Lys Glu Ser
            100                 105                 110

Ile Lys Gln Thr Lys Gln Gly Thr Trp Met Ser Pro Gly Phe Pro Pro
        115                 120                 125

Gln Asn Cys Gly Tyr Ala Thr Val Thr Asp Ser Val Ala Val Val Val
    130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                165                 170                 175

Thr Val His Asn Ser Thr Val Trp Tyr Ser Asp Tyr Lys Val Thr Gly
            180                 185                 190

Leu Cys Asp Ala Thr Leu Val Asp Thr Glu Ile Thr Phe Phe Ser Glu
        195                 200                 205

Asp Gly Lys Lys Glu Ser Ile Gly Lys Pro Asn Thr Gly Tyr Arg Ser
    210                 215                 220

Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
                245                 250                 255

Val Asp Gln Asp Val Tyr Ala Ala Lys Leu Pro Glu Cys Pro Val
            260                 265                 270

Gly Ala Thr Ile Ser Ala Pro Thr Gln Thr Ser Val Asp Val Ser Leu
        275                 280                 285

Ile Leu Asp Val Glu Arg Ile Leu Asp Tyr Ser Leu Cys Gln Glu Thr
    290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
        355                 360                 365

Thr Glu Arg Glu Leu Trp Thr Glu Trp Phe Pro Tyr Glu Gly Val Glu
    370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
        435                 440                 445

Lys Asn Pro Val Glu Leu Ile Glu Gly Trp Phe Ser Ser Trp Lys Ser
    450                 455                 460

```
Thr Val Val Thr Phe Phe Ala Ile Gly Val Phe Ile Leu Leu Tyr
465                 470                 475                 480

Val Val Ala Arg Ile Val Ile Ala Val Arg Tyr Arg Tyr Gln Gly Ser
            485                 490                 495

Asn Asn Lys Arg Ile Tyr Asn Asp Ile Glu Met Ser Arg Phe Arg Lys
            500                 505                 510
```

<210> SEQ ID NO 27
<211> LENGTH: 523
<212> TYPE: PRT
<213> ORGANISM: Vesicular stomatitis virus

<400> SEQUENCE: 27

```
Met Thr Ser Val Leu Phe Met Val Gly Val Leu Leu Gly Ala Phe Gly
1               5                   10                  15

Ser Thr His Cys Ser Ile Gln Ile Val Phe Pro Ser Glu Thr Lys Leu
            20                  25                  30

Val Trp Lys Pro Val Leu Lys Gly Thr Arg Tyr Cys Pro Gln Ser Ala
        35                  40                  45

Glu Leu Asn Leu Glu Pro Asp Leu Lys Thr Met Ala Phe Asp Ser Lys
50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
                85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
        115                 120                 125

Phe Pro Pro Glu Ser Cys Gly Tyr Ala Ser Ile Thr Asp Ser Glu Phe
130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205

Val Met Tyr Pro Gln Thr Lys Pro Thr Lys Gly Ala Asp Leu Thr Leu
210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
            260                 265                 270

Phe Pro Asp Cys Leu Val Gly Ser Val Val Lys Ser Thr Leu Leu Ser
        275                 280                 285

Glu Gly Val Gln Thr Ala Leu Trp Gly Thr Asp Arg Leu Leu Asp Tyr
290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335
```

```
Met Ala Tyr Ile Val Ala Asn Gly Ser Leu Met Ser Pro Ala Arg
            340                 345                 350

Tyr Ile Arg Val Trp Ile Asp Ser Pro Ile Leu Lys Glu Ile Lys Gly
            355                 360                 365

Lys Lys Glu Ser Ala Ser Gly Ile Asp Thr Val Leu Trp Glu Gln Trp
370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Gly Met Gly Ile Val
            405                 410                 415

Asp Gln Asp Leu Gln Glu Leu Ser Ser Val Asn Pro Val Asp His Pro
            420                 425                 430

His Val Pro Ile Ala Gln Ala Phe Val Ser Glu Gly Glu Glu Val Phe
            435                 440                 445

Phe Gly Asp Thr Gly Val Ser Lys Asn Pro Ile Glu Leu Ile Ser Gly
            450                 455                 460

Trp Phe Ser Asp Trp Lys Glu Thr Ala Ala Ala Leu Gly Phe Ala Ala
465                 470                 475                 480

Ile Ser Val Ile Leu Ile Ile Gly Leu Met Arg Leu Leu Pro Leu Leu
            485                 490                 495

Cys Arg Arg Arg Lys Gln Lys Lys Val Ile Tyr Lys Asp Val Glu Leu
            500                 505                 510

Asn Ser Phe Asp Pro Arg Gln Ala Phe His Arg
            515                 520

<210> SEQ ID NO 28
<211> LENGTH: 509
<212> TYPE: PRT
<213> ORGANISM: Vesicular stomatitis virus

<400> SEQUENCE: 28

Met Ser Ile Ile Ser Tyr Ile Ala Phe Leu Leu Ile Asp Ser Thr
1               5                   10                  15

Phe Gly Ile Pro Ile Phe Val Pro Ser Gly Gln Asn Ile Ser Trp Gln
            20                  25                  30

Pro Val Ile Gln Pro Phe Asp Tyr Gln Cys Pro Ile His Gly Asn Leu
        35                  40                  45

Pro Asn Thr Met Gly Leu Ser Ala Thr Lys Leu Thr Ile Lys Ser Pro
    50                  55                  60

Ser Val Phe Ser Thr Asp Lys Val Ser Gly Trp Ile Cys His Ala Ala
65                  70                  75                  80

Glu Trp Lys Thr Thr Cys Asp Tyr Arg Trp Tyr Gly Pro Gln Tyr Ile
                85                  90                  95

Thr His Ser Ile His Pro Ile Ser Pro Thr Ile Asp Glu Cys Lys Arg
            100                 105                 110

Ile Ile Ser Arg Ile Ala Ser Gly Thr Asp Glu Asp Leu Gly Phe Pro
        115                 120                 125

Pro Gln Ser Cys Gly Trp Ala Ser Val Thr Thr Val Ser Asn Thr Asn
    130                 135                 140

Tyr Lys Val Val Pro His Ser Val His Leu Glu Pro Tyr Gly Gly His
145                 150                 155                 160

Trp Ile Asp His Glu Phe Asn Gly Gly Glu Cys Arg Glu Lys Val Cys
                165                 170                 175

Glu Met Lys Gly Asn His Ser Ile Trp Ile Thr Asp Glu Thr Val Gln
            180                 185                 190
```

His Glu Cys Glu Lys His Ile Glu Glu Val Glu Gly Ile Met Tyr Gly
            195                 200                 205

Asn Ala Pro Arg Gly Asp Ala Ile Tyr Ile Asn Asn Phe Ile Ile Asp
        210                 215                 220

Lys His His Arg Val Tyr Arg Phe Gly Gly Ser Cys Arg Met Lys Phe
225                 230                 235                 240

Cys Asn Lys Asp Gly Ile Lys Phe Thr Arg Gly Asp Trp Val Glu Lys
                245                 250                 255

Thr Ala Glu Thr Leu Thr Asn Ile Tyr Ala Asn Ile Pro Glu Cys Ala
            260                 265                 270

Asp Gly Thr Leu Val Ser Gly His Arg Pro Gly Leu Asp Leu Ile Asp
        275                 280                 285

Thr Val Phe Asn Leu Glu Asn Val Val Glu Tyr Thr Leu Cys Glu Gly
    290                 295                 300

Thr Lys Arg Lys Ile Asn Asn Gln Glu Lys Leu Thr Ser Val Asp Leu
305                 310                 315                 320

Ser Tyr Leu Ala Pro Arg Ile Gly Gly Phe Gly Ser Val Phe Arg Val
                325                 330                 335

Arg Asn Gly Thr Leu Glu Arg Gly Ser Thr Thr Tyr Ile Lys Ile Glu
            340                 345                 350

Val Glu Gly Pro Ile Val Asp Ser Leu Asn Gly Thr Asp Pro Arg Thr
        355                 360                 365

Asn Ala Ser Arg Val Phe Trp Asp Asp Trp Glu Leu Asp Gly Asn Ile
    370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
                405                 410                 415

His Ala Phe Gln Ala Asp Ile Ile Pro His Pro His Tyr Asp Asp Asp
            420                 425                 430

Glu Ile Arg Glu Asp Asp Ile Phe Phe Asp Asn Thr Gly Glu Asn Gly
        435                 440                 445

Asn Pro Val Asp Ala Val Val Glu Trp Val Ser Gly Trp Gly Thr Ser
    450                 455                 460

Leu Lys Phe Phe Gly Thr Thr Leu Val Ala Leu Ile Leu Ile Phe Leu
465                 470                 475                 480

Leu Ile Arg Cys Cys Val Ala Cys Thr Tyr Leu Met Lys Lys Ser Lys
                485                 490                 495

Arg Pro Ala Thr Glu Ser His Glu Met Arg Ser Phe Val
            500                 505

<210> SEQ ID NO 29
<211> LENGTH: 4555
<212> TYPE: DNA
<213> ORGANISM: Artificial
<220> FEATURE:
<223> OTHER INFORMATION: Trip sEwnv vector
<220> FEATURE:
<221> NAME/KEY: misc_feature
<222> LOCATION: (1)..(4555)
<223> OTHER INFORMATION: Trip sEwnv vector

<400> SEQUENCE: 29
tggaagggct aattcactcc caacgaagac aagatatcct tgatctgtgg atctaccaca         60
cacaaggcta cttccctgat tagcagaact acacaccagg gccagggatc agatatccac        120
tgacctttgg atggtgctac aagctagtac cagttgagcc agagaagtta gaagaagcca        180

```
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360
gctgggggac tttccaggga ggcgtggcct gggcgggact ggggagtggc gagccctcag    420
atcctgcata taagcagctg ctttttgcct gtactgggtc tctctggtta gaccagatct    480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagacccct ttagtcagtg tggaaaatct ctagcagtgg cgcccgaaca gggacttgaa    660
agcgaaaggg aaaccagagg agctctctcg acgcaggact cggcttgctg aagcgcggaa    720
ttccgcgcca cggcaagagg cgaggggcgg cgactggtga gtacgccaaa aattttgact    780
agcggaggct agaaggagag agatgggtgc gagagcgtca gtattaagcg ggggagaatt    840
agatcgcgat gggaaaaaat tcggttaagg ccaggggaa agaaaaaata taaattaaaa     900
catatagtat gggcaagcag ggagctagaa cgattcgcag ttaatcctgg cctgttagaa    960
acatcagaag gctgtagaca atactgggga cagctacaac catcccttca gacaggatca    1020
gaagaactta gatcattata taatacagta gcaaccctct attgtgtgca tcaaaggata    1080
gagataaaag acaccaagga agctttagac aagatagagg aagagcaaaa caaaagtaag    1140
accaccgcac agcaagcggc cgctgatctt cagacctgga ggaggagata tgagggacaa    1200
ttggagaagt gaattatata aatataaagt agtaaaaatt gaaccattag gagtagcacc    1260
caccaaggca aagagaagag tggtgcagag agaaaaaaga gcagtgggaa taggagcttt    1320
gttccttggg ttcttgggag cagcaggaag cactatgggc gcagcgtcaa tgacgctgac    1380
ggtacaggcc agacaattat tgtctggtat agtgcagcag cagaacaatt gctgagggc     1440 tattgaggcg caacagcatc tgttgcaact cacagtctgg ggcatcaagc agctccaggc    1500
aagaatcctg gctgtggaaa gatacctaaa ggatcaacag ctcctgggga tttggggttg    1560
ctctggaaaa ctcatttgca ccactgctgt gccttggaat gctagttgga gtaataaatc    1620
tctggaacag atttggaatc acacgacctg gatggagtgg gacagagaaa ttaacaatta    1680
cacaagctta atacactcct taattgaaga atcgcaaaac cagcaagaaa agaatgaaca    1740
agaattattg gaattagata aatgggcaag tttgtggaat tggtttaaca taacaaattg    1800
gctgtggtat ataaaattat tcataatgat agtaggaggc ttggtaggtt taagaatagt    1860
ttttgctgta ctttctatag tgaatagagt taggcaggga tattcaccat tatcgtttca    1920
gacccacctc ccaaccccga ggggacccga caggcccgaa ggaatagaag aagaaggtgg    1980
agagagagac agagacagat ccattcgatt agtgaacgga tctcgacggt atcgccgaat    2040
tcacaaatgg cagtattcat ccacaatttt aaaagaaaag ggggggattgg ggggtacagt    2100 gcagggaaa gaatagtaga cataatagca acagacatac aaactaaaga attacaaaaa     2160
caaattacaa aaattcaaaa ttttcgggtt tattacaggg acagcagaga tccactttgg    2220
ggcgataagc ttgggagttc cgcgttacat aacttacggt aaatggcccg cctggctgac    2280
cgcccaacga cccccgccca ttgacgtcaa taatgacgta tgttcccata gtaacgccaa    2340
tagggacttt ccattgacgt caatgggtgg agtatttacg gtaaactgcc cacttggcag    2400
tacatcaagt gtatcatatg ccaagtacgc ccctattga cgtcaatgac ggtaaatggc     2460
ccgcctggca ttatgcccag tacatgacct tatgggactt tcctacttgg cagtacatct    2520
acgtattagt catcgctatt accatggtga tgcggttttg gcagtacatc aatgggcgtg    2580
```

```
gatagcggtt tgactcacgg ggatttccaa gtctccaccc cattgacgtc aatgggagtt    2640
tgttttggca ccaaaatcaa cgggactttc caaaatgtcg taacaactcc gccccattga    2700
cgcaaatggg cggtaggcgt gtacggtggg aggtctatat aagcagagct cgtttagtga    2760
accgtcagat cgcctggaga cgccatccac gctgttttga cctccataga agacaccgac    2820
tctagaggac gtacgatgag agttgtgttt gtcgtgctat tgcttttggt ggccccagct    2880
tacagcttca actgccttgg aatgagcaac agagacttct tggaaggagt gtctggagca    2940
acatgggtgg atttggttct cgaaggcgac agctgcgtga ctatcatgtc taaggacaag    3000
cctaccatcg atgtgaagat gatgaatatg gaggcggtca acctggcaga ggtccgcagt    3060
tattgctatt tggctaccgt cagcgatctc tccaccaaag ctgcgtgccc gaccatggga    3120
gaagctcaca atgacaaacg tgctgaccca gcttttgtgt gcagacaagg agtggtggac    3180
aggggctggg gcaacggctg cggattattt ggcaaaggaa gcattgacac atgcgccaaa    3240
tttgcctgct ctaccaaggc aataggaaga accatcttga aagagaatat caagtacgaa    3300
gtggccattt tgtccatgg accaactact gtggagtcgc acggaaacta ctccacacag    3360
gttggagcca ctcaggcagg gagattcagc atcactcctg cggcgccttc atacacacta    3420
aagcttggag aatatggaga ggtgacagtg gactgtgaac cacggtcagg gattgacacc    3480
aatgcatact acgtgatgac tgttggaaca aagacgttct tggtccatcg tgagtggttc    3540
atggacctca acctcccttg gagcagtgct ggaagtactg tgtggaggaa cagagagacg    3600
ttaatggagt tgaggaacc acacgccacg aagcagtctg tgatagcatt gggctcacaa    3660
gagggagctc tgcatcaagc tttggctgga gccattcctg tggaattttc aagcaacact    3720
gtcaagttga cgtcgggtca tttgaagtgt agagtgaaga tggaaaaatt gcagttgaag    3780
ggaacaacct atggcgtctg ttcaaaggct ttcaagtttc ttgggactcc cgcagacaca    3840
ggtcacggca ctgtggtgtt ggaattgcag tacactggca cggatggacc ttgcaaagtt    3900
cctatctcgt cagtggcttc attgaacgac ctaacgccag tgggcagatt ggtcactgtc    3960 aaccctttg tttcagtggc cacgccaac gctaaggtcc tgattgaatt ggaaccaccc    4020
tttggagact catacatagt ggtgggcaga ggagaacaac agatcaatca ccattggcac    4080
aagtctggaa gcagcattgg caaagccttt acaaccaccc tcaaaggagc cagagacta    4140 gccgctctag agacacagc ttgggacttt ggatcagttg gagggggtgtt cacctcagtt    4200 gggaaggctg tctaatgcgc gcggtacctt taagaccaat gacttacaag gcagctgtag    4260
atcttagcca ctttttaaaa gaaaagggggg gactggaagg gctaattcac tcccaacgaa    4320
gacaagatcg tcgagagatg ctgcatataa gcagctgctt tttgcttgta ctgggtctct    4380
ctggttagac cagatctgag cctggagct ctctggctaa ctagggaacc cactgcttaa    4440
gcctcaataa agcttgcctt gagtgcttca agtagtgtgt gcccgtctgt tgtgtgactc    4500
tggtaactag agatccctca gaccctttta gtcagtgtgg aaaatctcta gcagt         4555
```

<210> SEQ ID NO 30
<211> LENGTH: 4023
<212> TYPE: DNA
<213> ORGANISM: Artificial
<220> FEATURE:
<223> OTHER INFORMATION: Trip GFP

<400> SEQUENCE: 30

```
tggaagggct aattcactcc caacgaagac aagatatcct tgatctgtgg atctaccaca      60
cacaaggcta cttccctgat tagcagaact acacaccagg gccagggatc agatatccac     120
```

```
tgacctttgg atggtgctac aagctagtac cagttgagcc agagaagtta gaagaagcca    180
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360
gctgggggac tttccaggga ggcgtggcct gggcggact ggggagtggc gagccctcag     420
atcctgcata taagcagctg cttttttgcct gtactgggtc tctctggtta gaccagatct   480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagacccct tagtcagtg tggaaaatct ctagcagtgg cgcccgaaca gggacttgaa     660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc caggggggaaa gaaaaaatat aaattaaaac atatagtatg   900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat ggagaagtg    1200 aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcaggat attcaccatt atcgtttcag acccacctcc    1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aagaaaagg ggggattggg gggtacagtg caggggaaag    2100
aatagtagac ataatagcaa cagacataca aactaaagaa ttacaaaaac aaattacaaa   2160
aattcaaaat tttcgggttt attacaggga cagcagagat ccactttggg gcgataagct   2220
tgggagttcc gcgttacata acttacggta aatggcccgc ctggctgacc gcccaacgac   2280
ccccgcccat tgacgtcaat aatgacgtat gttcccatag taacgccaat agggactttc   2340
cattgacgtc aatgggtgga gtatttacgg taaactgccc acttggcagt acatcaagtg   2400
tatcatatgc caagtacgcc ccctattgac gtcaatgacg gtaaatggcc cgcctggcat   2460
tatgcccagt acatgacctt atgggacttt cctacttggc agtacatcta cgtattagtc   2520
```

```
atcgctatta ccatggtgat gcggttttgg cagtacatca atgggcgtgg atagcggttt    2580
gactcacggg gatttccaag tctccacccc attgacgtca atgggagttt gttttggcac    2640
caaaatcaac gggactttcc aaaatgtcgt aacaactccg ccccattgac gcaaatgggc    2700
ggtaggcgtg tacggtggga ggtctatata agcagagctc gtttagtgaa ccgtcagatc    2760
gcctggagac gccatccacg ctgttttgac ctccatagaa gacaccgact ctagaggatc    2820 ccaccggtc gccaccatgg tgagcaaggg cgaggagctg ttcaccgggg tggtgcccat     2880
cctggtcgag ctggacggcg acgtaaacgg ccacaagttc agcgtgtccg gcgagggcga    2940
gggcgatgcc acctacggca agctgaccct gaagttcatc tgcaccaccg gcaagctgcc    3000
cgtgccctgg cccaccctcg tgaccaccct gacctacggc gtgcagtgct tcagccgcta    3060
ccccgaccac atgaagcagc acgacttctt caagtccgcc atgcccgaag gctacgtcca    3120
ggagcgcacc atcttcttca aggacgacgg caactacaag acccgcgccg aggtgaagtt    3180
cgagggcgac accctggtga accgcatcga gctgaagggc atcgacttca aggaggacgg    3240
caacatcctg ggcacaagc tggagtacaa ctacaacagc cacaacgtct atatcatggc     3300
cgacaagcag aagaacggca tcaaggtgaa cttcaagatc cgccacaaca tcgaggacgg    3360
cagcgtgcag ctcgccgacc actaccagca gaacaccccc atcggcgacg gccccgtgct    3420
gctgcccgac aaccactacc tgagcaccca gtccgccctg agcaaagacc ccaacgagaa    3480
gcgcgatcac atggtcctgc tggagttcgt gaccgccgcc gggatcactc tcggcatgga    3540
cgagctgtac aagtaaagcg gccggactct agctcgagac ctagaaaaac atggagcaat    3600
cacaagtagc aatacagcag ctaccaatgc tgattgtgcc tggctagaag cacaagagga    3660
ggaggaggtg ggttttccag tcacacctca ggtacctta agaccaatga cttacaaggc     3720
agctgtagat cttagccact tttaaaaga aaaggggga ctggaagggc taattcactc     3780
ccaacgaaga caagatcgtc gagagatgct gcatataagc agctgctttt tgcttgtact    3840
gggtctctct ggttagacca gatctgagcc tgggagctct ctggctaact agggaaccca    3900
ctgcttaagc ctcaataaag cttgccttga gtgcttcaag tagtgtgtgc ccgtctgttg    3960
tgtgactctg gtaactagag atccctcaga ccctttagt cagtgtggaa aatctctagc     4020
agt                                                                  4023
```

<210> SEQ ID NO 31
<211> LENGTH: 1536
<212> TYPE: DNA
<213> ORGANISM: Vesicular stomatitis virus
<220> FEATURE:
<221> NAME/KEY: CDS
<222> LOCATION: (1)..(1536)

<400> SEQUENCE: 31

```
atg aaa tgc ctg ctc tat ctg gcc ttc ctc ttt atc ggc gtg aac tgt        48
Met Lys Cys Leu Leu Tyr Leu Ala Phe Leu Phe Ile Gly Val Asn Cys
1               5                   10                  15 aag ttc acg atc gtg ttt ccc cac aat cag aag gga aac tgg aag aac        96
Lys Phe Thr Ile Val Phe Pro His Asn Gln Lys Gly Asn Trp Lys Asn
            20                  25                  30 gtc ccg agc aac tac cac tac tgc cct agc tca agc gac ctg aac tgg       144
Val Pro Ser Asn Tyr His Tyr Cys Pro Ser Ser Ser Asp Leu Asn Trp
        35                  40                  45 cac aac gac ctg atc ggc acc gct atc cag gtg aag atg cca aag agc       192
His Asn Asp Leu Ile Gly Thr Ala Ile Gln Val Lys Met Pro Lys Ser
    50                  55                  60
```

```
cac aag gcc atc caa gcc gac ggc tgg atg tgt cac gcc agc aaa tgg        240
His Lys Ala Ile Gln Ala Asp Gly Trp Met Cys His Ala Ser Lys Trp
65                  70                  75                  80 gtg acg acg tgc gat ttt cgc tgg tat ggc ccc aag tac atc acc caa        288
Val Thr Thr Cys Asp Phe Arg Trp Tyr Gly Pro Lys Tyr Ile Thr Gln
                85                  90                  95 tca atc cgc tca ttt aca ccc agc gtg gag caa tgt aag gag agc atc        336
Ser Ile Arg Ser Phe Thr Pro Ser Val Glu Gln Cys Lys Glu Ser Ile
            100                 105                 110 gag cag acc aag cag ggg acc tgg ctc aac ccc ggc ttc cca ccg caa        384
Glu Gln Thr Lys Gln Gly Thr Trp Leu Asn Pro Gly Phe Pro Pro Gln
        115                 120                 125 agc tgc gga tac gcc acc gtg acc gac gct gag gcc gtc atc gtg cag        432
Ser Cys Gly Tyr Ala Thr Val Thr Asp Ala Glu Ala Val Ile Val Gln
    130                 135                 140 gtg acc ccg cac cac gtg ctg gtg gac gag tac acc ggc gag tgg gtg        480
Val Thr Pro His His Val Leu Val Asp Glu Tyr Thr Gly Glu Trp Val
145                 150                 155                 160 gat tca cag ttt atc aac gga aag tgt agc aat tac atc tgc ccc acc        528
Asp Ser Gln Phe Ile Asn Gly Lys Cys Ser Asn Tyr Ile Cys Pro Thr
                165                 170                 175 gtg cac aac agc acc acc tgg cac tca gac tat aag gtg aag ggc ctc        576
Val His Asn Ser Thr Thr Trp His Ser Asp Tyr Lys Val Lys Gly Leu
            180                 185                 190 tgc gac agc aat ctg atc tca atg gac atc acc ttc ttt agc gaa gac        624
Cys Asp Ser Asn Leu Ile Ser Met Asp Ile Thr Phe Phe Ser Glu Asp
        195                 200                 205 ggc gaa ctc tca agc ctc ggg aag gaa ggc acc ggg ttc cgc agc aat        672
Gly Glu Leu Ser Ser Leu Gly Lys Glu Gly Thr Gly Phe Arg Ser Asn
    210                 215                 220 tac ttt gct tac gaa acc ggc ggc aag gcc tgc aag atg caa tac tgc        720
Tyr Phe Ala Tyr Glu Thr Gly Gly Lys Ala Cys Lys Met Gln Tyr Cys
225                 230                 235                 240 aag cac tgg ggc gtg cgc ctg cca agc ggc gtg tgg ttt gag atg gct        768
Lys His Trp Gly Val Arg Leu Pro Ser Gly Val Trp Phe Glu Met Ala
                245                 250                 255 gat aag gac ctg ttc gcc gct gcc cgc ttc ccg gaa tgc ccc gag ggg        816
Asp Lys Asp Leu Phe Ala Ala Ala Arg Phe Pro Glu Cys Pro Glu Gly
            260                 265                 270 agc agc atc agc gcc ccc agc cag aca tca gtg gac gtg agc ctg atc        864
Ser Ser Ile Ser Ala Pro Ser Gln Thr Ser Val Asp Val Ser Leu Ile
        275                 280                 285 cag gat gtg gaa cgc atc ctg gac tac agc ctg tgt cag gaa acg tgg        912
Gln Asp Val Glu Arg Ile Leu Asp Tyr Ser Leu Cys Gln Glu Thr Trp
    290                 295                 300 agc aag atc cgc gcc gga ctg cct atc agc ccc gtg gat ctc agc tac        960
Ser Lys Ile Arg Ala Gly Leu Pro Ile Ser Pro Val Asp Leu Ser Tyr
305                 310                 315                 320 ctg gcc cca aag aac cca ggc acc gga ccc gcc ttt aca atc atc aac       1008
Leu Ala Pro Lys Asn Pro Gly Thr Gly Pro Ala Phe Thr Ile Ile Asn
                325                 330                 335 ggc acc ctg aag tac ttt gaa aca cgc tac atc cgc gtc gac atc gcc       1056
Gly Thr Leu Lys Tyr Phe Glu Thr Arg Tyr Ile Arg Val Asp Ile Ala
            340                 345                 350 gct ccc atc ctc tca cgc atg gtg ggc atg atc tca ggg acg acc acg       1104
Ala Pro Ile Leu Ser Arg Met Val Gly Met Ile Ser Gly Thr Thr Thr
        355                 360                 365 gag cgc gag ctg tgg gat gac tgg gcc ccg tat gaa gat gtg gag atc       1152
Glu Arg Glu Leu Trp Asp Asp Trp Ala Pro Tyr Glu Asp Val Glu Ile
    370                 375                 380
```

-continued

```
gga cct aac ggc gtg ctg cgc aca tca agc ggg tac aag ttc ccg ctg    1200
Gly Pro Asn Gly Val Leu Arg Thr Ser Ser Gly Tyr Lys Phe Pro Leu
385                 390                 395                 400 tac atg atc ggc cac ggc atg ctg gac agc gac ctg cac ctc agc tca    1248
Tyr Met Ile Gly His Gly Met Leu Asp Ser Asp Leu His Leu Ser Ser
            405                 410                 415 aag gcc cag gtc ttt gag cac cca cac atc cag gac gct gcc agc cag    1296
Lys Ala Gln Val Phe Glu His Pro His Ile Gln Asp Ala Ala Ser Gln
        420                 425                 430 ctc ccc gac gac gaa agc ctg ttc ttt gga gat aca ggg ctc agc aag    1344
Leu Pro Asp Asp Glu Ser Leu Phe Phe Gly Asp Thr Gly Leu Ser Lys
    435                 440                 445 aac ccc atc gag ctg gtc gag ggc tgg ttc tca agc tgg aag agc agc    1392
Asn Pro Ile Glu Leu Val Glu Gly Trp Phe Ser Ser Trp Lys Ser Ser
450                 455                 460 atc gct tca ttt ttt ttc atc atc ggc ctc atc atc ggg ctg ttt ctg    1440
Ile Ala Ser Phe Phe Phe Ile Ile Gly Leu Ile Ile Gly Leu Phe Leu
465                 470                 475                 480 gtg ctg cgc gtc ggc atc cac ctg tgc atc aag ctg aag cac acc aag    1488
Val Leu Arg Val Gly Ile His Leu Cys Ile Lys Leu Lys His Thr Lys
            485                 490                 495 aag cgc cag atc tat acc gac atc gag atg aat cgc ctg ggg aag taa    1536
Lys Arg Gln Ile Tyr Thr Asp Ile Glu Met Asn Arg Leu Gly Lys
        500                 505                 510
```

<210> SEQ ID NO 32
<211> LENGTH: 511
<212> TYPE: PRT
<213> ORGANISM: Vesicular stomatitis virus

<400> SEQUENCE: 32

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Ile Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
            85                  90                  95

Ser Ile Arg Ser Phe Thr Pro Ser Val Glu Gln Cys Lys Glu Ser Ile
        100                 105                 110

Glu Gln Thr Lys Gln Gly Thr Trp Leu Asn Pro Gly Phe Pro Pro Gln
    115                 120                 125

Ser Cys Gly Tyr Ala Thr Val Thr Asp Ala Glu Ala Val Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
            165                 170                 175

Val His Asn Ser Thr Thr Trp His Ser Asp Tyr Lys Val Lys Gly Leu
        180                 185                 190

Cys Asp Ser Asn Leu Ile Ser Met Asp Ile Thr Phe Phe Ser Glu Asp
    195                 200                 205

Gly Glu Leu Ser Ser Leu Gly Lys Glu Gly Thr Gly Phe Arg Ser Asn

```
                   210                 215                 220
Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 33
<211> LENGTH: 1554
<212> TYPE: DNA
<213> ORGANISM: Vesicular stomatitis virus
<220> FEATURE:
<221> NAME/KEY: CDS
<222> LOCATION: (1)..(1554)

<400> SEQUENCE: 33 atg ctg tca tat ctg atc ttt gcc ctg gct gtg agc cca atc ctc gga    48
Met Leu Ser Tyr Leu Ile Phe Ala Leu Ala Val Ser Pro Ile Leu Gly
1               5                   10                  15 aag atc gaa atc gtg ttc cca caa cac acc aca ggg gac tgg aag cgc    96
Lys Ile Glu Ile Val Phe Pro Gln His Thr Thr Gly Asp Trp Lys Arg
            20                  25                  30 gtg ccc cac gag tac aac tac tgc ccg acc tca gcc gac aag aat agc   144
Val Pro His Glu Tyr Asn Tyr Cys Pro Thr Ser Ala Asp Lys Asn Ser
        35                  40                  45 cac ggc acg cag acc ggc atc cct gtg gag ctg acc atg ccc aag ggg   192
```

-continued

| | | |
|---|---|---|
| His Gly Thr Gln Thr Gly Ile Pro Val Glu Leu Thr Met Pro Lys Gly<br>50                            55                            60 | | |
| ctc aca acg cac caa gtc gaa ggc ttc atg tgc cac agc gct ctc tgg<br>Leu Thr Thr His Gln Val Glu Gly Phe Met Cys His Ser Ala Leu Trp<br>65                            70                          75                        80 | 240 | |
| atg aca acc tgc gat ttt cgc tgg tat ggc ccc aag tac atc acg cac<br>Met Thr Thr Cys Asp Phe Arg Trp Tyr Gly Pro Lys Tyr Ile Thr His<br>                        85                          90                          95 | 288 | |
| agc atc cac aat gag gaa cca acc gac tac cag tgc ctc gaa gcc atc<br>Ser Ile His Asn Glu Glu Pro Thr Asp Tyr Gln Cys Leu Glu Ala Ile<br>                      100                       105                     110 | 336 | |
| aag tca tac aag gat ggg gtg agc ttc aac ccc ggc ttc ccg ccc caa<br>Lys Ser Tyr Lys Asp Gly Val Ser Phe Asn Pro Gly Phe Pro Pro Gln<br>        115                     120                       125 | 384 | |
| tca tgt ggc tac ggc acc gtg acc gac gcc gag gcc cac atc gtg acc<br>Ser Cys Gly Tyr Gly Thr Val Thr Asp Ala Glu Ala His Ile Val Thr<br>130                            135                          140 | 432 | |
| gtg aca ccc cac tca gtc aag gtg gac gag tac aca ggc gaa tgg atc<br>Val Thr Pro His Ser Val Lys Val Asp Glu Tyr Thr Gly Glu Trp Ile<br>145                            150                       155                     160 | 480 | |
| gac ccc cac ttc atc ggg ggc cgc tgt aag ggc caa atc tgc gag acc<br>Asp Pro His Phe Ile Gly Gly Arg Cys Lys Gly Gln Ile Cys Glu Thr<br>                      165                       170                     175 | 528 | |
| gtg cac aac agc acc aag tgg ttt acg tca tca gac ggc gaa agc gtg<br>Val His Asn Ser Thr Lys Trp Phe Thr Ser Ser Asp Gly Glu Ser Val<br>        180                     185                       190 | 576 | |
| tgc agc caa ctg ttt acg ctc gtg ggc ggc atc ttc ttt agc gac agc<br>Cys Ser Gln Leu Phe Thr Leu Val Gly Gly Ile Phe Phe Ser Asp Ser<br>               195                     200                     205 | 624 | |
| gag gag atc acc agc atg ggc ctc ccg gag aca gga atc cgc agc aac<br>Glu Glu Ile Thr Ser Met Gly Leu Pro Glu Thr Gly Ile Arg Ser Asn<br>210                            215                          220 | 672 | |
| tac ttt ccg tac atc agc acc gag gga atc tgt aag atg cct ttt tgc<br>Tyr Phe Pro Tyr Ile Ser Thr Glu Gly Ile Cys Lys Met Pro Phe Cys<br>225                            230                       235                     240 | 720 | |
| cgc aag cag gga tat aag ctg aag aat gac ctg tgg ttc cag atc atg<br>Arg Lys Gln Gly Tyr Lys Leu Lys Asn Asp Leu Trp Phe Gln Ile Met<br>               245                     250                     255 | 768 | |
| gac ccg gac ctg gac aag acc gtc cgc gat ctg ccc cac atc aag gac<br>Asp Pro Asp Leu Asp Lys Thr Val Arg Asp Leu Pro His Ile Lys Asp<br>            260                     265                     270 | 816 | |
| tgt gat ctg tca tca agc atc atc acc ccc gga gaa cac gcc acg gac<br>Cys Asp Leu Ser Ser Ser Ile Ile Thr Pro Gly Glu His Ala Thr Asp<br>275                            280                          285 | 864 | |
| atc agc ctc atc agc gat gtg gag cgc atc ctc gac tac gct ctc tgc<br>Ile Ser Leu Ile Ser Asp Val Glu Arg Ile Leu Asp Tyr Ala Leu Cys<br>290                            295                          300 | 912 | |
| cag aac aca tgg agc aag atc gaa agc ggc gaa ccc atc acc cca gtg<br>Gln Asn Thr Trp Ser Lys Ile Glu Ser Gly Glu Pro Ile Thr Pro Val<br>305                            310                       315                     320 | 960 | |
| gac ctg agc tat ctc ggc cca aag aac ccc ggc gtg ggc ccc gtg ttc<br>Asp Leu Ser Tyr Leu Gly Pro Lys Asn Pro Gly Val Gly Pro Val Phe<br>                      325                       330                     335 | 1008 | |
| acc atc atc aac ggg agc ctg cac tac ttt aca agc aag tat ctg cgc<br>Thr Ile Ile Asn Gly Ser Leu His Tyr Phe Thr Ser Lys Tyr Leu Arg<br>               340                     345                     350 | 1056 | |
| gtg gag ctc gaa agc cca gtc atc ccc cgc atg gag ggg aag gtg gcc<br>Val Glu Leu Glu Ser Pro Val Ile Pro Arg Met Glu Gly Lys Val Ala<br>355                            360                       365 | 1104 | |
| ggg acc cgc atc gtg cgc cag ctg tgg gac cag tgg ttc cct ttt ggc | 1152 | |

```
                                                    -continued

Gly Thr Arg Ile Val Arg Gln Leu Trp Asp Gln Trp Phe Pro Phe Gly
        370                 375                 380 gag gtg gaa atc ggc ccc aac ggc gtg ctg aag acc aag caa gga tat     1200
Glu Val Glu Ile Gly Pro Asn Gly Val Leu Lys Thr Lys Gln Gly Tyr
385                 390                 395                 400 aag ttc ccg ctg cac atc atc ggg acg ggc gaa gtg gac agc gat atc     1248
Lys Phe Pro Leu His Ile Ile Gly Thr Gly Glu Val Asp Ser Asp Ile
                    405                 410                 415 aag atg gag cgc gtg gtc aag cac tgg gag cac cca cac atc gag gct     1296
Lys Met Glu Arg Val Val Lys His Trp Glu His Pro His Ile Glu Ala
                420                 425                 430 gct cag acc ttt ctc aag aag gac gat acc ggc gaa gtc ctg tat tac     1344
Ala Gln Thr Phe Leu Lys Lys Asp Asp Thr Gly Glu Val Leu Tyr Tyr
            435                 440                 445 ggg gat acg gga gtg agc aag aac cct gtg gag ctg gtg gaa ggc tgg     1392
Gly Asp Thr Gly Val Ser Lys Asn Pro Val Glu Leu Val Glu Gly Trp
        450                 455                 460 ttc agc gga tgg cgc tca agc ctg atg ggc gtg ctg gcc gtc atc atc     1440
Phe Ser Gly Trp Arg Ser Ser Leu Met Gly Val Leu Ala Val Ile Ile
465                 470                 475                 480 gga ttt gtg atc ctg atg ttc ctc atc aag ctg atc ggc gtg ctg tca     1488
Gly Phe Val Ile Leu Met Phe Leu Ile Lys Leu Ile Gly Val Leu Ser
                    485                 490                 495 agc ctg ttc cgc cct aag cgc cgc cca atc tac aag agc gac gtc gag     1536
Ser Leu Phe Arg Pro Lys Arg Arg Pro Ile Tyr Lys Ser Asp Val Glu
                500                 505                 510 atg gcc cac ttt cgc taa                                             1554
Met Ala His Phe Arg
            515

<210> SEQ ID NO 34
<211> LENGTH: 517
<212> TYPE: PRT
<213> ORGANISM: Vesicular stomatitis virus

<400> SEQUENCE: 34

Met Leu Ser Tyr Leu Ile Phe Ala Leu Ala Val Ser Pro Ile Leu Gly
1               5                   10                  15

Lys Ile Glu Ile Val Phe Pro Gln His Thr Thr Gly Asp Trp Lys Arg
            20                  25                  30

Val Pro His Glu Tyr Asn Tyr Cys Pro Thr Ser Ala Asp Lys Asn Ser
        35                  40                  45

His Gly Thr Gln Thr Gly Ile Pro Val Glu Leu Thr Met Pro Lys Gly
    50                  55                  60

Leu Thr Thr His Gln Val Glu Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Glu Pro Thr Asp Tyr Gln Cys Leu Glu Ala Ile
            100                 105                 110

Lys Ser Tyr Lys Asp Gly Val Ser Phe Asn Pro Gly Phe Pro Pro Gln
        115                 120                 125

Ser Cys Gly Tyr Gly Thr Val Thr Asp Ala Glu Ala His Ile Val Thr
    130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175
```

```
Val His Asn Ser Thr Lys Trp Phe Thr Ser Ser Asp Gly Glu Ser Val
                180                 185                 190

Cys Ser Gln Leu Phe Thr Leu Val Gly Gly Ile Phe Phe Ser Asp Ser
            195                 200                 205

Glu Glu Ile Thr Ser Met Gly Leu Pro Glu Thr Gly Ile Arg Ser Asn
        210                 215                 220

Tyr Phe Pro Tyr Ile Ser Thr Glu Gly Ile Cys Lys Met Pro Phe Cys
225                 230                 235                 240

Arg Lys Gln Gly Tyr Lys Leu Lys Asn Asp Leu Trp Phe Gln Ile Met
                245                 250                 255

Asp Pro Asp Leu Asp Lys Thr Val Arg Asp Leu Pro His Ile Lys Asp
            260                 265                 270

Cys Asp Leu Ser Ser Ser Ile Ile Thr Pro Gly Glu His Ala Thr Asp
        275                 280                 285

Ile Ser Leu Ile Ser Asp Val Glu Arg Ile Leu Asp Tyr Ala Leu Cys
290                 295                 300

Gln Asn Thr Trp Ser Lys Ile Glu Ser Gly Glu Pro Ile Thr Pro Val
305                 310                 315                 320

Asp Leu Ser Tyr Leu Gly Pro Lys Asn Pro Gly

-continued

| | | |
|---|---|---|
| gtg ctg ctg atc agc ttc atc acc ccc ctg tac agc tac ctg agc att<br>Val Leu Leu Ile Ser Phe Ile Thr Pro Leu Tyr Ser Tyr Leu Ser Ile<br>10                    15                      20                      25 | 101 |
| gcc ttc ccc gag aac acc aag ctg gac tgg aag ccc gtg acc aag aac<br>Ala Phe Pro Glu Asn Thr Lys Leu Asp Trp Lys Pro Val Thr Lys Asn<br>               30                      35                      40 | 149 |
| acc cgg tac tgc ccc atg ggc ggc gag tgg ttt ctg gaa ccc ggc ctg<br>Thr Arg Tyr Cys Pro Met Gly Gly Glu Trp Phe Leu Glu Pro Gly Leu<br>                  45                      50                      55 | 197 |
| cag gaa gag agc ttc ctg agc agc acc ccc atc ggc gcc acc ccc agc<br>Gln Glu Glu Ser Phe Leu Ser Ser Thr Pro Ile Gly Ala Thr Pro Ser<br>                     60                      65                      70 | 245 |
| aag agc gac ggc ttc ctg tgc cac gcc gcc aag tgg gtg acc acc tgc<br>Lys Ser Asp Gly Phe Leu Cys His Ala Ala Lys Trp Val Thr Thr Cys<br>75                      80                      85 | 293 |
| gac ttc cgg tgg tac ggc ccc aag tac atc acc cac agc atc cac aac<br>Asp Phe Arg Trp Tyr Gly Pro Lys Tyr Ile Thr His Ser Ile His Asn<br>90                      95                     100                   105 | 341 |
| atc aag ccc acc aga agc gac tgc gac aca gcc ctg gcc tct tac aag<br>Ile Lys Pro Thr Arg Ser Asp Cys Asp Thr Ala Leu Ala Ser Tyr Lys<br>                   110                     115                   120 | 389 |
| agc ggc acc ctg gtg tcc ctg ggc ttc cct ccc gag agc tgc ggc tac<br>Ser Gly Thr Leu Val Ser Leu Gly Phe Pro Pro Glu Ser Cys Gly Tyr<br>            125                     130                     135 | 437 |
| gcc agc gtg acc gac agc gag ttc ctg gtg att atg att acc ccc cac<br>Ala Ser Val Thr Asp Ser Glu Phe Leu Val Ile Met Ile Thr Pro His<br>            140                     145                     150 | 485 |
| cac gtg ggc gtg gac gac tac cgg ggc cac tgg gtg gac cct ctg ttc<br>His Val Gly Val Asp Asp Tyr Arg Gly His Trp Val Asp Pro Leu Phe<br>155                     160                     165 | 533 |
| gtg gga ggg gaa tgc gac cag agc tac tgc gat acc atc cac aac tcc<br>Val Gly Gly Glu Cys Asp Gln Ser Tyr Cys Asp Thr Ile His Asn Ser<br>170                     175                     180                   185 | 581 |
| agc gtg tgg att ccc gcc gac cag acc aag aag aac atc tgc ggc cag<br>Ser Val Trp Ile Pro Ala Asp Gln Thr Lys Lys Asn Ile Cys Gly Gln<br>                   190                     195                   200 | 629 |
| agc ttc acc cct ctg acc gtg acc gtg gcc tac gac aag acc aaa gag<br>Ser Phe Thr Pro Leu Thr Val Thr Val Ala Tyr Asp Lys Thr Lys Glu<br>            205                     210                     215 | 677 |
| att gcc gcc gga ggg atc gtg ttc aag agc aag tac cac agc cac atg<br>Ile Ala Ala Gly Gly Ile Val Phe Lys Ser Lys Tyr His Ser His Met<br>            220                     225                     230 | 725 |
| gaa ggc gcc agg acc tgc aga ctg tcc tac tgc ggc cgg aac ggc atc<br>Glu Gly Ala Arg Thr Cys Arg Leu Ser Tyr Cys Gly Arg Asn Gly Ile<br>235                     240                     245 | 773 |
| aag ttc ccc aac ggc gag tgg gtg tcc ctg atg ctg aag ctg cgg agc<br>Lys Phe Pro Asn Gly Glu Trp Val Ser Leu Met Leu Lys Leu Arg Ser<br>250                     255                     260                   265 | 821 |
| aag cgg aac ctg tac ttc ccc tgc ctg aag atg tgc ccc acc ggc atc<br>Lys Arg Asn Leu Tyr Phe Pro Cys Leu Lys Met Cys Pro Thr Gly Ile<br>                   270                     275                   280 | 869 |
| cgg ggc gag atc tac ccc agc atc aga tgg gcc cag gtg ctg acc agc<br>Arg Gly Glu Ile Tyr Pro Ser Ile Arg Trp Ala Gln Val Leu Thr Ser<br>            285                     290                     295 | 917 |
| gag atc cag aga atc ctg gac tac agc ctg tgc cag aac acc tgg gac<br>Glu Ile Gln Arg Ile Leu Asp Tyr Ser Leu Cys Gln Asn Thr Trp Asp<br>            300                     305                     310 | 965 |
| aag gtg gag cgg aaa gag ccc ctg agc ccc ctg gac ctg agc tac ctg<br>Lys Val Glu Arg Lys Glu Pro Leu Ser Pro Leu Asp Leu Ser Tyr Leu<br>315                     320                     325 | 1013 |

```
gcc agc aag tcc ccc ggc aag ggc ctg gcc tac acc gtg atc aac ggc      1061
Ala Ser Lys Ser Pro Gly Lys Gly Leu Ala Tyr Thr Val Ile Asn Gly
330             335                 340                 345 acc ctg agc ttc gcc cac acc aga tac gtg cgg atg tgg atc gac ggc      1109
Thr Leu Ser Phe Ala His Thr Arg Tyr Val Arg Met Trp Ile Asp Gly
                350                 355                 360 ccc gtg ctg aaa gag ccc aag ggc aag aga gag agc ccc agc ggc atc      1157
Pro Val Leu Lys Glu Pro Lys Gly Lys Arg Glu Ser Pro Ser Gly Ile
            365                 370                 375 agc agc gac atc tgg acc cag tgg ttc aag tac ggc gac atg gaa atc      1205
Ser Ser Asp Ile Trp Thr Gln Trp Phe Lys Tyr Gly Asp Met Glu Ile
        380                 385                 390 ggc ccc aac ggc ctg ctg aaa aca gcc ggc gga tac aag ttt cct tgg      1253
Gly Pro Asn Gly Leu Leu Lys Thr Ala Gly Gly Tyr Lys Phe Pro Trp
    395                 400                 405 cac ctg atc ggc atg ggc atc gtg gac aac gag ctg cac gag ctg tcc      1301
His Leu Ile Gly Met Gly Ile Val Asp Asn Glu Leu His Glu Leu Ser
410                 415                 420                 425 gag gcc aac ccc ctg gat cac ccc cag ctg ccc cac gcc cag agc att      1349
Glu Ala Asn Pro Leu Asp His Pro Gln Leu Pro His Ala Gln Ser Ile
                430                 435                 440 gcc gac gac agc gag gaa atc ttc ttc ggc gac acc ggc gtg agc aag      1397
Ala Asp Asp Ser Glu Glu Ile Phe Phe Gly Asp Thr Gly Val Ser Lys
            445                 450                 455 aac ccc gtg gaa ctg gtg aca ggc tgg ttc acc agc tgg aaa gag agc      1445
Asn Pro Val Glu Leu Val Thr Gly Trp Phe Thr Ser Trp Lys Glu Ser
        460                 465                 470 ctg gcc gcc gga tct tgc ccc gac ctg cgg tgc ccc cct ctg ttc ccc      1493
Leu Ala Ala Gly Ser Cys Pro Asp Leu Arg Cys Pro Pro Leu Phe Pro
    475                 480                 485 ggc atc gtg tac tac ctg cag aaa gcc cag atg gaa gag cgg ggc gag      1541
Gly Ile Val Tyr Tyr Leu Gln Lys Ala Gln Met Glu Glu Arg Gly Glu
490                 495                 500                 505 cgg agc gac agc ttc gag atg cgg atc ttc aag ccc aac aac atg cgg      1589
Arg Ser Asp Ser Phe Glu Met Arg Ile Phe Lys Pro Asn Asn Met Arg
                510                 515                 520 gcc aga gtg tgatgagaat tcttaattaa                                    1618
Ala Arg Val <210> SEQ ID NO 36
<211> LENGTH: 524
<212> TYPE: PRT
<213> ORGANISM: Vesicular stomatitis virus

<400> SEQUENCE: 36

Met Thr Ser Ser Val Thr Ile Ser Val Val Leu Leu Ile Ser Phe Ile
1               5                   10                  15

Thr Pro Leu Tyr Ser Tyr Leu Ser Ile Ala Phe Pro Glu Asn Thr Lys
            20                  25                  30

Leu Asp Trp Lys Pro Val Thr Lys Asn Thr Arg Tyr Cys Pro Met Gly
        35                  40                  45

Gly Glu Trp Phe Leu Glu Pro Gly Leu Gln Glu Ser Phe Leu Ser
    50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
            100                 105                 110
```

-continued

```
Cys Asp Thr Ala Leu Ala Ser Tyr Lys Ser Gly Thr Leu Val Ser Leu
            115                 120                 125
Gly Phe Pro Pro Glu Ser Cys Gly Tyr Ala Ser Val Thr Asp Ser Glu
        130                 135                 140
Phe Leu Val Ile Met Ile Thr Pro His His Val Gly Val Asp Asp Tyr
145                 150                 155                 160
Arg Gly His Trp Val Asp Pro Leu Phe Val Gly Gly Glu Cys Asp Gln
                165                 170                 175
Ser Tyr Cys Asp Thr Ile His Asn Ser Ser Val Trp Ile Pro Ala Asp
            180                 185                 190
Gln Thr Lys Lys Asn Ile Cys Gly Gln Ser Phe Thr Pro Leu Thr Val
        195                 200                 205
Thr Val Ala Tyr Asp Lys Thr Lys Glu Ile Ala Ala Gly Gly Ile Val
    210                 215                 220
Phe Lys Ser Lys Tyr His Ser His Met Glu Gly Ala Arg Thr Cys Arg
225                 230                 235                 240
Leu Ser Tyr Cys Gly Arg Asn Gly Ile Lys Phe Pro Asn Gly Glu Trp
                245                 250                 255
Val Ser Leu Met Leu Lys Leu Arg Ser Lys Arg Asn Leu Tyr Phe Pro
            260                 265                 270
Cys Leu Lys Met Cys Pro Thr Gly Ile Arg Gly Glu Ile Tyr Pro Ser
        275                 280                 285
Ile Arg Trp Ala Gln Val Leu Thr Ser Glu Ile Gln Arg Ile Leu Asp
    290                 295                 300
Tyr Ser Leu Cys Gln Asn Thr Trp Asp Lys Val Glu Arg Lys Glu Pro
305                 310                 315                 320
Leu Ser Pro Leu Asp Leu Ser Tyr Leu Ala Ser Lys Ser Pro Gly Lys
                325                 330                 335
Gly Leu Ala Tyr Thr Val Ile Asn Gly Thr Leu Ser Phe Ala His Thr
            340                 345                 350
Arg Tyr Val Arg Met Trp Ile Asp Gly Pro Val Leu Lys Glu Pro Lys
        355                 360                 365
Gly Lys Arg Glu Ser Pro Ser Gly Ile Ser Ser Asp Ile Trp Thr Gln
    370                 375                 380
Trp Phe Lys Tyr Gly Asp Met Glu Ile Gly Pro Asn Gly Leu Leu Lys
385                 390                 395                 400
Thr Ala Gly Gly Tyr Lys Phe Pro Trp His Leu Ile Gly Met Gly Ile
                405                 410                 415
Val Asp Asn Glu Leu His Glu Leu Ser Glu Ala Asn Pro Leu Asp His
            420                 425                 430
Pro Gln Leu Pro His Ala Gln Ser Ile Ala Asp Ser Glu Glu Ile
        435                 440                 445
Phe Phe Gly Asp Thr Gly Val Ser Lys Asn Pro Val Glu Leu Val Thr
    450                 455                 460
Gly Trp Phe Thr Ser Trp Lys Glu Ser Leu Ala Ala Gly Ser Cys Pro
465                 470                 475                 480
Asp Leu Arg Cys Pro Pro Leu Phe Pro Gly Ile Val Tyr Tyr Leu Gln
                485                 490                 495
Lys Ala Gln Met Glu Glu Arg Gly Glu Arg Ser Asp Ser Phe Glu Met
            500                 505                 510
Arg Ile Phe Lys Pro Asn Asn Met Arg Ala Arg Val
        515                 520
```

<210> SEQ ID NO 37
<211> LENGTH: 1582
<212> TYPE: DNA
<213> ORGANISM: Vesicular stomatitis virus
<220> FEATURE:
<221> NAME/KEY: CDS
<222> LOCATION: (27)..(1568)

<400> SEQUENCE: 37

```
ggcgcgccgg atcctgatca gccacc atg aac ttt ctg ctg ctg aca ttc atc        53
                              Met Asn Phe Leu Leu Leu Thr Phe Ile
                               1               5 gtg ctg cct ctg tgc agc cac gcc aag ttc agc atc gtg ttc ccc cag        101
Val Leu Pro Leu Cys Ser His Ala Lys Phe Ser Ile Val Phe Pro Gln
 10                  15                  20                  25 agc cag aag ggc aac tgg aag aac gtg ccc agc agc tac cac tac tgc        149
Ser Gln Lys Gly Asn Trp Lys Asn Val Pro Ser Ser Tyr His Tyr Cys
                 30                  35                  40 ccc agc agc agc gac cag aac tgg cac aac gac ctg ctg ggc atc acc        197
Pro Ser Ser Ser Asp Gln Asn Trp His Asn Asp Leu Leu Gly Ile Thr
             45                  50                  55 atg aag gtg aaa atg ccc aag acc cac aag gcc att cag gct gac ggc        245
Met Lys Val Lys Met Pro Lys Thr His Lys Ala Ile Gln Ala Asp Gly
 60                  65                  70 tgg atg tgc cac gcc gcc aag tgg atc acc acc tgc gac ttc cgg tgg        293
Trp Met Cys His Ala Ala Lys Trp Ile Thr Thr Cys Asp Phe Arg Trp
 75                  80                  85 tac ggc ccc aag tac atc acc cac agc atc cac tcc atc cag ccc acc        341
Tyr Gly Pro Lys Tyr Ile Thr His Ser Ile His Ser Ile Gln Pro Thr
 90                  95                 100                 105 tcc gag cag tgc aaa gag agc atc aag cag acc aag cag ggc acc tgg        389
Ser Glu Gln Cys Lys Glu Ser Ile Lys Gln Thr Lys Gln Gly Thr Trp
                110                 115                 120 atg agc ccc ggc ttc cca ccc cag aac tgc ggc tac gcc acc gtg acc        437
Met Ser Pro Gly Phe Pro Pro Gln Asn Cys Gly Tyr Ala Thr Val Thr
            125                 130                 135 gac agc gtg gcc gtg gtg gtg cag gcc acc ccc cac cac gtg ctg gtc        485
Asp Ser Val Ala Val Val Val Gln Ala Thr Pro His His Val Leu Val
        140                 145                 150 gac gag tac acc ggc gag tgg atc gac agc cag ttc ccc aac ggc aag        533
Asp Glu Tyr Thr Gly Glu Trp Ile Asp Ser Gln Phe Pro Asn Gly Lys
    155                 160                 165 tgc gag aca gag gaa tgc gag aca gtg cac aac agc acc gtg tgg tac        581
Cys Glu Thr Glu Glu Cys Glu Thr Val His Asn Ser Thr Val Trp Tyr
170                 175                 180                 185 agc gac tac aag gtg acc ggc ctg tgc gac gcc acc ctg gtg gac acc        629
Ser Asp Tyr Lys Val Thr Gly Leu Cys Asp Ala Thr Leu Val Asp Thr
                190                 195                 200 gag atc acc ttt ttc agc gag gac ggc aag aaa gag tcc atc ggc aag        677
Glu Ile Thr Phe Phe Ser Glu Asp Gly Lys Lys Glu Ser Ile Gly Lys
            205                 210                 215 ccc aac acc ggc tac aga agc aac tac ttc gcc tac gag aag ggc gac        725
Pro Asn Thr Gly Tyr Arg Ser Asn Tyr Phe Ala Tyr Glu Lys Gly Asp
        220                 225                 230 aaa gtg tgc aag atg aac tac tgc aag cat gcc gga gtg agg ctg cct        773
Lys Val Cys Lys Met Asn Tyr Cys Lys His Ala Gly Val Arg Leu Pro
    235                 240                 245 agc ggc gtg tgg ttc gag ttc gtg gac cag gac gtg tac gcc gcc gcc        821
Ser Gly Val Trp Phe Glu Phe Val Asp Gln Asp Val Tyr Ala Ala Ala
250                 255                 260                 265 aag ctg ccc gag tgc ccc gtg ggc gcc acc atc agc gcc ccc acc cag        869
Lys Leu Pro Glu Cys Pro Val Gly Ala Thr Ile Ser Ala Pro Thr Gln
```

```
                       270                 275                 280
acc agc gtg gac gtg agc ctg atc ctg gac gtg gag aga atc ctg gac       917
Thr Ser Val Asp Val Ser Leu Ile Leu Asp Val Glu Arg Ile Leu Asp
            285                 290                 295 tac tct ctg tgt cag gaa acc tgg tcc aag atc aga tcc aag cag ccc       965
Tyr Ser Leu Cys Gln Glu Thr Trp Ser Lys Ile Arg Ser Lys Gln Pro
                300                 305                 310 gtg agc cct gtg gac ctg agc tac ctg gcc cct aag aac ccc ggc acc      1013
Val Ser Pro Val Asp Leu Ser Tyr Leu Ala Pro Lys Asn Pro Gly Thr
        315                 320                 325 ggc cct gcc ttc acc atc atc aac ggc acc ctg aag tac ttc gag aca      1061
Gly Pro Ala Phe Thr Ile Ile Asn Gly Thr Leu Lys Tyr Phe Glu Thr
330                 335                 340                 345 cgg tac atc cgg atc gac atc gac aac ccc atc atc agc aag atg gtg      1109
Arg Tyr Ile Arg Ile Asp Ile Asp Asn Pro Ile Ile Ser Lys Met Val
                350                 355                 360 ggc aag atc agc ggc agc cag acc gag cgg gag ctg tgg acc gag tgg      1157
Gly Lys Ile Ser Gly Ser Gln Thr Glu Arg Glu Leu Trp Thr Glu Trp
            365                 370                 375 ttc ccc tac gag ggc gtg gag atc ggc ccc aat ggc atc ctg aaa acc      1205
Phe Pro Tyr Glu Gly Val Glu Ile Gly Pro Asn Gly Ile Leu Lys Thr
        380                 385                 390 cct acc ggc tac aag ttc ccc ctg ttc atg atc ggc cac ggc atg ctg      1253
Pro Thr Gly Tyr Lys Phe Pro Leu Phe Met Ile Gly His Gly Met Leu
395                 400                 405 gac agc gac ctg cac aag acc tcc cag gcc gag gtg ttc gag cac ccc      1301
Asp Ser Asp Leu His Lys Thr Ser Gln Ala Glu Val Phe Glu His Pro
410                 415                 420                 425 cac ctg gcc gag gcc ccc aag cag ctg ccc gaa gag gaa acc ctg ttc      1349
His Leu Ala Glu Ala Pro Lys Gln Leu Pro Glu Glu Glu Thr Leu Phe
                430                 435                 440 ttc ggc gac acc ggc atc tcc aag aac cct gtg gag ctg atc gag ggc      1397
Phe Gly Asp Thr Gly Ile Ser Lys Asn Pro Val Glu Leu Ile Glu Gly
            445                 450                 455 tgg ttc agc agc tgg aag agc acc gtg gtg acc ttt ttc ttc gcc atc      1445
Trp Phe Ser Ser Trp Lys Ser Thr Val Val Thr Phe Phe Phe Ala Ile
        460                 465                 470 ggc gtg ttc atc ctg ctg tac gtg gtg gcc cgg atc gtg atc gcc gtg      1493
Gly Val Phe Ile Leu Leu Tyr Val Val Ala Arg Ile Val Ile Ala Val
475                 480                 485 cgg tac aga tac cag ggc agc aac aac aag cgg atc tac aac gac atc      1541
Arg Tyr Arg Tyr Gln Gly Ser Asn Asn Lys Arg Ile Tyr Asn Asp Ile
490                 495                 500                 505 gag atg agc cgg ttc cgg aag tga tga gaattcttaa ttaa                  1582
Glu Met Ser Arg Phe Arg Lys
                510

<210> SEQ ID NO 38
<211> LENGTH: 512
<212> TYPE: PRT
<213> ORGANISM: Vesicular stomatitis virus

<400> SEQUENCE: 38

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
                20                  25                  30

Asn Val Pro Ser Ser Tyr His Tyr Cys Pro Ser Ser Ser Asp Gln Asn
            35                  40                  45

Trp His Asn Asp Leu Leu Gly Ile Thr Met Lys Val Lys Met Pro Lys
```

-continued

```
                50                  55                  60
Thr His Lys Ala Ile Gln Ala Asp Gly Trp Met Cys His Ala Ala Lys
 65                  70                  75                  80

Trp Ile Thr Thr Cys Asp Phe Arg Trp Tyr Gly Pro Lys Tyr Ile Thr
                     85                  90                  95

His Ser Ile His Ser Ile Gln Pro Thr Ser Glu Gln Cys Lys Glu Ser
                    100                 105                 110

Ile Lys Gln Thr Lys Gln Gly Thr Trp Met Ser Pro Gly Phe Pro Pro
                    115                 120                 125

Gln Asn Cys Gly Tyr Ala Thr Val Thr Asp Ser Val Ala Val Val Val
                130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                    165                 170                 175

Thr Val His Asn Ser Thr Val Trp Tyr Ser Asp Tyr Lys Val Thr Gly
                180                 185                 190

Leu Cys Asp Ala Thr Leu Val Asp Thr Glu Ile Thr Phe Phe Ser Glu
    195                 200                 205

Asp Gly Lys Lys Glu Ser Ile Gly Lys Pro Asn Thr Gly Tyr Arg Ser
210                 215                 220

Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
                    245                 250                 255

Val Asp Gln Asp Val Tyr Ala Ala Ala Lys Leu Pro Glu Cys Pro Val
            260                 265                 270

Gly Ala Thr Ile Ser Ala Pro Thr Gln Thr Ser Val Asp Val Ser Leu
        275                 280                 285

Ile Leu Asp Val Glu Arg Ile Leu Asp Tyr Ser Leu Cys Gln Glu Thr
    290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                    325                 330                 335

Asn Gly Thr Leu Lys Tyr Phe Glu Thr Arg Tyr Ile Arg Ile Asp Ile
                340                 345                 350

Asp Asn Pro Ile Ile Ser Lys Met Val Gly Lys Ile Ser Gly Ser Gln
            355                 360                 365

Thr Glu Arg Glu Leu Trp Thr Glu Trp Phe Pro Tyr Glu Gly Val Glu
        370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                    405                 410                 415

Ser Gln Ala Glu Val Phe Glu His Pro His Leu Ala Glu Ala Pro Lys
                420                 425                 430

Gln Leu Pro Glu Glu Glu Thr Leu Phe Phe Gly Asp Thr Gly Ile Ser
            435                 440                 445

Lys Asn Pro Val Glu Leu Ile Glu Gly Trp Phe Ser Ser Trp Lys Ser
        450                 455                 460

Thr Val Val Thr Phe Phe Phe Ala Ile Gly Val Phe Ile Leu Leu Tyr
465                 470                 475                 480
```

```
Val Val Ala Arg Ile Val Ile Ala Val Arg Tyr Arg Tyr Gln Gly Ser
            485                 490                 495

Asn Asn Lys Arg Ile Tyr Asn Asp Ile Glu Met Ser Arg Phe Arg Lys
        500                 505                 510

<210> SEQ ID NO 39
<211> LENGTH: 1600
<212> TYPE: DNA
<213> ORGANISM: Vesicular stomatitis virus
<220> FEATURE:
<221> NAME/KEY: CDS
<222> LOCATION: (27)..(1586)

<400> SEQUENCE: 39
ggcgcgccgg atcctgatca gccacc atg acc gat aca gtg ctg ggc aag ttc        53
                              Met Thr Asp Thr Val Leu Gly Lys Phe
                              1               5 cag atc gtg ttc ccc gac cag aac gag ctg gaa tgg acc ccc gtc gtg        101
Gln Ile Val Phe Pro Asp Gln Asn Glu Leu Glu Trp Thr Pro Val Val
10              15                  20                  25 ggc gac agc cgg cat tgc cct cag tcc agc gag atg cag ttc gac ggc        149
Gly Asp Ser Arg His Cys Pro Gln Ser Ser Glu Met Gln Phe Asp Gly
                30                  35                  40 agc aga agc cag acc atc ctg acc ggc aag gcc ccc gtg ggc atc aca        197
Ser Arg Ser Gln Thr Ile Leu Thr Gly Lys Ala Pro Val Gly Ile Thr
            45                  50                  55 ccc agc aag agc gac ggc ttc atc tgc cac gcc gcc aag tgg gtg acc        245
Pro Ser Lys Ser Asp Gly Phe Ile Cys His Ala Ala Lys Trp Val Thr
        60                  65                  70 acc tgc gac ttc cgg tgg tac ggc ccc aag tac atc acc cac agc atc        293
Thr Cys Asp Phe Arg Trp Tyr Gly Pro Lys Tyr Ile Thr His Ser Ile
    75                  80                  85 cac cac ctg cgg ccc acc acc tcc gac tgc gag aca gcc ctg cag cgg        341
His His Leu Arg Pro Thr Thr Ser Asp Cys Glu Thr Ala Leu Gln Arg
90                  95                  100                 105 tac aag gac ggc agc ctg atc aac ctg ggc ttc cct ccc gag agc tgc        389
Tyr Lys Asp Gly Ser Leu Ile Asn Leu Gly Phe Pro Pro Glu Ser Cys
                110                 115                 120 ggc tac gcc acc gtg aca gac agc gag gcc atg ctg gtg cag gtg acc        437
Gly Tyr Ala Thr Val Thr Asp Ser Glu Ala Met Leu Val Gln Val Thr
            125                 130                 135 ccc cac cac gtg ggc gtg gac gac tac cgg ggc cac tgg atc gac ccc        485
Pro His His Val Gly Val Asp Asp Tyr Arg Gly His Trp Ile Asp Pro
        140                 145                 150 ctg ttc cct ggc ggc gag tgc agc acc aat ttc tgc gat acc gtg cac        533
Leu Phe Pro Gly Gly Glu Cys Ser Thr Asn Phe Cys Asp Thr Val His
    155                 160                 165 aac agc agc gtg tgg att ccc aag agc cag aaa acc gac atc tgc gcc        581
Asn Ser Ser Val Trp Ile Pro Lys Ser Gln Lys Thr Asp Ile Cys Ala
170                 175                 180                 185 cag agc ttc aag aac atc aag atg acc gcc agc tac ccc agc gag gga        629
Gln Ser Phe Lys Asn Ile Lys Met Thr Ala Ser Tyr Pro Ser Glu Gly
                190                 195                 200 gcc ctg gtg tcc gac cgg ttc gcc ttc cac agc gcc tac cac ccc aac        677
Ala Leu Val Ser Asp Arg Phe Ala Phe His Ser Ala Tyr His Pro Asn
            205                 210                 215 atg ccc ggc agc acc gtg tgc atc atg gat ttc tgc gag cag aag ggc        725
Met Pro Gly Ser Thr Val Cys Ile Met Asp Phe Cys Glu Gln Lys Gly
        220                 225                 230 ctg cgg ttc acc aac ggc gag tgg atg ggc ctg aac gtg gag cag agc        773
Leu Arg Phe Thr Asn Gly Glu Trp Met Gly Leu Asn Val Glu Gln Ser
    235                 240                 245
```

| | | | | | | | | | | | | | | | | |
|---|---|---|---|---|---|---|---|---|---|---|---|---|---|---|---|---|
| atc | cgg | gag | aag | aag | atc | agc | gcc | atc | ttc | ccc | aac | tgc | gtg | gcc | ggc | 821 |
| Ile | Arg | Glu | Lys | Lys | Ile | Ser | Ala | Ile | Phe | Pro | Asn | Cys | Val | Ala | Gly | |
| 250 | | | | | 255 | | | | 260 | | | | | 265 | | |
| acc | gag | atc | cgg | gcc | acc | ctg | gaa | tcc | gag | ggc | gcc | agg | acc | ctg | acc | 869 |
| Thr | Glu | Ile | Arg | Ala | Thr | Leu | Glu | Ser | Glu | Gly | Ala | Arg | Thr | Leu | Thr | |
| | | | 270 | | | | | 275 | | | | | 280 | | | |
| tgg | gag | aca | cag | cgg | atg | ctg | gac | tac | agc | ctg | tgc | cag | aac | acc | tgg | 917 |
| Trp | Glu | Thr | Gln | Arg | Met | Leu | Asp | Tyr | Ser | Leu | Cys | Gln | Asn | Thr | Trp | |
| | | 285 | | | | | 290 | | | | | 295 | | | | |
| gac | aag | gtg | tcc | cgg | aaa | gag | cct | ctg | tcc | ccc | ctg | gac | ctg | agc | tac | 965 |
| Asp | Lys | Val | Ser | Arg | Lys | Glu | Pro | Leu | Ser | Pro | Leu | Asp | Leu | Ser | Tyr | |
| | 300 | | | | | 305 | | | | | 310 | | | | | |
| ctg | agc | cct | aga | gcc | cct | ggc | aag | ggc | atg | gcc | tac | acc | gtg | atc | aac | 1013 |
| Leu | Ser | Pro | Arg | Ala | Pro | Gly | Lys | Gly | Met | Ala | Tyr | Thr | Val | Ile | Asn | |
| 315 | | | | | 320 | | | | | 325 | | | | | | |
| ggc | acc | ctg | cac | agc | gcc | cac | gcc | aag | tat | atc | cgg | acc | tgg | atc | gac | 1061 |
| Gly | Thr | Leu | His | Ser | Ala | His | Ala | Lys | Tyr | Ile | Arg | Thr | Trp | Ile | Asp | |
| 330 | | | | | 335 | | | | | 340 | | | | | 345 | |
| tac | ggc | gag | atg | aaa | gag | atc | aag | ggc | ggc | agg | ggc | gag | tac | agc | aag | 1109 |
| Tyr | Gly | Glu | Met | Lys | Glu | Ile | Lys | Gly | Gly | Arg | Gly | Glu | Tyr | Ser | Lys | |
| | | | 350 | | | | | 355 | | | | | 360 | | | |
| gcc | cct | gag | ctg | ctg | tgg | agc | cag | tgg | ttc | gac | ttc | ggc | ccc | ttc | aag | 1157 |
| Ala | Pro | Glu | Leu | Leu | Trp | Ser | Gln | Trp | Phe | Asp | Phe | Gly | Pro | Phe | Lys | |
| | | 365 | | | | | 370 | | | | | 375 | | | | |
| atc | ggc | ccc | aac | ggc | ctg | ctg | cac | acc | ggc | aag | acc | ttc | aag | ttc | cct | 1205 |
| Ile | Gly | Pro | Asn | Gly | Leu | Leu | His | Thr | Gly | Lys | Thr | Phe | Lys | Phe | Pro | |
| | 380 | | | | | 385 | | | | | 390 | | | | | |
| ctg | tat | ctg | atc | gga | gcc | ggc | atc | atc | gac | gag | gac | ctg | cac | gag | ctg | 1253 |
| Leu | Tyr | Leu | Ile | Gly | Ala | Gly | Ile | Ile | Asp | Glu | Asp | Leu | His | Glu | Leu | |
| 395 | | | | | 400 | | | | | 405 | | | | | | |
| gac | gaa | gcc | gcc | cct | atc | gac | cac | ccc | cag | atg | ccc | gac | gcc | aag | agc | 1301 |
| Asp | Glu | Ala | Ala | Pro | Ile | Asp | His | Pro | Gln | Met | Pro | Asp | Ala | Lys | Ser | |
| 410 | | | | | 415 | | | | | 420 | | | | | 425 | |
| gtg | ctg | ccc | gag | gac | gag | gaa | atc | ttc | ttc | ggc | gac | acc | ggc | gtg | agc | 1349 |
| Val | Leu | Pro | Glu | Asp | Glu | Glu | Ile | Phe | Phe | Gly | Asp | Thr | Gly | Val | Ser | |
| | | | 430 | | | | | 435 | | | | | 440 | | | |
| aag | aac | ccc | atc | gag | ctg | atc | cag | ggc | tgg | ttc | agc | aac | tgg | cgg | gag | 1397 |
| Lys | Asn | Pro | Ile | Glu | Leu | Ile | Gln | Gly | Trp | Phe | Ser | Asn | Trp | Arg | Glu | |
| | | 445 | | | | | 450 | | | | | 455 | | | | |
| agc | gtg | atg | gcc | atc | gtg | ggc | atc | gtg | ctg | ctg | atc | gtg | gtg | acc | ttc | 1445 |
| Ser | Val | Met | Ala | Ile | Val | Gly | Ile | Val | Leu | Leu | Ile | Val | Val | Thr | Phe | |
| | 460 | | | | | 465 | | | | | 470 | | | | | |
| ctg | gcc | atc | aag | acc | gtg | cgg | gtg | ctg | aac | tgc | ctg | tgg | cgg | ccc | agg | 1493 |
| Leu | Ala | Ile | Lys | Thr | Val | Arg | Val | Leu | Asn | Cys | Leu | Trp | Arg | Pro | Arg | |
| 475 | | | | | 480 | | | | | 485 | | | | | | |
| aag | aaa | cgg | atc | gtc | cgg | cag | gaa | gtg | gac | gtc | gag | agc | cgg | ctg | aac | 1541 |
| Lys | Lys | Arg | Ile | Val | Arg | Gln | Glu | Val | Asp | Val | Glu | Ser | Arg | Leu | Asn | |
| 490 | | | | 495 | | | | | 500 | | | | | | 505 | |
| cac | ttc | gag | atg | aga | ggc | ttc | ccc | gag | tac | gtg | aag | cgg | tga | tga | | 1586 |
| His | Phe | Glu | Met | Arg | Gly | Phe | Pro | Glu | Tyr | Val | Lys | Arg | | | | |
| | | | 510 | | | | | 515 | | | | | | | | |
| gaattcttaa | ttaa | | | | | | | | | | | | | | | 1600 |

<210> SEQ ID NO 40
<211> LENGTH: 518
<212> TYPE: PRT
<213> ORGANISM: Vesicular stomatitis virus

<400> SEQUENCE: 40

Met Thr Asp Thr Val Leu Gly Lys Phe Gln Ile Val Phe Pro Asp Gln

-continued

```
1               5                   10                  15
Asn Glu Leu Glu Trp Thr Pro Val Val Gly Asp Ser Arg His Cys Pro
                20                  25                  30

Gln Ser Ser Glu Met Gln Phe Asp Gly Ser Arg Ser Gln Thr Ile Leu
            35                  40                  45

Thr Gly Lys Ala Pro Val Gly Ile Thr Pro Ser Lys Ser Asp Gly Phe
        50                  55                  60

Ile Cys His Ala Ala Lys Trp Val Thr Thr Cys Asp Phe Arg Trp Tyr
65                  70                  75                  80

Gly Pro Lys Tyr Ile Thr His Ser Ile His His Leu Arg Pro Thr Thr
                    85                  90                  95

Ser Asp Cys Glu Thr Ala Leu Gln Arg Tyr Lys Asp Gly Ser Leu Ile
                100                 105                 110

Asn Leu Gly Phe Pro Pro Glu Ser Cys Gly Tyr Ala Thr Val Thr Asp
            115                 120                 125

Ser Glu Ala Met Leu Val Gln Val Thr Pro His His Val Gly Val Asp
        130                 135                 140

Asp Tyr Arg Gly His Trp Ile Asp Pro Leu Phe Pro Gly Gly Glu Cys
145                 150                 155                 160

Ser Thr Asn Phe Cys Asp Thr Val His Asn Ser Ser Val Trp Ile Pro
                165                 170                 175

Lys Ser Gln Lys Thr Asp Ile Cys Ala Gln Ser Phe Lys Asn Ile Lys
                180                 185                 190

Met Thr Ala Ser Tyr Pro Ser Glu Gly Ala Leu Val Ser Asp Arg Phe
            195                 200                 205

Ala Phe His Ser Ala Tyr His Pro Asn Met Pro Gly Ser Thr Val Cys
        210                 215                 220

Ile Met Asp Phe Cys Glu Gln Lys Gly Leu Arg Phe Thr Asn Gly Glu
225                 230                 235                 240

Trp Met Gly Leu Asn Val Glu Gln Ser Ile Arg Glu Lys Lys Ile Ser
                245                 250                 255

Ala Ile Phe Pro Asn Cys Val Ala Gly Thr Glu Ile Arg Ala Thr Leu
                260                 265                 270

Glu Ser Glu Gly Ala Arg Thr Leu Thr Trp Glu Thr Gln Arg Met Leu
            275                 280                 285

Asp Tyr Ser Leu Cys Gln Asn Thr Trp Asp Lys Val Ser Arg Lys Glu
        290                 295                 300

Pro Leu Ser Pro Leu Asp Leu Ser Tyr Leu Ser Pro Arg Ala Pro Gly
305                 310                 315                 320

Lys Gly Met Ala Tyr Thr Val Ile Asn Gly Thr Leu His Ser Ala His
                325                 330                 335

Ala Lys Tyr Ile Arg Thr Trp Ile Asp Tyr Gly Glu Met Lys Glu Ile
                340                 345                 350

Lys Gly Gly Arg Gly Glu Tyr Ser Lys Ala Pro Glu Leu Leu Trp Ser
            355                 360                 365

Gln Trp Phe Asp Phe Gly Pro Phe Lys Ile Gly Pro Asn Gly Leu Leu
        370                 375                 380

His Thr Gly Lys Thr Phe Lys Phe Pro Leu Tyr Leu Ile Gly Ala Gly
385                 390                 395                 400

Ile Ile Asp Glu Asp Leu His Glu Leu Asp Ala Ala Pro Ile Asp
                405                 410                 415

His Pro Gln Met Pro Asp Ala Lys Ser Val Leu Pro Glu Asp Glu Glu
            420                 425                 430
```

-continued

```
Ile Phe Phe Gly Asp Thr Gly Val Ser Lys Asn Pro Ile Glu Leu Ile
        435                 440                 445

Gln Gly Trp Phe Ser Asn Trp Arg Glu Ser Val Met Ala Ile Val Gly
450                 455                 460

Ile Val Leu Leu Ile Val Val Thr Phe Leu Ala Ile Lys Thr Val Arg
465                 470                 475                 480

Val Leu Asn Cys Leu Trp Arg Pro Arg Lys Lys Arg Ile Val Arg Gln
                485                 490                 495

Glu Val Asp Val Glu Ser Arg Leu Asn His Phe Glu Met Arg Gly Phe
            500                 505                 510

Pro Glu Tyr Val Lys Arg
            515

<210> SEQ ID NO 41
<211> LENGTH: 1600
<212> TYPE: DNA
<213> ORGANISM: Vesicular stomatitis virus
<220> F

```
gcc ctg gtg tcc gac cgg ttc gcc ttc cac agc gcc tac cac ccc aac      677
Ala Leu Val Ser Asp Arg Phe Ala Phe His Ser Ala Tyr His Pro Asn
            205                 210                 215 atg ccc ggc agc acc gtg tgc atc atg gat ttc tgc gag cag aag ggc      725
Met Pro Gly Ser Thr Val Cys Ile Met Asp Phe Cys Glu Gln Lys Gly
        220                 225                 230 ctg cgg ttc acc aac ggc gag tgg atg ggc ctg aac gtg gag cag agc      773
Leu Arg Phe Thr Asn Gly Glu Trp Met Gly Leu Asn Val Glu Gln Ser
    235                 240                 245 atc cgg gag aag aag atc agc gcc atc ttc ccc aac tgc gtg gcc ggc      821
Ile Arg Glu Lys Lys Ile Ser Ala Ile Phe Pro Asn Cys Val Ala Gly
250                 255                 260                 265 acc gag atc cgg gcc acc ctg gaa tcc gag ggc gcc agg acc ctg acc      869
Thr Glu Ile Arg Ala Thr Leu Glu Ser Glu Gly Ala Arg Thr Leu Thr
                270                 275                 280 tgg gag aca cag cgg atg ctg gac tac agc ctg tgc cag aac acc tgg      917
Trp Glu Thr Gln Arg Met Leu Asp Tyr Ser Leu Cys Gln Asn Thr Trp
            285                 290                 295 gac aag gtg tcc cgg aaa gag cct ctg tcc ccc ctg gac ctg agc tac      965
Asp Lys Val Ser Arg Lys Glu Pro Leu Ser Pro Leu Asp Leu Ser Tyr
        300                 305                 310 ctg agc cct aga gcc cct ggc aag ggc atg gcc tac acc gtg atc aac     1013
Leu Ser Pro Arg Ala Pro Gly Lys Gly Met Ala Tyr Thr Val Ile Asn
    315                 320                 325 ggc acc ctg cac agc gcc cac gcc aag tat atc cgg acc tgg atc gac     1061
Gly Thr Leu His Ser Ala His Ala Lys Tyr Ile Arg Thr Trp Ile Asp
330                 335                 340                 345 tac ggc gag atg aaa gag atc aag ggc ggc agg ggc gag tac agc aag     1109
Tyr Gly Glu Met Lys Glu Ile Lys Gly Gly Arg Gly Glu Tyr Ser Lys
                350                 355                 360 gcc cct gag ctg ctg tgg agc cag tgg ttc gac ttc ggc ccc ttc aag     1157
Ala Pro Glu Leu Leu Trp Ser Gln Trp Phe Asp Phe Gly Pro Phe Lys
            365                 370                 375 atc ggc ccc aac ggc ctg ctg cac acc ggc aag acc ttc aag ttc cct     1205
Ile Gly Pro Asn Gly Leu Leu His Thr Gly Lys Thr Phe Lys Phe Pro
        380                 385                 390 ctg tat ctg atc gga gcc ggc atc atc gac gag gac ctg cac gag ctg     1253
Leu Tyr Leu Ile Gly Ala Gly Ile Ile Asp Glu Asp Leu His Glu Leu
    395                 400                 405 gac gaa gcc gcc cct atc gac cac ccc cag atg ccc gac gcc aag agc     1301
Asp Glu Ala Ala Pro Ile Asp His Pro Gln Met Pro Asp Ala Lys Ser
410                 415                 420                 425 gtg ctg ccc gag gac gag gaa atc ttc ttc ggc gac acc ggc gtg agc     1349
Val Leu Pro Glu Asp Glu Glu Ile Phe Phe Gly Asp Thr Gly Val Ser
                430                 435                 440 aag aac ccc atc gag ctg atc cag ggc tgg ttc agc aac tgg cgg gag     1397
Lys Asn Pro Ile Glu Leu Ile Gln Gly Trp Phe Ser Asn Trp Arg Glu
            445                 450                 455 agc gtg atg gcc atc gtg ggc atc gtg ctg ctc atc gtg gtg acc ttc     1445
Ser Val Met Ala Ile Val Gly Ile Val Leu Leu Ile Val Val Thr Phe
        460                 465                 470 ctg gcc atc aag acc gtg cgg gtg ctg aac tgc ctg tgg cgg ccc agg     1493
Leu Ala Ile Lys Thr Val Arg Val Leu Asn Cys Leu Trp Arg Pro Arg
    475                 480                 485 aag aaa cgg atc gtc cgg cag gaa gtg gac gtc gag agc cgg ctg aac     1541
Lys Lys Arg Ile Val Arg Gln Glu Val Asp Val Glu Ser Arg Leu Asn
490                 495                 500                 505 cac ttc gag atg aga ggc ttc ccc gag tac gtg aag cgg tga tga         1586
His Phe Glu Met Arg Gly Phe Pro Glu Tyr Val Lys Arg
                510                 515
```
gaattcttaa ttaa                                                  1600

<210> SEQ ID NO 42
<211> LENGTH: 518
<212> TYPE: PRT
<213> ORGANISM: Vesicular stomatitis virus

<400> SEQUENCE: 42

Met Thr Asp Thr Val Leu Gly Lys Phe Gln Ile Val Phe Pro Asp Gln
1               5                   10                  15

Asn Glu Leu Glu Trp Thr Pro Val Val Gly Asp Ser Arg His Cys Pro
            20                  25                  30

Gln Ser Ser Glu Met Gln Phe Asp Gly Ser Arg Ser Gln Thr Ile Leu
        35                  40                  45

Thr Gly Lys Ala Pro Val Gly Ile Thr Pro Ser Lys Ser Asp Gly Phe
    50                  55                  60

Ile Cys His Ala Ala Lys Trp Val Thr Thr Cys Asp Phe Arg Trp Tyr
65                  70                  75                  80

Gly Pro Lys Tyr Ile Thr His Ser Ile His His Leu Arg Pro Thr Thr
                85                  90                  95

Ser Asp Cys Glu Thr Ala Leu Gln Arg Tyr Lys Asp Gly Ser Leu Ile
            100                 105                 110

Asn Leu Gly Phe Pro Pro Glu Ser Cys Gly Tyr Ala Thr Val Thr Asp
        115                 120                 125

Ser Glu Ala Met Leu Val Gln Val Thr Pro His His Val Gly Val Asp
    130                 135                 140

Asp Tyr Arg Gly His Trp Ile Asp Pro Leu Phe Pro Gly Gly Glu Cys
145                 150                 155                 160

Ser Thr Asn Phe Cys Asp Thr Val His Asn Ser Ser Val Trp Ile Pro
                165                 170                 175

Lys Ser Gln Lys Thr Asp Ile Cys Ala Gln Ser Phe Lys Asn Ile Lys
            180                 185                 190

Met Thr Ala Ser Tyr Pro Ser Glu Gly Ala Leu Val Ser Asp Arg Phe
        195                 200                 205

Ala Phe His Ser Ala Tyr His Pro Asn Met Pro Gly Ser Thr Val Cys
    210                 215                 220

Ile Met Asp Phe Cys Glu Gln Lys Gly Leu Arg Phe Thr Asn Gly Glu
225                 230                 235                 240

Trp Met Gly Leu Asn Val Glu Gln Ser Ile Arg Glu Lys Lys Ile Ser
                245                 250                 255

Ala Ile Phe Pro Asn Cys Val Ala Gly Thr Glu Ile Arg Ala Thr Leu
            260                 265                 270

Glu Ser Glu Gly Ala Arg Thr Leu Thr Trp Glu Thr Gln Arg Met Leu
        275                 280                 285

Asp Tyr Ser Leu Cys Gln Asn Thr Trp Asp Lys Val Ser Arg Lys Glu
    290                 295                 300

Pro Leu Ser Pro Leu Asp Leu Ser Tyr Leu Ser Pro Arg Ala Pro Gly
305                 310                 315                 320

Lys Gly Met Ala Tyr Thr Val Ile Asn Gly Thr Leu His Ser Ala His
                325                 330                 335

Ala Lys Tyr Ile Arg Thr Trp Ile Asp Tyr Gly Glu Met Lys Glu Ile
            340                 345                 350

Lys Gly Gly Arg Gly Glu Tyr Ser Lys Ala Pro Glu Leu Leu Trp Ser
        355                 360                 365

-continued

```
Gln Trp Phe Asp Phe Gly Pro Phe Lys Ile Gly Pro Asn Gly Leu Leu
    370                 375                 380

His Thr Gly Lys Thr Phe Lys Phe Pro Leu Tyr Leu Ile Gly Ala Gly
385                 390                 395                 400

Ile Ile Asp Glu Asp Leu His Glu Leu Asp Glu Ala Ala Pro Ile Asp
                405                 410                 415

His Pro Gln Met Pro Asp Ala Lys Ser Val Leu Pro Glu Asp Glu Glu
            420                 425                 430

Ile Phe Phe Gly Asp Thr Gly Val Ser Lys Asn Pro Ile Glu Leu Ile
        435                 440                 445

Gln Gly Trp Phe Ser Asn Trp Arg Glu Ser Val Met Ala Ile Val Gly
    450                 455                 460

Ile Val Leu Leu Ile Val Val Thr Phe Leu Ala Ile Lys Thr Val Arg
465                 470                 475                 480

Val Leu Asn Cys Leu Trp Arg Pro Arg Lys Lys Arg Ile Val Arg Gln
                485                 490                 495

Glu Val Asp Val Glu Ser Arg Leu Asn His Phe Glu Met Arg Gly Phe
            500                 505                 510

Pro Glu Tyr Val Lys Arg
        515
```

<210> SEQ ID NO 43
<211> LENGTH: 1573
<212> TYPE: DNA
<213> ORGANISM: Vesicular stomatitis virus
<220> FEATURE:
<221> NAME/KEY: CDS
<222> LOCATION: (27)..(1559)

<400> SEQUENCE: 43

```
ggcgcgccgg atcctgatca gccacc atg agc atc atc agc tat atc gcc ttt      53
                              Met Ser Ile Ile Ser Tyr Ile Ala Phe
                                1               5 ctg ctg ctg atc gac agc acc ctg ggc atc ccc atc ttc gtg ccc agc     101
Leu Leu Leu Ile Asp Ser Thr Leu Gly Ile Pro Ile Phe Val Pro Ser
 10              15                  20                  25 ggc cag aac atc agc tgg cag ccc gtg atc cag ccc ttc gac tac cag     149
Gly Gln Asn Ile Ser Trp Gln Pro Val Ile Gln Pro Phe Asp Tyr Gln
                 30                  35                  40 tgc ccc atc cac ggc aac ctg ccc aac acc atg ggc ctg agc gcc acc     197
Cys Pro Ile His Gly Asn Leu Pro Asn Thr Met Gly Leu Ser Ala Thr
             45                  50                  55 aag ctg acc atc aag agc ccc agc gtg ttc agc acc gac aag gtg tcc     245
Lys Leu Thr Ile Lys Ser Pro Ser Val Phe Ser Thr Asp Lys Val Ser
 60                  65                  70 ggc tgg atc tgc cac gcc gcc gag tgg aaa acc acc tgc gac tac cgg     293
Gly Trp Ile Cys His Ala Ala Glu Trp Lys Thr Thr Cys Asp Tyr Arg
 75                  80                  85 tgg tac ggc ccc cag tac atc acc cac agc atc cac ccc atc agc ccc     341
Trp Tyr Gly Pro Gln Tyr Ile Thr His Ser Ile His Pro Ile Ser Pro
 90                  95                 100                 105 acc atc gac gag tgc aag cgg atc atc agc cgg atc gcc agc ggc acc     389
Thr Ile Asp Glu Cys Lys Arg Ile Ile Ser Arg Ile Ala Ser Gly Thr
                110                 115                 120 gac gag gac ctg ggc ttc cca ccc cag agc tgc ggc tgg gcc agc gtg     437
Asp Glu Asp Leu Gly Phe Pro Pro Gln Ser Cys Gly Trp Ala Ser Val
            125                 130                 135 acc acc gtg agc aac acc aac tac aag gtg gtg ccc cac agc gtg cac     485
Thr Thr Val Ser Asn Thr Asn Tyr Lys Val Val Pro His Ser Val His
        140                 145                 150
```

|     |     |
| --- | --- |
| ctg gaa ccc tac ggc ggc cac tgg atc gac cac gac ttc aac ggc ggc<br>Leu Glu Pro Tyr Gly Gly His Trp Ile Asp His Asp Phe Asn Gly Gly<br>155                     160                     165 | 533 |
| gag tgc cgg gag aaa gtg tgc gag atg aag ggc aac cac agc atc tgg<br>Glu Cys Arg Glu Lys Val Cys Glu Met Lys Gly Asn His Ser Ile Trp<br>170                     175                     180                     185 | 581 |
| atc acc gac gag aca gtg cag cac gag tgc gag aag cac atc gag gaa<br>Ile Thr Asp Glu Thr Val Gln His Glu Cys Glu Lys His Ile Glu Glu<br>                      190                     195                     200 | 629 |
| gtg gag ggc atc atg tac ggc aac gcc ccc agg ggc gac gcc atc tac<br>Val Glu Gly Ile Met Tyr Gly Asn Ala Pro Arg Gly Asp Ala Ile Tyr<br>205                     210                     215 | 677 |
| atc aac aac ttc atc atc gac aag cac cac cgg gtg tac cgg ttc ggc<br>Ile Asn Asn Phe Ile Ile Asp Lys His His Arg Val Tyr Arg Phe Gly<br>         220                     225                     230 | 725 |
| ggc tcc tgc cgg atg aag ttc tgc aac aag gac ggc atc aag ttc acc<br>Gly Ser Cys Arg Met Lys Phe Cys Asn Lys Asp Gly Ile Lys Phe Thr<br>235                     240                     245 | 773 |
| aga ggc gac tgg gtg gag aaa acc gcc ggc acc ctg acc aac atc tac<br>Arg Gly Asp Trp Val Glu Lys Thr Ala Gly Thr Leu Thr Asn Ile Tyr<br>250                     255                     260                     265 | 821 |
| gag aac atc ccc gag tgc gcc gac ggc aca ctg gtg tcc ggc cac aga<br>Glu Asn Ile Pro Glu Cys Ala Asp Gly Thr Leu Val Ser Gly His Arg<br>                      270                     275                     280 | 869 |
| ccc ggc ctg gac ctg atc gac acc gtg ttc aac ctg gaa aac gtg gtg<br>Pro Gly Leu Asp Leu Ile Asp Thr Val Phe Asn Leu Glu Asn Val Val<br>285                     290                     295 | 917 |
| gag tac acc ctg tgc gag ggc acc aag cgg aag atc aac aag cag gaa<br>Glu Tyr Thr Leu Cys Glu Gly Thr Lys Arg Lys Ile Asn Lys Gln Glu<br>                      300                     305                     310 | 965 |
| aag ctg acc agc gtc gac ctg agc tac ctg gcc ccc agg atc ggc ggc<br>Lys Leu Thr Ser Val Asp Leu Ser Tyr Leu Ala Pro Arg Ile Gly Gly<br>315                     320                     325 | 1013 |
| ttc ggc agc gtg ttc cgc gtg cgg aat ggg acc ctg gaa aga gga agc<br>Phe Gly Ser Val Phe Arg Val Arg Asn Gly Thr Leu Glu Arg Gly Ser<br>330                     335                     340                     345 | 1061 |
| aca aca tac att cgg atc gaa gtg gaa ggc ccc gtg gtg gac agc ctg<br>Thr Thr Tyr Ile Arg Ile Glu Val Glu Gly Pro Val Val Asp Ser Leu<br>                      350                     355                     360 | 1109 |
| aac ggc atc gac ccc cgg acc aac gcc agc cgg gtg ttc tgg gac gac<br>Asn Gly Ile Asp Pro Arg Thr Asn Ala Ser Arg Val Phe Trp Asp Asp<br>365                     370                     375 | 1157 |
| tgg gag ctg gac ggc aac atc tac cag ggc ttc aat ggc gtg tac aag<br>Trp Glu Leu Asp Gly Asn Ile Tyr Gln Gly Phe Asn Gly Val Tyr Lys<br>                  380                     385                     390 | 1205 |
| ggc aag gat ggc aag atc cac atc ccc ctg aac atg atc gag agc ggc<br>Gly Lys Asp Gly Lys Ile His Ile Pro Leu Asn Met Ile Glu Ser Gly<br>395                     400                     405 | 1253 |
| atc atc gac gac gag ctg cag cac gcc ttc cag gcc gac atc atc ccc<br>Ile Ile Asp Asp Glu Leu Gln His Ala Phe Gln Ala Asp Ile Ile Pro<br>410                     415                     420                     425 | 1301 |
| cac ccc cac tac gac gac gac gag atc cgg gag gac gac atc ttc ttc<br>His Pro His Tyr Asp Asp Asp Glu Ile Arg Glu Asp Asp Ile Phe Phe<br>                      430                     435                     440 | 1349 |
| gac aac acc ggc gag aac ggc aac ccc gtg gac gcc gtg gtg gaa tgg<br>Asp Asn Thr Gly Glu Asn Gly Asn Pro Val Asp Ala Val Val Glu Trp<br>445                     450                     455 | 1397 |
| gtg tcc gga tgg ggc acc agc ctg aag ttc ttc ggc atg acc ctg gtg<br>Val Ser Gly Trp Gly Thr Ser Leu Lys Phe Phe Gly Met Thr Leu Val<br>460                     465                     470 | 1445 |

```
gcc ctg atc ctg atc ttc ctg ctg atc cgg tgc tgc gtg gcc tgc acc         1493
Ala Leu Ile Leu Ile Phe Leu Leu Ile Arg Cys Cys Val Ala Cys Thr
475                 480                 485 tac ctg atg aag aag agc aag agg ccc gcc acc gag agc cac gag atg         1541
Tyr Leu Met Lys Lys Ser Lys Arg Pro Ala Thr Glu Ser His Glu Met
490                 495                 500                 505 cgg agc ctg gtg tga tga gaattcttaa ttaa                                 1573
Arg Ser Leu Val <210> SEQ ID NO 44
<211> LENGTH: 509
<212> TYPE: PRT
<213> ORGANISM: Vesicular stomatitis virus

<400> SEQUENCE: 44

Met Ser Ile Ile Ser Tyr Ile Ala Phe Leu Leu Ile Asp Ser Thr
1               5                   10                  15

Leu Gly Ile Pro Ile Phe Val Pro Ser Gly Gln Asn Ile Ser Trp Gln
                20                  25                  30

Pro Val Ile Gln Pro Phe Asp Tyr Gln Cys Pro Ile His Gly Asn Leu
            35                  40                  45

Pro Asn Thr Met Gly Leu Ser Ala Thr Lys Leu Thr Ile Lys Ser Pro
        50                  55                  60

Ser Val Phe Ser Thr Asp Lys Val Ser Gly Trp Ile Cys His Ala Ala
65                  70                  75                  80

Glu Trp Lys Thr Thr Cys Asp Tyr Arg Trp Tyr Gly Pro Gln Tyr Ile
                85                  90                  95

Thr His Ser Ile His Pro Ile Ser Pro Thr Ile Asp Glu Cys Lys Arg
            100                 105                 110

Ile Ile Ser Arg Ile Ala Ser Gly Thr Asp Glu Asp Leu Gly Phe Pro
        115                 120                 125

Pro Gln Ser Cys Gly Trp Ala Ser Val Thr Thr Val Ser Asn Thr Asn
    130                 135                 140

Tyr Lys Val Val Pro His Ser Val His Leu Glu Pro Tyr Gly Gly His
145                 150                 155                 160

Trp Ile Asp His Asp Phe Asn Gly Gly Glu Cys Arg Glu Lys Val Cys
                165                 170                 175

Glu Met Lys Gly Asn His Ser Ile Trp Ile Thr Asp Glu Thr Val Gln
            180                 185                 190

His Glu Cys Glu Lys His Ile Glu Glu Val Glu Gly Ile Met Tyr Gly
        195                 200                 205

Asn Ala Pro Arg Gly Asp Ala Ile Tyr Ile Asn Asn Phe Ile Ile Asp
    210                 215                 220

Lys His His Arg Val Tyr Arg Phe Gly Gly Ser Cys Arg Met Lys Phe
225                 230                 235                 240

Cys Asn Lys Asp Gly Ile Lys Phe Thr Arg Gly Asp Trp Val Glu Lys
                245                 250                 255

Thr Ala Gly Thr Leu Thr Asn Ile Tyr Glu Asn Ile Pro Glu Cys Ala
            260                 265                 270

Asp Gly Thr Leu Val Ser Gly His Arg Pro Gly Leu Asp Leu Ile Asp
        275                 280                 285

Thr Val Phe Asn Leu Glu Asn Val Tyr Glu Tyr Thr Leu Cys Glu Gly
    290                 295                 300

Thr Lys Arg Lys Ile Asn Lys Gln Glu Lys Leu Thr Ser Val Asp Leu
305                 310                 315                 320
```

```
Ser Tyr Leu Ala Pro Arg Ile Gly Gly Phe Gly Ser Val Phe Arg Val
            325                 330                 335

Arg Asn Gly Thr Leu Glu Arg Gly Ser Thr Thr Tyr Ile Arg Ile Glu
        340                 345                 350

Val Glu Gly Pro Val Val Asp Ser Leu Asn Gly Ile Asp Pro Arg Thr
    355                 360                 365

Asn Ala Ser Arg Val Phe Trp Asp Asp Trp Glu Leu Asp Gly Asn Ile
370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
                405                 410                 415

His Ala Phe Gln Ala Asp Ile Ile Pro His Pro His Tyr Asp Asp Asp
            420                 425                 430

Glu Ile Arg Glu Asp Asp Ile Phe Phe Asp Asn Thr Gly Glu Asn Gly
        435                 440                 445

Asn Pro Val Asp Ala Val Val Glu Trp Val Ser Gly Trp Gly Thr Ser
    450                 455                 460

Leu Lys Phe Phe Gly Met Thr Leu Val Ala Leu Ile Leu Ile Phe Leu
465                 470                 475                 480

Leu Ile Arg Cys Cys Val Ala Cys Thr Tyr Leu Met Lys Lys Ser Lys
                485                 490                 495

Arg Pro Ala Thr Glu Ser His Glu Met Arg Ser Leu Val
            500                 505

<210> SEQ ID NO 45
<211> LENGTH: 1578
<212> TYPE: DNA
<213> ORGANISM: Artificial
<220> FEATURE:
<223> OTHER INFORMATION: VSV-G Indiana optimized

<400> SEQUENCE: 45
ctcggatcct gatcagccac catgaaatgc ctgctctatc tggccttcct ctttatcggc      60
gtgaactgta agttcacgat cgtgtttccc cacaatcaga agggaaactg gaagaacgtc     120
ccgagcaact accactactg ccctagctca agcgacctga actggcacaa cgacctgatc     180
ggcaccgcta tccaggtgaa gatgccaaag agccacaagg ccatccaagc cgacggctgg     240
atgtgtcacg ccagcaaatg ggtgacgacg tgcgatttc gctggtatgg ccccaagtac     300
atcacccaat caatccgctc atttacaccc agcgtggagc aatgtaagga gagcatcgag     360
cagaccaagc aggggaccctg gctcaacccc ggcttcccac cgcaaagctg cggatacgcc     420
accgtgaccg acgctgaggc cgtcatcgtg caggtgaccc cgcaccacgt gctggtggac     480
gagtacaccg gcgagtgggt ggattcacag tttatcaacg gaaagtgtag caattacatc     540
tgccccaccg tgcacaacag caccacctgg cactcagact ataaggtgaa gggcctctgc     600
gacagcaatc tgatctcaat ggacatcacc ttctttagcg aagacggcga actctcaagc     660
ctcgggaagg aaggcaccgg gttccgcagc aattactttg cttacgaaac cggcggcaag     720
gcctgcaaga tgcaatactg caagcactgg ggcgtgcgcc tgccaagcgg cgtgtggttt     780
gagatggctg ataaggacct gttcgccgct gcccgcttcc cggaatgccc cgaggggagc     840
agcatcagcg cccccagcca gatcagtg gacgtgagcc tgatccagga tgtggaacgc     900
atcctggact acagcctgtg tcaggaaacg tggagcaaga tccgcgccgg actgcctatc     960
agccccgtgg atctcagcta cctggccca aagaacccag gcaccggacc cgcctttaca    1020
```

-continued

```
atcatcaacg gcaccctgaa gtactttgaa acacgctaca tccgcgtcga catcgccgct    1080
cccatcctct cacgcatggt gggcatgatc tcagggacga ccacggagcg cgagctgtgg    1140
gatgactggg ccccgtatga agatgtggag atcggaccta acggcgtgct gcgcacatca    1200
agcgggtaca agttcccgct gtacatgatc ggccacggca tgctggacag cgacctgcac    1260
ctcagctcaa aggcccaggt cttttgagcac ccacacatcc aggacgctgc cagccagctc    1320
cccgacgacg aaagcctgtt cttttggagat acagggctca gcaagaaccc catcgagctg    1380
gtcgagggct ggttctcaag ctggaagagc agcatcgctt cattttttt catcatcggc    1440 ctcatcatcg ggctgtttct ggtgctgcgc gtcggcatcc acctgtgcat caagctgaag    1500
cacaccaaga agcgccagat ctataccgac atcgagatga atcgcctggg gaagtaagaa    1560
ttctgcagat atccagca                                                 1578
```

<210> SEQ ID NO 46
<211> LENGTH: 32
<212> TYPE: DNA
<213> ORGANISM: Artificial
<220> FEATURE:
<223> OTHER INFORMATION: Indiana oligonucleotide

<400> SEQUENCE: 46

```
agcagcatcg cttcattttt tttcatcatc gg                                   32
```

<210> SEQ ID NO 47
<211> LENGTH: 35
<212> TYPE: DNA
<213> ORGANISM: Artificial
<220> FEATURE:
<223> OTHER INFORMATION: Indiana oligonucleotide

<400> SEQUENCE: 47

```
gctggatatc tgcagaattc ttacttcccc aggcg                                35
```

<210> SEQ ID NO 48
<211> LENGTH: 160
<212> TYPE: DNA
<213> ORGANISM: Artificial
<220> FEATURE:
<223> OTHER INFORMATION: PCR fragment

<400> SEQUENCE: 48

```
agcagcatcg cttcattttt tttcatcatc ggcctcatca tcgggctgtt tctggtgctg    60
cgcgtcggca tccacctgtg catcaagctg aagcacacca agaagcgcca gatctatacc    120
gacatcgaga tgaatcgcct ggggaagtaa gaattctgca                          160
```

<210> SEQ ID NO 49
<211> LENGTH: 1597
<212> TYPE: DNA
<213> ORGANISM: Artificial
<220> FEATURE:
<223> OTHER INFORMATION: VSV-G New Jersey optimized

<400> SEQUENCE: 49
taccgagctc ggatcctgat cagccaccat gctgtcatat ctgatctttg ccctggctgt 60
gagcccaatc ctcggaaaga tcgaaatcgt gttcccacaa cacaccacag gggactggaa 120
gcgcgtgccc cacgagtaca actactgccc gacctcagcc gacaagaata gccacggcac 180
gcagaccggc atccctgtgg agctgaccat gcccaagggg ctcacaacgc accaagtcga 240
aggcttcatg tgccacagcg ctctctggat gacaacctgc gattttcgct ggtatggccc 300

-continued

```
caagtacatc acgcacagca tccacaatga ggaaccaacc gactaccagt gcctcgaagc    360
catcaagtca tacaaggatg gggtgagctt caacccggc ttcccgcccc aatcatgtgg    420
ctacggcacc gtgaccgacg ccgaggccca catcgtgacc gtgacacccc actcagtcaa    480
ggtggacgag tacacaggcg aatggatcga ccccccacttc atcggggcc gctgtaaggg    540 ccaaatctgc gagaccgtgc acaacagcac caagtggttt acgtcatcag acggcgaaag    600
cgtgtgcagc caactgttta cgctcgtggg cggcatcttc tttagcgaca gcaggagat    660 caccagcatg ggcctcccgg agacaggaat ccgcagcaac tactttccgt acatcagcac    720
cgagggaatc tgtaagatgc cttttttgccg caagcaggga tataagctga agaatgacct    780
gtggttccag atcatggacc cggacctgga caagaccgtc cgcgatctgc cccacatcaa    840
ggactgtgat ctgtcatcaa gcatcatcac ccccggagaa cacgccacgg acatcagcct    900
catcagcgat gtggagcgca tcctcgacta cgctctctgc cagaacacat ggagcaagat    960
cgaaagcggc gaacccatca ccccagtgga cctgagctat ctcggcccaa gaacccccgg   1020 cgtgggccc gtgttcacca tcatcaacgg gagcctgcac tactttacaa gcaagtatct   1080
gcgcgtggag ctcgaaagcc cagtcatccc ccgcatggag gggaaggtgg ccgggacccg   1140
catcgtgcgc cagctgtggg accagtggtt ccctttttggc gaggtggaaa tcggccccaa   1200
cggcgtgctg aagaccaagc aaggatataa gttcccgctg cacatcatcg ggacgggcga   1260
agtggacagc gatatcaaga tggagcgcgt ggtcaagcac tgggagcacc cacacatcga   1320
ggctgctcag acctttctca agaaggacga taccggcgaa gtcctgtatt acggggatac   1380
gggagtgagc aagaaccctg tggagctggt ggaaggctgg ttcagcggat ggcgctcaag   1440
cctgatgggc gtgctggccg tcatcatcgg atttgtgatc ctgatgttcc tcatcaagct   1500
gatcggcgtg ctgtcaagcc tgttccgccc taagcgccgc ccaatctaca agagcgacgt   1560
cgagatggcc cactttcgct aagaattctg cagatat                            1597
```

<210> SEQ ID NO 50
<211> LENGTH: 33
<212> TYPE: DNA
<213> ORGANISM: Artificial
<220> FEATURE:
<223> OTHER INFORMATION: New Jersey oligonucleotide

<400> SEQUENCE: 50

```
cgagctcgga tcctgatcag ccaccatgct gtc                                  33
```

<210> SEQ ID NO 51
<211> LENGTH: 51
<212> TYPE: DNA
<213> ORGANISM: Artificial
<220> FEATURE:
<223> OTHER INFORMATION: New Jersey oligonucleotide

<400> SEQUENCE: 51

```
gaaaaaaat gaagcgatgc tgctgcgcca tccgctgaac cagccttcca c              51
```

<210> SEQ ID NO 52
<211> LENGTH: 1456
<212> TYPE: DNA
<213> ORGANISM: Artificial
<220> FEATURE:
<223> OTHER INFORMATION: PCR product

<400> SEQUENCE: 52

```
cgagctcgga tcctgatcag ccaccatgct gtcatatctg atctttgccc tggctgtgag     60
```

```
cccaatcctc ggaaagatcg aaatcgtgtt cccacaacac accacagggg actggaagcg    120
cgtgccccac gagtacaact actgcccgac ctcagccgac aagaatagcc acggcacgca    180
gaccggcatc cctgtggagc tgaccatgcc caagggctc acaacgcacc aagtcgaagg     240
cttcatgtgc cacagcgctc tctgatgac aacctgcgat tttcgctggt atggccccaa     300
gtacatcacg cacagcatcc acaatgagga accaaccgac taccagtgcc tcgaagccat    360
caagtcatac aaggatgggg tgagcttcaa ccccggcttc cgccccaat catgtggcta     420 cggcaccgtg accgacgccg aggcccacat cgtgaccgtg acccccact cagtcaaggt     480 ggacgagtac acaggcgaat ggatcgaccc ccacttcatc gggggccgct gtaagggcca    540
aatctgcgag accgtgcaca acagcaccaa gtggtttacg tcatcagacg gcgaaagcgt    600
gtgcagccaa ctgtttacgc tcgtgggcgg catcttcttt agcgacagcg aggagatcac    660
cagcatgggc ctcccggaga caggaatccg cagcaactac tttccgtaca tcagcaccga    720
gggaatctgt aagatgcctt tttgccgcaa gcagggatat aagctgaaga atgacctgtg    780
gttccagatc atggacccgg acctggacaa gaccgtccgc gatctgcccc acatcaagga    840
ctgtgatctg tcatcaagca tcatcacccc cggagaacac gccacggaca tcagcctcat    900
cagcgatgtg gagcgcatcc tcgactacgc tctctgccag aacacatgga gcaagatcga    960
aagcggcgaa cccatcaccc cagtggacct gagctatctc ggcccaaaga accccggcgt    1020
ggggcccgtg ttcaccatca tcaacgggag cctgcactac tttacaagca gtatctgcg    1080 cgtggagctc gaaagcccag tcatccccg catggagggg aagtggccg ggacccgcat      1140 cgtgcgccag ctgtgggacc agtggttccc ttttggcgag gtggaaatcg gccccaacgg   1200
cgtgctgaag accaagcaag gatataagtt cccgctgcac atcatcggga cgggcgaagt   1260
ggacagcgat atcaagatgg agcgcgtggt caagcactgg gagcacccac acatcgaggc   1320
tgctcagacc tttctcaaga aggacgatac cggcgaagtc ctgtattacg gggatacggg   1380
agtgagcaag aaccctgtgg agctggtgga aggctggttc agcggatggc gcagcagcat   1440
cgcttcattt tttttc                                                    1456
```

<210> SEQ ID NO 53
<211> LENGTH: 1615
<212> TYPE: DNA
<213> ORGANISM: Artificial
<220> FEATURE:
<223> OTHER INFORMATION: PCR product

<400> SEQUENCE: 53

```
gagctcggat cctgatcagc caccatgctg tcatatctga tctttgccct ggctgtgagc     60
ccaatcctcg gaaagatcga aatcgtgttc cacaacaca ccacagggga ctggaagcgc     120
gtgccccacg agtacaacta ctgcccgacc tcagccgaca agaatagcca cggcacgcag    180
accggcatcc ctgtggagct gaccatgccc aaggggctca acgcacca agtcgaaggc      240 ttcatgtgcc acagcgctct ctggatgaca acctgcgatt ttcgctggta tggccccaag    300
tacatcacgc acagcatcca caatgaggaa ccaaccgact accagtgcct cgaagccatc    360
aagtcataca aggatggggt gagcttcaac cccggcttcc gccccaatc atgtggctac     420 ggcaccgtga ccgacgccga ggcccacatc gtgaccgtga cccccactc agtcaaggtg     480 gacgagtaca caggcgaatg gatcgacccc cacttcatcg ggggccgctg taagggccaa    540
atctgcgaga ccgtgcacaa cagcaccaag tggtttacgt catcagacgg cgaaagcgtg    600
tgcagccaac tgtttacgct cgtgggcggc atcttcttta gcgacagcga ggagatcacc    660
```

-continued

```
agcatgggcc tcccggagac aggaatccgc agcaactact ttccgtacat cagcaccgag    720
ggaatctgta agatgccttt ttgccgcaag cagggatata agctgaagaa tgacctgtgg    780
ttccagatca tggacccgga cctggacaag accgtccgcg atctgcccca catcaaggac    840
tgtgatctgt catcaagcat catcaccccc ggagaacacg ccacggacat cagcctcatc    900
agcgatgtgg agcgcatcct cgactacgct ctctgccaga acacatggag caagatcgaa    960
agcggcgaac ccatcacccc agtggacctg agctatctcg gcccaaagaa ccccggcgtg   1020
gggcccgtgt tcaccatcat caacgggagc ctgcactact ttacaagcaa gtatctgcgc   1080
gtggagctcg aaagcccagt catccccgc atggagggga aggtggccgg acccgcatc    1140 gtgcgccagc tgtgggacca gtggttccct tttggcgagg tggaaatcgg ccccaacggc   1200
gtgctgaaga ccaagcaagg atataagttc ccgctgcaca tcatcgggac gggcgaagtg   1260
gacagcgata tcaagatgga gcgcgtggtc aagcactggg agcacccaca catcgaggct   1320
gctcagacct ttctcaagaa ggacgatacc ggcgaagtcc tgtattacgg ggatacggga   1380
gtgagcaaga accctgtgga gctggtggaa ggctggttca gcggatggcg cagcagcatc   1440
gcttcatttt ttttcagcag catcgcttca ttttttttca tcatcggcct catcatcggg   1500
ctgtttctgg tgctgcgcgt cggcatccac ctgtgcatca agctgaagca caccaagaag   1560
cgccagatct ataccgacat cgagatgaat cgcctgggga agtaagaatt ctgca        1615
```

```
<210> SEQ ID NO 54
<211> LENGTH: 1563
<212> TYPE: DNA
<213> ORGANISM: Artificial
<220> FEATURE:
<223> OTHER INFORMATION: fusion VSV-G Chandipura / Indiana
<220> FEATURE:
<221> NAME/KEY: CDS
<222> LOCATION: (1)..(1563)

<400> SEQUENCE: 54 atg acc agc agc gtg acc atc agc gtg gtg ctg ctg atc agc ttc atc      48
Met Thr Ser Ser Val Thr Ile Ser Val Val Leu Leu Ile Ser Phe Ile
1               5                   10                  15 acc ccc ctg tac agc tac ctg agc att gcc ttc ccc gag aac acc aag      96
Thr Pro Leu Tyr Ser Tyr Leu Ser Ile Ala Phe Pro Glu Asn Thr Lys
            20                  25                  30 ctg gac tgg aag ccc gtg acc aag aac acc cgg tac tgc ccc atg ggc     144
Leu Asp Trp Lys Pro Val Thr Lys Asn Thr Arg Tyr Cys Pro Met Gly
        35                  40                  45 ggc gag tgg ttt ctg gaa ccc ggc ctg cag gaa gag agc ttc ctg agc     192
Gly Glu Trp Phe Leu Glu Pro Gly Leu Gln Glu Glu Ser Phe Leu Ser
    50                  55                  60 agc acc ccc atc ggc gcc acc ccc agc aag agc gac ggc ttc ctg tgc     240
Ser Thr Pro Ile Gly Ala Thr Pro Ser Lys Ser Asp Gly Phe Leu Cys
65                  70                  75                  80 cac gcc gcc aag tgg gtg acc acc tgc gac ttc cgg tgg tac ggc ccc     288
His Ala Ala Lys Trp Val Thr Thr Cys Asp Phe Arg Trp Tyr Gly Pro
                85                  90                  95 aag tac atc acc cac agc atc cac aac atc aag ccc acc aga agc gac     336
Lys Tyr Ile Thr His Ser Ile His Asn Ile Lys Pro Thr Arg Ser Asp
            100                 105                 110 tgc gac aca gcc ctg gcc tct tac aag agc ggc acc ctg gtg tcc ctg     384
Cys Asp Thr Ala Leu Ala Ser Tyr Lys Ser Gly Thr Leu Val Ser Leu
        115                 120                 125 ggc ttc cct ccc gag agc tgc ggc tac gcc agc gtg acc gac agc gag     432
Gly Phe Pro Pro Glu Ser Cys Gly Tyr Ala Ser Val Thr Asp Ser Glu
    130                 135                 140
```

```
ttc ctg gtg att atg att acc ccc cac cac gtg ggc gtg gac gac tac      480
Phe Leu Val Ile Met Ile Thr Pro His His Val Gly Val Asp Asp Tyr
145                 150                 155                 160 cgg ggc cac tgg gtg gac cct ctg ttc gtg gga ggg gaa tgc gac cag      528
Arg Gly His Trp Val Asp Pro Leu Phe Val Gly Gly Glu Cys Asp Gln
            165                 170                 175 agc tac tgc gat acc atc cac aac tcc agc gtg tgg att ccc gcc gac      576
Ser Tyr Cys Asp Thr Ile His Asn Ser Ser Val Trp Ile Pro Ala Asp
        180                 185                 190 cag acc aag aag aac atc tgc ggc cag agc ttc acc cct ctg acc gtg      624
Gln Thr Lys Lys Asn Ile Cys Gly Gln Ser Phe Thr Pro Leu Thr Val
    195                 200                 205 acc gtg gcc tac gac aag acc aaa gag att gcc gcc gga ggg atc gtg      672
Thr Val Ala Tyr Asp Lys Thr Lys Glu Ile Ala Ala Gly Gly Ile Val
210                 215                 220 ttc aag agc aag tac cac agc cac atg gaa ggc gcc agg acc tgc aga      720
Phe Lys Ser Lys Tyr His Ser His Met Glu Gly Ala Arg Thr Cys Arg
225                 230                 235                 240 ctg tcc tac tgc ggc cgg aac ggc atc aag ttc ccc aac ggc gag tgg      768
Leu Ser Tyr Cys Gly Arg Asn Gly Ile Lys Phe Pro Asn Gly Glu Trp
            245                 250                 255 gtg tcc ctg atg ctg aag ctg cgg agc aag cgg aac ctg tac ttc ccc      816
Val Ser Leu Met Leu Lys Leu Arg Ser Lys Arg Asn Leu Tyr Phe Pro
        260                 265                 270 tgc ctg aag atg tgc ccc acc ggc atc cgg ggc gag atc tac ccc agc      864
Cys Leu Lys Met Cys Pro Thr Gly Ile Arg Gly Glu Ile Tyr Pro Ser
    275                 280                 285 atc aga tgg gcc cag gtg ctg acc agc gag atc cag aga atc ctg gac      912
Ile Arg Trp Ala Gln Val Leu Thr Ser Glu Ile Gln Arg Ile Leu Asp
290                 295                 300 tac agc ctg tgc cag aac acc tgg gac aag gtg gag cgg aaa gag ccc      960
Tyr Ser Leu Cys Gln Asn Thr Trp Asp Lys Val Glu Arg Lys Glu Pro
305                 310                 315                 320 ctg agc ccc ctg gac ctg agc tac ctg gcc agc aag tcc ccc ggc aag     1008
Leu Ser Pro Leu Asp Leu Ser Tyr Leu Ala Ser Lys Ser Pro Gly Lys
            325                 330                 335 ggc ctg gcc tac acc gtg atc aac ggc acc ctg agc ttc gcc cac acc     1056
Gly Leu Ala Tyr Thr Val Ile Asn Gly Thr Leu Ser Phe Ala His Thr
        340                 345                 350 aga tac gtg cgg atg tgg atc gac ggc ccc gtg ctg aaa gag ccc aag     1104
Arg Tyr Val Arg Met Trp Ile Asp Gly Pro Val Leu Lys Glu Pro Lys
    355                 360                 365 ggc aag aga gag agc ccc agc ggc atc agc agc gac atc tgg acc cag     1152
Gly Lys Arg Glu Ser Pro Ser Gly Ile Ser Ser Asp Ile Trp Thr Gln
370                 375                 380 tgg ttc aag tac ggc gac atg gaa atc ggc ccc aac ggc ctg ctg aaa     1200
Trp Phe Lys Tyr Gly Asp Met Glu Ile Gly Pro Asn Gly Leu Leu Lys
385                 390                 395                 400 aca gcc ggc gga tac aag ttt cct tgg cac ctg atc ggc atg ggc atc     1248
Thr Ala Gly Gly Tyr Lys Phe Pro Trp His Leu Ile Gly Met Gly Ile
            405                 410                 415 gtg gac aac gag ctg cac gag ctg tcc gag gcc aac ccc ctg gat cac     1296
Val Asp Asn Glu Leu His Glu Leu Ser Glu Ala Asn Pro Leu Asp His
        420                 425                 430 ccc cag ctg ccc cac gcc cag agc att gcc gac gac agc gag gaa atc     1344
Pro Gln Leu Pro His Ala Gln Ser Ile Ala Asp Asp Ser Glu Glu Ile
    435                 440                 445 ttc ttc ggc gac acc ggc gtg agc aag aac ccc gtg gaa ctg gtg aca     1392
Phe Phe Gly Asp Thr Gly Val Ser Lys Asn Pro Val Glu Leu Val Thr
450                 455                 460
```

```
ggc tgg ttc acc agc tgg aaa agc agc atc gct tca ttt ttt ttc atc      1440
Gly Trp Phe Thr Ser Trp Lys Ser Ser Ile Ala Ser Phe Phe Phe Ile
465                 470                 475                 480 atc ggc ctc atc atc ggg ctg ttt ctg gtg ctg cgc gtc ggc atc cac      1488
Ile Gly Leu Ile Ile Gly Leu Phe Leu Val Leu Arg Val Gly Ile His
                485                 490                 495 ctg tgc atc aag ctg aag cac acc aag aag cgc cag atc tat acc gac      1536
Leu Cys Ile Lys Leu Lys His Thr Lys Lys Arg Gln Ile Tyr Thr Asp
            500                 505                 510 atc gag atg aat cgc ctg ggg aag taa                                  1563
Ile Glu Met Asn Arg Leu Gly Lys
        515                 520

<210> SEQ ID NO 55
<211> LENGTH: 520
<212> TYPE: PRT
<213> ORGANISM: Artificial
<220> FEATURE:
<223> OTHER INFORMATION: Synthetic Construct

<400> SEQUENCE: 55

Met Thr Ser Ser Val Thr Ile Ser Val Val Leu Leu Ile Ser Phe Ile
1               5                   10                  15

Thr Pro Leu Tyr Ser Tyr Leu Ser Ile Ala Phe Pro Glu Asn Thr Lys
            20                  25                  30

Leu Asp Trp Lys Pro Val Thr Lys Asn Thr Arg Tyr Cys Pro Met Gly
        35                  40                  45

Gly Glu Trp Phe Leu Glu Pro Gly Leu Gln Glu Ser Phe Leu Ser
    50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
            100                 105                 110

Cys Asp Thr Ala Leu Ala Ser Tyr Lys Ser Gly Thr Leu Val Ser Leu
        115                 120                 125

Gly Phe Pro Pro Glu Ser Cys Gly Tyr Ala Ser Val Thr Asp Ser Glu
    130                 135                 140

Phe Leu Val Ile Met Ile Thr Pro His His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
            180                 185                 190

Gln Thr Lys Lys Asn Ile Cys Gly Gln Ser Phe Thr Pro Leu Thr Val
        195                 200                 205

Thr Val Ala Tyr Asp Lys Thr Lys Glu Ile Ala Ala Gly Gly Ile Val
    210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Met Leu Lys Leu Arg Ser Lys Arg Asn Leu Tyr Phe Pro
            260                 265                 270

Cys Leu Lys Met Cys Pro Thr Gly Ile Arg Gly Glu Ile Tyr Pro Ser
        275                 280                 285
```

-continued

```
Ile Arg Trp Ala Gln Val Leu Thr Ser Glu Ile Gln Arg Ile Leu Asp
    290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
            340                 345                 350

Arg Tyr Val Arg Met Trp Ile Asp Gly Pro Val Leu Lys Glu Pro Lys
        355                 360                 365

Gly Lys Arg Glu Ser Pro Ser Gly Ile Ser Ser Asp Ile Trp Thr Gln
    370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
            420                 425                 430

Pro Gln Leu Pro His Ala Gln Ser Ile Ala Asp Asp Ser Glu Glu Ile
        435                 440                 445

Phe Phe Gly Asp Thr Gly Val Ser Lys Asn Pro Val Glu Leu Val Thr
    450                 455                 460

Gly Trp Phe Thr Ser Trp Lys Ser Ser Ile Ala Ser Phe Phe Phe Ile
465                 470                 475                 480

Ile Gly Leu Ile Ile Gly Leu Phe Leu Val Leu Arg Val Gly Ile His
                485                 490                 495

Leu Cys Ile Lys Leu Lys His Thr Lys Lys Arg Gln Ile Tyr Thr Asp
            500                 505                 510

Ile Glu Met Asn Arg Leu Gly Lys
        515                 520

<210> SEQ ID NO 56
<211> LENGTH: 1539
<212> TYPE: DNA
<213> ORGANISM: Artificial
<220> FEATURE:
<223> OTHER INFORMATION: fusion VSV-G Cocal / Indiana
<220> FEATURE:
<221> NAME/KEY: CDS
<222> LOCATION: (1)..(1539)

<400> SEQUENCE: 56 atg aac tt

-continued

```
                Trp Ile Thr Thr Cys Asp Phe Arg Trp Tyr Gly Pro Lys Tyr Ile Thr
                                85                  90                  95 cac agc atc cac tcc atc cag ccc acc tcc gag cag tgc aaa gag agc        336
His Ser Ile His Ser Ile Gln Pro Thr Ser Glu Gln Cys Lys Glu Ser
            100                 105                 110 atc aag cag acc aag cag ggc acc tgg atg agc ccc ggc ttc cca ccc        384
Ile Lys Gln Thr Lys Gln Gly Thr Trp Met Ser Pro Gly Phe Pro Pro
                115                 120                 125 cag aac tgc ggc tac gcc acc gtg acc gac agc gtg gcc gtg gtg gtg        432
Gln Asn Cys Gly Tyr Ala Thr Val Thr Asp Ser Val Ala Val Val Val
        130                 135                 140 cag gcc acc ccc cac cac gtg ctg gtc gac gag tac acc ggc gag tgg        480
Gln Ala Thr Pro His His Val Leu Val Asp Glu Tyr Thr Gly Glu Trp
145                 150                 155                 160 atc gac agc cag ttc ccc aac ggc aag tgc gag aca gag gaa tgc gag        528
Ile Asp Ser Gln Phe Pro Asn Gly Lys Cys Glu Thr Glu Glu Cys Glu
                165                 170                 175 aca gtg cac aac agc acc gtg tgg tac agc gac tac aag gtg acc ggc        576
Thr Val His Asn Ser Thr Val Trp Tyr Ser Asp Tyr Lys Val Thr Gly
            180                 185                 190 ctg tgc gac gcc acc ctg gtg gac acc gag atc acc ttt ttc agc gag        624
Leu Cys Asp Ala Thr Leu Val Asp Thr Glu Ile Thr Phe Phe Ser Glu
        195                 200                 205 gac ggc aag aaa gag tcc atc ggc aag ccc aac acc ggc tac aga agc        672
Asp Gly Lys Lys Glu Ser Ile Gly Lys Pro Asn Thr Gly Tyr Arg Ser
210                 215                 220 aac tac ttc gcc tac gag aag ggc gac aaa gtg tgc aag atg aac tac        720
Asn Tyr Phe Ala Tyr Glu Lys Gly Asp Lys Val Cys Lys Met Asn Tyr
225                 230                 235                 240 tgc aag cat gcc gga gtg agg ctg cct agc ggc gtg tgg ttc gag ttc        768
Cys Lys His Ala Gly Val Arg Leu Pro Ser Gly Val Trp Phe Glu Phe
                245                 250                 255 gtg gac cag gac gtg tac gcc gcc gcc aag ctg ccc gag tgc ccc gtg        816
Val Asp Gln Asp Val Tyr Ala Ala Ala Lys Leu Pro Glu Cys Pro Val
            260                 265                 270 ggc gcc acc atc agc gcc ccc acc cag acc agc gtg gac gtg agc ctg        864
Gly Ala Thr Ile Ser Ala Pro Thr Gln Thr Ser Val Asp Val Ser Leu
        275                 280                 285 atc ctg gac gtg gag aga atc ctg gac tac tct ctg tgt cag gaa acc        912
Ile Leu Asp Val Glu Arg Ile Leu Asp Tyr Ser Leu Cys Gln Glu Thr
290                 295                 300 tgg tcc aag atc aga tcc aag cag ccc gtg agc cct gtg gac ctg agc        960
Trp Ser Lys Ile Arg Ser Lys Gln Pro Val Ser Pro Val Asp Leu Ser
305                 310                 315                 320 tac ctg gcc cct aag aac ccc ggc acc ggc cct gcc ttc acc atc atc       1008
Tyr Leu Ala Pro Lys Asn Pro Gly Thr Gly Pro Ala Phe Thr Ile Ile
                325                 330                 335 aac ggc acc ctg aag tac ttc gag aca cgg tac atc cgg atc gac atc       1056
Asn Gly Thr Leu Lys Tyr Phe Glu Thr Arg Tyr Ile Arg Ile Asp Ile
            340                 345                 350 gac aac ccc atc atc agc aag atg gtg ggc aag atc agc ggc agc cag       1104
Asp Asn Pro Ile Ile Ser Lys Met Val Gly Lys Ile Ser Gly Ser Gln
        355                 360                 365 acc gag cgg gag ctg tgg acc gag tgg ttc ccc tac gag ggc gtg gag       1152
Thr Glu Arg Glu Leu Trp Thr Glu Trp Phe Pro Tyr Glu Gly Val Glu
370                 375                 380 atc ggc ccc aat ggc atc ctg aaa acc cct acc ggc tac aag ttc ccc       1200
Ile Gly Pro Asn Gly Ile Leu Lys Thr Pro Thr Gly Tyr Lys Phe Pro
385                 390                 395                 400 ctg ttc atg atc ggc cac ggc atg ctg gac agc gac ctg cac aag acc       1248
```

```
Leu Phe Met Ile Gly His Gly Met Leu Asp Ser Asp Leu His Lys Thr
            405                 410                 415 tcc cag gcc gag gtg ttc gag cac ccc cac ctg gcc gag gcc ccc aag    1296
Ser Gln Ala Glu Val Phe Glu His Pro His Leu Ala Glu Ala Pro Lys
        420                 425                 430 cag ctg ccc gaa gag gaa acc ctg ttc ttc ggc gac acc ggc atc tcc    1344
Gln Leu Pro Glu Glu Glu Thr Leu Phe Phe Gly Asp Thr Gly Ile Ser
            435                 440                 445 aag aac cct gtg gag ctg atc gag ggc tgg ttc agc agc tgg aag agc    1392
Lys Asn Pro Val Glu Leu Ile Glu Gly Trp Phe Ser Ser Trp Lys Ser
        450                 455                 460 agc atc gct tca ttt ttt ttc atc atc ggc ctc atc atc ggg ctg ttt    1440
Ser Ile Ala Ser Phe Phe Phe Ile Ile Gly Leu Ile Ile Gly Leu Phe
465                 470                 475                 480 ctg gtg ctg cgc gtc ggc atc cac ctg tgc atc aag ctg aag cac acc    1488
Leu Val Leu Arg Val Gly Ile His Leu Cys Ile Lys Leu Lys His Thr
                485                 490                 495 aag aag cgc cag atc tat acc gac atc gag atg aat cgc ctg ggg aag    1536
Lys Lys Arg Gln Ile Tyr Thr Asp Ile Glu Met Asn Arg Leu Gly Lys
            500                 505                 510 taa                                                                1539
```

<210> SEQ ID NO 57
<211> LENGTH: 512
<212> TYPE: PRT
<213> ORGANISM: Artificial
<220> FEATURE:
<223> OTHER INFORMATION: Synthetic Construct

<400> SEQUENCE: 57

```
Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
            20                  25                  30

Asn Val Pro Ser Ser Tyr His Tyr Cys Pro Ser Ser Ser Asp Gln Asn
        35                  40                  45

Trp His Asn Asp Leu Leu Gly Ile Thr Met Lys Val Lys Met Pro Lys
    50                  55                  60

Thr His Lys Ala Ile Gln Ala Asp Gly Trp Met Cys His Ala Ala Lys
65                  70                  75                  80

Trp Ile Thr Thr Cys Asp Phe Arg Trp Tyr Gly Pro Lys Tyr Ile Thr
                85                  90                  95

His Ser Ile His Ser Ile Gln Pro Thr Ser Glu Gln Cys Lys Glu Ser
            100                 105                 110

Ile Lys Gln Thr Lys Gln Gly Thr Trp Met Ser Pro Gly Phe Pro Pro
        115                 120                 125

Gln Asn Cys Gly Tyr Ala Thr Val Thr Asp Ser Val Ala Val Val
    130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                165                 170                 175

Thr Val His Asn Ser Thr Val Trp Tyr Ser Asp Tyr Lys Val Thr Gly
            180                 185                 190

Leu Cys Asp Ala Thr Leu Val Asp Thr Glu Ile Thr Phe Phe Ser Glu
        195                 200                 205

Asp Gly Lys Lys Glu Ser Ile Gly Lys Pro Asn Thr Gly Tyr Arg Ser
    210                 215                 220
```

```
Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
            245                 250                 255

Val Asp Gln Asp Val Tyr Ala Ala Lys Leu Pro Glu Cys Pro Val
                260                 265                 270

Gly Ala Thr Ile Ser Ala Pro Thr Gln Thr Ser Val Asp Val Ser Leu
            275                 280                 285

Ile Leu Asp Val Glu Arg Ile Leu Asp Tyr Ser Leu Cys Gln Glu Thr
290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
                355                 360                 365

Thr Glu Arg Glu Leu Trp Thr Glu Trp Phe Pro Tyr Glu Gly Val Glu
            370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
            435                 440                 445

Lys Asn Pro Val Glu Leu Ile Glu Gly Trp Phe Ser Ser Trp Lys Ser
            450                 455                 460

Ser Ile Ala Ser Phe Phe Phe Ile Ile Gly Leu Ile Ile Gly Leu Phe
465                 470                 475                 480

Leu Val Leu Arg Val Gly Ile His Leu Cys Ile Lys Leu Lys His Thr
                485                 490                 495

Lys Lys Arg Gln Ile Tyr Thr Asp Ile Glu Met Asn Arg Leu Gly Lys
            500                 505                 510

<210> SEQ ID NO 58
<211> LENGTH: 1518
<212> TYPE: DNA
<213> ORGANISM: Artificial
<220> FEATURE:
<223> OTHER INFORMATION: Fusion VSV-G Piry / Indiana
<220> FEATURE:
<221> NAME/KEY: CDS
<222> LOCATION: (1)..(1518)

<400> SEQUENCE: 58 atg acc gat aca gtg ctg ggc aag ttc cag atc gtg ttc ccc gac cag    48
Met Thr Asp Thr Val Leu Gly Lys Phe Gln Ile Val Phe Pro Asp Gln
1               5                   10                  15 aac gag ctg gaa tgg acc ccc gtc gtg ggc gac agc cgg cat tgc cct    96
Asn Glu Leu Glu Trp Thr Pro Val Val Gly Asp Ser Arg His Cys Pro
            20                  25                  30 cag tcc agc gag atg cag ttc gac ggc agc aga agc cag acc atc ctg    144
Gln Ser Ser Glu Met Gln Phe Asp Gly Ser Arg Ser Gln Thr Ile Leu
        35                  40                  45
```

```
acc ggc aag gcc ccc gtg ggc atc aca ccc agc aag agc gac ggc ttc    192
Thr Gly Lys Ala Pro Val Gly Ile Thr Pro Ser Lys Ser Asp Gly Phe
    50              55                  60 atc tgc cac gcc gcc aag tgg gtg acc acc tgc gac ttc cgg tgg tac    240
Ile Cys His Ala Ala Lys Trp Val Thr Thr Cys Asp Phe Arg Trp Tyr
65              70                  75                  80 ggc ccc aag tac atc acc cac agc atc cac cac ctg cgg ccc acc acc    288
Gly Pro Lys Tyr Ile Thr His Ser Ile His His Leu Arg Pro Thr Thr
                85                  90                  95 tcc gac tgc gag aca gcc ctg cag cgg tac aag gac ggc agc ctg atc    336
Ser Asp Cys Glu Thr Ala Leu Gln Arg Tyr Lys Asp Gly Ser Leu Ile
            100                 105                 110 aac ctg ggc ttc cct ccc gag agc tgc ggc tac gcc acc gtg aca gac    384
Asn Leu Gly Phe Pro Pro Glu Ser Cys Gly Tyr Ala Thr Val Thr Asp
        115                 120                 125 agc gag gcc atg ctg gtg cag gtg acc ccc cac cac gtg ggc gtg gac    432
Ser Glu Ala Met Leu Val Gln Val Thr Pro His His Val Gly Val Asp
    130                 135                 140 gac tac cgg ggc cac tgg atc gac ccc ctg ttc cct ggc ggc gag tgc    480
Asp Tyr Arg Gly His Trp Ile Asp Pro Leu Phe Pro Gly Gly Glu Cys
145                 150                 155                 160 agc acc aat ttc tgc gat acc gtg cac aac agc agc gtg tgg att ccc    528
Ser Thr Asn Phe Cys Asp Thr Val His Asn Ser Ser Val Trp Ile Pro
                165                 170                 175 aag agc cag aaa acc gac atc tgc gcc cag agc ttc aag aac atc aag    576
Lys Ser Gln Lys Thr Asp Ile Cys Ala Gln Ser Phe Lys Asn Ile Lys
            180                 185                 190 atg acc gcc agc tac ccc agc gag gga gcc ctg gtg tcc gac cgg ttc    624
Met Thr Ala Ser Tyr Pro Ser Glu Gly Ala Leu Val Ser Asp Arg Phe
        195                 200                 205 gcc ttc cac agc gcc tac cac ccc aac atg ccc ggc agc acc gtg tgc    672
Ala Phe His Ser Ala Tyr His Pro Asn Met Pro Gly Ser Thr Val Cys
    210                 215                 220 atc atg gat ttc tgc gag cag aag ggc ctg cgg ttc acc aac ggc gag    720
Ile Met Asp Phe Cys Glu Gln Lys Gly Leu Arg Phe Thr Asn Gly Glu
225                 230                 235                 240 tgg atg ggc ctg aac gtg gag cag agc atc cgg gag aag aag atc agc    768
Trp Met Gly Leu Asn Val Glu Gln Ser Ile Arg Glu Lys Lys Ile Ser
                245                 250                 255 gcc atc ttc ccc aac tgc gtg gcc ggc acc gag atc cgg gcc acc ctg    816
Ala Ile Phe Pro Asn Cys Val Ala Gly Thr Glu Ile Arg Ala Thr Leu
            260                 265                 270 gaa tcc gag ggc gcc agg acc ctg acc tgg gag aca cag cgg atg ctg    864
Glu Ser Glu Gly Ala Arg Thr Leu Thr Trp Glu Thr Gln Arg Met Leu
        275                 280                 285 gac tac agc ctg tgc cag aac acc tgg gac aag gtg tcc cgg aaa gag    912
Asp Tyr Ser Leu Cys Gln Asn Thr Trp Asp Lys Val Ser Arg Lys Glu
    290                 295                 300 cct ctg tcc ccc ctg gac ctg agc tac ctg agc cct aga gcc cct ggc    960
Pro Leu Ser Pro Leu Asp Leu Ser Tyr Leu Ser Pro Arg Ala Pro Gly
305                 310                 315                 320 aag ggc atg gcc tac acc gtg atc aac ggc acc ctg cac agc gcc cac   1008
Lys Gly Met Ala Tyr Thr Val Ile Asn Gly Thr Leu His Ser Ala His
                325                 330                 335 gcc aag tat atc cgg acc tgg atc gac tac ggc gag atg aaa gag atc   1056
Ala Lys Tyr Ile Arg Thr Trp Ile Asp Tyr Gly Glu Met Lys Glu Ile
            340                 345                 350 aag ggc ggc agg ggc gag tac agc aag gcc cct gag ctg ctg tgg agc   1104
Lys Gly Gly Arg Gly Glu Tyr Ser Lys Ala Pro Glu Leu Leu Trp Ser
        355                 360                 365
```

```
cag tgg ttc gac ttc ggc ccc ttc aag atc ggc ccc aac ggc ctg ctg    1152
Gln Trp Phe Asp Phe Gly Pro Phe Lys Ile Gly Pro Asn Gly Leu Leu
        370                 375                 380 cac acc ggc aag acc ttc aag ttc cct ctg tat ctg atc gga gcc ggc    1200
His Thr Gly Lys Thr Phe Lys Phe Pro Leu Tyr Leu Ile Gly Ala Gly
385                 390                 395                 400 atc atc gac gag gac ctg cac gag ctg gac gaa gcc gcc cct atc gac    1248
Ile Ile Asp Glu Asp Leu His Glu Leu Asp Glu Ala Ala Pro Ile Asp
                405                 410                 415 cac ccc cag atg ccc gac gcc aag agc gtg ctg ccc gag gac gag gaa    1296
His Pro Gln Met Pro Asp Ala Lys Ser Val Leu Pro Glu Asp Glu Glu
        420                 425                 430 atc ttc ttc ggc gac acc ggc gtg agc aag aac ccc atc gag ctg atc    1344
Ile Phe Phe Gly Asp Thr Gly Val Ser Lys Asn Pro Ile Glu Leu Ile
435                 440                 445 cag ggc tgg ttc agc aac tgg cgg agc agc atc gct tca ttt ttt ttc    1392
Gln Gly Trp Phe Ser Asn Trp Arg Ser Ser Ile Ala Ser Phe Phe Phe
                450                 455                 460 atc atc ggc ctc atc atc ggg ctg ttt ctg gtg ctg cgc gtc ggc atc    1440
Ile Ile Gly Leu Ile Ile Gly Leu Phe Leu Val Leu Arg Val Gly Ile
465                 470                 475                 480 cac ctg tgc atc aag ctg aag cac acc aag aag cgc cag atc tat acc    1488
His Leu Cys Ile Lys Leu Lys His Thr Lys Lys Arg Gln Ile Tyr Thr
                485                 490                 495 gac atc gag atg aat cgc ctg ggg aag taa                            1518
Asp Ile Glu Met Asn Arg Leu Gly Lys
        500                 505

<210> SEQ ID NO 59
<211> LENGTH: 505
<212> TYPE: PRT
<213> ORGANISM: Artificial
<220> FEATURE:
<223> OTHER INFORMATION: Synthetic Construct

<400> SEQUENCE: 59

Met Thr Asp Thr Val Leu Gly Lys Phe Gln Ile Val Phe Pro Asp Gln
1               5                   10                  15

Asn Glu Leu Glu Trp Thr Pro Val Val Gly Asp Ser Arg His Cys Pro
            20                  25                  30

Gln Ser Ser Glu Met Gln Phe Asp Gly Ser Arg Ser Gln Thr Ile Leu
        35                  40                  45

Thr Gly Lys Ala Pro Val Gly Ile Thr Pro Ser Lys Ser Asp Gly Phe
    50                  55                  60

Ile Cys His Ala Ala Lys Trp Val Thr Thr Cys Asp Phe Arg Trp Tyr
65                  70                  75                  80

Gly Pro Lys Tyr Ile Thr His Ser Ile His His Leu Arg Pro Thr Thr
                85                  90                  95

Ser Asp Cys Glu Thr Ala Leu Gln Arg Tyr Lys Asp Gly Ser Leu Ile
            100                 105                 110

Asn Leu Gly Phe Pro Pro Glu Ser Cys Gly Tyr Ala Thr Val Thr Asp
        115                 120                 125

Ser Glu Ala Met Leu Val Gln Val Thr Pro His His Val Gly Val Asp
    130                 135                 140

Asp Tyr Arg Gly His Trp Ile Asp Pro Leu Phe Pro Gly Gly Glu Cys
145                 150                 155                 160

Ser Thr Asn Phe Cys Asp Thr Val His Asn Ser Ser Val Trp Ile Pro
                165                 170                 175

Lys Ser Gln Lys Thr Asp Ile Cys Ala Gln Ser Phe Lys Asn Ile Lys
```

```
                180             185             190
Met Thr Ala Ser Tyr Pro Ser Glu Gly Ala Leu Val Ser Asp Arg Phe
            195                 200                 205

Ala Phe His Ser Ala Tyr His Pro Asn Met Pro Gly Ser Thr Val Cys
            210                 215                 220

Ile Met Asp Phe Cys Glu Gln Lys Gly Leu Arg Phe Thr Asn Gly Glu
225                 230                 235                 240

Trp Met Gly Leu Asn Val Glu Gln Ser Ile Arg Glu Lys Lys Ile Ser
                245                 250                 255

Ala Ile Phe Pro Asn Cys Val Ala Gly Thr Glu Ile Arg Ala Thr Leu
            260                 265                 270

Glu Ser Glu Gly Ala Arg Thr Leu Thr Trp Glu Thr Gln Arg Met Leu
        275                 280                 285

Asp Tyr Ser Leu Cys Gln Asn Thr Trp Asp Lys Val Ser Arg Lys Glu
    290                 295                 300

Pro Leu Ser Pro Leu Asp Leu Ser Tyr Leu Ser Pro Arg Ala Pro Gly
305                 310                 315                 320

Lys Gly Met Ala Tyr Thr Val Ile Asn Gly Thr Leu His Ser Ala His
                325                 330                 335

Ala Lys Tyr Ile Arg Thr Trp Ile Asp Tyr Gly Glu Met Lys Glu Ile
            340                 345                 350

Lys Gly Gly Arg Gly Glu Tyr Ser Lys Ala Pro Glu Leu Leu Trp Ser
        355                 360                 365

Gln Trp Phe Asp Phe Gly Pro Phe Lys Ile Gly Pro Asn Gly Leu Leu
    370                 375                 380

His Thr Gly Lys Thr Phe Lys Phe Pro Leu Tyr Leu Ile Gly Ala Gly
385                 390                 395                 400

Ile Ile Asp Glu Asp Leu His Glu Leu Asp Glu Ala Ala Pro Ile Asp
                405                 410                 415

His Pro Gln Met Pro Asp Ala Lys Ser Val Leu Pro Glu Asp Glu Glu
            420                 425                 430

Ile Phe Phe Gly Asp Thr Gly Val Ser Lys Asn Pro Ile Glu Leu Ile
        435                 440                 445

Gln Gly Trp Phe Ser Asn Trp Arg Ser Ser Ile Ala Ser Phe Phe Phe
    450                 455                 460

Ile Ile Gly Leu Ile Ile Gly Leu Phe Leu Val Leu Arg Val Gly Ile
465                 470                 475                 480

His Leu Cys Ile Lys Leu Lys His Thr Lys Lys Arg Gln Ile Tyr Thr
                485                 490                 495

Asp Ile Glu Met Asn Arg Leu Gly Lys
            500                 505

<210> SEQ ID NO 60
<211> LENGTH: 1560
<212> TYPE: DNA
<213> ORGANISM: Artificial
<220> FEATURE:
<223> OTHER INFORMATION: Fusion VSV-G Isfahan / Indiana
<220> FEATURE:
<221> NAME/KEY: CDS
<222> LOCATION: (1)..(1560)

<400> SEQUENCE: 60 atg aca tcc gtg ctg ttt atg gtg ggc gtg ctg ctc gga gct ttc gga        48
Met Thr Ser Val Leu Phe Met Val Gly Val Leu Leu Gly Ala Phe Gly
1               5                   10                  15 tct acc cac tgc agc atc cag atc gtg ttc ccc agc gag aca aag ctg        96
```

```
Ser Thr His Cys Ser Ile Gln Ile Val Phe Pro Ser Glu Thr Lys Leu
         20                  25                  30 gtg tgg aag ccc gtg ctg aag ggc acc cgg tac tgc ccc cag agc gcc      144
Val Trp Lys Pro Val Leu Lys Gly Thr Arg Tyr Cys Pro Gln Ser Ala
         35                  40                  45 gag ctg aac ctg gaa ccc gac ctg aaa acc atg gcc ttc gac agc aag      192
Glu Leu Asn Leu Glu Pro Asp Leu Lys Thr Met Ala Phe Asp Ser Lys
         50                  55                  60 gtg ccc atc ggc atc acc ccc agc aac agc gac ggc tac ctg tgc cac      240
Val Pro Ile Gly Ile Thr Pro Ser Asn Ser Asp Gly Tyr Leu Cys His
 65                  70                  75                  80 gcc gcc aag tgg gtg acc acc tgc gac ttc cgg tgg tac ggc ccc aag      288
Ala Ala Lys Trp Val Thr Thr Cys Asp Phe Arg Trp Tyr Gly Pro Lys
                 85                  90                  95 tac atc acc cac agc gtg cac agc ctg cgg ccc acc gtg agc gac tgc      336
Tyr Ile Thr His Ser Val His Ser Leu Arg Pro Thr Val Ser Asp Cys
                100                 105                 110 aag gcc gcc gtg gaa gct tac aac gct ggc acc ctg atg tac ccc ggc      384
Lys Ala Ala Val Glu Ala Tyr Asn Ala Gly Thr Leu Met Tyr Pro Gly
            115                 120                 125 ttc ccc ccc gag agc tgc ggc tac gcc agc atc acc gac agc gag ttc      432
Phe Pro Pro Glu Ser Cys Gly Tyr Ala Ser Ile Thr Asp Ser Glu Phe
        130                 135                 140 tac gtg atg ctg gtg acc ccc cac ccc gtg gga gtg gac gac tac cgg      480
Tyr Val Met Leu Val Thr Pro His Pro Val Gly Val Asp Asp Tyr Arg
145                 150                 155                 160 ggc cac tgg gtg gac cct ctg ttc ccc acc tcc gag tgc aac agc aac      528
Gly His Trp Val Asp Pro Leu Phe Pro Thr Ser Glu Cys Asn Ser Asn
                165                 170                 175 ttc tgc gag aca gtg cac aac gcc acc atg tgg att ccc aag gat ctg      576
Phe Cys Glu Thr Val His Asn Ala Thr Met Trp Ile Pro Lys Asp Leu
                180                 185                 190 aaa acc cac gac gtg tgc agc cag gac ttc cag acc atc aga gtg agc      624
Lys Thr His Asp Val Cys Ser Gln Asp Phe Gln Thr Ile Arg Val Ser
            195                 200                 205 gtg atg tac cct cag acc aag ccc acc aag gga gct gac ctg aca ctg      672
Val Met Tyr Pro Gln Thr Lys Pro Thr Lys Gly Ala Asp Leu Thr Leu
        210                 215                 220 aag agc aag ttc cac gcc cac atg aag ggc gac aga gtg tgc aag atg      720
Lys Ser Lys Phe His Ala His Met Lys Gly Asp Arg Val Cys Lys Met
225                 230                 235                 240 aag ttc tgc aac aag aac ggc ctg cgg ctg ggc aac ggc gag tgg atc      768
Lys Phe Cys Asn Lys Asn Gly Leu Arg Leu Gly Asn Gly Glu Trp Ile
                245                 250                 255 gaa gtg ggc gac gag gtg atg ctg gac aac agc aag ctg ctg tcc ctg      816
Glu Val Gly Asp Glu Val Met Leu Asp Asn Ser Lys Leu Leu Ser Leu
                260                 265                 270 ttc ccc gac tgc ctg gtg ggc agc gtg gtg aag agc acc ctg ctg tcc      864
Phe Pro Asp Cys Leu Val Gly Ser Val Val Lys Ser Thr Leu Leu Ser
            275                 280                 285 gag ggc gtg cag acc gcc ctg tgg gag aca gac cgg ctg ctg gac tac      912
Glu Gly Val Gln Thr Ala Leu Trp Glu Thr Asp Arg Leu Leu Asp Tyr
        290                 295                 300 agc ctg tgc cag aac acc tgg gag aag atc gac cgg aaa gag ccc ctg      960
Ser Leu Cys Gln Asn Thr Trp Glu Lys Ile Asp Arg Lys Glu Pro Leu
305                 310                 315                 320 agc gcc gtc gac ctg agc tac ctg gcc cct aga agc ccc ggc aag ggc     1008
Ser Ala Val Asp Leu Ser Tyr Leu Ala Pro Arg Ser Pro Gly Lys Gly
                325                 330                 335 atg gcc tac atc gtg gcc aac ggc agc ctg atg agc gcc cct gcc cgg     1056
```

```
Met Ala Tyr Ile Val Ala Asn Gly Ser Leu Met Ser Ala Pro Ala Arg
            340                 345                 350 tac atc aga gtg tgg atc gac agc ccc atc ctg aaa gag atc aag ggc      1104
Tyr Ile Arg Val Trp Ile Asp Ser Pro Ile Leu Lys Glu Ile Lys Gly
            355                 360                 365 aag aaa gag agc gcc agc ggc atc gac acc gtg ctg tgg gag cag tgg      1152
Lys Lys Glu Ser Ala Ser Gly Ile Asp Thr Val Leu Trp Glu Gln Trp
            370                 375                 380 ctg ccc ttc aac ggc atg gaa ctg ggc ccc aac ggc ctg atc aag acc      1200
Leu Pro Phe Asn Gly Met Glu Leu Gly Pro Asn Gly Leu Ile Lys Thr
385                 390                 395                 400 aag agc ggc tac aag ttc ccc ctg tac ctg ctg ggc atg ggc atc gtg      1248
Lys Ser Gly Tyr Lys Phe Pro Leu Tyr Leu Leu Gly Met Gly Ile Val
            405                 410                 415 gac cag gac ctg cag gaa ctg agc agc gtc aac ccc gtg gac cac ccc      1296
Asp Gln Asp Leu Gln Glu Leu Ser Ser Val Asn Pro Val Asp His Pro
            420                 425                 430 cac gtg cct atc gcc cag gcc ttc gtg agc gag ggc gag gaa gtg ttc      1344
His Val Pro Ile Ala Gln Ala Phe Val Ser Glu Gly Glu Glu Val Phe
            435                 440                 445 ttc ggc gac acc ggc gtg agc aag aac ccc atc gag ctg atc agc ggc      1392
Phe Gly Asp Thr Gly Val Ser Lys Asn Pro Ile Glu Leu Ile Ser Gly
450                 455                 460 tgg ttc agc gac tgg aaa agc agc atc gct tca ttt ttt ttc atc atc      1440
Trp Phe Ser Asp Trp Lys Ser Ser Ile Ala Ser Phe Phe Phe Ile Ile
465                 470                 475                 480 ggc ctc atc atc ggg ctg ttt ctg gtg ctg cgc gtc ggc atc cac ctg      1488
Gly Leu Ile Ile Gly Leu Phe Leu Val Leu Arg Val Gly Ile His Leu
            485                 490                 495 tgc atc aag ctg aag cac acc aag aag cgc cag atc tat acc gac atc      1536
Cys Ile Lys Leu Lys His Thr Lys Lys Arg Gln Ile Tyr Thr Asp Ile
            500                 505                 510 gag atg aat cgc ctg ggg aag taa                                       1560
Glu Met Asn Arg Leu Gly Lys
            515

<210> SEQ ID NO 61
<211> LENGTH: 519
<212> TYPE: PRT
<213> ORGANISM: Artificial
<220> FEATURE:
<223> OTHER INFORMATION: Synthetic Construct

<400> SEQUENCE: 61

Met Thr Ser Val Leu Phe Met Val Gly Val Leu Leu Gly Ala Phe Gly
1               5                   10                  15

Ser Thr His Cys Ser Ile Gln Ile Val Phe Pro Ser Thr Lys Leu
            20                  25                  30

Val Trp Lys Pro Val Leu Lys Gly Thr Arg Tyr Cys Pro Gln Ser Ala
            35                  40                  45

Glu Leu Asn Leu Glu Pro Asp Leu Lys Thr Met Ala Phe Asp Ser Lys
            50                  55                  60

Val Pro Ile Gly Ile Thr Pro Ser Asn Ser Asp Gly Tyr Leu Cys His
65                  70                  75                  80

Ala Ala Lys Trp Val Thr Thr Cys Asp Phe Arg Trp Tyr Gly Pro Lys
            85                  90                  95

Tyr Ile Thr His Ser Val His Ser Leu Arg Pro Thr Val Ser Asp Cys
            100                 105                 110

Lys Ala Ala Val Glu Ala Tyr Asn Ala Gly Thr Leu Met Tyr Pro Gly
            115                 120                 125
```

```
Phe Pro Pro Glu Ser Cys Gly Tyr Ala Ser Ile Thr Asp Ser Glu Phe
    130                 135                 140

Tyr Val Met Leu Val Thr Pro His Pro Val Gly Val Asp Asp Tyr Arg
145                 150                 155                 160

Gly His Trp Val Asp Pro Leu Phe Pro Thr Ser Glu Cys Asn Ser Asn
                165                 170                 175

Phe Cys Glu Thr Val His Asn Ala Thr Met Trp Ile Pro Lys Asp Leu
            180                 185                 190

Lys Thr His Asp Val Cys Ser Gln Asp Phe Gln Thr Ile Arg Val Ser
        195                 200                 205

Val Met Tyr Pro Gln Thr Lys Pro Thr Lys Gly Ala Asp Leu Thr Leu
    210                 215                 220

Lys Ser Lys Phe His Ala His Met Lys Gly Asp Arg Val Cys Lys Met
225                 230                 235                 240

Lys Phe Cys Asn Lys Asn Gly Leu Arg Leu Gly Asn Gly Glu Trp Ile
                245                 250                 255

Glu Val Gly Asp Glu Val Met Leu Asp Asn Ser Lys Leu Leu Ser Leu
                260                 265                 270

Phe Pro Asp Cys Leu Val Gly Ser Val Val Lys Ser Thr Leu Leu Ser
            275                 280                 285

Glu Gly Val Gln Thr Ala Leu Trp Glu Thr Arg Leu Leu Asp Tyr
    290                 295                 300

Ser Leu Cys Gln Asn Thr Trp Glu Lys Ile Asp Arg Lys Glu Pro Leu
305                 310                 315                 320

Ser Ala Val Asp Leu Ser Tyr Leu Ala Pro Arg Ser Pro Gly Lys Gly
                325                 330                 335

Met Ala Tyr Ile Val Ala Asn Gly Ser Leu Met Ser Ala Pro Ala Arg
                340                 345                 350

Tyr Ile Arg Val Trp Ile Asp Ser Pro Ile Leu Lys Glu Ile Lys Gly
                355                 360                 365

Lys Lys Glu Ser Ala Ser Gly Ile Asp Thr Val Leu Trp Glu Gln Trp
        370                 375                 380

Leu Pro Phe Asn Gly Met Glu Leu Gly Pro Asn Gly Leu Ile Lys Thr
385                 390                 395                 400

Lys Ser Gly Tyr Lys Phe Pro Leu Tyr Leu Leu Gly Met Gly Ile Val
                405                 410                 415

Asp Gln Asp Leu Gln Glu Leu Ser Ser Val Asn Pro Val Asp His Pro
            420                 425                 430

His Val Pro Ile Ala Gln Ala Phe Val Ser Glu Gly Glu Val Phe
        435                 440                 445

Phe Gly Asp Thr Gly Val Ser Lys Asn Pro Ile Glu Leu Ile Ser Gly
    450                 455                 460

Trp Phe Ser Asp Trp Lys Ser Ser Ile Ala Ser Phe Phe Ile Ile
465                 470                 475                 480

Gly Leu Ile Ile Gly Leu Phe Leu Val Leu Arg Val Gly Ile His Leu
                485                 490                 495

Cys Ile Lys Leu Lys His Thr Lys Lys Arg Gln Ile Tyr Thr Asp Ile
            500                 505                 510

Glu Met Asn Arg Leu Gly Lys
        515

<210> SEQ ID NO 62
<211> LENGTH: 1536
<212> TYPE: DNA
```

-continued

```
<213> ORGANISM: Artificial
<220> FEATURE:
<223> OTHER INFORMATION: Fusion VSV-G New Jersey / Indiana
<220> FEATURE:
<221> NAME/KEY: CDS
<222> LOCATION: (1)..(1536)

<400> SEQUENCE: 62 atg agc atc atc agc tat atc gcc ttt ct

```
acc gtg ttc aac ctg gaa aac gtg gtg gag tac acc ctg tgc gag ggc    912
Thr Val Phe Asn Leu Glu Asn Val Val Glu Tyr Thr Leu Cys Glu Gly
290                 295                 300 acc aag cgg aag atc aac aag cag gaa aag ctg acc agc gtc gac ctg    960
Thr Lys Arg Lys Ile Asn Lys Gln Glu Lys Leu Thr Ser Val Asp Leu
305                 310                 315                 320 agc tac ctg gcc ccc agg atc ggc ggc ttc ggc agc gtg ttc cgc gtg   1008
Ser Tyr Leu Ala Pro Arg Ile Gly Gly Phe Gly Ser Val Phe Arg Val
                325                 330                 335 cgg aat ggg acc ctg gaa aga gga agc aca aca tac att cgg atc gaa   1056
Arg Asn Gly Thr Leu Glu Arg Gly Ser Thr Thr Tyr Ile Arg Ile Glu
            340                 345                 350 gtg gaa ggc ccc gtg gtg gac agc ctg aac ggc atc gac ccc cgg acc   1104
Val Glu Gly Pro Val Val Asp Ser Leu Asn Gly Ile Asp Pro Arg Thr
        355                 360                 365 aac gcc agc cgg gtg ttc tgg gac gac tgg gag ctg gac ggc aac atc   1152
Asn Ala Ser Arg Val Phe Trp Asp Asp Trp Glu Leu Asp Gly Asn Ile
370                 375                 380 tac cag ggc ttc aat ggc gtg tac aag ggc aag gat ggc aag atc cac   1200
Tyr Gln Gly Phe Asn Gly Val Tyr Lys Gly Lys Asp Gly Lys Ile His
385                 390                 395                 400 atc ccc ctg aac atg atc gag agc ggc atc atc gac gac gag ctg cag   1248
Ile Pro Leu Asn Met Ile Glu Ser Gly Ile Ile Asp Asp Glu Leu Gln
                405                 410                 415 cac gcc ttc cag gcc gac atc atc ccc cac ccc cac tac gac gac gac   1296
His Ala Phe Gln Ala Asp Ile Ile Pro His Pro His Tyr Asp Asp Asp
            420                 425                 430 gag atc cgg gag gac gac atc ttc ttc gac aac acc ggc gag aac ggc   1344
Glu Ile Arg Glu Asp Asp Ile Phe Phe Asp Asn Thr Gly Glu Asn Gly
        435                 440                 445 aac ccc gtg gac gcc gtg gtg gaa tgg gtg tcc gga tgg ggc agc agc   1392
Asn Pro Val Asp Ala Val Val Glu Trp Val Ser Gly Trp Gly Ser Ser
450                 455                 460 atc gct tca ttt ttt ttc atc atc ggc ctc atc atc ggg ctg ttt ctg   1440
Ile Ala Ser Phe Phe Phe Ile Ile Gly Leu Ile Ile Gly Leu Phe Leu
465                 470                 475                 480 gtg ctg cgc gtc ggc atc cac ctg tgc atc aag ctg aag cac acc aag   1488
Val Leu Arg Val Gly Ile His Leu Cys Ile Lys Leu Lys His Thr Lys
                485                 490                 495 aag cgc cag atc tat acc gac atc gag atg aat cgc ctg ggg aag taa   1536
Lys Arg Gln Ile Tyr Thr Asp Ile Glu Met Asn Arg Leu Gly Lys
            500                 505                 510
```

<210> SEQ ID NO 63
<211> LENGTH: 511
<212> TYPE: PRT
<213> ORGANISM: Artificial
<220> FEATURE:
<223> OTHER INFORMATION: Synthetic Construct

<400> SEQUENCE: 63

```
Met Ser Ile Ile Ser Tyr Ile Ala Phe Leu Leu Leu Ile Asp Ser Thr
1               5                   10                  15

Leu Gly Ile Pro Ile Phe Val Pro Ser Gly Gln Asn Ile Ser Trp Gln
            20                  25                  30

Pro Val Ile Gln Pro Phe Asp Tyr Gln Cys Pro Ile His Gly Asn Leu
        35                  40                  45

Pro Asn Thr Met Gly Leu Ser Ala Thr Lys Leu Thr Ile Lys Ser Pro
    50                  55                  60

Ser Val Phe Ser Thr Asp Lys Val Ser Gly Trp Ile Cys His Ala Ala
```

```
                     65                  70                  75                  80
Glu Trp Lys Thr Thr Cys Asp Tyr Arg Trp Tyr Gly Pro Gln Tyr Ile
                         85                  90                  95

Thr His Ser Ile His Pro Ile Ser Pro Thr Ile Asp Glu Cys Lys Arg
                    100                 105                 110

Ile Ile Ser Arg Ile Ala Ser Gly Thr Asp Glu Asp Leu Gly Phe Pro
                    115                 120                 125

Pro Gln Ser Cys Gly Trp Ala Ser Val Thr Thr Val Ser Asn Thr Asn
        130                 135                 140

Tyr Lys Val Val Pro His Ser Val His Leu Glu Pro Tyr Gly Gly His
145                 150                 155                 160

Trp Ile Asp His Asp Phe Asn Gly Gly Glu Cys Arg Glu Lys Val Cys
                165                 170                 175

Glu Met Lys Gly Asn His Ser Ile Trp Ile Thr Asp Glu Thr Val Gln
                180                 185                 190

His Glu Cys Glu Lys His Ile Glu Glu Val Glu Gly Ile Met Tyr Gly
            195                 200                 205

Asn Ala Pro Arg Gly Asp Ala Ile Tyr Ile Asn Asn Phe Ile Ile Asp
210                 215                 220

Lys His His Arg Val Tyr Arg Phe Gly Gly Ser Cys Arg Met Lys Phe
225                 230                 235                 240

Cys Asn Lys Asp Gly Ile Lys Phe Thr Arg Gly Asp Trp Val Glu Lys
                245                 250                 255

Thr Ala Gly Thr Leu Thr Asn Ile Tyr Glu Asn Ile Pro Glu Cys Ala
                260                 265                 270

Asp Gly Thr Leu Val Ser Gly His Arg Pro Gly Leu Asp Leu Ile Asp
            275                 280                 285

Thr Val Phe Asn Leu Glu Asn Val Val Glu Tyr Thr Leu Cys Glu Gly
        290                 295                 300

Thr Lys Arg Lys Ile Asn Lys Gln Glu Lys Leu Thr Ser Val Asp Leu
305                 310                 315                 320

Ser Tyr Leu Ala Pro Arg Ile Gly Gly Phe Gly Ser Val Phe Arg Val
                325                 330                 335

Arg Asn Gly Thr Leu Glu Arg Gly Ser Thr Thr Tyr Ile Arg Ile Glu
                340                 345                 350

Val Glu Gly Pro Val Val Asp Ser Leu Asn Gly Ile Asp Pro Arg Thr
            355                 360                 365

Asn Ala Ser Arg Val Phe Trp Asp Asp Trp Glu Leu Asp Gly Asn Ile
        370                 375                 380

Tyr Gln Gly Phe Asn Gly Val Tyr Lys Gly Lys Asp Gly Lys Ile His
385                 390                 395                 400

Ile Pro Leu Asn Met Ile Glu Ser Gly Ile Ile Asp Asp Glu Leu Gln
                405                 410                 415

His Ala Phe Gln Ala Asp Ile Ile Pro His Pro His Tyr Asp Asp Asp
                420                 425                 430

Glu Ile Arg Glu Asp Asp Ile Phe Phe Asp Asn Thr Gly Glu Asn Gly
            435                 440                 445

Asn Pro Val Asp Ala Val Val Glu Trp Val Ser Gly Trp Gly Ser Ser
        450                 455                 460

Ile Ala Ser Phe Phe Phe Ile Ile Gly Leu Ile Gly Leu Phe Leu
465                 470                 475                 480

Val Leu Arg Val Gly Ile His Leu Cys Ile Lys Leu Lys His Thr Lys
                485                 490                 495
```

-continued

```
             Lys Arg Gln Ile Tyr Thr Asp Ile Glu Met Asn Arg Leu Gly Lys
                 500                 505                 510
```

<210> SEQ ID NO 64
<211> LENGTH: 1557
<212> TYPE: DNA
<213> ORGANISM: Artificial
<220> FEATURE:
<223> OTHER INFORMATION: Fusion VSV-G New Jersey / Indiana
<220> FEATURE:
<221> NAME/KEY: CDS
<222> LOCATION: (1)..(1557)

<400> SEQUENCE: 64

```
atg ctg t

```
gac ccg gac ctg gac aag acc gtc cgc gat ctg ccc cac atc aag gac       816
Asp Pro Asp Leu Asp Lys Thr Val Arg Asp Leu Pro His Ile Lys Asp
        260                 265                 270 tgt gat ctg tca tca agc atc atc acc ccc gga gaa cac gcc acg gac       864
Cys Asp Leu Ser Ser Ser Ile Ile Thr Pro Gly Glu His Ala Thr Asp
    275                 280                 285 atc agc ctc atc agc gat gtg gag cgc atc ctc gac tac gct ctc tgc       912
Ile Ser Leu Ile Ser Asp Val Glu Arg Ile Leu Asp Tyr Ala Leu Cys
290                 295                 300 cag aac aca tgg agc aag atc gaa agc ggc gaa ccc atc acc cca gtg       960
Gln Asn Thr Trp Ser Lys Ile Glu Ser Gly Glu Pro Ile Thr Pro Val
305                 310                 315                 320 gac ctg agc tat ctc ggc cca aag aac ccc ggc gtg ggg ccc gtg ttc      1008
Asp Leu Ser Tyr Leu Gly Pro Lys Asn Pro Gly Val Gly Pro Val Phe
                325                 330                 335 acc atc atc aac ggg agc ctg cac tac ttt aca agc aag tat ctg cgc      1056
Thr Ile Ile Asn Gly Ser Leu His Tyr Phe Thr Ser Lys Tyr Leu Arg
            340                 345                 350 gtg gag ctc gaa agc cca gtc atc ccc cgc atg gag ggg aag gtg gcc      1104
Val Glu Leu Glu Ser Pro Val Ile Pro Arg Met Glu Gly Lys Val Ala
        355                 360                 365 ggg acc cgc atc gtg cgc cag ctg tgg gac cag tgg ttc cct ttt ggc      1152
Gly Thr Arg Ile Val Arg Gln Leu Trp Asp Gln Trp Phe Pro Phe Gly
    370                 375                 380 gag gtg gaa atc ggc ccc aac ggc gtg ctg aag acc aag caa gga tat      1200
Glu Val Glu Ile Gly Pro Asn Gly Val Leu Lys Thr Lys Gln Gly Tyr
385                 390                 395                 400 aag ttc ccg ctg cac atc atc ggg acg ggc gaa gtg gac agc gat atc      1248
Lys Phe Pro Leu His Ile Ile Gly Thr Gly Glu Val Asp Ser Asp Ile
                405                 410                 415 aag atg gag cgc gtg gtc aag cac tgg gag cac cca cac atc gag gct      1296
Lys Met Glu Arg Val Val Lys His Trp Glu His Pro His Ile Glu Ala
            420                 425                 430 gct cag acc ttt ctc aag aag gac gat acc ggc gaa gtc ctg tat tac      1344
Ala Gln Thr Phe Leu Lys Lys Asp Asp Thr Gly Glu Val Leu Tyr Tyr
        435                 440                 445 ggg gat acg gga gtg agc aag aac cct gtg gag ctg gtg gaa ggc tgg      1392
Gly Asp Thr Gly Val Ser Lys Asn Pro Val Glu Leu Val Glu Gly Trp
    450                 455                 460 ttc agc gga tgg cgc agc agc atc gct tca ttt ttt ttc atc atc ggc      1440
Phe Ser Gly Trp Arg Ser Ser Ile Ala Ser Phe Phe Phe Ile Ile Gly
465                 470                 475                 480 ctc atc atc ggg ctg ttt ctg gtg ctg cgc gtc ggc atc cac ctg tgc      1488
Leu Ile Ile Gly Leu Phe Leu Val Leu Arg Val Gly Ile His Leu Cys
                485                 490                 495 atc aag ctg aag cac acc aag aag cgc cag atc tat acc gac atc gag      1536
Ile Lys Leu Lys His Thr Lys Lys Arg Gln Ile Tyr Thr Asp Ile Glu
            500                 505                 510 atg aat cgc ctg ggg aag taa                                           1557
Met Asn Arg Leu Gly Lys
        515

<210> SEQ ID NO 65
<211> LENGTH: 518
<212> TYPE: PRT
<213> ORGANISM: Artificial
<220> FEATURE:
<223> OTHER INFORMATION: Synthetic Construct

<400> SEQUENCE: 65

Met Leu Ser Tyr Leu Ile Phe Ala Leu Ala Val Ser Pro Ile Leu Gly
1               5                   10                  15
```

-continued

```
Lys Ile Glu Ile Val Phe Pro Gln His Thr Thr Gly Asp Trp Lys Arg
             20                  25                  30
Val Pro His Glu Tyr Asn Tyr Cys Pro Thr Ser Ala Asp Lys Asn Ser
         35                  40                  45
His Gly Thr Gln Thr Gly Ile Pro Val Glu Leu Thr Met Pro Lys Gly
     50                  55                  60
Leu Thr Thr His Gln Val Glu Gly Phe Met Cys His Ser Ala Leu Trp
 65                  70                  75                  80
Met Thr Thr Cys Asp Phe Arg Trp Tyr Gly Pro Lys Tyr Ile Thr His
                 85                  90                  95
Ser Ile His Asn Glu Glu Pro Thr Asp Tyr Gln Cys Leu Glu Ala Ile
            100                 105                 110
Lys Ser Tyr Lys Asp Gly Val Ser Phe Asn Pro Gly Phe Pro Pro Gln
        115                 120                 125
Ser Cys Gly Tyr Gly Thr Val Thr Asp Ala Glu Ala His Ile Val Thr
    130                 135                 140
Val Thr Pro His Ser Val Lys Val Asp Glu Tyr Thr Gly Glu Trp Ile
145                 150                 155                 160
Asp Pro His Phe Ile Gly Gly Arg Cys Lys Gly Gln Ile Cys Glu Thr
                165                 170                 175
Val His Asn Ser Thr Lys Trp Phe Thr Ser Ser Asp Gly Glu Ser Val
            180                 185                 190
Cys Ser Gln Leu Phe Thr Leu Val Gly Gly Ile Phe Phe Ser Asp Ser
        195                 200                 205
Glu Glu Ile Thr Ser Met Gly Leu Pro Glu Thr Gly Ile Arg Ser Asn
    210                 215                 220
Tyr Phe Pro Tyr Ile Ser Thr Glu Gly Ile Cys Lys Met Pro Phe Cys
225                 230                 235                 240
Arg Lys Gln Gly Tyr Lys Leu Lys Asn Asp Leu Trp Phe Gln Ile Met
                245                 250                 255
Asp Pro Asp Leu Asp Lys Thr Val Arg Asp Leu Pro His Ile Lys Asp
            260                 265                 270
Cys Asp Leu Ser Ser Ser Ile Ile Thr Pro Gly Glu His Ala Thr Asp
        275                 280                 285
Ile Ser Leu Ile Ser Asp Val Glu Arg Ile Leu Asp Tyr Ala Leu Cys
    290                 295                 300
Gln Asn Thr Trp Ser Lys Ile Glu Ser Gly Glu Pro Ile Thr Pro Val
305                 310                 315                 320
Asp Leu Ser Tyr Leu Gly Pro Lys Asn Pro Gly Val Gly Pro Val Phe
                325                 330                 335
Thr Ile Ile Asn Gly Ser Leu His Tyr Phe Thr Ser Lys Tyr Leu Arg
            340                 345                 350
Val Glu Leu Glu Ser Pro Val Ile Pro Arg Met Glu Gly Lys Val Ala
        355                 360                 365
Gly Thr Arg Ile Val Arg Gln Leu Trp Asp Gln Trp Phe Pro Phe Gly
    370                 375                 380
Glu Val Glu Ile Gly Pro Asn Gly Val Leu Lys Thr Lys Gln Gly Tyr
385                 390                 395                 400
Lys Phe Pro Leu His Ile Ile Gly Thr Gly Val Asp Ser Asp Ile
                405                 410                 415
Lys Met Glu Arg Val Val Lys His Trp Glu His Pro His Ile Glu Ala
            420                 425                 430
Ala Gln Thr Phe Leu Lys Lys Asp Asp Thr Gly Glu Val Leu Tyr Tyr
```

```
                435                 440                 445
Gly Asp Thr Gly Val Ser Lys Asn Pro Val Glu Leu Val Glu Gly Trp
    450                 455                 460

Phe Ser Gly Trp Arg Ser Ser Ile Ala Ser Phe Phe Ile Ile Gly
465                 470                 475                 480

Leu Ile Ile Gly Leu Phe Leu Val Leu Arg Val Gly Ile His Leu Cys
                485                 490                 495

Ile Lys Leu Lys His Thr Lys Lys Arg Gln Ile Tyr Thr Asp Ile Glu
                500                 505                 510

Met Asn Arg Leu Gly Lys
            515

<210> SEQ ID NO 66
<211> LENGTH: 493
<212> TYPE: PRT
<213> ORGANISM: Artificial
<220> FEATURE:
<223> OTHER INFORMATION: delta myr-GAG antigen

<400> SEQUENCE: 66

Met Ala Ser Val Leu Ser Gly Gly Glu Leu Asp Arg Trp Glu Lys Ile
1               5                   10                  15

Arg Leu Arg Pro Gly Gly Lys Lys Tyr Lys Leu Lys His Ile Val
            20                  25                  30

Trp Ala Ser Arg Glu Leu Glu Arg Phe Ala Val Asn Pro Gly Leu Leu
        35                  40                  45

Glu Thr Ser Glu Gly Cys Arg Gln Ile Leu Gly Gln Leu Gln Pro Ser
    50                  55                  60

Leu Gln Thr Gly Ser Glu Glu Leu Arg Ser Leu Tyr Asn Thr Val Ala
65                  70                  75                  80

Thr Leu Tyr Cys Val His Gln Arg Ile Glu Val Lys Asp Thr Lys Glu
                85                  90                  95

Ala Leu Asp Lys Ile Glu Glu Glu Gln Asn Lys Ser Lys Lys Lys Ala
                100                 105                 110

Gln Gln Ala Ala Ala Asp Thr Asn His Ser Ser Gln Val Ser Gln Asn
            115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Val Glu Glu Lys Ala
145                 150                 155                 160

Phe Ser Pro Glu Val Ile Pro Met Phe Ser Ala Leu Ser Glu Gly Ala
                165                 170                 175

Thr Pro Gln Asp Leu Asn Thr Met Leu Asn Thr Val Gly Gly His Gln
                180                 185                 190

Ala Ala Met Gln Met Leu Lys Glu Thr Ile Asn Glu Glu Ala Ala Glu
            195                 200                 205

Trp Asp Arg Leu His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Gly Trp Met Thr Asn Asn Pro Pro Ile Pro Val Gly
                245                 250                 255

Glu Ile Tyr Lys Arg Trp Ile Ile Leu Gly Leu Asn Lys Ile Val Arg
                260                 265                 270

Met Tyr Ser Pro Thr Ser Ile Leu Asp Ile Arg Gln Gly Pro Lys Glu
            275                 280                 285
```

```
Pro Phe Arg Asp Tyr Val Asp Arg Phe Tyr Lys Thr Leu Arg Ala Glu
    290                 295                 300

Gln Ala Ser Gln Glu Val Lys Asn Trp Met Thr Glu Thr Leu Leu Val
305                 310                 315                 320

Gln Asn Ala Asn Pro Asp Cys Lys Thr Ile Leu Lys Ala Leu Gly Pro
                325                 330                 335

Ala Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Val Thr
        355                 360                 365

Asn Ser Ala Thr Ile Met Met Gln Arg Gly Asn Phe Arg Asn Gln Arg
370                 375                 380

Lys Thr Val Lys Cys Phe Asn Cys Gly Lys Glu Gly His Ile Ala Lys
385                 390                 395                 400

Asn Cys Arg Ala Pro Arg Lys Lys Gly Cys Trp Lys Cys Gly Lys Glu
                405                 410                 415

Gly His Gln Met Lys Asp Cys Thr Glu Arg Gln Ala Asn Phe Leu Gly
            420                 425                 430

Lys Ile Trp Pro Ser His Lys Gly Arg Pro Gly Asn Phe Leu Gln Ser
        435                 440                 445

Arg Pro Glu Pro Thr Ala Pro Pro Glu Glu Ser Phe Arg Phe Gly Glu
450                 455                 460

Glu Thr Thr Thr Pro Ser Gln Lys Gln Glu Pro Ile Asp Lys Glu Leu
465                 470                 475                 480

Tyr Pro Leu Ala Ser Leu Arg Ser Leu Phe Gly Asn Asp
                485                 490

<210> SEQ ID NO 67
<211> LENGTH: 109
<212> TYPE: PRT
<213> ORGANISM: Artificial
<220> FEATURE:
<223> OTHER INFORMATION: Pol-derived antigen

<400> SEQUENCE: 67

Lys Lys Ser Val Thr Val Leu Asp Val Gly Asp Ala Tyr Phe Ser Val
1               5                   10                  15

Pro Leu Asp Lys Asp Phe Arg Lys Tyr Thr Ala Phe Thr Ile Pro Ser
                20                  25                  30

Ile Asn Asn Glu Thr Pro Gly Ile Arg Tyr Gln Tyr Asn Val Leu Pro
            35                  40                  45

Gln Gly Trp Lys Gly Ser Pro Ala Ile Phe Gln Ser Ser Met Thr Lys
        50                  55                  60

Ile Leu Glu Pro Phe Arg Lys Gln Asn Pro Asp Ile Val Ile Tyr Gln
65                  70                  75                  80

Tyr Met Asp Asp Leu Tyr Val Gly Ser Asp Leu Glu Ile Gly Gln His
                85                  90                  95

Arg Thr Glu Ile Leu Lys Glu Pro Val His Gly Val Tyr
            100                 105

<210> SEQ ID NO 68
<211> LENGTH: 136
<212> TYPE: PRT
<213> ORGANISM: Artificial
<220> FEATURE:
<223> OTHER INFORMATION: NEF-derived antigen

<400> SEQUENCE: 68
```

Val Gly Phe Pro Val Arg Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30

Glu Gly Leu Ile Tyr Ser Gln Lys Arg Gln Asp Ile Leu Asp Leu Trp
        35                  40                  45

Val Tyr His Thr Gln Gly Tyr Phe Pro Asp Trp Gln Asn Tyr Thr Pro
    50                  55                  60

Gly Pro Gly Ile Arg Tyr Pro Leu Thr Phe Gly Trp Cys Phe Lys Leu
65                  70                  75                  80

Val Pro Val Asp Pro Glu Lys Glu Val Leu Val Trp Lys Phe Asp Ser
                85                  90                  95

Arg Leu Ala Phe His His Met Ala Arg Glu Leu His Pro Glu Tyr Tyr
                100                 105                 110

Ala Pro Val Lys Gln Thr Leu Asn Phe Asp Leu Leu Lys Leu Ala Gly
            115                 120                 125

Asp Val Glu Ser Asn Pro Gly Pro
            130                 135

<210> SEQ ID NO 69
<211> LENGTH: 512
<212> TYPE: PRT
<213> ORGANISM: Artificial
<220> FEATURE:
<223> OTHER INFORMATION: GAG antigen

<400> SEQUENCE: 69

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Gln Asn Lys Ser Lys
                100                 105                 110

Lys Lys Ala Gln Gln Ala Ala Ala Asp Thr Gly His Ser Ser Gln Val
            115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

```
Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
        260                 265                 270

Ile Val Arg Met Tyr Ser Pro Thr Ser Ile Leu Asp Ile Arg Gln Gly
    275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
        340                 345                 350

Val Gly Gly Pro Gly His Lys Ala Arg Val Leu Ala Glu Ala Met Ser
    355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
        420                 425                 430

Phe Leu Gly Lys Ile Trp Pro Ser Tyr Lys Gly Arg Pro Gly Asn Phe
    435                 440                 445

Leu Gln Ser Arg Pro Glu Pro Thr Ala Pro Pro Phe Leu Gln Ser Arg
450                 455                 460

Pro Glu Pro Thr Ala Pro Pro Glu Glu Ser Phe Arg Ser Gly Val Glu
465                 470                 475                 480

Thr Thr Thr Pro Ser Gln Lys Gln Glu Pro Ile Asp Lys Glu Leu Tyr
            485                 490                 495

Pro Leu Thr Ser Leu Arg Ser Leu Phe Gly Asn Asp Pro Ser Ser Gln
        500                 505                 510

<210> SEQ ID NO 70
<211> LENGTH: 1539
<212> TYPE: DNA
<213> ORGANISM: Artificial
<220> FEATURE:
<223> OTHER INFORMATION: coding sequence of GAG antigen

<400> SEQUENCE: 70
atgggtgcga gagcgtcagt attaagcggg ggagaattag atcgatggga aaaaattcgg      60
ttaaggccag ggggaaagaa aaatataaa  ttaaaacata tagtatgggc aagcagggag     120
ctagaacgat tcgcagttaa tcctggcctg ttagaaacat cagaaggctg tagacaaata     180
ctgggacagc tacaaccatc ccttcagaca ggatcagaag aacttagatc attatataat     240
acagtagcaa ccctctattg tgtgcatcaa aggatagaga taaaagacac caaggaagct     300
ttagacaaga tagaggaaga gcaaaacaaa agtaagaaaa agcacagca  agcagcagct     360 gacacaggac acagcagcca ggtcagccaa aattacccta gtgtgcagaa catccagggg     420
caaatggtac atcaggccat atcacctaga actttaaatg catgggtaaa agtagtagaa     480
```

```
gagaaggctt tcagcccaga agtgatacccc atgtttttcag cattatcaga aggagccacc    540
ccacaagatt taaacaccat gctaaacaca gtgggggggac atcaagcagc catgcaaatg    600
ttaaaagaga ccatcaatga ggaagctgca gaatgggata gagtgcatcc agtgcatgca    660
gggcctattg caccaggcca gatgagagaa ccaaggggaa gtgacatagc aggaactact    720
agtacccttc aggaacaaat aggatggatg acaaataatc cacctatccc agtaggagaa    780
atttataaaa gatggataat cctgggatta aataaaatag taagaatgta tagccctacc    840
agcattctgg acataagaca aggaccaaaa gaacccttta gagactatgt agaccggttc    900
tataaaactc taagagccga gcaagcttca caggaggtaa aaaattggat gacagaaacc    960
ttgttggtcc aaaatgcgaa cccagattgt aagactattt taaaagcatt gggaccagca   1020
gctacactag aagaaatgat gacagcatgt caggagtgtgg gaggacccgg ccataaggca   1080
agagttttgg ctgaagcaat gagccaagta acaaattcag ctaccataat gatgcaaaga   1140
ggcaatttta ggaaccaaag aaagattgtt aagtgtttca attgtggcaa agaagggcac   1200
atagccagaa attgcagggc ccctaggaaa aagggctgtt ggaaatgtgg aaaggaagga   1260
caccaaatga aagattgtac tgagagacag gctaattttt tagggaagat ctggccttcc   1320
tacaagggaa ggccagggaa ttttcttcag agcagaccag agccaacagc cccaccattt   1380
cttcagagca gaccagagcc aacagcccca ccagaagaga gcttcaggtc tggggtagag   1440
acaacaactc cctctcagaa gcaggagccg atagacaagg aactgtatcc tttaacttcc   1500
ctcagatcac tctttggcaa cgacccctcg tcacaataa                           1539

<210> SEQ ID NO 71
<211> LENGTH: 5322
<212> TYPE: DNA
<213> ORGANISM: Artificial
<220> FEATURE:
<223> OTHER INFORMATION: Plasmid

<400> SEQUENCE: 71
tggaagggct aattcactcc caacgaagac aagatatcct tgatctgtgg atctaccaca     60
cacaaggcta cttccctgat tagcagaact acacaccagg gccagggatc agatatccac    120
tgacctttgg atggtgctac aagctagtac cagttgagcc agagaagtta gaagaagcca    180
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360
gctgggggac tttccaggga ggcgtggcct gggcgggact ggggagtggc gagccctcag    420
atcctgcata taagcagctg ctttttgcct gtactgggtc tctctggtta gaccagatct    480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagaccctt ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc caggggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
```

```
atcattatat aatacagtag caaccctcta ttgtgtgcat caaaggatag agataaaaga    1080
caccaaggaa gctttagaca agatagagga agagcaaaac aaaagtaaga ccaccgcaca    1140
gcaagcggcc gctgatcttc agacctggag gaggagatat gagggacaat tggagaagtg    1200
aattatataa atataaagta gtaaaaattg aaccattagg agtagcaccc accaaggcaa    1260
agagaagagt ggtgcagaga gaaaaaagag cagtgggaat aggagctttg ttccttgggt    1320
tcttgggagc agcaggaagc actatgggcg cagcgtcaat gacgctgacg gtacaggcca    1380
gacaattatt gtctggtata gtgcagcagc agaacaattt gctgagggct attgaggcgc    1440
aacagcatct gttgcaactc acagtctggg gcatcaagca gctccaggca agaatcctgg    1500
ctgtggaaag atacctaaag gatcaacagc tcctggggat ttggggttgc tctggaaaac    1560
tcatttgcac cactgctgtg ccttggaatg ctagttggag taataaatct ctggaacaga    1620
tttggaatca cacgacctgg atggagtggg acagagaaat taacaattac acaagcttaa    1680
tacactcctt aattgaagaa tcgcaaaacc agcaagaaaa gaatgaacaa gaattattgg    1740
aattagataa atgggcaagt ttgtggaatt ggtttaacat aacaaattgg ctgtggtata    1800
taaaattatt cataatgata gtaggaggct tggtaggttt aagaatagtt tttgctgtac    1860
tttctatagt gaatagagtt aggcagggat attcaccatt atcgtttcag acccacctcc    1920
caaccccgag gggacccgac aggcccgaag gaatagaaga agaaggtgga gagagagaca    1980
gagacagatc cattcgatta gtgaacggat ctcgacggta tcgccgaatt cacaaatggc    2040
agtattcatc cacaatttta aaagaaaagg ggggattggg gggtacagtg caggggaaag    2100
aatagtagac ataatagcaa cagacataca aactaaagaa ttacaaaaac aaattacaaa    2160
aattcaaaat tttcgggttt attacaggga cagcagagat ccactttggg gcgataagct    2220
tgggagttcc gcgttacata acttacggta aatggcccgc ctggctgacc gcccaacgac    2280
ccccgcccat tgacgtcaat aatgacgtat gttcccatag taacgccaat agggactttc    2340
cattgacgtc aatgggtgga gtatttacgg taaactgccc acttggcagt acatcaagtg    2400
tatcatatgc caagtacgcc ccctattgac gtcaatgacg gtaaatggcc cgcctggcat    2460
tatgcccagt acatgacctt atgggacttt cctacttggc agtacatcta cgtattagtc    2520
atcgctatta ccatggtgat gcggttttgg cagtacatca atgggcgtgg atagcggttt    2580
gactcacggg gatttccaag tctccacccc attgacgtca atgggagttt gttttggcac    2640
caaaatcaac gggactttcc aaaatgtcgt aacaactccg ccccattgac gcaaatgggc    2700
ggtaggcgtg tacggtggga ggtctatata agcagagctc gtttagtgaa ccgtcagatc    2760
gcctggagac gccatccacg ctgttttgac ctccatagaa gacaccgact ctagaggatc    2820
tgccaccatg gtgagaaact ccgtcttgtc agggaagaaa gcagatgaat tagaaaaaat    2880
taggctacga cccaacggaa agaaaaagta catgttgaag catgtagtat gggcagcaaa    2940
tgaattagat agatttggat tagcagaaag cctgttggag aacaaagaag gatgtcaaaa    3000
aatactttcg gtcttagctc cattagtgcc aacaggctca gaaaatttaa aaagccttta    3060
taatactgtc tgcgtcatct ggtgcattca cgcagaagag aaagtgaaac acactgagga    3120
agcaaaacag atagtgcaga gacacctagt ggtggaaaca ggaacaacag aaactatgcc    3180
aaaaacaagt agaccaacag caccatctag cggcagagga ggaaattacc cagtacaaca    3240
aataggtggt aactatgtcc acctgccatt aagcccgaga acattaaatg cctgggtaaa    3300
attgatagag gaaagaaat ttggagcaga agtagtgcca ggatttcagg cactgtcaga    3360
aggttgcacc ccctatgaca ttaatcagat gttaaattgt gtgggagacc atcaagcggc    3420
```

| | |
|---|---|
| tatgcagatt atcagagata ttataaacga ggaggctgca gattgggact tgcagcaccc | 3480 |
| acaaccagct ccacaacaag gacaacttag ggagccgtca ggatcagata ttgcaggaac | 3540 |
| aactagttca gtagatgaac aaatccagtg gatgtacaga caacagaacc ccataccagt | 3600 |
| aggcaacatt tacaggagat ggatccaact ggggttgcaa aaatgtgtca gaatgtataa | 3660 |
| cccaacaaac attctagatg taaaacaagg gccaaaagag ccatttcaga gctatgtaga | 3720 |
| caggttctac aaaagtttaa gagcagaaca gacagatgca gcagtaaaga attggatgac | 3780 |
| tcaaacactg ctgattcaaa atgctaaccc agattgcaag ctagtgctga aggggctggg | 3840 |
| tgtgaatccc accctagaag aaatgctgac ggcttgtcaa ggagtagggg ggccgggaca | 3900 |
| gaaggctaga ttaatggcag aagccctgaa agaggccctc gcaccagtgc caatcccttt | 3960 |
| tgcagcagcc caacagaggg gaccaagaaa gccaattaag tgttggaatt gtgggaaaga | 4020 |
| gggacactct gcaaggcaat gcagagcccc aagaagacag ggatgctgga aatgtggaaa | 4080 |
| aatggaccat gttatggcca aatgcccaga cagacaggcg ggttttttag gccttggtcc | 4140 |
| atggggaaag aagccccgca atttccccat ggctcaagtg catcaggggc tgatgccaac | 4200 |
| tgctcccca gaggacccag ctgtggatct gctaaagaac tacatgcagt tgggcaagca | 4260 |
| gcagagagaa aagcagagag aaagcagaga gaagccttac aaggaggtga cagaggattt | 4320 |
| gctgcacctc aattctctct tggaggaga ccagtagctc gagctcaagc ttcgaattcc | 4380 |
| cgataatcaa cctctggatt acaaaatttg tgaaagattg actggtattc ttaactatgt | 4440 |
| tgctcctttt acgctatgtg gatacgctgc tttaatgcct ttgtatcatg ctattgcttc | 4500 |
| ccgtatggct ttcattttct cctccttgta taaatcctgg ttgctgtctc tttatgagga | 4560 |
| gttgtggccc gttgtcaggc aacgtggcgt ggtgtgcact gtgtttgctg acgcaacccc | 4620 |
| cactggttgg ggcattgcca ccacctgtca gctcctttcc gggactttcg ctttcccct | 4680 |
| ccctattgcc acggcggaac tcatcgccgc ctgccttgcc cgctgctgga caggggctcg | 4740 |
| gctgttgggc actgacaatt ccgtggtgtt gtcggggaag ctgacgtcct ttccatggct | 4800 |
| gctcgcctgt gttgccacct ggattctgcg cgggacgtcc ttctgctacg tccccttcggc | 4860 |
| cctcaatcca gcggaccttc cttcccgcgg cctgctgccg ctctgcggc ctcttccgcg | 4920 |
| tcttcgcctt cgccctcaga cgagtcggat ctccctttgg gccgcctccc cgcgtcgacg | 4980 |
| cgtgaattcg gtacctttaa gaccaatgac ttacaaggca gctgtagatc ttagccactt | 5040 |
| tttaaaagaa aagggggggac tggaagggct aattcactcc caacgaagac aagatcgtcg | 5100 |
| agagatgctg catataagca gctgcttttt gcttgtactg ggtctctctg gttagaccag | 5160 |
| atctgagcct gggagctctc tggctaacta gggaacccac tgcttaagcc tcaataaagc | 5220 |
| ttgccttgag tgcttcaagt agtgtgtgcc cgtctgttgt gtgactctgg taactagaga | 5280 |
| tccctcagac ccttttagtc agtgtggaaa atctctagca gt | 5322 |

<210> SEQ ID NO 72
<211> LENGTH: 5335
<212> TYPE: DNA
<213> ORGANISM: Artificial
<220> FEATURE:
<223> OTHER INFORMATION: Plasmid

<400> SEQUENCE: 72

| | |
|---|---|
| tggaagggct aattcactcc caacgaagac aagatatcct tgatctgtgg atctaccaca | 60 |
| cacaaggcta cttccctgat tagcagaact acacaccagg gccagggatc agatatccac | 120 |
| tgacctttgg atggtgctac aagctagtac cagttgagcc agagaagtta gaagaagcca | 180 |

```
acaaaggaga gaacaccagc ttgttacaac ctgtgagcct gcatgggatg gatgacccgg    240
agagagaagt gttagagtgg aggtttgaca gccgcctagc atttcatcac ggtggcccga    300
gagctgcatc cggagtactt caagaactgc tgatatcgag cttgctacaa gggactttcc    360 gctggggac tttccaggga ggcgtggcct gggcgggact ggggagtggc gagccctcag     420
atcctgcata taagcagctg cttttttgcct gtactgggtc tctctggtta gaccagatct   480
gagcctggga gctctctggc taactaggga acccactgct taagcctcaa taaagcttgc    540
cttgagtgct tcaagtagtg tgtgcccgtc tgttgtgtga ctctggtaac tagagatccc    600 tcagacccctt ttagtcagtg tggaaaatct ctagcagtgg cgcccgaaca gggacttgaa   660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat ggagaagtg    1200 aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccaccctcc   1920 caacccgag ggacccgac aggcccgaag gaatagaaga agaaggtgga gagagagaca    1980
gagacagatc cattcgatta gtgaacggat ctcgacggta tcgccgaatt cacaaatggc   2040
agtattcatc cacaatttta aagaaaagg ggggattggg gggtacagtg caggggaaag    2100
aatagtagac ataatagcaa cagacataca aactaaagaa ttacaaaaac aaattacaaa   2160
aattcaaaat tttcgggttt attacaggga cagcagagat ccactttggg gcgataagct   2220
tgggagttcc gcgttacata acttacggta aatggcccgc ctggctgacc gcccaacgac   2280
ccccgcccat tgacgtcaat aatgacgtat gttcccatag taacgccaat agggactttc   2340
cattgacgtc aatgggtgga gtatttacgg taaactgccc acttggcagt acatcaagtg   2400
tatcatatgc caagtacgcc ccctattgac gtcaatgacg gtaaatggcc cgcctggcat   2460
tatgcccagt acatgacctt atgggacttt cctacttggc agtacatcta cgtattagtc   2520
atcgctatta ccatggtgat gcggttttgg cagtacatca atgggcgtgg atagcggttt   2580
```

```
gactcacggg gatttccaag tctccacccc attgacgtca atgggagttt gttttggcac   2640
caaaatcaac gggactttcc aaaatgtcgt aacaactccg ccccattgac gcaaatgggc   2700
ggtaggcgtg tacggtggga ggtctatata agcagagctc gtttagtgaa ccgtcagatc   2760
gcctggagac gccatccacg ctgttttgac ctccatagaa gacaccgact ctagaggatc   2820
tcgatcggcc accatgggcg tgcgcaacag cgtgctgagc ggcaagaagg ccgacgagct   2880
ggagaagatc cgcctgcgcc ccaacggcaa gaagaagtac atgctgaagc acgtggtgtg   2940
ggccgctaac gagctggacc ggttcggcct ggccgagagc ctgctggaga caaggaggg   3000 ctgccagaag atcctgagcg tgctggcccc tctggtgccc accggcagcg agaacctgaa   3060
gagcctgtac aacaccgtgt gcgtgatctg gtgcatccac gccgaggaga aggtgaagca   3120
caccgaggag gccaagcaga tcgtgcagcg ccacctggtg gtggagaccg gcaccaccga   3180
gaccatgccc aagaccagca ggcccaccgc ccctagcagc ggcagaggcg ggaactaccc   3240
cgtgcagcag atcggcggca actacgtgca cctgcccctg agcccagga ccctgaacgc   3300 ctgggtgaag ctgatcgagg agaagaagtt cggcgctgag gtggtgcccg gcttccaggc   3360
cctgagcgag ggctgcaccc cctacgacat caaccagatg ctgaactgcg tgggcgacca   3420
ccaggccgcc atgcagatca tccgcgacat catcaacgag gaagccgccg actgggacct   3480
gcagcacccc cagcctgccc ccagcaggg ccagctgcgc gagcccagcg gctccgacat   3540
cgccggcacc accagcagcg tcgacgagca gatccagtgg atgtaccgcc agcagaaccc   3600
catccccgtg gcaacatct accgccgctg gatccagctg ggcctgcaga agtgcgtgcg   3660
catgtacaac cccaccaaca tcctggacgt gaagcaggc cccaaggagc ccttccagag   3720
ctacgtggac cgcttctaca agagcctgag ggccgagcag accgatgccg ccgtgaagaa   3780
ctggatgacc cagaccctgc tgatccagaa cgccaacccc gactgcaagc tggtgctgaa   3840
gggcctgggc gtgaaccca ccctggagga gatgctgacc gcctgccagg gcgtgggagg   3900
acctggccag aaggccaggc tgatggccga agccctgaag gaggccctgg ccctgtgcc   3960 catcccttc gccgctgccc agcagagggg ccctcgcaag cccatcaagt gttggaactg   4020
cggcaaggag ggccacagcg ccaggcagtg ccgcgctccc cgcaggcagg ctgctggaa   4080 gtgtgggaag atggaccacg tgatggccaa gtgccccgac cgccaggccg gcttcctggg   4140
cctgggcccc tggggaaga agccccgcaa cttccctatg gcgcaggtgc caggggcct   4200 catgcctacc gcccctcccg aggaccctgc cgtggacctg ctgaagaact acatgcagct   4260
gggcaagcag cagcgcgaga agcagcgcga gagccgcgaa aagccctaca aggaggtgac   4320
cgaggacctg ctgcacctga acagcctgtt cggcggagac cagtaatgaa ctcgagctca   4380
agcttcgaat tccgataat caacctctgg attacaaaat ttgtgaaaga ttgactggta   4440
ttcttaacta tgttgctcct tttacgctat gtggatacgc tgctttaatg cctttgtatc   4500
atgctattgc ttcccgtatg ctttcatt tctcctcctt gtataaatcc tggttgctgt   4560
ctctttatga ggagttgtgg cccgttgtca ggcaacgtgg cgtggtgtgc actgtgtttg   4620
ctgacgcaac ccccactggt tggggcattg ccaccacctg tcagctcctt ccgggactt   4680 tcgctttccc cctccctatt gccacggcgg aactcatcgc cgcctgcctt gcccgctgct   4740
ggacaggggc tcggctgttg ggcactgaca attccgtggt gttgtcgggg aagctgacgt   4800
cctttccatg gctgctcgcc tgtgttgcca cctggattct gcgcgggacg tccttctgct   4860
acgtcccttc ggccctcaat ccagcggacc ttccttcccg cggcctgctg ccggctctgc   4920
ggcctcttcc gcgtcttcgc cttcgccctc agacgagtcg gatctccctt tgggccgcct   4980
```

```
ccccgcgtcg acgcgtgaat tcggtacctt taagaccaat gacttacaag gcagctgtag     5040
atcttagcca cttttttaaaa gaaaaggggg gactggaagg gctaattcac tcccaacgaa     5100
gacaagatcg tcgagagatg ctgcatataa gcagctgctt tttgcttgta ctgggtctct     5160
ctggttagac cagatctgag cctgggagct ctctggctaa ctaggaacc cactgcttaa     5220 gcctcaataa agcttgcctt gagtgcttca agtagtgtgt gcccgtctgt tgtgtgactc     5280
tggtaactag agatccctca gacccttttta gtcagtgtgg aaaatctcta gcagt         5335
```

<210> SEQ ID NO 73
<211> LENGTH: 510
<212> TYPE: PRT
<213> ORGANISM: Artificial
<220> FEATURE:
<223> OTHER INFORMATION: SIVmac 239 GAG protein

<400> SEQUENCE: 73

```
Met Gly Val Arg Asn Ser Val Leu Ser Gly Lys Lys Ala Asp Glu Leu
1               5                   10                  15

Glu Lys Ile Arg Leu Arg Pro Asn Gly Lys Lys Lys Tyr Met Leu Lys
            20                  25                  30

His Val Val Trp Ala Ala Asn Glu Leu Asp Arg Phe Gly Leu Ala Glu
        35                  40                  45

Ser Leu Leu Glu Asn Lys Glu Gly Cys Gln Lys Ile Leu Ser Val Leu
    50                  55                  60

Ala Pro Leu Val Pro Thr Gly Ser Glu Asn Leu Lys Ser Leu Tyr Asn
65                  70                  75                  80

Thr Val Cys Val Ile Trp Cys Ile His Ala Glu Glu Lys Val Lys His
                85                  90                  95

Thr Glu Glu Ala Lys Gln Ile Val Gln Arg His Leu Val Val Glu Thr
            100                 105                 110

Gly Thr Thr Glu Thr Met Pro Lys Thr Ser Arg Pro Thr Ala Pro Ser
        115                 120                 125

Ser Gly Arg Gly Gly Asn Tyr Pro Val Gln Gln Ile Gly Gly Asn Tyr
    130                 135                 140

Val His Leu Pro Leu Ser Pro Arg Thr Leu Asn Ala Trp Val Lys Leu
145                 150                 155                 160

Ile Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
            180                 185                 190

Val Gly Asp His Gln Ala Ala Met Gln Ile Ile Arg Asp Ile Ile Asn
        195                 200                 205

Glu Glu Ala Ala Asp Trp Asp Leu Gln His Pro Gln Pro Ala Pro Gln
    210                 215                 220

Gln Gly Gln Leu Arg Glu Pro Ser Gly Ser Asp Ile Ala Gly Thr Thr
225                 230                 235                 240

Ser Ser Val Asp Glu Gln Ile Gln Trp Met Tyr Arg Gln Gln Asn Pro
                245                 250                 255

Ile Pro Val Gly Asn Ile Tyr Arg Arg Trp Ile Gln Leu Gly Leu Gln
            260                 265                 270

Lys Cys Val Arg Met Tyr Asn Pro Thr Asn Ile Leu Asp Val Lys Gln
        275                 280                 285

Gly Pro Lys Glu Pro Phe Gln Ser Tyr Val Asp Arg Phe Tyr Lys Ser
    290                 295                 300

Leu Arg Ala Glu Gln Thr Asp Ala Ala Val Lys Asn Trp Met Thr Gln
```

```
            305                 310                 315                 320
Thr Leu Leu Ile Gln Asn Ala Asn Pro Asp Cys Lys Leu Val Leu Lys
                    325                 330                 335
Gly Leu Gly Val Asn Pro Thr Leu Glu Glu Met Leu Thr Ala Cys Gln
                340                 345                 350
Gly Val Gly Gly Pro Gly Gln Lys Ala Arg Leu Met Ala Glu Ala Leu
            355                 360                 365
Lys Glu Ala Leu Ala Pro Val Pro Ile Pro Phe Ala Ala Ala Gln Gln
        370                 375                 380
Arg Gly Pro Arg Lys Pro Ile Lys Cys Trp Asn Cys Gly Lys Glu Gly
385                 390                 395                 400
His Ser Ala Arg Gln Cys Arg Ala Pro Arg Arg Gln Gly Cys Trp Lys
                405                 410                 415
Cys Gly Lys Met Asp His Val Met Ala Lys Cys Pro Asp Arg Gln Ala
                420                 425                 430
Gly Phe Leu Gly Leu Gly Pro Trp Gly Lys Lys Pro Arg Asn Phe Pro
            435                 440                 445
Met Ala Gln Val His Gln Gly Leu Met Pro Thr Ala Pro Pro Glu Asp
        450                 455                 460
Pro Ala Val Asp Leu Leu Lys Asn Tyr Met Gln Leu Gly Lys Gln Gln
465                 470                 475                 480
Arg Glu Lys Gln Arg Glu Ser Arg Glu Lys Pro Tyr Lys Glu Val Thr
                485                 490                 495
Glu Asp Leu Leu His Leu Asn Ser Leu Phe Gly Gly Asp Gln
                500                 505                 510

<210> SEQ ID NO 74
<211> LENGTH: 21
<212> TYPE: DNA
<213> ORGANISM: Artificial
<220> FEATURE:
<223> OTHER INFORMATION: Primer

<400> SEQUENCE: 74
ggctaactag ggaacccact g                                             21

<210> SEQ ID NO 75
<211> LENGTH: 25
<212> TYPE: DNA
<213> ORGANISM: Artificial
<220> FEATURE:
<223> OTHER INFORMATION: primer

<400> SEQUENCE: 75
gctagagatt ttccacactg actaa                                         25

<210> SEQ ID NO 76
<211> LENGTH: 27
<212> TYPE: DNA
<213> ORGANISM: Artificial
<220> FEATURE:
<223> OTHER INFORMATION: Probe

<400> SEQUENCE: 76
cacaacagac gggcacacac tacttga                                       27

<210> SEQ ID NO 77
<211> LENGTH: 25
<212> TYPE: DNA
<213> ORGANISM: Artificial
<220> FEATURE:
```

<223> OTHER INFORMATION: Probe

<400> SEQUENCE: 77
cactcaaggc aagctttatt gaggc                                       25

<210> SEQ ID NO 78
<211> LENGTH: 23
<212> TYPE: DNA
<213> ORGANISM: Artificial
<220> FEATURE:
<223> OTHER INFORMATION: primer

<400> SEQUENCE: 78
ggctatcatt cttcttcaag gta                                         23

<210> SEQ ID NO 79
<211> LENGTH: 22
<212> TYPE: DNA
<213> ORGANISM: Artificial
<220> FEATURE:
<223> OTHER INFORMATION: primer

<400> SEQUENCE: 79
cctctcttca gccatttaag ta                                          22

<210> SEQ ID NO 80
<211> LENGTH: 34
<212> TYPE: DNA
<213> ORGANISM: Artificial
<220> FEATURE:
<223> OTHER INFORMATION: probe

<400> SEQUENCE: 80
ggctgaaggt tagggatacc aatattcctg tctc                             34

<210> SEQ ID NO 81
<211> LENGTH: 30
<212> TYPE: DNA
<213> ORGANISM: Artificial
<220> FEATURE:
<223> OTHER INFORMATION: probe

<400> SEQUENCE: 81
ctagtgatgg gctcttccct tgagcccttc                                  30

<210> SEQ ID NO 82
<211> LENGTH: 24
<212> TYPE: DNA
<213> ORGANISM: Artificial
<220> FEATURE:
<223> OTHER INFORMATION: primer

<400> SEQUENCE: 82
gcagaggagg aaattaccca gtac                                        24

<210> SEQ ID NO 83
<211> LENGTH: 25
<212> TYPE: DNA
<213> ORGANISM: Artificial
<220> FEATURE:
<223> OTHER INFORMATION: Primer

<400> SEQUENCE: 83
caattttacc caggcattta atgtt                                       25

<210> SEQ ID NO 84

```
<211> LENGTH: 23
<212> TYPE: DNA
<213> ORGANISM: Artificial
<220> FEATURE:
<223> OTHER INFORMATION: Primer

<400> SEQUENCE: 84
tgtccacctg ccattaagcc cga                                            23
```

LENTIVIRAL GENE TRANSFER VECTORS AND THEIR MEDICINAL APPLICATIONS

The invention relates to the design of gene transfer vectors and especially provides lentiviral gene transfer vectors suitable for either a unique administration or, for iterative administration in a host, and to their medicinal application.

In a particular embodiment, the invention especially relies on the results obtained in pre-clinical trials conducted with lentiviral gene transfer vectors in a homologous model, with a follow-up over a period of more than 5 months, to design candidates for vaccination against Immunodeficiency Virus, especially suitable in human hosts.

The invention especially relates to the use of gene transfer vectors for unique or for multiple in vivo administration into a host in need thereof. The field of application of the present application concerns in particular animal treatment or treatment of human being (e.g. prophylactic or therapeutic or symptomatic or curative treatment).

The combination of lentiviral vectors according to the invention is in particular suitable for use in the field of gene therapy or vaccination in vivo. It is however also more generally suitable for any medicinal treatment which requires in vivo unique or multiple injections of the vectors.

The invention especially provides means suitable for use of the lentiviral vectors in iterative administration, either for prevention or for treatment of a disease in a mammalian host, especially in human beings. A particular application of these vectors is to elicit an immune response to prevent or to treat a pathogenic state, including virus infections, parasite and bacterial infections or cancers, and preferably to elicit a protective, long-lasting immune response. According to a particular embodiment of the present invention, the designed vectors are especially of interest in the field of treatment or prevention against Immunodeficiency Virus and especially against AIDS.

Another aspect of the invention is that the gene transfer vectors are either integrative or non-integrative (NI) vectors. The choice of either form of vectors should be dependent upon the purpose of their use.

Viruses, in particular RNA-viruses, and especially lentiviruses have been used in the past to design gene transfer vectors especially due to the ability of lentiviruses to achieve mitosis-independent nuclear import that enables them to replicate efficiently in non dividing target cells. Accordingly, lentivirus based vectors have been explored for various applications including prophylactic or therapeutic vaccination or with a view to use these vectors as tools for gene therapy.

When testing lentiviral vectors in vivo, it has however been observed that the number of in vivo injections is limited by the humoral response of the host elicited against the envelope protein used for pseudotyping the vector particles.

The response which is elicited in the host against the envelope of the pseudotyped vector particles is accordingly a drawback for the efficient use of such vectors, when in vivo multiple administrations are required.

The present invention proposes means that are intended to remedy, at least in part, to the drawbacks due to the immune response against the envelope of the pseudotyped vector particles, when administrated several times to a host in the context of prophylaxy or treatment.

The invention thus relates to different structures of lentiviral vectors, and also especially to their association in a combination of compounds (also designated as a kit of compounds), suitable for use in a host in need thereof, in conditions allowing either unique or iterative administration of said lentiviral vectors.

In particular, the invention takes advantage of the sequential use of different lentiviral vectors to deliver a transgene in a host.

The lentiviral vectors according to the invention and especially their combination, is in particular suitable for use in the field of medicinal treatment where especially an immune response, including a cellular immune response, elicited by endogenously expressed antigen is beneficial or necessary; accordingly, the invention provides tools for the design of vaccination protocols for use in hosts in need of preventive or curative treatment against intracellular pathogenic organisms, including viruses especially retroviruses, or more generally against a pathogenic state, including to perform gene therapy in vivo. It is in particular suitable for any medicinal treatment which requires in vivo multiple injections of the vectors.

The inventors have in particular provided evidence that the lentiviral vectors as defined herein, especially when used in a combination, are appropriate to elicit a cellular immune response in a non-human primate model, which may be protective in the context of viral challenge, when the lentiviral vectors express an antigen of said virus.

In a particular embodiment of the invention, the inventors have especially shown that a cellular protective immune response has been obtained in a non-human primate model in the context of viral challenge with Simian Immunodeficiency Virus. The inventors have especially shown in a prime-boost strategy using lentiviral vectors pseudotyped with a glycoprotein G from two non-cross reactive VSV serotypes that these vectors elicited robust and broad cellular immune responses against the vector-encoded antigen. This has been shown in a model consisting of cynomolgus macaque, and adapted vectors have thus been designed in particular with respect to the vector-encoded antigen, to provide vectors suitable for the application in human hosts especially.

In view of these results, the inventors have designed tools which would be suitable to elicit an efficient and preferably protective immune response when administered to a host, especially in situations of prevention or treatment of viral infections and in particular in human hosts, to provide an immune response against such viral infections, in particular retroviral, for example lentiviral including against Human Immunodeficiency Virus and possibly to prevent development of pathogenesis associated with the infection.

Accordingly, the combination of lentiviral vectors of the invention, provides especially an efficient prime-boost system for use for iterative administration, enabling successively priming and boosting the immune response in a host, especially after injections in a host in need thereof. "Iterative" means that the active principle, i.e., the heterologous polynucleotide contained in the lentiviral vector of the invention is administered twice or more, especially three times, to the host, as a result of the administration of lentiviral vectors disclosed herein.

The invention is accordingly directed to a combination of compounds comprising at least:
 (i) lentiviral vector particles (also designated as lentiviral vectors), pseudotyped with a first determined heterologous viral envelope protein or viral envelope proteins;
 (ii) lentiviral vector particles (also designated as "lentiviral vectors"), pseudotyped with a second determined heterologous viral envelope protein or viral envelope proteins different from said first determined envelope protein or envelope proteins;
wherein said lentiviral vector particles of (i) and (ii) encode (i.e., contain) a heterologous determined polynucleotide which is in particular a recombinant polynucleotide (or transgene) encoding one or several polypeptides and;

wherein said first and second viral envelope protein(s) do not sero-neutralize with each other and are suitable for in vivo transduction of mammalian cells.

The polynucleotide encoded (contained) by the lentiviral vector particles is said "heterologous" because it is brought as an insert in the vector genome construct. In particular embodiments, the genome vector and the polynucleotide may originate from the same group of lentiviruses, even from the same type.

In a particular embodiment of the invention, the heterologous determined polynucleotide, encodes one or several polypeptides comprising at least one antigen derived from a GAG antigen of an Immunodeficiency Virus. Especially, the antigen is or comprises one or more immunogenic epitopes. The antigen derived from GAG is defined in the present application and illustrated in the examples. It encompasses in particular fragments of GAG. The GAG antigen illustrated in the examples originates from SIV, in accordance with the design of the model for assaying protection against SIV infection. When intended for the design of a vector suitable for a human host, the GAG antigen is derived from a GAG polyprotein of a Human Immunodeficiency Virus, especially HIV-1 or HIV-2.

In a particular embodiment of the invention, the heterologous determined polynucleotide which is a recombinant polynucleotide (or transgene) encoding one or several polypeptides does not encode a biologically active POL antigen of an Immunodeficiency Virus.

In a particular embodiment, the encoded antigen derived from GAG, especially immunogenic epitope(s) derived from GAG, is not a biological functional GAG antigen and does not comprise such a biologically functional GAG; in other words the antigen is a biologically non functional GAG.

The lentiviral vectors defined in the present invention are pseudotyped lentiviral vectors consisting of vector particles (accordingly also designated as "lentiviral vector particles") bearing envelope protein or envelope proteins (of a particular polyprotein envelope), wherein said envelope protein(s) originate from a virus which is different from the particular lentivirus which provides the vector genome of the lentiviral vector. Accordingly, said envelope protein or envelope proteins, are so-called "heterologous viral envelope protein or viral envelope proteins". In the following pages, reference will also be made to "envelope protein(s)" to encompass any type of envelope protein or envelope proteins suitable to perform the invention.

The lentiviral vectors according to the invention are replacement vectors, meaning that the sequences of the original lentivirus encoding the lentiviral proteins are essentially deleted from the genome of the vector or, when present, are modified, and especially prevent expression of biologically active POL antigen and optionally of further structural and/or accessory and/or regulatory proteins of the lentivirus.

The "vector genome" of the vector particles also comprises the polynucleotide or transgene of interest. In a particular embodiment, said transgene is also devoid of a polynucleotide encoding biologically active POL proteins. As a consequence, the vector genome does not enable to recover biologically active POL antigens. A biologically active POL antigen comprises the viral enzymes protease (RT), reverse tanscriptase (RT and RNase H) and integrase (IN) produced by cleavage of the GAG-POL polyprotein. The POL antigen is not biologically active, when the biological activity of at least one of these enzymes is not enabled. The biological activity is described with these enzymes in Fields (Virology—Vol 2 Chapter 60, pages 1889-1893 Edition 1996).

In a particular embodiment, the polynucleotide or transgene in the vector genome is devoid of the functional pol gene, and especially does not contain a complete pol gene.

The vector genome as defined herein contains, apart from the so-called heterologous polynucleotide of therapeutic interest placed under control of proper regulatory sequences, the sequences of the lentiviral genome which are non-coding regions of said genome, and are necessary to provide recognition signals for DNA or RNA synthesis and processing. These sequences are cis-acting sequences. The structure and composition of the vector genome used to prepare the lentiviral vectors of the invention are based on the principles described in the art. Examples of such lentiviral vectors are disclosed in (Zennou et al, 2000; Firat H. et al, 2002; VandenDriessche T. et al). Especially, minimum lentiviral gene delivery vectors can be prepared from a vector genome, which only contains, apart from the heterologous polynucleotide of therapeutic interest under control of proper regulatory sequences, the sequences of the lentiviral genome which are non-coding regions of said genome, necessary to provide recognition signals for DNA or RNA synthesis and processing.

Hence, a vector genome may be a replacement vector in which all the viral protein coding sequences between the 2 long terminal repeats (LTRs) have been replaced by the polynucleotide of interest.

Unless otherwise stated, or unless technically not relevant, the characteristics disclosed in the present application with respect to any of to the various features, embodiments or examples of the structure or use of the lentiviral vectors, especially regarding their envelope protein(s), or the heterologous polynucleotide, may be combined according to any possible combinations.

The expression "combination of compounds" or "kit of compounds" means that the lentiviral vectors constituting active ingredients of the kits or combinations, are provided as separate compounds in said kit or combination, and are intended for separate administration to a host, especially separate administration in time. Accordingly the invention enables to perform a prime-boost administration in a host in need thereof, where the first administration step elicits an immune, especially cellular, immune response and the later administration step(s) boost(s) the immune reaction.

The compounds of the kit thus are provided separately to the host in need thereof, especially to a mammalian host, in particular a human patient.

Accordingly, said lentiviral vectors can be provided in separate packages or can be presented in a common package for a separate use thereof.

Therefore, the notice included in the packages and comprising the directions for use, may indicate that said lentiviral vector particles which are pseudotyped with distinct envelope protein or envelope proteins are for separate administration in time, especially for priming and subsequently boosting an immune reaction in a host.

In accordance with the invention, it is provided lentiviral vector particles which are pseudotyped with a first determined heterologous viral envelope protein, or viral envelope proteins, and lentiviral viral vector particles which are pseudotyped with a second determined heterologous viral envelope protein or viral envelope proteins. Accordingly, said first and second heterologous viral envelope protein(s) are different and in particular are originating from different virus strains. Thus, the lentiviral vector particles of the kit of compounds of the invention are distinct, at least due to the particular envelope protein(s) used for pseudotyping the vector particles.

In a particular embodiment of the invention, the combination of compounds comprises a third or a further type of lentiviral vector particles wherein the envelope protein(s) of the third lentiviral vector is different from said first and second envelope protein(s) and especially originates from a different virus strain.

Apart from their pseudotyping envelope protein(s), the lentiviral vectors of the invention may be identical and especially may have identical vector genomes.

Alternatively, their vector genomes may be different, provided they carry the same heterologous determined polynucleotide (also designated as transgene), especially the same polynucleotide having a therapeutic interest.

In another embodiment of the invention, the vector genomes of the lentiviral vectors are different by having a different polynucleotide, provided said different polynucleotides encode polypeptides having common antigenic determinants, or common epitopes. Hence the different polynucleotides may be variants from each other.

As specified above, the expression "vector genome" refers to the nucleic acid i.e., the nucleic acid of lentiviral origin, which constitutes the genome of the lentiviral vector particles. Accordingly the expression relates to any appropriate nucleic acid, i.e., DNA or RNA, either double or single stranded, including in the form containing the DNA flap as a triplex sequence. The nature of the nucleic acid (DNA, RNA) and its organization depend upon the stage of the cycle of the particles, and includes the vector plasmid—used for cotransfection of cells with the encapsidation plasmid and the envelope plasmid—for expression of the particles, or the RNA genome of the particles when formed, or the various forms (including the genomic mRNA transcript, linear unintegrated DNA retrotranscript, or unintegrated one or two LTR DNA circular forms or integrated proviruses) (see in Fields Virology) of nucleic acid of this genome in the transduced cells of the host to whom particles are administered, including the vector pre-integration complex.

As a result of administration of particles to the host, the heterologous polynucleotide allows endogeneous expression of the polypeptides that it encodes in the cells of the host that are transduced by the lentiviral vectors.

Said first and second viral and if any said third and possibly further, envelope protein(s), are selected for their capacity not to sero-neutralize with each other (i.e., not to cross-react). Accordingly, each of said first and second viral and if any said third or further, envelope protein(s), used for pseudotyping the vector particles in the combination, does not react with and especially is not recognized by antibodies directed against the other of said first and second and if any said third or further, envelope protein(s). Accordingly, each of said first and second and if any said third or further, viral envelope protein(s), when administered within a lentiviral vector, does not elicit the production of antibodies, that recognize the other viral envelope protein(s) where such production of said anti-envelope antibodies (so-called antivector immunity) would result in a failure to elicit an immune response against the product expressed from the polynucleotide.

In a particular embodiment, in the kit of compounds, said first and second viral and if any said third or further, envelope protein(s) originate from human viruses, either DNA or RNA viruses.

In a particular embodiment of the kit of compounds of the invention, said first and second and if any said third or further, envelope protein(s) originate from viruses of the same virus family.

In accordance with a particular embodiment of the invention, said first and second envelope viral protein(s) originate from different strain types of the same virus, or from non cross-reactive serotypes of the same virus.

In another embodiment of said kit of compounds, said first and second and if any said third or further, envelope protein(s) originate from viruses of different genus.

In another embodiment of said kit of compounds, said first and second and if any said third or further, envelope protein(s) originate from the same genus or from the same serotype but from different strain types, or from non cross-reactive serotypes of the virus.

The invention especially relates to a kit of compounds, wherein said first and second and if any said third or further, viral envelope protein or viral envelope proteins originate from Rhabdoviridae (including Rabies), especially from a Vesiculovirus, including Vesicular Stomatitis Virus (VSV) from Paramyxoviridae, especially from Measles Virus (MV) Respiratory Syncytia Virus (RSV), or from non-human retroviruses or from Orthomyxoviridae such as Influenza virus.

The above-cited viruses are RNA-viruses, capable of infecting mammalian hosts, especially human hosts. Some of them, such as viruses of the order of Mononegavirales, and especially viruses of the family of Rabdoviridae in particular of the genus of Vesiculoviruses in particular VSV have been proposed to provide envelope protein(s), also designated as surface proteins, to pseudotype viral vectors, especially lentiviral vector particles.

The glycoprotein of the vesicular stomatisis virus (VSV-G) is a transmembrane protein that functions as the surface coat of the wild type viral particles. It is also a common coat protein for engineered lentiviral vectors. Presently, nine virus species are definitively classified in the VSV gender, and nineteen rhabdoviruses are provisionally classified in this gender (see hereafter), all showing various degrees of cross-neutralisation. When sequenced, the protein G genes indicate sequence similarities. The VSV-G protein presents a N-terminal ectodomain, a transmembrane region and a C-terminal cytoplasmic tail. It is exported to the cell surface via the transGolgi network (endoplasmic reticulum and Golgi apparatus).

The VSV strains include several serotypes that may provide envelope protein(s) for the preparation of the lentiviral vectors: The VSV-G glycoprotein may especially be chosen among species classified in the vesiculovirus genus: Carajas virus (CJSV), Chandipura virus (CHPV), Cocal virus (COCV), Isfahan virus (ISFV), Maraba virus (MARAV), Piry virus (PIRYV), Vesicular stomatitis Alagoas virus (VSAV), Vesicular stomatitis Indiana virus (VSIV) and Vesicular stomatitis New Jersey virus (VSNJV) and/or stains provisionally classified in the vesiculovirus genus as Grass carp rhabdovirus, BeAn 157575 virus (BeAn 157575), Boteke virus (BTKV), Calchaqui virus (CQIV), Eel virus American (EVA), Gray Lodge virus (GLOV), Jurona virus (JURY), Klamath virus (KLAV), Kwatta virus (KWAV), La Joya virus (LJV), Malpais Spring virus (MSPV), Mount Elgon bat virus (MEBV), Perinet virus (PERV), Pike fry rhabdovirus (PFRV), Porton virus (PORV), Radi virus (RADIV), Spring viremia of carp virus (SVCV), Tupaia virus (TUPV), Ulcerative disease rhabdovirus (UDRV) and Yug Bogdanovac virus (YBV).

Vesicular stomatitis Indiana virus (VSIV) and Vesicular stomatitis New Jersey virus (VSNJV) are preferred strains to pseudotype the lentiviral vectors of the invention, or to design recombinant envelope protein(s) to pseudotype the lentiviral vectors. However, Isfahan and SVCV envelopes provide also good candidates for the preparation of the pseudotyped particles. Cocal is also interested, to the extent where it is not used in the particles which would be administered first and especially would be preferred for a late or last administration in a prime-boost regimen. When particles are successively administered which have different pseudotyping envelopes, the following order of administration with respect to said envelopes could be preferred, Indiana; New Jersey; Isfahan; SVCV/Cocal. Because Cocal pseudotyped lentiviral vectors seroneutralize several other envelopes, it is preferable, in the vaccination chronology, when Cocal envelopes are to be used in the preparation of particles, to administer them as the last one.

The VSV strains of Indiana and New Jersey serotypes are particularly interesting to be used in the lentiviral vectors of the invention. Their VSV-G proteins are disclosed in Genebank, where several strains are presented. For VSV-G New Jersey strain reference is especially made to the sequence having accession number V01214.

Among VSV, Chandipura virus (CHPV), Cocal virus (COCV), Perinet virus (PERV), Piry virus (PIRYV), SVCV or Isfahan virus may be good candidates to design alternative envelope proteins, and especially to design a third envelope protein or third envelope proteins, or further envelope protein(s). However, it has been shown in the examples that Chandipura virus (CHPV) and Piry virus (PIRYV) provides envelope proteins having low pseudotyping ability when comparing the vector titers obtained with particles prepared with different envelopes. Therefore in a first approach these envelopes may be excluded from the choice of envelopes in order to prepare particles with an efficient transduction capacity.

According to another embodiment, the viral envelope protein(s) originate from other RNA-viruses, for example non-human retroviruses, such as murine retroviruses or from Influenza viruses.

Other examples of envelope protein(s) suitable for lentiviral pseudotyping are given later in the description, especially with a reference to their target cells in a host.

According to a particular embodiment, the kit of compounds of the invention makes use of first and second and if any said third or further, viral envelope protein(s), that originate from Rhabdoviridae, in particular VSV or from Paramyxoviridae wherein the first and second and if any said third or further, envelope protein(s) originate from viruses of different genus, or originate from different virus strains in the same serogroup, especially in the vesicular stomatitis serogroup or alternatively originate from different serotypes of the same genus.

In a particular embodiment of the invention, protein(s) or glycoprotein(s), suitable for use in the design of pseudotyped lentiviral vectors of the kit of compounds are especially produced as monomeric or multimeric protein(s).

In a particular embodiment of the invention, said first and second and if any said third or further, viral envelope protein(s) are capable of uptake by antigen presenting cells and especially by dendritic cells by mean of fusion and/or of endocytosis. In a particular embodiment, the efficiency of the uptake may be used as a feature to choose the envelope of a VSV for pseudotyping. In this respect the relative titer of transduction (Titer DC/Titer of other transduced cells e.g. 293T cells) may be considered and envelope having a relative good ability to fuse with DC would be preferred. Relative titers of transduction are illustrated in the examples.

Antigen Presenting Cells (APC) and especially Dentritic cells (DC) are proper target cells for pseudotyped lentiviral vectors which are used as vaccine compositions, either for a prophylactic or a therapeutic purpose.

The envelope protein(s) used to pseudotype the lentiviral vector particles may thus be selected with respect to the target cells in a host.

Polynucleotide encoding VSV envelope protein(s) (VSV-G) also targets splenocytes, in particular Antigen Presenting Cells (APC) or Dendritic Cells (DC), or liver cells including hepatocytes or non parenchymal cells.

Other target cells may be activated or proliferating cardiomyocytes.

Polynucleotides encoding envelope protein(s) suitable to target determined cells and to be used for pseudotyping the lentiviral vector of the invention are illustrated hereafter: polynucleotides encoding envelope protein(s) of VSV (VSV-G), LCMV (Lymphocytic choriomeningitis Virus), or RRV (Ross River Virus) may be used to prepare vectors suitable to target liver cells (Park 2003) (Kang et al, 2002).

Envelope protein(s) of Ebola or Marburg viruses may be used to target apical surface airway epithelium (Kobinger et al, 2001).

Envelope protein(s) of viruses of the Rhabdoviridae family (including Rabies or Rabies-related viruses like Mokola virus) or of the VSV family may provide neurotropic lentiviral vectors.

Envelope glycoprotein(s) of an Arenavirus such as Lymphocytic Choriomeningitis Virus (LCMV) may be used to transduce fibroblasts, epithelial cells, hematopoietic cells, neuroblastoma and glioma cell lines.

Alphaviruses envelope protein(s) such as the protein(s) of RRV or SFV (Semliki Forest Virus) may target Antigen Presenting Cells (APC), neurons or muscle cells.

Other envelope protein(s) may be used to pseudotype the lentiviral vector of the invention, such as HA protein (influenza hemaglutinin), RD114 protein, envelope protein(s) of Togaviridae, of Orthomyxoviridae (such as Influenza virus), Coronaviridae, Flaviridae, Filoviridae.

The envelope protein(s), also designated sometimes as surface protein in particular viruses, are said to "originate" from a different organism, and especially from different RNA virus strains, meaning that in said protein(s), essential features of the corresponding protein(s) expressed in a determined RNA virus are maintained. Said essential features, relate to the structure or to the function of the protein and are those which enable especially the obtained protein(s) to be expressed at the surface of the vector particles for pseudotyping said vectors. The envelope proteins are then capable of being recognized and internalized in the target cells of the hosts when present on the vector particles.

In a particular embodiment, protein(s) or glycoprotein(s), suitable for use in the design of pseudotyped lentiviral vectors of the kit of compounds are used as multimeric proteins, such as VSV-G protein which is trimeric.

The envelope protein(s) are expressed from a polynucleotide containing the coding sequence for said protein(s), which polynucleotide is inserted in a plasmid (envelope expression plasmid or pseudotyping env plasmid) used for the preparation of the lentiviral vector of the invention. The polynucleotide encoding the envelope protein(s) is under the control of regulatory sequences for the transcription and/or expression of the coding sequence (including optionally a polynucleotide such as WPRE sequence from Invitrogen).

The invention thus relates to a nucleic acid construct which comprises an internal promoter suitable for the use in mammalian, especially in human, cells, in vivo and the nucleic acid encoding the envelope protein under the control of said promoter. The invention also concerns a plasmid containing this construct. Promoters may in particular be selected for their properties as constitutive promoters, tissue-specific promoters, or inducible promoters. Examples of suitable promoters encompass the promoters of the following genes: EF1α, human PGK, PPI (preproinsulin), thiodextrin, HLA DR invariant chain (P33), HLA DR alpha chain, Ferritin L chain or Ferritin H chain, Beta 2 microglobulin, Chymosin beta 4, Chymosin beta 10, or Cystatin Ribosomal Protein L41.

The nucleotide sequence used for the expression of the envelope protein(s) required for pseudotyping the lentiviral vector particles may also be modified with respect to the nucleic acid encoding the native envelope protein(s) used as reference. The modification may be carried out to improve the codons usage (codon optimization) in the cells for the preparation of the vector particles and/or in the transduced cells of the host It may be modified to express a protein different from the native protein(s), especially one which has an improved pseudotyping capacity, an improved capacity in the level of production, or an improved capacity with respect to prevention of sero-neutralization with other envelope protein(s) used in the kit of compounds.

Such a modification of the envelope protein(s) may affect and especially improve their level of production in a cell host or their ability to pseudotype the vector particles possibly by improving the density of envelope protein(s) associated with pseudovirions. Said modification may derive from a mutation in the amino acid sequence of said protein(s), for instance by addition, deletion or substitution of one or several nucleotides or nucleotidic fragments or may relate to post translational modifications and in particular to the glycosylation status of said envelope protein(s).

The envelope protein(s) used to pseudotype the lentiviral vectors of the invention are indeed especially glycoproteins.

It has already been shown that pseudotyping viral vectors with Vesicular Stomatitis Virus glycoprotein (VSV-G) enables the transduction of a large range of cell types from different species. This VSV-G glycoprotein, in addition to its broad tropism, has an interesting stability when used for vector pseudotyping. Therefore, VSV-G have been used as a standard for evaluating the efficiency of other pseudotypes (Cronin J. et al, 2005). Accordingly, VSV-G is an appropriate candidate for pseudotyping the lentiviral vectors of the invention.

The invention especially relates to a kit of compounds as defined in the present application, wherein both said first and second and if any, said third or further viral envelope proteins are transmembrane glycosylated (G) proteins of a VSV virus, said G proteins having different VSV type-specificity in the lentiviral vectors of the kit.

In particular, said first G protein originates from a VSV-Indiana serotype and said second G protein originates from a VSV-New-Jersey serotype, or vice-versa.

It has been shown and reported in the following examples that having recourse in a kit, to pseudotyped viral particles wherein the envelope protein(s), are G proteins of respectively the VSV-Indiana serotype and the VSV-New Jersey serotype enables to prime and boost an immunological reaction when the lentiviral vectors pseudotyped with either of said G proteins are successively used to elicit a reaction in a host to whom they are administered. In such a case, it has been shown that no humoral response (no cross-reactive humoral response) or a low humoral response (low cross-reactive humoral response) is produced against the first envelope protein(s) used which could harm the response elicited in the host against the expression product of the polynucleotide, when said lentiviral vector peudotyped with a second, distinct, envelope protein(s) is administered. This is enabled by the fact that said distinct envelope protein(s) do not cross-neutralize or do not significantly cross-react with each other and accordingly does not give rise to an antivector immune response.

In a particular embodiment, the invention concerns a G protein originating from a VSV which is modified with respect to its native form, and/or is encoded by a nucleic acid molecule which is modified with respect to the natural one, in order to improve pseudotyping. It may be as a result of improvement of envelope protein(s) uptake by the lentiviral particles which allows improvement of transduction of the lentiviral particles by the cells of the host to whom they are administered.

A particular kit of compounds comprises lentiviral vectors wherein one or two or more of them is (are) pseudotyped with recombinant envelope protein(s) comprising domains or fragments originating from different envelope protein(s) of different viruses, especially of different genus of different species of VSV.

In a particular embodiment of the invention, at least one the first, second and if any third or further envelope protein(s) is (are) recombinant envelope protein(s) comprising the export determinant of the VSV-G of Indiana strain.

The export determinant of the VSV-G of the Indiana strain is a polypeptide encoded by the cytoplasmic fragment of the open reading frame of the envelope.

The export determinant of the VSV-G of the Indiana strain is a polypeptide comprising or having amino acid sequence YTDIE in the cytoplasmic tail (Nishimua N. et al. 2002).

Said recombinant envelope protein(s) may comprise the cytoplasmic tail of the VSV-G of an Indiana strain which is the intracellular portion of VSV-G delimited by a hydrophobic transmembrane domain.

A particular kit of compounds comprises lentiviral vectors wherein one or two or more of them is (are) pseudotyped with recombinant envelope protein(s) comprising the cytoplasmic domain of the indiana VSV and the ectodomain of a strain of a different VSV serotype. The transmembrane domain may also be the one of the Indiana VSV-G.

A particular kit of compounds comprises lentiviral vectors wherein one or both of them is (are) pseudotyped with recombinant envelope protein(s) comprising the transmembrane domain and the cytoplasmic domain of the Indiana VSV and the ectodomain of the New-Jersey VSV.

Appropriate other modifications encompass mutations, especially point mutations, that improve pseudotyping. Such mutations for the VSV-G proteins may be carried out in the transmembrane domain by substituting or deleting one or several amino acid residues. Other examples of appropriate mutations are disclosed in Fredericksen B. L. et al (1995) or Nishimura N. et al (2003).

When reference is made to "fragments" in the present description, it refers to polynucleotides or polypeptides having respectively a nucleotide sequence or an amino acid sequence of at least or longer than 6 nucleotides, respectively of at least or longer than 2 amino acid residues.

It is also especially possible to modify the glycosylation status of the VSV-G, in order to improve transduction efficiency of the lentiviral vector pseudotyped with these VSV-G proteins, when administered to a host.

VSV-G proteins from various strains of VSV are disclosed in the figures and their sequences can also be derived from databases, especially from Genebank.

Considering the glycoproteins of the New-Jersey and Indiana strains of VSV, it has been proposed that glycosylation at two asparagine residues (N180 and N336) favour the efficient pseudotyping of lentiviral vectors. This particular feature may be applied in the preparation of the lentiviral vectors of the invention.

Figure 6C:
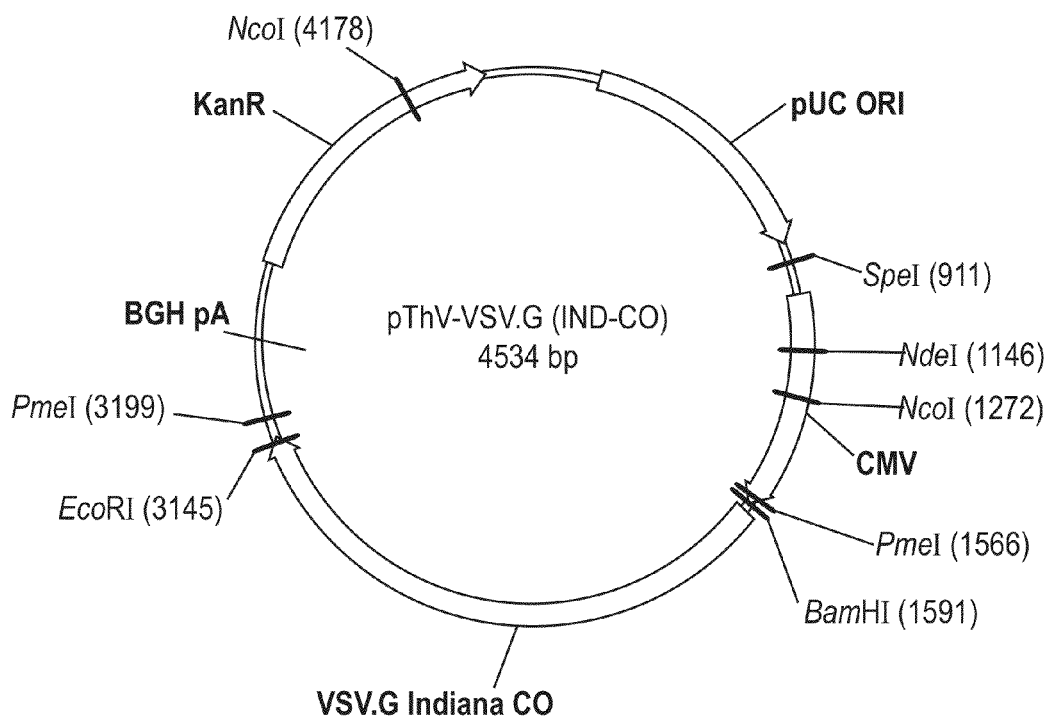

The invention especially relates to the following constructs encoding VSV-G derived envelope proteins, and to their use in the preparation of the combination of lentiviral vector particles of the invention. The invention also relates to the envelope proteins encoded by said constructs:

A VSV-G Indiana gene codon optimized is disclosed in FIG. 6 and is part of the invention. The invention also relates to encapsidation plasmids containing an envelope gene for VSV-G Indiana. A particular encapsidation plasmid is pThV-VSV.G (IND-CO) deposited at the CNCM (Paris, France) on Oct. 10, 2007, under number I-3842 or in an alternative version of the plasmid construct, on Jul. 31, 2008, under number CNCM I-4056. Other constructs may be derived from this particular plasmid, especially by substituting the promoter for a promoter among those listed in the present application.

Figure 7C:
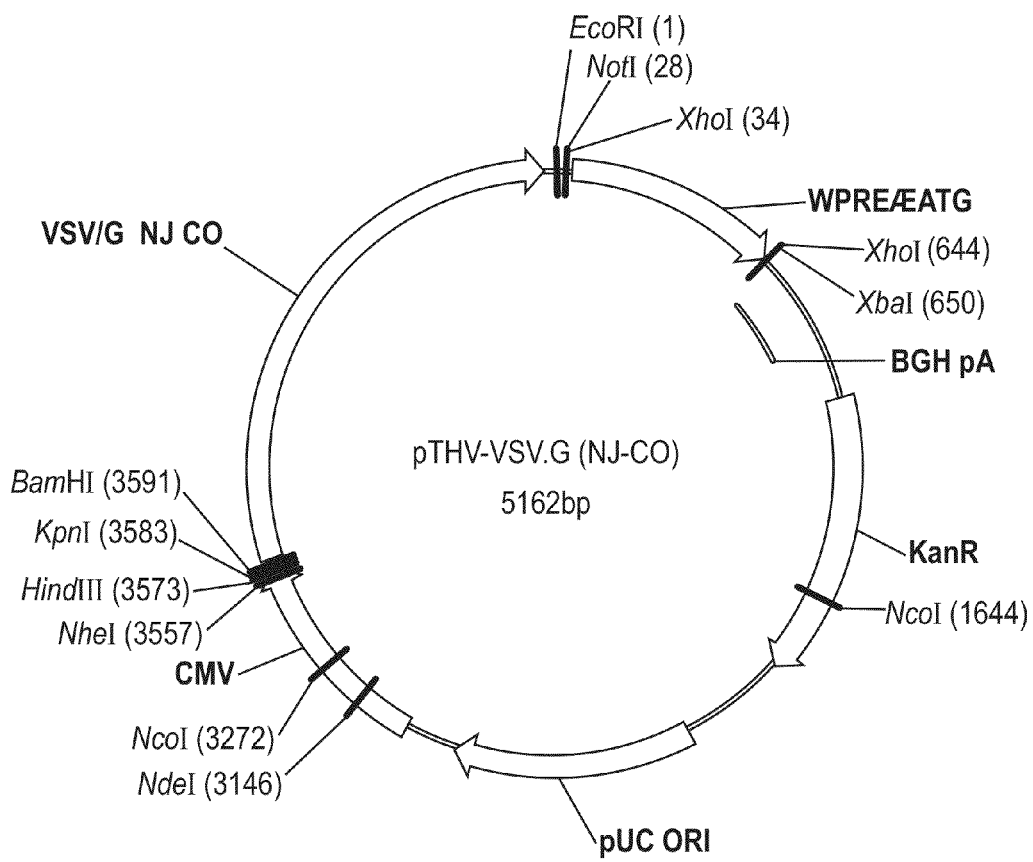

A VSV-G New-Jersey gene codon optimized is disclosed in FIG. 7 and is part of the invention. The invention also relates to encapsidation plasmids containing an envelope gene for VSV-G New jersey. A particular encapsidation plasmid is pThV-VSV.G (NJ-CO) deposited at the CNCM (Paris, France) on Oct. 10, 2007, under number I-3843 or in an alternative version of the plasmid construct, on Jul. 31, 2008, under number CNCM I-4058. Other constructs may be derived from this particular plasmid, especially by substituting the promoter for a promoter among those listed in the present application. The invention concerns these plasmids and the insert which they contain, which encodes the VSV-G envelope protein.

Other envelope genes suitable to carry out the invention having codon optimized sequences are illustrated in FIGS. 6 to 12 and 14 to 19 and especially encompass VSV-G Chandipura gene and its expression product, VSV-G Cocal gene and its expression product, VSV-G Piry gene and its expression product, VSV-G Isfahan gene and its expression product, VSV-G Spring viremia carp virus gene and its expression product. A particular encapsidation plasmid, containing an envelope gene for VSV-G Cocal, is pThV-VSV.G (COCAL-CO) deposited at the CNCM (Paris, France) on Jul. 31, 2008, under number CNCM I-4055. Another particular encapsidation plasmid, containing an envelope gene for VSV-G Isfahan, is pThV-VSV.G (ISFA-CO) deposited at the CNCM (Paris, France) on Jul. 31, 2008, under number CNCM I-4057. Another particular encapsidation plasmid, containing an envelope gene for VSV-G Spring viremia carp virus, is pThV-VSV.G (SVCV-CO) deposited at the CNCM (Paris, France) on Jul. 31, 2008, under number CNCM I-4059. The invention concerns these plasmids and the insert which they contain, which encodes the VSV-G envelope protein.

The invention is also directed to fusion envelope proteins, especially fusion proteins involving several different fragments of VSV-G proteins of different viruses and to the nucleic acid constructs encoding such proteins. A particular fusion envelope is the fusion between the ectodomain of the New-Jersey envelope protein and the transmembrane domain and cytoplasmic domain of the Indiana envelope protein as illustrated in the figures.

Another fusion envelope protein according to the invention comprises the ectodomain of one VSV-G protein selected among VSV-G Chandipura, VSV-G Cocal, VSV-G Pyri, VSV-G Isfahan, or VSV-G SVCV and the tranmembrane and cytoplasmic domains of VSV-G Indiana. The invention also relates to a nucleic acid molecule encoding said fusion protein illustrated in the figures, and especially a codon optimized nucleic acid encoding the fusion protein also described in the figures.

The invention also concerns the expression vectors, especially the plasmids containing the nucleic acid constructs encoding the fusion proteins.

Basic, essential features characterizing the vector genome used in the construction of the pseudotyped lentiviral vector particles of the invention have been described hereabove. Additional features for the preparation of suitable vector genome (also designated as transfer vector) are disclosed hereafter, including in the examples and in the drawings.

In a particular embodiment of the invention, the pseudotyped lentiviral vectors are human lentivirus based vectors. Accordingly their genome is derived from a human lentivirus, especially from the HIV lentivirus. In particular, the pseudotyped lentiviral vector is an HIV-based vector, such as an HIV-1, or HIV-2 based vector, in particular is derived from HIV-1M, for example from the BRU or LAI isolates.

In another embodiment, the pseudotyped lentiviral vectors are primate or feline lentivirus based vectors.

As stated above, when considering it apart from the transgene that it finally contains, the vector genome is a replacement vector in which the nucleic acid between the 2 long terminal repeats (LTRs) in the original lentivirus genome have been restricted to cis-acting sequences for DNA or RNA synthesis and processing, or at least are deleted or mutated for essential nucleic acid segments that would enable the expression of lentiviral structure proteins including biological functional GAG polyprotein and possibly POL and ENV proteins.

In a particular embodiment, the vector genome is defective for the expression of biologically functional Gag, and advantageously for biologically functional POL and ENV proteins.

The 5' LTR and 3' LTR sequences of the lentivirus are used in the vector genome, but the 3'-LTR at least is modified with respect to the 3'LTR of the original lentivirus at least in the U3 region. The 5'LTR may also be modified, especially in its promoter region.

In a particular embodiment the vector genome is accordingly devoid of the coding sequences for Vif-, Vpr, Vpu- and Nef-accessory genes (for HIV-1 lentiviral vectors), or of their complete or functional genes.

In a preferred embodiment, the vector genome of the lentiviral vector particles comprises, as an inserted cis-acting fragment, at least one polynucleotide consisting in the DNA flap or containing such DNA flap. In a particular embodiment, the DNA flap is inserted upstream of the polynucleotide of interest, advantageously but not necessarily to be located in an approximate central position in the vector genome. A DNA flap suitable for the invention may be obtained from a retrovirus, especially from a lentivirus, in particular a human lentivirus, or from a retrovirus-like organism such as retrotransposon. It may be alternatively obtained from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. The DNA flap may be either prepared synthetically (chemical synthesis) or by amplification of the DNA providing the DNA Flap from the appropriate source as defined above such as by Polymerase chain reaction (FOR). In a more preferred embodiment, the DNA flap is obtained from an HIV retrovirus, for example HIV-1 or HIV-2 virus including any isolate of these two types.

The DNA flap (defined in Zennou V. et al., 2000, Cell vol 101, 173-185 or in WO 99/55892 and WO 01/27304), is a structure which is central in the genome of some lentiviruses especially in HIV, where it gives rise to a 3-stranded DNA structure normally synthesized during especially HIV reverse transcription and which acts as a cis-determinant of HIV genome nuclear import. The DNA flap enables a central strand displacement event controlled in cis by the central polypurine tract (cPPT) and the central termination sequence (CTS) during reverse transcription. When inserted in lentiviral-derived vectors, the polynucleotide enabling the DNA flap to be produced during reverse-transcription, stimulates gene transfer efficiency and complements the level of nuclear import to wild-type levels (Zennou et al., Cell, 2000).

Sequences of DNA flaps have been disclosed in the prior art, especially in the above cited patent applications. These sequences are also disclosed in the attached figures as SEQ ID NO 1 to SEQ ID NO 7. They are preferably inserted as fragment possibly with additional flanking sequences in the vector genome in a position which is near the centre of said vector genome. Alternatively they may be inserted immediately upstream from the promoter controlling the expression of the polynucleotide of the invention. Said fragments comprising the DNA flap, inserted in the vector genome may have a sequence of about 80 to about 200 bp, depending on its origin and preparation.

According to a particular embodiment, a DNA flap has a nucleotide sequence of about 90 to about 140 nucleotides.

In HIV-1, the DNA flap is a stable 99-nucleotide-long plus strand overlap. When used in the genome vector of the lentiviral vector of the invention, it may be inserted as a longer sequence, especially when it is prepared as a PCR fragment. A particular appropriate polynucleotide comprising the structure providing the DNA flap is a 178-base pair polymerase chain reaction (PCR) fragment encompassing the cPPT and CTS regions of the HIV-1 DNA (Zennou et al 2000).

This PCR fragment may especially be derived from infective DNA clone of HIV-1 LAI especially pLAI3 of HIV1, as a fragment corresponding to the sequence from nucleotide 4793 to 4971. If appropriate, restriction sites are added to one or both extremities of the obtained fragment, for cloning. For example, Nar I restriction sites may be added to the 5' extremities of primers used to perform the PCR reaction.

Therefore, the DNA flap is used, in the present invention, deleted from the unnecessary 5' and 3' parts of the pol gene and is recombined with sequences of different origin. The DNA flap may be either prepared synthetically (chemical synthesis) or by amplification of the DNA providing the DNA flap from the appropriate source as defined above such as by Polymerase chain reaction (PCR). In a more preferred embodiment, the DNA flap is obtained from an HIV retrovirus, for example HIV-1 or HIV-2 virus including any isolate of these two types.

It is specified that the DNA flap used in the genome vector and the polynucleotides of the encapsidation plasmid encoding the GAG and POL polyproteins should originate from the same lentivirus sub-family or from the same retrovirus-like organism.

Preferably, the other cis-activating sequences of the genome vector also originate from the same lentivirus or retrovirus-like organism, as the one providing the DNA flap.

The vector genome may further comprise one or several unique restriction site(s) for cloning the polynucleotide of interest.

According to the invention, the pseudotyped lentiviral vector is a replication-incompetent lentiviral vector as a result of the fact that gag and pol functional genes are exclusively provided in trans and therefore not present on the vector genome. In such a case, when the lentiviral vector has been administered to the host, it is not capable of replicating in the host cells. Accordingly, it provides the polynucleotide of therapeutic interest into the host cells for expression but does not form further lentiviral vector particles. This replication-incompetent of the lentiviral vector status is achieved especially when the lentiviral gag, pol, env genes are not provided in the vector genome or are not provided as functional genes. By "functional" it is meant a gene that is correctly transcribed, and/or correctly expressed. Thus, the lentiviral vector genome of the invention in this embodiment contains at least one of the gag, pol and env genes that is either not transcribed or incompletely transcribed; the expression "incompletely transcribed" refers to the alteration in the transcripts gag, gag-pro or gag-pro-pol, one of these or several of these being not transcribed. Other sequences involved in lentiviral replication may also be mutated in the vector genome, in order to achieve this status.

In a preferred embodiment, in said vector genome, the 3' LTR sequence of the lentiviral vector genome is devoid of at least the activator (enhancer) and possibly the promoter of the U3 region. In another particular embodiment, the 3' LTR region is devoid of the U3 region (delta U3). In this respect, reference is made to WO 01/27300 and WO 01/27304.

In a particular embodiment, in the vector genome, the U3 region of the LTR 5' is replaced by a non lentiviral U3 or by a promoter suitable to drive tat-independent primary transcription. In such a case, the vector is independent of tat transactivator.

The vector genome also comprises the psi (ψ) packaging signal. The packaging signal is derived from the N-terminal fragment of the gag ORF. In a particular embodiment, its sequence could be modified by frameshift mutation(s) in order to prevent any interference of a possible transcription/translation of gag peptide, with that of the transgene.

The vector genome may optionally also comprise elements selected among a splice donor site (SD), a splice acceptor site (SA) and/or a Rev-responsive element (RRE).

According to a particular embodiment, the vector plasmid (or added genome vector) comprises the following cis-acting sequences for a transgenic expression cassette:
1. The LTR sequence (Long-Terminal Repeat), required for reverse transcription, viral DNA integration and transcription. The 3' LTR has been deleted in the U3 region, without perturbing the functions necessary for gene transfer, for two major reasons: first, to avoid transactivation of a host gene, once the DNA is integrated in the genome and secondly to allow self-inactivation of the viral cis-sequences after retrotranscription. Optionally, the tat dependent U3 sequence from the 5'-LTR which drives transcription of the genome is replaced by a promoter sequence. Thus, in target cells only sequences from the internal promotor will be transcribed (transgene) (FIGS. 23 and 24),
2. The ψ region, necessary for viral RNA encapsidation,
3. The RRE sequence (REV Responsive Element) allowing export of viral messenger RNA from the nucleus to the cytosol after binding of the Rev protein.
4. The DNA flap sequence (cPPT/CTS, normally contained in Pol) to facilitate nuclear import.
5. Optionally, the WPRE cis-active sequence (Woodchuck hepatitis B virus Post-Responsive Element) also added to optimize stability of mRNA (Zufferey et al., 1999). WPRE is not translated.

In a particular embodiment, apart from the polynucleotide of therapeutic interest which may be derived from a coding region of a lentivirus, the vector plasmid disclosed with respect to the above-cited cis-acting sequences, is devoid from other lentiviral nucleotide sequences.

The lentiviral vector of the invention is non replicative i.e., the vector and lentiviral vector genome are not able to form new particles budding from the infected host cell. This may be achieved by the absence in the lentiviral genome of the gag, pol or env genes, as indicated in the above paragraph; this can also be achieved by deleting other viral coding sequence(s) and/or cis-acting genetic elements needed for particles formation. The absence of replication of the lentiviral vector should be distinguished from the replication of the lentiviral genome. Indeed, as described before, the lentiviral genome may contain an origin of replication ensuring the replication of the lentiviral vector genome without ensuring necessarily the replication of the vector (or particle).

In a further embodiment, particularly when the polynucleotide encoding the at least one antigenic polypeptide originates from a lentivirus, said lentiviral vector genome does not comprise a complete lentiviral gag, pol or env coding polynucleotide, meaning that said lentiviral vector genome comprises a polynucleotide shorter than the lentiviral gag, pol or env genes. Therefore, the gag coding sequence is shorter than 1500 by for HIV-1 or HIV-2; the pol coding sequence is shorter than 3000 by for HIV-1 and 3300 by for HIV-2; the env coding sequence is shorter than 2700 by for HIV-1 and 2500 by for HIV-2. This size refers to the longest continuous nucleotide sequence found as such in the native lentiviral genome. However, in another particular embodiment, the lentiviral genome is devoid of all endogenous coding lentiviral sequences.

In order to obtain lentiviral vectors according to the invention, the vector genome (as a vector plasmid) must be encapsidated in particles or pseudo-particles. Accordingly, lentiviral proteins, except the envelope proteins, have to be provided in trans to the vector genome in the producing system, especially in producing cells, together with the vector genome, having recourse to at least one encapsidation plasmid carrying the gag and pol lentiviral genes or integrative—incompetent pol gene, and preferably lacking the coding sequences for Vif-, Vpr, Vpu- and Nef-accessory genes (for HIV-1 lentiviral vectors).

A further plasmid is used, which carries a polynucleotide encoding the envelope protein(s) selected for pseudotyping each lentiviral vector.

In a preferred embodiment, the packaging plasmid encodes only the lentiviral proteins essential for viral particle synthesis. Accessory genes whose presence in the plasmid could raise safety concerns are accordingly removed. Viral proteins brought in trans are respectively as illustrated for HIV-1:
 1. Gag proteins for building of the matrix (MA, with apparent Molecular Weight p17), the capsid (CA, p24) and nucleocapsid (NC, p6).
 2. Pol encoded enzymes: integrase, protease and reverse transcriptase.
 3. Tat and Rev coding regulatory proteins, Tat is necessary for the initiation of LTR-mediated transcription; it may be omitted if the U3 region of 5'LTR is substituted for a promoter driving tat-independent transcription.

In order to avoid any packaging of the mRNA generated from the genes contained in the packaging plasmid in the viral particles, the ψ region is removed from the packaging plasmid. A heterologous promoter is inserted in the plasmid to avoid recombination issues and a poly-A tail is added 3' from the sequences encoding the proteins.

The envelope plasmid encodes the envelope protein(s) for pseudotyping which are disclosed herein, under the control of an internal promoter.

Any or all the described plasmids for the preparation of the lentiviral vector particles of the invention may be codon optimized (CO) in the segment encoding proteins. Codon optimization according to the invention is preferably performed to improve translation of the coding sequences contained in the plasmids, in mammalian cells, especially human cells. According to the invention, codon optimization is especially suited to directly or indirectly improve the preparation of the vector particles or to improve their uptake by the cells of the host to whom they are administered, or to improve the efficiency of the transfer of the polynucleotide of interest (transgene) in the genome of the transduced cells of the host. Methods for optimizing codons are well known in the art and codon optimization is especially performed using available programs to that effect. Codon optimization is illustrated for the coding sequences contained in the described pTRIP plasmids and pThV plasmids of the invention illustrated in the figures.

In a particular embodiment of the invention, the pseudotyped lentiviral vector is also, or alternatively, integrative-incompetent. In such a case, the vector genome and thus the heterologous polynucleotide of therapeutic interest do not integrate into the genome of the transduced cells or in the cells of the host to whom it has been administered.

The present invention relates to the use of a lentiviral vector wherein the expressed integrase protein is defective and which further comprises a polynucleotide especially encoding at least one antigenic polypeptide, to produce an immunogenic composition suitable for eliciting an immune response against said at least one polypeptide, in a host in need thereof. The polynucleotide is one having the features disclosed herein.

Said polynucleotide (or lentiviral vector genome) comprises all the elements necessary for the nucleic import and the correct expression of the polynucleotide encoding at least one antigenic polypeptide. As examples of elements that can be inserted in the lentiviral genome of the lentiviral vector of the invention are at least one (preferably two) long terminal repeats (LTR), such as a LTR5' and a LTR3', a psi sequence involved in the lentiviral genome encapsidation, and optionally at least one DNA flap comprising a cPPT and a CTS domains. The lentiviral vector genome may also comprise elements selected among a splice donor site (SD), a splice acceptor site (SA) and/or a Rev-responsive element (RRE).

In a particular embodiment, said lentiviral vector is pseudotyped with a VSV-G protein, as described herein.

By "defective", it is meant that the integrase, preferably of lentiviral origin, is devoid of the capacity of integration of the lentiviral genome into the genome of the host cells i.e., an integrase protein mutated to specifically alter its integrase activity.

Integration-incompetent lentiviral vectors are obtained by modifying the pol gene encoding the Integrase, resulting in a mutated pol gene encoding an integrative deficient integrase, said modified pol gene being contained in the encapsidation plasmid. Such integration-incompetent lentiviral vectors have been described in patent application WO 2006/010834. Accordingly the integrase capacity of the protein is altered whereas the correct expression from the encapsidation plasmid of the GAG, PRO and POL proteins and/or the formation of the capsid and hence of the vector particles, as well as other steps of the viral cycle, preceding or subsequent to the integration step, such as the reverse transcription, the nuclear import, stay intact. An integrase is said defective when the integration that it should enable is altered in a way that an integration step takes place less than 1 over 1000, preferably less than 1 over 10000, when compared to a lentiviral vector containing a corresponding wild-type integrase.

In a particular embodiment of the invention, the defective integrase results from a mutation of class 1, preferably amino acid substitutions (one-amino acid substitution) or short deletions fulfilling the requirements of the expression of a defective integrase. The mutation is carried out within the poi gene. These vectors may carry a defective integrase with the mutation D64V in the catalytic domain of the enzyme, which specifically blocks the DNA cleaving and joining reactions of the integration step. The D64V mutation decreases integration of pseudotyped HIV-1 up to 1/10,000 of wild type, but keep their ability to transduce non dividing cells, allowing efficient transgene expression.

Other mutations in the pol gene which are suitable to affect the integrase capacity of the integrase of HIV-1 are the following: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D-35-E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In a particular embodiment, mutation in the pol gene is performed at either of the following positions D64, D116 or E152, or at several of these positions which are in the catalytic site of the protein. Any substitution at these positions is suitable, including those described above.

Another proposed substitution is the replacement of the amino acids residues RRK (positions 262 to 264) by the amino acids residues AAH.

In a particular embodiment of the invention, when the lentiviral vector is integration-incompetent, the lentiviral genome further comprises an origin of replication (ori), whose sequence is dependent on the nature of cells where the lentiviral genome has to be expressed. Said origin of replication may be from eukaryotic origin, preferably of mammalian origin, most preferably of human origin. It may alternatively be of viral origin, especially coming from DNA circular episomic viruses, such as SV40 or RPS. It is an advantageous embodiment of the invention to have an origin or replication inserted in the lentiviral genome of the lentiviral vector of the invention. Indeed, since the lentiviral genome does not integrate into the cell host genome (because of the defective integrase), the lentiviral genome is lost in cells undergoing frequent cell divisions; this is particularly the case in immune cells, such as B or T cells. The presence of an origin of replication ensures that at least one lentiviral genome is present in each cell, even after cell division, maximazing the efficiency of the immune response.

In a particular embodiment of the invention, the lentiviral vector genome is a HIV-based genome and has the sequence features represented on FIG. 2 or 23 to 25, wherein said sequence of interest is selected for its therapeutic interest and the internal promoter enabling its expression (represented in the figures by a CMV promoter) is advantageously selected to be suitable for administration in human.

The internal promoter contained in the transgene or in the expression cassette of the vector genome may be selected from the promoters of the following genes: EF1α, human PGK, PPI (preproinsulin), thiodextrin, HLA DR invariant chain (P33), HLA DR alpha chain, Ferritin L chain or Ferritin H chain, Beta 2 microglobulin, Chymosin beta 4, Chimosin beta 10, or Cystatin Ribosomal Protein L41.

The lentiviral vector genome of said lentiviral vectors of the invention may especially be derived from HIV-1 plasmid pTRIPΔ3.CMV-GFP deposited at the CNCM (Paris, France) on Oct. 11, 1999 under number I-2330. The structure and restriction sites of the various sequences contained in the plasmid are shown on FIG. 2D. The sequence of pTRIPΔU3.CMV-GFP is provided on FIG. 6.

In a particular embodiment of the invention, the lentiviral vector genome may be derived from HIV-1 plasmid pTRIP [delta]U3EF1[alpha]-GFP deposited at the CNCM on Oct. 11, 1999 under number I-2328. A description of the constituting sequences of the plasmid is depicted in FIG. 2E, with the restriction sites of the various sequences.

When the vector genome is derived from these particular plasmids, a sequence of a heterologous polynucleotide as disclosed in the present application is inserted therein, in addition or in replacement of the GFP coding fragment. The GFP coding sequence may also be substituted by a different marker. The CMV promoter may also be substituted by another promoter, especially one of the promoters disclosed above, especially in relation to the expression of the transgene.

Other lentiviral vector genomes suitable to carry out the invention are those contained in the deposited material listed hereafter or are derived from these deposited plasmids, especially by substituting the transgene either for a different polynucleotide of interest and/or for a different internal promoter. The WPRE sequence also contained in the particular deposited pTRIP vectors may also be deleted.

The invention thus concerns the lentiviral vector genome provided by plasmid pTRIPDeltaU3-CMV-SIV-GAGco-WPRE deposited at the CNCM (Paris, France) on Oct. 10, 2007 under Number I-3841. The composition of the plasmid is disclosed in the figures and its sequence is provided. This plasmid expresses the GAG protein of SIV as a non-myristilated protein. The ORF of the transgene has been codon optimized for the expression in human cells.

The invention also concerns the lentiviral vector genome provided by plasmid pTRIPDelta U3-CMV-SIV-GAG-WPRE deposited at the CNCM (Paris, France) on Oct. 10, 2007 under Number I 3840. The composition of the plasmid is disclosed in the figures and its sequence is provided. This plasmid expresses the GAG protein of SIV as a non-myristilated protein. The ORF of the transgen is not codon optimized.

Vector particles may be produced after transfection of appropriate cells, such as 293 T cells, by said plasmids, or by other processes. In the cells used for the expression of the lentiviral particles, all or some of the plasmids may be used to stably express their coding polynucleotides, or to transiently or sem-stably express their coding polynucleotides.

The concentration of particles produced can be determined by measuring the P24 (capsid protein for HIV-1) content of cell supernatants.

The lentiviral vector of the invention, once administered into the host, infects cells of the host, possibly specific cells, depending on the envelope proteins it was pseudotyped with. The infection leads to the release of the lentiviral genome into the cytoplasm of the host cell where the retrotranscription takes place. Once under a triplex form (via the DNA flap), the lentiviral genome is imported into the nucleus, where the polynucleotide of interest is expressed via the cellular machinery. When non-dividing cells are transduced (such as DC), the expression may be stable. When dividing cells are transduced, such as B cells, the expression is temporary in absence of origin of replication in the lentiviral genome, because of nucleic acid dilution and cell division. The expression may be longer by providing an origin of replication ensuring a proper diffusion of the lentiviral genome into daughter cells after cell division. The stability and/or expression may also be increased by insertion of MAR (Matrix Associated Region) or SAR (Scaffold Associated Region) elements.

Indeed, these SAR or MAR regions are AT-rich sequences enable to anchor the lentiviral genome to the matrix of the cell chromosome, thus regulating the transcription of the polynucleotide encoding at least one antigenic polypeptide, and particularly stimulating gene expression of the transgene and improving chromatin accessibility.

If the lentiviral genome is non integrative, it does not integrate into the host cell genome. Nevertheless, the at least one polypeptide encoded by the transgene is sufficiently expressed and longer enough to be processed, associated with MHC molecules and finally directed towards the cell surface. Depending on the nature of the polynucleotide of interest, the at least one polypeptide epitope associated with the MHC molecule triggers a humoral or a cellular immune response. The preparation of integrative-incompetent lentiviral vector, has been disclosed herein: the encapsidation plasmid used to transcomplement the vector genome is mutated in the region of the integrase protein, in such a way that said integrase is not expressed or is not functionally expressed in the lentiviral vector when said vector is produced as pseudotyped particles in a cell host, after said lentiviral vector has been administered to a patient.

The expression "immunogenic composition" refers to a composition comprising at least the lentiviral vector of the invention as active principle, said composition being suitable for administration into a host. This composition may comprise further a pharmaceutically suitable excipient or carrier and/or vehicle, when used for systemic or local administration. A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed and is compatible with other ingredients of the formulation; Suitable carriers include, but are not limited to, phosphate buffered saline solutions, distilled water, emulsions such as an oil/water emulsions, various types of wetting agents sterile solutions and the like, dextrose, glycerol, saline, ethanol, and combinations thereof.

The immunogenic composition of the invention has the capacity, despite the absence of integration of the transgene into the genome of the host cell, to elicit an immune response i.e., any reaction by the immune system of the host against said at least one polypeptide (encoded by said transgene).

The immune response can be a humoral response i.e., antibodies, elicited by said composition, are produced against said at least one polypeptide of the lentiviral vector. In a particular embodiment, said humoral response is a protective humoral response. The protective humoral response results mainly in maturated antibodies, having a high affinity for their antigen, such as IgG. In a particular aspect, the protective humoral response is T-cell dependent. In a particular embodiment, the protective humoral response induces the production of neutralizing antibodies.

The immune response can be a cellular immune response (T-cell immune response), particularly a CD8-mediated cellular immune response or a CD4-mediated cellular immune response i.e., an immune response which is mediated by activated cells harbouring CD8 or CD4 receptors, preferably Cytotoxic T lymphocytes (CTL).

In a particular embodiment of the invention, the lentiviral vector of the invention, despite the defective integrase, is able to elicit an early immune response. The expression "early immune response" refers to a protective immune response (protection against the pathogen or tumoral cell bearing said at least one polypeptide) that is conferred within about one week after the administration of the composition.

In another embodiment, the immune response conferred by the composition of the invention is a long lasting immune response i.e., said immune response can be still detected at least two months, preferably at least 3 months and most preferably at least 6 months after the administration of the composition. When the immune response is humoral, the long lasting response can be shown by the detection of specific antibodies, by any suitable methods such as ELISA, immunofluorescence (IFA), focus reduction neutralization tests (FRNT), immunoprecipitation, or Western blotting.

In another embodiment, independent of the above-embodiment, the strength of the immune response conferred by the composition of the invention is dependent upon the injected doses of the lentiviral vectors; the higher the dose, the higher the immune response strength.

Interestingly, said immune response, either humoral or cellular, early immune response and/or long lasting immune response, is elicited with the non-integrative gene transfer vector, after a single administration of the composition of the invention.

With a view to use the lentiviral vector particles and especially the kit of compounds in the design of medicinal treatment protocols, the lentiviral vectors of the invention carry in their vector genome, a heterologous polynucleotide (or transgene) having a therapeutic interest. By the expression "heterologous polynucleotide", it is meant that the vector genome comprises, irrespective from the ci-acting sequences in the vector genome that originate from the lentivirus genome and which are necessary or useful for the vector activity, at least one polynucleotide which is not necessary or which is not useful for the vector activity but which is suitable to obtain a biological effect, especially a medicinal effect when it is expressed in a host especially a human host. In a preferred embodiment, the polynucleotide of interest encodes a polypeptide and is preferably included in an expression cassette.

The heterologous polynucleotide of the invention encodes one polypeptide or several polypeptides which is (are) suitable for eliciting an immune response in a host, said immune response being a cellular immune response and possibly a humoral response. The encoded polypeptide(s) (i.e. antigen) comprise(s) one or several epitopes or consist(s) in epitope(s) of an antigen. In a particular embodiment, it may be a polyepitope. It (they) may be processed in the cells of the host for presentation by the APC, especially the DC, of the host to give rise to an immune response, or it (they) may directly elicit an immune response. Accordingly, the polynucleotide of interest comprises or consists of sequences of B epitope(s) and/or T epitope(s) of one or several antigens, including association of both categories of epitopes, possibly giving rise to a chimeric (i., e., non natural) polypeptide.

The epitope may depend either from a specific three-dimensional antigenic conformation (conformational epitope), or may correspond to a simple primary sequence region (linear epitope). The size of the polypeptide ranges from at least 9 amino acids up to 500 amino acids, and is preferably less than 200 amino acids.

In a particular embodiment, the heterologous polynucleotide encodes an antigen or several antigens or fragments thereof including epitopes (B and/or T epitopes) of a pathogenic organism such as a virus, especially a retrovirus, lentivirus, flavivirus or corona virus, bacteria or parasite, or of a pathogenic agent or compound. It may encode an antigen of the pathogenic organism or recombinant antigens, to the extent that it does not enable expression of the pathogenic organism when the lentiviral vector is administered.

The heterologous polynucleotide may be expressed as endogenous antigen in the cells of the host especially after transfer of said polynucleotide in the genome of the host cells and processed in said cells for presentation in association with MHC molecules.

The polynucleotide of interest may be chosen so that the immune response elicited with the vector, possibly after presentation by APC, may especially encompass an elicitation of T lymphocytes response, including T helper or CTL cells (cytotoxic). A CD8+ T cell response, against the processed expression product of said polynucleotide, in a host is especially of interest.

A CD4+ T cell response may also be expressed (induced or elicited).

Particular cells targeted by the lentiviral vectors of the present invention either in integrative or in non-integrative version are cells involved in immune response, such as antigen presenting cells (APC), dendritic cells (DC), including conventional DC (cDC) or plasmacytoid (pDC), T cells, including CD4+ or CD8+, B cells, monocytes, macrophages, Natural Killer cells, Natural Killer T cells, endothelial cells and epithelial cells. Interestingly, B cells have been recently shown to interact with circulating mature DC, thus activating these B cells, that in turn efficiently present antigens to naïve T cells (amplification of the mature APC population); therefore, this points out the critical role of B cells in priming cells involved in cellular immune response, and particularly naïve CD8+ T cells (Diaz de Durana; 2006).

The polynucleotide of interest may be chosen so that the lentivirus vector of the invention may also or alternatively be used to elicit a humoral immune response, especially a neutralizing humoral immune response, against the expression product of said polynucleotide, in a host.

In a particular embodiment of the invention wherein the lentiviral vector particles are intended for prevention or treatment of non lentiviral infections, the heterologous polynucleotide having a biological or a therapeutic interest is of a different origin than the polynucleotide constituting the vector genome. Especially, it is originating from a different organism than the lentivirus providing the sequences of the vector genome.

In a particular embodiment, where prevention or treatment of a lentiviral infection is sought, the heterologous polynucleotide may be originating from the same family or the same serotype of lentivirus providing the vector, especially when the lentiviral vector particles are HIV-based lentiviral vectors.

In a particular embodiment, the heterologous polynucleotide encodes an antigen derived from a lentiviral protein or an antigenic fragment thereof or a combination of such antigens. In such a case, said lentiviral protein antigen derived thereof or antigenic fragment thereof is used in conditions which prevent formation of native or replicative-competent lentiviral particles.

In a particular embodiment, it is used in conditions which also prevent the formation of lentivirus pseudo particles such as GAG or GAG-POL pseudo particles. These antigens may be derived from the same lentivirus, especially HIV, in particular HIV-1, as the one used for the design of the lentiviral vector.

Accordingly, the polynucleotide can be a coding sequence of one or several a HIV polypeptide(s) or polyepitopes, especially HIV-1 polypeptides or polyepitopes, suitable to elicit a cellular, especially a cytotoxic T-lymphocyte (CTL) response, and possibly T helper response in a host.

In a preferred embodiment of the invention, the lentiviral vectors comprise in their genome, a recombinant polynucleotide encoding one or several polypeptides comprising at least one antigen derived from a GAG antigen or polyprotein of an Immunodeficiency Virus, especially from HIV, SIV or Fly.

GAG polyprotein encompasses the Matrix protein (MA), the Capsid protein (CA), and the Nucleocapsid protein (NP). It may also comprise the p7 protein.

GAG derived antigens as defined above encompasses polypeptides derived from each of theses proteins, including fragments thereof or mutated (by deletion, substitution or addition) versions thereof. It also encompasses combinations of such polypeptides derived from each of these proteins.

In a particular embodiment, an antigen derived from GAG of an immunodeficiency virus has the amino acid sequence of the natural GAG antigens, especially of the GAG polyprotein or the Matrix protein or the Capsid protein or the nucleocapsid protein, or is a fragment of such polyprotein or of such protein, or is a GAG antigen which is modified with respect to the natural GAG antigen, especially by mutation, including by deletion, substitution or addition of one or several amino acid residues in the amino acid sequence, or which is modified by post translational modifications. The modified GAG antigen is selected to be either biologically functional or biologically non-functional.

In a particular embodiment, the recombinant polynucleotide encoding one or several polypeptides comprising at least one antigen derived from a GAG polyprotein of an Immunodeficiency Virus encodes a polypeptide which is a biologically non-functional GAG polypeptide (including an antigenic fragment of GAG) of SIV especially $SIV_{MAC}$, or of FIV, or of HIV in particular HIV-1 or HIV-2, and which is not capable of forming biologically functional capsids proteins within cells transduced with the lentiviral vectors, and especially does not induce secretion of capsid proteins from these cells that would enable formation of GAG pseudo particles or GAG-POL pseudo-particles.

In a particular embodiment, the polynucleotide including the nucleic acid encoding the antigen derived from GAG does not enable the expression of POL biologically active polypeptides (polyprotein also designated as precursor) and thus does not comprise the pol native genes or an equivalent functional gene.

In a particular embodiment, the recombinant polynucleotide encoding one or several polypeptides comprising at least one antigen derived from a GAG antigen of an Immunodeficiency Virus also encodes a polypeptide derived from a NEF, TAT or REV antigens of an Immunodeficiency Virus, and/or optionally from a POL antigen of an Immunodeficiency Virus or a combination thereof. These polypeptides are especially antigenic fragments of said antigens.

Examples of recombinant polynucleotide encoding an antigen derived from GAG (of HIV-1) and further nucleotide fragments encoding other antigens of HIV-1 in a fusion protein, is one which encodes a GAG protein as illustrated in FIG. 21 and a POL fragment or/and a NEF fragment or a fusion of such POL and NEF fragments also described on FIG. 21. These fragments may be fused 5' and/or 3' of the GAG antigen, may be contiguous to each other and/or to the GAG antigen or may be separated by a peptide such as the 2A peptide from picornavirus. Such construct is illustrated in the figures. The sequence of the 2A peptide is the following: APVKQTLNFDLLKLAGDVESNPGP (SEQ ID NO:8). A particular organization of the structure of the fusion protein is one of the following: 5' GAG POL NEF 3', or 5' POL NEF GAG 3' or 5' POL GAG NEF 3', or 5' NEF GAG POL 3' or 5' NEF POL GAG 3' or 5' GAG NEF POL 3'.

In a preferred embodiment, the antigens derived from GAG and/or NEF and/or POL antigens are derived from a Human Immunodeficiency Virus (HIV), in particular HIV-1 or HIV-2.

In a particular embodiment, the polypeptide derived from the GAG antigen is a GAGΔmyr protein which is not myristylated contrary to native GAG.

Non myristylated HIV-1 GAG may be obtained by mutating the coding sequence of GAG at codon 2 to change Gly residue [GGA] to Ala residue [GCA], or by deletion of said codon 2.

Other GAG derived antigen of interest for the invention are antigens formed of fragments of at least one of the Matrix, Capsid and Nucleocapsid proteins of GAG, especially are formed of a fusion of fragments of each of said proteins.

It is observed that the encoded derived antigen may be derived from GAG antigen of HIV-1, especially of HIV-1 subtype B or from HIV-1 group 0 (FIG. 21) and be used in a combination of compounds to elicit an immune response against various HIV groups, including different HIV-1 subtypes, HIV-1 and possibly HIV-2.

The invention also relates to a lentiviral vector as defined herein which comprises in its genome, a recombinant polynucleotide which has a human codon optimized sequence encoding an antigen derived from a GAG polyprotein of a Human Immunodeficiency Virus (HIV), or encoding a fusion antigen including an antigen derived from GAG and from at least an antigenic fragment of NEF, TAT, REV or POL as disclosed herein.

A chimeric HIV-1 derived antigen of the invention is, in a particular embodiment, a fusion protein comprising or consisting in the combination of the GAG derived antigen having the sequence of FIG. 21, with an antigen derived from NEF, POL, TAT or REV of a HIV-1 virus strain or with a combination of such antigens.

A particular fusion protein as disclosed above is one wherein POL derived antigen comprises or has the amino acid sequence of FIG. 21.

A particular fusion protein as disclosed above is one wherein the NEF derived antigen comprises or has the amino acid sequence of FIG. 21.

The antigens encoded by the polynucleotide of the vector genome, and especially the GAG derived antigen, may be of natural, synthetic or recombinant origin and accordingly expressed by any conventional methods.

The invention also relates to nucleotidic constructs encoding such fusion antigen, including in their codon optimized version for expression in mammalian, especially in human cells.

According to a particular embodiment, the recombinant polynucleotide encodes an antigen derived from the GAG polyprotein of HIV-1 consensus B strain.

In another particular embodiment, the recombinant polynucleotide encodes an antigen derived from a GAG polyprotein and a cluster of epitopes of NEF antigen of HIV and optionally a cluster of epitopes of POL polyprotein of HIV.

The invention relates to nucleic acid molecules encoding the antigen disclosed herein. It relates in particular to the nucleic acid molecules inserted in plasmids deposited at the CNCM and especially the plasmids pTRIPDelta U3-CMV-SIV-GAG-WPRE or pTRIPDelta U3-CMV-SIV-GAG co-WPRE, deposited at the CNCM or the plasmids pThV-VSV-G(IND-co), pThV-VSV-G(NJ-co), pThV-VSV-G(COCAL-co) pThV-VSV-G(ISFA-co) or pThV-VSV-G(SVCV-co) deposited at the CNCM, or to sequences hybridizing in stringent conditions with these nucleic acid molecules and especially having the same length or being shorter, Particular acid nucleics encode at least a GAG antigen or a fragment thereof and especially encodes a HIV-1 or HIV-2 GAG antigen or a fragment thereof.

The specificity of the cellular response is measured when comparing the response obtained with the lentivirus vector particles expressing a heterologous polynucleotide encoding an antigen of HIV or an antigen derived therefrom with the response obtained with particles not expressing said antigen. It is observed that the administration of the particles capable of expressing said HIV antigen or HIV-derived antigen elicit a T cell immune response which is not elicited with the particles not expressing the antigen.

This is illustrated in the examples with particles expressing an SIV derived antigen.

The response is advantageously protective which means that it enables to achieve a decrease in the viral load or to control the viral load measured in the plasma of the host infected with an Immunodeficiency Virus, who has received at least a prime and one or several boosting administrations of the compounds of the combination of compounds for a prophylactic or therapeutic use against infection by an immunodeficiency virus, especially by a HIV in a human host or by a $SIV_{MAC}$ in a non-human primate host.

In other words, when used for prophylactic or therapeutic treatment of an infection by an Immunodeficiency Virus, especially an HIV, the administered combination of compounds allows elimination of the virus from the body, or control of the viral load, for a long lasting period of time (over six months) and preferably enables protection against AIDS disease in vivo. The inventors have especially shown that, when administrated to a host who is infected to the Immunodeficiency Virus, the combination of compounds according to the invention enables the preservation of the Central Memory CD4+ T cell response during acute phase of the infection, which is a valuable correlation with protection against the pathogenesis of the retrovirus, i.e., against the development of AIDS in a human host (Letvin, N. L., et al, 2006).

The ability of the combination of compounds to provide tools to elicit a protective specific cellular immune response in a human host, is derived from the experimental results which have been obtained in a macaque/SIVmac non-human primate model in conditions which essentially resemble those observed in the human/HIV-1 situation.

Accordingly, the invention relates to the use of a combination of compounds for the preparation of a medicinal product for sequential administration to a mammalian host, to elicit a protective specific cellular immune response against an Immunodeficiency Virus, especially HIV.

Particular lentiviral vectors have been designed according to the invention, to elicit a specific cellular immune response which is shown to be protective in the context of a virus challenge. Although for obvious reason, this demonstration has not yet been carried out in human being, the disclosed results on the non-human primate are highly in favour of similar expectation in human.

The particular lentiviral vectors obtained provide specific interesting candidates for therapeutic vaccination or for prophylactic vaccination against AIDS.

In a particular aspect of the invention, polynucleotides encoding B epitopes and/or T epitopes originating from a pathogenic organism are polynucleotides encoding the envelope E-glycoprotein ($E_{WNV}$) of the West Nile Virus (WNV) or the envelope of the Yellow Fever Virus, or of the Dengue virus (DV), the Japanese encephalitis virus (JEV) or the SARS-associated coronavirus. Other interesting viral polypeptides are from the capsid of HIV.

In a particular embodiment, the at least one polypeptide is encoded by a polynucleotide of lentiviral origin (for example from gag as disclosed above or pol, or for example from env). In a particular embodiment, said coding polynucleotides are not the complete gag or pol gene or not the complete env gene, or are not a functional version of these genes i.e., a gene encoding a functional protein. For example, they have a size ranging from 30 to 1000, preferably from 30 to 500 bp, preferably 30 to 300 bp, more preferably 30 to 100 by or its soluble form or encoding epitopes thereof. Insertion of the coding sequence of the soluble E glycoprotein of WNV ($sE_{WNV}$) may be achieved following the disclosure in Reimann et al. (J. Virol.; 2005), using $sE_{WNV}$ as described in Hel et al. (J. immunol.; 2006).

According to another particular aspect of the invention, the heterologous polynucleotide encodes a polypeptide which is a tumor associated antigen (TAA) or a fragment thereof.

Non-limiting known examples of TAA are especially:
mutated peptides found in melanoma such as β-catetin, MART-2, or leukaemia such as brc-abl,
tissue specific proteins such as gp100, MART-1, tyrosinase, found in melanoma, or PSA, PAP, PSM, PSMA found in prostate cancer,
cancer-testis antigen such as MAGE,
Molecules related to tumorigenesis such as Survivin, hTERT, found in various cancers,
Mucins like MUC-1 found in breast, ovarian or pancreas cancer,
viral proteins of virus that transforms a normal cell in tumor cell (tumor virus) including those of HPV (Human Papilloma Virus), especially HPV16 or HPV18, including the HPV16-E7 antigen (found expressed in cervical cancer), EBV (Epstein-Barr virus) causing lymphoma including EBV-EBMA protein (in lymphoma), HBV (Hepatitis B Virus), HCV (Hepatitis C Virus), HHV (Human Herpes Virus) such as HHV8 or HTLV (Human T Leukemia Virus) such as HTLV-1, such HTLV-1 tax protein (in Acute T Leukemia).

More generally, these polynucleotides may be derived from the peptide sequences disclosed in the peptide database entitled Cancer Immunity. The polynucleotides may especially be selected among shared tumor-specific antigens, differenciation antigens, antigens overexpressed in tumors or tumor antigens resulting from mutations These polypeptides (or part thereof) may originate from the cell (self peptide) either in a wild type or mutated form.

In a particular embodiment, the polynucleotide of interest encodes human antigens.

In another embodiment of the invention, the polynucleotide of interest may encode a polypeptide whose expression or functional expression is harmed in the host affected with the considered pathology. In a particular embodiment, the lentiviral vectors of the invention are used to deliver the polynucleotide to target cells in the host to seek for genetic correction in a medicinal treatment of gene therapy, for example of genetic diseases that result in serum protein deficiencies, or for genetic vaccination strategies against cancer or infectious, viral or autoimmune diseases. In another embodiment, other pathologies such as diabetes may be treated with the kit of compounds of the invention.

Finally said at least one polypeptide may be an artificial (non-natural) polypeptide, preferably a multiepitope polypeptide. This multiepitope polypeptide encodes at least two epitopes, originating from a pathogenic organism, including viruses, and/or of tumoral-origin. In a particular embodiment, said at least two epitopes originate from the same virus or from the same tumor cell; in that case, said at least two epitopes may be selected for their different CMH (HLA) restriction. In another embodiment, said at least two epitopes originate from different viruses, or from different tumor cells. Said epitopes can be arranged consecutively, i.e., the 3' end of the epitope is directly linked to the 5' end of the second epitope (and so on), corresponding to a polynucleotide encoding a peptide sequence exclusively composed of consecutive epitopes. The at least two epitopes of the invention can alternatively be separated by a one-amino acid spacer or a peptide spacer i.e., meaning that the different polynucleotide units are separated by one or several codon(s) encoding respectively one or several amino acid(s). As spacers improving the processing of multiple epitopes, 4 amino acid-peptides composed of an arginine (R) in the C terminal position and hydrophilic residues (A, K, D and/or T) in other positions are preferred. Especially, 4 amino acid-peptides having a positively charged residue or an acidic residue in the C terminal position may be used, dependently or independently of hydrophilic residues (A, K, D and/or T) in other positions. In a particular embodiment, said spacers are internal processing sequences such as endosomal or lysosomal processing sequences, enabling the better processing of the multiple epitopes and avoiding the processing of new peptides resulting from overlapping cutting. Such a separation having recourse to a spacer can be used to separate all or part of the epitopes.

The heterologous polynucleotide is inserted in the vector genome, under the control of regulatory sequences for transcription and expression, including a promoter and for possibly an enhancer. In a particular embodiment, the regulatory sequences are not of lentiviral origin. Suitable promoters encompass CMV, also referred to as CMVie promoter, or EF1α promoter, CGA promoter, CD11c promoter and house keeping gene promoters such as PGK promoter, ubiquitin promoter, actin promoter, histone promoter, alpha-tubulin promoter, beta-tubulin promoter, superoxide dismutase 1 (SOD-1) promoter, dihydrofolate reductase (DHFR) promoter, hypoxanthine phosphorybosyltransferase (HPRT) promoter, adenosine deaminase promoter, thymidylate synthetase promoter, dihydrofolate reductase P1 promoter, glucose-6-phosphate dehydrogenase promoter or nucleolin promoter. Other suitable promoters encompass the promoters of the following genes: EF1α, human PGK, PPI (preproinsulin), thiodextrin, HLA DR invariant chain (P33), HLA DR alpha chain, Ferritin L chain or Ferritin H chain, Beta 2 microglobulin, Chymosin beta 4, Chymosin beta 10, or Cystatin Ribosomal Protein L41.

The kit of compounds of the invention is especially suited for use in a medicinal treatment, wherein said lentiviral vector pseudotyped with said first viral envelope protein(s) is administered separately in time from said lentiviral vector pseudotyped with said second viral envelope protein(s), and if appropriate said prime and first boost are followed by one or several boosting step(s), later in time.

Accordingly, the kit of compounds of the invention is especially suited for iterative administration of active principles, especially in a prime-boost(s) type reaction, possibly encompassing several boosting steps.

In particular, the compounds of the kit are such that said lentiviral vectors pseudotyped either with said first viral envelope protein(s) or with said second viral envelope proteins are respectively used for priming an immunogenic reaction or alternatively for boosting said immunogenic reaction in a host in need thereof. The immune reaction may be further boosted by using a lentiviral vector having a third envelope protein(s) as described herein, and optionally additional boosting steps with further envelope proteins which do not sero-neutralize with the one of the other lentiviral vectors.

In a particular embodiment, the lentiviral vector pseudotyped with the VSV-G of the Indiana strain is administered first, in order to prime the immunological reaction, and the lentiviral vector pseudotyped with the VSV-G of the New Jersey strain or with the recombinant or modified VSV-G as disclosed herein is administered in second instance, to boost the immunological reaction.

In another particular embodiment, the lentiviral vector pseudotyped with the VSV-G of the New Jersey strain or with the recombinant or modified VSV-G as disclosed herein is administered first, in order to prime the immunological reaction, and the lentiviral vector pseudotyped with the VSV-G of the Indiana strain is administered in second instance, to boost the immunological reaction.

The invention especially relates to an embodiment corresponding to an administration protocol with one round of administration of both compounds of the kit may be sufficient to elicit a strong response.

To possibly improve the intensity or the spectrum or the duration of the response, further administration steps may be performed. In particular, a lentiviral vector pseudotyped with an envelope chosen among VSV-G, Cocal, Perinet, SVCV or Isfahan viruses or a recombinant envelope comprising a domain of one of these envelopes, as described herein, may be used.

The kit of compounds of the invention is suitable for use in prophylactic treatment or therapeutic, including curative, treatment against a viral disease or against an infectious or tumoral disease, wherein said lentiviral vector comprises a polynucleotide encoding one or several viral antigens or fragments thereof suitable to elicit an immune response.

In addition to being suitable to prepare a combination of compounds for the therapeutic treatment of mammalian hosts infected with an Immunodeficiency Virus, in particular a human host infected with a HIV or a non-human primate host infected with a $SIV_{MAC}$ or an animal infected with FIV, the lentiviral vectors disclosed herein also provide tools for the design of a combination of compounds for a prophylactic use against infection by an immunodeficiency virus, especially by a HIV in a human host or by a $SIV_{MAC}$ in a non-human primate host or by FIV in an animal.

The combination of compounds disclosed herein may especially be used for the therapeutic treatment of human hosts infected with a HIV-1 or HIV-2.

The combination of compounds disclosed herein may especially be used for the prophylactic treatment of human hosts against infection by a HIV-1 or HIV-2.

The data provided in the experimental section hereafter provide indeed strong evidence of the relevancy of the designed lentiviral vector for transposition to medicinal applications in human. The level of protection achieved on the non-human primate model depicted in the examples is stronger than results reported in the literature with other vaccine candidates and it is noteworthy that it was obtained in the context of virus challenge with a particular high dose of infectious SIVmac virus.

From the experimental data obtained, it is even observed that the combination of compounds for the elicitation of a protective specific cellular immune response against an immunodeficiency virus may be prepared without adding an adjuvant of the immune response.

The skilled person may however decide to include in the combination of compounds, in association to all or part of the lentiviral vectors or/and as a further separate compound, an immunomodulating agent. For example, a cytokine such as Il12 may be included in the combination.

The invention especially provides a combination of compounds wherein said lentiviral vectors are formulated in compositions suitable for injection to a host, especially for sub-cutaneous injection. In another embodiment, the administration of the compounds of the invention may be advantageously carried out by intramuscular route, especially by injection. The inventors have shown, in an experimental mouse model, that the immune response elicited when the compounds including the gene transfer vector particles expressing a SIV GAG antigen are administered through intramuscular route, is higher than when they are administered in the same model, by sub-cutaneous injection.

The combination of compounds is thus in particular for use in an administration regimen involving injection to the host and encompassing priming the immune response and subsequently boosting the immune response in a mammalian host, wherein said (i) lentiviral vector pseudotyped with said first viral envelope protein(s) is administered separately in time from said (ii) lentiviral vector pseudotyped with said second viral envelope protein(s), and if any from said (iii) lentiviral vectors pseudotyped with said third viral envelope protein(s), each of said lentiviral vectors (i) and (ii) and if any (iii) being administered either for priming or for boosting the immune response.

The choice of the administration regimen may be adapted by the skilled person in view of the intensity and spectrum of the response obtained with selected doses used and number of boosting steps carried out.

In a particular embodiment, the invention concerns a combination of compounds for sequential administration to a human host, to elicit a protective specific cellular immune response against a HIV and the administration regimen encompasses administering the same dose of lentiviral vector for prime and boost steps.

According to another embodiment, the kit of compounds is suitable for use in gene therapy in vivo. Examples of diseases that may be treated with the compounds of the kit of the invention for in vivo gene therapy are neurodegenerative diseases such as Parkinson disease, Amyotrophic lateral sclerosis (ALS), Spinal Muscular Atrophy (SMA) which are motor neurone diseases. Another example of disease that can be treated with the kits of compounds of the invention is the spinal cord'injury.

The kit of compounds of the invention is also suitable for the treatment of cancer, wherein iterative administration of the lentiviral vector may be necessary.

The invention also relates to an immunogenic composition compring a lentiviral particle as defined in the present application, suitable for inhibiting in vivo a HIV-1 or HIV-2 infection or a SIV or a HIV infection in a mammalian host.

The invention also relates to a method of treatment of a host or patient in need thereof, which comprises the successive administration to the host of:
(i) a lentiviral vector, pseudotyped with a first determined heterologous viral envelope protein or viral envelope proteins; followed by,
(ii) a lentiviral vector, pseudotyped with a second determined heterologous viral envelope protein or viral envelope proteins different from said first determined envelope protein or envelope proteins;

wherein said lentiviral vector of (i) and (ii) encodes a heterologous polynucleotide having a therapeutic interest.

In a particular embodiment, a third step of administration to the host of a lentiviral vector pseudotyped with a third envelope protein(s) as disclosed herein is carried out.

According to a particular embodiment of the invention, additional administration steps are performed in order to boost the immune reaction further.

The time left between the two first administration steps may be in the range of 3 to 12 weeks or more depending on the response to the prime. The time left between the first boost and the last boosting step may be in the range of a few weeks, especially more than 12 weeks, for example 6 months, and even may be one or even several years.

According to another embodiment, the gene transfer vectors of the invention may be used as a single active principle, i.e., for a single administration to a host.

Accordingly, the description of the embodiments of the invention, of the features of the gene transfer vectors or of their properties, apply to the vectors when used as a unique administered compound (in contrast to a combination), especially in their non-integrative version.

A treatment or a medicinal treatment according to the invention aims at improving the clinical condition of a patient, especially a human being, in need thereof, who has been diagnosed as infected (even at a stage of primo-infection) by a pathogen or as suffering from a pathological state, or this treatment aims at the elimination of the causative agent or organism of the disease, or at lowering said agent or organism. In a situation of viral infection, the treatment may result in a significant decrease of the viral load in the plasma of the host and possibly in a plasma viral load which is less than what can be detected when measured or, at lowering the size or the development of the tumor if any.

Medicinal treatment includes, when referring to a patient diagnosed with a pathological state, improving the clinical status of said patient and in a preferred embodiment, restoring to health.

It also encompasses a prophylactic treatment of a host in need thereof, especially vaccination to prevent the occurrence of a pathological state in a host.

The experimental results obtained by the inventors, enable to define specific uses for the combination of compounds, kits, methods and generally therapeutic or prophylactic applications disclosed in the present application, especially in the field of medical applications related to the Immunodeficiency Virus, especially HIV and in particular HIV-1 or HIV-2.

These specific uses according to the invention include, independently of each other, or in combination, the following indications, possibly associated with different stages of the infection by an Immunodeficiency Virus, especially by HIV or prior to said infection or prior to the exposure to the retrovirus:

the control of the viremia after exposition to and especially after infection by the retrovirus, and in particular limiting or reducing the viral load in the host;

the induction of protective cellular immunity against the retrovirus in a host, especially against HIV in a human host;

the protection against viral replication after exposure to or infection by the retrovirus, especially the HIV retrovirus;

the protection against depletion of the Central Memory CD4+ T cell response, especially in the acute phase of infection by the retrovirus, especially HIV;

the preservation of the Central Memory CD4+ T cell response, especially in the chronic phase of infection by the retrovirus, especially HIV;

the elicitation of an earlier and/or higher rebound of the naïve and Central Memory CD8+ T cell response during primary infection by the retrovirus, especially HIV;

the prevention against viral escape from immune pressure thereby allowing long-term control of the infection by a retrovirus, especially HIV.

These specific uses are beneficial for the development of an efficient immune response in a prophylactic or therapeutic application, in the field of infection by an Immunodeficiency Virus, They also allow targeting the applications of the invention to various categories of hosts, depending on their clinical profile, in relation to the stage of infection by the retrovirus (including prior to infection or to exposure to the retrovirus) or pathogenesis, because they impact on various compartments of the immune system, which are involved at different stages of the immune response depending on the stage of the infection.

Although it seems not to be necessary in the case of administering lentiviral vectors expressing SIV or HIV antigens, it may be decided, in other applications to further include in the combination of compounds, adjuvant and/or vehicle when used for systemic or local administration, or it may be devoid of such components.

In any cases suitable excipients for the formulation of the medicinal compositions may be added.

The compositions quoted above can be injected in a host via different routes: subcutaneous (s.c.), intradermal (i.d.), intramuscular (i.m.) or intravenous (i.v.) injection, oral administration and mucosal administration, especially intranasal administration or inhalation. The quantity to be administered (dosage) depends on the subject to be treated, including considering the condition of the patient, the state of the individual's immune system, the route of administration and the size of the host. Suitable dosages range expressed with respect to the content in equivalent p24 antigen of vector particles (for HIV-1 lentiviral vectors) and can be determined.

When used for a single administration, the vector of the invention may be administered in dosages which range from 1 to 100 µg, preferably 1 to 50 µg and most preferably 1 to 10 µg, and can be modified by one skilled in the art, depending on circumstances. When, formulated for subcutaneous injection, the immunogenic composition of the invention preferably comprises between 1 and 100 µg of the lentiviral vector per body weight of the host, more preferably from 1 to 30 µg/dose, especially around 10 µg/dose, in a sole injection.

Other examples and features of the invention will become apparent in the examples and figures.

FIG. 1: Various examples of DNA flap sequences derived from different viruses.

FIG. 2: (A) vector genome construct organization for the purpose of the invention, based on a typical HIV-1 genome sequence; (B) Schematic representation of the TRIP/sEwnv vector (C) Schematic representation of the TRIP/Es(WNV); (D) Schematic representation of plasmid pTRIPΔU3.CMV-GFP; (E) Schematic representation of plasmid pTRIP[delta]U3EF1 [alpha]-GFP.

The following abbreviations are used: U3, R and U5 represent the domains of the LTR; ΔU3: deletion of the U3 domain: RRE: Rev-responsive element; ψ: encapsidation signal; cPPT and CTS represent the DNA flap; CMVie: cytomegalovirus immediate early promoter.

Details on the construct and especially on the DNA flap and on its insertion in a HIV-1 based genome are available in (Zennou et al 2000).

FIG. 3: (A) Alignment of VSV-G protein sequences from various serotypes known in the Vesiculovirus genus for VSV species: Indiana (NCB' Accession Number J02428), Chandipura (J04350), Piry (D26175), New Jersey, Cocal (AF045556), Isfahan (AJ810084) and Spring viremia of carp virus (SVCV)(AY527273). The Indiana protein and New Jersey protein are those used in the examples. (B) VSV-G protein sequences from various serotypes known in the Vesiculovirus genus for VSV species: Indiana, Chandipura, Piry, New Jersey, Cocal, Isfahan and Spring viremia of carp virus (SVCV).

FIG. 4: Nucleotide sequence of the TRIPsEwnv vector. The cPPT/CTS region is underlined. In this region, cPPT and CTS domains appear in lowercase. The sEwnv sequence, represented in bold, is a BsiWi-BssHII DNA insert. This vector has been deposited at the CNCM (Paris, France), under number I-3076, on Aug. 27, 2003.

FIG. 5: Nucleotide sequence of the TRIP GFP vector. The cPPT/CTS region is underlined. In this region, cPPT and CTS domains appear in lowercase. The GFP sequence is located between nucleotides 2816 to 3573. This vector has been deposited at the CNCM, under number I-2330, on Oct. 11, 1999 (pTRIP [deltaU3] CMV GFP).

FIGS. 6-12: VSV-G protein sequence (with transmembrane domain underlined) (A) and coding codon optimized nucleic acid (B) for various strains of VSV. An envelope plasmid comprising each codon optimized sequence is described (C). The plasmid is derived from pThV plasmid and comprises A CMV promoter that may be substituted by another promoter;

A codon optimized polynucleotide encoding VSV-G;

A WPRE (ΔATG) sequence which is optional;

A polyA sequence

A kanR (kanamycine resistance gene) that may be substituted or deleted

An origin of replication (pUC ORI)

The VSV-G envelope represented are respectively:

FIG. 6: Indiana VSV-G (SEQ ID NO: 31 & SEQ ID NO: 32). This envelope has been inserted into plasmid pThV-VSV-G (IND-CO) deposited under I-3842.

FIG. 7: New Jersey VSV-G (SEQ ID NO: 33 & SEQ ID NO: 34). This envelope has been inserted into plasmid pThV-VSV-G (NJ-CO) deposited under I-3843. The deposited plasmids are in *E. coli* cells. Their suitable growth medium is LB Kanamycin 10 µg/ml and the incubation temperature is 37° C. For storage they may be suspended in fluid with 50% LB and 50% Glycerol.

FIG. 8: Chandipura VSV-G (SEQ ID NO: 35 & SEQ ID NO: 36)

Figure 9C:
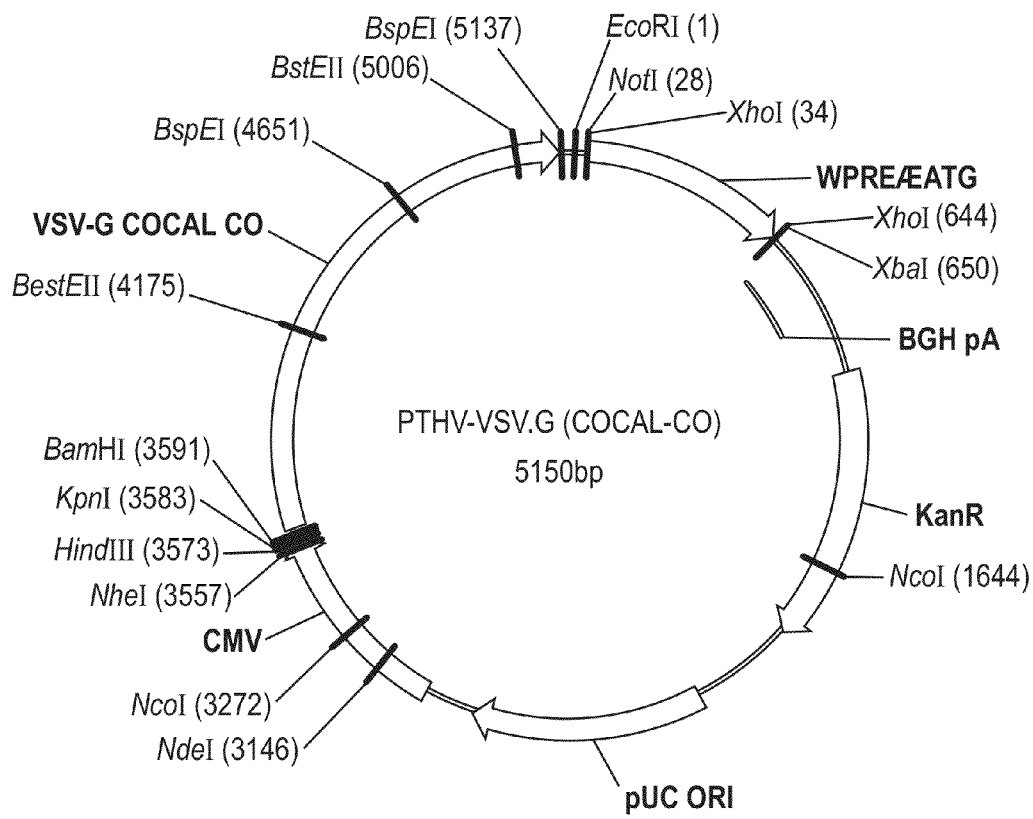
Figure 9C:
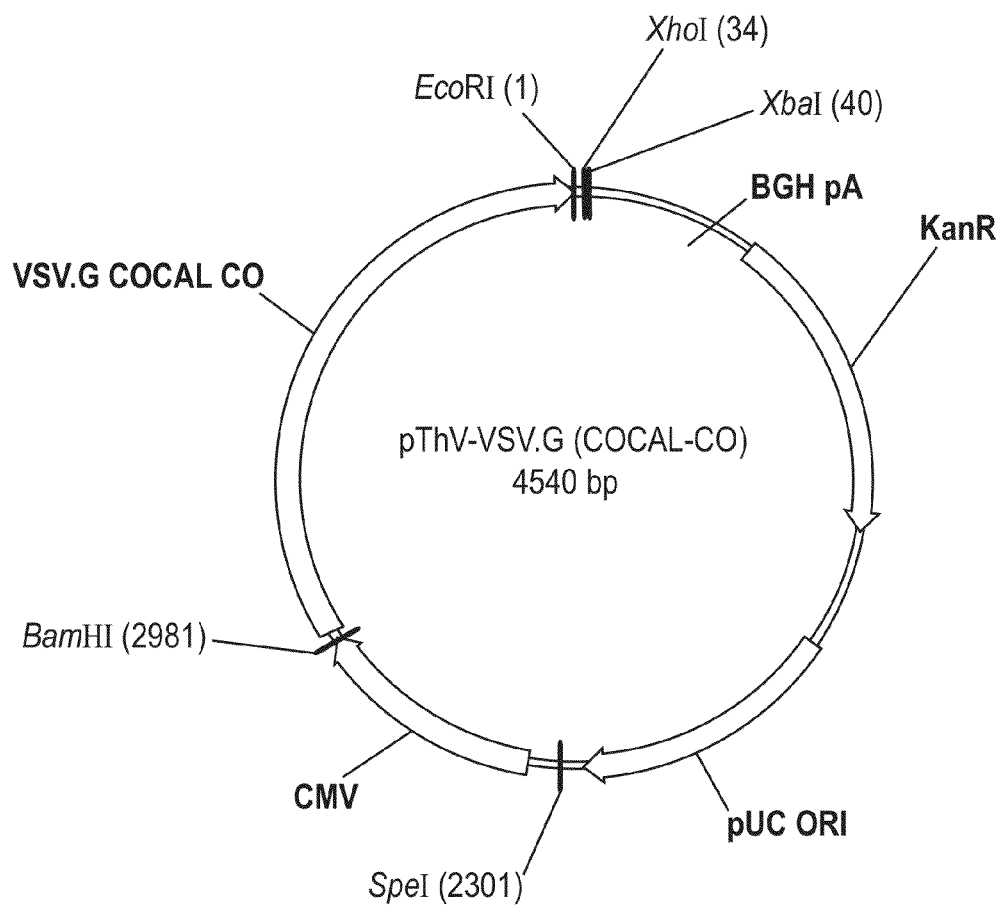

FIG. 9: Cocal VSV-G (SEQ ID NO: 37 & SEQ ID NO: 38)

Figure 10C:
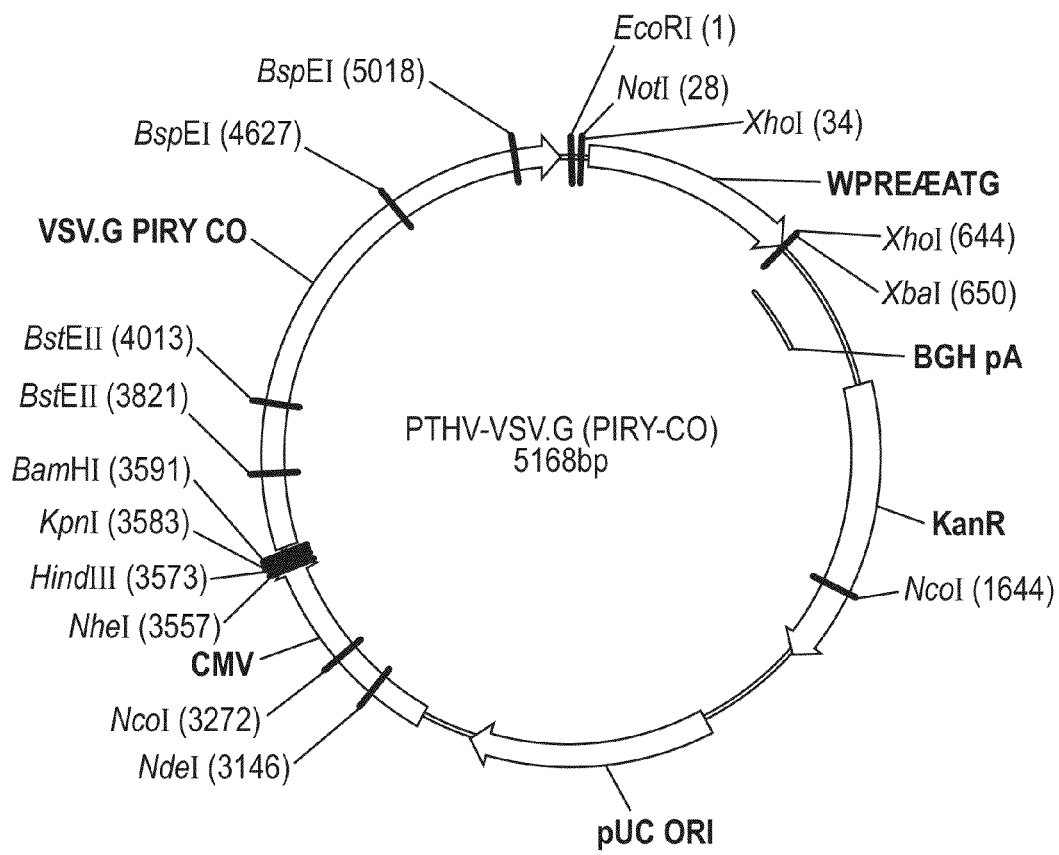
Figure 10C:
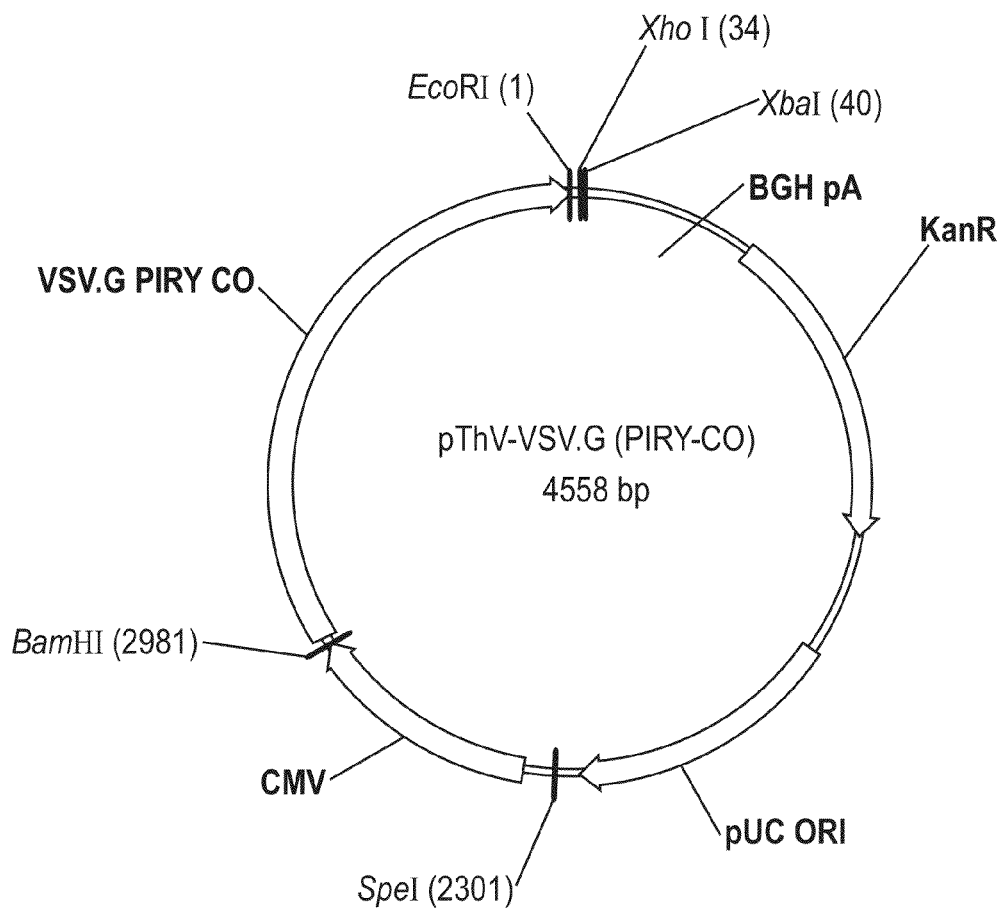

FIG. 10: Piry VSV-G (SEQ ID NO: 39 & SEQ ID NO: 40)

Figure 11C:
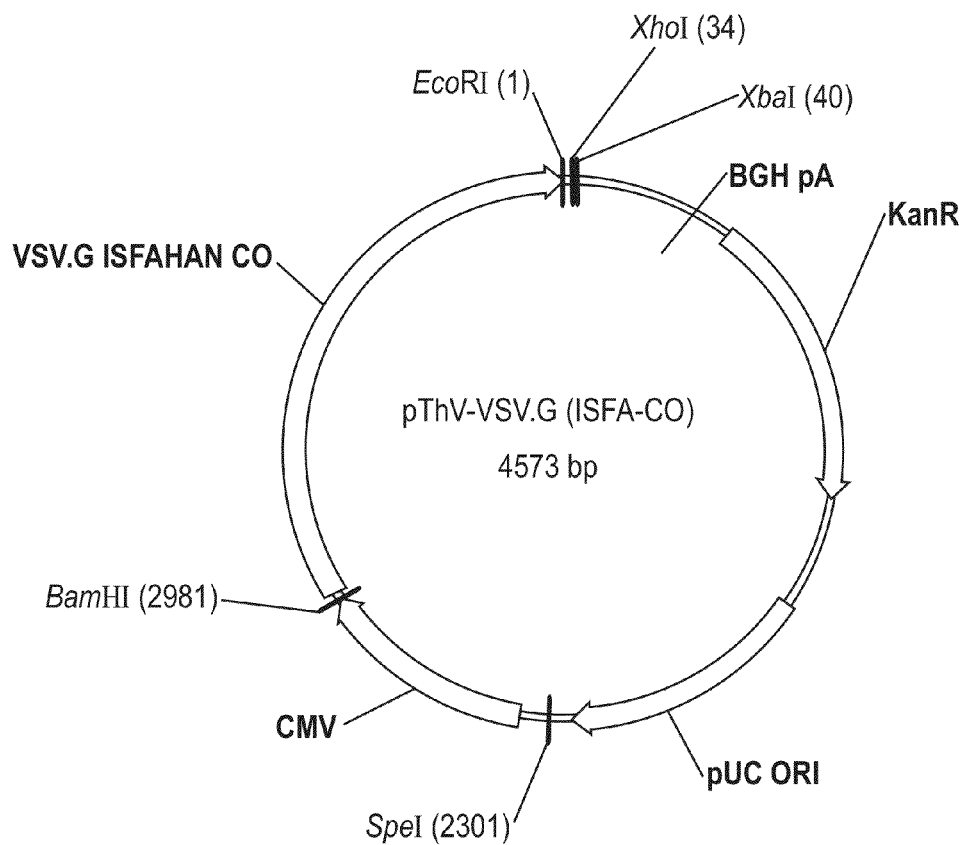

FIG. 11: Isfahan VSV-G (SEQ ID NO: 41 & SEQ ID NO: 42)

FIG. 12: SVCV-VSV-G (SEQ ID NO: 43 & SEQ ID NO: 44)

FIG. 13 represents a fusion gene between the VSV-G New Jersey and the VSV-G Indiana genes. The transmembrane domain is in bold and is underlined. The PCR strategy for the preparation of the fusion gene is disclosed. The oligonucleotides used as primers are described.

FIGS. 14 to 19 disclose fusion proteins obtained by recombining different domains of various VSV-G proteins. For each protein, the codon optimized (for expression in human cells) nucleic acid (A) is provided, together with a plasmid (B) comprising said nucleic acid.

Figure 14:
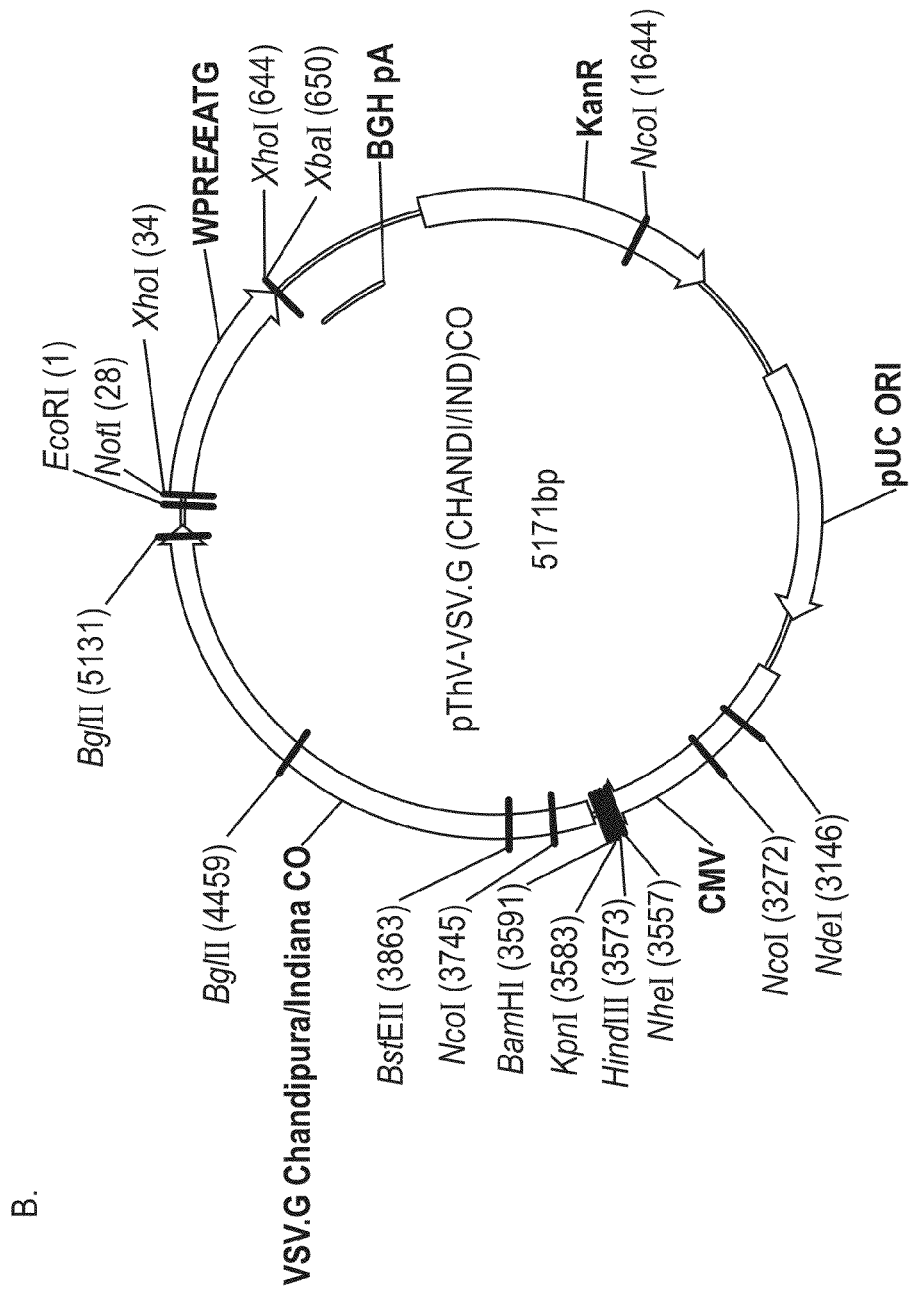

FIG. 14: fusion protein of VSV-G Chandipura/Indiana (SEQ ID NO: 54 & SEQ ID NO: 55)

FIG. 15: fusion protein of VSV-G Cocal/Indiana (SEQ ID NO: 56 & SEQ ID NO: 57)

Figure 16C:
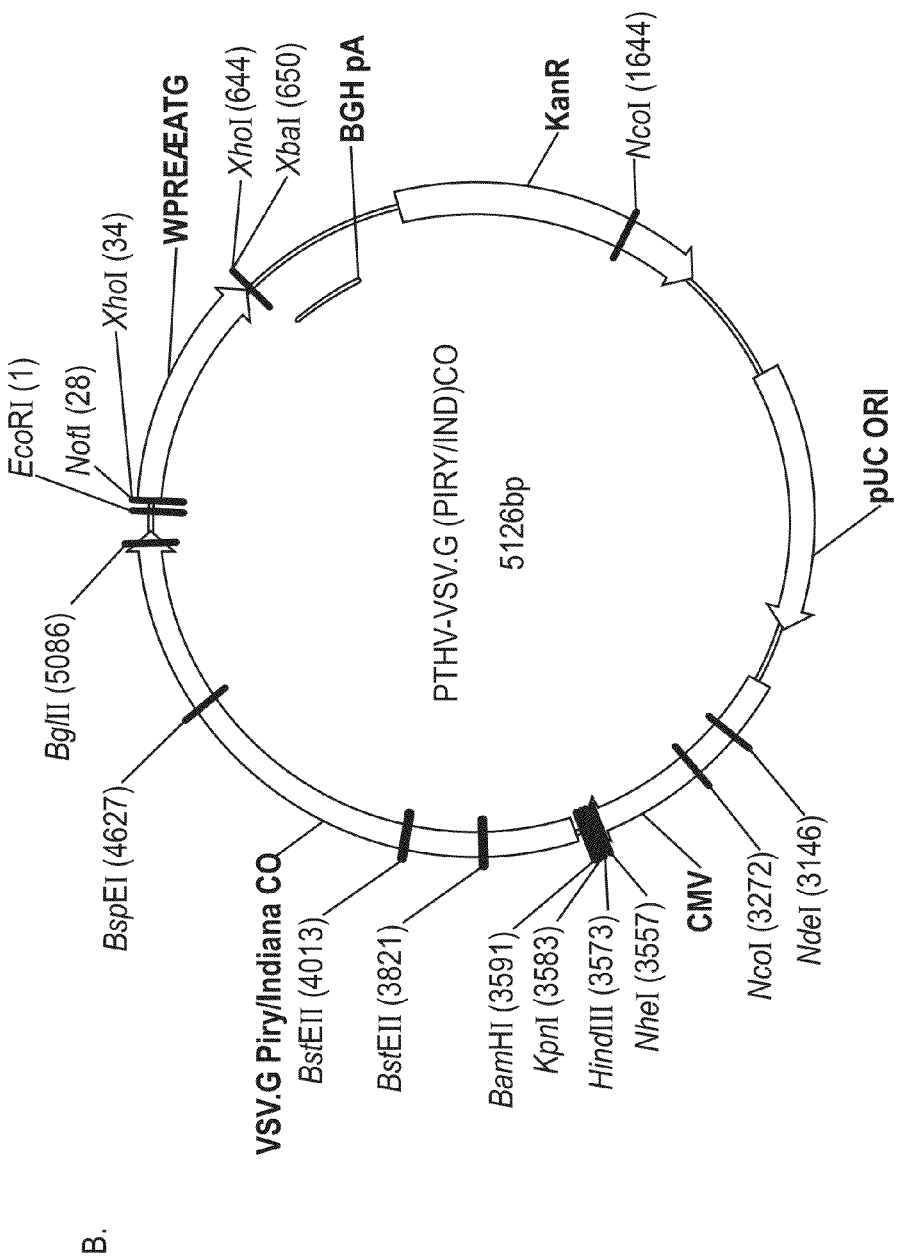

FIG. 16: fusion protein of VSV-G Piry/Indiana (SEQ ID NO: 58 & SEQ ID NO: 59)

FIG. 17: fusion protein of VSV-G Isfahan/Indiana (SEQ ID NO: 60 & SEQ ID NO: 61)

FIG. 18: fusion protein of VSV-G SVCV/Indiana (SEQ ID NO: 62 & SEQ ID NO: 63)

Figure 19C:
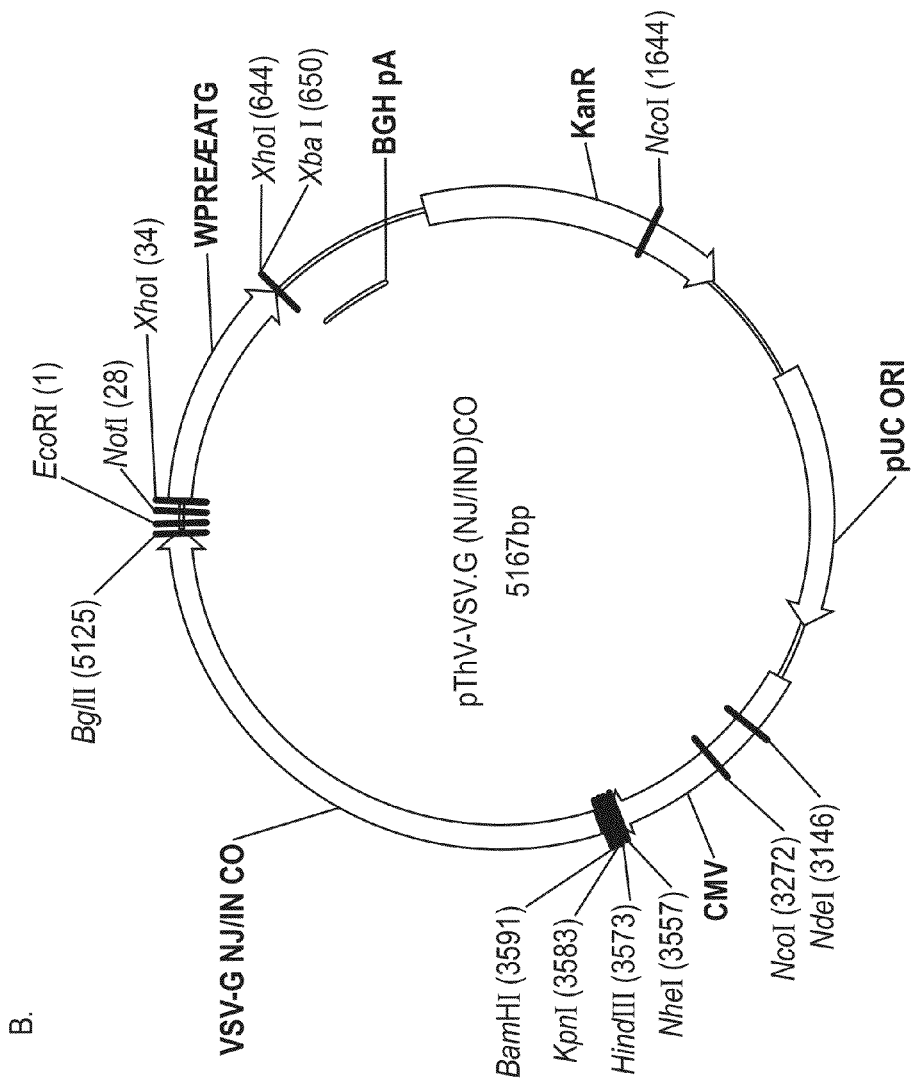

FIG. 19: fusion protein of VSV-G New Jersey/Indiana (SEQ ID NO: 64 & SEQ ID NO: 65).

FIG. 20: shows the effect of codon-optimization upon lentiviral vectors pseudotyped with New-Jersey VSV-G-glycoprotein. The human codon-optimization of the VSV-G gene (NJ serotype) stimulates gene transfer of a 100× factor.

FIG. 21: illustrates sequences of antigens of interest for the invention. The nucleic acids encoding these antigens, especially in a codon-optimized version for human cells may be inserted in the heterologous polynucleotide of the vector genome. The illustrated antigens are: A native GAG antigen of HIV-1 LAI isolate (sub type B) (D) (SEQ ID NO: 69) and the corresponding nucleic acid sequence (E) (SEQ ID NO: 70); a modified HIV-1 GAG, which is a delta Myr-GAG antigen prohibiting myristilation, and derived from the consensus sequence of the B subtype (A) (SEQ ID NO: 66); an antigen derived from HIV-1 POL, which is a fragment of POL polyprotein (B)SEQ ID NO: 67); an antigen derived from HIV-1 NEF, which is a fragment of NEF protein (C) (SEQ ID NO: 68). These antigens may be used in combination in a fusion protein. The POL and/or NEF fragments may be inserted 5' or 3' of the GAG derived antigen. They may be contiguous to each other and inserted 5' or 3' from the GAG derived antigen. They may be separated and inserted, one in 5', the other in 3' from the GAG derived antigen. The POL, NEF and GAG derived antigens may be separated or not by a peptide, especially one enabling auto-cleavage. A suitable separating peptide is a 2A peptide from picronavirus having sequence: APVKQTLNFDLLKLAGDVESNPGP (SEQ ID NO: 8).

Figure 22:
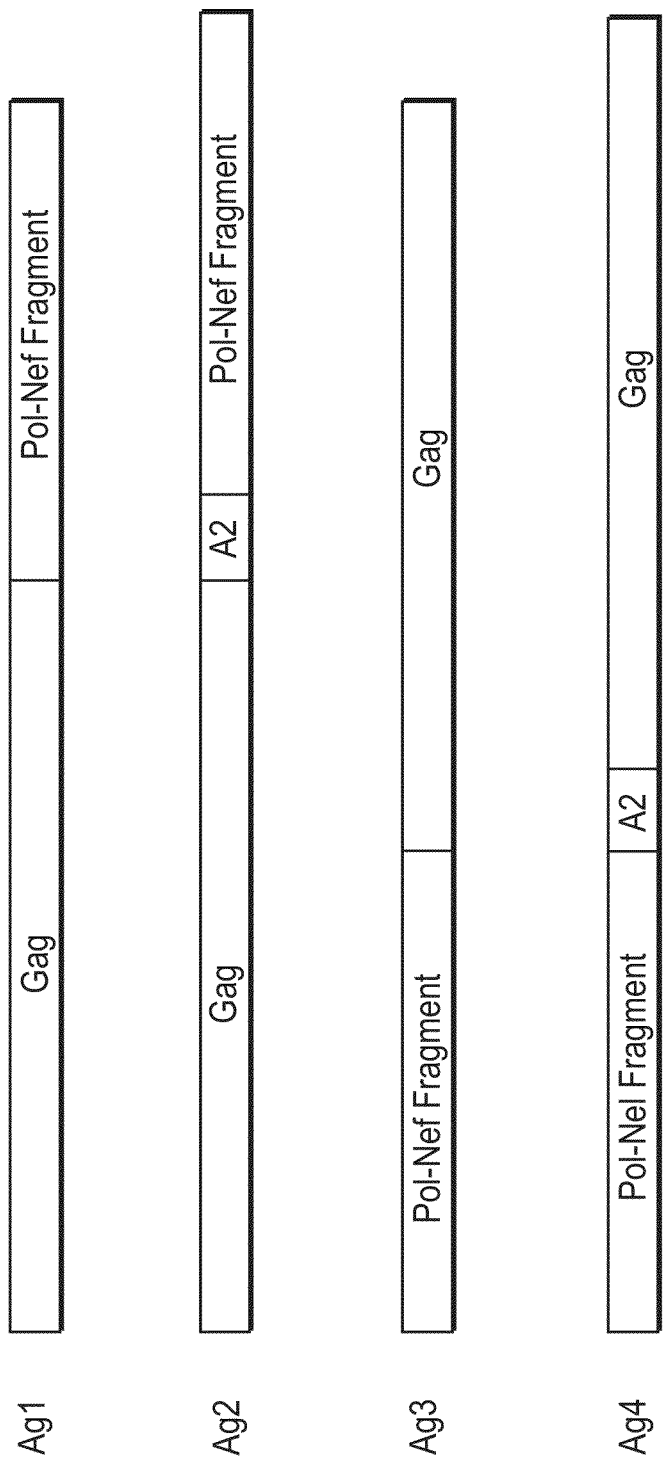

FIG. 22 illustrates various antigen constructs according to FIG. 21, for the design of human HIV-1 antigen for vaccination against AIDS.

Figure 23:
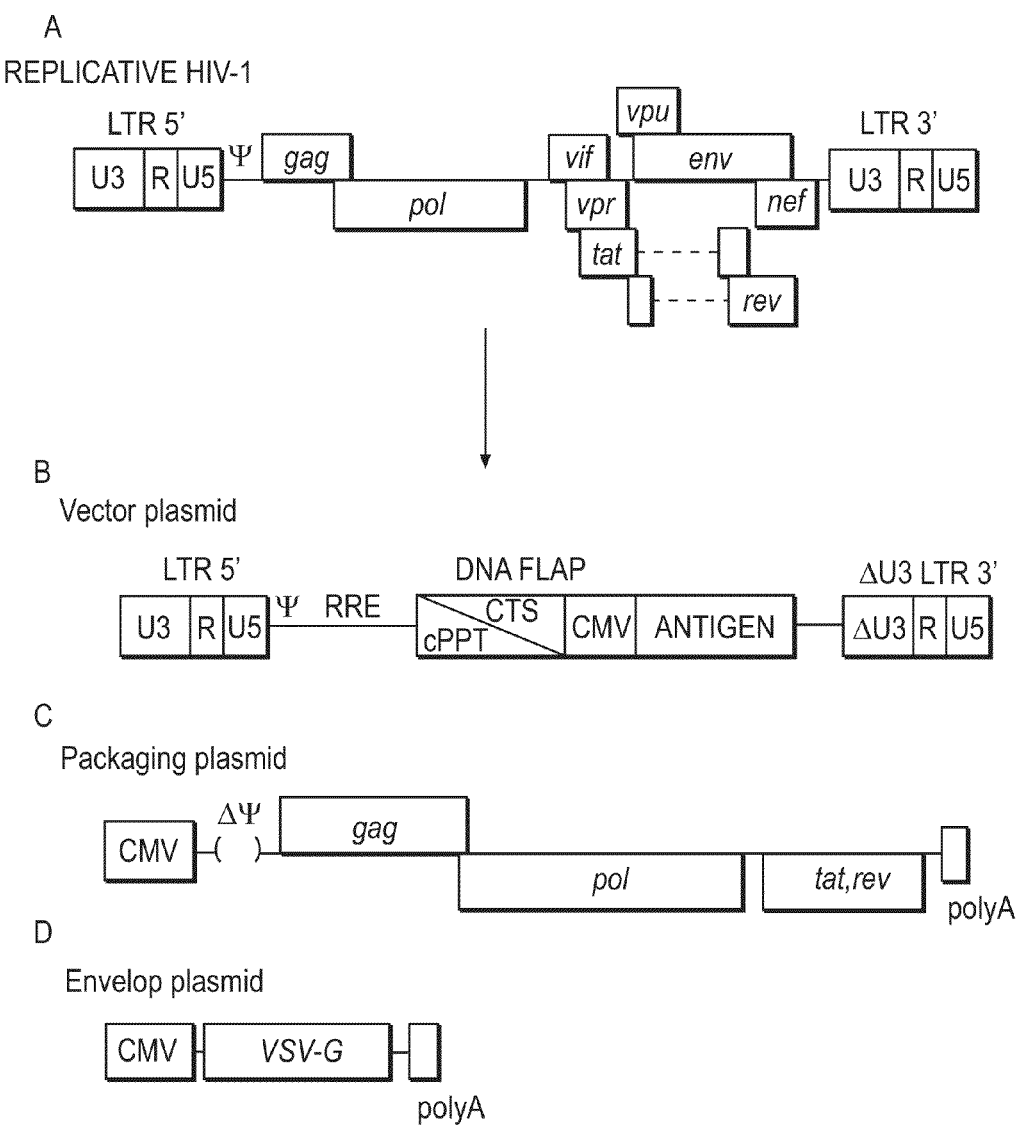

FIGS. 23 to 27: Principle of TRIP Lentiviral Vectors generation and application for the preparation of Lentiviral vector particles expressing an antigen derived from SIVmac239 GAG polyprotein. The same principle would apply for other antigens. The figures describe especially the following features:

FIG. 23: Principle of TRIP Lentiviral Vectors generation.

HIV-1 genome (A) is split into a vector plasmid (B), containing the cis-acting sequences (LTR, encapsidation signal, RRE, DNA Flap) and the gene of interest (antigen for vaccination) under the control of an heterologous promoter (CMV) or another promoter, a packaging plasmid (C) containing genes gag, pol, tat and rev, necessary for encapsidation (during vector particle production) and for the early step of viral replication cycle (in transduced cells) and an envelop plasmid (D), containing an Indiana serotype of the glycoprotein G from the VSV. Packaging plasmid and envelop plasmid have heterologous transcriptional regulation elements from CMV and are deleted in encapsidation sequence, in cPPT, and CTS.

Figure 24:
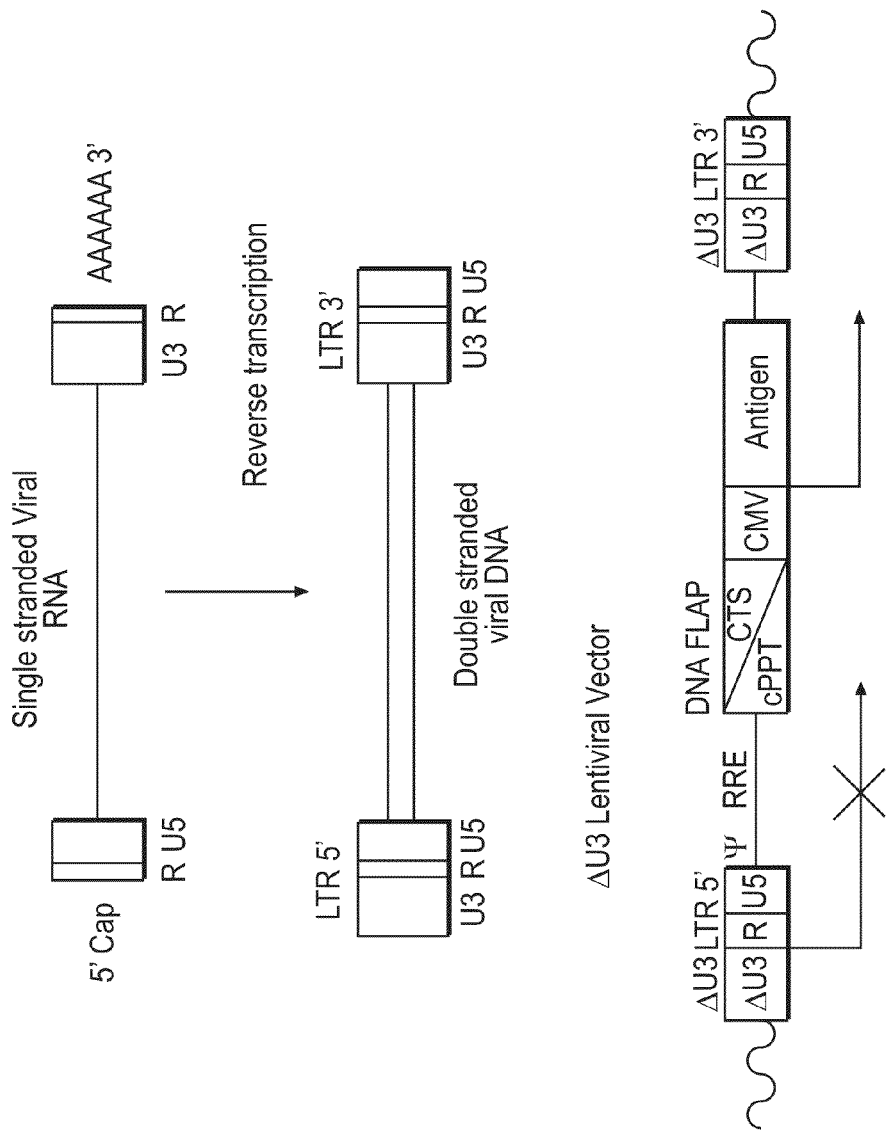

FIG. 24: Principle of U3' deleted Lentiviral Vector

During reverse transcription of viral single stranded RNA, there is a duplication of U3' and U5' sequences which allow then forming the 5'LTR and 3'LTR in the double stranded viral DNA. Transcription of viral DNA begins in the cell from the LTR 5'. If the U3' region is deleted in vector plasmid (ΔU3), viral RNA is also ΔU3, consequently, after reverse transcription, viral DNA misses the U3 sequence in the 5'LTR, no transcription can begin from the viral LTR promoter. As a consequence, transcription is mediated only via the internal promoter of the transgene.

Figure 25B:
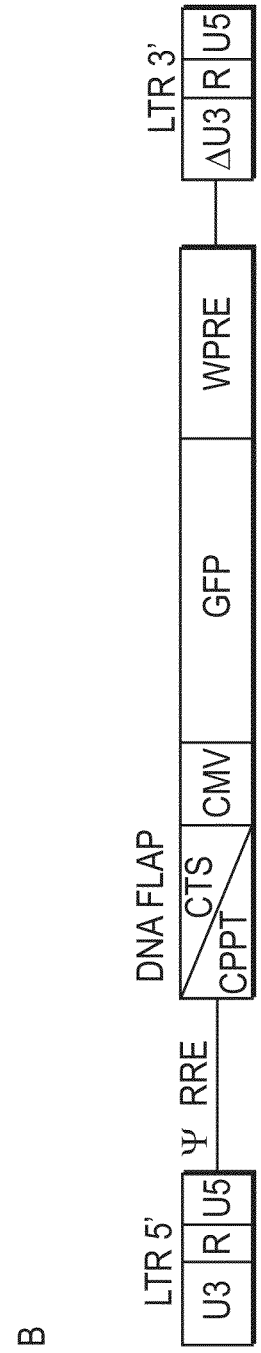

FIG. 25: Schematic representation of the 2 vector plasmids used for TRIP vectors production
A: TRIP-SIVmac239 Gag. This vector plasmid contains the sequence encoding the antigen, SIVmac239 gag, deleted in the myristilation sequence. This allows to work only in L1, P1 bio-safety level because it abrogates protein secretion in transfected cells and in transduced cells.
B: TRIP-GFP. This vector plasmid contains the irrelevant antigen Green Fluorecent Protein (GFP).

Both vector plasmid contain upstream the CMV promoter for antigen expression and downstream the WPRE sequence to improve antigen expression. They also contain the viral sequences necessary for vector particle formation and early steps of viral replication. in transduced cells: Long Terminal Repeat (LTR), DNA Flap (cPPt, CTS), RRE, encapsidation signal ψ.
C. pTRIP DeltaU3-CMV-SIVGag-WPRE restriction map of the vector genome (C1) and its nucleic acid sequence (C2). The vector construct has been deposited at the CNCM under I-3840.
D. pTRIP DeltaU3-CMV-SIVGag co-WPRE restriction map of the vector genome (D1) and its nucleic acid sequence (D2). The vector construct has been deposited at the CNCM under I-3841;

The plasmids of the deposits are introduced in E. coli cells. The culture medium of the cell is LB Ampi 100 µg/ml and the incubation is at 37° C. Storage is in suspending fluid with 50% LB 50% Glycerol, FIG. 26: Schematic representation of the SIVmac239 GAG protein divided in 15mer long peptides The SIV mac239 GAG protein is 511 Amino Acid long (SEQ ID NO: 73). This protein was divided into 125 peptides. These Peptides are 15 amino acids in length; there is 11 amino acids overlap between sequential peptides. Peptides are dispatched into 11 pools named from letter M to W, containing 5 to 12 peptides.

FIG. 27: (A) Sequences of primers and probes and qPCR program used for vector titration (SEQ ID NOs: 74-81); (B) Scheme of the standardisation plasmid used for building standard curve in Q-PCR vector titration with localization of probes and primers annealing sites.

FIG. 28(1): A prime/boost lentiviral vector-based vaccination strategy induces robust cellular immunity The longitudinal follow-up of the SIVmac239 GAG specific T cells responses was performed at various time points post-prime, post-boost and post-challenge by IFN-γ ELISPOT assay after restimulation of whole PBMC with pools of overlapping peptides encompassing SIVmac239 GAG p55. The individual GAG-specific cumulative responses of all 6 vaccinated animals injected with TRIP-SIVmac239 GAG (low dose: 20022, 20089; medium dose: 20293, 20056; high dose, 20195 and 20158, FIG. 28a), 2 control animals immunized with an irrelevant antigen (TRIP-GFP) at a high p24 dose (21544 and 20456, FIG. 28b) and unvaccinated animals (15661, 14184, 15885 and 14468, FIG. 28c) are shown.

Briefly, 0.2 10$^6$ PBMC per well were restimulated in vitro for 40 hours with 11 pools of 5 to 12 overlapping 15-mers peptides (2 µg/ml of each peptide). The mean number of IFN-γ spots forming cells (SFC) per million PBMC was calculated from triplicate wells after subtracting the one from control wells (no peptide). The cumulative responses shown correspond to the sum of IFN-γ SFC/million PBMC obtained with each pool of peptides. The symbol + indicates an underestimation of the cumulative response due to saturated ELISPOT wells for at least one pool of peptides (see FIG. 29(2)). Two weeks post-challenge, it was not possible to quantify the number of spots in the control wells and thus to calculate the cumulative response for animal 20022 (noted ++) (nd, not determined).

FIG. 28(2): Subcutaneous injection of lentiviral vector did not result in systemic inflammation The presence of IFN-α (PBL Biomedical Laboratories) (FIG. 28(2)a), IL-6(U-Cytech Bioscience) (FIG. 28(2)b) and TNF-α (U-Cytech Bioscience) (FIG. 28(2)c) in the plasma shortly after subcutaneous injection was measured by ELISA. The absence of either significant (IFN-α and TNF-α) or major (IL-6) increase in their level suggested there was not systemic inflammation induced by the in vivo administration of lentiviral vector particles, even at high dose (2.5 10$^8$ TU/animal). These data did not exclude a local inflammation likely triggered by intrinsic PAMP (Brown B, D et al, 2007; Pichlmair A et al, 2007; Georgel P. et al, 2007).

FIG. 29(1): Vaccinated macaques have an improved control of viremia compared to unvaccinated and control animals Plasma viral loads were followed for 5 months post-challenge, twice a week during the first 3 weeks, then once a week during the next 3 weeks and finally once a month. Viremia of unvaccinated (FIG. 29a 15661; 14184; 15885; 14468 lines marqued with □; ◊; Δ; ∇), control (FIG. 29a 21544 with x) and vaccinated animals (FIG. 29b), as well as the mean for the naive and control group (in black) versus the vaccinated group (in grey) (FIGS. 29a, 29b and 29c) are shown. The mean of viral replication levels was lower in the vaccinated group at all time points tested (FIG. 29c). P. values <0.05 are noted *. An average of 2 log 10 fold reduction of viremia was observed at the peak of primo-infection (FIG. 29e). The mean viremia of the vaccinated animals (in grey) was also compared to the mean viremia of progressor animals (14184-21544-20456) in orange and to the mean viremia of non-progressor animals (15661-15885-14468) in light blue (FIG. 29d). Post-acute viremia were lower in vaccinated animals in comparison to progressor animals. P. values <0.05 are noted *. A measure of viral replication during the first 154 days after infection was determined by integrating viral loads between day 0 and day 154 (area under the curve, AUC) to compare the vaccinated animals to the naive control ones (FIG. 29f).

Briefly, viral RNA was isolated from plasma (200 µl) with TRI Reagent BD (Molecular Research Center). The number of RNA copies was determined in a quantitative one-step RT-PCR using the Taqman EZ RT-PCR (Applied Biosystem) and the Mastercycler ep realplex (Eppendorf). The primers were respectively at position 389 and 456 of SIVmac251 GAG mRNA genome (forward, TGTCCACCTGCCAT-TAAGCCCGA (SEQ ID NO: 9); reverse, GCAGAGGAG-GAAATTACCCAGTAC) (SEQ ID NO: 10). The Taqman quantification method was chosen with an internal probe containing the Fam and Tamra fluorophores respectively in 5' and 3' (TGTCCACCTGCCATTAAGCCCGA) (SEQ ID NO: 11). The quantity of viral RNA copies was assessed by extrapolation of threshold fluorescence values onto an internal standard curve prepared from serial dilutions in dH$_2$O of RNA obtained by in vitro transcription with the MAXIscript kit (Ambion) of a SpeI linearized pGEM-5Zf(+) GAG plasmid. The threshold of detection was 375 RNA copies/ml (2.57 log 10 RNA copies/ml).

FIG. 29(2): Saturation of the ELISPOT assay

An IFN-γ ELISPOT assay was performed using serial dilutions of PBMC to determine the saturation curve of the ELISPOT reader (280 spots/well corresponding to 1400 spots/million PBMC since 200,000 cells are used) FIG. 29(2)a). When the frequency of specific T cells was high and spots overlapped (acquisition), the number of IFN-γ SFC/million was therefore underestimated to 1400 before substracting the background (analysis). The example of PBMC from animal 20056 restimulated with the peptide pools covering SIVmac339 GAG:385-443 and SIVmac339 GAG:443-491 2 weeks post-challenge is given (FIG. 29(2)b).

FIG. 30(1): The central memory CD4+ T cells compartment is well preserved in vaccinated macaques.

Changes in the numbers of central memory (CM) CD4+ T cells in the peripheral blood, a strong correlate of progression, were followed for 5 months post-challenge. Dynamics of other cell compartments (total CD4+, naive CD4+total CD8, naive CD8+, CM CD8+, and effector memory (EM) CD8+ T cells) are available on FIG. 32(2).

The % of baseline CM CD4+ T cells of naive (FIG. 30a 15661-14184-15885-14468), control (FIG. 30a 21544-20456 marqued with ○ or x) and vaccinated animals (FIG. 30b all the lines but the one with ♦), as well as the mean for the naive and control group (marqued with ▲ in black) versus the vaccinated group (marqued with ♦ in grey) (FIGS. 30a, 30b and 30c) are shown. Vaccinated animals showed a full preservation of their CM CD4+ T cells compartment during primo-infection and no gradual depletion in the chronic phase in contrast to naive and control animals (FIG. 30c) and to progressor animals (14184-21544-20456) with ▲ (FIG. 30d) (p. values <0.05 are noted *). CM CD4+ T cells for all animals are compared at the peak of primo-infection (FIG. 30e).

The quantifications of absolute lymphocyte counts, proportions of CD3+CD4+ T cells and of naive, EM and CM T cells (defined as CD28+CD95−, CD28+CD95+ and CD28− $^{CD}$ 95+ cells) were described previously (Karlsson I et al 2007).

FIG. 30(2): Vaccine-induced T cells responses were broad and they recognized antigen derived from AT2-inactivated SIV The diversity and the relative contribution of the proteins encoded by GAG (matrix MA, capsid CA, nucleocapsid NC and p6) to the vaccine-induced, virus-induced and virus-recalled GAG-specific T cells responses were studied by IFN-γ ELISPOT assay at the peak of the primary responses (2 weeks post-prime, FIG. 30(2)a), a week after the boost (FIG. 30(2)b) and during the acute phase of infection (3 weeks post-challenge, FIG. 30(2)c). AT-2 inactivated SIVmac251 (5 μg/ml of total viral proteins) was also used to restimulate GAG-specific CD4+ and CD8+ T cells 2 weeks post-boost in a whole PBMC IFN-γ ELISPOT assay (FIG. 30(2)d). Background after coculture with the control microvesicles was substracted. Saturated responses were indicated with +. AT-2-inactivated SIVmac 251 and its control microvesicles were obtained from JD Lifson (Frederick, Mass.) through the EU Program EVA Centralized Facility for AIDS Reagents (NIBSC, Potters Bar, UK)

FIG. 31(1): Immune correlates of protection

Control of plasma viral loads at the peak of primo-infection was tested for correlation (Spearman's rank) with GAG-specific T cell responses. A high frequency of IFN-γ secreting T cells after the prime injection (FIG. 31a), the boost injection (FIG. 31b) and after challenge (FIG. 31c) correlated with a better control of viremia at the peak of primo-infection. The significances of correlations are under-estimated due to occasional satutation of ELISPOT wells, The preservation of central memory CD4+ T cells (CM) during the acute phase also strongly correlated with reduction of viral loads at the peak of primo-infection (FIG. 31d).

FIG. 31(2): Injected animals develop humoral responses toward the glycoprotein G from VSV used to pseudotype the vector particles The presence of neutralizing antibody against the envelope used for pseudotyping was measured with an in vitro transduction assay. P4 cells (HeLa derived) were cultured in the presence of lentiviral vectors encoding GFP pseudotyped with VSV-G Indiana (FIG. 31(2)a) or VSV-G New Jersey (FIG. 31(2)b) pre-incubated with plasma diluted at 1:20 from immunized animals collected at various time points. The transduction efficacy was assessed by flow cytometry. In the absence of plasma and at the dose of vector used, 61% and 23% of P4 cells were GFP+ after transduction with lentiviral vectors encoding GFP pseudotyped with VSV-G Indiana and New Jersey respectively.

Figure 32:
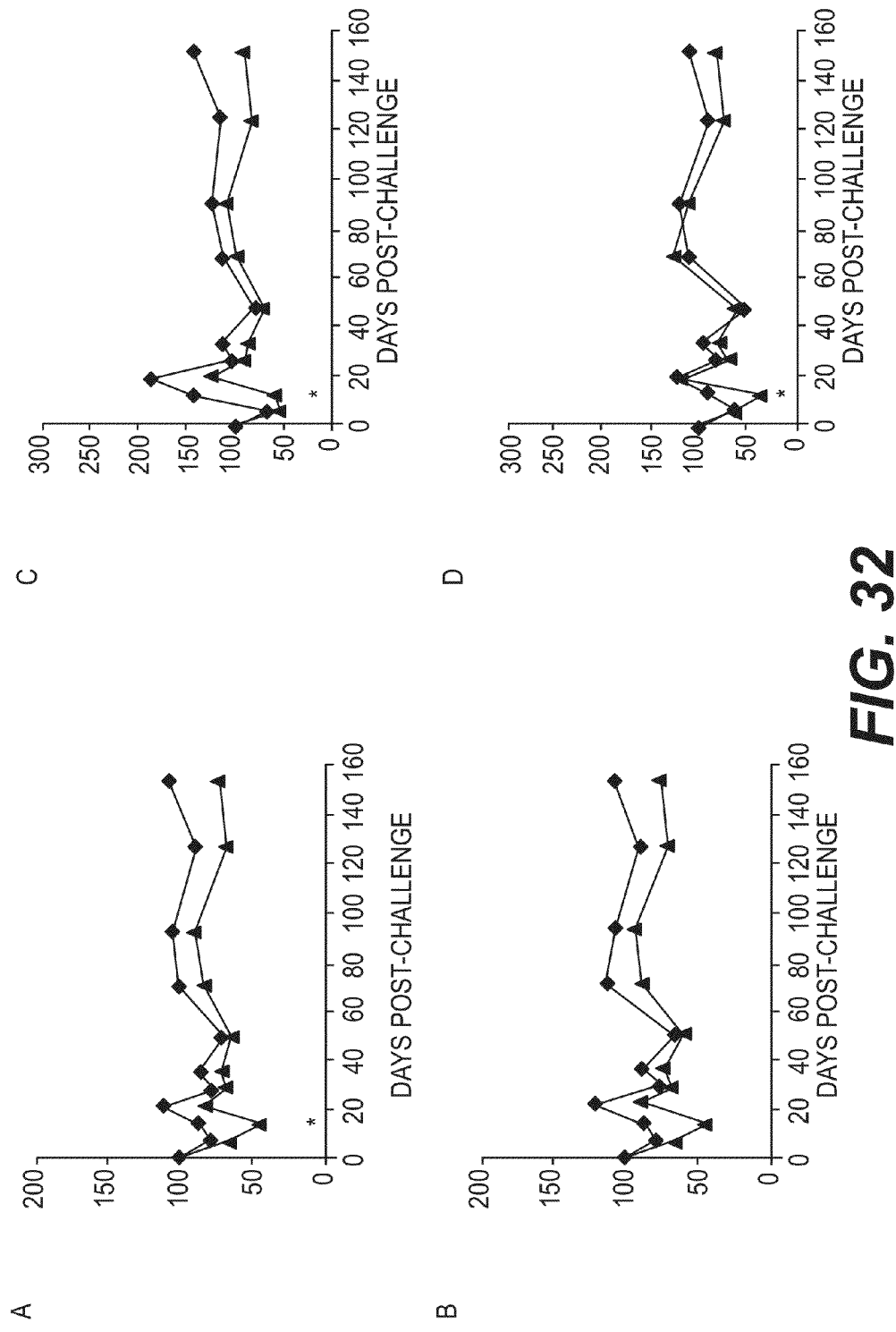
Figure 32:
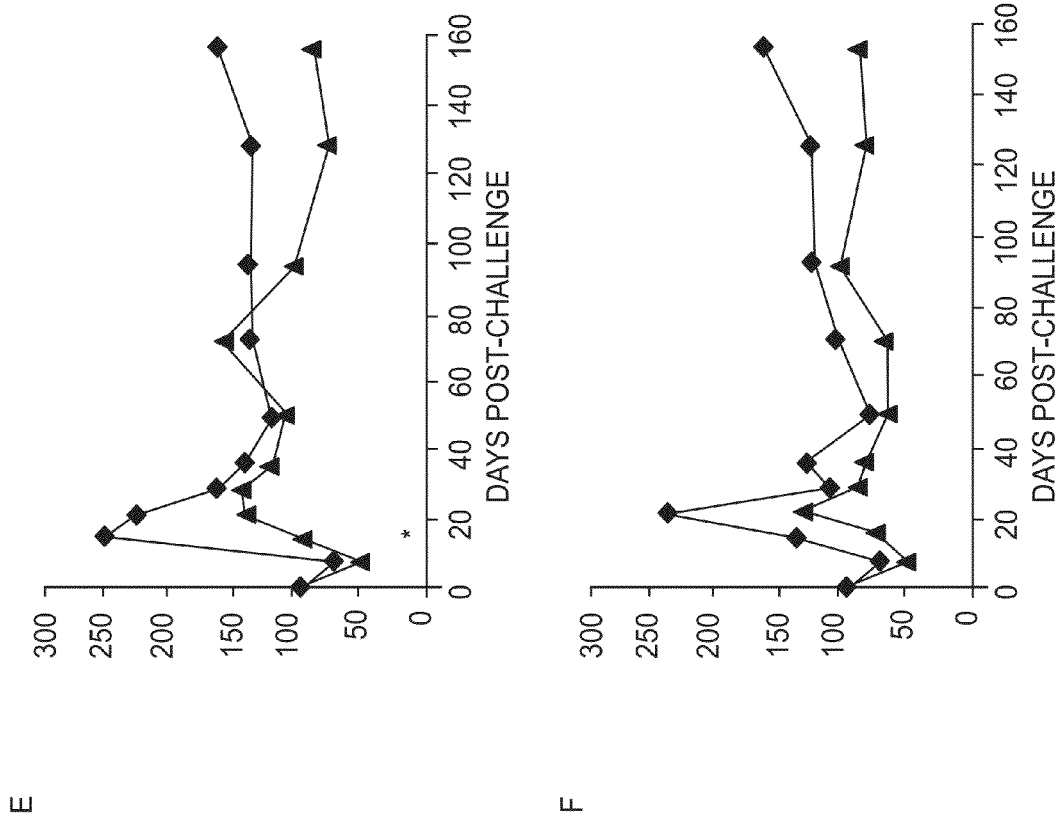

FIG. 32: The dynamics of total, naive and memory CD4+ and CD8+ T cells in vaccinees differ from those of unvaccinated and control macaques after infection The % of baseline total CD4+ T cells (FIG. 32a), naive CD4+ T cells (FIG. 32b), total CDS+ T cells (FIG. 32c), naive CD8' T cells (FIG. 32d), central memory (CM) CD8+ T cells (FIG. 32e) and effector memory (EM) CD8+ T cells (FIG. 32f) were followed. The mean for the naive and control group (black triangle) versus the vaccinated group (grey diamond) are shown. P. values <0.05 are noted *.

Figure 33:
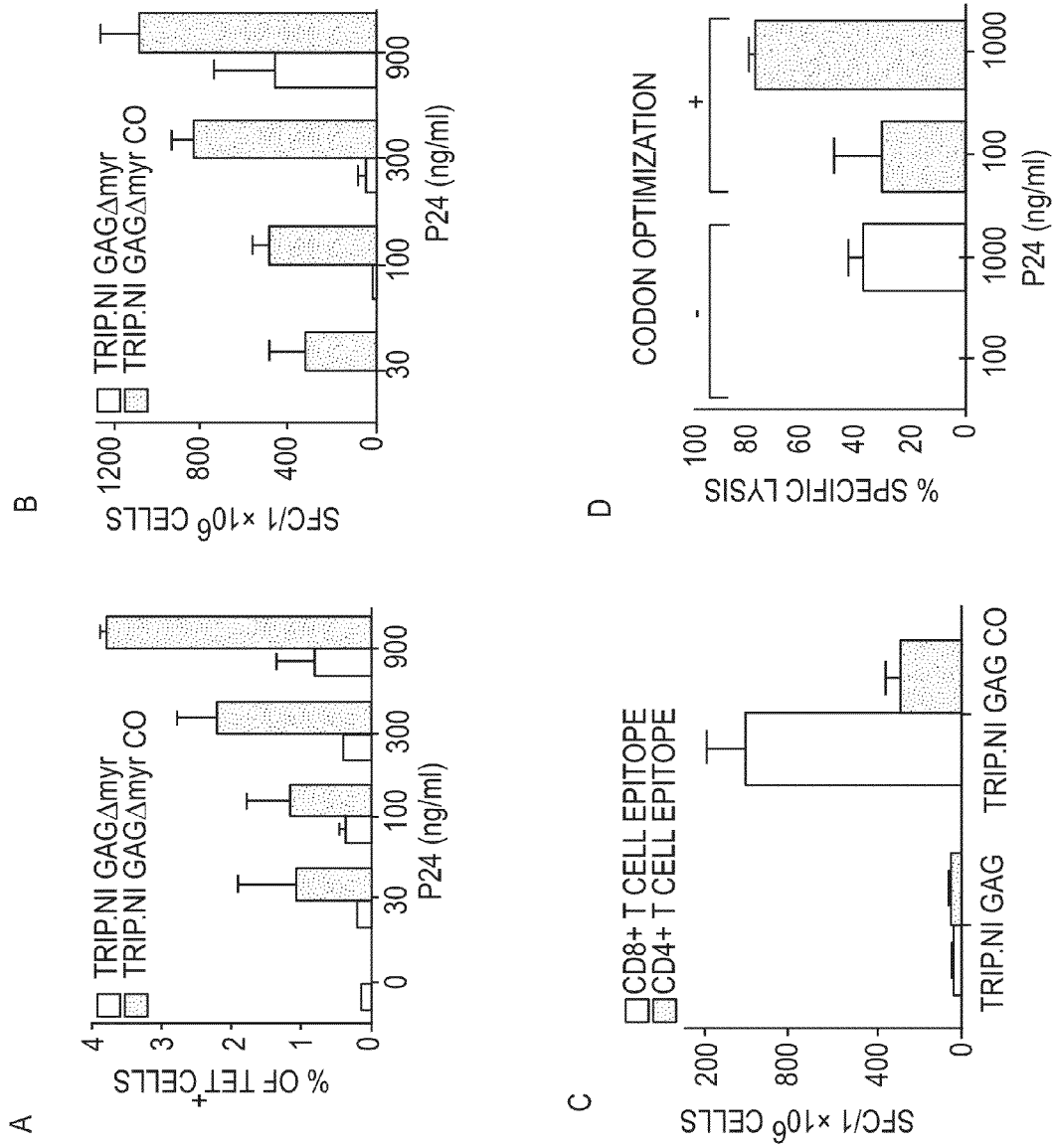

FIG. 33: Codon optimization critically improves the CTL response induced by TRIP.NI LV-based vaccines. Gag-specific cellular immune responses against the immunodominant gag CD8+ T cell epitope were assessed by tetramer staining (A) or IFN-γ ELISPOT (B). SFC, spot-forming cells. (C) IFN-γ ELISPOT assays in response to the CD8+ T cell immunodominant epitope and the CD4+ T cell epitope of gag. Mice were primed i.p. with 100 ng of TRIP.NI gagΔmyr LV or TRIP.NI gagΔmyr CO LV. 10 days later, splenocytes from immunized mice were stimulated with the corresponding peptides and analyzed by ELISPOT assays. Background frequencies were substracted prior to plotting. Error bars represent SD for 3 mice per group. (D)

Comparison of gag specific lytic activities induced by TRIP.NI gagΔmyr LV versus TRIP.NI gagΔmyr CO LV immunization. CTL activity was measured 10 days after immunization using a 20 hours in vivo CTL assay as described in Materials and Methods. Mean+/−SD of three mice is shown.

Figure 34:
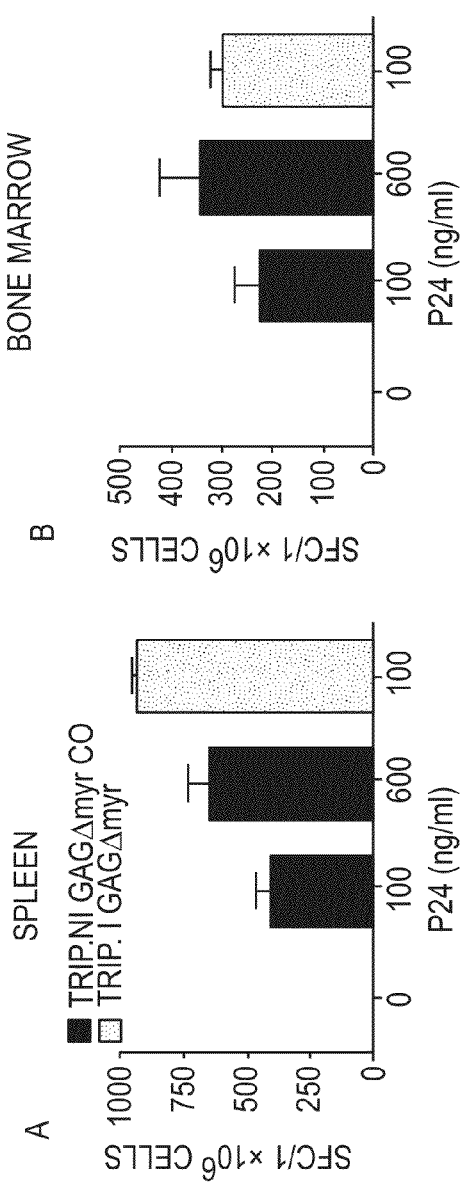

FIG. 34: A single immunization with TRIP.NI GAGΔmyr CO particles induces strong and durable cellular immune responses. ELISPOT assay on splenocytes (A) or bone-marrow cells (B) from mice immunized or not with TRIP.NI GAGΔmyr CO or TRIP.I GAGΔmyr wild-type particles at 8 weeks post-injection.

Figure 35:
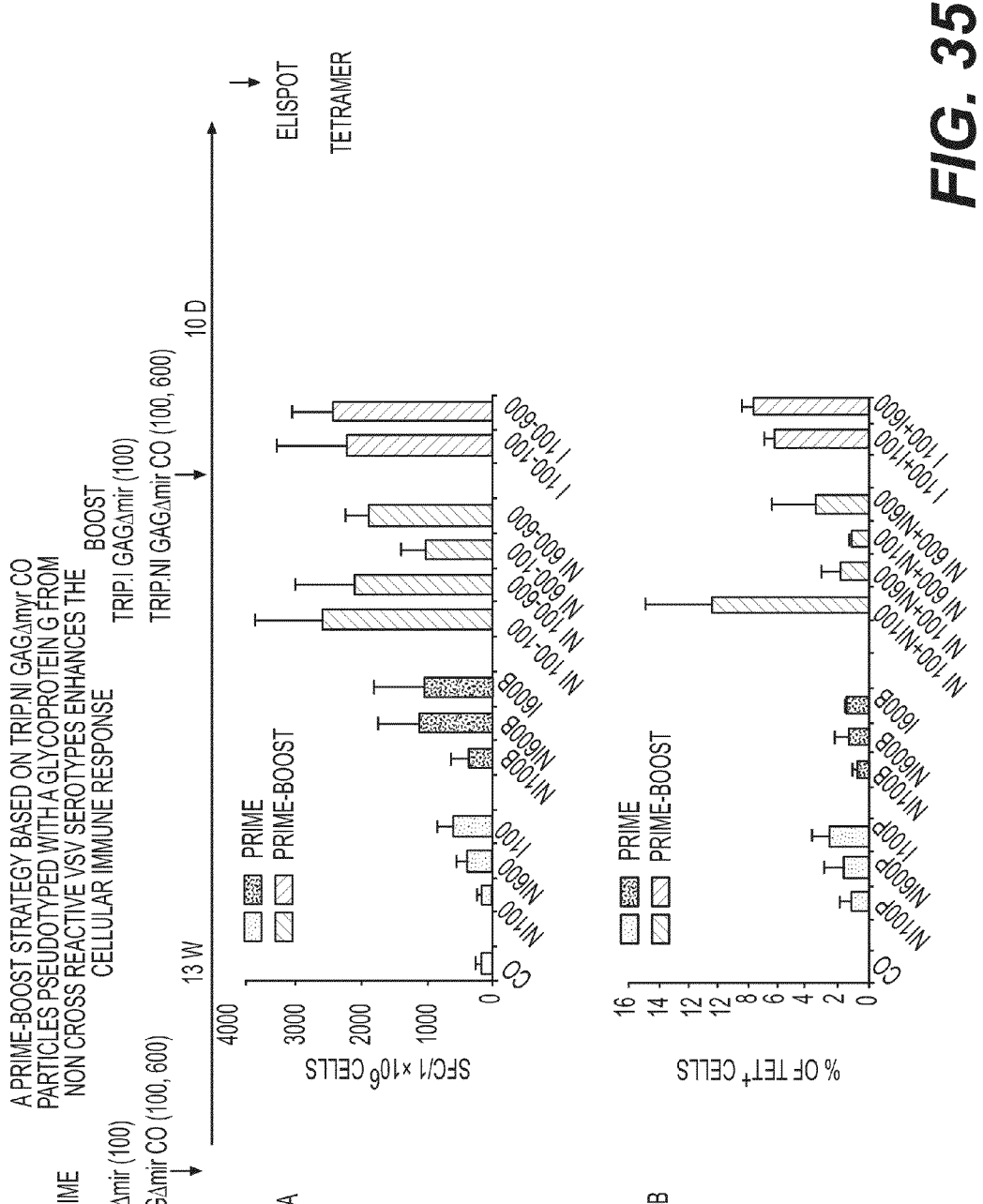

FIG. 35: Mice were immunized with TRIP.NI GAGΔmyr CO or TRIP.I GAG wild-type particles pseudotyped with VSV-G Indiana and 13 weeks later were boosted with respectively TRIP.NI GAGΔmyr CO or TRIP.I GAG wild-type particles pseudotyped with VSV-G New Jersey. Control groups for the prime-boost protocol include mice injected only one time with TRIP particles pseudotyped with VSV-G Indiana (grey diagrams) or TRIP particles pseudotyped with VSV-G New Jersey (blue diagrams). All the mice were sacrified at 10 days post-immunization, and the cellular immune response against GAG was evaluated by IFN-γ ELISPOT (A) or tetramer staining (B).

Figure 36:
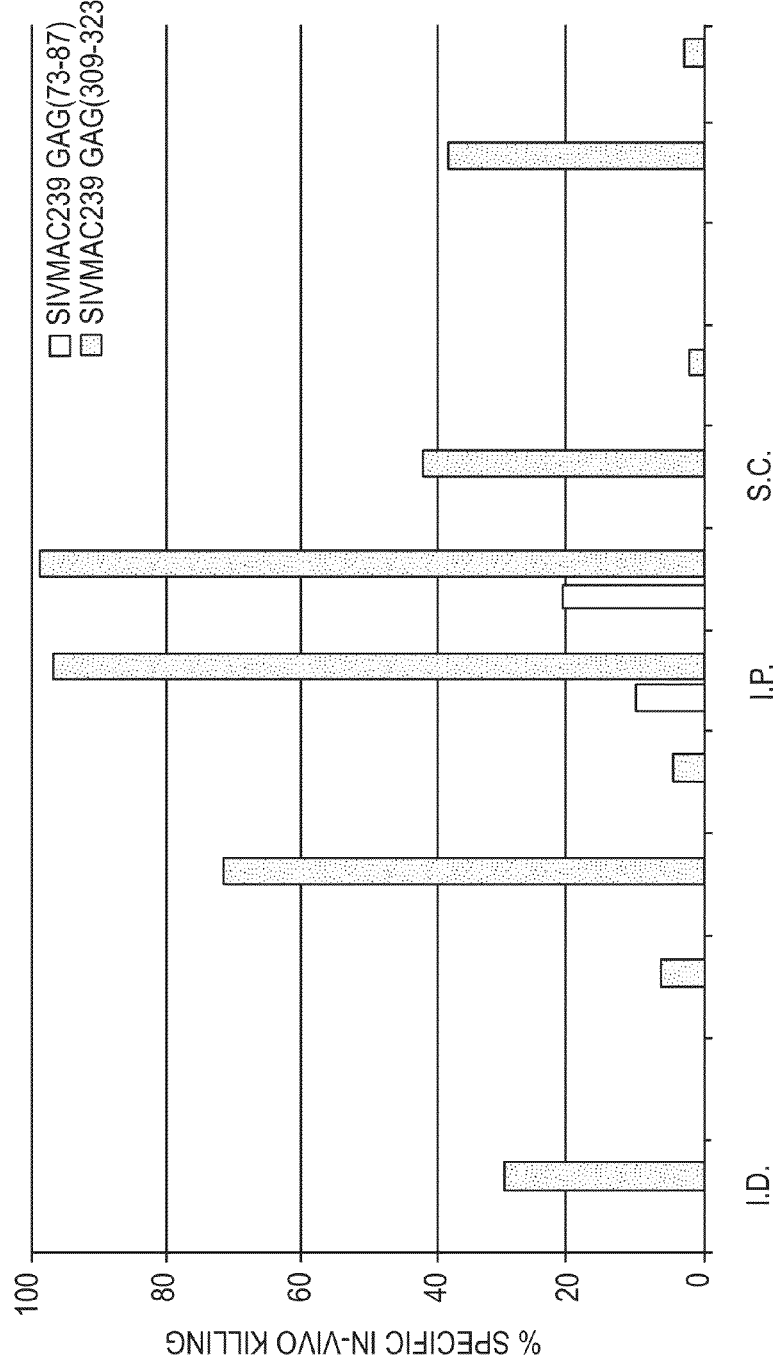

FIG. 36: Vaccination of mice with a lentiviral vector encoding SIVmac239 GagΔMyr WPRE. Groups of 2 to 5 129 mice were vaccinated once with 1.10$^{e7}$ TU per mouse. Ten days after a single administration, the specific immune responses were analyzed by an in-vivo cytotoxicity assay using congenic naïve splenocytes stained with CFSE and pulsed with 15-mer peptides (SIVmac239 Gag(73-87) and SIVmac239

Gag(309-323) containing a subdominant or an immunodominant CTL epitope) as target cells. i.d., intradermal; i.p., intraperitoneal; s.c., subcutaneous.

Figure 37:
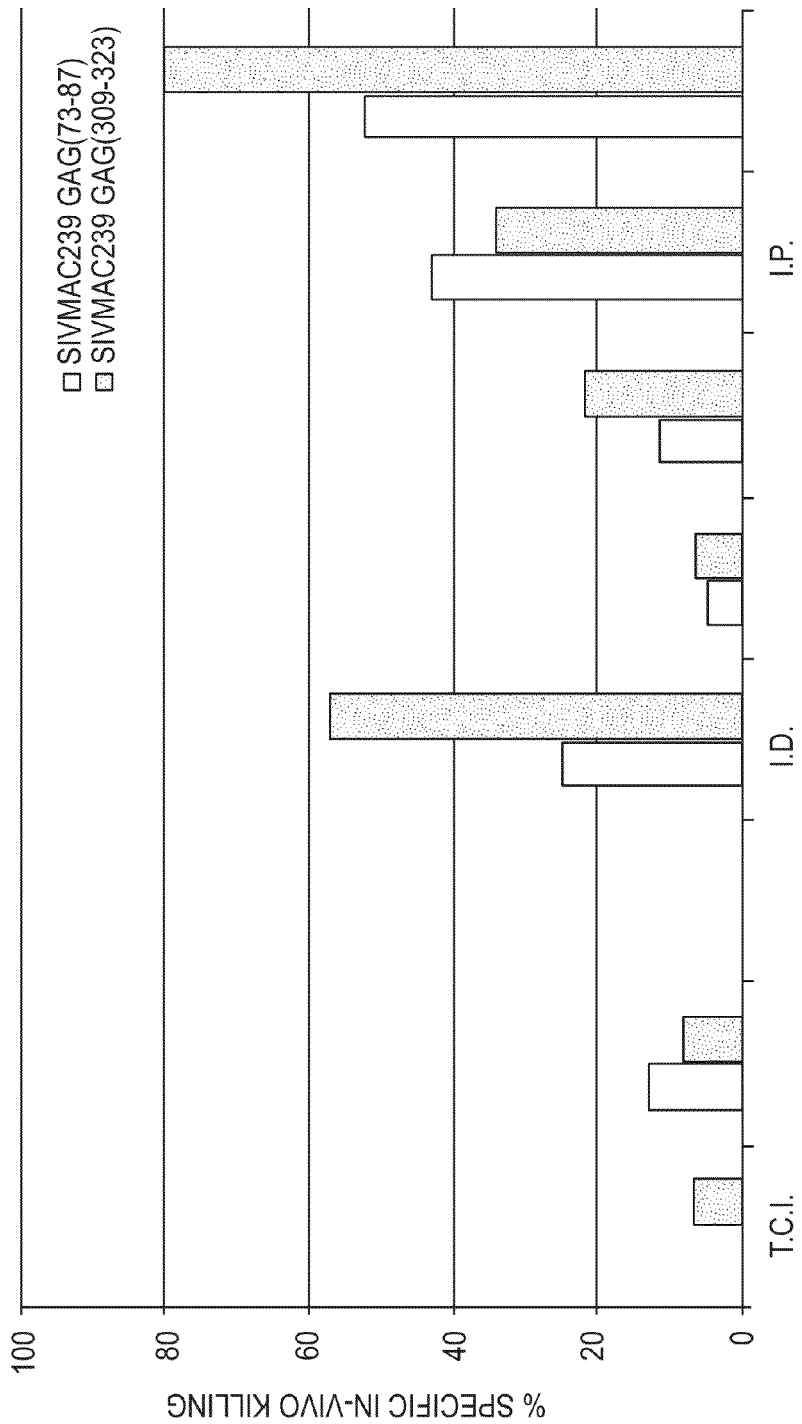

FIG. 37: Vaccination of mice with a lentiviral vector encoding SIVmac239 GagΔMyr WPRE. Groups of 2 to 3 129 mice were vaccinated once with 300 ng p24 per mouse. Ten days after a single administration, the specific immune responses were analyzed by an in-vivo cytotoxicity assay using congenic naive splenocytes stained with CFSE and pulsed with 15-mer peptides (SIVmac239 Gag(73-87) and SIVmac239 Gag(309-323) containing a subdominant or an immunodominant CTL epitope) as target cells. t.c.i., transcutaneous, i.d., intradermal; i.p., intraperitoneal.

Figure 38:
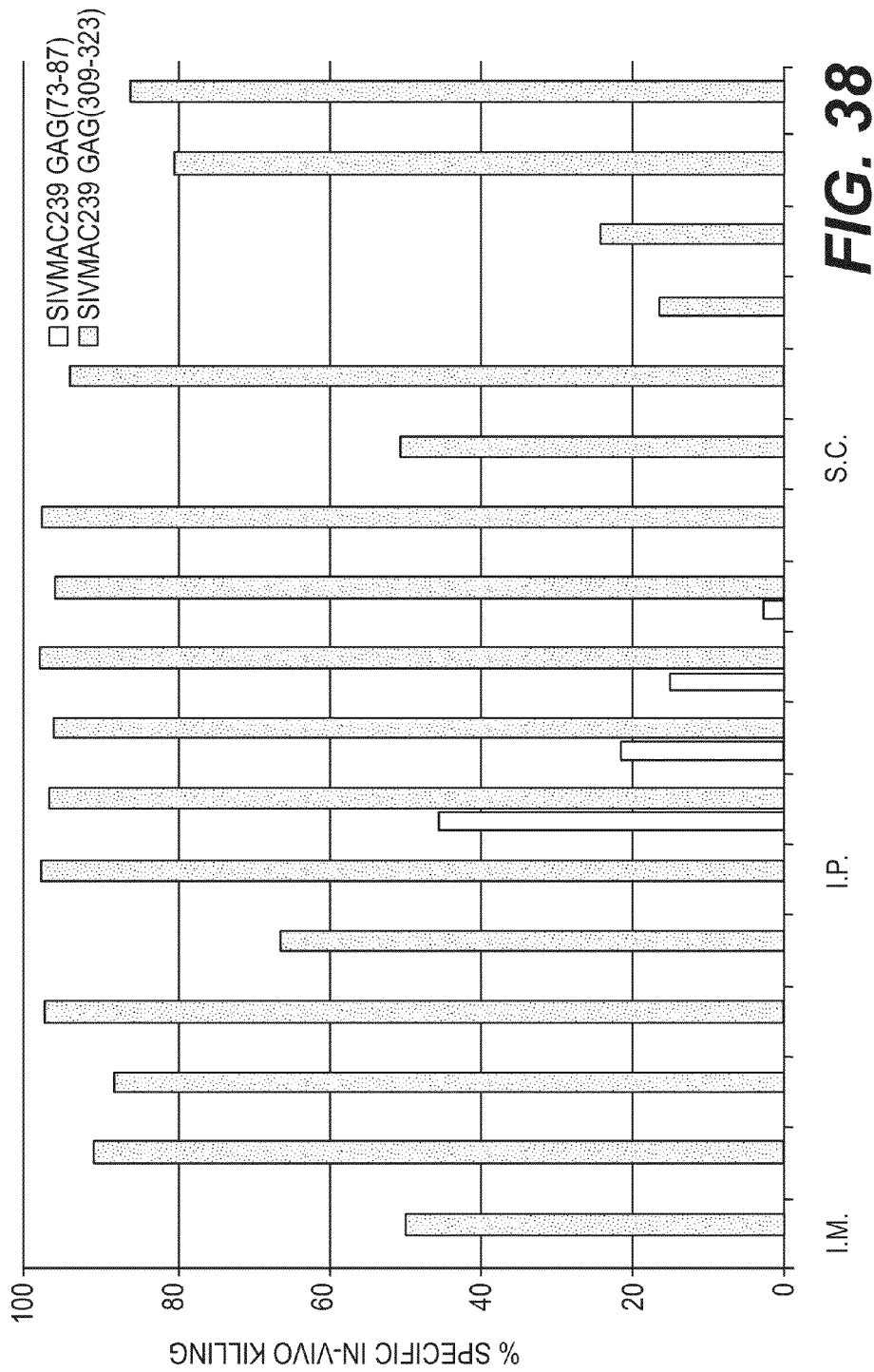

FIG. 38: Vaccination of mice with a lentiviral vector encoding SIVmac239 GagΔMyr WPRE. Groups of 5 to 6 C57BL/6j mice were vaccinated once with $1.10^{e}7$ TU per mouse. Ten days after a single administration, the specific immune responses were analyzed by an in-vivo cytotoxicity assay using congenic naïve splenocytes stained with CFSE and pulsed with 15-mer peptides (SIVmac239 Gag(73-87) and SIVmac239 Gag(309-323) containing a subdominant or an immunodominant CTL epitope) as target cells, i.m., intramuscular; i.p., intraperitoneal; s.c., subcutaneous.

Figure 39:
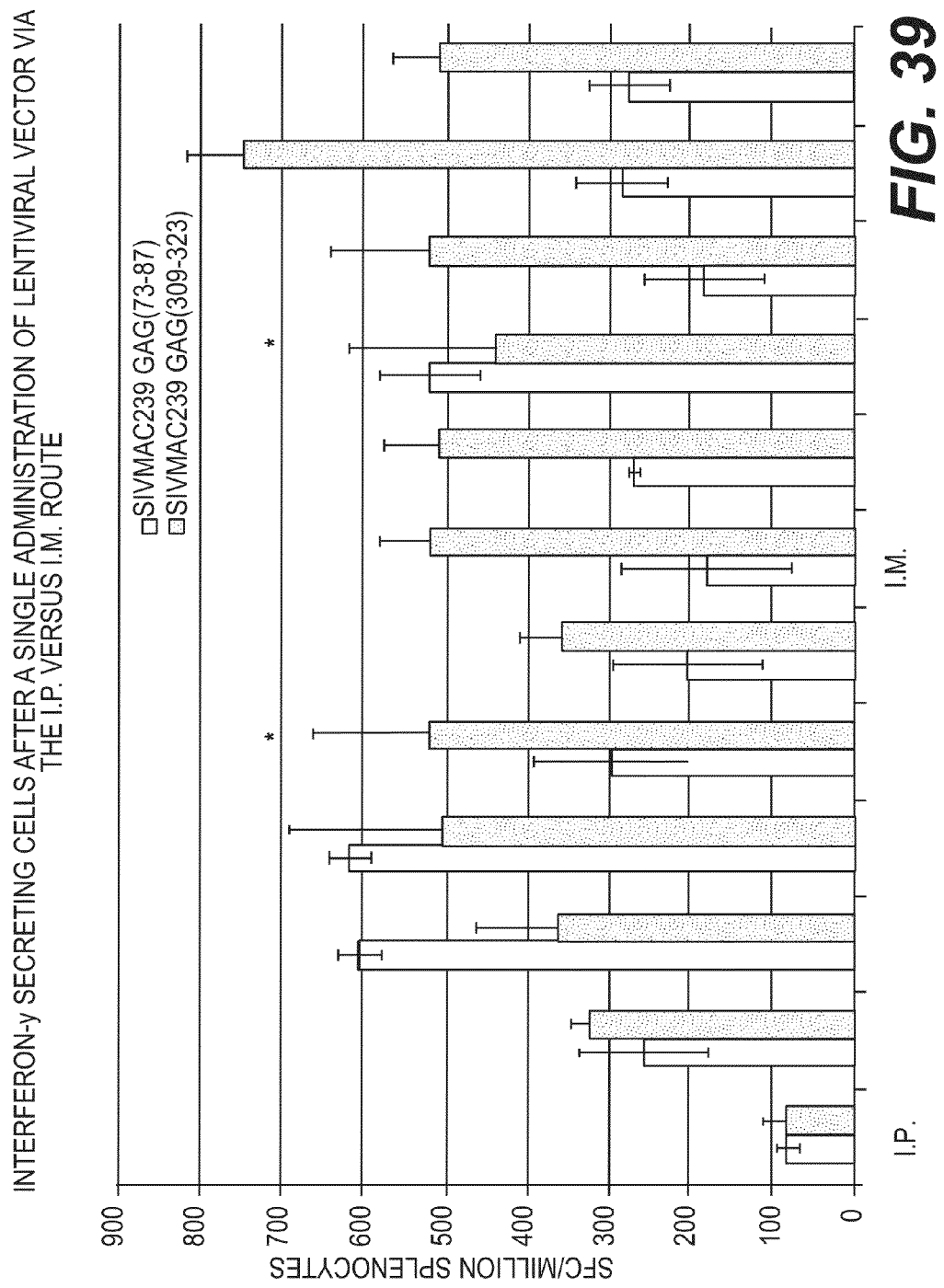

FIG. 39: Vaccination of mice with a lentiviral vector encoding SIVmac239 GagΔMyr WPRE. Groups of 6 C57Bl/6j mice were vaccinated once with $2.10^{e}6$ TU per mouse. Twelve days after a single administration, the specific immune responses were analyzed by an INFgamma ELISPOT assay stimulating the cells with 15-mer peptides (SIVmac239 Gag(73-87) and SIVmac239 Gag(309-323) containing a subdominant or an immunodominant CTL epitope). i.p., intraperitoneal; i.m., intramuscular. The symbol "star" indicates an underestimation of the response due to saturated ELISPOT wells.

Figure 40:
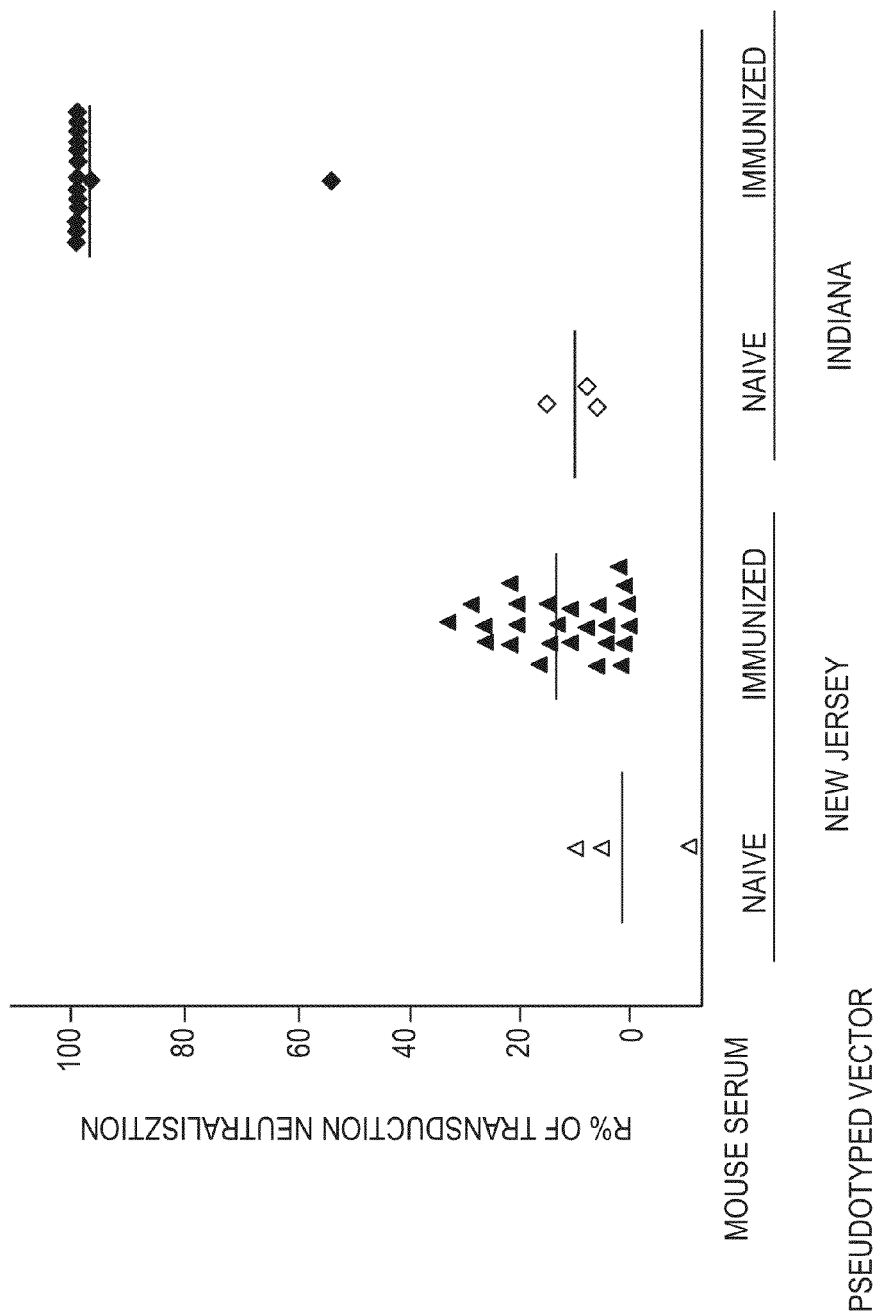

FIG. 40: in vitro neutralization of transduction of cells with a lentiviral vector pseudotyped with the Indiana VSV-G or with the New Jersey VSV-G, wherein the cells are from a naïve mice or from a mice previously immunized with a lentiviral vector pseudotyped with the Indiana VSV-G.

Figure 41:
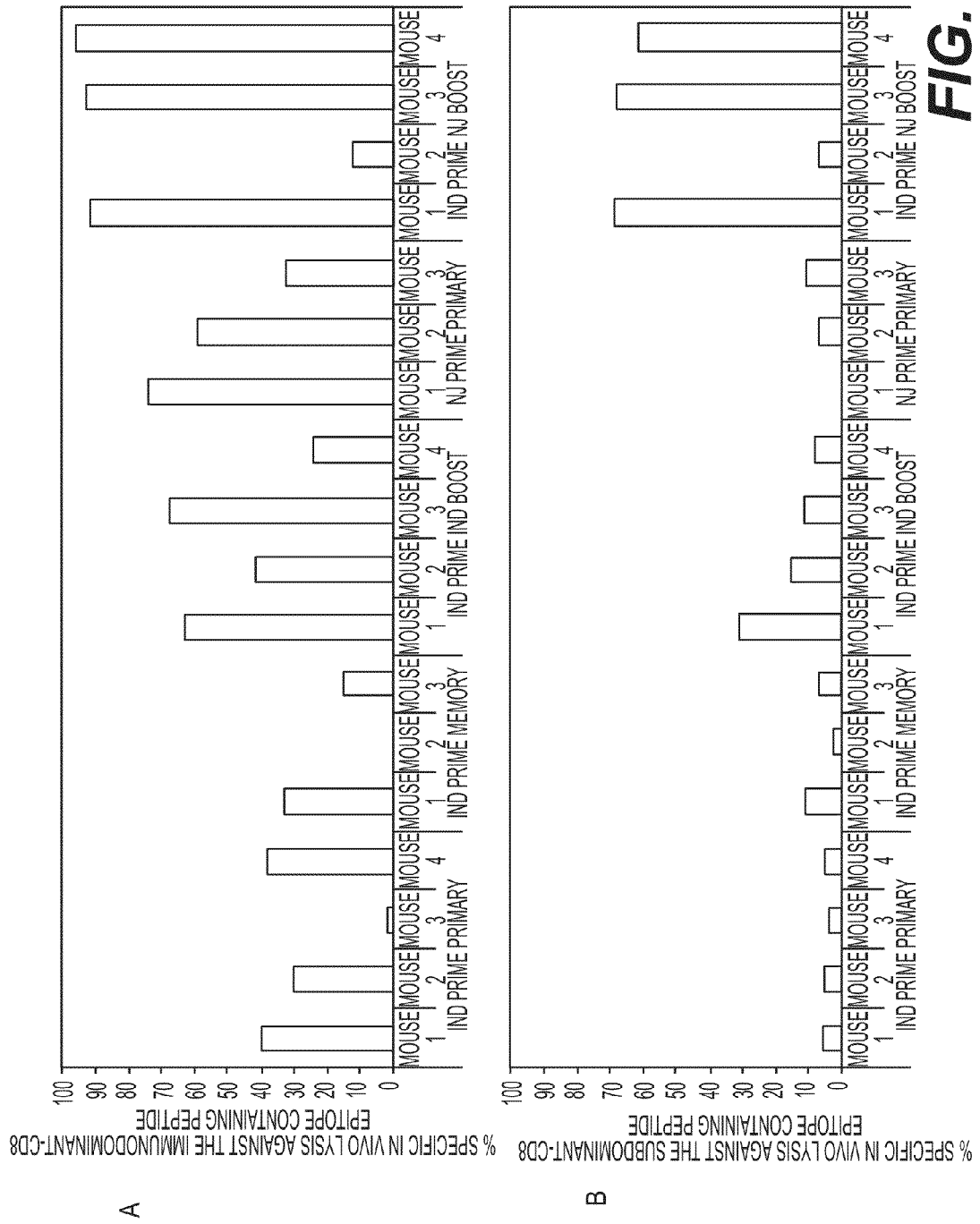

FIG. 41: in vivo specific lysis against an immunodominant—CD8 epitope containing peptide (A) or against a subdominant CD8 epitope containing peptide (B). Prime or Prime-Boost reactions were performed on individual mice, either with lentiviral vectors having the same VSV-G envelope or with lentiviral vectors having different VSV-G envelopes in the prime and boost reactions.

Figure 42:
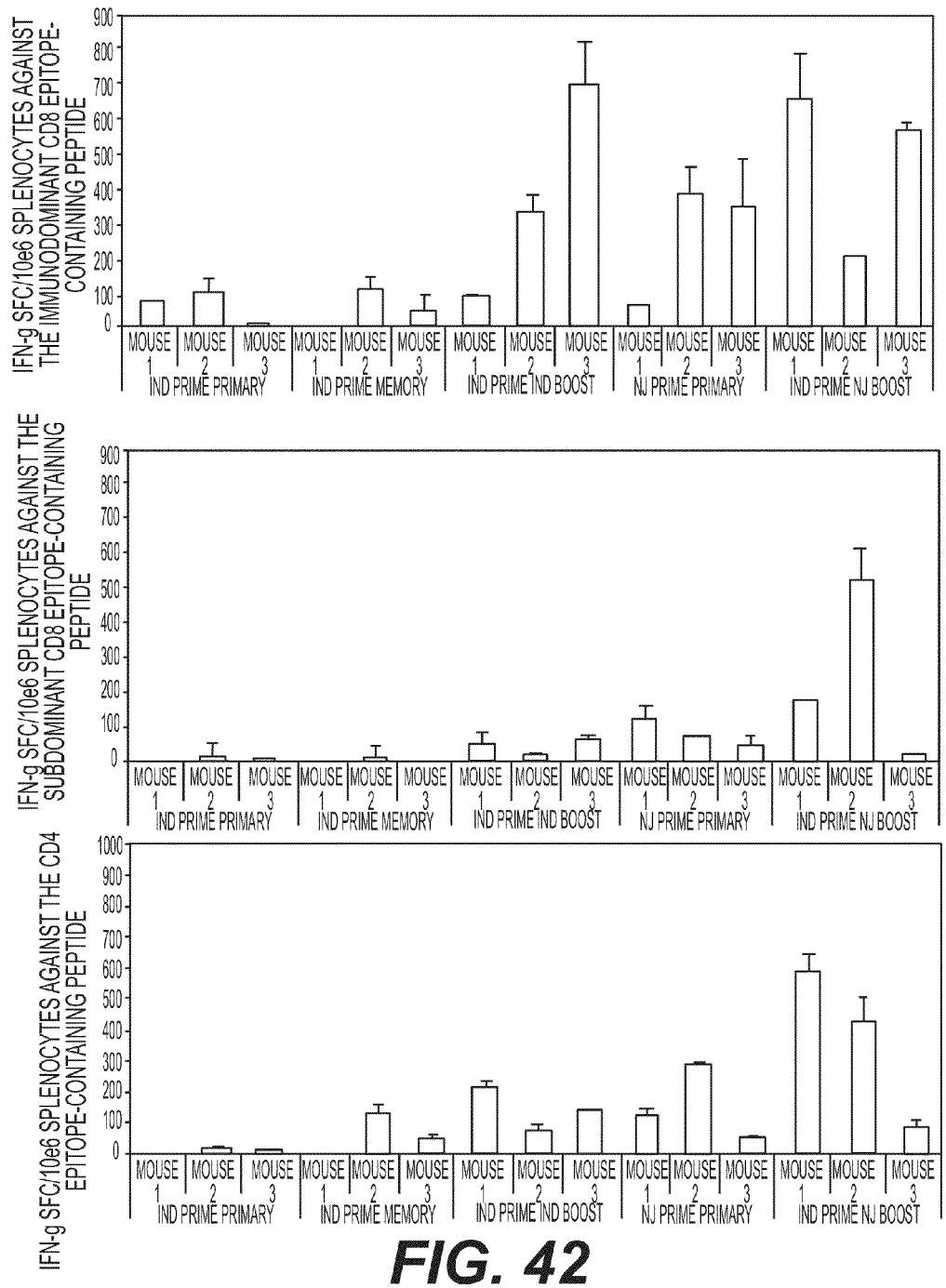

FIG. 42: IFN-gamma Elispot test for determining the CTL activity against an immunodominant—CD8 epitope containing peptide (A) or against a subdominant CD8 epitope containing peptide (B) or against a CD4 containing peptide (C). Prime or Prime-Boost reactions were performed on individual mice, either with lentiviral vectors having the same VSV-G envelope or with lentiviral vectors having different VSV-G envelopes in the prime and boost reactions.

Figure 43:
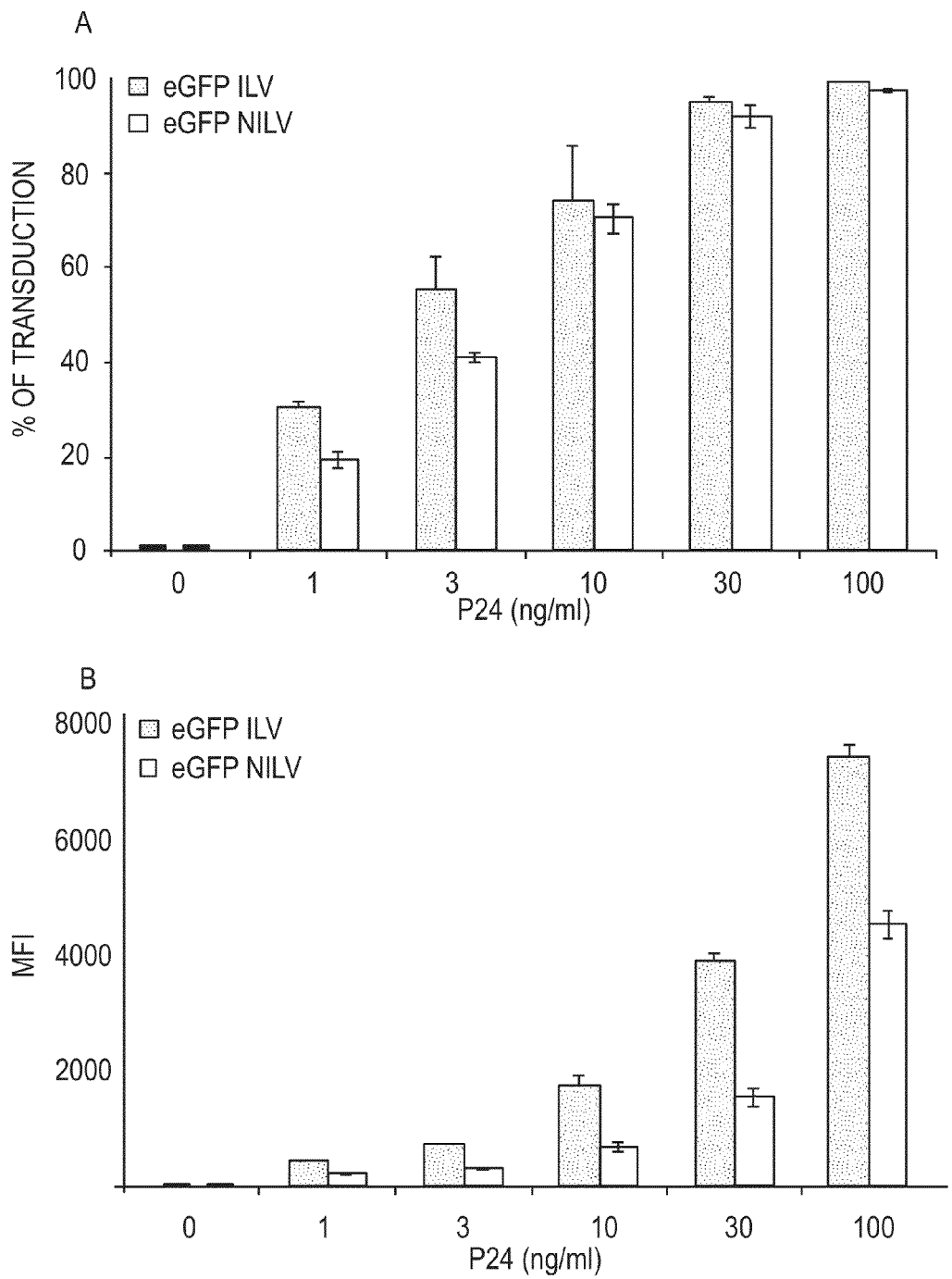

FIG. 43: Efficient transduction of nondividing cells with LV defective for integration. Aphidicolin-treated HeLa cells were transduced with graded doses (from 1 to 100 ng of p24 antigen per ml of medium) of eGFP-integrative LV (eGFP-ILV) or eGFP-nonintegrative LV (eGFP-NILV). At 48 hours post-transduction, eGFP expression was analyzed by flow cytometry. The upper panel shows the percentage of GFP positive cells and the lower panel shows MFI (mean fluorescent intensity) of the GFP positive cells.

FIG. 44: Lentiviral vector transduction leads to effective antigen expression both In conventional dendritic cells (cDC) and in plasmacytoid DC (pDC). (A) Dose-response transduction experiments (from 0 to 300 ng/ml) with eGFP-integrative LV (eGFP-ILV) or eGFP-non integrative LV (eGFP-NILV) or with 300 ng/ml of heat-inactivated (HI) eGFP-ILV or eGFP-NILV. On day 6, FL-DC were exposed to vector particles for 48 hours and transduction of CD11c positive cells was assessed by measuring eGFP expression by flow cytometry. Numbers indicate the percentage of CD11c cells expressing eGFP. (B) Transduction of pDC and cDC by LV. Expression of eGFP by cDC($CD11c^{+}$ $B220^{-}$) and pDC($CD11c^{+}B220^{+}$) is shown. Thin lines, control cells (Ctl); filled profiles, FL-DC transduced with 300 ng/ml of vector particles.

Figure 53A:
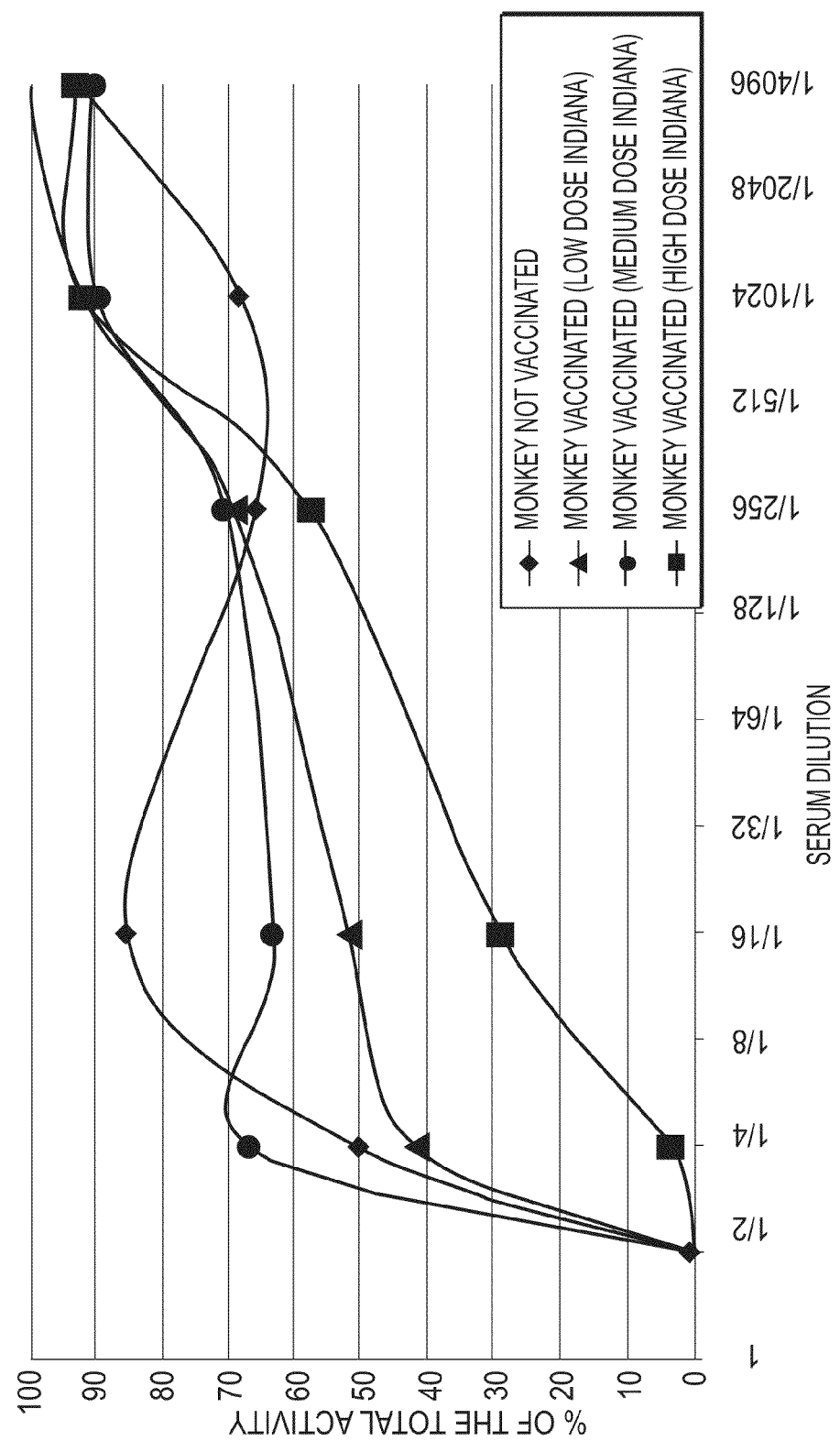
Figure 53B:
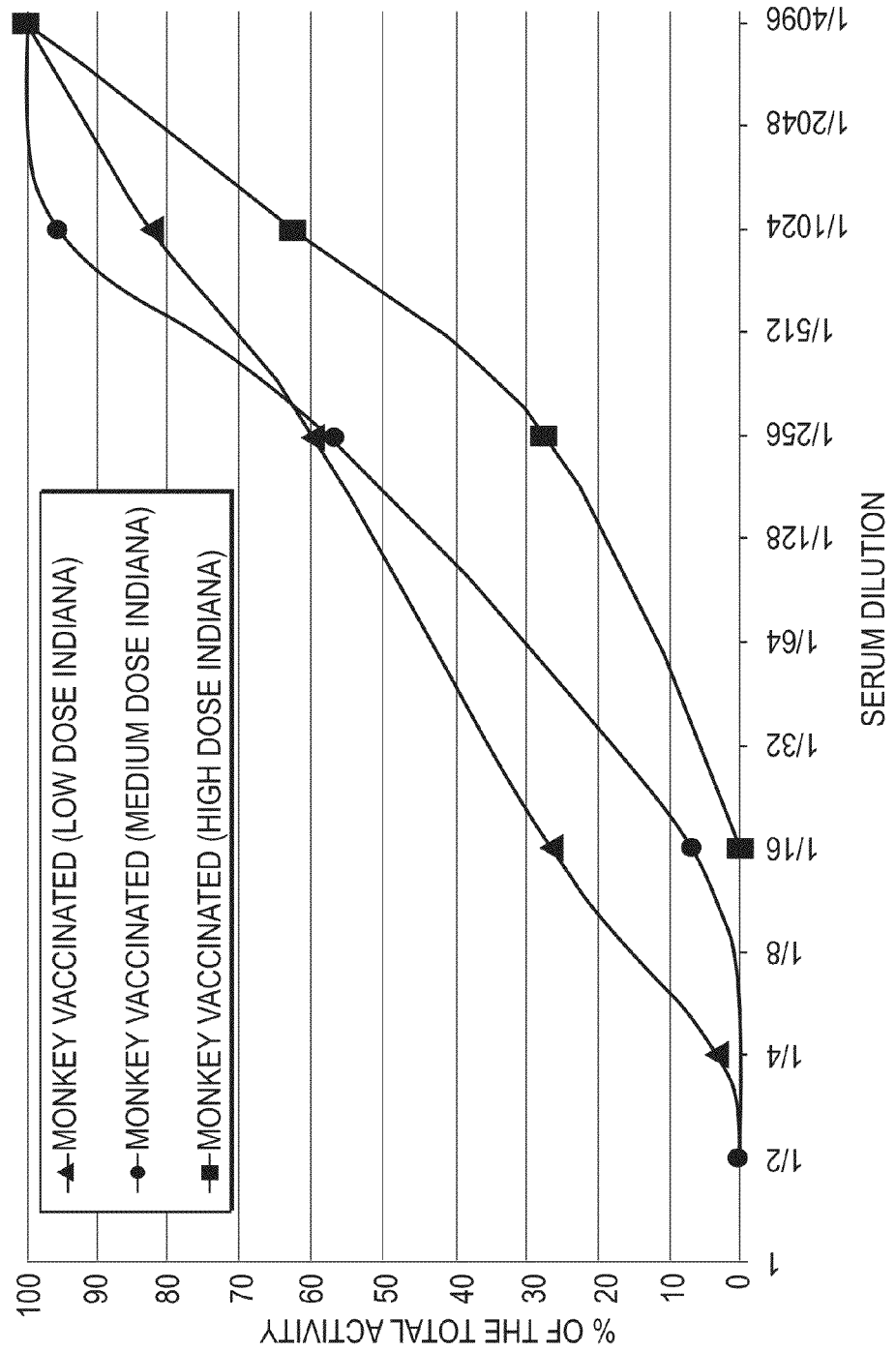
Figure 53C:
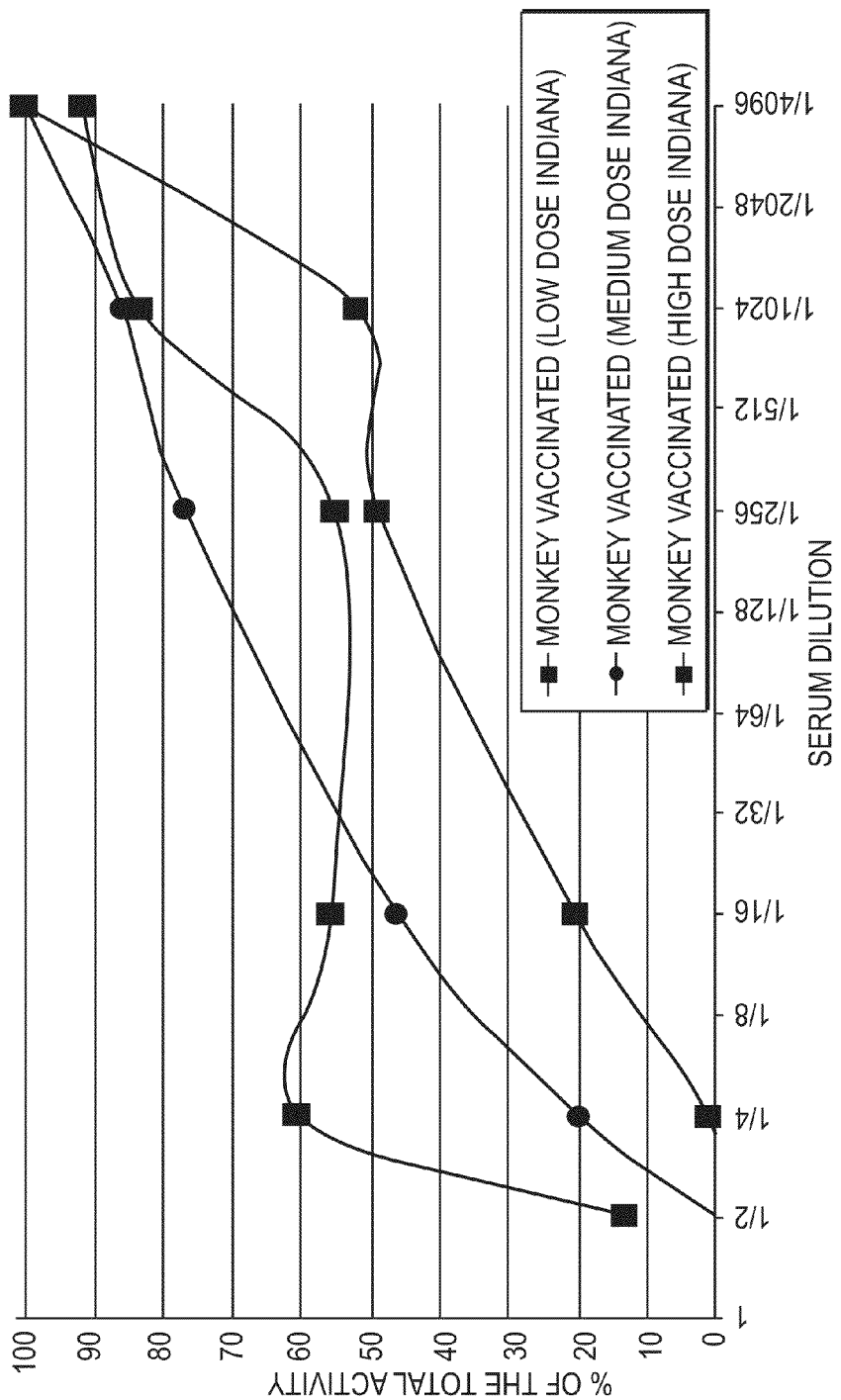

FIG. 45: A single dose of ${}_{s}E_{WNV}$-NILV elicits a strong and specific antibody response. Groups of adult mice were immunized i.p. with graded doses of ${}_{s}E_{WNV}$-NILV (from 1 to 100 ng of p24 antigen) (A, B) or ${}_{s}E_{WNV}$-ILV (B). Control mice were injected with heat-inactivated ${}_{s}E_{WNV}$-LV NI (A, B) or I (B) (HI 100). After 21 days, pooled sera (6 mice per group) were assessed for WNV-specific antibodies.

FIG. 46: Rapid protection against WNV infection conferred by sEwnv-NILV immunization. Six mice/group were vaccinated with 100 ng of sEwnv-NILV or 100 ng of sEwnv-ILV. A control group of mice inoculated with phosphate-buffered saline (PBS) was included. One week after the vaccination, mice were challenged with 1,000i.p. $LD_{50}$s of WNV strain IS-98-ST1. Survival was recorded for 21 days.

FIG. 47: Efficient long-term protection by $sE_{WNV}$-NILV against WNV infection. Two months post-immunization with graded doses of $sE_{WNV}$-NILV (1-100 ng of p24 antigen) (A, B) or ${}_{s}E_{WNV}$-ILV (B), mice were inoculated with 1,0001.p. $LD_{50}$s of WNV strain IS-98-ST1. Survival was recorded for 21 days.

FIG. 48: Impact of the codon-optimization on the level of expression of gagΔmyr. 293 T cells were cotransfected with TRIP vector plasmids containing either a wild-type sequence (left panel) or a codon-optimized sequence (right panel) of gagΔmyr, the encapsidation plasmid p8.7 D64V and the VSV-G expression plasmid.

FIG. 49: Groups of mice (n=5) were immunized or not (Naive) with TRIP.NI GAGΔmyr CO (100 ng) or TRIP.I GAG wild-type particles (100 ng) pseudotyped with VSV-G Indiana and 13 weeks later were boosted with respectively TRIP.NI GAGΔmyr CO (100 ng) or TRIP.I GAG wild-type particles (100 ng) pseudotyped with VSV-G New Jersey. All the mice were sacrified at 10 days post-immunization, and the cellular immune response against GAG was evaluated by IFN-γ ELISPOT (A) or tetramer staining (B).

FIG. 50: Titration of the lentiviral vector particles pseudotyped by various VSV-G serotypes codon optimized (CO) or wild type (WT), when available FIG. 51: In vitro assay for quantification of sera neutralizing activities. Mice sera were collected from animals injected twice, at two months interval, with 300 ng P24 of lentiviral vector particles per injection, pseudotyped by the VSV.G proteins of the different serotypes. Luciferase encoding vector particles, again pseudotyped with the various serotypes of VSV.G proteins, were incubated in the presence of dilutions of sera for 1 hour at 37° C. After incubation, luciferase encoding lentiviral vector particles were used to transduce 293T cells in 96 wells plates with 1 ng P24 per well. After a 48 hour-incubation, luciferase activity was measured using a luminescence detection kit according to the manufacturer instructions (Boehringer). Results are expressed as percentage of luminescence activity after incubation without serum.

FIG. 52: Cross neutralization of lentiviral vector particles with different mouse sera: Viral particles pseudotyped with the different VSV.G proteins are tested in transduction experiments in presence of various mouse sera. A: The transduction is either totally (++), partially (+ or +/−) or not (−) inhibited. B: details of these experiments.

FIG. 53: Activity of Indiana pseudotyped particles in presence of various monkey sera. A: Sera from pre-immunized monkeys, B: sera from monkeys injected with Indiana pseudotyped particles at various doses (prime) and C: monkey sera after an injection with New Jersey pseudotyped particles (boost)

Figure 54A:
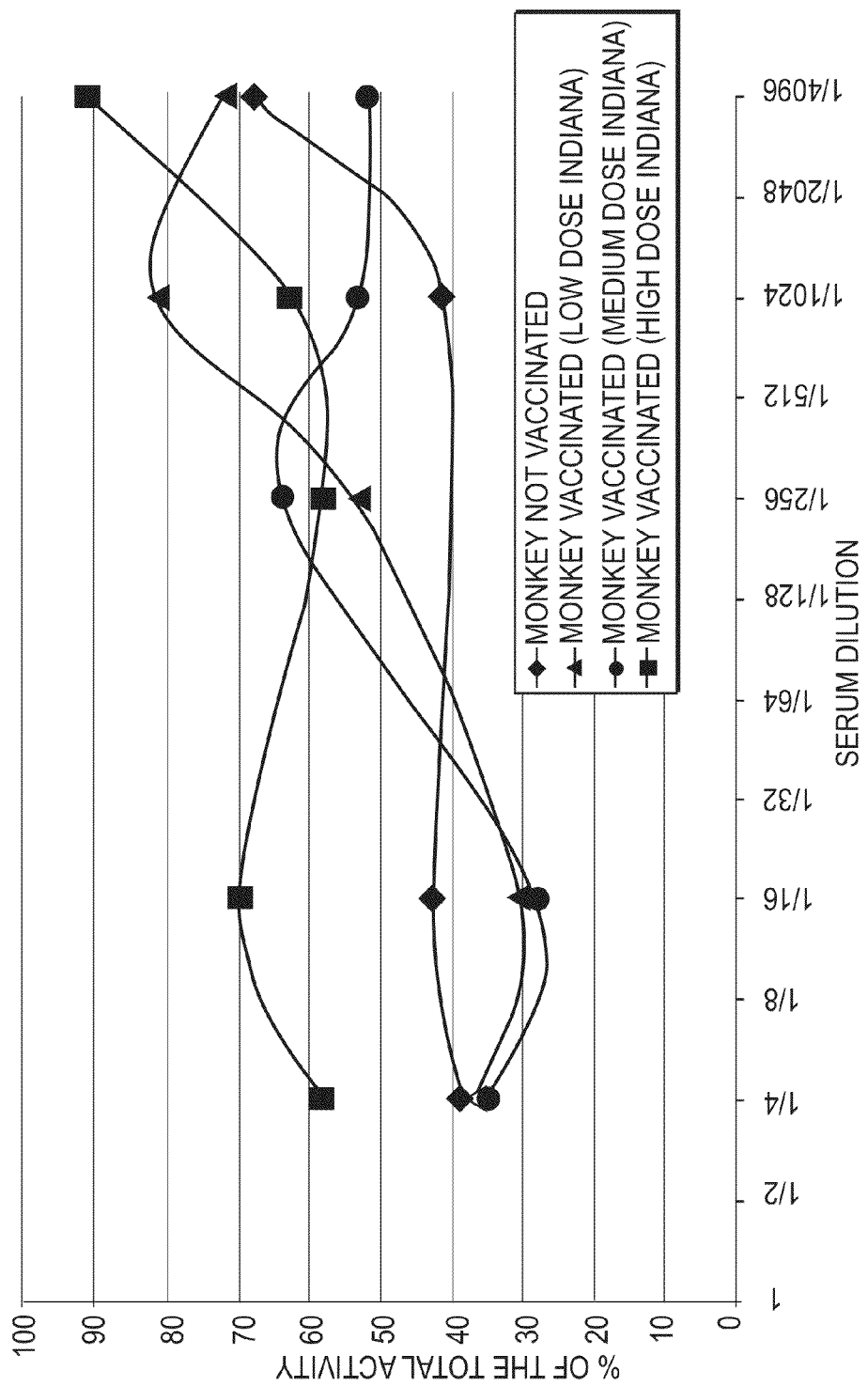
Figure 54B:
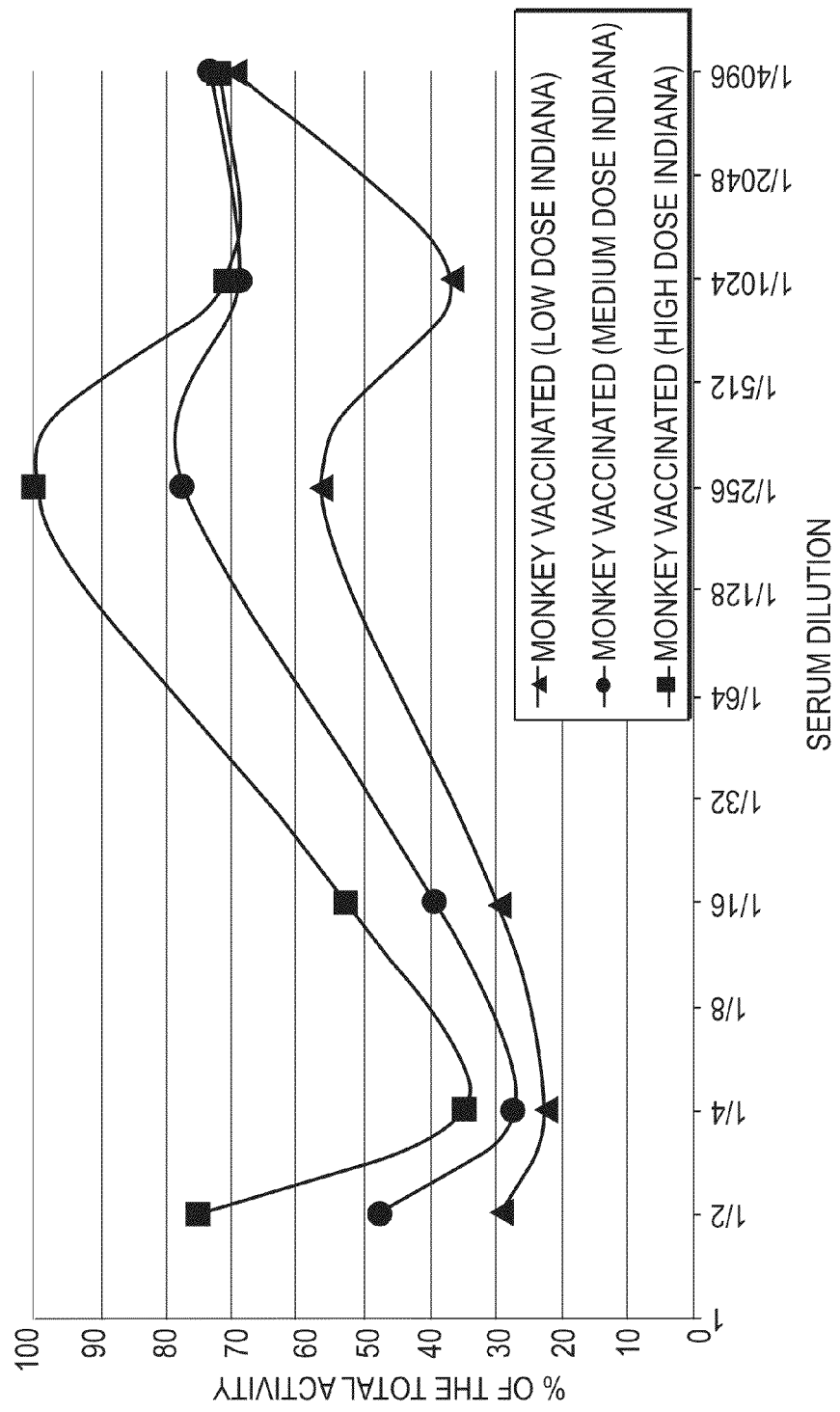
Figure 54C:
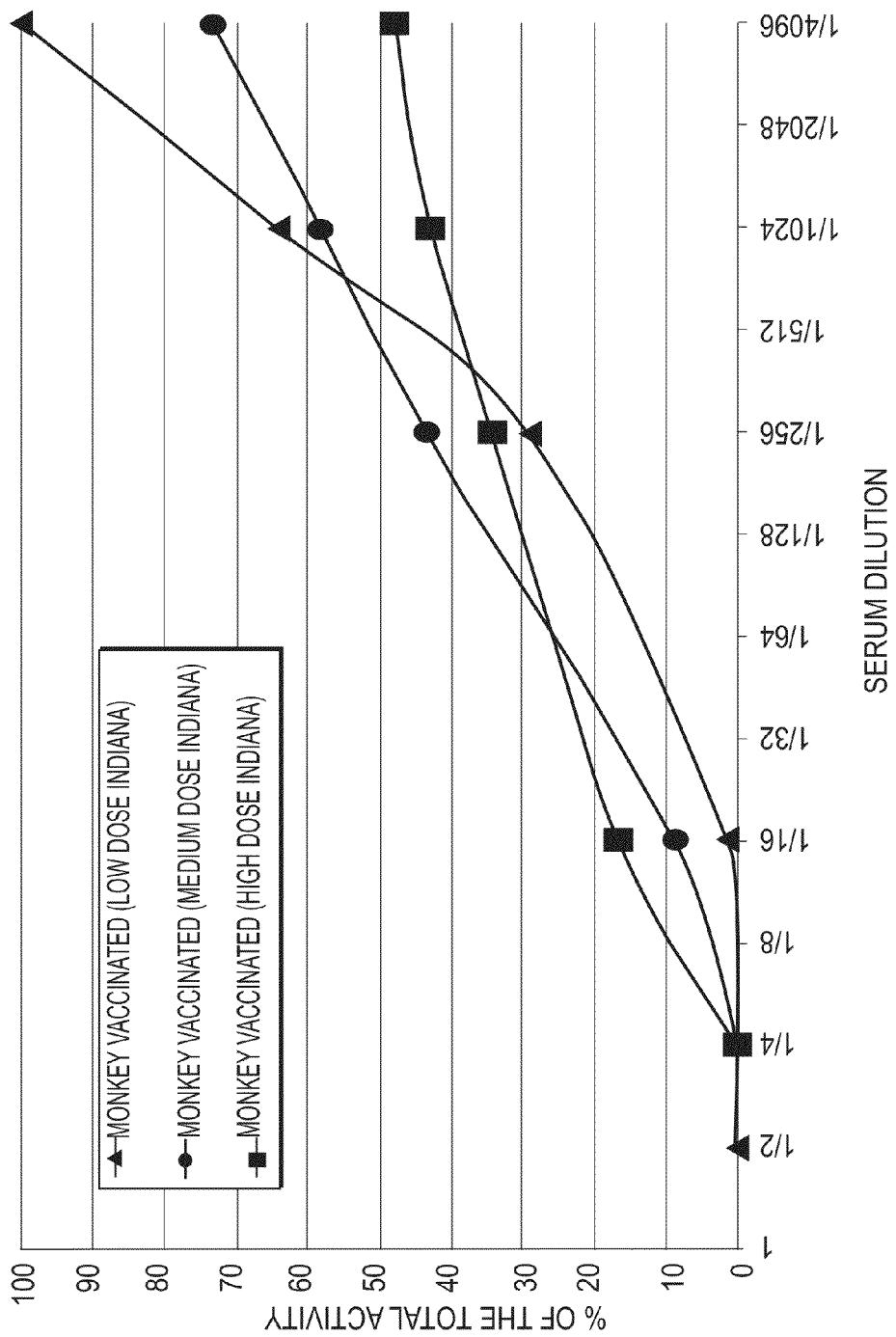

FIG. 54: Activity of New Jersey pseudotyped particles in presence of various monkey sera. A: Sera from pre-immunized monkeys, B: sera from monkeys injected with Indiana pseudotyped particles at various doses (prime) and C: monkey sera after an injection with New Jersey pseudotyped particles (boost)

Figure 55A:
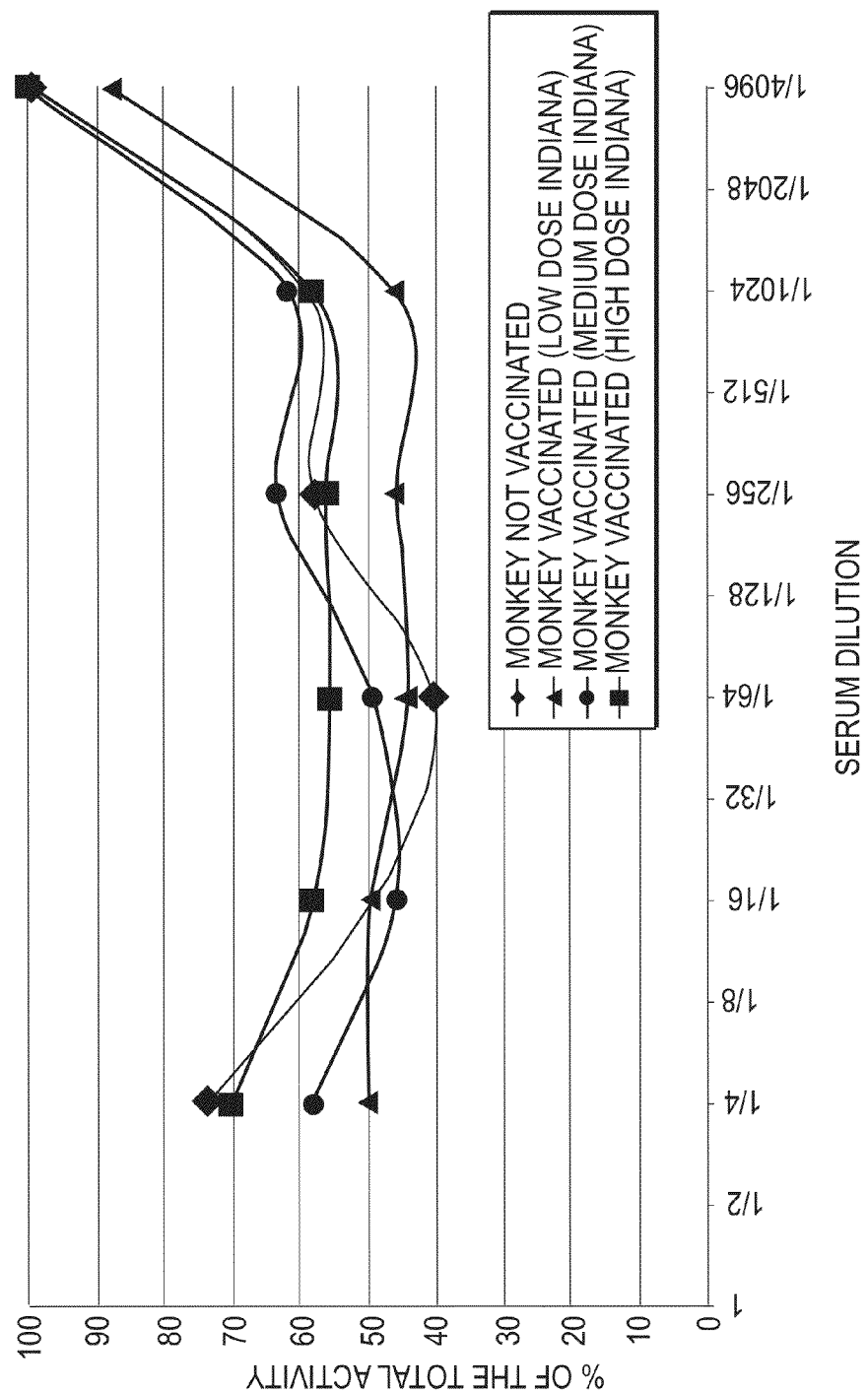
Figure 55B:
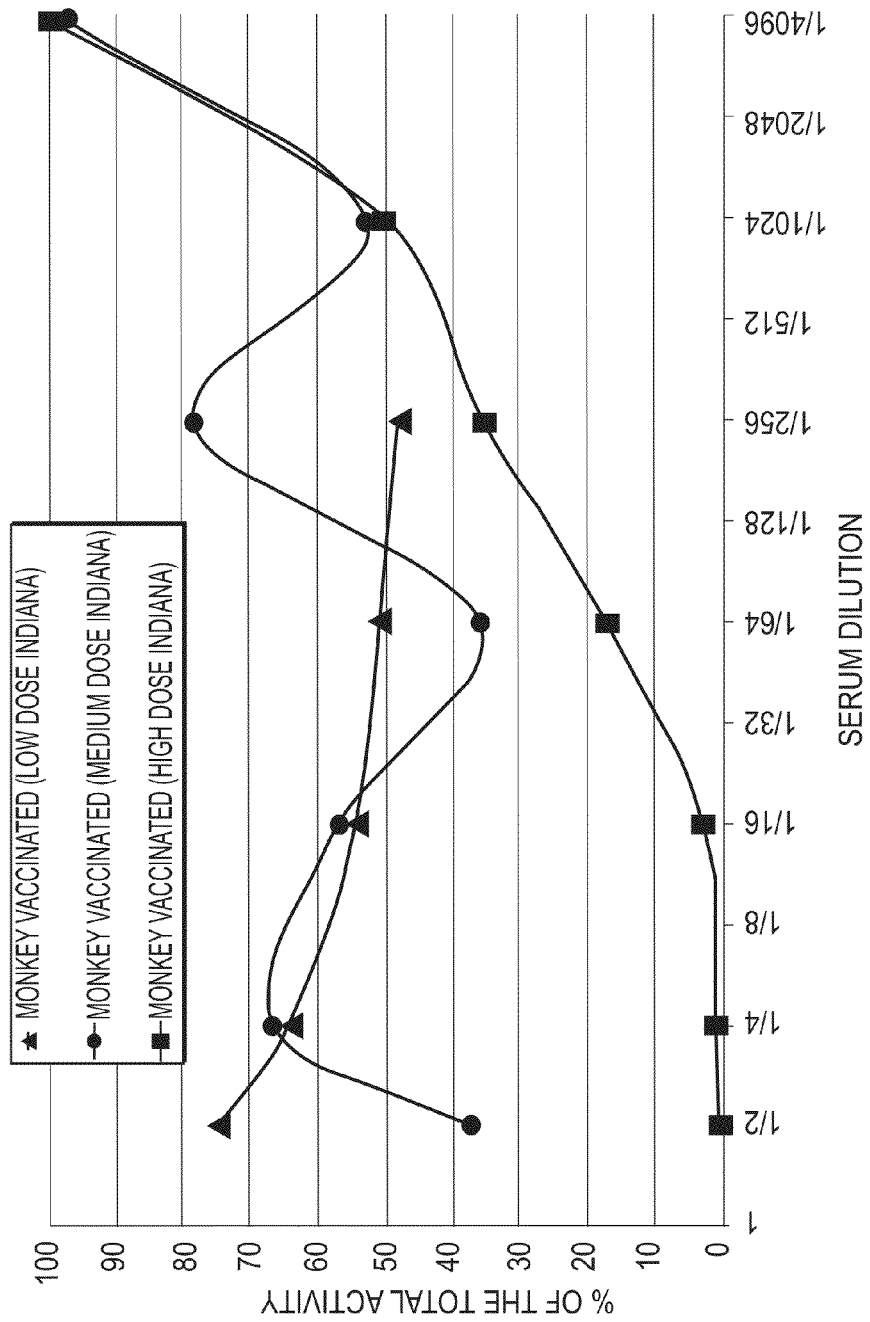
Figure 55C:
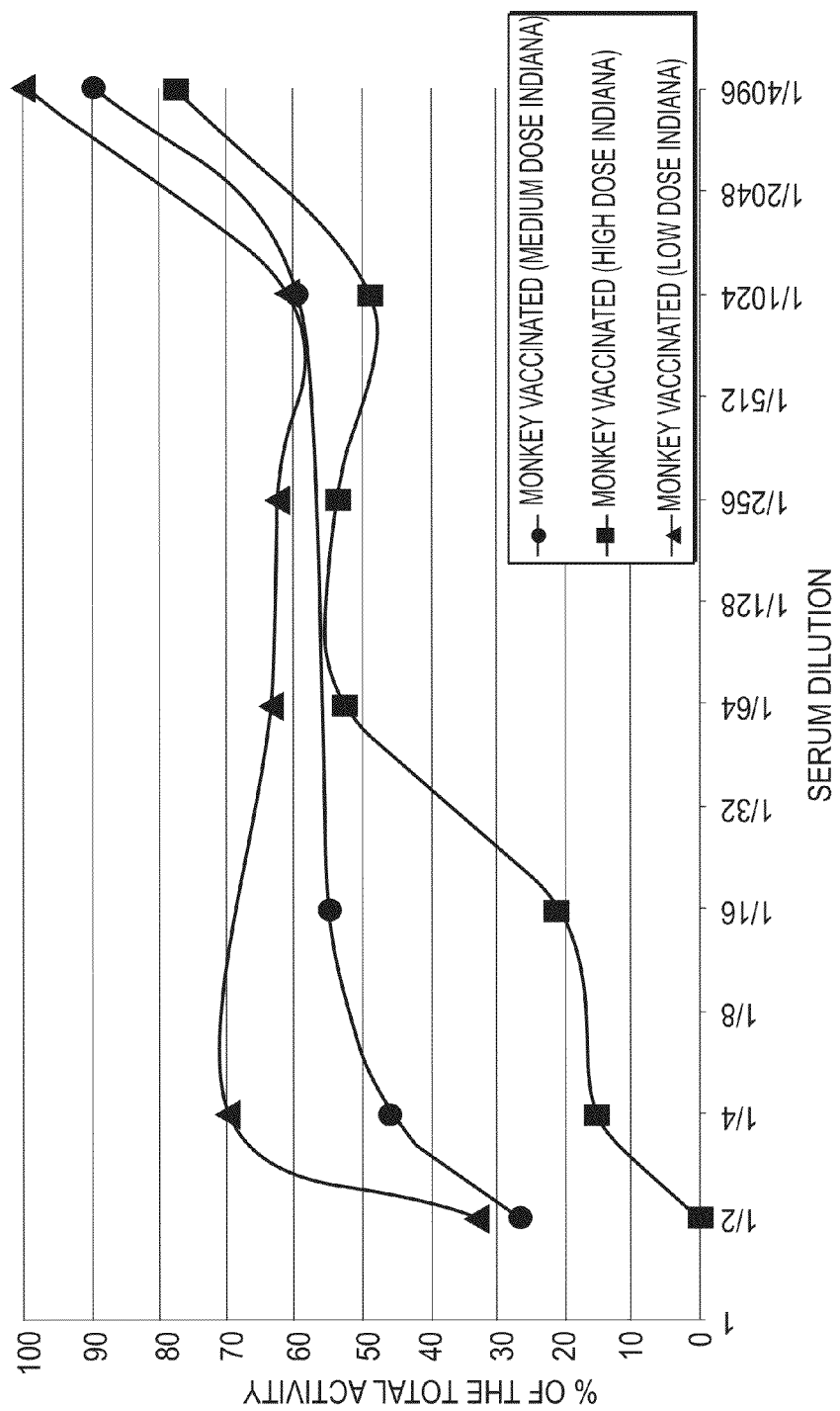

FIG. 55: Activity of Cocal pseudotyped particles in presence of various monkey sera. A: Sera from pre-immunized monkeys, B: sera from monkeys injected with Indiana pseudotyped lentiviral vector particles at various doses (prime) and C: monkey sera after an injection with New Jersey pseudotyped lentiviral vector particles (boost)

Figure 56A:
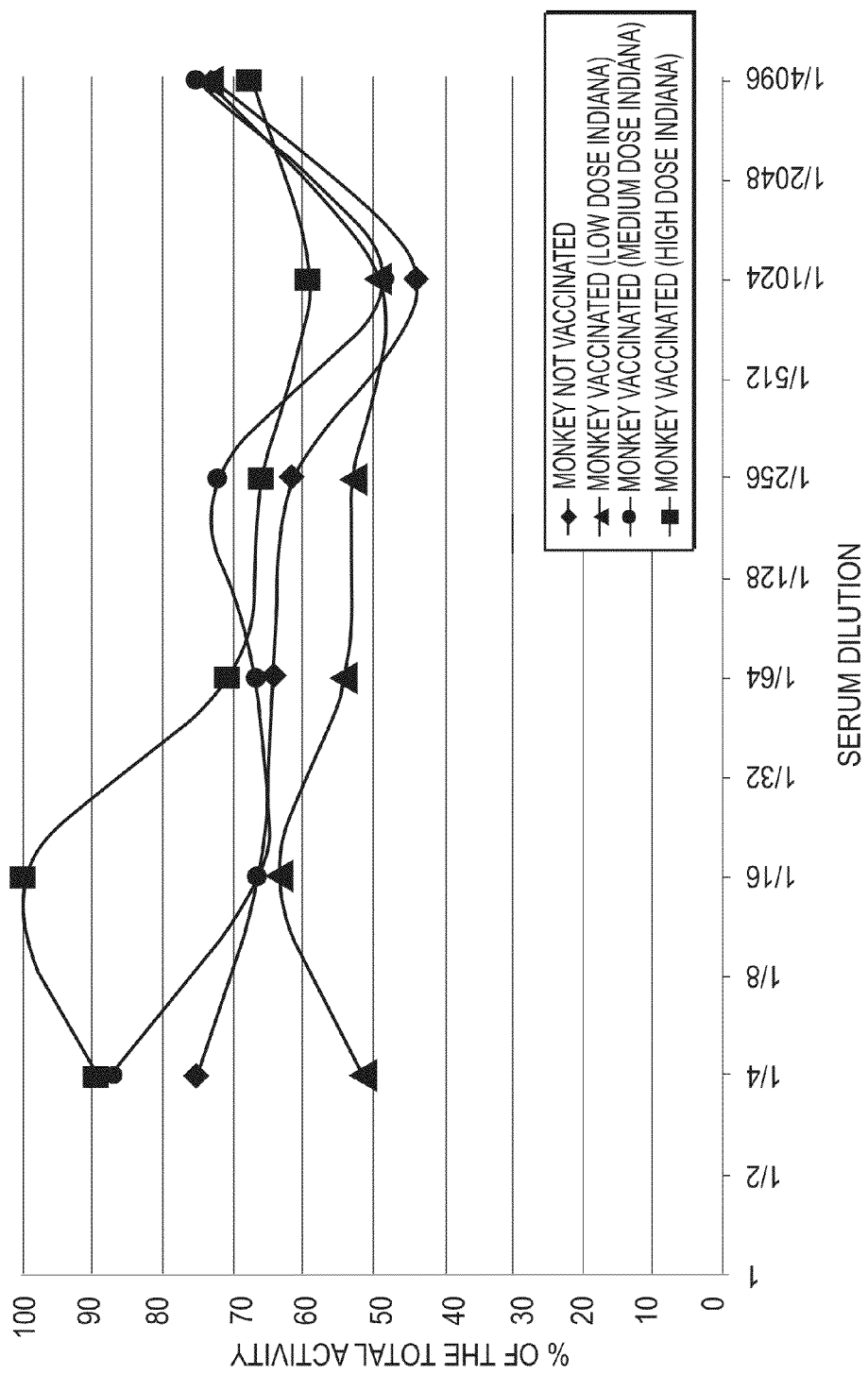
Figure 56B:
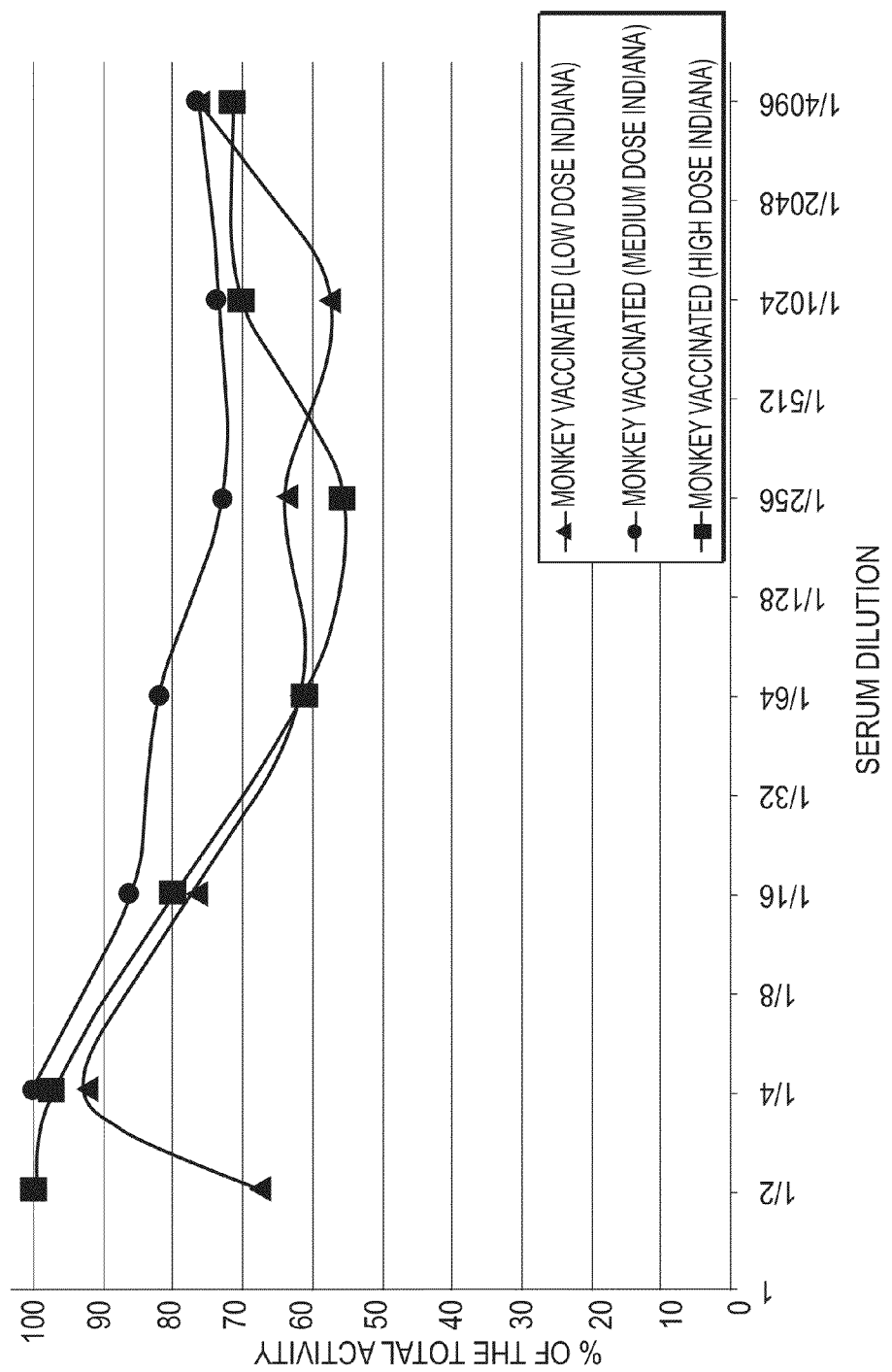
Figure 56C:
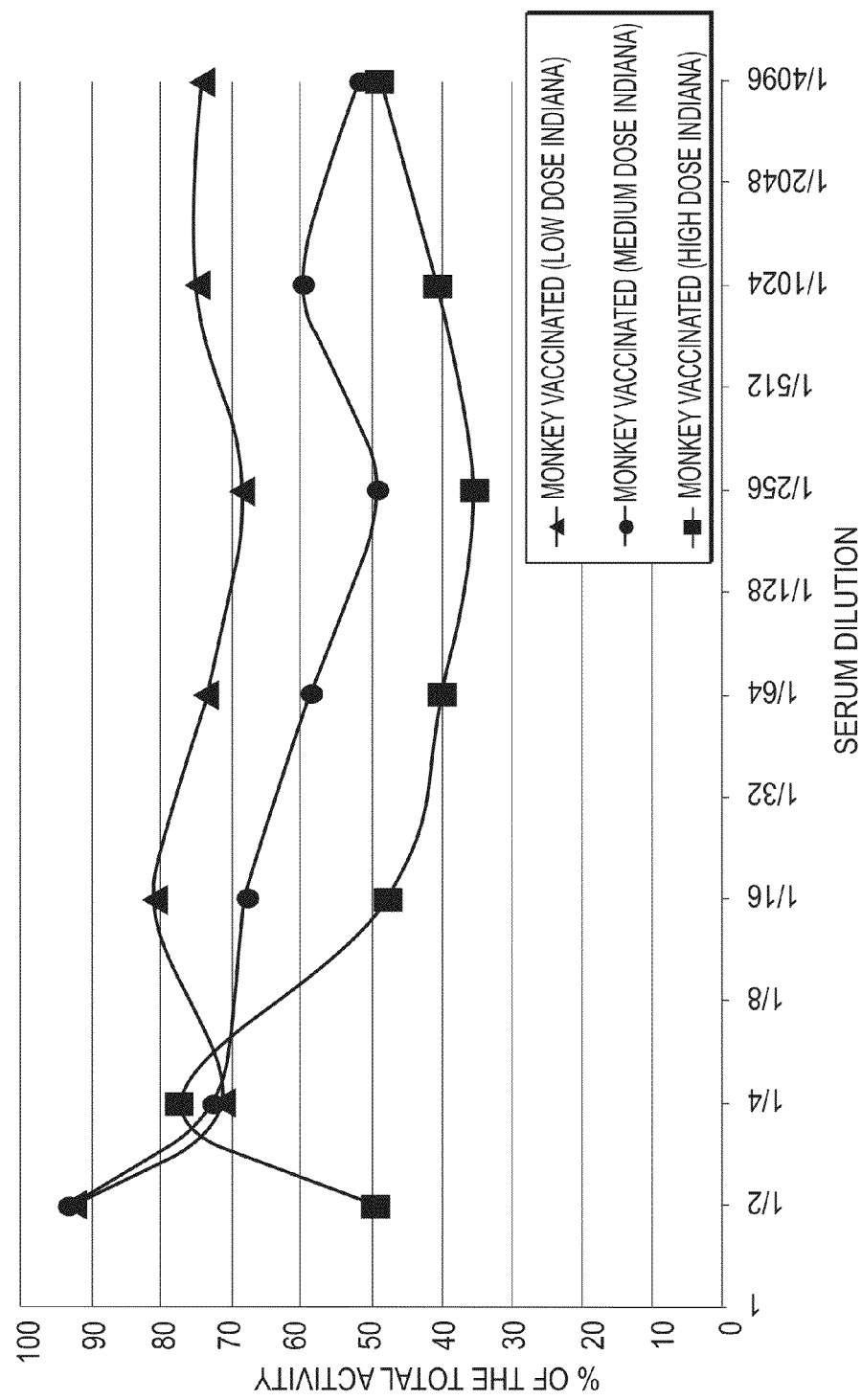

FIG. 56: Activity of Isfahan pseudotyped particles in presence of various monkey sera. A: Sera from pre-immunized monkeys, B: sera from monkeys injected with Indiana pseudotyped particles at various doses (prime) and C: monkey sera after an injection with New Jersey pseudotyped particles (boost)

Figure 57A:
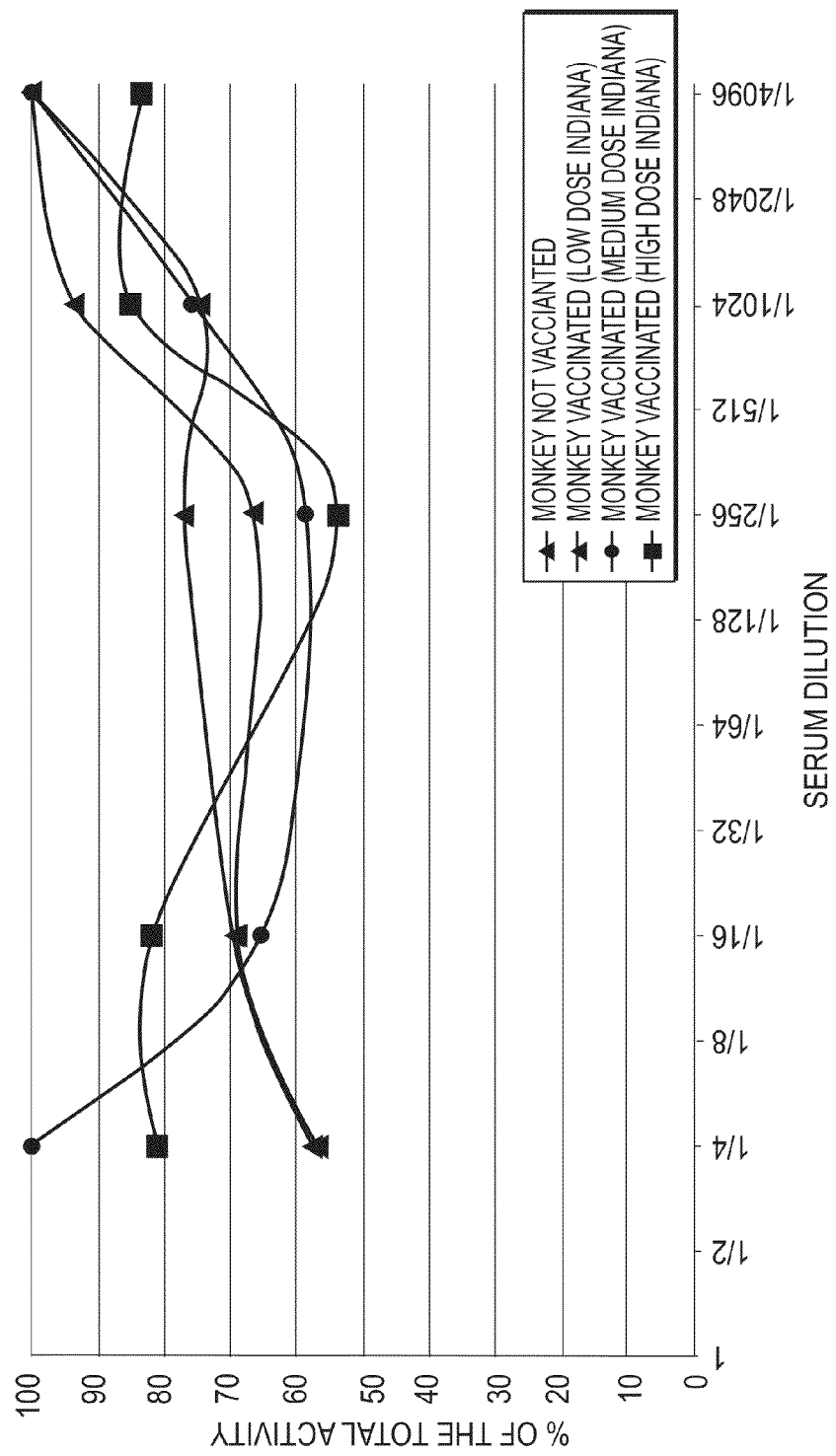
Figure 57B:
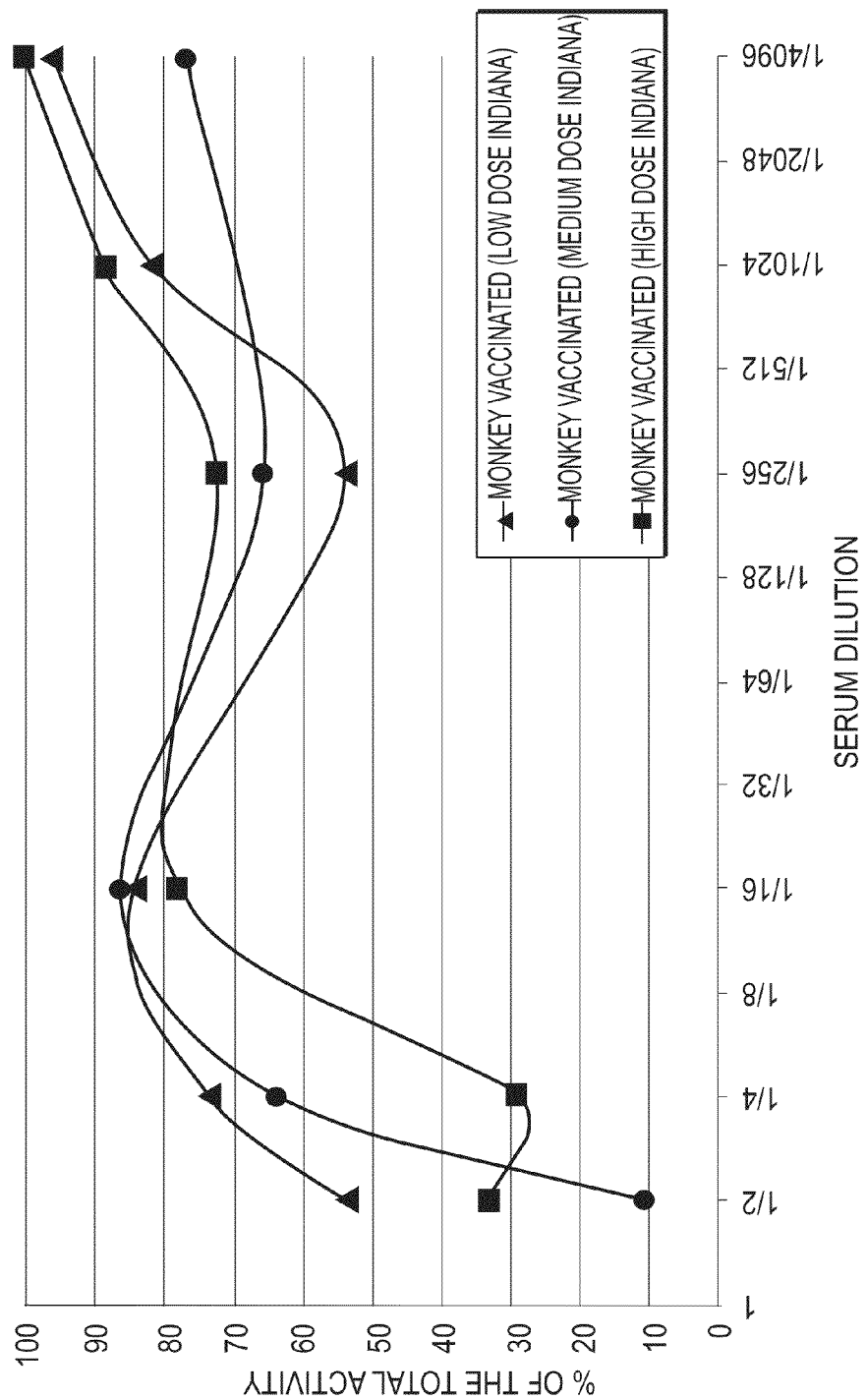
Figure 57C:
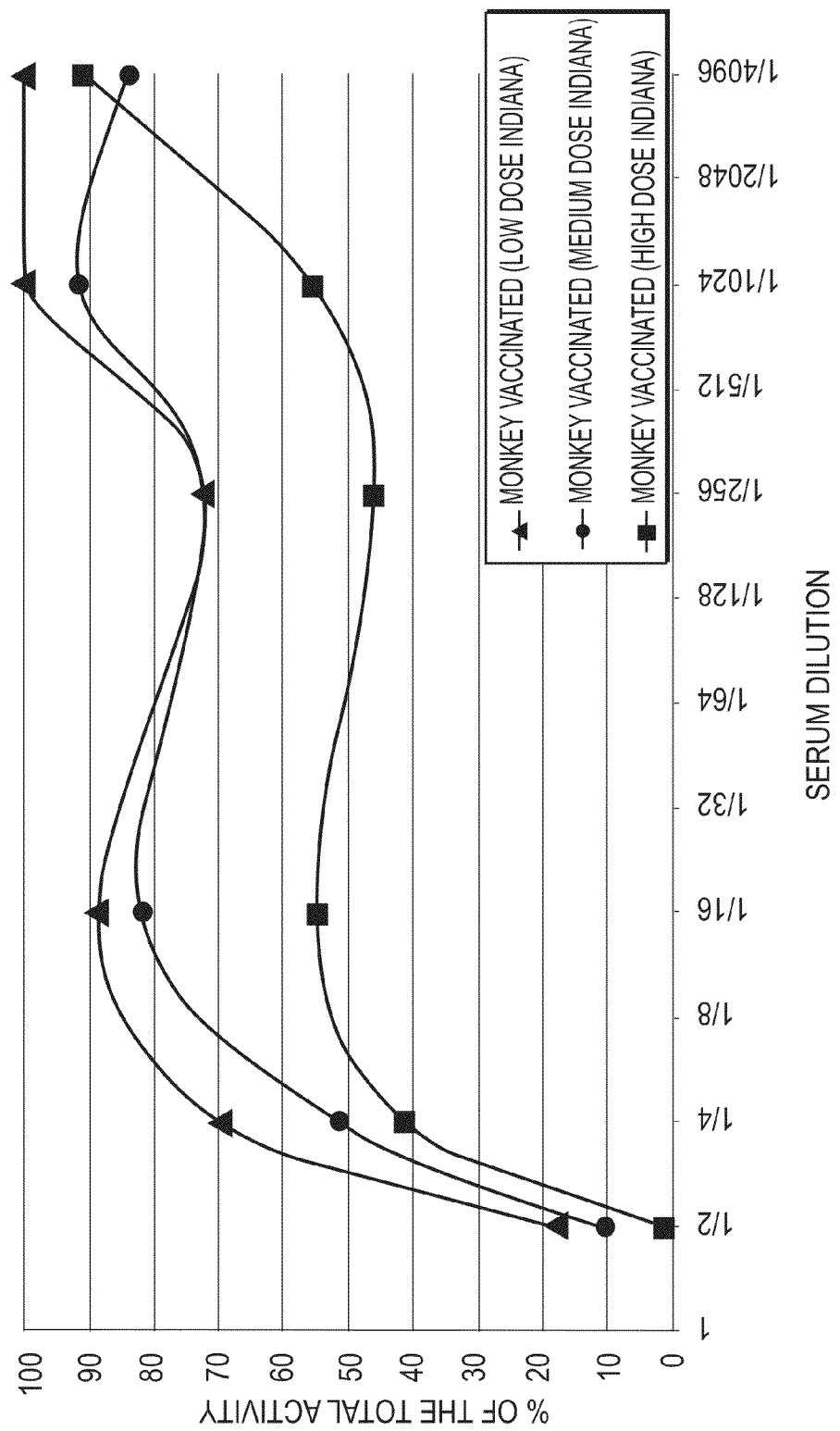
Figure 59A:
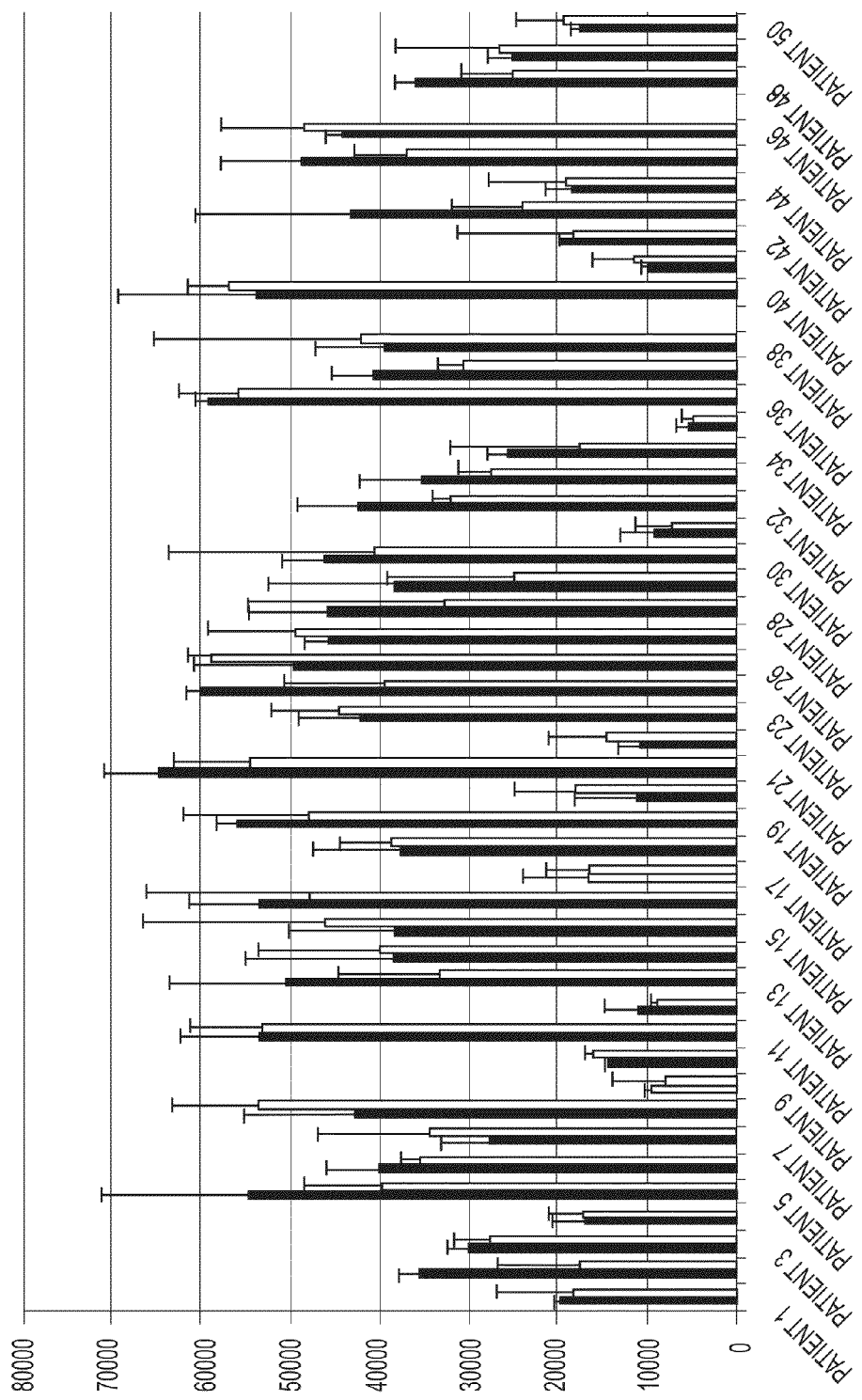
Figure 59A:
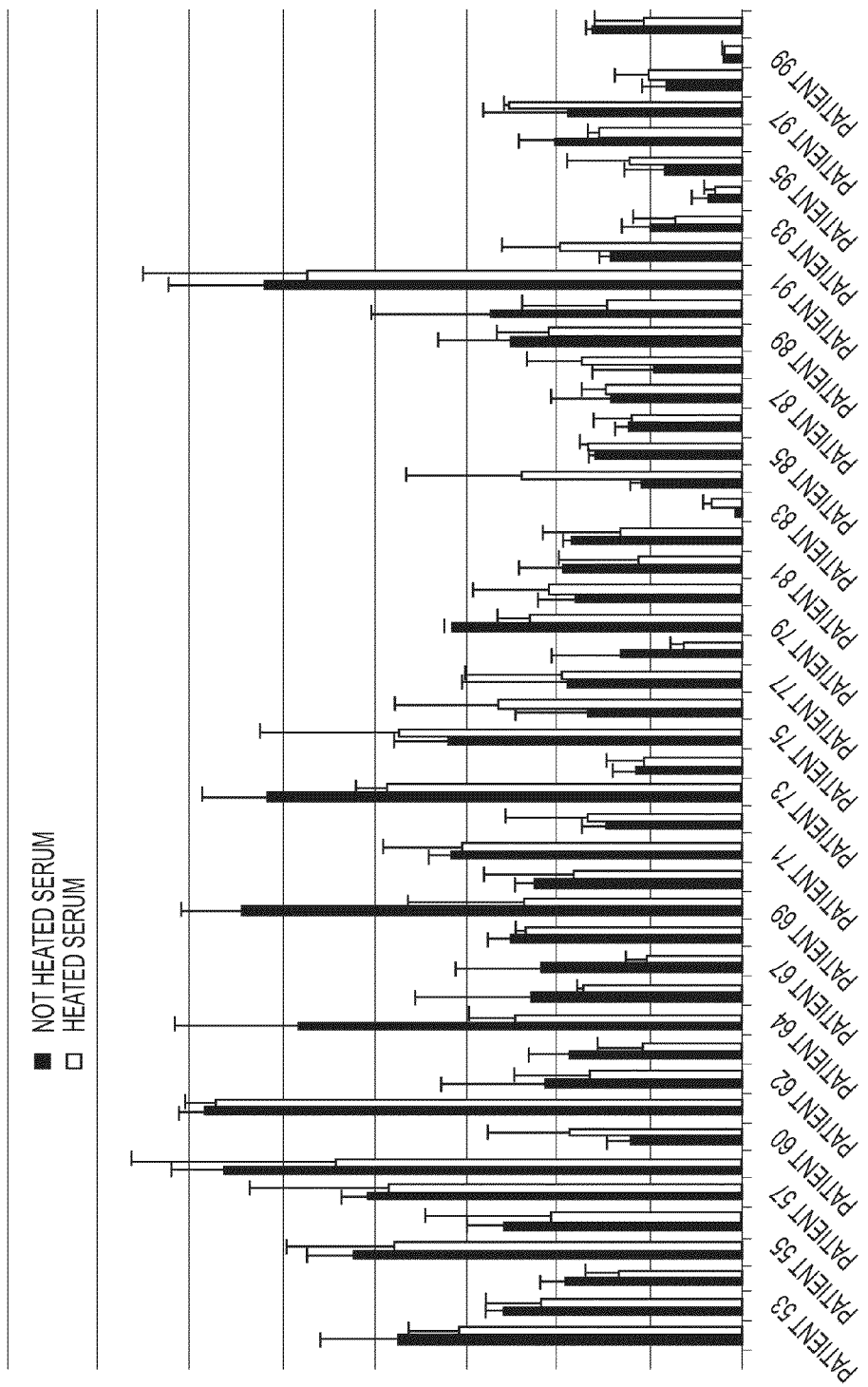
Figure 59B:
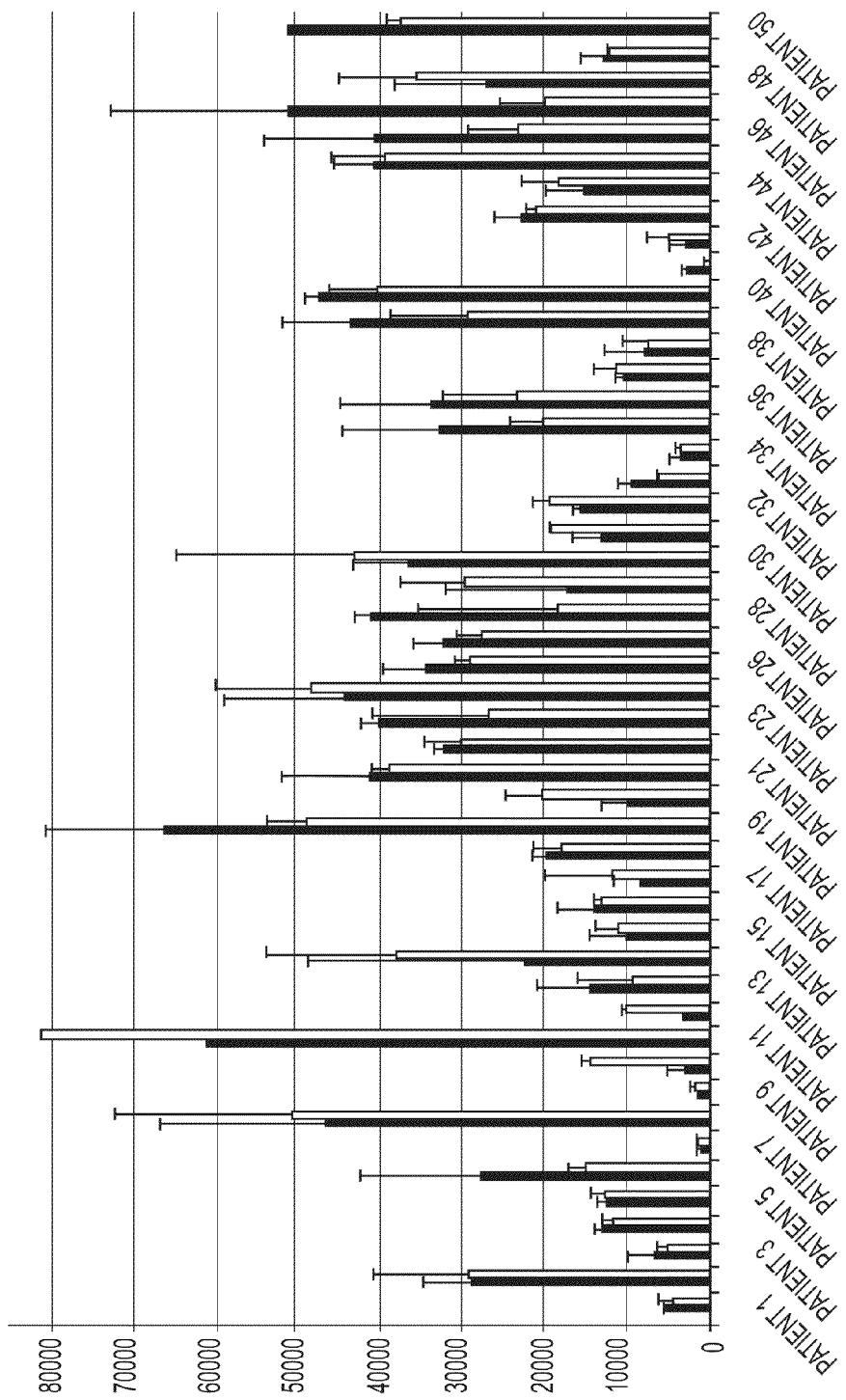
Figure 59B:
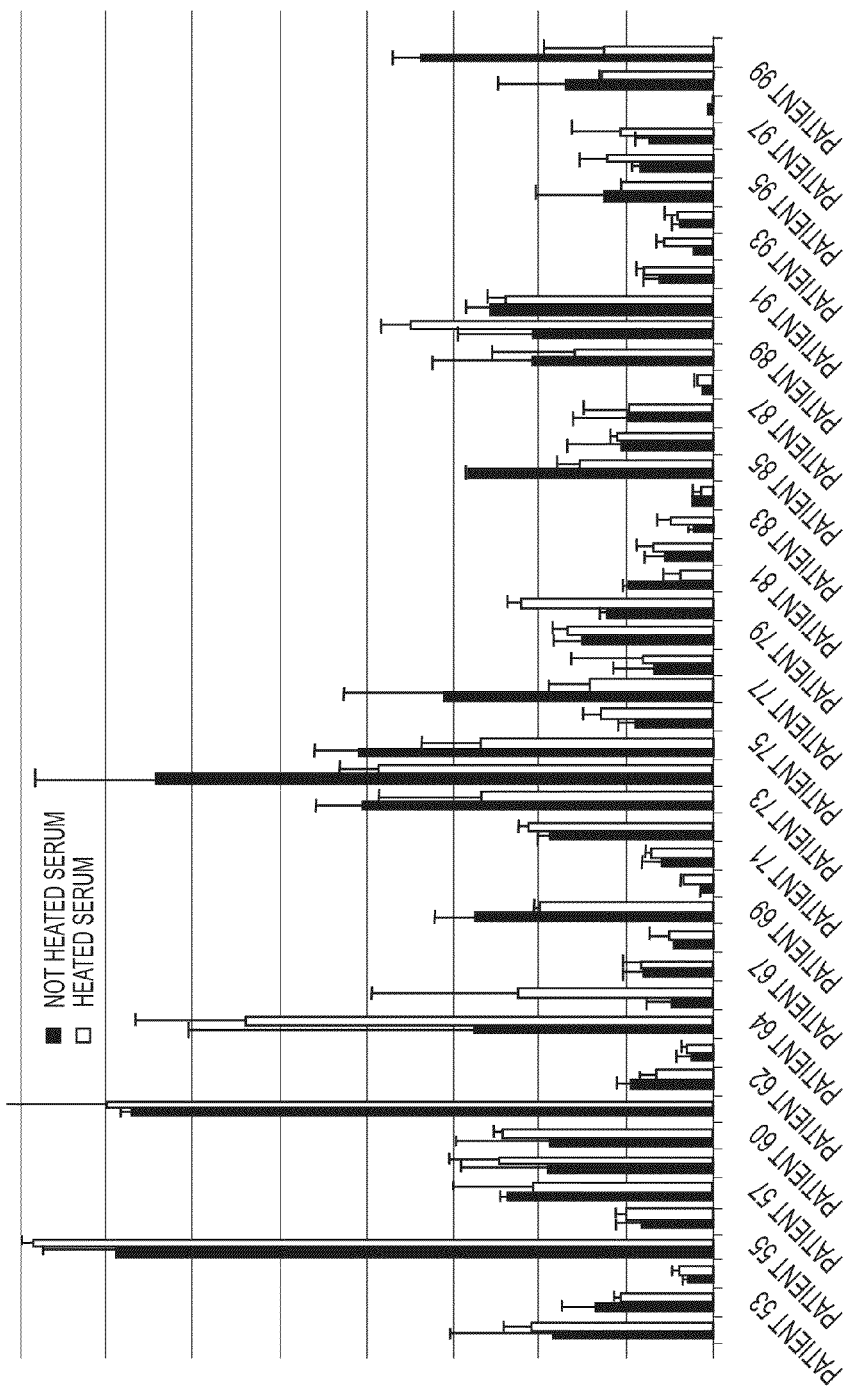
Figure 59C:
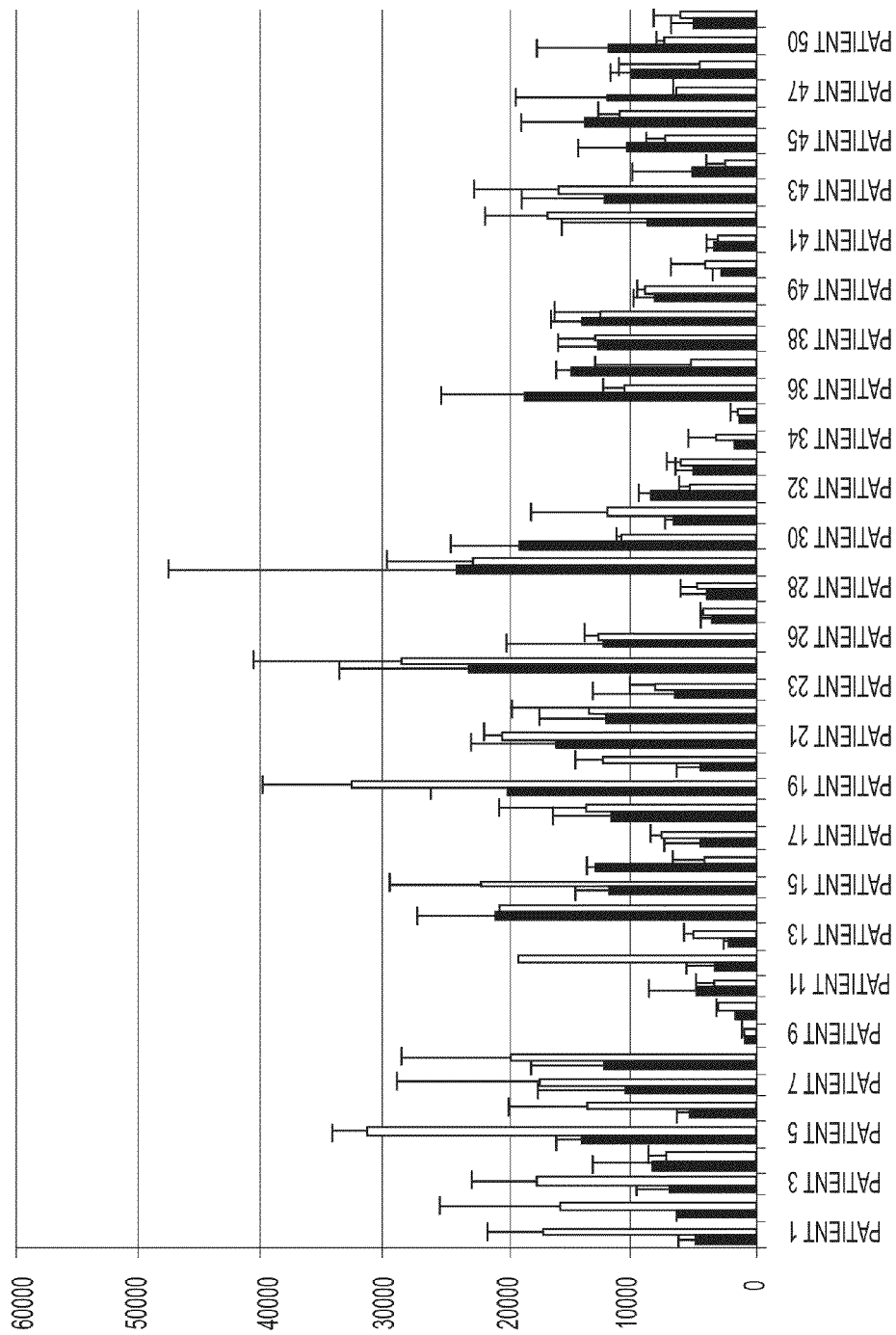
Figure 59C:
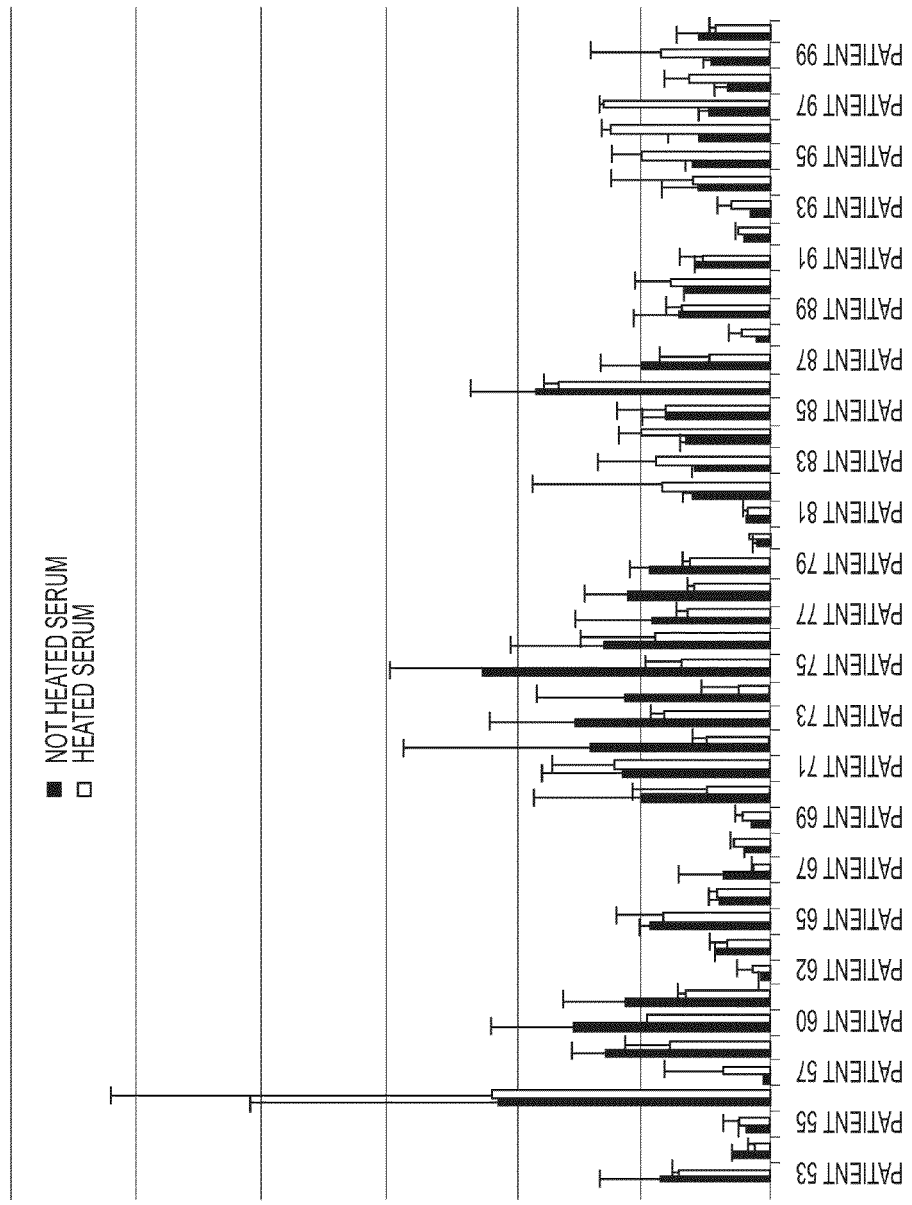
Figure 59D:
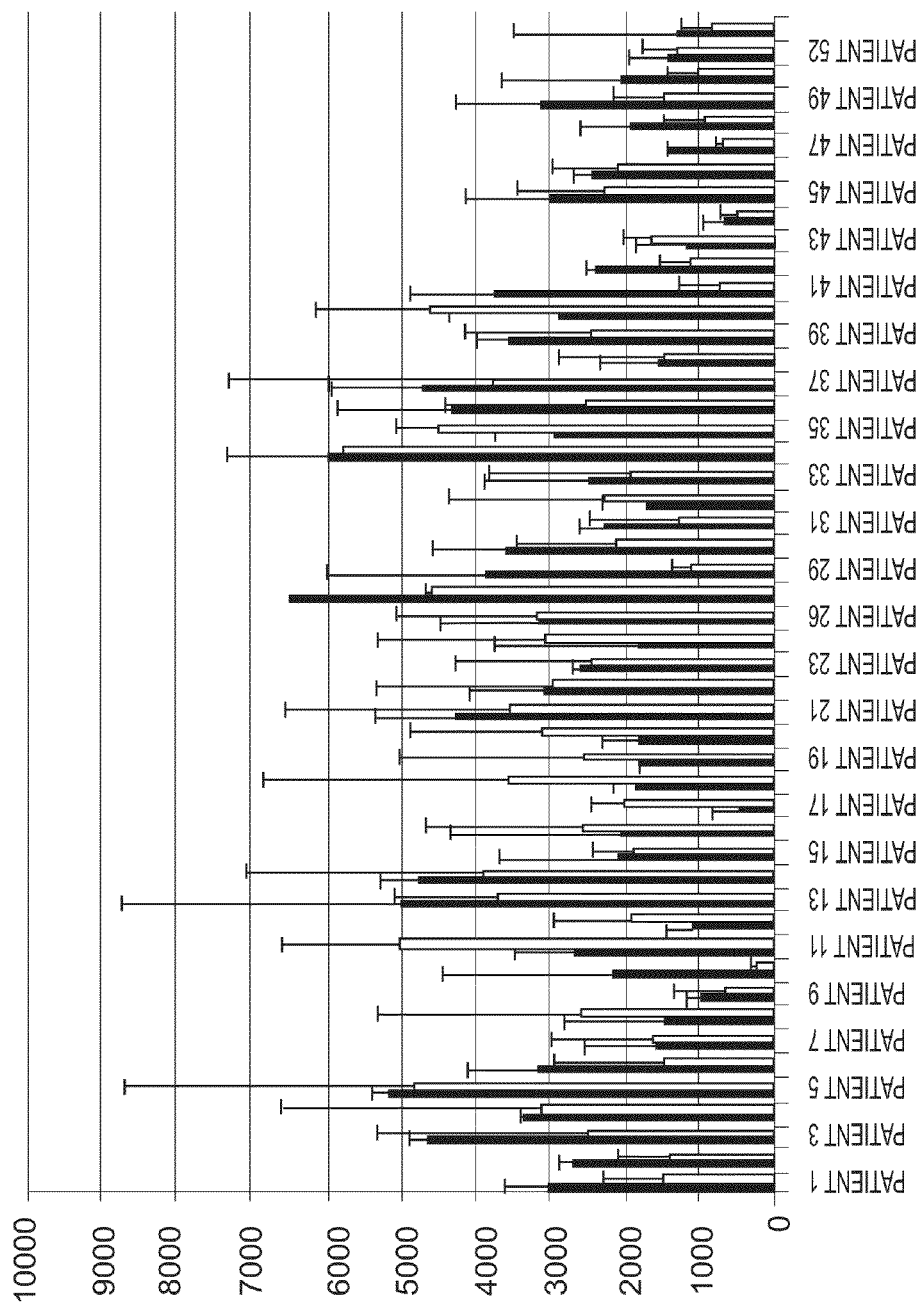
Figure 59D:
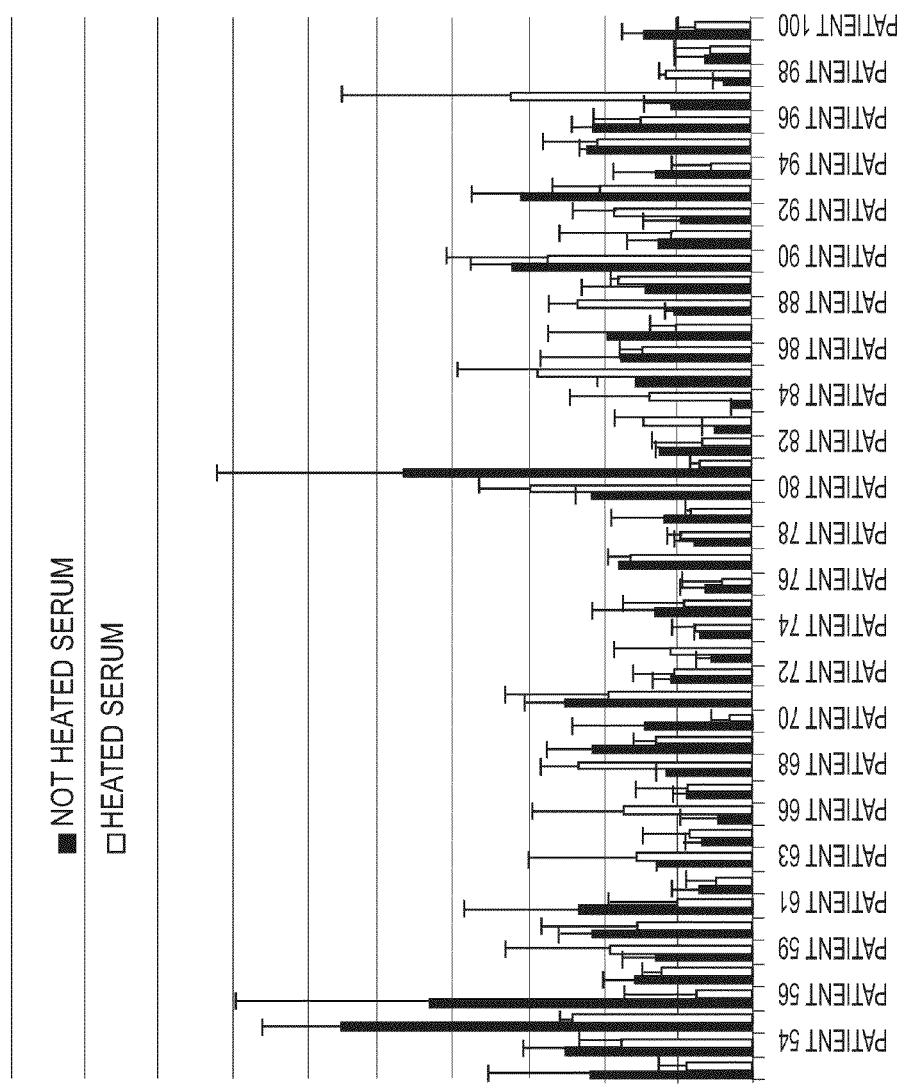
Figure 59E:
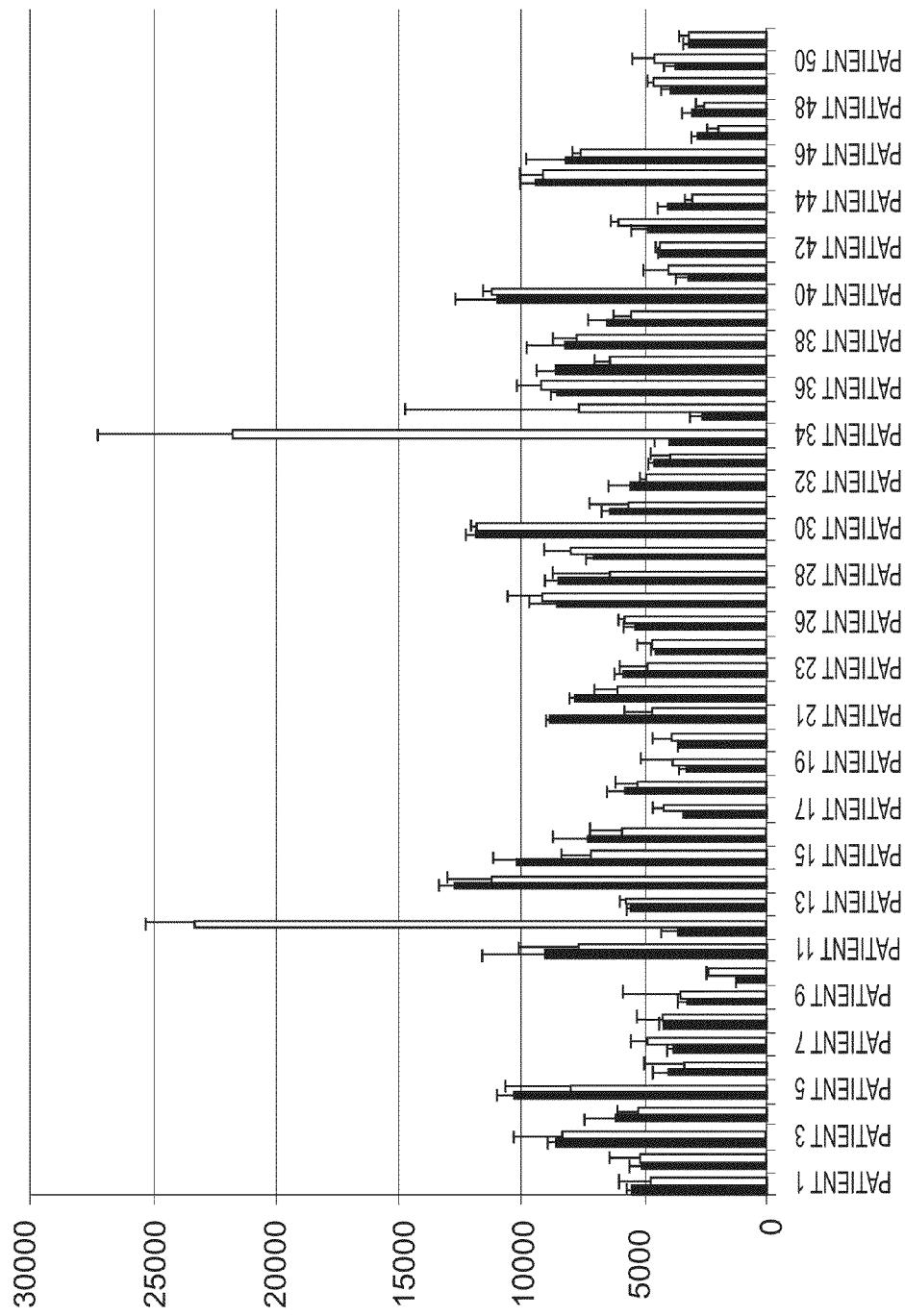
Figure 59E:
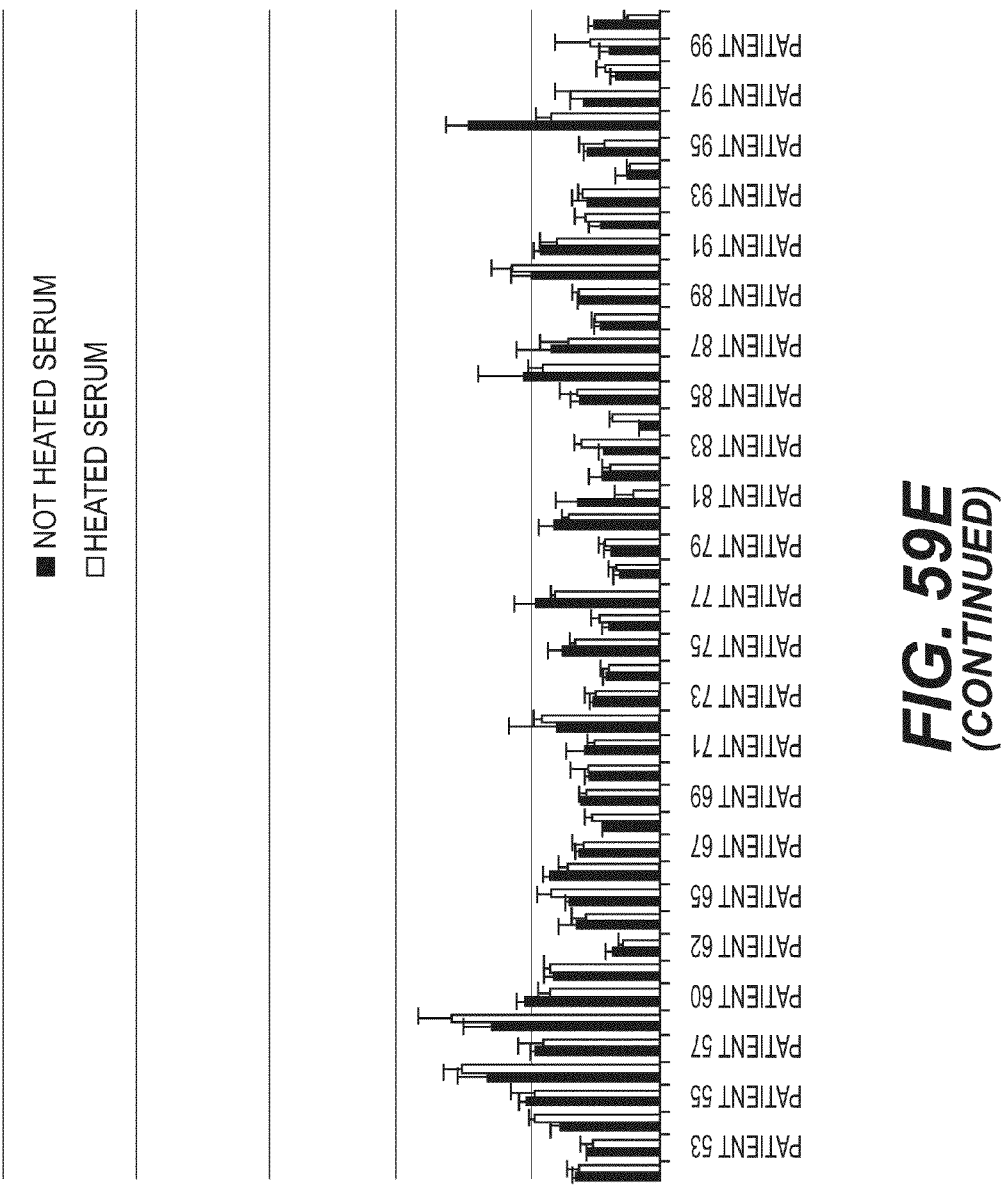
Figure 60A:
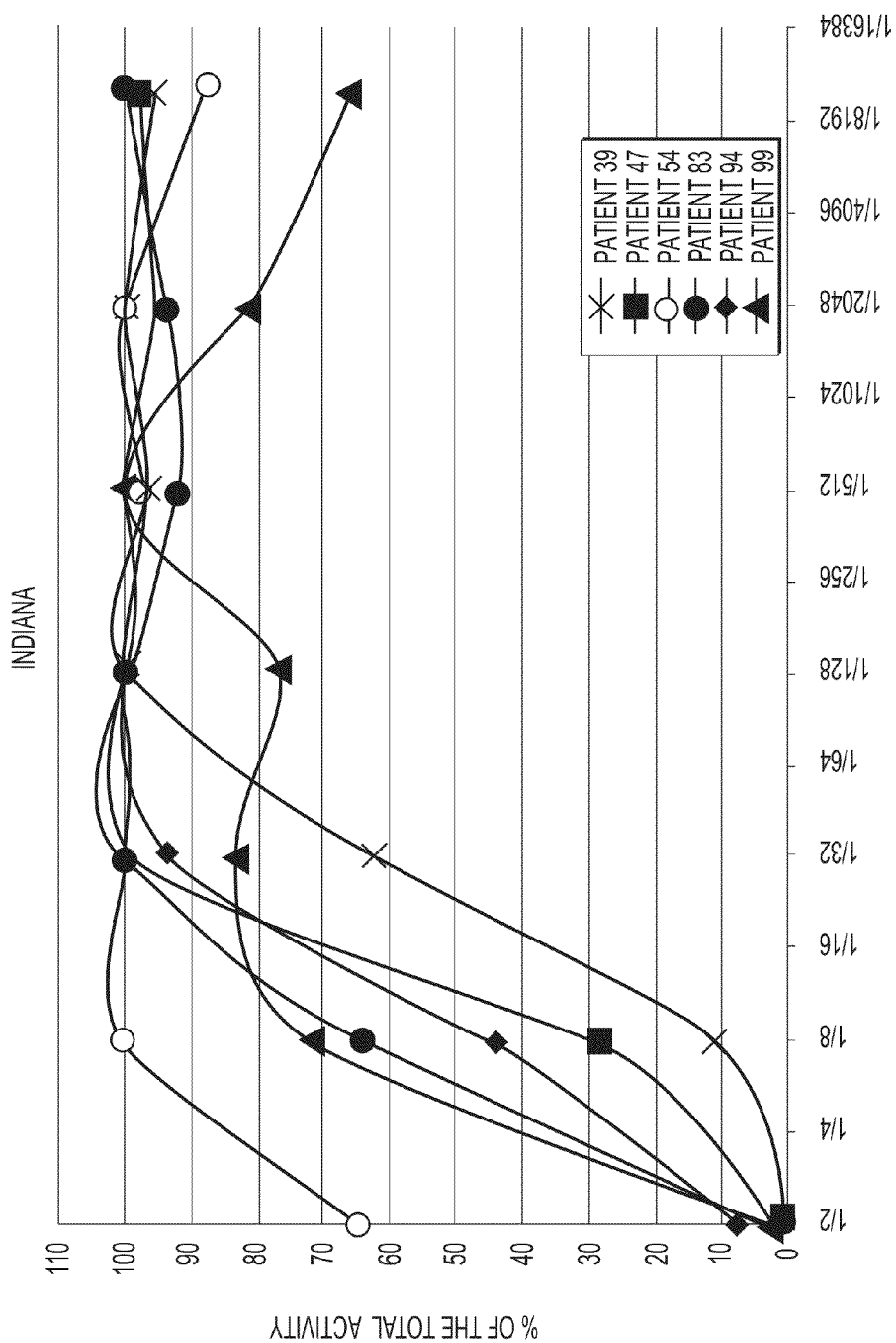
Figure 60B:
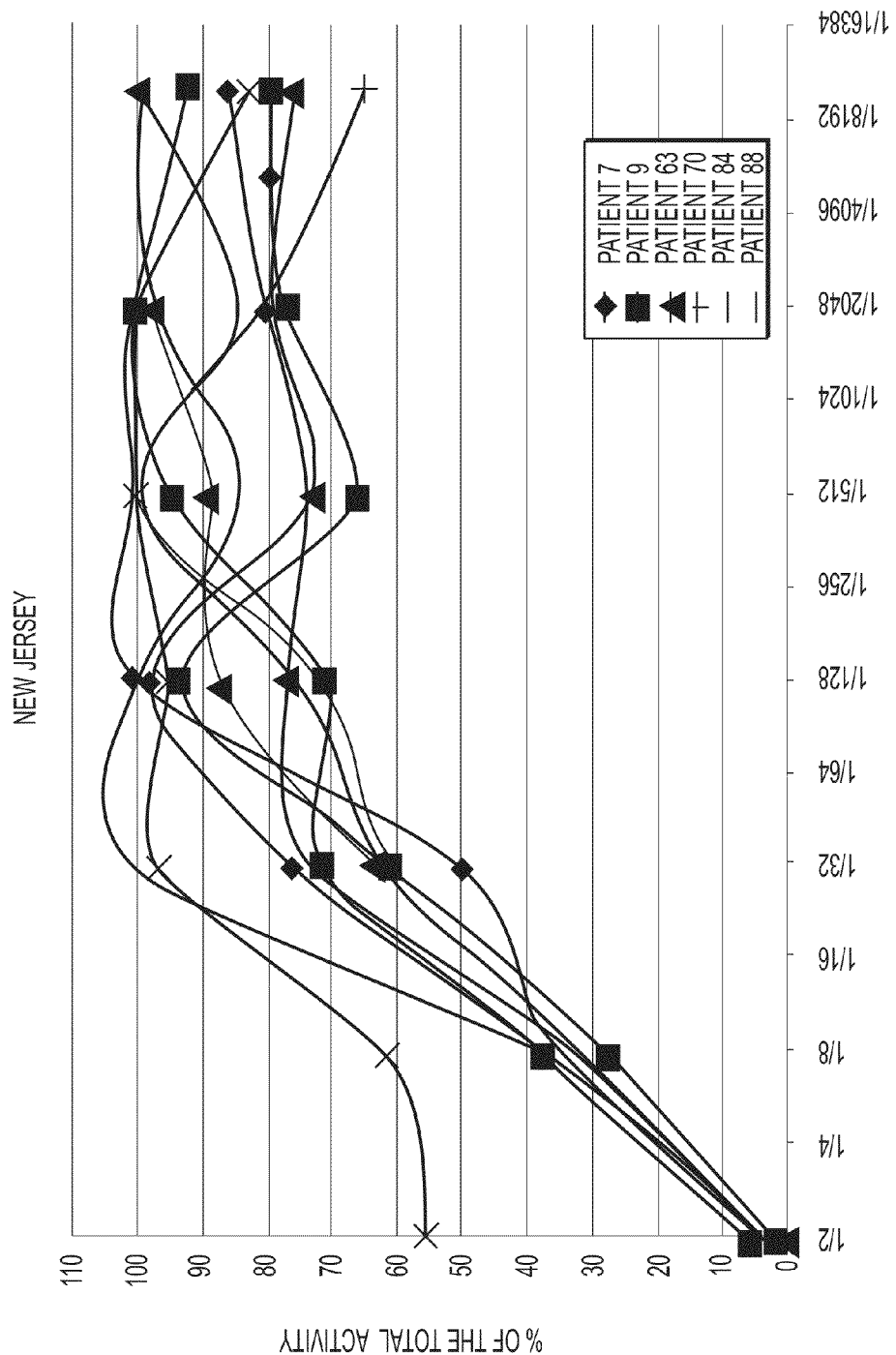
Figure 60C:
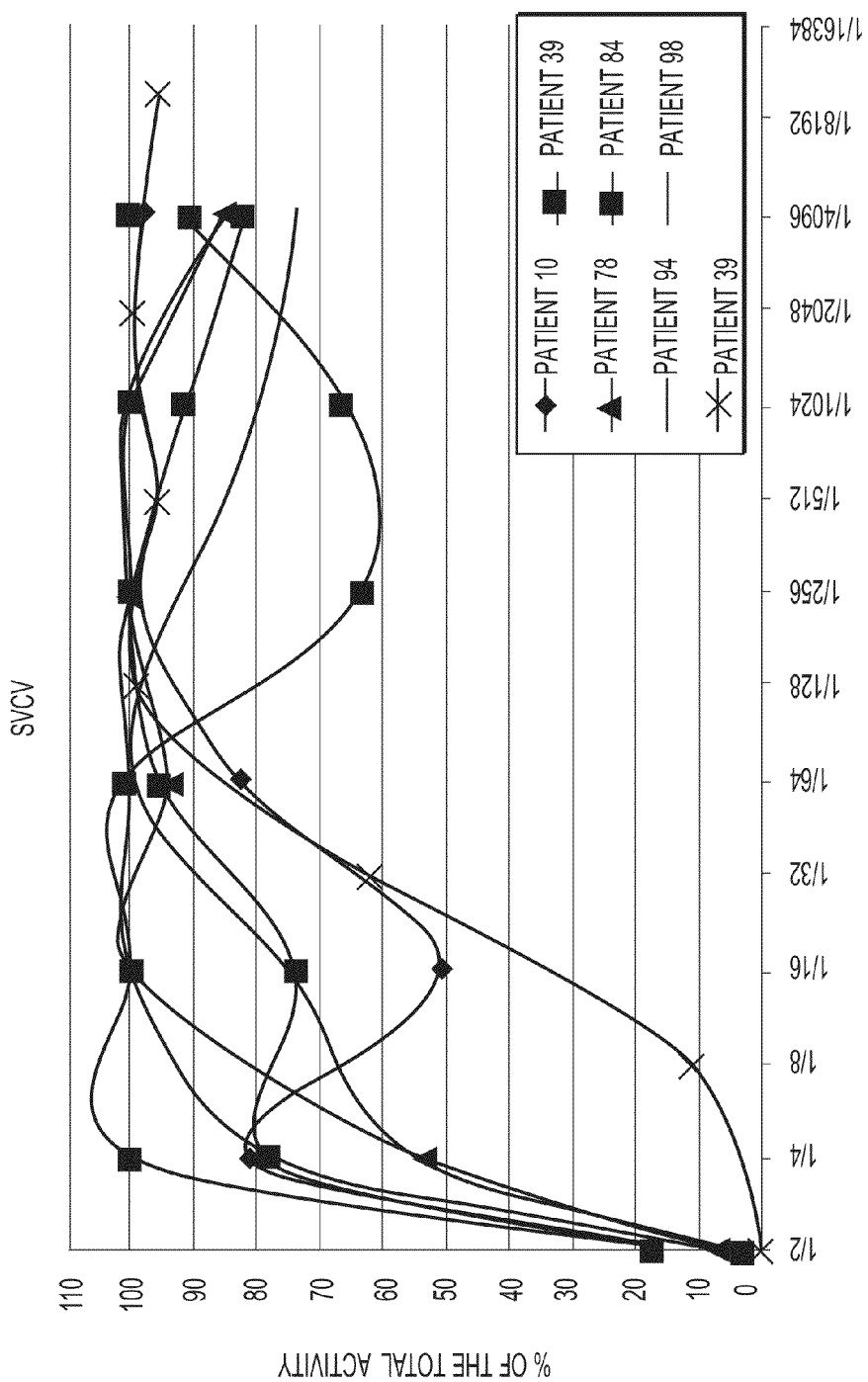
Figure 60D:
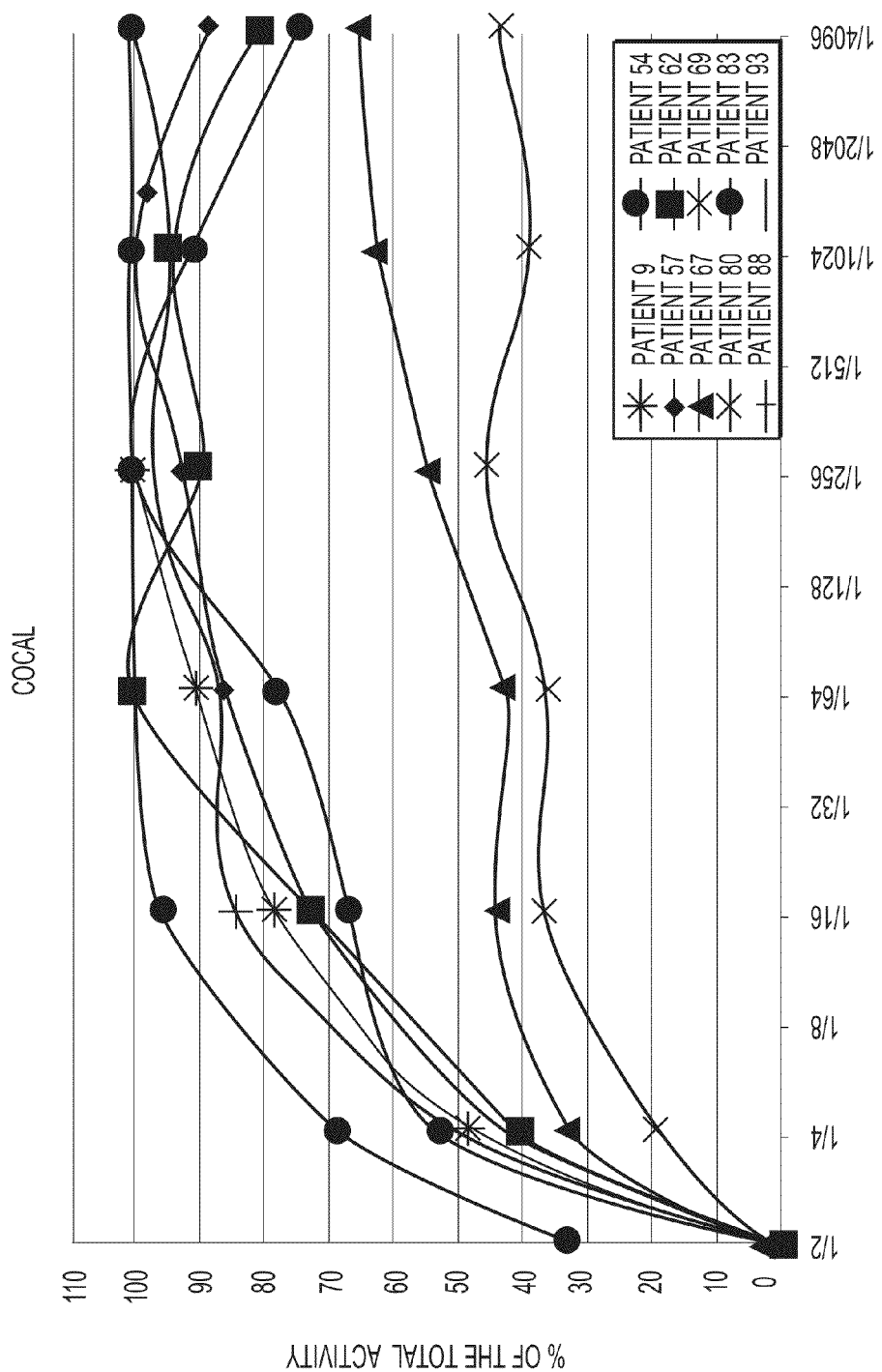
Figure 60E:
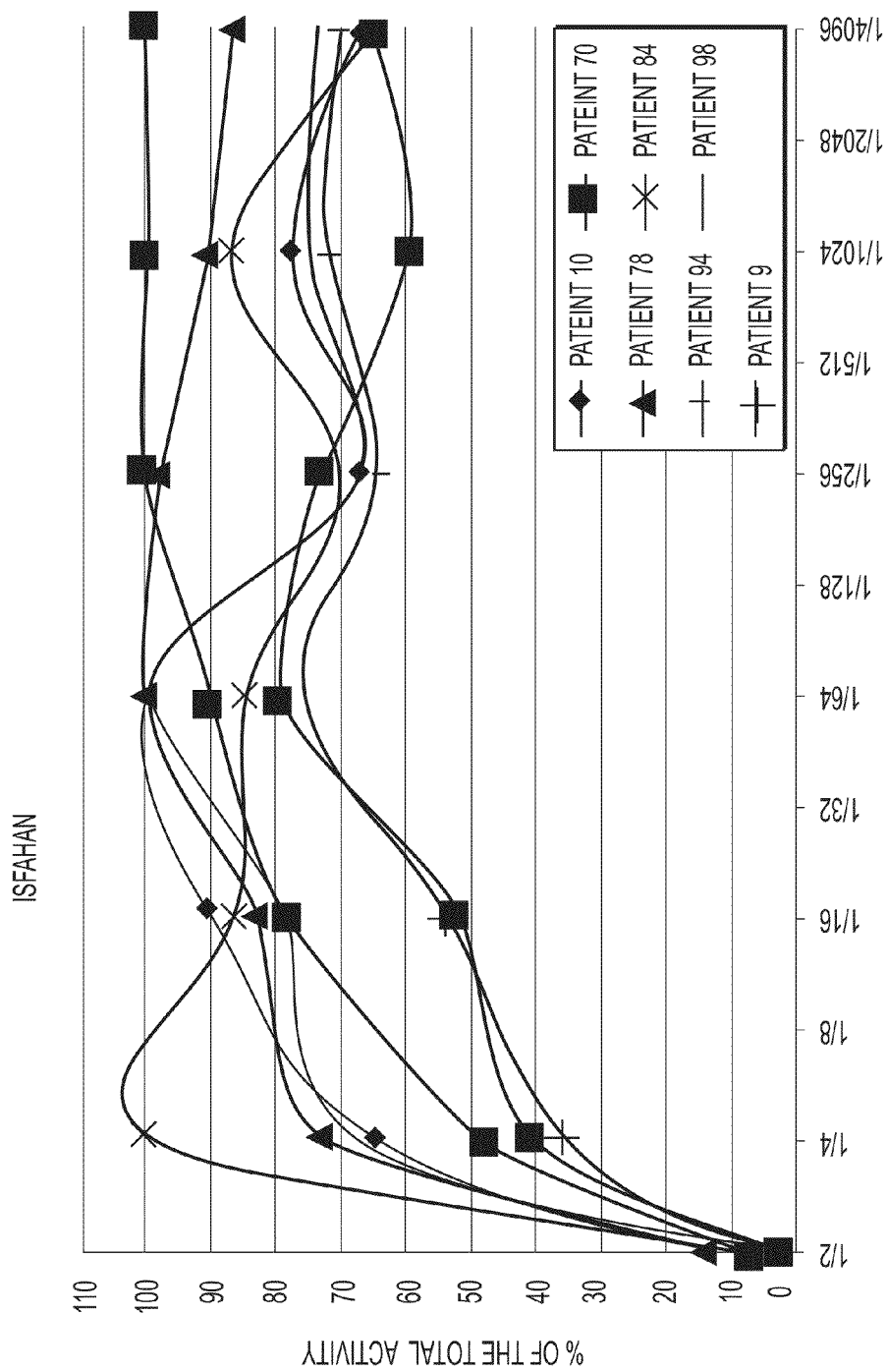

FIG. 57: Activity of SVCV pseudotyped particles in presence of various monkey sera. A: Sera from pre-immunized monkeys, B: sera from monkeys injected with Indiana pseudotyped particles at various doses (prime) and C: monkey sera after an injection with New Jersey pseudotyped particles (boost)

FIG. 58: Prevalence of antibodies against the VSV.G proteins in human sera. The presence of neutralizing antibodies against VSV-G proteins was determined by transduction assays of particles pseudotyped with A: VSV-G Indiana, B: VSV-G New jersey, C: VSV-G Cocal, D: VSV-G SVCV and E: VSV-G Isfahan, in presence of various human sera, heated or not heated.

FIG. 59: Prevalence of antibodies against the Cocal VSV.G protein in human sera. 96 human sera (both heated and not heated) were tested in transduction experiments (in 1/2 dilution) in presence of viral particles pseudotyped with A: Indiana, B: New Jersey, C: Cocal, D: Isfahan and E: SVCV VSV.G proteins. These experiments have been done twice for each conditions.

Figure 61A:
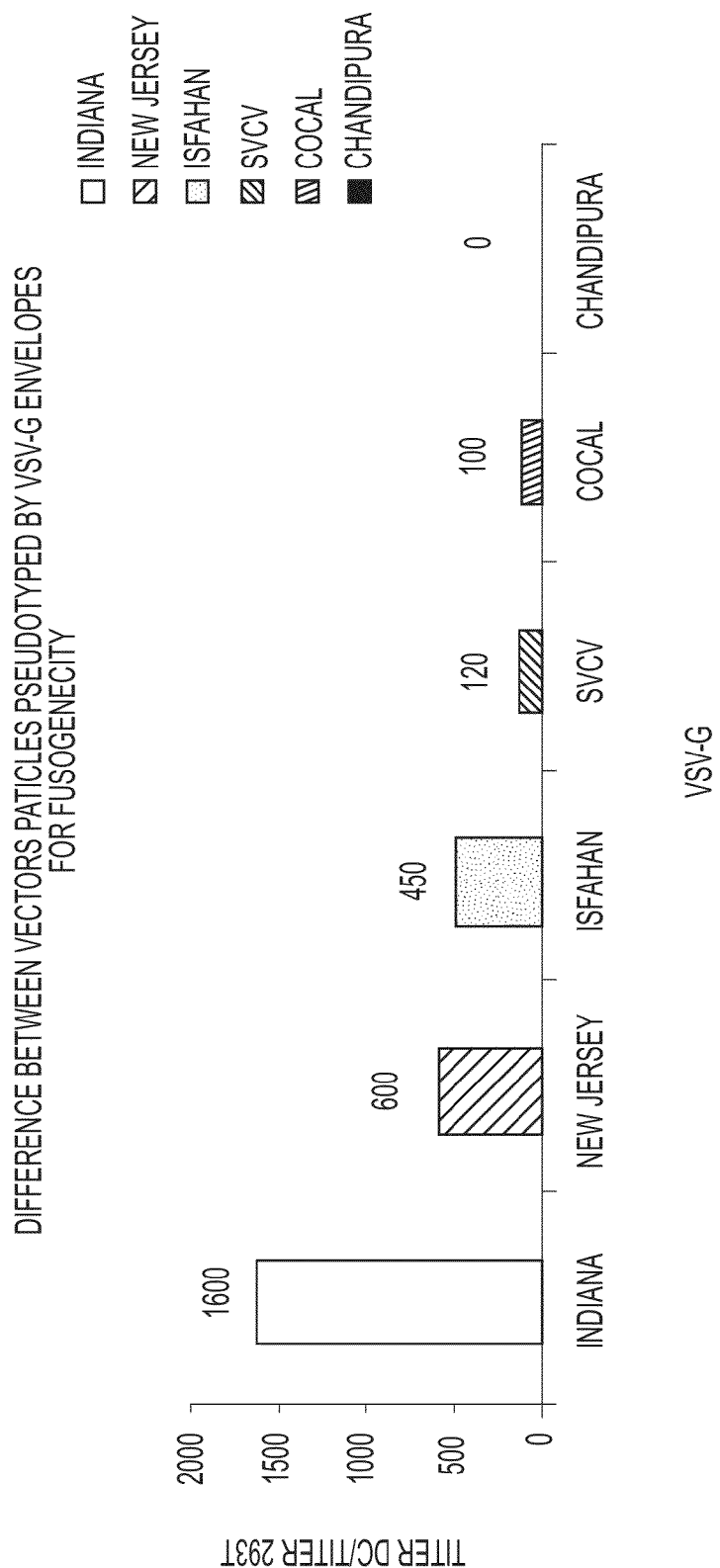
Figure 61B:
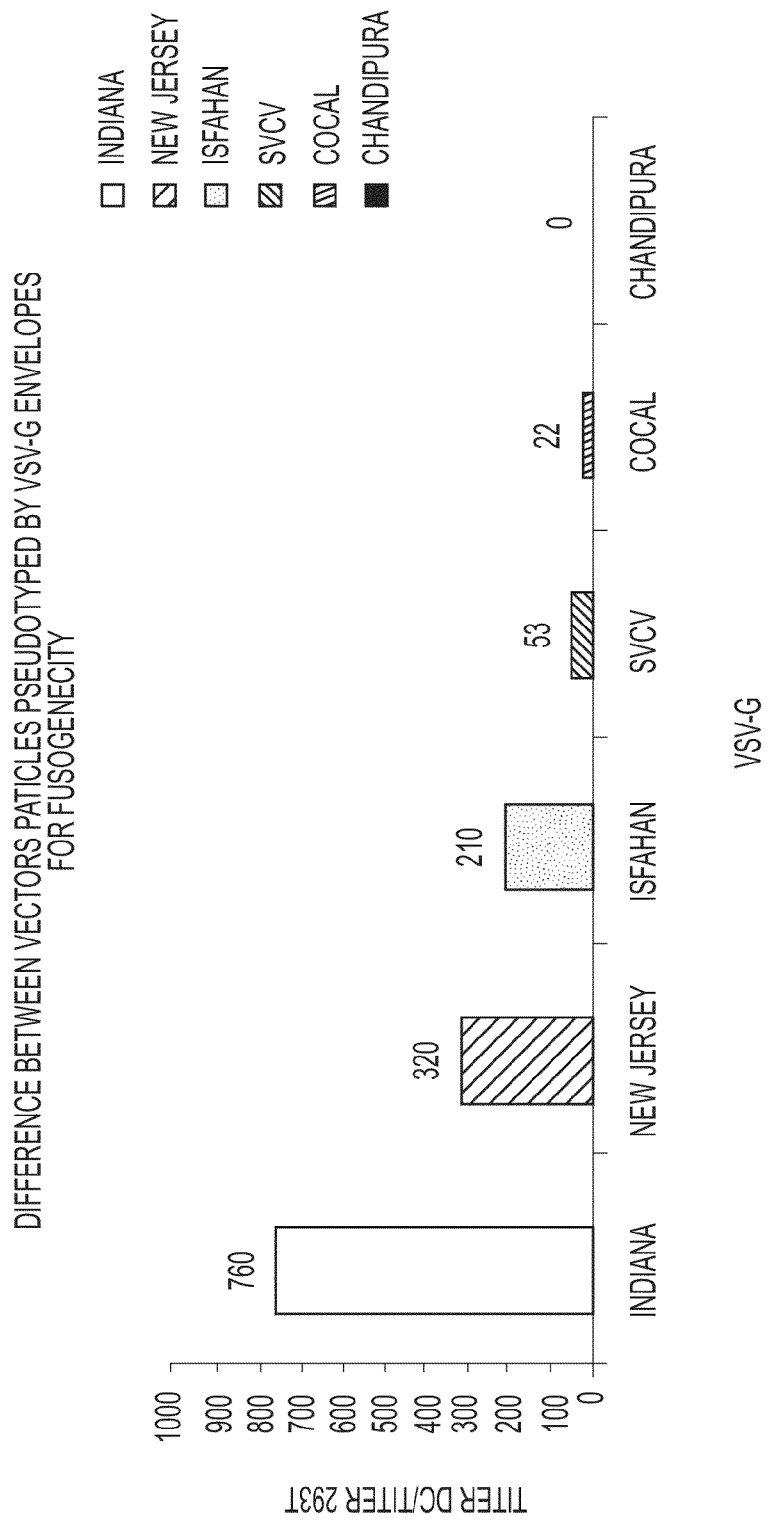

FIG. 60: Analysis of the human sera from patients neutralizing the VSV-G proteins. Patients whose serum are presenting a neutralizing activity against VSV-G proteins are investigated by transduction assays (A: Indiana, B: New Jersey, C: SVCV, D Cocal and E: Isfahan particles in serial dilutions FIG. 61: Ability of vector particles pseudotyped by different VSV-G envelope to fuse or not with mDCh. The human monocyte derived DCs (mDCs) was transduced with GFP vector particles pseudotyped by VSV-G envelope of Indiana, New Jersey, Isfahan, SVCV, Cocal and Chandipura. Five days after transduction, mDCs were analyzed by flow cytometry to determine the titer. Relative titer are expressed as a ratio between the titer determined on mDCs and the titer determined in 293T cells.

THE APPLICATION OF TRIP LENTIVIRAL VECTORS IN A VACCINATION STRATEGY AGAINST SIV INFECTION AS A MODEL FOR ILLUSTRATION OF VACCINATION AGAINST HIV INFECTION

I. Potential of the Trip Vector to Induce Anti-SIV Specific T Cells Responses in Mice Models.

To determine if lentivirus vectors harbouring an envelope protein originating from a VSV virus could be modified to allow boosting of immune responses, we developed a new vector strategy based on lentiviral vectors expressing the glycoprotein from different VSV serotypes expected not to be cross-reactive.

Isolates of Vesicular stomatitis virus (VSV) are enveloped, non segmented, negative-strand RNA viruses that belong to the genus Vesiculovirus in the Rhabdoviridae family. VSV infects domestic animals such as cattle, swine, and horses, causing vesicular lesions in the tongue, oral tissues, udders, and hooves. The VSV genome is delivered to the cytoplasm of host cells, where replication occurs, via receptor-mediated endocytosis of viral particles and subsequent pH-induced fusion of the viral envelope with the endosomal membrane. The VSV G protein, the sole viral surface glycoprotein, is required for attachment and fusion. There are two major serotypes of VSV, Indiana and New Jersey, which are distinguished by neutralizing antibodies against the G glycoprotein. In addition to their antigenic structures, the Indiana and New Jersey glycoproteins also differ in the number (511 and 517, respectively) and composition of amino acids (only 50% identity), in posttranslational modifications, and in folding. Correspondingly, Indiana and New Jersey strains are not equally important regarding VSV pathogenesis. Outbreaks caused by New Jersey strains are more frequent and more severe than those caused by Indiana strains.

Materials and Methods

Mice. Female C57B1J6 mice (élevage Janvier, France) were bred at the Pasteur Institute facilities.

Cell culture. HeLa (human cervical adenocarcinoma) available at the ECACC) and human embryonic kidney 293T cells (available at the ATCC), used for lentiviral vector production, were grown in Dulbecco's modified Eagle medium (DMEM) Glutamax (GIBCO) supplemented with 10% heat-inactivated fetal calf serum (FCS) and antibiotics (penicillin-streptomycin).

Vector Construction and Production

The vector plasmid pTRIP.ΔU3.CMV.SIVmac239gagΔmyr contain a non myristoylated form of SIVmac239 gag sequence under the control of the cytomegalovirus immediate early promoter (CMVie). Vector particles were produced by transient calcium phosphate co-transfection of 293T cells with the vector plasmid, an encapsidation plasmid (p8.7) and a VSV-G envelope expression plasmid, Indiana serotype (pHCMV-G) (10) vs New Jersey serotype (pcDNA3.1(−) NJ-G) (derived from commercialized pcDNA3.1 plasmid available from Invitrogen). The protein sequence is disclosed on FIG. 3.

Cloning strategy encompassed the following steps:

A plasmid containing the gene from the glycoprotein from the New Jersey VSV serotype (pBS VSV-G NJ) has been used.

It was cloned into a pcDNA 3.1 (−) vector (Invitrogen) after XhoI/NotI digestion. The plasmid derived by this method was designated pcDNA3.1(−) VSV-G NJ.

The WPRE sequence (Woodchuck hepatitis virus postregulatory element) (11) is a posttranscriptional regulatory element known to significantly increase gene expression. It was cloned into a TOPO® Cloning vector (Invitrogen).

The WPREsequence was cloned into the pcDNA3.1(−) VSV-G NJ after EcoRI digestion and dephosphorylation. The plasmid derived by this method was designated pcDNA3.1(−) VSV-G NJ WPRE.

WPRE Quantification of p24 antigen content of concentrated vector particles was done with a commercial HIV-1 p24 ELISA kit (Perkin-Elmer Life Sciences). For vector stock titration, 293T cells were transduced with different vector concentrations for 72 h, and lysed. Lysats were treated with Rnase and proteinase K and then used for quantitative PCR (Lightcycler).

In vitro transduction inhibition assay. HeLa cells were plated at 10,000 cells per 96wells-plates. A day later, cells were transduced with lentiviral vectors encoding eGFP (enhanced G FP) and pseudotyped with the glycoprotein from VSV Indiana or New Jersey serotype, after 30 min preincubation with decomplemented mouse serum diluted at 1:6. Mice were either naive mice or mice immunized once with 0.25 $10^7$ transduction units (TU) of lentiviral vector coding for a non myristoylated form of SIVmac239 Gag and pseudotyped with the glycoprotein from VSV Indiana serotype and bled 14 days post-immunization. After 72 h, transduction was assayed by flow cytometry. The percentage of transduction neutralization was calculated in comparison to transduction in the absence of serum.

Mice immunization. All animal experiments were conducted in accordance with the guidelines of the Office Laboratory of Animal Care at the Pasteur institute. Nine-weeks-old mice were intraperitoneally (i.p.) inoculated with 0.25 $10^7$ transduction units (TU) of pTRIP.ΔU3.CMV.SIVmac239gagΔmyr vector particles in 0.2 ml Dulbecco's PBS twice on day 0 and then on day 21. Mice were bled on day 14. Immune responses were analyzed on day 28.

For the prime, a lentiviral vector encoding a non myristoylated form of SIVmac239 Gag and pseudotyped with the glycoprotein from VSV Indiana serotype was administered, whereas for the boost, the same vector but pseudotyped with the glycoprotein from VSV New Jersey serotype was injected.

The comparison was done with the homologous prime/boost strategy using two subsequent injections of lentiviral vector pseudotyped with the glycoprotein from VSV Indiana serotype. As controls, the primary (day 7) and memory (day 28) responses were characterized after a single injection of lentiviral vector pseudotyped with the glycoprotein from VSV Indiana serotype. The primary (day 7) response of mice immunized only once with lentiviral vector pseudotyped with the glycoprotein from VSV New Jersey serotype was also assayed.

IFN-γ Elispot Assay

Nitrocellulose microplates (MAHA S4510, Millipore) were coated overnight with capture antibody (Mouse IFN-γ Elispot pair, BD Pharmingen) and blocked with complete medium composed of RPMI1640 Glutamax supplemented with 10% FCS, antibiotics, hepes, non essential amino-acids, b-mercaptoethanol and sodium pyruvate. Splenocytes from vector-immunized mice were added to the plates in triplicates at $0.25 \times 10^6$ cells/well and stimulated with SIVmac239 gag peptides (NIH AIDS Research and Reference Reagent Program), concanavalin A (1 µg/ml). Forty hours later, spots were revealed with the biotine-conjugated antibody (Mouse IFN-γ Elispot pair, BD Pharmingen) followed by streptavidin-AP (Roche) and BCIP/NBT substrate solution (Promega). Spots were counted using a Bioreader 2000 (Biosys, Karben, Germany) and results were expressed as IFN-g spot-forming cells (SFC) per million splenocytes.

In-vivo Cytotoxicity Assay

For target cell preparation, splenocytes from naïve mice were labelled with various concentrations (high, 5 µM; medium, 1 µM; low, 0.2 µM) of CFSE (carbosyfluoresceindiacetate succinimidyl ester, Vybrant CFDA-SE cell-tracer kit, Molecular Probes) Splenocytes were then pulsed with peptides at 5 µg/ml. Each mouse received $10^7$ CFSE-labelled cells of a mix containing an equal number of cells from each fraction, through the retroorbital vein. After 15-18 h, single-cell suspensions from spleens were analyzed by flow cytometry (Becton Dickinson, CellQuest software). The disappearance of peptide-pulsed cells was determined by comparing the ratio of pulsed (high/medium CFSE fluorescence intensity) to non-pulsed (low CFSE fluorescence intensity) populations in immunized versus naïve mice. The percentage of specific killing was established according to the following calculation:

$$[1-[(CFSE_{low}\text{naïve}/CFSE_{high/medium}\text{naïve})/(CFSE_{low}\text{immunized}/CFSE_{high/medium}\text{immunized})]] \times 100.$$

Results (FIGS. 40 to 42)

We first showed that mice immunized only once and with a low dose (0.25 10e7 TU/mouse, corresponding to 650 ng p24 for this batch) of lentiviral vector pseudotyped with the glycoprotein from VSV Indiana serotype do develop strong humoral response which neutralize the in vitro transduction of cells with a lentiviral vector pseudotyped with the same envelope. On the contrary, there was only a low sero-neutralization of transduction by vector pseudotyped with the glycoprotein from VSV New Jersey serotype detectable.

A preliminary dose response experiment using the lentiviral vector encoding a non myristoylated form of SIVmac239 Gag and pseudotyped with the glycoprotein from VSV Indiana serotype allowed us to characterize the immune responses and identify peptides containing an immunodominant CD8 epitope (SIVmac239 gag: 309-323 (QTDAAVKNWMTQTLL) (SEQ ID NO: 12)) as well as a subdominant CD8 epitope (SIVmac239 gag: 73-97 (ENLKSLYNTVCVIWC) (SEQ ID NO: 13) (data not shown). A dose as low as 0.45 $10^7$ TU/mouse was sufficient to reach a plateau of 100% responding mice with a specific lysis of almost 100% for the immunodominant CD8 epitope-containing peptide. In contrast, even high doses (up to 23 $10^7$ TU/mouse) were not enough to stimulate an in vivo cytolytic activity of 100% in the case of the subdominant-CD8 epitope-containing peptide In parallel, a recently published paper using adenoviral vectors coding for the same antigen characterized a peptide containing a CD4 epitope (SIVmac239 gag: 297-311 (YVDRFYKSLRAEQTD) (SEQ ID NO: 14)).

Therefore, we choosed to monitor immunity directed against these 3 peptides and to immunize mice with a sub-optimal dose of vector (0.25 $10^7$ TU/mouse) in order to be able to detect a boosting effect both in terms of number of responding mice and amplitude of the responses.

II—Protective Response Against SIVMAC in Non-human Primate Model

Introduction

1 HIV Infection and AIDS 1.1 HIV and its Impacts 1.1.1 Epidemiology

Since the first cases of acquired immunodeficiency syndrome (AIDS) were reported in 1981, the global spread of Human Immunodeficiency Virus (HIV) has reached pandemic proportions and represents now a global developmental and public health threat (Girard et al., 2006). Indeed, the number of people living with HIV throughout the world is nowadays around 39.5 million and is still growing exponentially, with 4.3 million people infected in the previous year and an estimated 14,000 people becoming infected every day (http//www.unaids.org).

1.1.2 HIV Biology

The physiopathology of the infection is directly correlated with the characteristics of the HIV. This virus belongs to the family of Retroviridae, genus lentivirus. It is an enveloped virus of around 110 to 120 nm in diameter. The gp120 glycoprotein is responsible for the virus tropism; indeed it allows the fixation to the cellular receptor CD4 and co-receptors CCR5 or CXCR4, making thus $CD4^+$ lymphocytes its major target cells. Once virus attaches to $CD4^+$ lymphocytes, the viral cycle is divided in 2 major steps: early and late step. In the cytoplasm, viral RNA is reverse transcribed into double stranded DNA inside the viral capsid and actively imported to the nucleus where it can integrate in the cell genome (Arhel et al., 2007). Transcription of viral DNA and translation of viral mRNA allows the formation of new viral particles.

Most studies of AIDS pathogenesis are carried-out in non-human primates with an HIV simian equivalent: SIV. Indeed, SIV viral structure and biology are closely related to HIV ones.

1.1.3 Physiopathology of HIV Infection

Disease progression is accurately defined by combined measurement of plasma HIV-1 RNA and CD4$^+$lymphocytes. Natural HIV infection can be divided into 3 major phases: primo infection or acute infection, characterized by a peak in viral load (around $10^6$ copies RNA/ml of blood) and by a rapid but transient decrease in circulating T CD4$^+$(Weber, 2001). Moreover, at this early stage of infection, HIV specific CD4$^+$ T cells are the major targets of the virus and are preferentially destroyed in the absence of any treatment (Rosenberg et al., 2000). However, this increase in viral load is generally well controlled by a specific immune response, principally cellular. Indeed, there is evidence for a temporal correlation between the appearance of HIV-specific CD8$^+$ T cells and the decline of primary viremia (Koup et al., 1994). As a consequence, T CD4$^+$ number gets back to a higher level (inferior to the one prior to infection) and viremia stabilizes (between $10^3$ and $10^6$ RNA copies/ml): the set-point (SP) is reached; its level often correlates with the evolution of the disease (Mellors, 1996). The infected individual then enters an asymptomatic period, which can last anything from months to years. This period is characterized by a slow and linear decrease in the number of circulating CD4$^+$, due to an equilibrium between the immune system and HIV replication. In absence of treatment, this asymptomatic phase is followed by AIDS. At this point, viremia progressively returns to a high level and an inflection in the CD4$^+$ T cells depletion slope is observed (CD4 count inferior to 200 cells/mm$^3$ of blood). Eventually, the immune system collapses and disease causing agents that are usually either completely controlled or easily cleared become potentially lethal.

2. Medical Treatments

2.1 From Monotherapy to HAART

In order to slow-down the progression of the disease to AIDS, new medications were put on the market in 1986. They were called antiretroviral drugs, their goal was to prevent HIV replication and thus to postpone CD4$^+$ T cells depletion. The most famous of these drugs was certainly AZT (Zidovudine), an inhibitor of the virus Reverse Transcriptase (RT). However, this monotherapeutic approach was eventually found to be of limited effectiveness, as HIV is a virus that has the potential to quickly develop a resistance (through mutations) to any antiretroviral medication. In 1996, new inhibitors of RT were commercialized; they were chemically different from AZT-like inhibitors. Eventually, a new class of HIV medication appeared in 1995, protease inhibitors (PI). The combination that is nowadays the "standard" in anti-HIV therapy, called Highly Active Antiretroviral Therapy (HAART), consists of an association of 3 classes of antiretroviral medications, usually 2 different inhibitors of RT and one of PI. HAART allows a powerful long-lasting viral load decrease (FIG. 5B), for most of the patients, virus copies in blood can even become undetectable (Gulick et al., 2000). As a consequence, CD4 count increases, the immune system recovers partially and can again push back opportunistic pathogens (Autran et al., 1997). For patients who have access to the treatment, HAART has allowed an impressive reduction of AIDS related morbidity (Palella et al., 1998).

2.2 HAART limits

Although HAART success is irrefutable, it presents some limits and questions can be raised concerning its long-term use. First of all, HAART treatment is really expensive and is still non accessible to developing countries. Then, the toxicity of these medications is relatively high, they often triggers major side effects (diabetes, lipodystrophia, diarrhoea, headaches . . . ). Moreover, it has been shown that HIV was capable of developing resistances against HAART treatment. Mutations often appear in regions of HIV constrained by the treatment. HAART treatment also limits the production of HIV antigens, apparently to a threshold below what is needed to stimulate HIV-specific effector T cells or to expand HIV-specific naïve T cells. Immune memory to HIV still persists however, as indicated by the transient restoration of CD4 and CD8 immune responses to HIV when the immune system is re-exposed to the virus after treatment interruptions (Autran et al., 2004).

2.3 HIV Vaccination

2.3.1. Prophylactic/Therapeutic Vaccine

Because the efficacy of drugs is still limited and because HAART should become a lifelong therapy, too expensive and difficult to administer in most Third World settings, other strategies have to be found to durably prevent the onset of AIDS. The development of an HIV vaccine may represent the only way to slow the pandemic. Two different strategies of vaccination are being tested. On the one hand, a prophylactic vaccine should be capable of inducing sterilizing immunity, and would prevent both infection and its complications. Such a vaccine should be able to operate at the time of virus entry and at the very early stage of infection, before the virus can disseminate to lymphoid organs. On the other hand, a therapeutic vaccine is designed for chronically infected patients under HAART treatment (Autran et al., 2004). It would consist of first treating patients with HAART to restore immune competence, and then immunize them to subsequently boost their rested immune responses to HIV before interrupting treatment. Eventually, if immune control of the virus could be enhanced, disease progression would be attenuated, allowing treatment interruptions, and consequently a limitation in the use of HAART, thus minimizing their toxicity and cost.

2.3.2 State of Current AIDS Vaccine Research

Whatever strategy is chosen, vaccine development is facing huge scientific challenges, such as high genetic variability of the virus, lack of immune correlates of protection and limitations in the existing animal models. Until now, more than fifty vaccine candidates have been tested in phase I/II clinical trials (www.iavi.org) (See appendix 1 for a summary of anti HIV-1 on going trials). Multiple vaccination strategies have been tested so far (Tonks, 2007). At first, traditional live attenuated vaccines were tested because of their past success against small pox, polio or measles. A live attenuated virus with a deletion in the Nef gene (SIV-Δnef) has been the most effective vaccine in the SIV/macaque model. However, its application is restricted since the vaccine virus persists at a low level indefinitely in vaccinated macaques and can be pathogenic to neonates. In addition SIV-☐nef can cause disease in adults several years after vaccination. Nevertheless these live attenuated vaccines provide a critical proof of principle for the feasibility of HIV vaccine development and allow the characterization of the nature of protective immunity (Koff et al., 2006). Another traditional vaccine strategy was to induce broad and long-lasting neutralizing antibodies to disable viral entry and prevent infection. To this end, subunit vaccines were developed. They were composed of HIV proteins or peptides, often recombinant. We can cite here the VaxGen trial, evaluated in phase II in the USA, with a vaccine based on a monomeric gp120 administered in alum. However, none of these subunits vaccine trials showed a statistically significant reduction of the HIV infection in the vaccinees. As vaccines eliciting humoral responses failed to give encouraging results, researchers have turned instead to the cell-mediated arm. Indeed, it was shown previously that CD8+ cytotoxic effector T cells could clear infected cells displaying viral peptides on their class I MHC molecules. Moreover, CD8+ T cells are known to be important in controlling SIV and HIV infection because (i) the depletion of CD8+ T cells during chronic SIV infection in monkeys increases the viral load (Jin et al., 1999), (ii) HIV-positive patients who are heterozygous at class I HLA loci have slower rates of disease progression (Carrington et al., 1999) and (iii) the virus accumulates mutations in CM8+ T cells epitopes (Goulder and Watkins, 2004). A vaccine stimulating T cell responses would not prevent infection in the traditional way but could at least suppress it long enough to prevent the onsets of AIDS. Among T cell vaccines are found the DNA vaccines, currently in phase I trials, using isolated HIV genes encoded by plasmids, but which face problems of immunogenicity. The most commonly used strategy to elicit T cells responses is the one of recombinant vectors. It consists of using viral vectors (derived from pox, vaccinia or adenovirus) to transport isolated HIV genes into human cells.

Finally, it is also worth mentioning the technique of dendritic cell-based vaccination, whose results against SIV challenges were very encouraging. It consists of immunizing macaques with autologous dendritic cells (DC) pulsed with chemically in activated SIV (inactivation with aldrithiol-2, AT-2). The inactivated virus is not capable of reverse transcription but the viral particles conserve their structure intact and most of all fusion capacity. This technique was even tested with success in chronically infected and non-treated humans, with autologous DC pulsed with inactivated autologous HIV (Andrieu and Lu, 2007). Despite its efficiency, this technique is rather expensive and time-consuming.

2.3.3 Problems Encountered by Prior Vaccine Strategies

Although many types of vaccines have been and are still being tested, none of them has been completely successful until now. Indeed, no long-term effect on viral load has ever been observed with DNA vaccines, even if CTL specific responses were stimulated. Vaccines eliciting a humoral response suffer from the huge variability of the virus and even if antibodies were generated, they were never versatile enough to cope with HIV genetic diversity. Even passive immunization of HIV-infected individuals with neutralizing monoclonal antibodies failed, underlining the limits of humoral immunity in controlling HIV-1 infection (Trkola et al., 2005). Pox vectors succeeded in eliciting specific CD4+ and CD8+ T cells responses, but did not allow a better control of viral load after many weeks of HAART interruption. Consequently, other vaccination strategies need to be tested. We propose here to test a new HIV-1 vaccine strategy, based on the use of a Lentiviral Vectors (LV) derived from HIV-1 as candidate vaccine.

3. Lentiviral Vectors as Candidates for HIV Vaccination 3.1 Technology of Lentiviral Vectors LV were described for the first time 20 years ago (Poznansky et al., 1991). As a recombinant vector, a LV is capable of integrating a transgene (until 8-10 kb) into the DNA of the host cell. The unique particularity of HIV-1 derived vectors and of all LV is their ability to transduce non-dividing cells. Indeed, LV like lentiviruses, are able to integrate independently of the cell mitosis. This capacity derives from an active nuclear-import of the viral DNA (or vector DNA) through the nuclear membrane of the host cell. One explanation for this active nuclear import is the formation of an unique triple-stranded DNA, called DNA Flap or Triplex via two cis-active sequences in the pol sequence: cPPT (central Polypurine Tract) and CTS (Central Termination Sequence) discovered in the laboratory (Zennou et al., 2000).

Our vaccination project uses an HIV-1 derived LV commonly named TRIP (because it contains the central DNA Flap/Triplex structure). This vector, belonging to the third generation of LV, has been optimized in term of design, production, transduction efficiency and bio-safety parameters (Delenda, 2004).

One major interest for using HIV-1 as a gene transfer vector is that retroviruses, contrary to RNA positive or DNA viruses are not directly infectious. Indeed a RNA positive genome needs reverse transcription and many accessory proteins to begin viral replication and pathogenesis in vivo. However, in order to be used as a gene transfer vector, HIV-1 genome has been reduced to the minimal viral sequences necessary for transgene expression and packaging (FIG. 8). The cis-acting sequences necessary for a transgenic expression cassette are the following ones:

The LTR sequence (Long-Terminal Repeat) is required for reverse transcription, viral DNA integration and transcription. This 3'LTR has been deleted in the U3 region, without perturbing the functions necessary for gene transfer, for two major reasons: first, to avoid trans-activation of a host gene, once the DNA integrated in the genome and secondly to allow self-inactivation of the viral cis-sequences after. retrotranscription. Thus, in target cells only sequences from the internal promoter will be transcribed (transgene) (FIG. 9).

The ψ region is necessary for viral RNA encapsidation.

The RRE sequence (REV Responsive Element) allows export of viral messenger RNA from the nucleus to the cytosol after binding of the Rev protein.

The DNA flap sequence (cPPT/CTS, normally contained in Pol) facilitates nuclear import.

The WPRE cis-active sequence (Woodchuck hepatitis B virus Post-Responsive Element) is also added to optimize stability of mRNA (Zufferey et al., 1999). WPRE is not translated.

The gene of interest (i.e. encoding the antigen) is inserted in the transfer vector plasmid under the control of a strong and often ubiquitous promoter.

In order to generate viral particles (RNA, capsid and envelope), certain HIV-1 helper packaging proteins have to be brought concomitantly within producer cells. They are encoded by two additional plasmids called the packaging or encapsidation plasmid and the envelope expression plasmid. The packaging plasmid encodes only the viral proteins essential for viral particle synthesis. Accessory genes whose presence in the plasmid could raise safety concerns were removed. Viral proteins brought in trans are respectively:

Gag proteins for building of the matrix (MA, p17), the capsid (CA, p24) and nucleocapsid (NC, p6).

Pol encoded enzymes: integrase, protease and reverse transcriptase.

Tat and Rev coding regulatory proteins, Tat is necessary for the initiation of LTR-mediated transcription.

In order to avoid any packaging of these generated mRNA in the viral particles, the ψ region was removed. An heterologous promoter was chosen to avoid recombination issues.

The envelope expression plasmid does not encode the HIV-1 natural env proteins (gp120, gp41). Indeed, these proteins are too labile to allow an efficient production and concentration by ultracentrifugation of vector particles. Moreover, the env proteins of HIV-1 have a limited tropism (CD4, CCR5, CXCR4). To counter these issues, LV production uses a process called pseudotyping. It consists in generating viral particles with an heterologous envelope glycoprotein. Among the first and still most widely used glycoproteins for pseudotyping LV is the Vesicular Stomatitis Virus Glycoprotein G (VSV-G) from the Indiana serotype. LV pseudotyped with VSV-G offer significant advantages in that VSV-G interacts with an ubiquitous cellular receptor on cells, endowing the vector with a broad host cells range. Moreover, VSV-G confers high vector particle stability allowing downstream processing of viral particles: principally concentration by ultracentrifugation.

3.2. Why are Lentiviral Vectors Promising Candidates for Vaccination Against HIV-1?

3.2.1 Transduction of DC

LV were initially used in gene therapy and their unique capacities as gene-transfer system are today undeniable.

First and contrary to adenovirus and vaccinia virus-derived vectors, there is no pre-existing immunity in humans against lentiviral viruses. Since their emergence, LV have been tested with success in vitro in a large variety of cells and tissues of therapeutic importance, including liver, brain and dendritic cells (DC) in the context of gene therapy protocols.

DC are a heterogeneous group of Antigen Presenting Cells (APC) which plays a crucial role in innate immunity as well as in initiating adaptive immune responses. DC act as sentinels of the immune system by continuously capturing antigens in peripheral tissues. Once activated by microbial products or inflammatory signals, they undergo maturation, migrate to draining lymphoid tissues where they subsequently process and present the captured antigens in the context of MHC I and II to CD8+ and CD4+ T cells. Interestingly, among the cell types that could be efficiently transduced by LV were found the mitotically hypoactive human CD34+- and monocyte-derived DC as well as mouse bone marrow derived DC. In vitro, transduction by LV did not affect their viability. Eventually, stable transduction of DC allows an endogenous presentation of the antigen during the whole lifespan of the cells. Thus, it makes LV good candidate vaccines.

3.2.2 History of the Use of LV for Vaccination Purposes

Besides efficient expression of a transgenic protein, DC transduced in vitro with LV were shown to efficiently process and present peptides derived from the protein. Indeed, both human and murine lentivirally transduced DC were capable of restimulating specific T cell lines or clones in vitro. More importantly, several groups reported in vitro priming of naïve T cells against relevant antigens when using human DC.

Many groups then evaluated the use of lentivirally transduced DC as immunotherapeutic agents in vivo, principally in mouse models but also more recently in a primate model. It has consisted in immunizing animals with ex vivo lentivirally transduced DC, and in analyzing the resulting CD8+ T cells responses in vitro. When possible the capacity of protection was also tested in vivo in the context of a challenge. The majority of these studies used tumor antigens as models and tested the capacity of induced CTL responses to eliminate tumor cells. Very few research teams have proved the pertinence of ex vivo lentivirally transduced DC against viral infections. Zarei et al. for example demonstrated the capacity of protection against a LCMV challenge in mice immunized with DC transduced with LV encoding the virus glycoprotein (Zarei et al., 2004).

However, this technique seemed to be difficult to apply in a human vaccination protocol, consequently LV were rapidly tested via direct in vivo administration. Many groups have demonstrated the efficacy of in vivo injection of LV in mice in order to elicit a transgene-specific immune response. Once again, tumor antigens were principally used. For example, it was shown by the lab that direct in vivo inoculation of melanoma poly-epitope encoding lentiviruses in HLA-A*0201 transgenic mice could elicit vigorous CTL responses against most of the melanoma epitopes encoded (Firat et al., 1999). It has even been demonstrated that injection of LV was superior to the ex vivo transduced DC injection, both in terms of amplitude and longevity of the CTL response (Esslinger et al., 2003). Furthermore, a functional CD8' T cells memory response could be generated after direct in vivo immunization with the TRIP vector even in the absence of CD4' T cells, undeniable advantage towards HIV vaccination (Iglesias et al., 2007). Many research teams are now investigating the intricate mechanisms that could contribute to the high potential of LV as vaccination tools. The sustained antigenic expression, particularly in DC, as well as the activation of innate immunity might play a critical role (Breckpot et al., 2003).

4. Vaccinal Trial in Cynomolgus Macaques 4.1 Previous Work in the Laboratory, Early Days of the Project In the laboratory, immunogenicity studies have demonstrated the potential of anti-SIV specific T cells responses in inbred mice immunized with TRIP vector encoding a non-myristoylated form of SIVmac239 Gag (above). These murine models allowed to underline the potential of TRIP vectors as candidates for vaccination against HIV. However, they did not permit to test the capacity of protection of TRIP vector immunizations in the context of a viral challenge.

4.2. The Macaque Model

For this purpose, a non-human primate model was chosen for protective efficacy studies, more particularly the Cynomolgus macaque. The human/HIV-1 model was translated to the macaque/SIVmac non human primate model. Macaques are highly susceptible to SIVmac infection and progressively develop an immunodeficiency syndrome, which mimics human AIDS. Interestingly, plasma viral loads during primary and chronic infection parallel those observed in humans, as in HIV-1 infected people long-term non-progressors as well as rapid progressors can be observed. As in humans infected with HIV-1 the cellular immune responses to SIVmac during primary and chronic infection differ significantly and evidence of immune escape is readily documented. As in HIV-1 infected individuals, gut-associated lymphoid tissues is the major site of viral replication and CD4+ T cell depletion.

Nowadays, AIDS vaccine/challenge data are essentially generated in 3 main macaque species: mainly rhesus macaques of Indian origin, but also rhesus macaques of Chinese origin and Cynomolgus macaques. Each species model presents advantages and drawbacks for studying responses to viral infection. Cynomolgus macaques were chosen for our trial because they are more readily available in Europe than rhesus macaques. Reinman et al. showed that the pathogenicity of SIV was attenuated in Cynomolgus macaques compared to Indian rhesus (lower plasma viremia, preservation of CD4+ T cells number, increased survival time). This attenuated pathogenicity was associated with earlier and stronger IFN-γ ELISPOT responses to GAG and ENV than in rhesus species. These observations support thus a role of early T cells immune responses. Finally, despite lower plasma viral load, viremia after challenge can be significantly used as experimental endpoint in Cynomolgus macaques, assuming that the dose of virus used for the challenge is high enough and that the naïve group is big enough to limit the statistical significance of spontaneous controllers. Interestingly, Cynomolgus macaques display viral loads more similar to those seen in the human infection. (Reimann et al., 2005).

4.3. Choice of the Antigen

In the context of a vaccinal trial in non-human primates, the question of the choice of the antigen has to be raised. The GAG SIVmac239 non myristyllated protein was chosen as antigen. Previous results and observations, as well as data concerning natural HIV-1 infection and viral structure could justify the choice of this protein as potentially efficient antigen. First of all, the important variability in HIV-1 strains constrained us to choose a protein well conserved among the different HIV-1/SIV strains. Only GAG, POL and NEF could fulfil this criteria. However, it has been shown that CTL recognise principally epitopes located on gag and nef (Addo et al., 2003). More recently, it was demonstrated that of the HIV-1 proteins targeted, only GAG specific responses were associated with lowering viremia and that independently of the particular HLA-type (Kiepiela et al., 2007). In addition, the more diversified the GAG specific responses were, the lower was the plasma viremia. Moreover, as it composes the viral matrix, GAG is the first protein to be processed and presented by MHC class I (Sacha et al., 2007), because entry/capture is sufficient and that there is no need of virus replication. GAG is also the most represented among HIV-1 proteins (1000-1500 CA) (Briggs et al., 2004). All these data justified the choice of this protein as relevant antigen for our first vaccinal trial. In addition, this trial was designed to give the proof of concept of the efficiency of TRIP vectors as vaccination tools. To this end, a simple antigen was voluntarily chosen in order to highlight the protective role played by the vector itself (gene transfer efficacy). Moreover, having the simple GAG protein as antigen allows to make comparisons with previous vaccine studies.

4.4. Vaccination Protocol

A prime-boost strategy was chosen in order to strengthen primary responses. A second injection is supposed to increase the number of responders, the frequency and avidity of antigen specific T cells and the intensity of T cells responses. It should also improve the diversity of responses as well as T cells functions such as killing or migration to the periphery.

For the prime, 3 groups of 2 macaques were immunized with the LV vector TRIP-SIVmac239 Gag pseudotyped with an Indiana serotype VSV-G, at 3 different doses. Two animals received a TRIP-GFP vector pseudotyped with Indiana serotype VSV-G as irrelevant vector. For the boost, 3 months after the prime, all immunized animals received a similar dose of TRIP-SIVmac239 Gag or TRIP-GFP pseudotyped with an Indiana non cross-reactive serotype VSV-G.

In order to test the capacities of protection triggered by this TRIP vector based vaccine, two months after the boost the 8 animals were challenged intra-rectally with 500 Animal Infectious Dose 50 (AID50) of SIVmac251. The inoculation route and the very high dose of virus for the challenge were justified by the size of the cohort, indeed by increasing the infectious dose, we hoped to limit the number of spontaneous controllers in the naïve animals arm of the study composed only of 4 macaques.

A longitudinal follow-up of the cellular immune response after prime, boost and challenge by IFN-γ ELISPOT on PBMC has been performed.

Materials and Methods
1. Materials
1.1 Antigens

The SIVmac239 GAGΔmyr protein was chosen as antigen. It is a 511 amino-acid protein. The protein myristylation domain was deleted to permit manipulations in biosafty levels L1, labs, and to promote class I presentation by APC. The complete sequence of the GAG polyprotein from SIV mac239 can be found via the protein ID: AAA47632. The GFP protein was chosen as irrelevant antigen.

1.2. Plasmids

All plasmids used for transfections were produced in strain JM109 *E. coli* K12 bacteria (F' traD36 proA$^+$B$^+$ lacI$^q$ Δ(lacZ)M15/Δ(lac-proAB) glnV44 e14$^-$ gyrA96 recA1 relA1 endA1 thi hsdR17), grown in LB medium supplemented with ampicillin and extracted with the Maxi-prep Nucleobound kit from Macherey-Nagel (Hoerdt, France).

Three plasmid constructs were used to generate the particles of TRIP-ΔU3-CMV-Gag Δmyr-WPRE (named here TRIP-SIVmac239 Gag, FIG. 25 A) or TRIP-ΔU3-CMV-eGFP-WPRE (named here TRIP-GFP, FIG. 25 B). A vector plasmid, containing HIV-1 cis-active genes (LTR, ΔU3 in 3', encapsidation signal ψ, RRE and DNA Flap i.e., cPPT/CTS), and the transgene encoding either the SIVmac239 GAG Δmyr protein or the GFP, under control of heterologous transcriptional regulator elements: Cytomegalovirus promoter. The WPRE (Woodchuck hepatitis virus postregulatory element) (Donella J. E. et al, 1998) sequence was added to increase transgene expression.

A packaging plasmid (encapsidation plasmid), containing the HIV-1 genes gag, pol, tat and rev, necessary for building of viral particles in the production cell line, which can be designed as p. 8.7.1 in Zufferey et al, 1998.

An envelope plasmid (envelope expression plasmid), encoding the Glycoprotein G from Vesicular Stomatitis Virus (VSV-G) serotype Indiana (ph CMV VSV-G) (Yee J. et al, 1994, Genebank AJ318514) or Indiana non cross reactive serotype such as serotype New-Jersey (pcDNA3.1(−)NJ-G WPRE). pcDNA 3.1(−)NJG is derived from pcDNA3.1 plasmid available from Invitrogen. Especially, to construct the pcDNA3.1(−)NJ WPRE, pBS-NJG (Genebank V01214)[17] was digested with XhoI and NotI and cloned into the pcDNA3.1(−) vector (Invitrogen). To increase expression, a WPRE (woodchuck post-transcriptional regulatory element) sequence, pre-amplified by PCR and cloned into a TOPO TA Cloning vector was added by EcoRI digestion.

Packaging and envelope plasmids have heterologous transcriptional elements (CMV promoter, and polyadenylation signal). All plasmids contain the ampicillin resistance gene to ease growth selection in bacteria.

1.3 Cell Culture

The human embryonic kidney cell line (human 293T) was used for TRIP vector production. For inhibition of transduction assays, the P4 cell line, a HeLa derived cell line, was used.

These cells were grown in complete medium composed of Dulbecco's modified Eagle's Medium containing glutamine (DMEM, GlutaMAX-I Supplement, GIBCO), supplemented with 10% heat-inactivated Fetal Calf Serum (FCS) (PAA Laboratories GmbH, Pasching, Austria) and penicillin, streptomycin (100 Units/ml of penicillin G (sodium salt) and 100 U/ml of streptomycin sulphate, GIBCO, Invitrogen). Macaques primary cells were cultured in RPMI GlutaMAX-I complete medium (10% FCS and antibiotics, similar concentrations as in DMEM).

1.4 Non-human Primates

Twelve adult Cynomolgus macaques (*Macaca fascicularis*), males from the Indian Ocean Island of Mauritius were included in the vaccination trial. They were negative for SIV Herpes Virus B, filovirus, STLV-1, SRV-1, SRV-2, measles, hepatitis B-HbsAg, and hepatitis B-HBcAb before inclusion in this study. Immunizations, challenge and blood collection were handled, in accordance to the EC guidelines for experiments using non human primates.

1.5 SIV Virus for Challenge

The SIVmac251 strain (complete proviral genome and flanking sequence: accession number: M19499) was used for challenge.

1.6 SIVmac239 GAG and SIVmac251 NEF Peptides Sets

PBMC in vitro restimulation in ELISPOT were carried out with either a SIV mac239 GAG or SIVmac251 NEF peptide sets containing 125 peptides or 64 peptides respectively (NIH AIDS Research and Reference Reagent Program). Peptides were 15 amino acids in length, with 11 amino acids overlaps between sequential peptides. GAG peptides were dispatched into 11 pools containing 5 to 12 consecutive and overlapping peptides, named in order from letter M to W and recovering the SIVmac239 GAG protein (FIG. 26). NEF peptides were divided into 12 pools of 8 peptides recovering the NEF SIV mac251 protein and named in order from letter a to h. Most of the peptides were more than 80% pure. They were delivered lyophilized at 1 mg each. At reception, they were resuspended at 2 mg/ml in 5% DMSO for GAG peptides and at 1 mg/ml in pure DMSO for NEF peptides, based on percentage of peptide content and HPLC purity.

2. Methods 2.1 Vectors Production

Vector particles were produced by transcient calcium phosphate transfection of 293T cells (CaCl$_2$ 0, 125 mM, 1× HEPES-buffered saline pH 7.10, 70 mM NaCl, 0.75 mM Na$_2$HPO$_4$ 2H$_2$O, 25 mM HEPES). Ten μg of vector plasmid encoding either GAGΔmyr or GFP was required with 5 to 10 μg of the plasmid encoding the VSV-G glycoprotein envelope, and 10 μg of the packaging plasmid as described previously by Zennou et al 2000 (Zennou et al., 2000) Cells were seeded in 10 cm$^2$ polystyrene-treated tissue culture Petri dishes (Falcon) at $6.10^6$ in complete medium 24 h before transfection, and medium was changed prior to transfection. Cells were at least 80% confluent. Twenty-four hours after transfection, complete medium without FCS was added to the cells at a smaller volume to concentrate the particles. Forty-eight hours post-transfection, supernatants were collected from Petri-dishes, centrifuged to pellet floating cells (2500 rpm, 5 min) and treated 15 min at 37° C. with DNAse I (Roche Boehringer, 20 U) and MgCl$_2$ (Sigma, 1 mM) in order to eliminate residual plasmids DNA. Vectors were collected after ultracentrifugation of the supernatant (22 000 rpm; 1 hour) and resuspended in cold PBS. Vectors were conserved at −80° C. in aliquots of small volume.

2.2 Measurement of p24 GAG Antigen Production

Vectors HIV-1 p24 GAG antigen contents were determined by Enzymed-Linked-Immunosorbent Assay (Perkin-Elmer Life Sciences, Paris, France). p24 concentrations were given in ng/ml of vector.

2.3 Vector Titration

Titration was performed by transduction of 293T cells (seeded 24 h prior to transduction at $5.10^5$ cells/well in 6 well-Petri dishes) with 3 different volumes of vector. Cells were also transduced with the same amount of vector previously heat inactivated at 70° C. Seventy-two hours after transduction, cells were lysed with a lysing-buffer 1× (Tris 20 mM pH=8.8; NP40 0.1%; Tween 0.1% final) containing RNAse, Dnase-free (Roche Boehringer, 50 μg/ml final). Cellular proteins were degraded by addition of Proteinase K (Proteinase K stabilised 100 μg/ml final, Eurobio).

Vector titers were assessed by performing a real-time PCR on cells lysates, using the Light Cycler Instrument (Roche Diagnostics, Meylan France). Total HIV-1 DNA copy number was determined by detection of a viral DNA sequence, localized in the LTR U5 region (primers AASM reverse and M667 forward). Two hybridization probes were used for each PCR run, one probe labelled with Fluorescein (FL) as 3' end donor and the other labelled with the LightCycler Red 640 (FC) as 5' acceptor. Normalization to cell number was done by detecting the CD3 sequence (house keeping gene), with primers CD3 in 3' and CD3 in 5' and probes FL and FC. For PCR, 5 μL of lysate were tested in duplicates for each condition, in a 15 pL PCR-mix (Jumpstart taq readmix for Q-PCR, Sigma 1×, MgCl$_2$ 1.9 mM, 1.5 U of Taq polymerase (Invitrogen), 1.5 μM forward and reverse primers and 0.2 μM fluorogenic hybridization probes). Copy number was determined in reference to a standard curve prepared by amplification of $10^2$ to $10^8$ of cloned plasmid diluted in mouse cells lysate (3T3) with matching sequences (U5R and CD3) (FIG. 27 and as shown in the table below; SEQ ID NOs: 74-81).

| PCR | Oligos | Sequence 5'→3' |
|---|---|---|
| U5R forward primer | M667 | GGCTAACTAGGGAACCCACTG |
| U5R reverse primer | AASM | GCTAGAGATTTTCCACACTGACTAA |
| U5R 3' end LTR donor probe | FL | CACAACAGACGGGCACACACTACTTGA-FL |
| U5R 5' end LTR donor probe | LC | LC-CACTCAAGGCAAGCTTTATTGAGGC |
| CD3 forward primer | CD3 in 5' | GGCTATCATTCTTCTTCAAGGTA |
| CD3 reverse primer | CD3 in 3' | CCTCTCTTCAGCCATTTAAGTA |
| CD3 3' end donor probe | CD3 FL | GGCTGAAGGTTAGGGATACCAATATTCCTGTCTC-FL |
| CD3 5' end donor probe | CD3 LC | LC-CTAGTGATGGGCTCTTCCCTTGAGCCCTTC |

| Step and number of cycles | | Temperature | duration |
|---|---|---|---|
| 1 cycle | 1: Denaturation | 95° C. | 3 min |
| 40 cycles | 2: Denaturation | 95° C. | 5 sec |
| | 3: Annealing | 57° C. | 10 sec |
| | 4: Elongation | 72° C. | 8 sec |

2.4 Macaques Immunization

Macaques were divided into four groups of 2 animals (Table A) and were sub-cutaneously injected in 2 points with TRIP-SIVmac239 Gag pseudotyped with the VSV-G envelope serotype Indiana, at 3 different doses (high dose $2.5.10^8$ Transduction Unit (TU), 6863 ng p24; medium dose $1.10^8$ TU, 2745 ng p24 or low dose $2.5 \times 10^7$ TU, 686 ng p24) or with TRIP-GFP at the same p24 dose than the high dose of TRIP-SIVmac239 Gag (6863 ng p24).

For the second immunization performed 87 days post prime, animals were injected sub-cutaneously in 4 points with a vector pseudotyped with an Indiana non cross-reactive VSV-G glycoprotein serotype (VSV-G serotype New-Jersey). Macaques received either $1.10^8$ TU of TRIP-SIVmac239 Gag, 60185 ng p24 when primed with the GAGdeltamyr antigen, or 60185 ng p24 of TRIP-GFP vector when primed with the G FP antigen.

TABLE A

Repartition of Cynomolgus macaques used in TRIP vaccination trial

| Cynomolgus macaque tatoo number | Vector received at the prime | Category |
|---|---|---|
| 20022 | TRIP-SIVmac239 Gag $2.5\ 10^7$ TU | LOW DOSE |
| 20089 | TRIP-SIVmac239 Gag $2.5\ 10^7$ TU | |
| 20293 | TRIP-SIVmac239 Gag $1\ 10^8$ TU | MEDIUM DOSE |
| 20056 | TRIP-SIVmac239 Gag $1\ 10^8$ TU | |
| 20195 | TRIP-SIVmac239 Gag $2.5\ 10^8$ TU | HIGH DOSE |
| 20158 | TRIP-SIVmac239 Gag $2.5\ 10^8$ TU | |
| 21544 | TRIP-GFP 6862 ng p24 | CONTROL |
| 20456 | TRIP-GFP 6862 ng p24 | |
| 15661 | None | UNVACCINATED |
| 14184 | None | |
| 15885 | None | |
| 14468 | None | |

The animals are ranged according to the tattoo number and the nature/dose of the TRIP vector received at the prime immunization.

2.5. SIV mac251 Challenge

Immunized and naïve macaques (12 macaques in total) were challenged intra-rectally 57 days post-boost (ie 136-days post prime) with a single dose of 500 AID50 in 1 ml (Animal Infectious dose sufficient to infect 50% of the animals) of pathogenic SIVmac 251 (stock from A.M. AUBERTIN, Université Louis Pasteur, Strasbourg, France distributed by ANRS- or equivalent stock available from NIH). Animals were anaesthetized with 10 to 20 mg/kg of Ketamine (Imalgène, Rhône-Mérieux) and the whole procedure was done according to the EU regulations and guidelines of Animal Care and Use. After inoculation macaques were housed separately with precautions bound to a Level 3 bio security animal house.

2.6 IFN-γ ELISPOT

Animals were anaesthetized with 10 to 20 mg/Kg of Ketamine (Imalgène, Rhone-Mérieux) for blood collection. 8 ml of blood were collected for each macaque in Cell Preparation Tubes with Sodium Citrate (BD Vacutainer™ CPT™) for PBMC and citrate-plasma collection and 3 ml in serum separator tube (Vacuette®) for serum collection. After centrifugation (10 min, 2500 rpm for Vacuette® tubes and 30 min, 3000 rpm, no brake, for CPT™), and red blood cells lysis with 3 to 5 ml 1× lysis buffer (IOtest 10× lysis buffer, Beckman-Coulter), PBMC were pelleted by a 10 min 1600 rpm centrifugation, and then numerated in a Kova's chamber Hycor®, and distributed to 96-well ELISPOT plates in triplicates at $2.10^5$ cells/well if enough cells were available.

96-well plates with Immobilon®-P (Polyvinylidene Fluoride, PVFD) membrane (MultiScreen HTS Assay System, MSIP; Millipore), were prewetted (ethanol 35%) and coated overnight at 4° C. with capture antibody (mouse IgG1 anti-human-monkey-IFN-γ monoclonal antibody GZ-4 purified (Mabtech), 10 μg/ml final in PBS; 50μL per well). Plates were washed 4 times in Dulbecco's PBS 1× and blocked with complete RPMI.

Cells were restimulated either by addition of one pool of peptides (2 μg/ml of each peptide), AT-2 inactivated SIVmac251 (5 μg/ml of total viral proteins), (or PMA-iono (0.1 μM PMA and 1 μM ionomycin) as positive control (4000 cells/well), or mocked stimulated with DMSO/RPMI.

After 40 hours, spots were revealed with a biotin-conjugated antibody (mouse IgG1 anti-human-monkey interferon-γ monoclonal antibody 7-B6-1 purified (Mabtech); 1 μg/ml final in PBS 0.5% FCS; 100 μL per well 2 h at 37° C.), followed by streptavidin-AP (1 h, 1/5000 in PBS 0.5% FCS, 100μL per well, 1 h, 37° C.) and BCIP/NBT substrate solution (Ready to use mixture, 60μL per well; 15 min, RT, in the dark). Spots were numerated using a Bioreader 4000 (Biosys, Karben, Germany). Results were expressed as IFN-γ Spot-Forming-Cells (SFC) per million PBMC. The IFN-γ SFC/million PBMC resulting from a 5% DMSO/RPMI stimulation were subtracted from the results as a background signal.

2.7 ELISA

Quantification of innate cytokines (IL6; TNF-α and IFN-α was performed via ELISA using commercial kits (Monkey IL-6 and TNF-α ELISA kit from U-Cytech Bioscience (Utrech, Netherlands), human IFN-α kit from PBL Biomedical Laboratories (New Jersey, United States)). Plasma were tested for each animal 40 days before prime injection, 1 hour, 6 hours, 24 hours and 7 days post prime injection.

2.8. In vitro Seroneutralization Assays

P4 cells were seeded at $1.10^5$/well in 96-well plates in complete medium 24 h prior to transduction. On the day of transduction, cells were cultured with TRIP-GFP (pseudotyped with an Indiana serotype VSV-G or with an Indiana non cross-reactive VSV-G such as New-Jersey VSV-G) preincubated with different dilutions of plasma. Cells were mocked transduced with the same volume of complete medium. Seventy-two hours after transduction, efficiency of transduction was assessed by analysing the GFP fluorescence by flowcytometry using a FACScalibur (BD).

2.9 Viral Load Determination

Briefly, viral RNA was isolated from citrate-plasma (200μL in total) with the High Pure Viral RNA Kit from Roche. Elution was carried out in 50μL elution buffer (Nuclease-free, sterile, double distilled water). The number of SIV-RNA isolated from plasma was determined in a quantitative single-step RT-PCR using the Platinium qRT-PCR from Invitrogen Reactions were performed in duplicates in the Mastercycler ep realplex (Eppendorf) in 96-well plates from ABgene (AB1100) in a final volume of 25μL (10μL RNA extract and 15 μL Mix). The Taqman quantification method was chosen, with an internal probe (500 nM final) containing the Fam and Tamra fluorophores respectively in 5' and 3'. The primers (450 nM final) were respectively at position 389 and 456 of SIVmac 251 GAG mRNA genome (Table B).

The quantity of viral RNA copies initially presents was assessed by extrapolation of threshold fluorescence values onto an internal standard curve prepared from serial dilutions in $dH_2O$ of a virus stock SIVmac251 previously titered by the technique of "branched DNA". As positive control for PCR, the TRIP-SIVmac239 Gag vector plasmid was used ($10^4$ copies/μL). The primers (SEQ ID NOs: 82-84) are shown in the table below.

| Name | Sequence 5'→3' | size |
|---|---|---|
| Primer Forward: SIVmac389F | GCAGAGGAGGAAATTACCCAGTAC | 24 bp |
| Primer Reverse: SIVmac456R | CAATTTTACCCAGGCATTTAATGTT | 25 bp |
| Taqman probe: SIVmac TM | Fam-TGTCCACCTGCCATTAAGCCCGA-Tamra | 23 bp |

TABLE B

Sequences of primers and probers and Taqman RT-PCR program used for plasma viral load determination.

| | Step and number of cycles | Temperature | duration |
|---|---|---|---|
| 1 cycle | 1: Reverse transcription (1 Cycle) | 46° C. | 30 min |
| | 2: Enzyme activation | 95° C. | 4 min |
| 50 cycles | 3: Step one, PCR denaturation | 95° C. | 15 s |
| | 3: Step two, PCR annealing and elongation | 60° C. | 1 min |
| 1 cycle | 4: Cooling | 20° C. | Hold |

Results: Lentiviral Vector Prime-boost Vaccination Confers Strong Protection Against Massive SIVmac 251 Challenge in Macaques Many studies have highlighted the critical role played by $CD8^+$ T cells in controlling HIV infection and suggested that an effective vaccine should induce vigorous, broad and long-lasting $CD8^+$ T cell responses. Yet, several viral vectors shown to elicit specific SIV $CD8^+$ T cell responses have subsequently failed to control viremia in SIV/macaques models (Schoenly, K. A. & Weiner, 2007). Since we and others have demonstrated that lentiviral vectors are very potent to induce cellular immunity (reviewed by He, Y. & Falo, L. D., 2007 and by Breckpot, K, Aerts, J. L. & Thielemans, K., 2007), we assessed whether they could confer protective cellular immunity against SIV infection and simian AIDS. We opted for the model of SIVmac251 infection of cynomolgus macaques which displays viral load levels and a variety of progression rates similar to those seen in HIV-1 infection in humans (Karlsson, I. et al, 2007 and Reimann, K. A., et al, 2005).

Six cynomolgus macaques were immunized twice by subcutaneous injections of HIV-1 derived lentiviral vectors encoding a non-secreted SIVmac239 GAG protein in its native sequence (TRIP-SIVmac239 GAG). This single and non-optimized antigen was chosen to highlight the potential of the lentiviral vector system for vaccination. In order to circumvent the presence of neutralizing anti-vector antibodies, and hence to allow an efficient boost effect, a strategy of envelope exchange was designed. Indeed, preparatory experiments in mice had shown that a prime-boost regimen using TRIP-SIVmac239 GAG particles pseudotyped with VSV-G from two non-cross reactive serotypes, Indiana followed by New Jersey, was more efficient than a homologous prime-boost. The immunization groups and experimental design are summarized in Table 1 hereafter.

A single injection of lentiviral vector was sufficient to induce robust cellular immunity in every immunized animal, regardless of the dose received (FIG. 28a) and without stimulating systemic inflammation (FIG. 28(2)). SIVmac239 GAG specific T cell responses peaked at 16 days post-prime, reaching a high frequency of IFN-γ secreting cells (up to 3,000 IFN-γ SFC/million PBMC), and returned to pre-immunization levels two months after immunization (FIGS. 28(1)a and 28(1)b). In addition to the robustness of primary response, these were also found to be broad, covering several peptides pools (FIG. 30(2)a and Table 2a). In our outbred cohort, we observed that the SIVmac239 GAG specific IFN-γ responses were preferentially directed against two pools within the C-terminal region of GAG covering a part of p27 CA and p9 NC. All 6 vaccines mounted a vigorous response against the pool SIVmac239 GAG: 337-395 and 4 out of 6 against the pool SIVmac239 GAG: 385-443.

Animals also developed neutralizing humoral responses against VSV-serotype Indiana (FIG. 31(2)a), but importantly, sera from vaccinated animals did not neutralize vectors pseudotyped with VSV-G New Jersey in vitro (FIG. 31(2)b). Macaques were therefore then injected with a medium dose of TRIP-SIVmac239 GAG particles pseudotyped with VSV-G New Jersey 11 weeks post-prime. SIVmac239GAG (15-mers) Peptides-Complete Set was obtained through the AIDS Research and Reference Reagent Program, Division of AIDS, NIAID, NIH. SIVmac239 GAG-specific T cell responses were efficiently restimulated by the second injection (FIG. 28(1)a). The magnitude of responses was increased with kenetics typical of secondary responses, that is faster onset and longer persistence. IFN-γ secreting cells were detected as early as one week following the second immunization and up to 2 months and more. The breadth of the cellular responses was not improved (FIG. 30(2)b or Table 2b). To mimic more closely the processing and trafficking steps that occur in infected cells for antigen presentation but which are bypassed by peptide pulsing, A T-2 inactivated SIVmac251 was also used as antigen. Weak (macaque 20089) to strong (macaques 20022, 20195 and 20056) responses were observed (FIG. 30(2)d). Intracellular stainings performed 10 weeks post-boost indicated that both $CD4^+$ and $CD8^+$ T cells contributed to IFN-γ production in response to peptide pools (data not shown).

Given the robust and broad cellular immune responses induced by the vaccine, we tested its protective efficacy against SIV infection. Macaques were challenged 11 weeks post-boost by intra-rectal inoculation of a high dose of SIVmac251 (500 $AID_{50}$) (Table 1). Massive anamnestic SIV GAG specific responses were observed in the peripheral blood of immunized animals shortly after challenge (within a week) in contrast to unvaccinated and control animals. These responses peaked earlier and more vigourously (more than 4,000 SIV GAG specific IFN-γ SFC/million PBMC) (FIG. 28). An earlier and higher rebound of total, naïve and central memory $CD8^+$ T cells was also documented during primary infection in vaccinated animals in comparison to unvaccinated and control (TRIP GFP) ones (FIG. 32(2)). GAG regions mapped after immunizations were recalled by the challenge and new immunogenic regions were also detected after infection. The diversity of the GAG-specific responses was comparable between vaccinated and unvaccinated or control animals (FIG. 30(2)c and Table 2c).

Although viral challenge led to infection in all animals, immunization conferred strong protection against viral replication and depletion of the central memory $CD4^+$ T cells during the acute phase. TRIP GFP injected control animals had a course of infection very comparable to unvaccinated macaques and were therefore gathered as a single group. In the plasma of these naïve and control animals, the peak of viral replication was high with a mean of $1.02 \ 10^7$ RNA copies/ml. Viral loads then decreased in all 6 unvaccinated and control animals to reach low to moderate set-point plasma viral RNA levels (days 70 to 154) with a mean of $3.44 \ 10^5$ RNA copies/ml (FIGS. 29(1)a and 29(1)c). In contrast, viremia at the peak of primo-infection of all 6 immunized animals were lower than in naïve and control animals by at least two orders of magnitude with a mean of 9.25 $10^4$ RNA copies/ml (FIGS. 29(1)b and 29(1)c). From the 6 vaccinated macaques, 4 suppressed peak viremia by more than 2 log 10 fold (20022, 20293, 20158), 2 by more than 3 log 10 fold (20293 and 20158) and 1 by more than 4 log 10 fold (20195) (FIG. 29(1)e). After resolution of peak viremia, viral loads decreased and remained persistently below those of unvaccinated and control animals by around a 10 fold factor, and statistically lower at day 49 post-infection (FIG. 29(1)c). When the cumulative replications during the first 154 days of infection (expressed as area under the curve of viral load as a function of time) were compared, the benefit provided by vaccination was statistically significant (FIG. 29(1)f).

We also monitored the evolution of $CD4^+$ T cells in the peripheral blood during the course of infection, and more particularly the central memory (CM) $CD4^+$ T cells, because their depletion correlates with plasma viral loads (Karlsson, I. et al, 2007) and their preservation during acute and chronic SIV infection predicts long-term survival of vaccinated monkeys, betten than set-point viral load levels (Mattapallil, J. J. et al, 2006 and Letvin, N. L., et al, 2006).

During acute infection, there was a rapid and profound decline of CM $CD4^+$ T cells in the peripheral blood of the unvaccinated and control animals (FIG. 30a). CM $CD4^+$ T cell counts remained low with signs of gradual depletion for 3 of them (21544, 14184 and 20456), whereas depletion was transient and followed by a return to baseline for the 3 others (15661, 15885 and 14468). These two subgroups further demonstrated moderate and low post-acute viremia correspondingly and were therefore classified as progressor (14184-21544-20456) and non-progressor animals (15661-15885-14468).

In contrast, vaccinated animals showed full preservation or only low depletion of their CM $CD4^+$ T cells during peak viremia and all rapidly recovered their CM $CD4^+$ T lymphocytes, except macaque 20089 (FIGS. 30(1)b and 30(1)c).

All naïve and control animals experienced a profound CM $CD4^+$ T cell loss and high viremia at the peak of primo-infection, but half of them rapidly recovered their CM $CD4^+$ T cell compartment whereas the other half on contrary showed slow decline of CM $CD4^+$ T cell number. These two subgroups demonstrated low and moderate post-acute viremia correspondingly and were therefore classified as non-progressor (15661-15885-14468) and progressor animals (14184-21544-20456). Importantly, viremia of vaccinated animals at late time points was reduced by around a 2 $\log_{10}$ fold factor when compared to progressor unvaccinated animals, whereas post-acute viremia and CM $CD4^+$ T cell counts were similar between vaccines and non-progressor unvaccinated animals (FIGS. 29d and 30d).

Correlations between the vaccine-induced immune responses and viral loads were found despite the under-evaluation of cellular responses due to saturation of some ELISPOT wells (FIG. 29(2)). Importantly, there was an inverse correlation between the level of peak viremia and the magnitude of GAG specific IFN-γ responses measured 2 weeks post-prime, 1 week post-boost and 1 week post-challenge (FIGS. 32a, 32b and 32c). These findings are in perfect agreement with studies in large HIV-1 infected patients cohorts showing a correlation between HIV61 GAG-specific $CD8^+$ T cells and low viral loads and slow disease progression (Kiepiela, P. et al, 2007). We also observed a strong correlation between the preservation of CM $CD4^+$ T cells and viral loads during acute infection (FIG. 32d).

In summary, this study provides evidence that a lentiviral vector-based prime/boost vaccination regimen elicits strong and broad cellular immunity in cynomolgus macaques and confers efficient protection against massive SIVmac251 infection by lowering viremia and by entirely preventing loss of $CD4^+$ T cells and CM $CD4^+$ T cells at the peak of primo-infection.

A long-term follow-up will tell whether or not viral escape from immune pressure can happen in this macaque cohort. After 5 months follow-up, the stability of the $CD4^+$ T cell numbers and the tendency for decrease of viral loads in vaccinated animals argue for long-term control. This first pre-clinical trial in an albeit limited macaque cohort is very encouraging given that protection relied solely on responses directed against a non-optimized GAG antigen. We expect an improvement of the control of replication by increasing antigen expression and immunogenicity by codon-optimization (Deml, L. et al, 2001 and zur Megede, J. et al, 2000), and by increasing the diversity of the cellular responses by fusing other SIV antigens with GAG (Wilson, N. A. et al, 2006 and Hel, Z. et al, 2006). In this respect some results are presented hereafter on a mouse model, and nn optimised version of this vaccination strategy, with complete fulfillment of both efficacy and safety requirements, will thereafter enter therapeutic vaccination clinical trials in humans.

TABLE 1

Immunization groups and experimental design

| group | vaccine | subgroup | animal # | prime particles pseudotyped with VSV-G Indiana day 0 | boost particles pseudotyped with VSV-G New Jersey day 79 post-prime | challenge day 76 post-boost |
|---|---|---|---|---|---|---|
| vaccinated n = 6 | TRIP-SIVmac239 GAG | low dose | 20022, 20089 | 2.5 $10^7$ TU | 1.2 $10^8$ TU | 500 $AID_{50}$ SIVmac251 |
| | | medium dose | 20293, 20056 | 1 $10^8$ TU | | |
| | | high dose | 20195, 20158 | 2.5 $10^8$ TU | | |
| control n = 2 | TRIP-GFP | | 21544, 20456 | 6863 ng p24 | 6018 ng p24 | 500 $AID_{50}$ SIVmac251 |

TABLE 1-continued

Immunization groups and experimental design

| group | vaccine | subgroup | animal # | prime particles pseudotyped with VSV-G Indiana day 0 | boost particles pseudotyped with VSV-G New Jersey day 79 post-prime | challenge day 76 post-boost |
|---|---|---|---|---|---|---|
| unvaccinated n = 4 | none | | 15661, 14184 15885, 14468 | none | none | 500 AID$_{50}$ SIVmac251 |

Twelve outbred males and adult cynomolgus macaques (*Macaca fascicularis*) from the Indian Ocean Island of Mauritius were included in the preclinical trial. They were negative for SIV, Herpes Virus B, filovirus, STLV-1, SRV-1, SRV-2, measles, hepatitis N" 2001-486). B-HbsAg, and hepatitis B-HBcAb before inclusion in the study. Immunizations, blood collections and challenge were handled in accordance to the EU guidelines for experiments using non human primates (décretthe glycoproteins G from 2 non-cross-reactive serotypes of VSV, Immunizations were done by subcutaneous injections on day 0 and day 79 of lentiviral particles pseudotyped with 2 different envelopes, Indiana and New Jersey. The dose of lentiviral vector particles were expressed as transduction unit (TU)/animal and ng p24/animal. Six animals were immunized with 3 doses of lentiviral vectors encoding a non-secreted form of SIVmac239 GAG (myristoylation-deficient). Because of the absence of dose-response after the first injection, all 6 vaccinated animals received the very same medium dose of vector for the second injection. Two control animals were immunized with lentiviral vector encoding an irrelevant antigen, GFP, at the same p24 dose than the high dose relevant subgroup. Vaccinated, control and unvaccinated macaques were challenged intra-rectally 76 days post-boost with a high dose of pathogenic SIVmac251 (A-M Aubertin, Université Louis Pasteur, Strasbourg, France) expressing a GAG protein that is closely matched to the vaccine (homologous challenge). A high dose of virus (500 AID$_{50}$ compared to 20-50 AID$_{50}$ usually used in studies of protective efficacy of vaccines) was chosen to limit the number of spontaneous controllers[5].

TABLE 2

Vaccine-induced T cell responses were broad

Table 2a

| | | p17 MA 1-132 | | | p27 CA:133-380 | | | | p9 NC and p6: 381-511 | | | |
|---|---|---|---|---|---|---|---|---|---|---|---|---|
| | | GAG: 1-59 | GAG: 49-107 | GAG: 97-165 | GAG: 145-203 | GAG: 193-251 | GAG: 243-293 | GAG: 289-347 | GAG: 317-399 | GAG: 385-443 | GAG: 433-91 | GAG: 481-511 | |
| low dose | 20022 | 140 | 113 | 90 | 160 | 17 | 100 | 63 | 743 | 613 | 1190 | 23 | 2/11 |
| | 20049 | 158 | 133 | 11 | 138 | 0 | 0 | 1 | 433 | 185 | 70 | 68 | 1/11 |
| medium dose | 20293 | 28 | 542 | 27 | 180 | 0 | 10 | 45 | 388 | 265 | 37 | 62 | 2/11 |
| | 20056 | 100 | 35 | 102 | 405 | 77 | 60 | 15 | 1280 | 843 | 325 | 0 | 3/11 |
| high dose | 20195 | 255 | 1060 | 32 | 245 | 28 | 203 | 95 | 690 | 543 | 31 | 24 | 3/11 |
| | 20058 | 92 | 150 | 165 | 297 | 55 | 47 | 218 | 900 | 503 | 128 | 8 | 2/11 |
| | | 0/6 | 2/6 | 0/6 | 1/6 | 0/6 | 0/6 | 0/6 | 6/6 | 4/6 | 1/6 | 0/6 | |

Table 2b

| | | p17 MA 1-132 | | | p27 CA: 133-380 | | | | | p9 NC and p6: 381-511 | | | |
|---|---|---|---|---|---|---|---|---|---|---|---|---|---|
| | | GAG 1-59 | GAG 49-107 | GAG 97-155 | GAG 145-203 | GAG 193-251 | GAG: 243-293 | GAG 289-347 | GAG 317-399 | GAG 385-443 | GAG 433-91 | GAG 81-4511 | |
| low dose | 20022 | 173 | 153 | 207 | 132 | 93 | 123 | 85 | 623 | 402 | 1347 | 65 | 3/11 |
| | 20049 | 321 | 291 | 150 | 198 | 59 | 176 | 49 | 449 | 434 | 135 | 72 | 2/11 |
| medium dose | 20293 | 167 | 41 | 0 | 3 | 49 | 0 | 27 | 140 | 302 | 45 | 79 | 0/11 |
| | 20056 | 168 | 82 | 88 | 160 | 222 | 125 | 109 | 1275 | 1150 | 308 | 62 | 2/11 |
| high dose | 20195 | 84 | 430 | 2 | 21 | 11 | 4 | 9 | 432 | 432 | 432 | 432 | 5/11 |
| | 20058 | 197 | 70 | 24 | 134 | 279 | 30 | 88 | 1029 | 909 | 177 | 46 | 2/11 |
| | | 0/6 | 1/6 | 0/6 | 0/6 | 0/6 | 0/6 | 0/6 | 5/6 | 5/6 | 2/6 | 1/6 | |

Table 2c

| | | p17 MA 1-132 | | | p27 CA: 133-380 | | | | | p9 NC and p6: 381-511 | | | |
|---|---|---|---|---|---|---|---|---|---|---|---|---|---|
| | | GAG 1-59 | GAG 49-107 | GAG 97-165 | GAG 145-203 | GAG 193-251 | GAG 241-393 | GAG 289-347 | GAG 337-399 | GAG: 385-443 | GAG 433-91 | GAG 481-511 | |
| low dose | 2002 | 190 | 85 | 78 | 82 | 182 | 103 | 55 | 850 | 873 | 1197 | 92 | 3/11 |
| | 2004 | 735 | 161 | 93 | 52 | 523 | 322 | 106 | 513 | 550 | 187 | 110 | 4/11 |
| medium dose | 2029 | 0 | 495 | 40 | 12 | 0 | 40 | 240 | 510 | 520 | 40 | 128 | 3/11 |
| | 2005 | 60 | 0 | 4 | 270 | 0 | 117 | 33 | 602 | 788 | 530 | 9 | 3/11 |
| high dose | 2019 | 99 | 34 | 0 | 16 | 0 | 3 | 172 | 58 | 14 | 60 | 62 | 0/11 |
| | 2005 | 142 | 135 | 4 | 447 | 65 | 58 | 192 | 586 | 658 | 633 | 178 | 4/11 |
| control | 2154 | 147 | 178 | 142 | 647 | 70 | 118 | 147 | 513 | 807 | 198 | 192 | 3/11 |
| | 2045 | 13 | 252 | 18 | 205 | 105 | 119 | 272 | 217 | 152 | 123 | 59 | 0/11 |
| naive | 15661 | 288 | 911 | 408 | 228 | 0 | 513 | 161 | 906 | 893 | 503 | 102 | 6/11 |
| | 14184 | 170 | 173 | 78 | 268 | 33 | 88 | 403 | 312 | 288 | 137 | 292 | 1/11 |
| | 15885 | 148 | 136 | 159 | 251 | 188 | 598 | 326 | 491 | 331 | 229 | 12 | 2/11 |
| | 14468 | 0 | 46 | 122 | 72 | 29 | 0 | 153 | 37 | 320 | 1033 | 92 | 1/11 |
| | | 1/12 | 2/12 | 1/12 | 2/12 | 1/12 | 2/12 | 1/12 | 8/12 | 7/12 | 5/12 | 0/12 | |

The diversity and the relative contribution of the proteins encoded by GAG (matrix MA, capsid CA, nucleocapsid NC and p6) to the vaccine-induced, virus-induced and virus-recalled GAG-specific T cell responses were studied by IFN-γ ELISPOT assay at the peak of the primary responses (2 weeks post-prime, Supplementary Table 1a), a week after the boost (Supplementary Table 1b) and during the acute phase of infection (3 weeks post-challenge, Supplementary Table 1c) using 11 pools of peptides shown in the second line of the tables. The first 2 columns indicate the animal identifier. The numbers correspond to IFN-γ SFC/million PBMC. The underscore indicates saturated ELISPOT wells. The light grey-shaded boxes correspond to positive responses (>375 IFN-g SFC/million PBMC) and the dark grey-shaded boxes represent the strongest response in an individual animal. The far-right column shows the number of pools of peptides recognized by each animal, whereas the bottom row represents the number of animal of the cohort which mounted a response against each individual pool of peptides.

Comparison of the Immune Response Obtained in Mice Immunized with a Lentiviral Vector Encoding a Gag Antigen or a Codon Optimized Form of Said Antigen 1. Codon Optimization of the Polynucleotide Encoding the Antigen Improves the CTL Response Naïve mice (n=3/group) were immunized i.p. with a single injection of various doses of TRIP.NI gag delta myr or TRIP.NI LV coding for a codon-optimized form of gag delta myr (TRIP.NI gagΔmyr CO).At 10 days post immunization, gag-specific cellular immune responses against the immunodominant gag CD8+ T cell epitope were assessed (FIG. 33) by tetramer staining (A) or IFN-γ ELISPOT (B). SFC spot-forming cells (C) IFN-γ ELISPOT assays in response to the CD8+ T cell immunodominant epitope and the CD4+ T cell epitope of gag. Mice were primed i.p. with 100 ng of TRIP.N gagΔmyr LV or TRIP.NI gagΔmyr CO LV. 10 days later, splenocytes from immunized mice were stimulated with the corresponding peptides and analyzed by ELISPOT assays. Background frequencies were substracted prior to plotting. Error bars represent SD for 3 mice per group. (D) Comparison of gag specific lytic activities induced by TRIP.NI gagΔmyr LV versus TRIP.NI gagΔmyr CO LV immunization. CTL activity was measured 10 days after immunization using a 20 hours in vivo CTRL assay as described in Materials and Methods, Mean+/−SD three mice is shown.

The obtained results show that codon optimization critically improves the CTL response induced by TRIP.NI LV-based vaccines.

2. Lentiviral Vector Particles Encoding Codon Optimized Antigen Induce a Strong and Durable Cellular Immune Response after Even a Single Injection The obtained results show that codon optimization critically improves the CTL response induced by TRIP.NI LV-based vaccines.

The Memory T cell responses induced by non integrative lentiviral vectors were assayed in mice, after a single injection of TRIP.NI gag Δmyr or TRIP.NI gag Δmyr CO particles. FIG. 34 shows that lentiviral vector particles encoding codon optimized antigen induce a strong and durable cellular immune response after even a single injection 3. Prime-boost Strategy Based on TRIP.NI gagΔmyr CO Particles Pseudotyped with a Glycoprotein G from Non Cross Reactive VSV Serotypes Enhances the Cellular Immune Response Mice were immunized with TRIP.NI GAGΔmyr CO or TRIP.I GAG wild-type particles pseudotyped with VSV-G Indiana and 13 weeks later were boosted with respectively TRIP.NI GAGΔmyr CO or TRIP.I GAG wild-type particles pseudotyped with VSV-G New Jersey, Control groups for the prime-boost protocol include mice injected only one time with TRIP particles pseudotyped with VSV-G Indiana (grey diagrams) or TRIP particles pseudotyped with VSV-G New Jersey (blue diagrams). All the mice were sacrified at 10 days post-immunization, and the cellular immune response against GAG was evaluated by IFN-γ ELISPOT (A) or tetramer staining (B) (FIG. 35). The results obtained show that codon optimization of the lentiviral based particles enhances the prime-boost vaccine regimen.

The data obtained on mice show that codon optimization of the polynucleotide encoding the antigen in the lentiviral vector particles provides improvement in the level of the cellular immune response and especially the CTL response in the host, after a single injection or after a prime-boost injection. In addition, the obtained response is strong and durable.

Comparison of the Immune Response Obtained in Mice Immunized Through Different Routes Several groups of two different types of mice were vaccinated with lentiviral vector particles encoding SIVmac239GagΔ. The elicited immune response was analyzed in each group 10 days after a single injection of the particles performed either intramuscularly (i.m.), intradermally (i.d.), intraperitoneally (i.p.), subcutaneously (s.c.) or transcutaneously (t.c.i.).

Especially the response was analyzed in an in vivo cytotoxicity assay (FIGS. 36-38) or in an IFNgamma ELISPOT.

In the groups of mice (C57Bl/6j) where the injection was performed through the intramuscular route a stronger response was elicited than when the injection was carried out through another route.

Non-Integrative Lentiviral Vectors for Use to Elicit Immune Response when administered for protection in a vaccine Regimen.

Materials and Methods

Cell Culture and Virus Preparations

Hela cells (ATCC CCL-2), Human 293T cells and African green monkey kidney Vero cells (ATCC CCL-81) were cultured in Dulbecco modified Eagle medium (DMEM) supplemented with 10% (Hela cells, 293T cells) or 5% (Vero cells) heat-inactivated fetal calf serum (FCS), penicillin, streptomycin and Glutamax (GIBCO). West Nile Virus (WNV) strain IS-98-ST1 (GenBank accession number AF 481 864), a closely related variant of NY99 strain$^{10}$, was propagated in mosquito *Aedes pseudoscutellaris* AP61 cell monolayers. Purification in sucrose gradients and virus titration on AP61 cells (*Aedes pseudoscutellaris* cells) by focus immunodetection assay (FIA) using anti-WNV hyperimmune mouse ascitic fluid (HMAF) were performed as previously described. Infectivity titers were expressed as focus forming units (FFU).

Lentiviral Vector Production

The TRIP$_{sEWNV}$ (FIG. 2) and TRIP$_{GFP}$ vector plasmids were constructed as previously described (Iglesias et al. J. Gene Med. 2006 March; 8(3): 265-74). The nucleotide sequences of these two vectors are presented respectively on FIGS. 4 and 5. Vector particles were produced by transient calcium phosphate co-transfection of 293T cells with the vector plasmid pTRIP$_{sEwnv}$ or pTRIP$_{GFP}$, a VSV-G envelope expression plasmid (pHCMV-G) and an encapsidation plasmid (p8.74 or pD64V for the production of integration-proficient or integration-deficient vectors respectively) as previously described. Quantification of the p24 antigen content of concentrated vector particles was performed with a commercial HIV-1 p24 enzyme-linked immunosorbent assay (ELISA) kit (Perkin Elemer Life Sciences). Vector titers of TRIP.I and TRIP.NI particles were determined by transducing HeLa cells treated with aphidicolin and performing a quantitative PCR as previously described in Iglesias et al. (J. Gene Med. 2006 March; 8(3): 265-74). The titers of integrative and non-integrative lentiviral vectors were similar according to p24 content and quantitative PCR measured in growth arrested cells.

Preparation of Bone Marrow-Derived DCs

Bone marrow cells were isolated by flushing mice femurs and tibiae with RPMI supplemented with 10% FCS. Cells were then passed through a 45μm cell strainer, centrifuged and resuspended in 10Test® 3 lysing solution (an erythrocyte lysing solution, mixture of ammonium chloride, potassium bicarbonate and ethylenediamine tetraacetic acid (EDTA); Beckman Coulter) and incubated at 4DC for 5 min to lyze red blood cells. The cells were centrifuged and cultured for 8 days at $1 \times 10^6$ cells/ml in culture medium consisting of RPMI with 10% FCS, L-glutamine, penicillin, streptomycin, 1 mM sodium pyruvate, 10 mM HEPES, and 50 μM 2-mercaptoethanol supplemented with 100 ng/ml of recombinant mouse FLT3 ligand (R&D Systems).

Transduction Experiments and Flow Cytometry Analysis

For transduction experiments on non-dividing cells, Hela cells were seeded in 48 wells plates at 40,000 cells/well in the presence of 8 μM of aphidicolin (Sigma). Cells were transduced with lentiviral vectors at a concentration ranging from 1 to 100 ng/ml, 24 hours after the aphidicolin block, which was replenished in the medium at the time of transduction. At 2 days post-transduction, cells were harvested and eGFP expression was analyzed by flow cytometry.

For DC transduction experiments, 500,000 FLT3L-generated-bone marrow-derived DC (FL-DC) were transduced at day 6 of the differentiation, with lentiviral vectors at a concentration ranging from 50 to 300 ng/ml. At 2 days post-transduction, FL-DC were harvested and resuspended in PBS with 2% FCS and 0.01% sodium azide (staining buffer). Cells were strained with an APC(allophycocyanine)-conjugated anti-CD11c antibody and a PerCP(Peridinin chlorophyll protein)-conjugated anti-B220 antibody, washed twice and analyzed by flow cytometry on a FACSCalibur (BD biosciences, Franklin Lakes, N.J.).

Mice Immunization

All animal experiments were conducted in accordance with the guidelines of the Office Laboratory of Animal Care at the Pasteur Institute. Six-week-old C57/Bl6 mice were intraperitoneally (i.p.) inoculated with varying doses of TRIP/sE WNV vector particles (from 1 to 100 ng/ml) in 0.1 ml Dulbecco's phosphate-buffered saline (DPBS; pH 7.5) supplemented with buffered 0.2% bovine serum albumin (DPBS/0.2% BSA, Sigma).

Measurement of Serum Antibody Responses

Mice were bled via the periorbital route and serum samples were heat-inactivated 30 min at 56° C. Anti-WNV antibodies were detected by ELISA, by use of microtitration plates coated with sucrose-purified WNV IS-98-ST1. Peroxydase goat anti-mouse immunoglobulin ($H_+L$) (Jackson Immuno Research) was used at a 1:4,000 dilution as secondary antibodies. The endpoint titer was calculayed as the reciprocal of the last dilution eliciting twice the optical density (OD) of sera from nonimmunized mice.

WNV challenge

WNV challenge was performed by i.p. inoculation of neurovirulent WNV strain IS-98-ST1 (i.p. LD 50=10 FFU) as previously described, either one week or two months after lentiviral vector vaccination. The challenged mice were monitored daily for signs of morbidity or mortality, for up to 21 days after the WNV strain inoculation.

Results

Transduction of nondividing cells with TRIP vectors deficient for Integration results in high transgene expression levels To test the hypothesis that integration deficient LV (TRIP.NI vectors) could be efficient tools to deliver antigen (Ags) to nondividing APC such as DC, we initially evaluated their transduction efficiency of growth-arrested cells. For this purpose, HeLa cells treated with aphidicolin, a specific inhibitor of cell cycle, were exposed to graded doses of TRIP.NI or TRIP.I particles encoding eGFP. The transduction efficiency was then determined by flow cytometry. As shown in FIG. 43 (upper panel), TRIP.NI vectors transduced nondividing cells with high efficiency and in a dose dependent manner. Moreover, analysis of the percent of eGFP positive cells revealed marginal differences in the capacities of transduction of TRIP.NI vectors compared to that of TRIP.I vectors. Transduction with TRIP.NI particles yielded also high levels of expression of the transgene (FIG. 43, lower panel), although significantly lower by a 2-fold factor compared to TRIP.I-transduced cells.

Figure 44A:
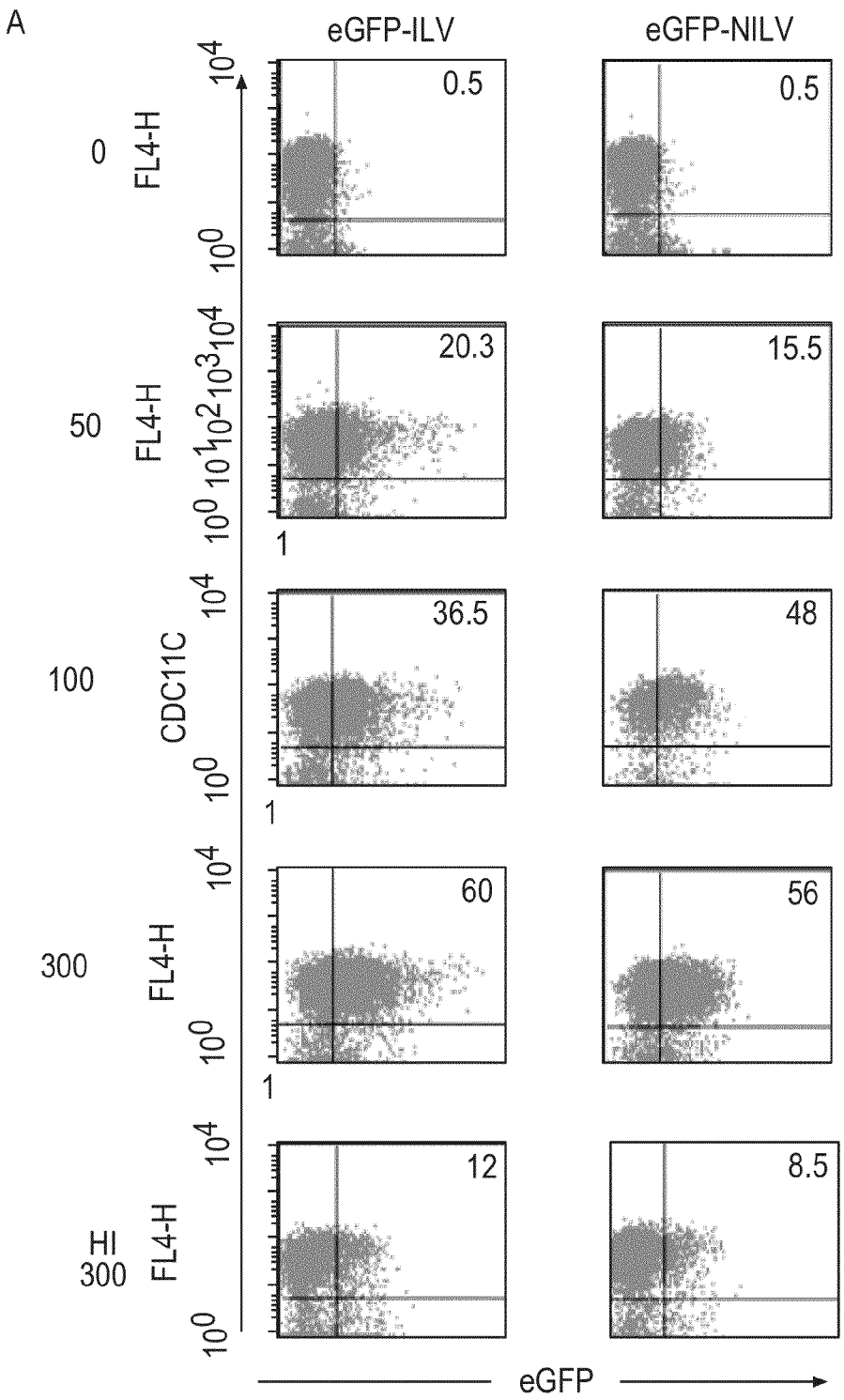

TRIP Nonintegrative Lentiviral Vector Transduction Leads to Effective Antigen Expression Both in Conventional and in Plasmacytoid Dendritic Cells We next studied the ability of TRIP.NI vectors to transduce DC. DC are categorized as conventional (cDC) ($CD11c^{+B}$ $220^-$) and plasmacytoid (pDC) ($CD11c^+B220^+$) and both these DC subtypes are able to stimulate Ag-specific immune responses. We then investigated the transduction of bone marrow-derived DC differentiated in presence of Flt3L (FL-DC), which allows the generation of large numbers of pDC and cDC. FL-DC were exposed to graded doses of $TRIP.NI_{GFP}$ or $TRIP.I_{GFP}$ particles. As shown in FIG. 44A, both TRIP.I and TRIP.NI vectors were capable of transducing FL-DC with maximal transduction of efficiency of 60% and 56% respectively. Interestingly, we observed that transduction with TRIP.I particles led to a small proportion of DC expressing high levels of eGFP whereas transduction experiments with TRIP.NI did not (see the presence of dots in the right top corner of the dot blot, in experiments where cells have been transduced with the lentiviral vectors of the invention as compared to HI vectors). To rule out the possibility of pseudo-transduction conferred by residual eGFP proteins contaminating the vector stock, we also evaluated the percentage of transduced DC after exposure to particles submitted prior to a heat-treatment, which has been shown to abrogate the transduction capabilities of LV on different cell types. As expected, the heat-treatment decreased drastically the percentage of eGFP positive cells (FIG. 2A).

Figure 44B:
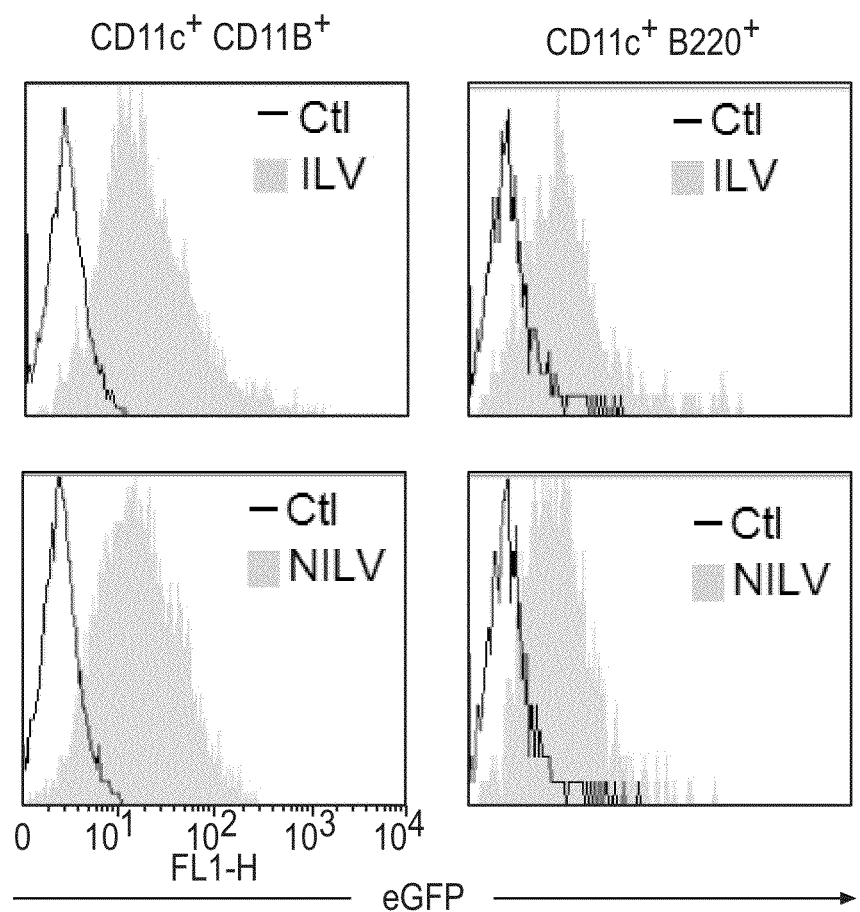

We next gated on $CD11c^+B220^+$ dendritic cells and $CD11c^{+B}220^-$ dendritic cells to evaluate the capacity of LV to transduce each DC subset. As shown in FIG. 44B, not only FL-derived cDC but also FL-derived pDC could be efficiently transduced with LV, regardless of their integration proficiencies.

Transduction efficiency with TRIP.NI particles was dose dependent and slightly but insignificantly lower than those obtained with TRIP.I particles. Interestingly, we observed that transduction with TRIP.I vectors led to a small proportion of DC expressing high levels of the transgene, whereas exposure of DC to TRIP.NI vectors did not (FIG. 44A). This cellular population which was only observed in transduction experiments with TRIP.I vectors could be the consequence of multiple-vector integrations or integration of the vector in active transcription regions of the genome.

TRIP Nonintegrative Lentiviral Vectors Induce the Production of Ag-Specific Antibodies Taking into account that TRIP.NI could efficiently deliver a foreign gene to DC, we next explored their ability to mount a specific immune response. In a recent study, we have designed TRIP.I vectors coding for a secreted form of WNV envelope (TRIP.I $E_{WNV}$) which possesses neutralizing epitopes and we have demonstrated that TRIP.I $E_{WNV}$ could stimulate an antibody-based protective immunity in a mouse model of WNV infection. To investigate the ability of TRIP.NI vectors to initiate a B cell response, animals were immunized with various doses of TRIP.NI $E_{WNV}$ particles ranging from 1 to 100 ng of p24 antigen per mouse. As a control, mice were inoculated with 100 ng of TRIP.NI $E_{WNV}$ particles inactivated by heating (HI) to abrogate their transduction capacities. Three weeks after immunization, mice were bled periorbitally and individual or pooled sera were tested by ELISA for anti-WNV total antibodies. As expected, immunizations with heat-inactivated TRIP.NI $E_{WNV}$ vectors were not followed by the production of Abs (FIG. 45A). By contrast, mice immunized with a dose as low as 10 ng of TRIP.NI $E_{WNV}$ vectors displayed detectable levels of anti-WNV antibodies and immunizations with 100 ng of sE-NILV induced a massive secretion of anti-WNV Ig with a mean titer reaching $8 \times 10^4$.

We next compared the strength of the immune response elicited by TRIP.NI $E_{WNV}$ and TRIP.I $E_{WNV}$ vectors. As shown in FIG. 45B, vaccination with TRIP.I $E_{WNV}$ at a dose as low as 3 ng of particles generated a very high secretion of anti-WNV antibodies and titers were relatively constant within the range of immunizing doses from 3 to 100 ng, with no dose response evident. By contrast and contrary to all expectations, titers in sera from mice immunized with TRIP.NI $E_{WNV}$ vectors were proportional to the dose of particles injected. Although TRIP.I vectors elicited a higher immune response than TRIP.NI vectors at doses below 30 ng, vaccinations with 100 ng of either vectors led to an equivalent response.

Taken together, these results demonstrated that a single immunization with TRIP.NI vectors was sufficient to elicit a humoral specific immune response with a strength comparable to that obtained with TRIP.I vectors, above a threshold dose of particles. Interestingly and surprisingly, use of non-integrative vectors enable to obtain an immune response whose strength is dependent upon the dose of injected lentiviral vectors.

Immunizations of mice with a single dose of TRIP.NisEwnv give the following antibody titers:

| Dose | WNV specific antibody titer (O.D.) |
| --- | --- |
| HI NI 100 | 0 |
| NI 1 | 0 |
| NI 3 | 0 |
| NI 10 | 152 |
| NI 30 | 569 |
| NI 100 | 83000 |

Figure 46:
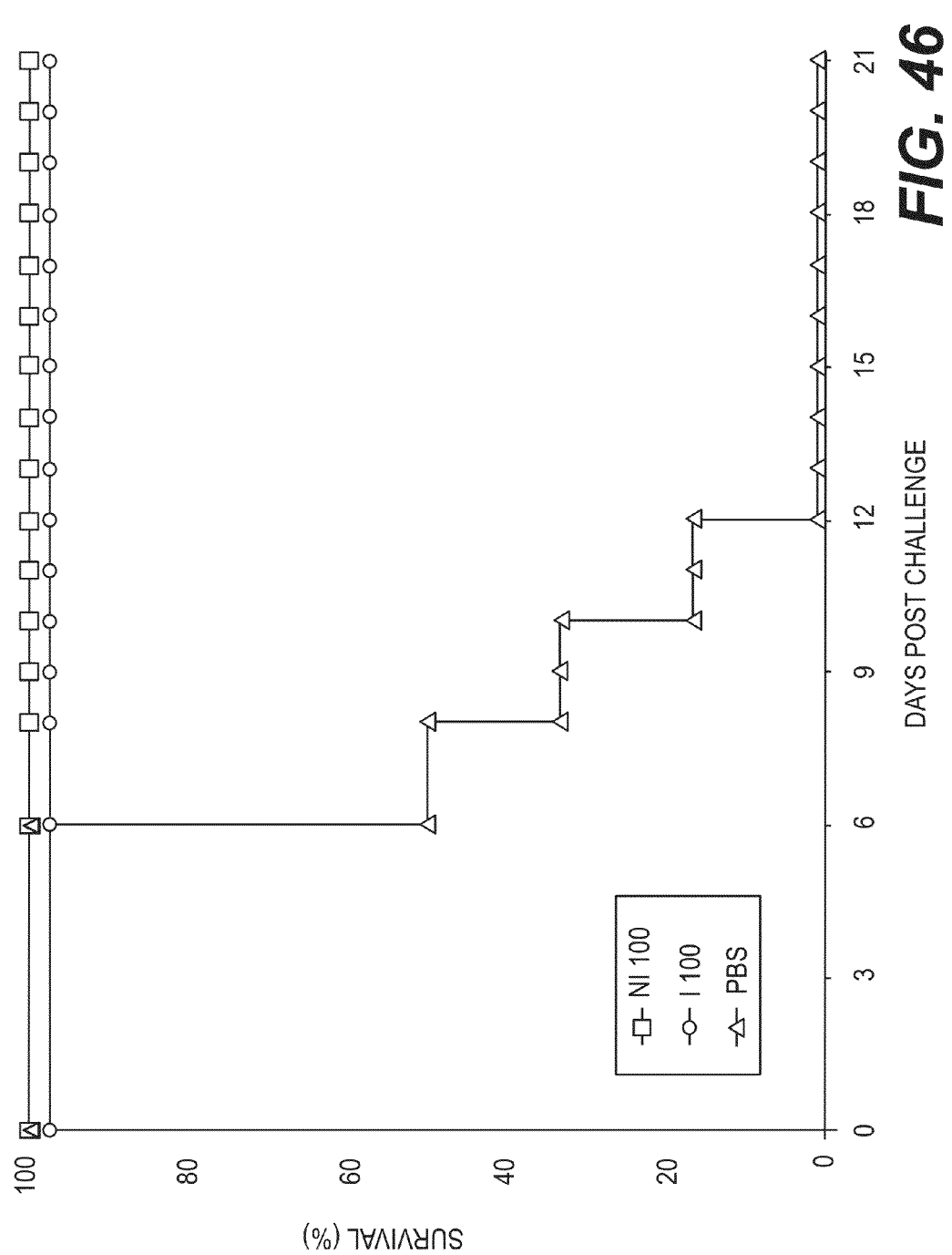
Figure 48:
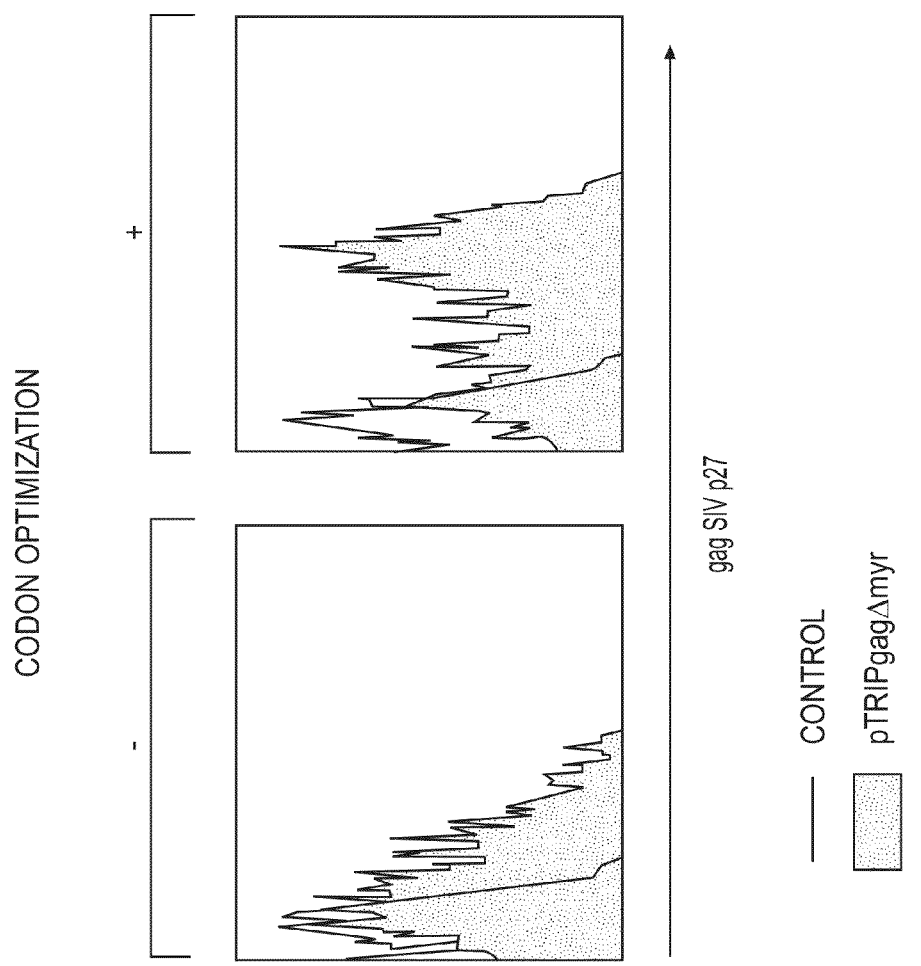
Figure 49:
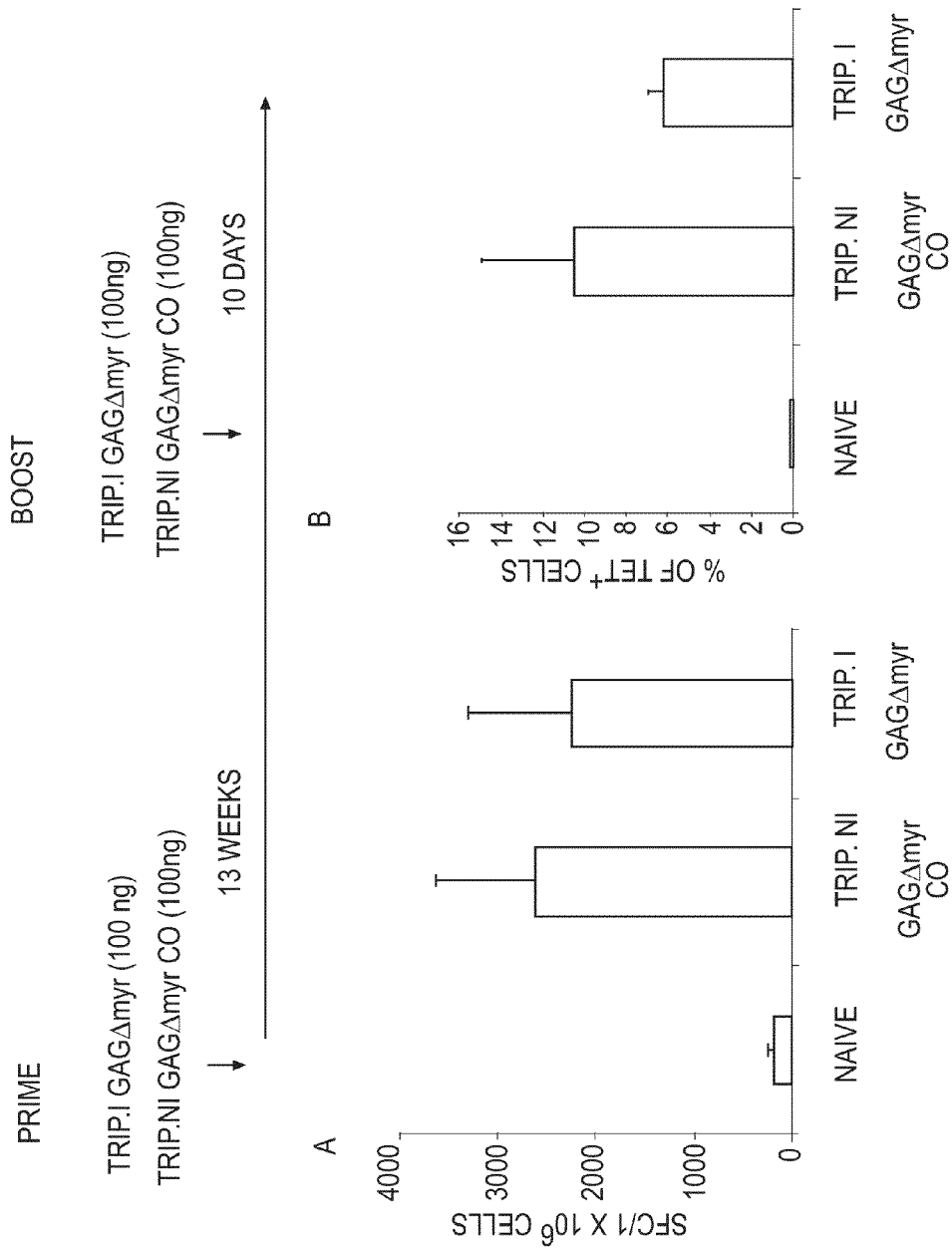

As shown on FIG. 45A, a potent secretion of specific WNV antibodies, with a mean titer reaching $8 \times 10^4$ at a dose of 100 ng of p24 antigen is obtained. At this dose, immunizations with TRIP.NI led to an equivalent response to that obtained with TRIP.I. However, dose-response experiments revealed that the minimal dose required for the induction of a B cell response was lower with TRIP.I particles compared to the TRIP.NI particles. One possible explanation for this result could be related to the ability of TRIP.I vectors to generate Ag-highly-expressing DC since, on theorical grounds, high expression levels of the Ag in the DC could favor a more sustained presentation of antigenic peptides and thus may explain why low doses of TRIP.I particles were sufficient to elicit a specific immune response. This hypothesis may also explain the non-linearity of the WNV antibody production observed in dose-response immunization experiments with TRIP.I vectors (FIG. 45B). Indeed, the in vitro dose response experiments performed on DC revealed that the appearance of Ag-highly-expressing DC do not seem to be correlated to the dose of TRIP.I particle (FIG. 44A). Thus, the capacity to generate Ag-highly-expressing DC may contribute to explain the differences observed between TRIP.I and TRIP.NI with low doses of particles injected. Another possibility is linked to the fact that VSV-G pseudotyped LV have a large cellular tropism and thus, may transduce at the site of injection other cell types than DC, including dividing cells. This could result in a more sustained expression of the Ag in vaccination experiments with TRIP.I particles. Which cell types are transduced after in vivo injections of LV and to what extend they are involved in the magnitude of the immune response elicited by TRIP.I and TRIP.NI vectors is the subject of ongoing research Immunization with TRIP.NI $E_{WNV}$ vectors confers early protection against WNV challenge We have previously shown that TRIP.I $E_{WNV}$ confers an early protective immunity against a WNV challenge. To determine if the immune response elicited by TRIP.NI vectors could also lead to a rapid protection, mice were immunized with 100 ng of TRIP.NI $E_{WNV}$ particles and challenged 7 days after with 10,000 FFU of the highly virulent WNV strain IS-98-ST1 (thousand times the dose required to kill 50% of infected animals). We included also in this challenge experiment a group of mice immunized with 100 ng of TRIP.I $E_{WNV}$ as a positive control of protection and another group of mice inoculated with D-PBS as a negative control. As expected, all mice that received D-PBS died within 12 days post-challenge (FIG. 46). In contrast, all mice immunized with a single dose of TRIP.NI $E_{WNV}$ were protected from the challenge, as were mice immunized with TRIP.I $E_{WNV}$.

Mice protected from WNV challenge did not develop clinical signs of illness during the 3-weeks post-challenge observation period. These results demonstrated that an early protective immunity against WNV was achieved with a single administration of TRIP. $E_{WNV}$ defective for integration.

TRIP.NI $E_{WNV}$ Induces Long-Lasting Protection

As demonstrated earlier, immunization of mice with TRIP.I $E_{WNV}$ resulted in the establishment of long-term protective immunity against WNV challenge. To evaluate the duration of the protective immunity elicited by TRIP.NI $E_{WNV}$, and the minimum dose of particles required to induce long-term protection, mice were immunized with different amounts of particles (1, 3, 10, 30 and 100 ng of p24 antigen) and were challenged after 2-month waiting period after immunization. As shown in FIG. 47A, there was a dose-dependent relationship between the dose of TRIP.NI $E_{WNV}$ particles administrated and the degree of protection, with a fully protection achieved at a dose of 100 ng of vaccine particles injected.

Thus, TRIP.NI $E_{WNV}$ vectors induced long-lasting immunity against WNV infection Discussion An important result of the present experiments is the demonstration that vaccination with TRIP.NI particles can provide an efficient and strong immune response that is both an early and long lasting immune response, and further antigen dose-dependent, despite the absence of integration of the lentiviral genome administered. Therefore, a fully protection against a challenge with a lethal dose of WNV was demonstrated.

As expected, memory protective immunity was directly correlated to the titer of anti WNV antibodies induced by TRIP.NI particles (FIG. 45 and FIG. 47). Indeed, it is well established that humoral immunity is a critical component for the establishment of a fully protective immunity against WNV, as specific antibodies limit dissemination of the infection. Intriguingly, heat-inactivated TRIP.NI particles as well as HI-TRIP.I particles were able to confer a partial protection (30%) against WNV challenge (data not shown), although no WNV-antibodies were detected in the sera of animals 3 weeks after injection of HI-TRIP particles (FIGS. 45A, B). This suggests that cellular immunity could also play a partial role in the establishment of protection against WNV. Consistent with this hypothesis, mice that lack $CD8^+$ cells have increased mortality after WNV infection (Shoresta and Diamonds, unpublished data). Moreover, cytotoxic T cell epitopes have been defined in the domain III of the envelope of several flaviviruses. Additional works are required to clarify the relative contribution of CTL responses to the long term protection conferred by TRIP.NI and TRIP.I vaccines. Moreover, further studies are also needed to define the molecular mechanisms allowing the entry of HI-TRIP particles in DC since the heat-treatment denatures the VSV-G envelope and has been shown to abrogate the transduction capacities of LV in different cell lines. However, it is tempting to speculate that, in regards to the exceptional internalization capacities of DC, a fraction of HI TRIP particles could be incorporated in DC by a VSV-G independent mechanism, allowing a low but sufficient Ag expression to explain the partial protection conferred by HI-TRIP particles.

Kinetic challenge experiments on vaccinated mice revealed that TRIP.NI vaccines not only conferred a long term protective immunity but elicited also protection as early as one week after a single injection of particles. Although the exact mechanisms involved in this early protection are not fully understood, we have detected specific WNV antibodies one week after immunizations with TRIP.NI and TRIP.I particles. We have previously shown that this early wave of antibodies were exclusively composed of specific IgM, derived from mice 4 days after injection, completely protected mice against WNV infection.

In our study, a vaccination regimen based on a direct injection of a single dose of TRIP.NI particles elicited a robust, rapid and long term specific immune response, achieving fully protection against WNV. Thus, TRIP.NI based vaccine strategy represents a safe and efficacious platform for the development of vaccines against pathogens agents such as flaviviruses that require B cell immunity.

Codon Optimization Enables to Improve the Cellular Immune Response of Non Integrative Vectors. Further Improvement is Obtained with a Prime-Boost Regimer
Material and Methods Intracellular staining of gag p27. 293 T cells were cotransfected with TRIP vector plasmids containing either a wild-type sequence or a codon-optimized sequence of gagΔmyr, the encapsidation plasmid p8.7 D64V and the VSV-G Indiana expression plasmid. 48 hours later, cells were washed and permeabilized for 20 min in Cytofix-Cytoperm solution (BD Pharmingen). After two washes with PermWash buffer (BD Pharmingen), permeabilized cells were incubated with Anti-gagSIV p27 antibody (55-2F12, AIDS Research and Reference Reagent Program) for 30 min at 4° C. at a 1:3 dilution in PermWash buffer. Cells were washed twice and incubated with FITC-conjugated rat IgG2b kappa monoclonal antibody (553988, BD Biosciences) for 30 min at 4° C. at a 1:30 dilution in PermWash buffer. After two additional washes, cells were analyzed by flow cytometry.

Mice immunization. For prime experiments, groups of mice were intraperitoneally inoculated with various doses of TRIP.NI gagΔmyr wild-type or codon optimized (CO) particles pseudotyped with the glycoprotein from VSV Indiana serotype. For prime-boost experiments, groups of mice were intraperitoneally inoculated with 100 ng of p24 of TRIP.NI gagΔmyr codon optimized (CO) or 100 ng of p24 of TRIP.I gagΔmyr particles pseudotyped with the glycoprotein from VSV indiana serotype. 13 weeks later, mice primed with TRIP.NI gagΔmyr CO particles were boosted with 100 ng of p24 of TRIP.NI gagΔmyr CO particles pseudotyped with the glycoprotein from VSV New Jersey serotype. In parallel, mice primed with TRIP.I gagΔmyr particles were boosted with 100 ng of p24 of TRIP.I gagΔmyr particles pseudotyped with the glycoprotein from VSV New Jersey serotype.

Elispot Assay. Nitrocellulose microplates (MAHA S4510, Millipore) were coated with capture antibody (Mouse IFNg Elispot pair, BD Pharmingen) and blocked with complete medium composed of RPMI 1640 Glutamax supplemented with 10% FCS, antibiotic, Hepes, non-essential amino-acids, b-mercaptoethanol and sodium pyruvate. Splenocytes from vector-immunized mice were added to the plates in triplicates at $0.25 \times 10^6$ cells/well and stimulated with SIVmac 239 gag peptides (NIH AIDS Research and Reference Reagent Program). Forty hours later, spots were revealed with the biotine-conjugated antibody (Mouse IFNg Elispot pair, BD Pharmingen) followed by streptavidin-AP (Roche) and BCIP/NB substrate solution (Promega). Spots were counted using a Bioreader 2000 (Biosys, Karben, Germany) and results were expressed as IFNg spot-forming cells (SFC) per million splenocytes.

In vivo cytotoxic assay. For target cell preparation, splenocytes from naive mice were labelled with various concentrations (high, 5 μM; Low, 1 μM) of CFSE (carbosyfluorescein-diacetate succinimydel ester, Vybrant CFDA-SE cell-tracer kit, Molecular Probes). Splenocytes labelled with high concentrations of CFSE were pulsed with peptides at 5 μg/ml. The control population stained with low doses of CFSE was incubated in medium without peptides. Each mouse received $10^7$ CFSE-labelled cells of a mix containing an equal number of cells from each fraction, through the retroorbital vein. After 15-18 h, single-cell suspensions from spleen were analyzed by flow cytometry (Becton Dickinson, CellQuest software). The disappearance of peptide-pulsed cells was determined by comparing the ratio of pulsed (High CFSE fluorescence intensity) to unpulsed (Low CFSE fluorescence intensity) populations in immunized versus naive mice. The percentage of specific killing was established according to the following calculation: $(1-((CFSE_{low}\ naive/CFSE_{high}\ naive)/(CFSE_{low}\ immunized/CFSE_{high}\ immunized)))*100$.

Tetramer staining. $2 \times 10^6$ splenocytes from immunized mice were stained at room temperature for 5 min with anti-CD3-FITC (Becton Dickinson), an anti-CD8-APC (Becton Dickinson) and a PE-tetramer specific of the immunodominant peptide of $GAG_{SIV}$. Data was collected using FACSCalibur and analyzed using CellQuest.

Conclusion

The invention provides a solution to improve the cellular immune response induced with nonintegrative lentiviral vectors by the use of:
1. a codon-optimized form of the transgene coding for the antigen and/or
2. a prime-boost regimen 1. We have demonstrated that nonintegrative lentiviral vectors coding for the gagdmyr$_{SIV}$ wild-type antigen are far less potent at inducing specific T cell responses than integrative lentiviral vectors coding for the same antigen. More importantly, we have demonstrated that this poor immunogenicity can be overcome by the use of a codon-optimized form of the trangene coding for Gagdmyr$_{SIV}$. The absolute requirement of a codon-optimized antigen with nonintegrative lentiviral vectors to induce strong T cell responses could not be anticipated. This result was unexpected since we have demonstrated that nonintegrative lentiviral vectors could efficiently transduce nondividing cells and especially dendritic cells, the most efficient antigen-presenting cells, as well as integrative lentiviral vectors. However, the expression of a non-codon-optimized transgene was lower by a 2-fold factor in transduced cells with nonintegrative lentiviral vectors compared to cells transduced with integrative lentiviral vectors. This result suggested that in vivo, the response induced by nonintegrative lentiviral vectors could be less strong by a 2-fold factor compared to the response induced by integrative lentiviral vectors and it could be anticipated that the injection of twice more nonintegrative lentiviral vectors could give similar responses to that obtained with integrative lentiviral vectors. This was absolutely not the case, since specific T cell responses elicited by nonintegrative lentiviral vectors are 5 to 10 fold lower than that observed with integrative lentiviral vectors. Moreover, the induction of specific T cell responses responses with nonintegrative lentiviral vectors could only be achieved with high doses of injected particles (the minimal dose required to induce a quantifiable T cell response with nonintegrative lentiviral vectors is at least 10-fold higher than the minimal dose required with integrative lentiviral vectors). Codon-optimization(CO) overcomes this poor immunogenicity. Thus, at a dose of 100 ng, nonintegrative lentiviral vectors bearing a codon-optimized form of gagdmyr$_{SIV}$ induced memory T cell responses against the antigen, whereas vectors bearing the wild-type form did not. However, the response elicited by TRIP.NI gagdmyr$_{SIV}$ CO is still lower by a 2-fold factor than that elicited by TRIP.I gagdmyr$_{SIV}$ wild-type.

2. A prime-boost regimen based on TRIP.NI gagdmyr$_{SIV}$ CO elicits similar response in term of intensity than a prime-boost regimen based on TRIP.I gagdmyr$_{SIV}$ wild-type. In prime-boost experiments, mice were immunized with 100 ng of TRIP.NI gagdmyr$_{SIV}$ CO or 100 ng of TRIP.I gagdmyr$_{SIV}$ wild-type. Lentiviral vectors were pseudotyped with the VSV-G Indiana envelope. 13 weeks later, mice immunized with TRIP.NI particles were boosted with 100 ng of TRIP.NI gagdmyr$_{SIV}$ CO particles pseudotyped with the noncrossreactive VSV-G New Jersey envelope. In parallel, mice primed with TRIP.I particles were boosted with 100 ng of TRIP.I gagdmyr$_{SIV}$ wild-type pseudotyped with the VSV-G New Jersey envelope. Analysis of Gagdmyr$_{SIV}$ specific immune response (IFNg ELISPOT, tetramer staining) performed on splenocytes from immunized mice revealed that a prime-boost regimen based on TRIP.NI gagdmyr$_{SIV}$ CO elicits at least similar responses in term of amplitude than a prime-boost regimen based on TRIP.I gagdmyr$_{SIV}$ wild-type particles. This result has never been published and could not be anticipated since a single injection with TRIP.NI gagdmyr$_{SIV}$ CO particles induced lower responses compared to a single injection of TRIP.I gagdmyr$_{SIV}$ wild-type particles.

Use of the VSV-G Envelope Protein of Different Serotypes for Pseudotyping Lentiviral Vector Particles The G glycoprotein of the vesicular stomatisis virus (VSV-G) of the Indiana serotype is a transmembrane protein commonly used as a coat protein for engineering lentiviral vector vectors.

Presently, nine virus species are definitively classified in the VSV gender, and nineteen rhabdoviruses provisionally classified in this gender, all showing various degrees of cross-neutralisation. When sequenced, the protein G genes indicate sequence similarities. The VSV-G protein presents a N-terminal ectodomain, a transmembrane region and a C-terminal cytoplasmic tail. It is exported to the cell surface via the transgoigi network (endoplasmic reticulum and Golgi apparatus).

A codon optimized gene have been generated, and cloned between the BamH1 and EcoR1 sites of the pThV vector, generating the pThV-VSV.G (IND-CO) (FIG. 6). The codon optimization for the expression of the VSV-G proteins in human cells can stimulate gene transfer efficiency of a 100 fold factor, as shown in the case of the New Jersey serotype (FIG. 20). We further show that several serotypes of VSV-G proteins, in the specific context of pseudotyped lentiviral vector particles, do not induce croos-neutralizing antibodies after in vivo injections.

When further VSV-G serotypes are required to design a suitable combination for use in the vaccine assay including at least one a boost injection, other VSV-G serotypes have been tested for particles coating. The first one used was the VSV-G$_{NewJersey}$ serotype. A codon optimized gene have been synthesized, and cloned between the BamH1 and EcoR1 sites of the pThV-plasmid, generating the pThV-VSV.G (NJ CO) vector (FIG. 7).

Presently, five other VSV-G genes are sequenced (Chandipura, Cocal, Piry, Isfahan and spring viremia of carp virus, FIG. 3), and have been prepared in a codon optimized version.

Materials and Methods
1. Materials
1.1 Plasmids

Figure 12C:
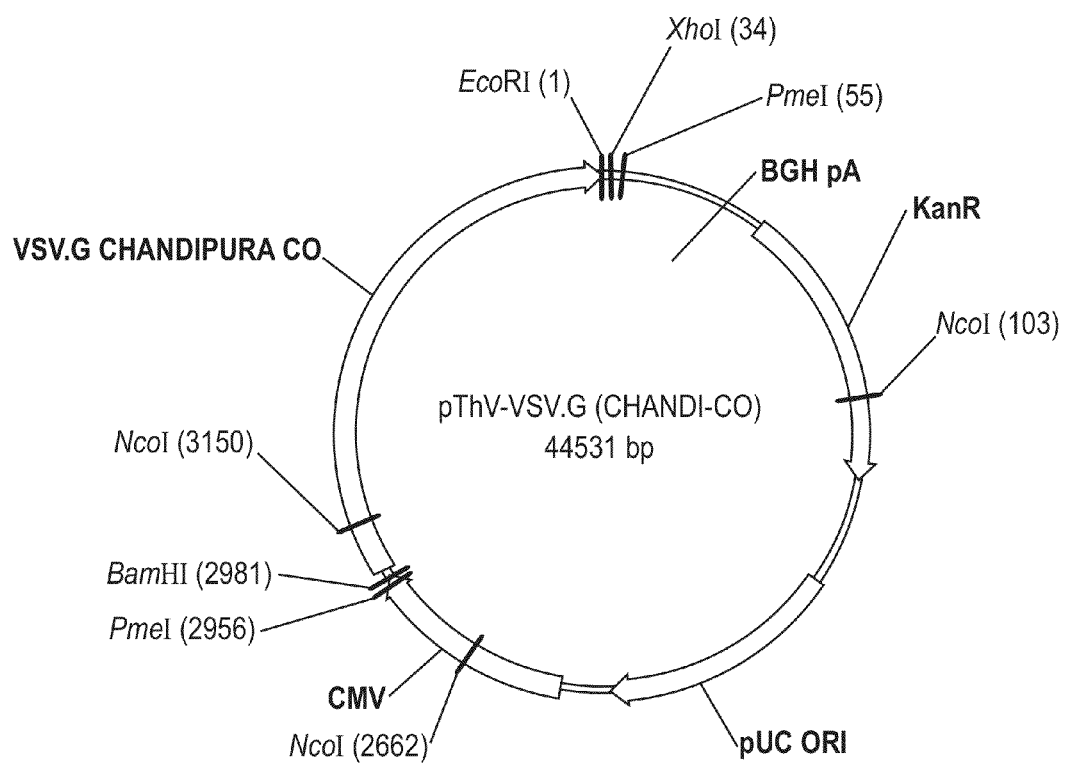

Codon optimized genes have been generated by Gene Art AG (Germany) for the five characterized VSV-G serotypes. The genes were cloned between the BamH1 and EcroR1 sites of the pThV plasmid, generating the following vectors: pThV-VSV.G (CHANDI-CO; FIG. 8), pThV-VSV.G (COCAL-CO; FIG. 9), pThV-VSV.G (PIRY-CO; FIG. 10), pThV-VSV.G (ISFA-CO; FIG. 11) and pThV-VSV.G (SVCV-CO; FIG. 12).

2. Methods
2.1 Cross neutralization assays

Mice C57Bl/6 mice (haplotype H2b, between 12 and 23 weeks old) were intraperitoneally injected with the lentiviral vector particles pseudotyped with the VSV-G serotypes (Indiana, New Jersey, Isfahan, Cocal and SVCV, 6 mice per group, 450µL/mouse). 4 weeks later, the mice were boosted with the same particles (500 µL/mouse). A first retro orbital blood collection (in Capiject tubes) is done 15 days post boost, and a second 21 days post boost. The blood is centrifuged 6 min at 3500 rpm and the serum is collected and kept at −20° C.

Transduction assays were made in presence of various dilutions of these sera.

2.2 Generation of Human Monocyte-Derived DCs

Buffy coats were obtained from French Blood Bank (EFS-Rungis) with informed consent from all subjects and according to ethical guidelines. PBMCs are isolated by Ficoll density centrifugation. Monocytes cells are enriched by adhesion on tissue-culture-treated plates. After the adhesion step cells are cultured in RPMI media containing 10% FCS, Peni strptomycine, Pyruvate 0.1 mM+Hepes 1 mM and supplemented with granulocyte-macrophage rhGM-CSF (50 ng/ml, R&D systems) and rIL-4 (20 ng/ml, R&D systems). This medium was replaced with fresh media containing rhGM-CSF (50 ng/ml) and rhIL-4 (20 ng/ml) four days after. On day 7, cells were phenotyped and transduced with lentilentiviral vector vectors. Two hours after transductions RPMI (INVITROGEN) media containing rhGM-CSF and rhIL-4 was added. Cells were harvested 5 days after transduction and were analyzed by LSR II flow cytometry (Becton Dickinson). Expression of GFP by DCs, was examined directly by flow cytometry in the fluorescein isothiocyanate channel.

2.3 Phenotypic Analysis of Human Monocyte-Derived DCs

For phenotypic analysis, DCs ($1\times10^6$ cells in 100 µl) were incubated for 5 min at room temperature with anti CD14, CD86, CD1a and HLA-dr antibody labeled with FITC- or PE at a concentration of 0.1 µg/µl (Becton Dickinson). Stained cells were analyzed by LSR II flow cytometry (Becton Dickinson).

Results

1. Evaluation of the Pseudotyping Abilities of the Different VSV-G Serotypes

Figure 50:
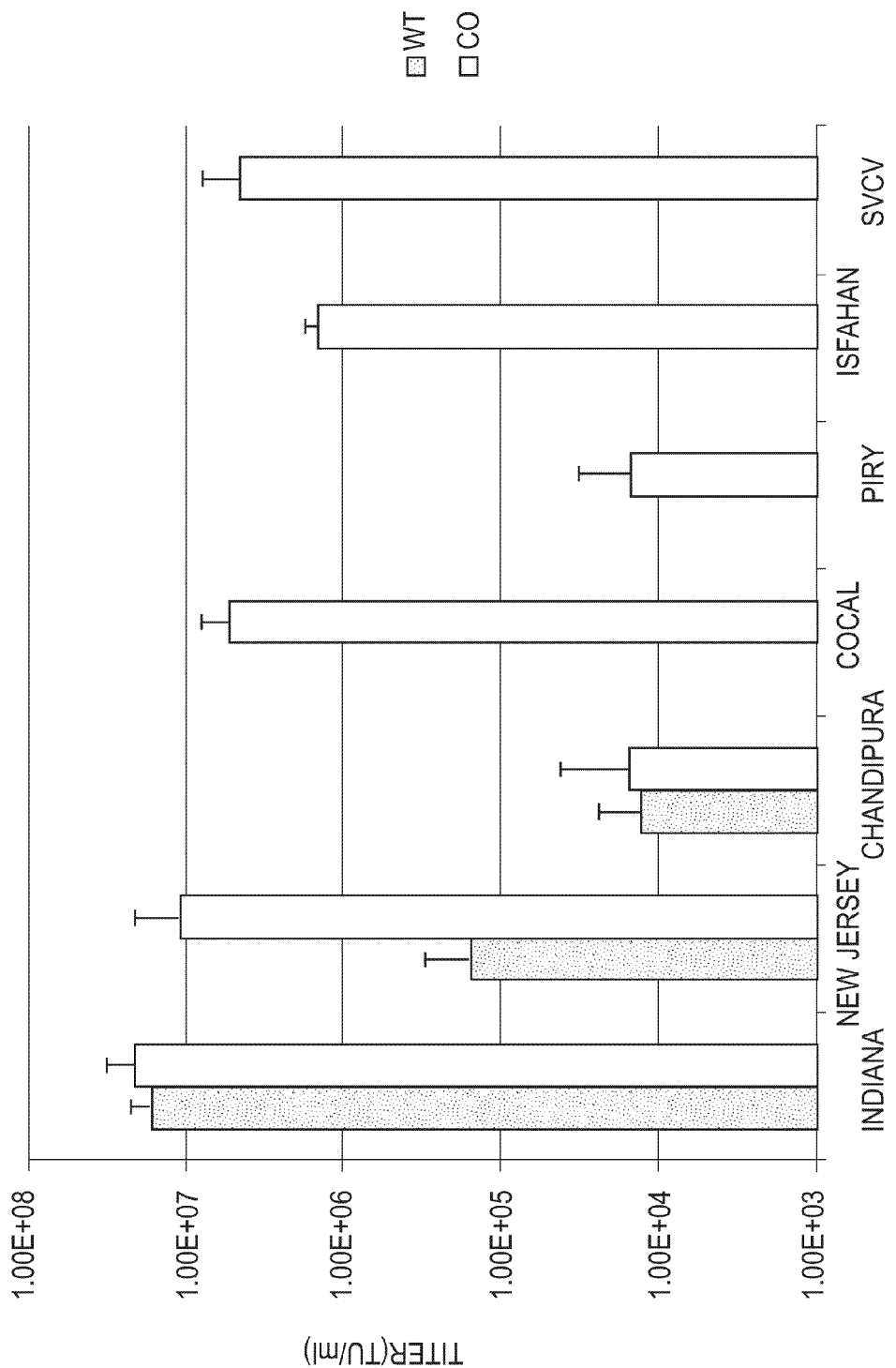

Human codon-optimized genes have been generated for the five characterized VSV-G serotypes, and cloned inside the pThV plasmid, generating the following vectors: pThV-VSV.G (CHANDI-CO), pThV-VSV.G (COCAL-CO), pThV-VSV.G (PIRY-CO), pThV-VSV.G (ISFA-CO) and pThV-VSV.G (SVCV-CO), (FIGS. 8 to 12). These envelope plasmids have been used for lentiviral vector particles productions, and their pseudotyping abilities have been evaluated by determining the vector titers (TU/ml). As shown in FIG. 50, in addition to the VSV-G Indiana and New Jersey, only three out of the five VSV-G proteins are able to efficiently pseudotype our lentiviral vector particles: the Cocal, Isfahan and SVCV serotypes. The best titer is observed with the Indiana serotype (no significant difference can be observed between the wild type and the codon optimized protein). The other serotypes give rise to 54% (New Jersey), 25% (Cocal), 22% (SVCV) and 7% (Isfahan) of the Indiana titer.

The Chandipura and Piry VSV-G serotypes both give rise to only 0.07% of the Indiana titer. It appears that their very low fusion activity would prevent their effective use to pseudotype our lentiviral vector particles, as they won't be able to transduce enough target cells. This low efficiency of the Chandipura VSV-G protein can explain its reported lack of ability to boost an immune response in the context of VSV-G pseudotyped replication-defective human immunodeficiency virus particles (Baliga CS, at al, Molecular Therapy, 2006).

2. Cross Neutralization Assays

Characterizing the aptitude of our VSV-G proteins to generate neutralizing antibodies and checking whether these antibodies potentially cross neutralize heterologous VSV-G serotypesmay be of help to settle on a preferred order in which the pseudotyped vectors should be injected in vaccination trials.

Figure 51A:
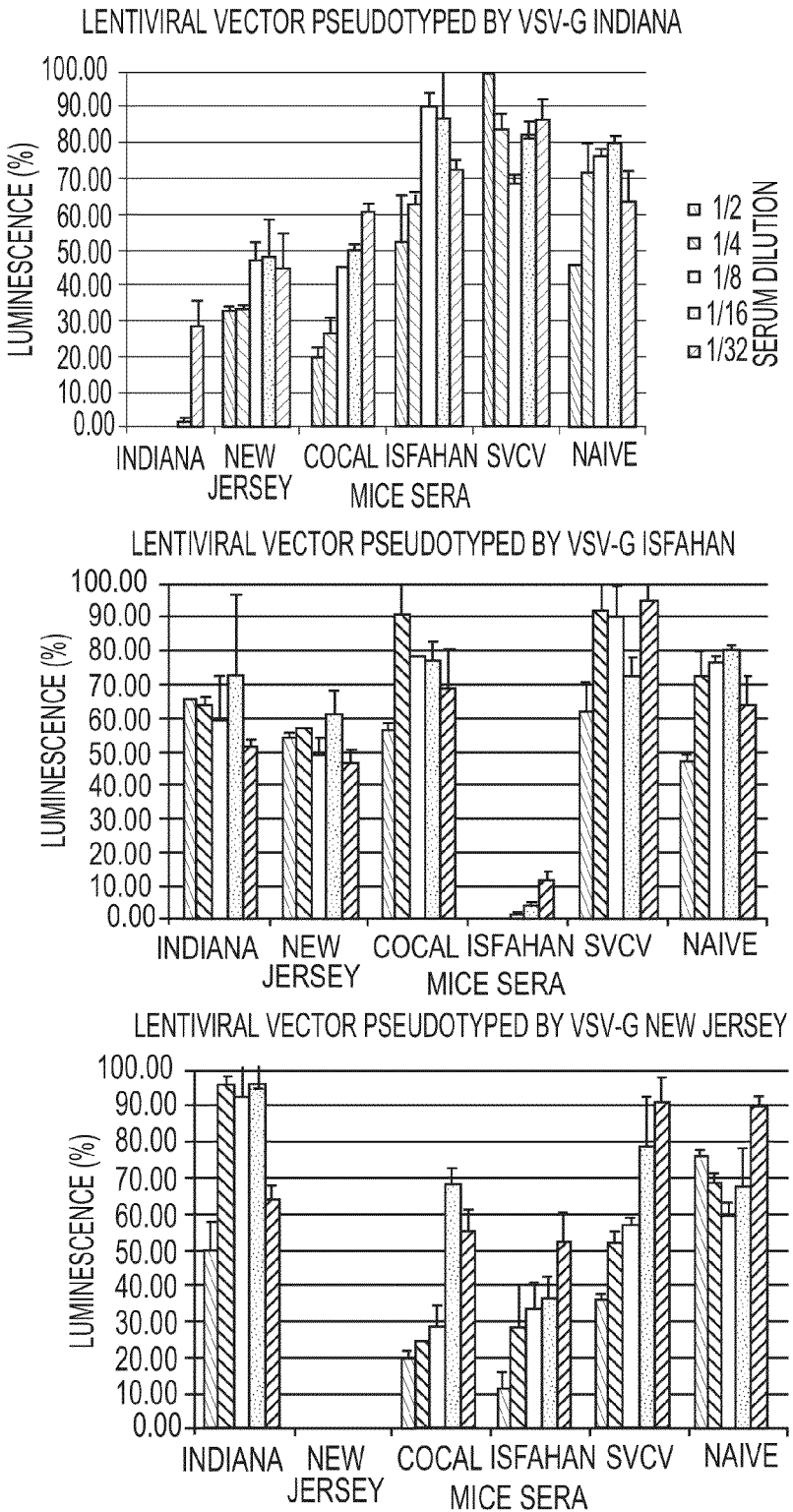

Lentiviral vector particles pseudotyped with the efficient VSV-G proteins (Indiana, New Jersey, Cocal, Isfahan and SVCV) were injected twice in C57Bl/6 mice, with a four week interval between injections. 15 days after the second injection, blood was collected from mice and its ability to neutralize lentiviral vector particles pseudotyped with various VSV-G proteins was tested. As shown in FIGS. 51 and 52, the VSV-G Indiana, New Jersey, SVCV and Isfahan pseudotypes don't induce detectible antibodies against any other VSV-G proteins. Hence they can be used in any order for the first injection. In contrast, the anti-Cocal antibodies strongly inhibit the Indiana and SVCV pseudotyped particles. Therefore, if used, the Cocal pseudotyped particles should be used for the last injection, in order to avoid any neutralizing reaction inhibiting the effect of vaccination. In summary, when the various tested VSV-G proteins are successively used in prime-boost regimen the combinations of pseudotyped particles would in particular take into account the fact that the VSV-G pseudotyped particles should be injected in the following order: Indiana-New Jersey-Isfahan-SVCV/Cocal.

3. Antibody Prevalence in Monkeys and Human Sera

The presence in human sera of antibodies able to neutralize the VSV-G proteins should be determined prior to use them for pseudotyping our vector particles. In order to evaluate the intensity of the neutralizing responses that may be obtained with human sera, we first decided to test our particles pseudotyped with the selected VSV-G proteins in presence of various monkey sera, obtained from the animals used in our trial. Hence we collected sera from four monkeys (one not vaccinated, three vaccinated with various doses of particles pseudotyped with VSV-G Indiana—low, medium and high doses—and boosted with a unique dose of VSV-G New jersey pseudotyped particles), at various time (before injection, post prime and post boost). The ability of these monkey sera to neutralize particles pseudotyped with the selected VSV-G proteins (Indiana, New Jersey, Cocal, Isfahan and SVCV) has then been tested and the results are shown in FIGS. 53 to 57, respectively. As expected, a strong neutralizing activity against VSV-G Indiana was found in sera from monkeys which have been vaccinated with Indiana pseudotyped particles (FIG. 53) in a dose dependant manner, and also against New Jersey particles in sera from monkeys boosted with New Jersey pseudotyped particles (FIG. 54). Hence we can see that a homologous neutralizing activity is characterized by an IC 50 around 1/1024 serum dilution (50% of the total activity is obtained with a serum dilution of 1/1024). In FIG. 55, we can see that a neutralizing activity against the VSV-G Cocal serotype has been specifically developed by the monkey which had received a high dose of Indiana particles (this response is not observed with lower doses of Indiana particles). Nevertheless, no specific neutralizing activity against the Isfahan nor SVCV serotypes has been found in sera from pre immunized or vaccinated monkeys (FIGS. 56 and 57).

The presence in human serum of antibodies able to neutralize the VSV-G proteins has been determined in 96 human sera randomly selected. Transduction experiments with lentiviral vector particles pseudotyped with the selected VSV-G proteins were done in presence of human sera (heated and not heated). Results summarized in FIG. 58 (details of the experiments are shown in FIG. 59) show that some patients' sera presented strong neutralizing activities against VSV-G proteins (2 patients against Indiana, 4 against New Jersey and 3 against Cocal). In order to determine if this neutralizing activity is homologous or not specific, these patients were further investigated and transduction assays of particles pseudotyped with different VSV-G were done in presence of serial dilutions of these sera. As shown in FIG. 60, the patients who presented a neutralizing activity against the VSV-G Indiana in presence of a 2 fold dilution of their serum (patients #39, 47, 54, 83, 94 and 99) did not show this neutralization activity anymore at further dilution factor. The same observation could be done with the patients previously showing neutralizing activity against the New Jersey VSV-G protein (patients #7, 9, 63, 70, 84 and 88), the SVCV VSV-G protein (patients 10, 78, 94, 39, 84 and 98) and the Isfahan VSV-G protein (patients #10, 78, 9, 94, 70, 84 and 98). In contrast, out of the patients presenting a neutralizing activity against the Cocal VSV-G protein (patients #9, 57, 67, 80, 88, 54, 62, 69, 83 and 93), two were still presenting a neutralizing activity at high serum dilutions (patients #67 and 69) with an IC 50 at around the 1/512 serum dilution. These results indicate that an anti-Cocal prevalence may have to be determined in patients if the Cocal serotype is used for pseudotyping our lentiviral vector particles.

4. Transduction of Human Monocyte-Derived Dendritic Cells with Vector Particles Pseudotyped by Different VSV-G Envelopes In a proposed vaccination protocol of the invention, the lentiviral vector pseudotyped with the Indiana VSV-G pseudotype is injected first to prime the immunological reaction. In order to boost the immunological reaction, a lentiviral vector pseudotyped with one of the previously described VSV-G serotype is used for the second injection of lentiviral vector particles. Dendritic cells play central role in innate and adaptive immunities. Hence we characterized the capacity of vector particles pseudotyped by different VSV-G proteins to fuse with human DCs. Therefore, human monocytes derived dendritic cells (mDCs) were transduced with lentiviral vectors pseudotyped with various VSV-G proteins (New Jersey, Isfahan, SVCV, Cocal or Chandipura), leading to the determination of the titers (TU/mL) for the different particles, which correlates directly with the fusogenicity of each VSV-G. Besides, the titer of vector particles classically done on 293 T cells was also characterized to establish the relative titer of transduction (Titer DC/Titer 293T). The experiments demonstrated that all the VSV-G envelopes tested presented a relative ability to fuse with mDCs with the notable exception of the Chandipura serotype of VSV-G (FIG. 61). VSV-G Indiana appears to be the most fusogenic envelope compared to the other tested. Nevertheless, VSV-G New Jersey, Isfahan, SVCV and Cocal present also a good ability to fuse with mDCs. Considering different envelopes, the data provided (FIG. 61) by 2 different experiments showed the same pattern of fusogenicity whatever the value of relative titer (DC titer/293 T titer) was. This is due to the difference on the physiological state of mDCs used at the time of the transduction.

Bibliography

Addo, M. M., Yu, X. G., Rathod, A., Cohen, D., Eldridge, R. L., Strick, D., Johnston, M. N., Corcoran, C., Wurcel, A. G., Fitzpatrick, C. A., et al. (2003). Comprehensive epitope analysis of human immunodeficiency virus type 1 (HIV-1)-specific T-cell responses directed against the entire expressed HIV-1 genome demonstrate broadly directed responses, but no correlation to viral load. J Virol 77, 2081-2092.

Andrieu, J. M., and Lu, W. (2007). A dendritic cell-based vaccine for treating HIV infection: background and preliminary results. J Intern Med 261, 123-131.

Arhel, N.J., Souquere-Besse, S., Munier, S., Souque, P., Guadagnini, S., Rutherford, S., Prevost, M. C., Allen, T. D., and Charneau, P. (2007). HIV-1 DNA Flap formation promotes uncoating of the pre-integration complex at the nuclear pore. Embo J 26, 3025-3037.

Autran, B., Carcelain, G., Combadiere, B., and Debre, P. (2004). Therapeutic vaccines for chronic infections. Science 305, 205-208.

Autran, B., Carcelain, G., Li, T. S., Blanc, C., Mathez, D., Tubiana, R., Katlama, C., Debre, P., and Leibowitch, J. (1997). Positive effects of combined antiretroviral therapy on CD4+ T cell homeostasis and function in advanced HIV disease. Science 277, 112-116.

Andreas Bergthaler, Nicolas U. Gerber, Doron Merkler, Edit Horvath, Juan Carlos de la Torre, Daniel D. Pinschewer, 3-PloS Pathogens Vol. 2, No. 6, e51, Envelope Exchange for the Generation of Live-Attenuated Arenavirus Vaccines Betts, M. R., Nason, M. C., West, S. M., De Rosa, S. C., Migueles, S. A., Abraham, J., Lederman, M. M., Benito, J. M., Goepfert, P. A., Connors, M., et al. (2006). HIV non-progressors preferentially maintain highly functional HIV-specific CDB+ T cells. Blood 107, 4781-4789.

Breckpot, K., Dullaers, M., Bonehill, A., van Meirvenne, S., Heirman, C., de Greef, C., van der Bruggen, P., and Thielemans, K. (2003). Lentivirally transduced dendritic cells as a tool for cancer immunotherapy. J Gene Med 5, 654-667.

(3) Breckpot, K., Aerts, J. L. & Thielemans, K. Lentiviral vectors for cancer immunotherapy: transforming infectious particles into therapeutics. Gene Ther 14, 847-62 (2007).

Brenchley, J. M., Price, D. A., Schacker, T. W., Asher, T. E., Silvestri, G., Rao, S., Kazzaz, Z., Bornstein, E., Lambotte, O., Altmann, D., et al. (2006). Microbial translocation is a cause of systemic immune activation in chronic HIV infection. Nat Med 12, 1365-1371.

Briggs, J. A., Simon, M. N., Gross, I., Krausslich, H. G., Fuller, S. D., Vogt, V. M., and Johnson, M. C. (2004). The stoichiometry of Gag protein in HIV-1. Nat Struct Mol Biol 11, 672-675.

Brown, B. D. et al. In vivo administration of lentiviral vectors triggers a type I interferon response that restricts hepatocyte gene transfer and promotes vector clearance. Blood 109, 2797-805 (2007).

Carrington, M., Nelson, G. W., Martin, M. P., Kissner, T., Vlahov, D., Goedert, J. J., Kaslow, R., Buchbinder, S., Hoots, K., and O'Brien, S. J. (1999). HLA and HIV-1: heterozygote advantage and B*35-Cw*04 disadvantage. Science 283, 1748-1752.

Cronin J. et al, Curr Gene Ther. 2005, August; 5(4): 387-398 *Altering the Tropism of Lentiviral Vectors through Pseudotyping*

Day, C. L., Kaufmann, D. E., Kiepiela, P., Brown, J. A., Moodley, E. S., Reddy, S., Mackey, E. W., Miller, J. D., Leslie, A. J., DePierres, C., et al. (2006). PD-1 expression on HIV-specific T cells is associated with T-cell exhaustion and disease progression. Nature 443, 350-354.

Delenda, C. (2004). Lentiviral vectors: optimization of packaging, transduction and gene expression. J Gene Med 6 *Suppl* 1, S125-138.

(9) Deml, L. et al. Multiple effects of codon usage optimization on expression and immunogenicity of DNA candidate vaccines encoding the human immunodeficiency virus type 1 Gag protein. J Virol 75, 1 0991-1 001 (2001).

Despres P. et al. Infect Dis. 2005; 191: 207-214

Donello J. E. et al, J. Virol. 1998, June; 72(6): 5085-92

Dullaers, M., and Thielemans, K. (2006). From pathogen to medicine: HIV-1-derived lentiviral vectors as vehicles for dendritic cell based cancer immunotherapy. J Gene Med 8, 3-17.

Esslinger, C., Chapatte, L., Finke, D., Miconnet; I., Guillaume, P., Levy, F., and MacDonald, H. R. (2003). In vivo administration of a lentiviral vaccine targets DCs and induces efficient CD8(+) T cell responses. J Clin Invest 111, 1673-1681.

Firat, H., Garcia-Pons, F., Tourdot, S., Pascolo, S., Scardino, A., Garcia, Z., Michel, M. L., Jack, R. W., Jung, G., Kosmatopoulos, K., et al. (1999). H-2 class I knockout, HLA-A2.1-transgenic mice: a versatile animal model for preclinical evaluation of antitumor immunotherapeutic strategies. Eur J Immunol 29, 3112-3121.

Firat H. et al. The Journal of Gene Medicine 2002; 4: 38-45

Frank, I., Santos, J. J., Mehlhop, E., Villamide-Herrera, L., Santisteban, C., Gettie, A., Ignatius, R., Lifson, J. D., and Pope, M. (2003). Presentation of exogenous whole inactivated simian immunodeficiency virus by mature dendritic cells induces CD4+ and CD8+T-cell responses. J Acquir Immune Defic Syndr 34, 7-19.

Fredericksen B. L. et al. J. Virol. (1995) 69: 1435-1443

Gauduin, M. C., Yu, Y., Barabasz, A., Carville, A., Piatak, M., Lifson, J. D., Desrosiers, R. C., and Johnson, R. P. (2006). Induction of a virus-specific effector-memory CD4+ T cell response by attenuated SIV infection. J Exp Med 203, 2661-2672.

Girard, M. P., Osmanov, S. K., and Kieny, M. P. (2006). A review of vaccine research and development: the human immunodeficiency virus (HIV). Vaccine 24, 4062-4081.

Goulder, P. J., and Watkins, D. I. (2004). HIV and SIV CTL escape: implications for vaccine design. Nat Rev Immunol 4, 630-640.

Gulick, R. M., Mellors, J. W., Havlir, D., Eron, J. J., Meibohm, A., Condra, J. H., Valentine, F. T., McMahon, D., Gonzalez, C., Jonas, L., et al. (2000). 3-year suppression of HIV viremia with indinavir, zidovudine, and lamivudine. Ann Intern Med 133, 35-39.

Hacein-Bey-Abina, S., Von Kalle, C., Schmidt, M., McCormack, M. P., Wulffraat, N., Leboulch, P., Lim, A., Osborne, C. S., Pawliuk, R., Morillon, E., et al. (2003). LMO2-associated clonal T cell proliferation in two patients after gene therapy for SCID-X1. Science 302, 415-419.

He, Y. & Falo, L. D., Jr. Lentivirus as a potent and mechanistically distinct vector for genetic Immunization. Curr Opin Mol Ther 9, 439-46 (2007).

Hel, Z. et al. improved vaccine protection from simian AIDS by the addition of nonstructural simian immunodeficiency virus genes. J Immunol 176, 85-96 (2006).

Iglesias, M. C., Mollier, K., Beignon, A. S., Souque, P., Adotevi, O., Lemonnier, F., and Charneau, P. (2007). Lentiviral vectors encoding HIV-1 polyepitopes induce broad CTL responses in vivo. Mol Ther 15, 1203-1210.

Iglesias, M. C. et al. A single immunization with a minute dose of a lentiviral vector-based vaccine is highly effective at eliciting protective humoral immunity against West Nile virus. J Gene Med 8, 265-74 (2006).

Jin, X., Bauer, D. E., Tuttleton, S. E., Lewin, S., Gettie, A., Blanchard, J., Irwin, C. E., Safrit, J. T., Mittler, J., Weinberger, L., et al. (1999). Dramatic rise in plasma viremia after CD8(+) T cell depletion in simian immunodeficiency virus-infected macaques. J Exp Med 189, 991-998.

Karlsson, I. et al. Dynamics of T-cell responses and memory T cells during primary simian immunodeficiency virus infection in cynomolgus macaques. J Virol Si, 13456-68 (2007).

Kiepiela, P., Ngumbela, K., Thobakgale, C., Ramduth, D., Honeyborne, I., Moodley, E., Reddy, S., de Pierres, C., Mncube, Z., Mkhwanazi, N., et al. (2007). CD8+ T-cell responses to different HIV proteins have discordant associations with viral load. Nat Med 13, 46-53.

Koff, W. C., Johnson, P. R., Watkins, D. I., Burton, D. R., Lifson, J. D., Hasenkrug, K. J., McDermott, A. B., Schultz, A., Zamb, T. J., Boyle, R., and Desrosiers, R. C. (2006). HIV vaccine design: insights from live attenuated SIV vaccines. Nat Immune 7, 19-23.

Koup, R. A., Safrit, J. T., Cao, Y., Andrews, C. A., McLeod, G., Borkowsky, W., Farthing, C., and Ho, D. D. (1994). Temporal association of cellular immune responses with the initial control of viremia in primary human immunodeficiency virus type 1 syndrome. J Virol 68, 4650-4655.

Gallione, C. J. and Rose, J. K.—J. Virol. 46(1), 162-169.

Georgel, P. et al. Vesicular stomatitis virus glycoprotein G activates a specific antiviral Toll-like receptor 4-dependent pathway. Virology 362, 304-13 (2007).

Iglesias, M. C. et al. Lentiviral vectors encoding HIV-1 polyepitopes induce broad CTL responses in vivo. Mol Ther 15, 1203-10 (2007).

Iglesias M C, et al, A single immunization with a minute dose of a lentiviral vector-based vaccine is highly effective protective humoral immunity against West Nile virus. J. Gene Med. 2006 March; 8(3):265-274.

Iglesias M C et al, Polyepitopes Induce Broad CTL Responses In Vivo. Mol. Ther. 2007 June, 15(6) 1203-10.

Isidoro Martinez and Gail W. Wertz, The Journal of Virology, March 2005, p. 3578-3585 Vol. 79, No. 6, Biological Differences between Vesicular Stomatitis Virus Indiana and New Jersey Serotype Glycoproteins: Identification of Amino acid Residues Modulating pH-Dependent Infectivity Kiepiela, P. et al. CD8+T-cell responses to different HIV proteins have discordant associations with viral load. Nat Med 13, 46-53 (2007).

Letvin, N. L. et al. Preserved CD4+central memory T cells and survival in vaccinated SIV-challenged monkeys. Science 312, 1530-3 (2006).

Mattapallil, J. J. et al. Vaccination preserves CD4 memory T cells during acute simian immunodeficiency virus challenge. J Exp Med 203, 1533-41 (2006).

zur Megede, J. et al. Increased expression and immunogenicity of sequence-modified human immunodeficiency virus type 1 gag gene. J Virol 74, 2628-35 (2000).

Mellors, J. W. (1996). Closing in on human immunodeficiency virus-1. Nat Med 2, 274-275.

Montini, E., Cesana, D., Schmidt, M., Sanvito, F., Ponzoni, M., Bartholomae, C., Sergi Sergi, L., Benedicenti, F., Ambrosi, A., Di Serio, C., et al. (2006). Hematopoietic stem cell gene transfer in a tumor-prone mouse model uncovers low genotoxicity of lentiviral vector integration. Nat Biotechnol 24, 687-696.

Palella, F. J., Jr., Delaney, K. M., Moorman, A. C., Loveless, M. O., Fuhrer, J., Satten, G. A., Aschman, D. J., and Holmberg, S. D. (1998). Declining morbidity and mortality among patients with advanced human immunodeficiency virus infection. HIV Outpatient Study Investigators. N Engl J Med 338, 853-860.

Pichlmair, A. et al. Tubulovesicular structures within vesicular stomatitis virus G protein-pseudotyped lentiviral vector preparations carry DNA and stimulate antiviral responses via Toll-Uke receptor 9. J Virol 81, 539-47 (2007).

Poznansky, M., Lever, A., Bergeron, L., Haseltine, W., and Sodroski, J. (1991). Gene transfer into human lymphocytes by a defective human immunodeficiency virus type 1 vector. J Virol 65, 532-536.

Reimann, K. A., Parker, R. A., Seaman, M. S., Beaudry, K., Beddall, M., Peterson, L., Williams, K. C., Veazey, R. S., Montefiori, D.C., Mascola, J. R., et al. (2005). Pathogenicity of simian-human immunodeficiency virus SHIV-89.6P and SIVmac is attenuated in cynomolgus macaques and associated with early T-lymphocyte responses. J Virol 79, 8878-8885.

Rose, N. F, et al. An effective AIDS vaccine based on live attenuated vesicular stomatitis virus recombinants. Cell 106, 539-49 (2001).

Nina F. Rose, Anjeanette Roberts, Linda Buonocore, and John K. Rose, The Journal of Virology, December 2000, p. 10903-10910 Vol. 74, No. 23, Glycoprotein Exchange Vectors based on Vesicular Stomatitis Virus Allow Effective Boosting and Generation of Neutralizing Antibodies to a Primary Isolate of Human Immunodeficiency Virus Type 1
Nina F. Rose, Preston A. Marx, Amara Luckay, Douglas F. Nixon, Walter J. Moretto, Sean M. Donahoe, David Montefiori, Anjeanette Roberts, Linda Buonocore, and John K. Rose, Cell, Vol. 106, 539-549, Sep. 7, 2001, An Effective AIDS Vaccine Based on Live Attenuated Vesicular Stomatitis Virus Recombinants
Nishimura N. et al (PNAS (2002) 99: 6755-6760
Rosenberg, E. S., Altfeld, M., Poon, S. H., Phillips, M. N., Wilkes, B. M., Eldridge, R. L., Robbins, G. K., D'Aquila, R. T., Goulder, P. J., and Walker, B. D. (2000). Immune control of HIV-1 after early treatment of acute infection. Nature 407, 523-526.
Saag, M. S. (1997). Use of virologic markers in clinical practice. J Acquir Immune Defic Syndr Hum Retrovirol 16 *Suppl* 1, S3-13.
Sacha, J. B., Chung, C., Rakasz, E. G., Spencer, S. P., Jonas, A. K., Bean, A. T., Lee, W., Burwitz, B. J., Stephany, J. J., Loffredo, J. T., et al. (2007). Gag-specific CD8+ T lymphocytes recognize infected cells before AIDS-virus integration and viral protein expression. J Immunol 178, 2746-2754.
Schoenly, K. A. & Weiner, D. B. HIV-1 Vaccine Development: Recent Advances in the CTL Platform "Spotty Business". J Viral (2007).
Steven AC. And Spear P G, Viral Glycoproteins and an Evolutionary Conundrum.
Tonks, A. (2007). Quest for the AIDS vaccine. Bmj 334, 1346-1348.
Trkola, A., Kuster, H., Rusert, P., Joos, B., Fischer, M., Leemann, C., Manrique, A., Huber, M., Rehr, M., Oxenius, A., et al., (2005). Delay of HIV-1 rebound after cessation of antiretroviral therapy through passive transfer of human neutralizing antibodies. Nat Med 11, 615-622.
VandenDriessche T. et al. Blood, 1 Aug. 2002-vol. 100, n° 3, p. 813-822

Vargas, J., Jr., Gusella, G. L., Najfeld, V., Klotman, M. E., and Cara, A. (2004). Novel integrase-defective lentiviral episomal vectors for gene transfer. Hum Gene Ther 15, 361-372.
Weber, J. (2001). The pathogenesis of HIV-1 infection. Br Med Bull 58, 61-72.
Wei, X., Ghosh, S. K., Taylor, M. E., Johnson, V. A., Emini, E. A., Deutsch, P., Lifson, J. D., Bonhoeffer, S., Nowak, M. A., Hahn, B. H., and et al. (1995). Viral dynamics in human immunodeficiency virus type 1 infection. Nature 373, 117-122.
Wilson, N. A. et al. Vaccine-induced cellular immune responses reduce plasma viral concentrations after repeated low-dose challenge with pathogenic simian immunodeficiency virus SIVmac239. J Virol 80, 5875-85 (2006).
Wiseman, R. W., Wojcechowskyj, J. A., Greene, J. M., Blasky, A. J., Gopon, T., Soma, T., Friedrich, T. C., O'Connor, S. L., and O'Connor, D. H. (2007). Simian immunodeficiency virus SIVmac239 Infection of major histocompatibility complex-identical cynomolgus macaques from Mauritius. J Virol 81, 349-361.
Yee J. et al, 1994, Proc. Natl. Acad. Sci. USA 91, 9564-9568.
Zarei, S., Abraham, S., Arrighi, J. F., Haller, O., Calzascia, T., Walker, P. R., Kundig, T. M., Hauser, C., and Piguet, V. (2004). Lentiviral transduction of dendritic cells confers protective antiviral immunity in vivo. J Virol 78, 7843-7845.
Zennou, V., Petit, C., Guetard, D., Nerhbass, U., Montagnier, L., and Charneau, P. (2000). HIV-1 genome nuclear import is mediated by a central DNA flap. Cell 101, 173-185.
Zufferey, R., Donello, J. E., Trono, D., and Hope, T. J. (1999). Woodchuck hepatitis virus posttranscriptional regulatory element enhances expression of transgenes delivered by retroviral vectors. J Virol 73, 2886-2892.
Zufferey, R., Dull, T., Mandel, R. J., Bukovsky, A., Quiroz, D., Naldini, L., and Trono, D. (1998). Self-inactivating lentivirus vector for safe and efficient in vivo gene delivery. J Virol 72, 9873-9880.

The invention claimed is:

1. A combination of compounds for sequential administration to a mammalian host comprising:
 (i) lentiviral vector particles, pseudotyped with a first vesicular stomatitis virus G protein, for a first administration; and
 (ii) lentiviral vector particles, pseudotyped with a different, second vesicular stomatitis virus G protein, for a second administration;
 wherein neither of the vesicular stomatitis virus G proteins is of the Chadipura strain or Piry strain, and
 wherein the first the vesicular stomatitis virus G protein does not sero-neutralize the second vesicular stomatitis virus G protein.

2. The combination of compounds of claim 1, wherein the first vesicular stomatitis virus G protein is of the Indiana strain.

3. The combination of compounds of claim 2, wherein the second vesicular stomatitis virus G protein is of the New Jersey strain.

4. The combination of compounds of claim 2, wherein the second vesicular stomatitis virus G protein is of the SVCV strain.

5. The combination of compounds of claim 2, wherein the second vesicular stomatitis virus G protein is of the Isfahan strain.

6. The combination of compounds of claim 2, wherein the second vesicular stomatitis virus G protein is of the Cocal strain.

7. The combination of compounds of claim 1, wherein the first vesicular stomatitis virus G protein is of the New Jersey strain.

8. The combination of compounds of claim 7, wherein the second vesicular stomatitis virus G protein is of the Indiana strain.

9. The combination of compounds of claim 7, wherein the second vesicular stomatitis virus G protein is of the SVCV strain.

10. The combination of compounds of claim 7, wherein the second vesicular stomatitis virus G protein is of the Isfahan strain.

11. The combination of compounds of claim 7, wherein the second vesicular stomatitis virus G protein is of the Cocal strain.

12. The combination of compounds of claim 1, wherein the first vesicular stomatitis virus G protein is of the Isfahan strain.

13. The combination of compounds of claim 12, wherein the second vesicular stomatitis virus G protein is of the Indiana strain.

14. The combination of compounds of claim 12, wherein the second vesicular stomatitis virus G protein is of the SVCV strain.

15. The combination of compounds of claim 12, wherein the second vesicular stomatitis virus G protein is of the New Jersey strain.

16. The combination of compounds of claim 12, wherein the second vesicular stomatitis virus G protein is of the Cocal strain.

17. The combination of compounds of claim 1, wherein the first vesicular stomatitis virus G protein is of the SVCV strain.

18. The combination of compounds of claim 17, wherein the second vesicular stomatitis virus G protein is of the Indiana strain.

19. The combination of compounds of claim 17, wherein the second vesicular stomatitis virus G protein is of the Isfahan strain.

20. The combination of compounds of claim 17, wherein the second vesicular stomatitis virus G protein is of the New Jersey strain.

21. The combination of compounds of claim 17, wherein the second vesicular stomatitis virus G protein is of the Cocal strain.

22. The combination of compounds of claim 1, wherein the first vesicular stomatitis virus G protein is of the Cocal strain.

23. The combination of compounds of claim 22, wherein the second vesicular stomatitis virus G protein is of the Isfahan strain.

24. The combination of compounds of claim 22, wherein the second vesicular stomatitis virus G protein is of the New Jersey strain.

25. The combination of compounds of claim 1, wherein the lentiviral vector particles for the first or second administration comprise a nucleic acid that encodes at least one human immunodeficiency virus Gag antigen.

26. The combination of compounds of claim 25, wherein the Gag antigen is a GagΔmyr protein devoid of myristylation.

27. The combination of compounds of claim 1, wherein one of the vesicular stomatitis virus G proteins comprises the cytoplasmic tail of the vesicular stomatitis virus G protein of the Indiana strain.

28. The combination of compounds of claim 1, wherein one of the vesicular stomatitis virus G proteins comprises the transmembrane domain of the vesicular stomatitis virus G protein of the Indiana strain.

29. The combination of compounds of claim 1, wherein one of the vesicular stomatitis virus G proteins comprises the transmembrane and cytoplasmic domain of the vesicular stomatitis virus G protein of the Indiana strain and the ectodomain of the vesicular stomatitis virus G protein of the New Jersey strain.

30. The combination of compounds of claim 1, wherein the lentiviral vector particles for the first or second administration comprise a nucleic acid comprising a functional lentiviral DNA flap.

31. The combination of compounds of claim 30, wherein the functional lentiviral DNA flap is an HIV-1 DNA flap.

32. The combination of compounds of claim 1, wherein the lentiviral vector particles for the first or second administration comprise a nucleic acid comprising a β2 microglobulin promoter.

33. The combination of compounds of claim 1, wherein the lentiviral vector particles for the first and second administration comprise a nucleic acid comprising a β2 microglobulin promoter.

34. The combination of compounds of claim 1, wherein the lentiviral vector particles for the first or second administration comprise a nucleic acid comprising an LTR devoid of the enhancer of the U3 region.

35. The combination of compounds of claim 1, wherein the lentiviral vector particles for the first or second administration comprise a nucleic acid that encodes at least one human immunodeficiency virus Nef, Tat, Rev, or Pol antigen.

36. The combination of compounds of claim 1, wherein the lentiviral vector particles for the first or second administration are HIV vector particles.

37. The combination of compounds of claim 1, wherein the lentiviral vector particles for the first and second administration are HIV vector particles.

38. A method for priming and subsequently boosting an immune response in a mammalian host comprising sequentially administering the combination of compounds of claim 1, wherein the first administration and second administration are administered at different times to a mammalian host.

39. A method for inducing an immune response in a human comprising administering the combination of compounds of claim 1 to a human.

40. The method of claim 39, wherein the human is infected with a human immunodeficiency virus.

* * * * *

UNITED STATES PATENT AND TRADEMARK OFFICE
CERTIFICATE OF CORRECTION

PATENT NO. : 8,420,104 B2
APPLICATION NO. : 12/671898
DATED : April 16, 2013
INVENTOR(S) : Charneau et al.

Page 1 of 1

It is certified that error appears in the above-identified patent and that said Letters Patent is hereby corrected as shown below:

In the Claims

Col. 241:

Line 24, Claim 1, replace "the first the vesicular" with -- the first vesicular --.

Signed and Sealed this
Twenty-fifth Day of June, 2013

Teresa Stanek Rea
*Acting Director of the United States Patent and Trademark Office*